US010172549B2

(12) United States Patent
Waldhauser et al.

(10) Patent No.: US 10,172,549 B2
(45) Date of Patent: Jan. 8, 2019

(54) METHODS OF FACILITATING POSITIONING OF ELECTRODES

(71) Applicant: Cardionomic, Inc., New Brighton, MN (US)

(72) Inventors: Steven L. Waldhauser, Savage, MN (US); Steven C. Christian, St. Paul, MN (US)

(73) Assignee: Cardionomic, Inc., New Brighton, MN (US)

( * ) Notice: Subject to any disclaimer, the term of this patent is extended or adjusted under 35 U.S.C. 154(b) by 0 days.

(21) Appl. No.: 15/893,038

(22) Filed: Feb. 9, 2018

(65) Prior Publication Data

US 2018/0168503 A1    Jun. 21, 2018

Related U.S. Application Data

(63) Continuation of application No. PCT/US2017/021214, filed on Mar. 7, 2017.
(Continued)

(51) Int. Cl.
*A61B 5/00* (2006.01)
*A61B 6/12* (2006.01)
(Continued)

(52) U.S. Cl.
CPC ........ *A61B 5/4836* (2013.01); *A61B 5/02028* (2013.01); *A61B 5/02158* (2013.01);
(Continued)

(58) Field of Classification Search
CPC ... A61B 5/4836; A61B 5/7246; A61B 5/4848; A61B 5/02028; A61B 5/02158;
(Continued)

(56) References Cited

U.S. PATENT DOCUMENTS

| 4,718,423 A | 1/1988 | Willis et al. |
| 4,947,866 A | 8/1990 | Lessar et al. |

(Continued)

FOREIGN PATENT DOCUMENTS

| CA | 2 848 781 | 3/2013 |
| EP | 1 871 469 | 10/2013 |

(Continued)

OTHER PUBLICATIONS

Ardell et al., "Differential sympathetic regulation of automatic, conductile, and contractile tissue in dog heart," American Journal of Physiology (Nov. 1988) 255 (5): H1050-H1059.
(Continued)

*Primary Examiner* — Julian W Woo
(74) *Attorney, Agent, or Firm* — Knobbe Martens Olson & Bear, LLP

(57) ABSTRACT

A device includes a handle, an expandable structure including a plurality of splines extending from a proximal hub to a distal hub, a first electrode on a first spline of the plurality of splines, an outer tube extending from the handle to the proximal hub, and a shaft extending through the outer tube from the handle to the distal hub. The expandable structure has a collapsed state and a self-expanded state. The handle is configured to retract the shaft. Retracting the shaft may expand the expandable structure outward of the self-expanded state.

20 Claims, 108 Drawing Sheets

Related U.S. Application Data

(60) Provisional application No. 62/464,039, filed on Feb. 27, 2017, provisional application No. 62/343,302, filed on May 31, 2016, provisional application No. 62/305,988, filed on Mar. 9, 2016.

(51) Int. Cl.

| | | |
|---|---|---|
| *A61N 1/05* | (2006.01) | |
| *A61N 1/36* | (2006.01) | |
| *A61B 6/00* | (2006.01) | |
| *A61B 5/08* | (2006.01) | |
| *A61B 5/0215* | (2006.01) | |
| *A61B 5/02* | (2006.01) | |
| *A61M 25/10* | (2013.01) | |
| *A61B 5/042* | (2006.01) | |
| *A61B 5/0452* | (2006.01) | |
| *A61B 18/14* | (2006.01) | |
| *A61N 1/362* | (2006.01) | |
| *A61N 1/365* | (2006.01) | |
| *A61B 18/00* | (2006.01) | |
| *A61M 25/00* | (2006.01) | |

(52) U.S. Cl.
CPC .......... *A61B 5/0422* (2013.01); *A61B 5/0452* (2013.01); *A61B 5/0823* (2013.01); *A61B 5/4848* (2013.01); *A61B 5/6858* (2013.01); *A61B 5/6859* (2013.01); *A61B 5/7246* (2013.01); *A61B 6/12* (2013.01); *A61B 6/487* (2013.01); *A61B 18/1492* (2013.01); *A61M 25/10* (2013.01); *A61N 1/056* (2013.01); *A61N 1/0573* (2013.01); *A61N 1/3627* (2013.01); *A61N 1/36114* (2013.01); *A61N 1/36139* (2013.01); *A61N 1/36585* (2013.01); *A61B 2018/00214* (2013.01); *A61B 2018/00267* (2013.01); *A61B 2018/00279* (2013.01); *A61B 2018/00285* (2013.01); *A61B 2018/00351* (2013.01); *A61B 2018/00839* (2013.01); *A61B 2562/028* (2013.01); *A61B 2562/0247* (2013.01); *A61M 2025/0003* (2013.01); *A61N 1/0558* (2013.01); *A61N 1/36017* (2013.01); *A61N 1/36117* (2013.01); *A61N 1/36135* (2013.01); *A61N 1/36146* (2013.01); *A61N 1/36185* (2013.01); *A61N 2001/058* (2013.01)

(58) Field of Classification Search
CPC ......... A61B 6/12; A61B 5/0823; A61B 6/487; A61B 2562/0247; A61B 2562/028; A61N 1/056; A61N 1/36139; A61N 1/36114; A61M 25/10; A61M 2025/0003
See application file for complete search history.

(56) References Cited

U.S. PATENT DOCUMENTS

| | | | |
|---|---|---|---|
| 4,950,227 A | 8/1990 | Savin et al. | |
| 5,067,957 A | 11/1991 | Jervis | |
| 5,156,154 A | 10/1992 | Valenta, Jr. et al. | |
| 5,190,546 A | 3/1993 | Jervis | |
| 5,197,978 A | 3/1993 | Hess | |
| 5,213,098 A | 5/1993 | Bennett et al. | |
| 5,224,491 A | 7/1993 | Mehra | |
| 5,259,387 A | 11/1993 | Depinto | |
| 5,336,244 A | 8/1994 | Weijand | |
| 5,345,936 A | 9/1994 | Pomeranz et al. | |
| 5,365,926 A | 11/1994 | Desai | |
| 5,423,881 A | 6/1995 | Breyen et al. | |
| 5,431,649 A | 7/1995 | Mulier et al. | |
| 5,554,139 A | 9/1996 | Okajima | |
| 5,564,434 A | 10/1996 | Halperin et al. | |
| 5,598,848 A | 2/1997 | Swanson et al. | |
| 5,711,316 A | 1/1998 | Elsberry et al. | |
| 5,725,570 A | 3/1998 | Heath | |
| 5,755,766 A | 5/1998 | Chastain et al. | |
| 5,782,239 A | 7/1998 | Webster | |
| 5,853,411 A | 12/1998 | Whayne et al. | |
| 5,948,007 A | 9/1999 | Starkebaum et al. | |
| 5,954,761 A | 9/1999 | Machek et al. | |
| 5,968,040 A | 10/1999 | Swanson et al. | |
| 5,997,563 A | 12/1999 | Kretzers | |
| 6,036,697 A | 3/2000 | Dicaprio | |
| 6,038,480 A | 3/2000 | Hrdlicka et al. | |
| 6,058,331 A | 5/2000 | King et al. | |
| 6,059,810 A | 5/2000 | Brown et al. | |
| 6,071,308 A | 6/2000 | Ballou et al. | |
| 6,136,021 A | 10/2000 | Tockman et al. | |
| 6,152,882 A | 11/2000 | Prutchi | |
| 6,161,029 A | 12/2000 | Spreigl et al. | |
| 6,223,072 B1 | 4/2001 | Mika et al. | |
| 6,231,516 B1 | 5/2001 | Keilman et al. | |
| 6,233,484 B1 | 5/2001 | Ben-haim et al. | |
| 6,233,487 B1 | 5/2001 | Mika et al. | |
| 6,236,887 B1 | 5/2001 | Ben-haim et al. | |
| 6,241,724 B1 | 6/2001 | Fleischman et al. | |
| 6,254,610 B1 | 7/2001 | Darvish et al. | |
| 6,263,242 B1 | 7/2001 | Mika et al. | |
| 6,266,564 B1 | 7/2001 | Hill et al. | |
| 6,285,906 B1 | 9/2001 | Ben-haim et al. | |
| 6,292,693 B1 | 9/2001 | Darvish et al. | |
| 6,292,695 B1 | 9/2001 | Webster et al. | |
| 6,292,704 B1 | 9/2001 | Malonek et al. | |
| 6,295,475 B1 | 9/2001 | Morgan | |
| 6,298,268 B1 | 10/2001 | Ben-haim et al. | |
| 6,304,777 B1 | 10/2001 | Ben-haim et al. | |
| 6,317,631 B1 | 11/2001 | Ben-haim et al. | |
| 6,319,241 B1 | 11/2001 | King et al. | |
| 6,330,476 B1 | 12/2001 | Ben-haim et al. | |
| 6,335,538 B1 | 1/2002 | Prutchi et al. | |
| 6,348,045 B1 | 2/2002 | Malonek et al. | |
| 6,353,762 B1 | 3/2002 | Baudino et al. | |
| 6,360,123 B1 | 3/2002 | Kimchi et al. | |
| 6,360,126 B1 | 3/2002 | Mika et al. | |
| 6,363,279 B1 | 3/2002 | Ben-haim et al. | |
| 6,370,430 B1 | 4/2002 | Mika et al. | |
| 6,415,178 B1 | 7/2002 | Ben-Haim et al. | |
| 6,424,866 B2 | 7/2002 | Mika et al. | |
| 6,428,537 B1 | 8/2002 | Swanson et al. | |
| 6,442,424 B1 | 8/2002 | Ben-haim et al. | |
| 6,447,478 B1 | 9/2002 | Maynard | |
| 6,459,928 B2 | 10/2002 | Mika et al. | |
| 6,463,324 B1 | 10/2002 | Ben-haim et al. | |
| 6,473,653 B1 | 10/2002 | Schallhorn et al. | |
| 6,480,737 B1 | 11/2002 | Policker et al. | |
| 6,522,904 B1 | 2/2003 | Mika et al. | |
| 6,522,926 B1 | 2/2003 | Kieval et al. | |
| 6,529,778 B2 | 3/2003 | Prutchi | |
| 6,542,774 B2 | 4/2003 | Hill et al. | |
| 6,547,788 B1 | 4/2003 | Maguire et al. | |
| 6,564,096 B2 | 5/2003 | Mest | |
| 6,571,127 B1 | 5/2003 | Ben-haim et al. | |
| 6,574,492 B1 | 6/2003 | Shlomo et al. | |
| 6,587,721 B1 | 7/2003 | Prutchi et al. | |
| 6,597,952 B1 | 7/2003 | Mika et al. | |
| 6,600,953 B2 | 7/2003 | Flesler et al. | |
| 6,662,055 B1 | 12/2003 | Prutchi | |
| 6,669,693 B2 | 12/2003 | Friedman | |
| 6,675,043 B1 | 1/2004 | Prutchi et al. | |
| 6,684,105 B2 | 1/2004 | Cohen et al. | |
| 6,694,192 B2 | 2/2004 | Policker et al. | |
| 6,712,831 B1 | 3/2004 | Kaplan et al. | |
| 6,725,093 B1 | 4/2004 | Ben-haim et al. | |
| 6,738,655 B1 | 5/2004 | Sen et al. | |
| 6,740,113 B2 | 5/2004 | Vrba | |
| 6,748,271 B2 | 6/2004 | Spinelli et al. | |
| 6,749,600 B1 | 6/2004 | Levy | |
| 6,754,532 B1 | 6/2004 | Ferek-Petric | |
| RE38,654 E | 11/2004 | Hill et al. | |
| 6,832,478 B2 | 12/2004 | Anderson et al. | |

(56) References Cited

U.S. PATENT DOCUMENTS

| | | |
|---|---|---|
| 6,850,801 B2 | 2/2005 | Kieval et al. |
| 6,887,266 B2 | 5/2005 | Williams et al. |
| 6,912,419 B2 | 6/2005 | Hill et al. |
| 6,932,930 B2 | 8/2005 | Desimone et al. |
| 6,944,490 B1 | 9/2005 | Chow |
| 6,947,792 B2 | 9/2005 | Ben-haim et al. |
| 6,950,689 B1 | 9/2005 | Willis et al. |
| 6,985,774 B2 | 1/2006 | Kieval et al. |
| 6,993,385 B1 | 1/2006 | Routh et al. |
| 7,027,863 B1 | 4/2006 | Prutchi et al. |
| 7,062,318 B2 | 6/2006 | Ben-haim et al. |
| 7,072,720 B2 | 7/2006 | Puskas |
| 7,082,336 B2 | 7/2006 | Ransbury et al. |
| 7,092,753 B2 | 8/2006 | Darvish et al. |
| 7,092,759 B2 | 8/2006 | Nehls et al. |
| 7,096,070 B1 | 8/2006 | Jenkins et al. |
| 7,097,665 B2 | 8/2006 | Stack et al. |
| 7,111,627 B2 | 9/2006 | Stack et al. |
| 7,121,283 B2 | 10/2006 | Stack et al. |
| 7,141,061 B2 | 11/2006 | Williams et al. |
| 7,146,984 B2 | 12/2006 | Stack et al. |
| 7,152,607 B2 | 12/2006 | Stack et al. |
| 7,158,832 B2 | 1/2007 | Kieval et al. |
| 7,163,554 B2 | 1/2007 | Williams et al. |
| 7,167,748 B2 | 1/2007 | Ben-haim et al. |
| 7,171,263 B2 | 1/2007 | Darvish et al. |
| 7,187,970 B2 | 3/2007 | Shemer et al. |
| 7,190,997 B1 | 3/2007 | Darvish et al. |
| 7,195,594 B2 | 3/2007 | Eigler et al. |
| 7,195,637 B2 | 3/2007 | Mika |
| 7,218,963 B2 | 5/2007 | Ben-haim et al. |
| 7,231,260 B2 | 6/2007 | Wallace et al. |
| 7,260,431 B2 | 8/2007 | Libbus et al. |
| 7,277,757 B2 | 10/2007 | Casavant et al. |
| 7,277,761 B2 | 10/2007 | Shelchuk |
| 7,279,007 B2 | 10/2007 | Nikolic |
| 7,285,287 B2 | 10/2007 | Williams et al. |
| 7,295,881 B2 | 11/2007 | Cohen et al. |
| 7,308,303 B2 | 12/2007 | Whitehurst et al. |
| 7,310,555 B2 | 12/2007 | Ben-haim et al. |
| 7,321,793 B2 | 1/2008 | Ben Ezra et al. |
| 7,354,454 B2 | 4/2008 | Stack et al. |
| 7,363,082 B2 | 4/2008 | Ransbury et al. |
| 7,377,939 B2 | 5/2008 | Williams et al. |
| 7,389,149 B2 | 6/2008 | Rossing et al. |
| 7,412,289 B2 | 8/2008 | Malonek et al. |
| 7,431,725 B2 | 10/2008 | Stack et al. |
| 7,460,906 B2 | 12/2008 | Libbus |
| 7,460,907 B1 | 12/2008 | Darvish et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,529,589 B2 | 5/2009 | Williams et al. |
| 7,542,800 B2 | 6/2009 | Libbus et al. |
| 7,547,286 B2 | 6/2009 | Choate |
| 7,561,923 B2 | 7/2009 | Libbus et al. |
| 7,616,997 B2 | 11/2009 | Kieval et al. |
| 7,617,003 B2 | 11/2009 | Caparso et al. |
| 7,617,007 B2 | 11/2009 | Williams et al. |
| 7,623,926 B2 | 11/2009 | Rossing et al. |
| 7,630,760 B2 | 12/2009 | Libbus et al. |
| 7,634,317 B2 | 12/2009 | Ben-David et al. |
| 7,643,875 B2 | 1/2010 | Heil, Jr. et al. |
| 7,647,102 B2 | 1/2010 | Routh et al. |
| 7,658,709 B2 | 2/2010 | Anderson et al. |
| 7,668,602 B2 | 2/2010 | Ben-David et al. |
| 7,676,266 B1 | 3/2010 | Kroll |
| 7,704,276 B2 | 4/2010 | Williams et al. |
| 7,706,884 B2 | 4/2010 | Libbus |
| 7,734,343 B2 | 6/2010 | Ransbury et al. |
| 7,734,348 B2 | 6/2010 | Zhang et al. |
| 7,747,335 B2 | 6/2010 | Williams |
| 7,765,000 B2 | 7/2010 | Zhang et al. |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,801,614 B2 | 9/2010 | Rossing et al. |
| 7,805,194 B1 | 9/2010 | Schecter |
| 7,805,203 B2 | 9/2010 | Ben-David et al. |
| 7,813,812 B2 | 10/2010 | Kieval et al. |
| 7,840,262 B2 | 11/2010 | Mika et al. |
| 7,840,271 B2 | 11/2010 | Kieval et al. |
| 7,840,282 B2 | 11/2010 | Williams et al. |
| 7,848,812 B2 | 12/2010 | Crowley et al. |
| 7,857,748 B2 | 12/2010 | Williams et al. |
| 7,869,881 B2 | 1/2011 | Libbus et al. |
| 7,873,413 B2 | 1/2011 | McCabe et al. |
| 7,881,782 B2 | 2/2011 | Libbus et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,892,292 B2 | 2/2011 | Stack et al. |
| 7,899,554 B2 | 3/2011 | Williams et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,919,162 B2 | 4/2011 | Desimone et al. |
| 7,925,352 B2 | 4/2011 | Stack et al. |
| 7,949,400 B2 | 5/2011 | Kieval et al. |
| 7,953,481 B1 | 5/2011 | Shemer et al. |
| 7,966,067 B2 | 6/2011 | Rousso et al. |
| 7,974,693 B2 | 7/2011 | Ben-David et al. |
| 8,000,793 B2 | 8/2011 | Libbus |
| 8,005,542 B2 | 8/2011 | Ben-Ezra et al. |
| 8,005,545 B2 | 8/2011 | Ben-David et al. |
| 8,014,858 B1 | 9/2011 | Ben-haim et al. |
| 8,014,874 B2 | 9/2011 | Rossing et al. |
| 8,024,050 B2 | 9/2011 | Libbus et al. |
| 8,027,724 B2 | 9/2011 | Wei et al. |
| 8,032,215 B2 | 10/2011 | Libbus et al. |
| 8,036,745 B2 | 10/2011 | Ben-David et al. |
| 8,060,197 B2 | 11/2011 | Ben-David et al. |
| 8,060,206 B2 | 11/2011 | Kieval et al. |
| 8,060,218 B2 | 11/2011 | Singh et al. |
| 8,086,314 B1 | 12/2011 | Kieval |
| 8,116,881 B2 | 2/2012 | Cohen et al. |
| 8,116,883 B2 | 2/2012 | Williams et al. |
| 8,121,693 B2 | 2/2012 | Libbus |
| 8,126,560 B2 | 2/2012 | Schiener et al. |
| 8,131,373 B2 | 3/2012 | Libbus |
| 8,145,304 B2 | 3/2012 | Moffitt et al. |
| 8,150,521 B2 | 4/2012 | Crowley et al. |
| 8,152,843 B2 | 4/2012 | Williams et al. |
| 8,155,744 B2 | 4/2012 | Rezai |
| 8,175,705 B2 | 5/2012 | Libbus |
| 8,195,289 B2 | 6/2012 | Heil, Jr. et al. |
| 8,195,290 B2 | 6/2012 | Brockway et al. |
| 8,204,591 B2 | 6/2012 | Ben-David et al. |
| 8,204,596 B2 | 6/2012 | Ransbury et al. |
| 8,206,456 B2 | 6/2012 | Stack et al. |
| 8,224,444 B2 | 7/2012 | Ben-David et al. |
| 8,229,564 B2 | 7/2012 | Rezai |
| 8,239,037 B2 | 8/2012 | Glenn et al. |
| 8,239,045 B2 | 8/2012 | Ransbury et al. |
| 8,244,355 B2 | 8/2012 | Bennett et al. |
| 8,249,706 B2 | 8/2012 | Koh |
| 8,260,416 B2 | 9/2012 | Ben-haim et al. |
| 8,290,595 B2 | 10/2012 | Kieval et al. |
| 8,301,247 B2 | 10/2012 | Ben-haim et al. |
| 8,306,616 B2 | 11/2012 | Ben-haim et al. |
| 8,306,617 B2 | 11/2012 | Ben-haim et al. |
| 8,311,629 B2 | 11/2012 | Ben-haim et al. |
| 8,311,633 B2 | 11/2012 | Ransbury et al. |
| 8,321,013 B2 | 11/2012 | Darvish et al. |
| 8,326,416 B2 | 12/2012 | Mika et al. |
| 8,335,571 B2 | 12/2012 | Singh et al. |
| 8,352,031 B2 | 1/2013 | Rousso et al. |
| 8,369,954 B2 | 2/2013 | Stack et al. |
| 8,372,325 B2 | 2/2013 | Williams et al. |
| 8,386,053 B2 | 2/2013 | Kornet |
| 8,386,056 B2 | 2/2013 | Ben-David et al. |
| 8,401,672 B2 | 3/2013 | Libbus et al. |
| 8,406,864 B2 | 3/2013 | Rousso et al. |

(56) References Cited

U.S. PATENT DOCUMENTS

| | | |
|---|---|---|
| 8,406,877 B2 | 3/2013 | Smith et al. |
| 8,412,326 B2 | 4/2013 | Arcot-Krishnamurthy et al. |
| 8,417,354 B2 | 4/2013 | Zhang et al. |
| 8,428,730 B2 | 4/2013 | Stack et al. |
| 8,437,867 B2 | 5/2013 | Murney et al. |
| 8,452,398 B2 | 5/2013 | Libbus et al. |
| 8,473,076 B2 | 6/2013 | Libbus et al. |
| 8,498,703 B2 | 7/2013 | Spinelli et al. |
| 8,527,042 B2 * | 9/2013 | Libbus ............... A61B 5/02028 607/118 |
| 8,538,535 B2 | 9/2013 | Gross et al. |
| 8,548,583 B2 | 10/2013 | Rousso et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,583,236 B2 | 11/2013 | Kieval et al. |
| 8,606,359 B2 | 12/2013 | Rossing et al. |
| 8,609,082 B2 | 12/2013 | Ben-David et al. |
| 8,615,294 B2 | 12/2013 | Ben-David et al. |
| 8,620,426 B2 | 12/2013 | Moffitt et al. |
| 8,626,290 B2 | 1/2014 | Dagan et al. |
| 8,626,299 B2 | 1/2014 | Gross et al. |
| 8,634,921 B2 | 1/2014 | Chavan et al. |
| 8,639,332 B2 | 1/2014 | Kuhn et al. |
| 8,655,444 B2 | 2/2014 | Ben-haim et al. |
| 8,682,430 B2 | 3/2014 | Libbus et al. |
| 8,682,434 B2 | 3/2014 | Libbus |
| 8,706,230 B2 | 4/2014 | Rousso et al. |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,771,337 B2 | 7/2014 | Williams et al. |
| 8,784,354 B2 | 7/2014 | Stack et al. |
| 8,784,500 B2 | 7/2014 | Stack et al. |
| 8,788,066 B2 | 7/2014 | Cates et al. |
| 8,798,738 B2 | 8/2014 | Machado et al. |
| 8,805,501 B2 | 8/2014 | Libbus |
| 8,818,501 B2 | 8/2014 | Machado et al. |
| 8,825,152 B2 | 9/2014 | Shemer et al. |
| 8,838,246 B2 | 9/2014 | Kieval |
| 8,855,783 B2 | 10/2014 | Dagan et al. |
| 8,880,190 B2 | 11/2014 | Kieval et al. |
| 8,886,340 B2 | 11/2014 | Williams et al. |
| 8,901,878 B2 | 12/2014 | Prutchi et al. |
| 8,906,286 B2 | 12/2014 | Desimone et al. |
| 8,918,172 B2 | 12/2014 | Moffitt et al. |
| 8,929,990 B2 | 1/2015 | Moffitt et al. |
| 8,934,956 B2 | 1/2015 | Glenn et al. |
| 8,934,968 B2 | 1/2015 | Whitehurst et al. |
| 8,958,872 B2 | 2/2015 | Ben-haim et al. |
| 8,972,015 B2 | 3/2015 | Stack et al. |
| 8,977,353 B2 | 3/2015 | Rousso et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-haim et al. |
| 9,216,289 B2 | 12/2015 | Libbus et al. |
| 9,248,038 B2 | 2/2016 | Stack et al. |
| 9,289,618 B1 | 3/2016 | Ben-haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 2003/0045909 A1 | 3/2003 | Gross et al. |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0100668 A1 | 5/2006 | Ben-David et al. |
| 2006/0116737 A1 | 6/2006 | Libbus |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0135875 A1 | 6/2007 | Demarais et al. |
| 2007/0255364 A1 | 11/2007 | Gerber et al. |
| 2008/0015659 A1 | 1/2008 | Zhang et al. |
| 2008/0046016 A1 | 2/2008 | Ben-David et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0161894 A1 | 7/2008 | Ben-David et al. |
| 2008/0167693 A1 | 7/2008 | Kieval et al. |

(56) References Cited

U.S. PATENT DOCUMENTS

| | | |
|---|---|---|
| 2008/0177338 A1 | 7/2008 | Ben-David et al. |
| 2008/0275349 A1* | 11/2008 | Halperin ............. A61B 5/0205 |
| | | 600/484 |
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0276022 A1 | 11/2009 | Burnes et al. |
| 2009/0281608 A1 | 11/2009 | Foster |
| 2010/0222832 A1 | 9/2010 | Zhang et al. |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1 | 2/2012 | Haverkost |
| 2012/0232563 A1 | 9/2012 | Williams et al. |
| 2012/0303080 A1 | 11/2012 | Ben-David et al. |
| 2012/0310304 A1 | 12/2012 | Brockway et al. |
| 2013/0012863 A1 | 1/2013 | Stack et al. |
| 2013/0110208 A1 | 5/2013 | Inagaki et al. |
| 2013/0172715 A1 | 7/2013 | Just et al. |
| 2013/0172953 A1 | 7/2013 | Machado et al. |
| 2013/0218221 A1 | 8/2013 | Zhang et al. |
| 2013/0253616 A1 | 9/2013 | Libbus et al. |
| 2013/0289686 A1 | 10/2013 | Masson et al. |
| 2013/0331919 A1 | 12/2013 | Zhang et al. |
| 2013/0338748 A1 | 12/2013 | Dagan |
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0172006 A1 | 6/2014 | Stack et al. |
| 2014/0214135 A1 | 7/2014 | Ben-David et al. |
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0324115 A1 | 10/2014 | Ziegler et al. |
| 2015/0018908 A1 | 1/2015 | Williams et al. |
| 2015/0039058 A1 | 2/2015 | Masson et al. |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2016/0022890 A1 | 1/2016 | Schwammenthal et al. |
| 2016/0051741 A1 | 2/2016 | Schwammenthal et al. |
| 2016/0174864 A1 | 6/2016 | Levin et al. |
| 2017/0001015 A1 | 1/2017 | Marnfeldt et al. |
| 2017/0065812 A1 | 3/2017 | Goedeke et al. |
| 2017/0065818 A1 | 3/2017 | Ransbury et al. |
| 2017/0143227 A1 | 5/2017 | Marecki et al. |
| 2017/0173338 A1 | 6/2017 | Waldhauser et al. |
| 2017/0173339 A1 | 6/2017 | Waldhauser et al. |
| 2017/0189642 A1 | 7/2017 | Masson et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0050206 A1 | 2/2018 | Waldhauser et al. |
| 2018/0147408 A1 | 5/2018 | Machado et al. |
| 2018/0161577 A1 | 6/2018 | Goedeke et al. |
| 2018/0169414 A1 | 6/2018 | Goedeke et al. |
| 2018/0214696 A1 | 8/2018 | Cuchiara et al. |
| 2018/0214697 A1 | 8/2018 | Cuchiara et al. |
| 2018/0214698 A1 | 8/2018 | Cuchiara et al. |
| 2018/0236220 A1 | 8/2018 | Glenn et al. |

FOREIGN PATENT DOCUMENTS

| | | |
|---|---|---|
| EP | 2 316 525 | 1/2016 |
| WO | WO 1997/024983 | 7/1997 |
| WO | WO 2005/041748 | 5/2005 |
| WO | WO 2006/007048 | 1/2006 |
| WO | WO 2006/058253 | 6/2006 |
| WO | WO 2008/054448 | 5/2008 |
| WO | WO 2009/135083 | 11/2009 |
| WO | WO 2012/068273 | 5/2012 |
| WO | WO 2012/149511 | 11/2012 |
| WO | WO 2015/179634 | 11/2015 |
| WO | WO 2016/040037 | 3/2016 |
| WO | WO 2016/040038 | 3/2016 |
| WO | WO 2016/111940 | 7/2016 |
| WO | WO 2017/156039 | 9/2017 |

OTHER PUBLICATIONS

Casadei, "Vagal control of myocardial . . . in humans," The Physiological Society (Mar. 2001): 817-823.

De Ferrari et al., "Vagus nerve stimulation . . . future directions," Heart Fail Rev. (2011) 16: 195-203.

Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprIW.mjjo, downloaded on Oct. 30, 2017.

Klein et al., "Vagus nerve stimulation . . . heart failure," Cariology Journal (2010) 17 (6): 638-643.

Koizumi et al., "Functional significance of coactivation . . . ," National Academy of Sciences (Mar. 1982) 79 (6): 2116-2120.

Lawo et al., "Electrical Signals Applied During the Absolute Refractory Period", JACC, Dec. 20, 2005, vol. 46, No. 21, pp. 2229-2236.

Meyer et al., "Augmentation of left ventricular . . . ," Americ. Heart Assoc. (2010): 1286-1294.

Murphy, "Preliminary observations of the effects of simulation of . . . in man," CA Journal of Phys. and Pharmac (Jun. 1985). 63 (6): 649-655.

Randall et al., "Regional cardiac distribution . . . ," Federation Proceedings (Jul.-Aug 1972) 31 (4): 1199-1208.

Randall, "Augmentor action to the sympathetic . . . ," Journal of Applied Physiology (Jul. 1960) 15 (4): 629-631.

Rudski et al., "Guidelines for the Echocardiographic Assessment of the Right Heart in Adults: A Report from the American Society of Echocardiography", J Am Soc Echocardiogr, 2010, vol. 23, pp. 685-713.

Triposkiadis et al., "Sympathetic nervous . . . failure," Journal of Amer. Coll. of Cardiology (Nov. 3, 2009) 54 (19): 1747-1762.

Zarse, "Selective increase . . . sympathetic tone," Journal of Amer. Coll. of Cardiology (2005) 46 (7): 1354-1359.

International Search Report and Written Opinion issued in PCT Application No. PCT/US2017/021214, dated Jul. 21, 2017, in 22 pages.

Karamanoglu, "A System for Analysis of Arterial Blood Pressure Waveforms in Humans", Computers and Biomedical Research, 1997, vol. 30, pp. 244-255.

Karamanoglu et al., "Estimation of cardiac output in patients with congestive heart failure by analysis of right ventricular pressure waveforms", Biomedical Engineering Online, 2011, vol. 10, No. 36.

Karamanoglu et al., "Right Ventricular Pressure Waveform and Wave Reflection Analysis in Patients With Pulmonary Arterial Hypertension", Chest Jour., Jul. 2007, vol. 132, No. 1, pp. 37-43.

\* cited by examiner

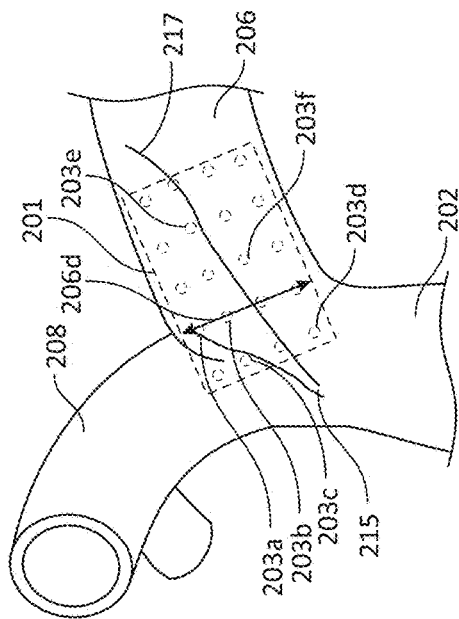
FIG. 2I
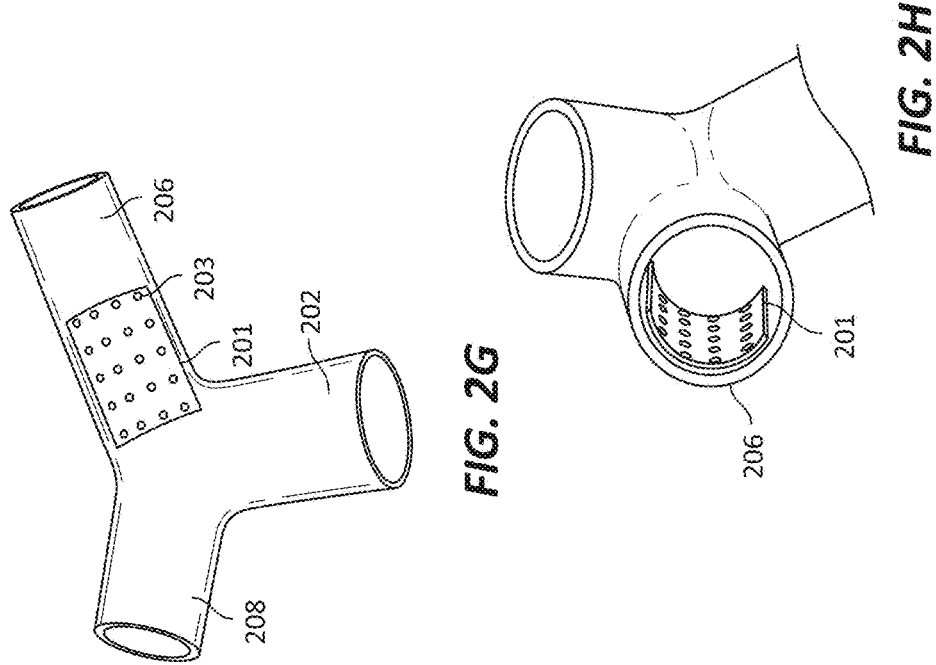
FIG. 2G
FIG. 2H

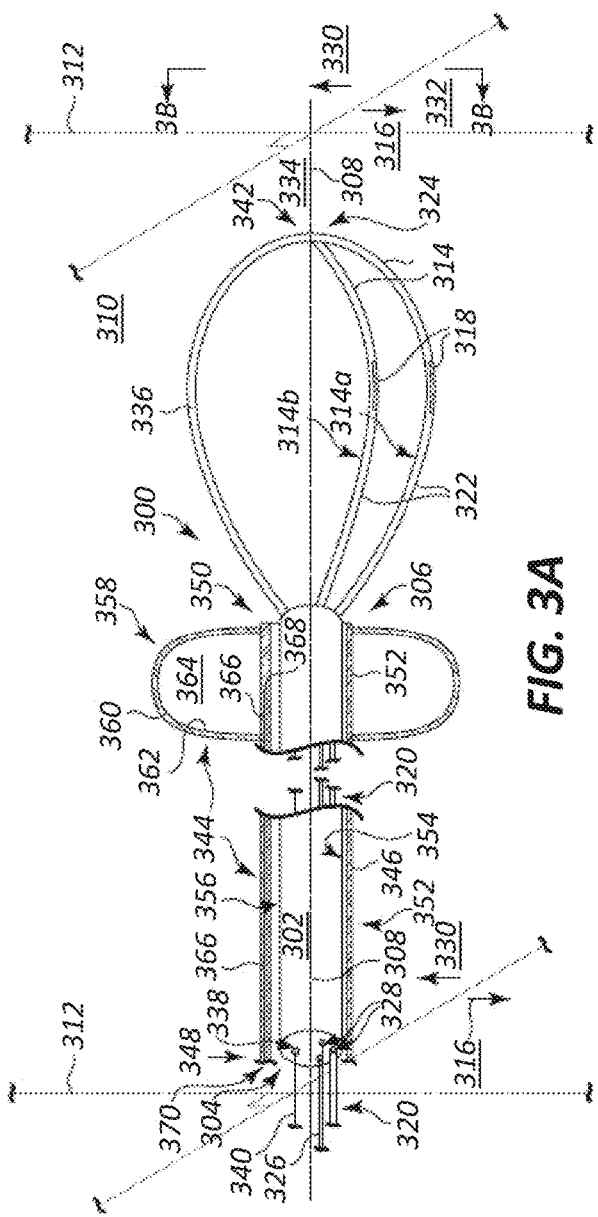
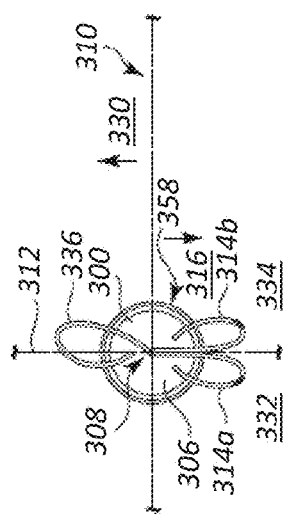
FIG. 3A
FIG. 3B

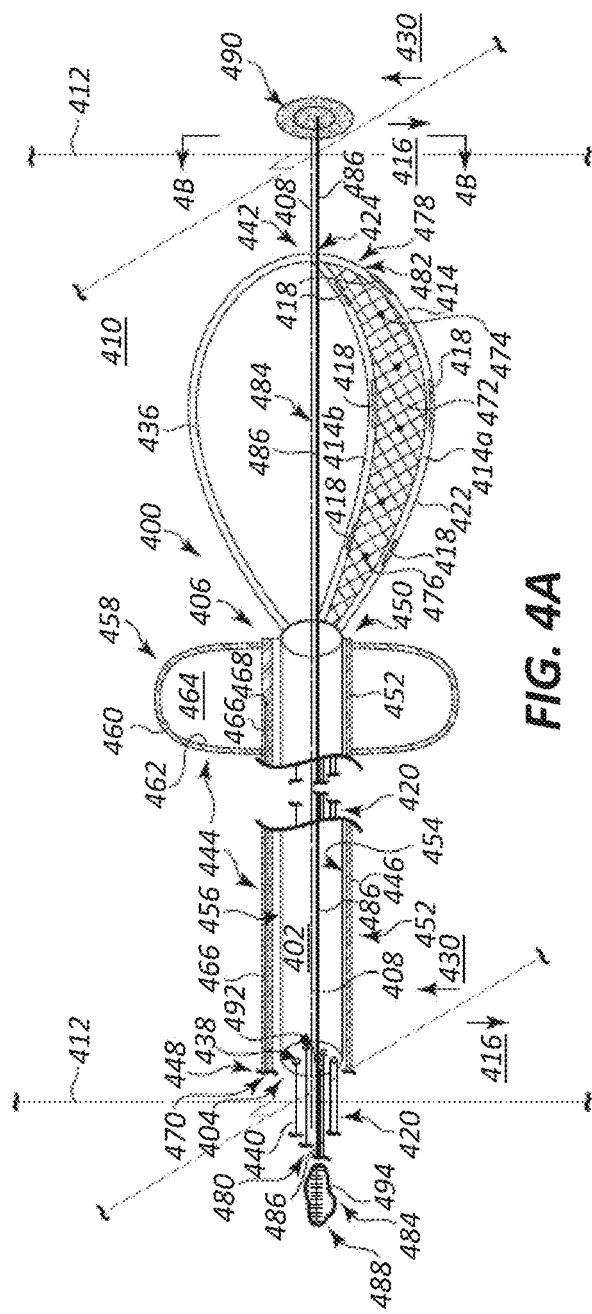
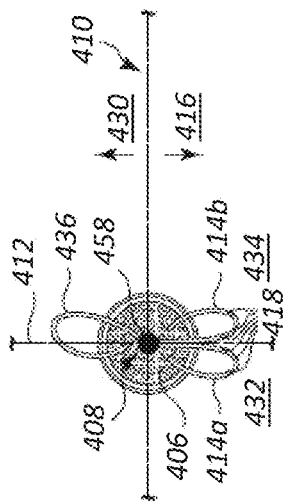
FIG. 4A
FIG. 4B

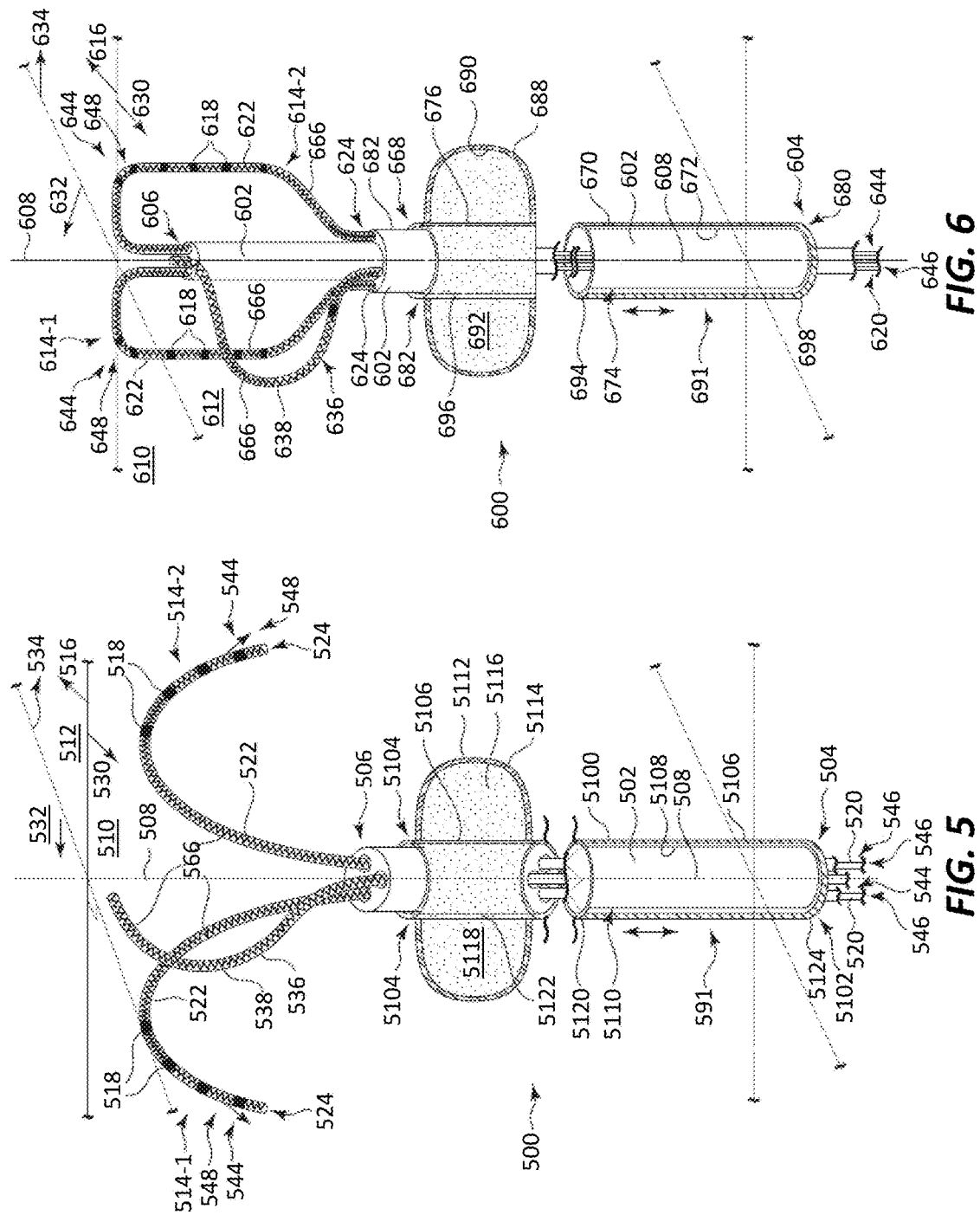

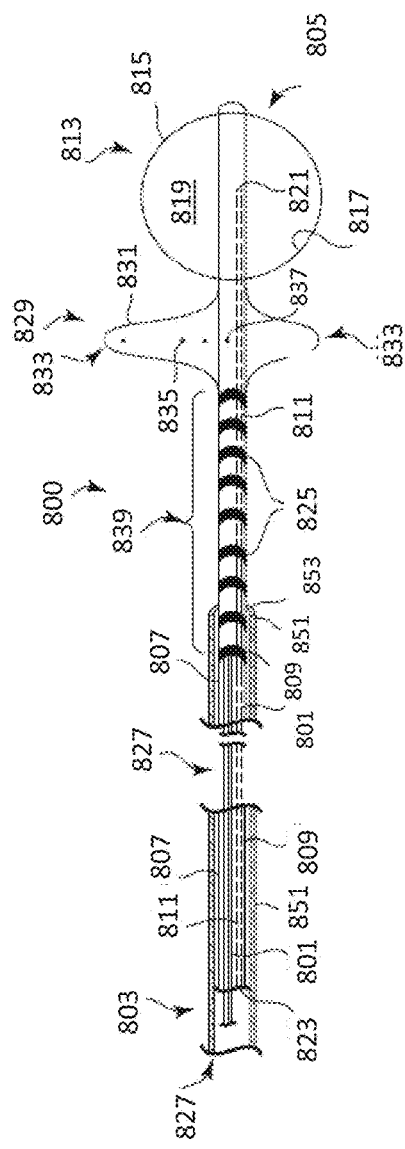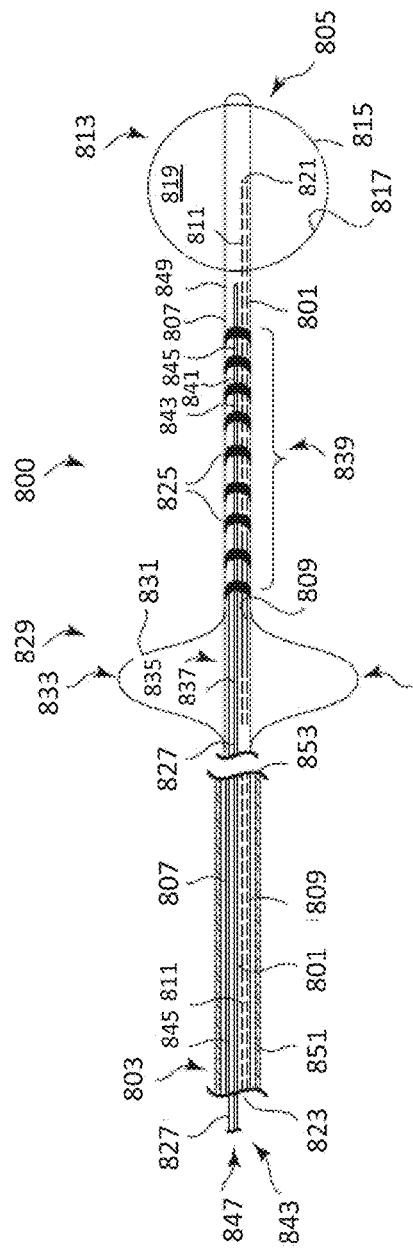

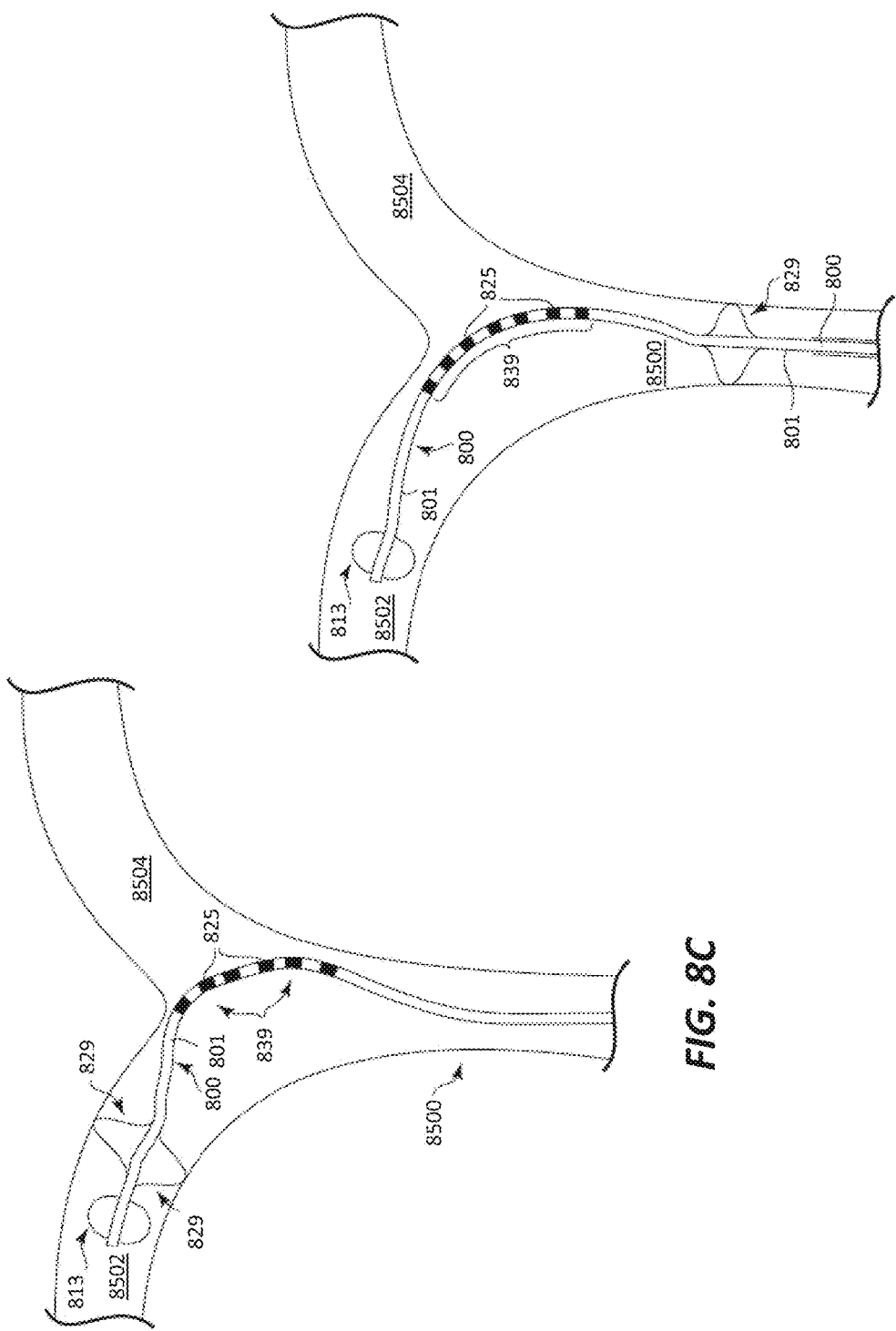

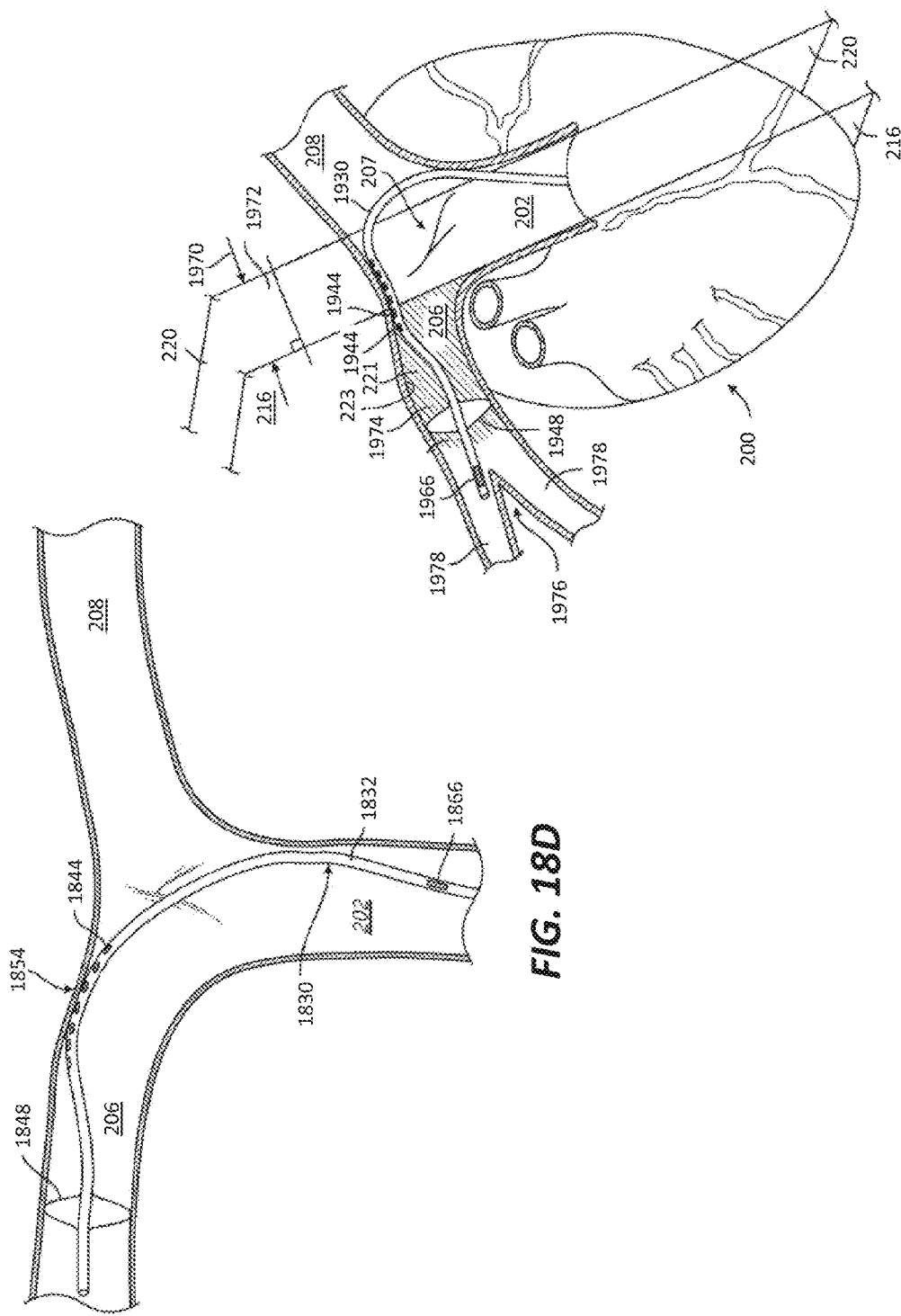

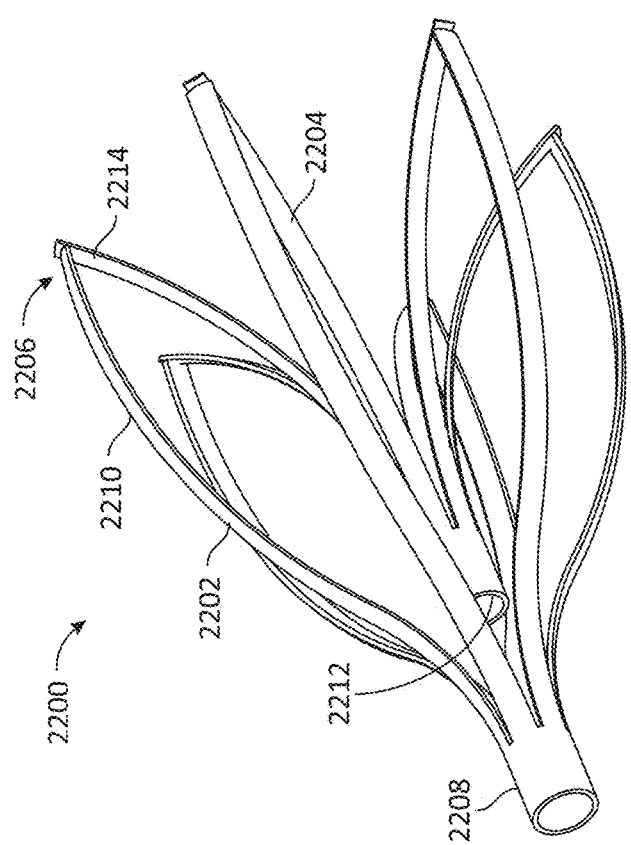
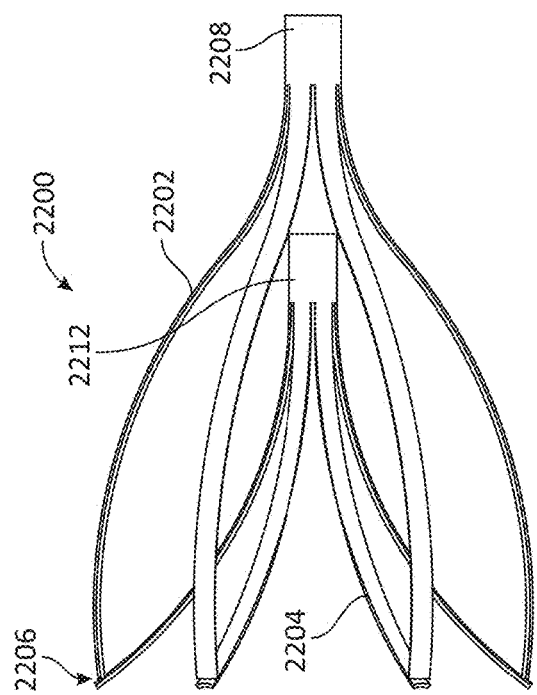
FIG. 22A
FIG. 22B

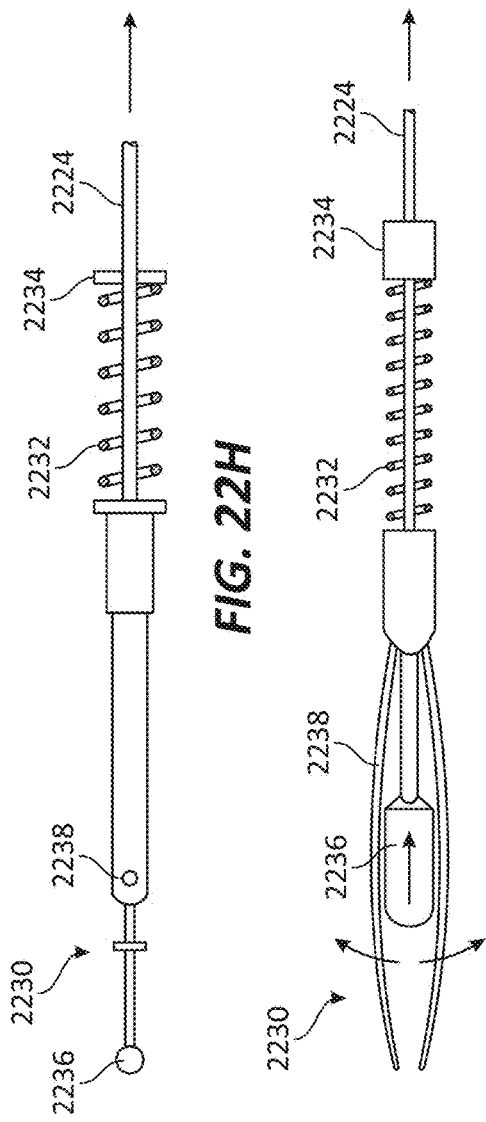
FIG. 22H
FIG. 22I
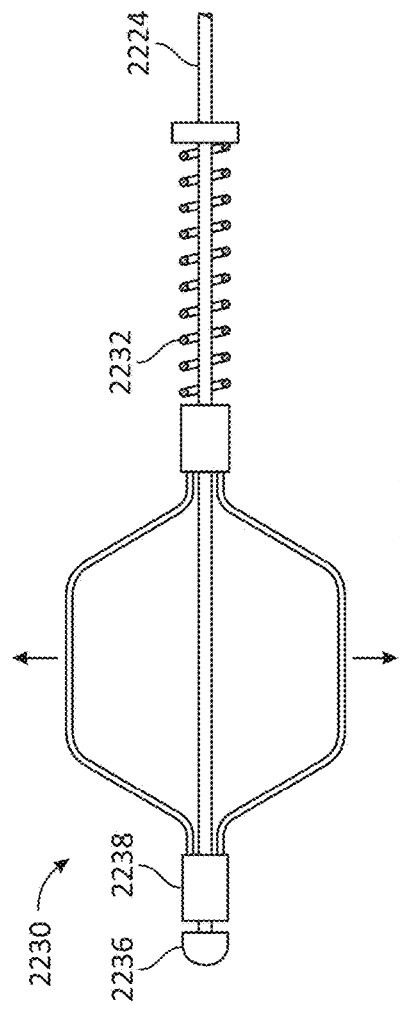
FIG. 22J

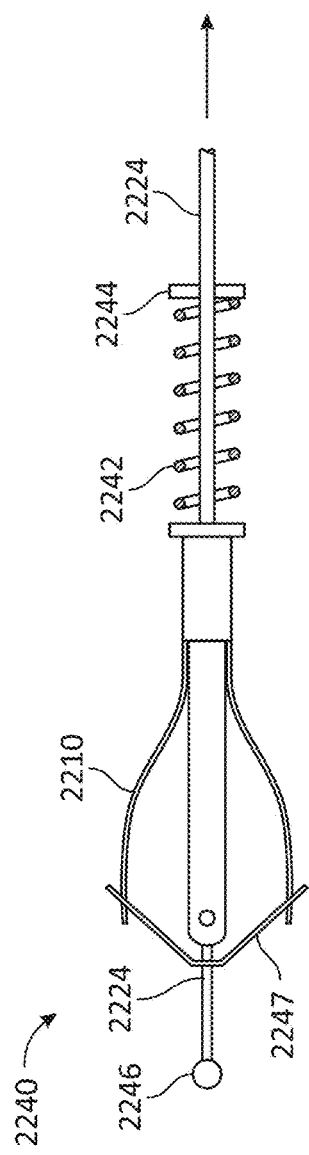
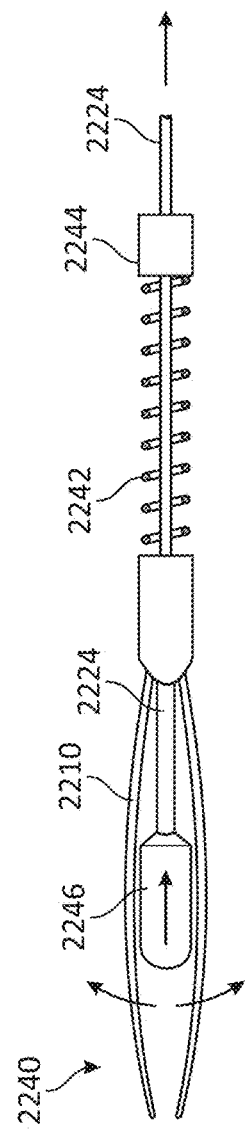

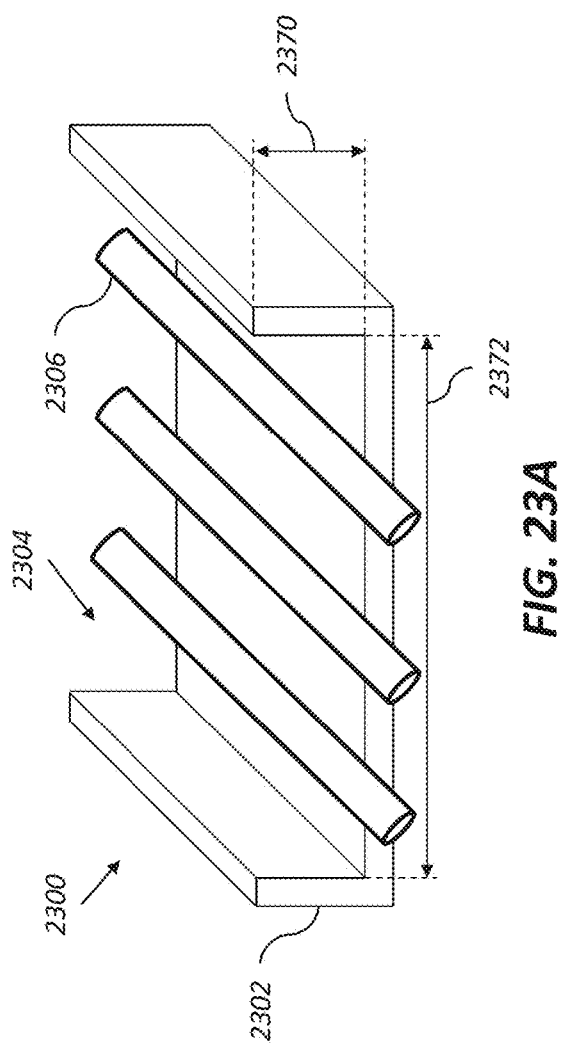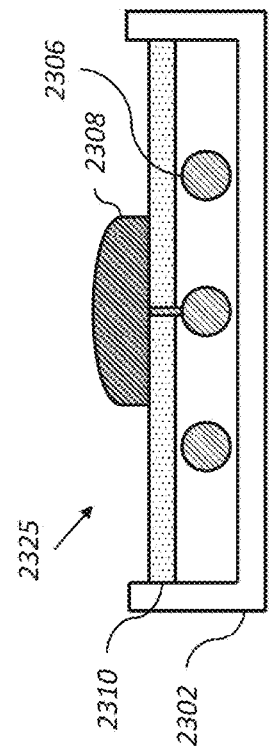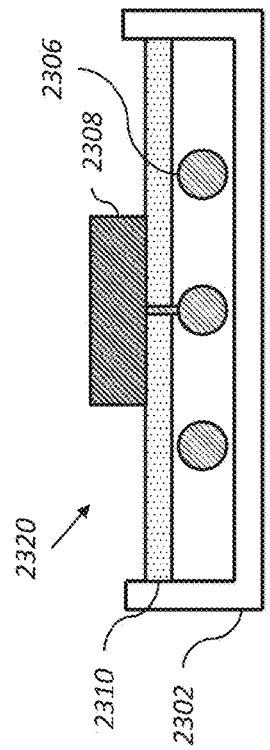
FIG. 23A
FIG. 23B
FIG. 23C

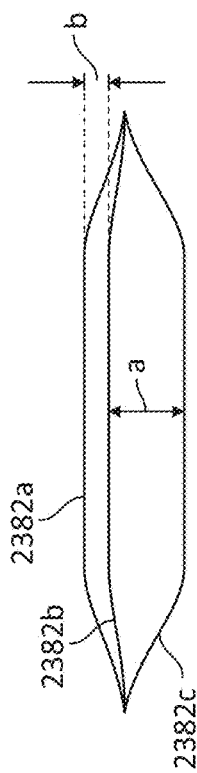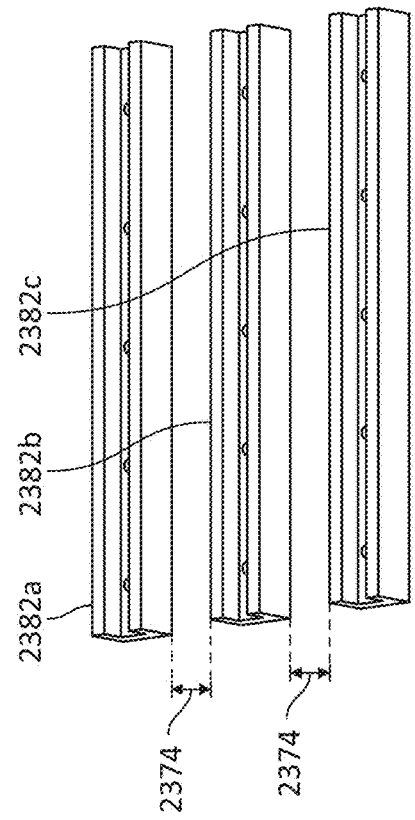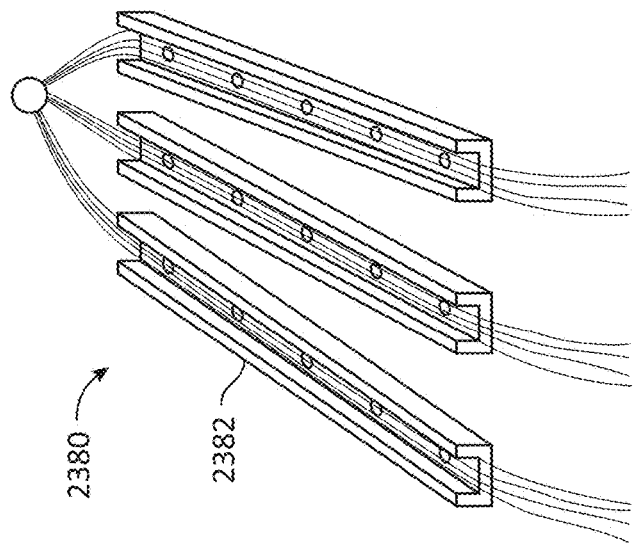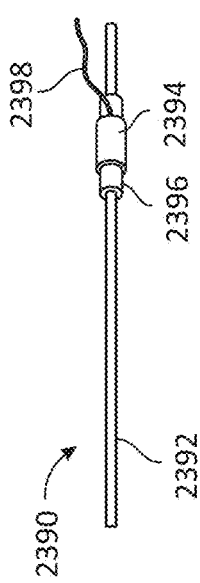
FIG. 23I
FIG. 23J
FIG. 23H
FIG. 23K

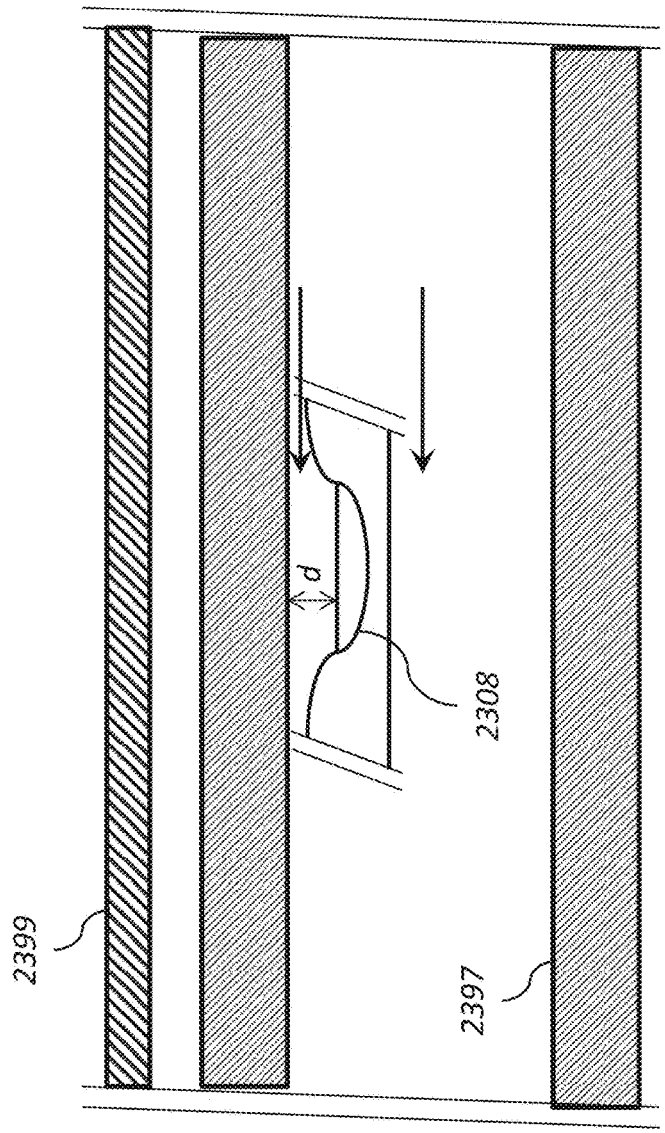

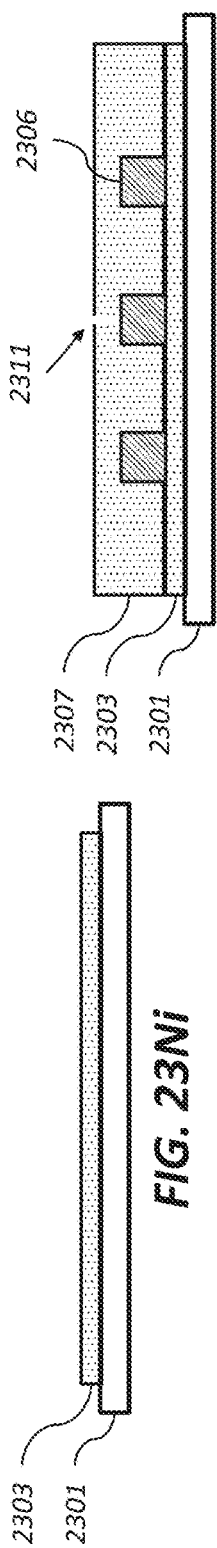

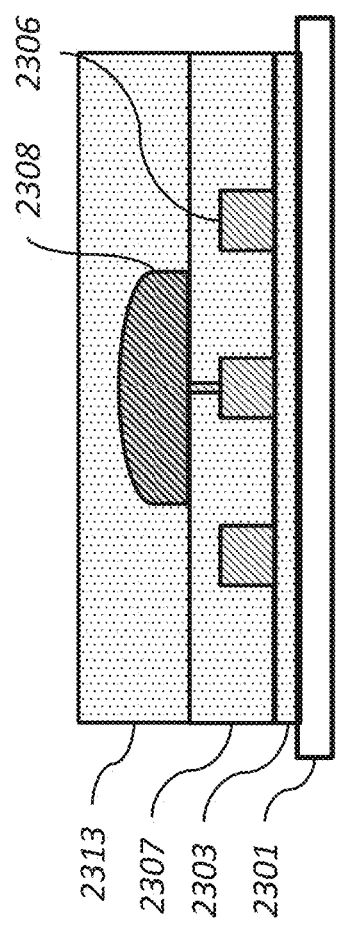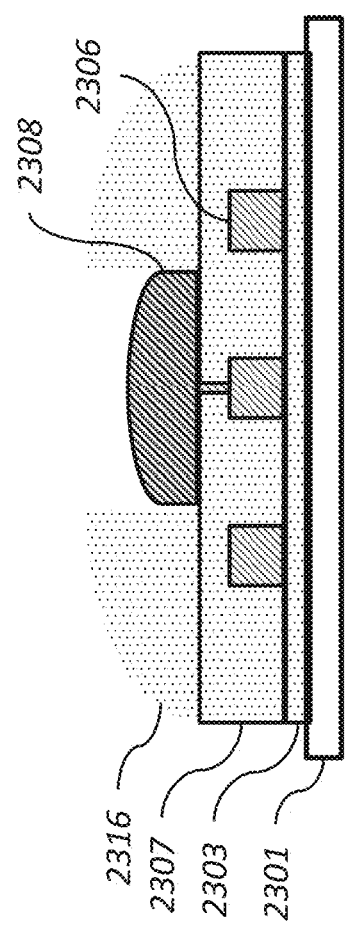

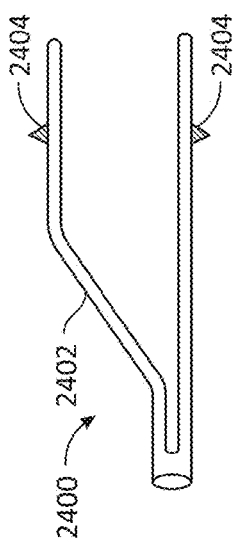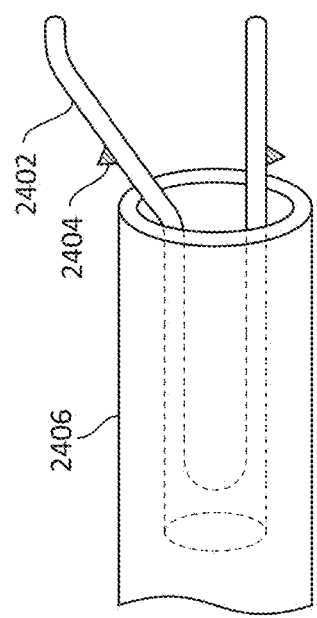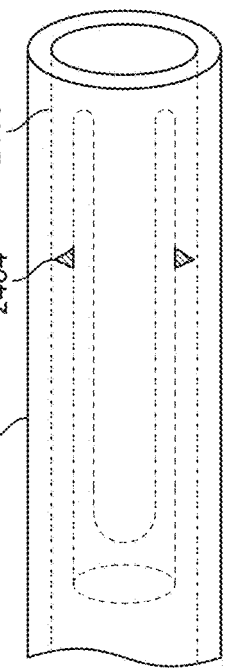
FIG. 24A
FIG. 24B
FIG. 24C

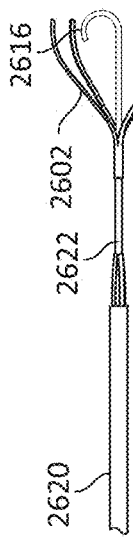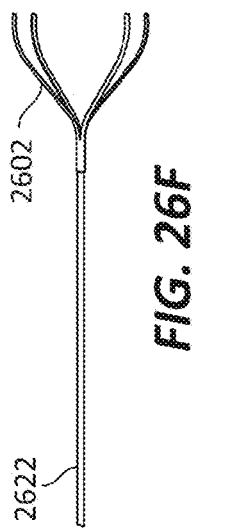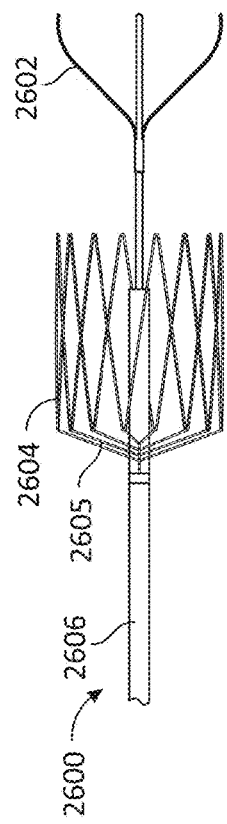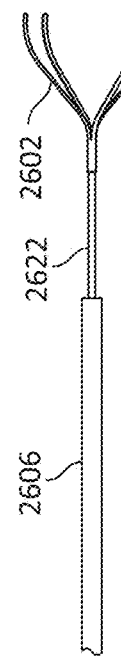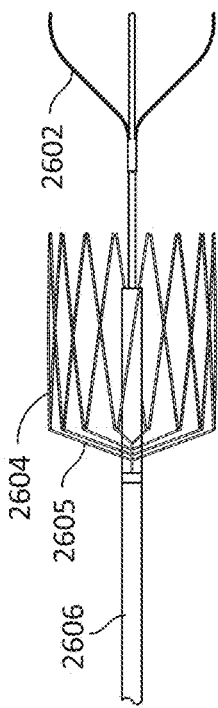
FIG. 26A  FIG. 26B  FIG. 26C  FIG. 26D  FIG. 26E  FIG. 26F  FIG. 26G  FIG. 26H

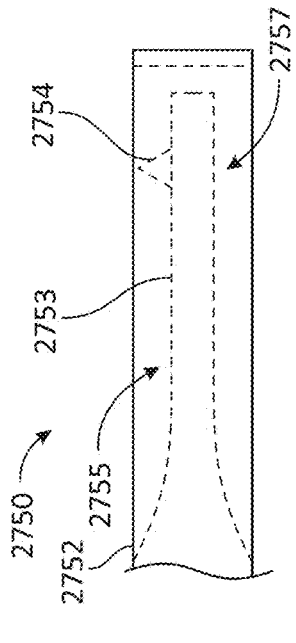
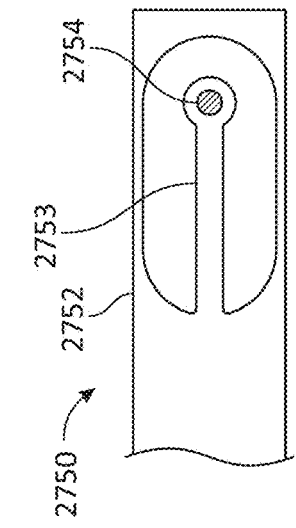
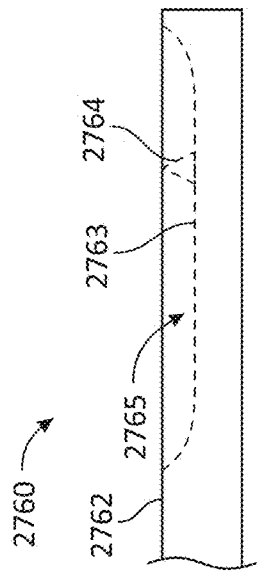

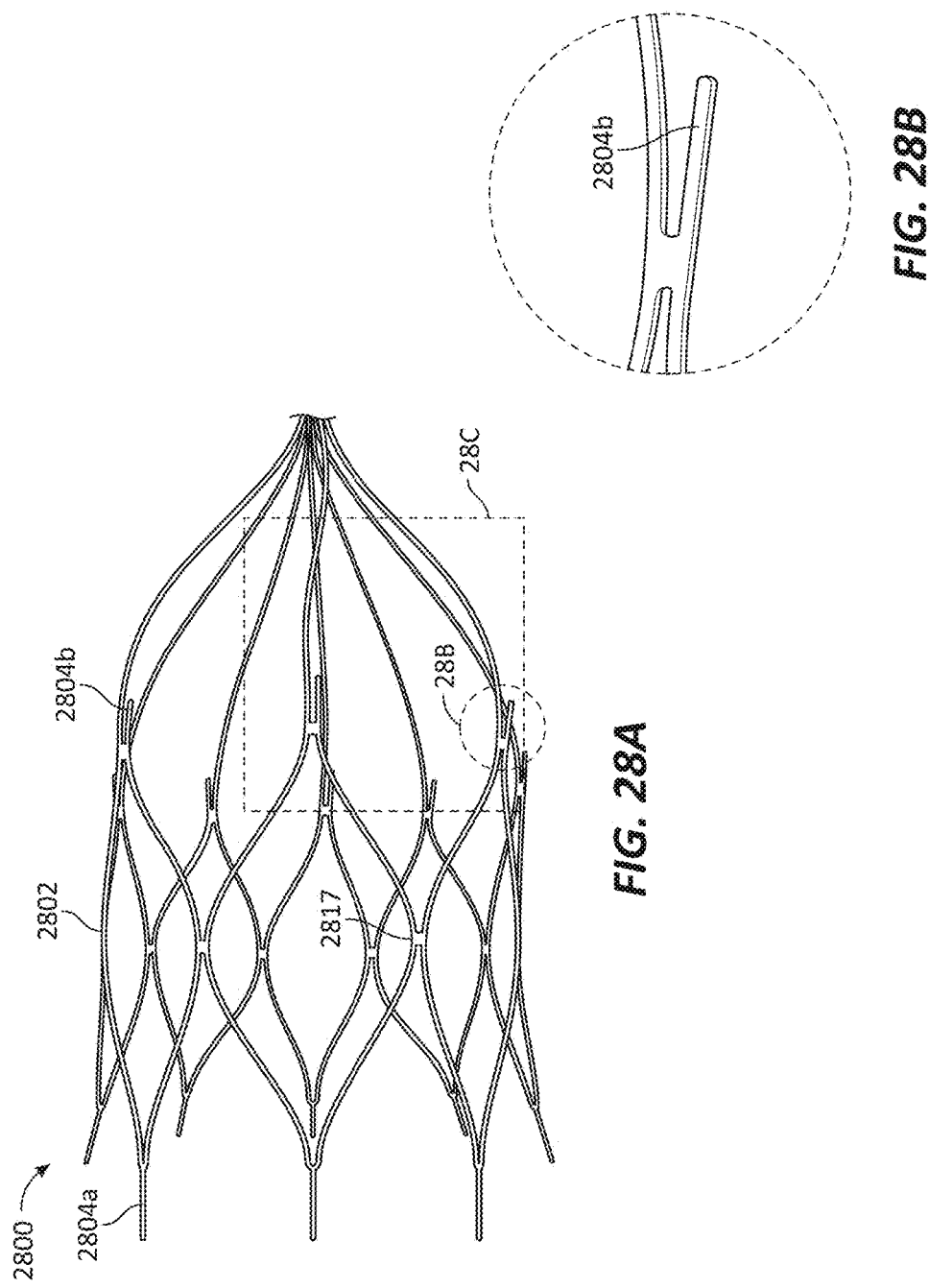

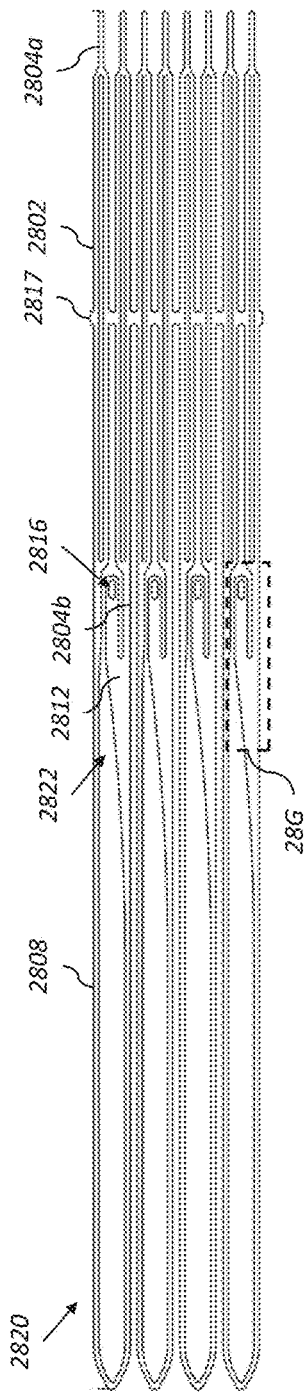
FIG. 28F
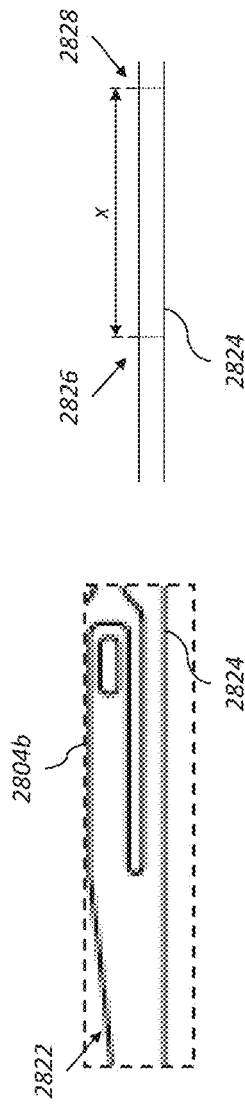
FIG. 28G
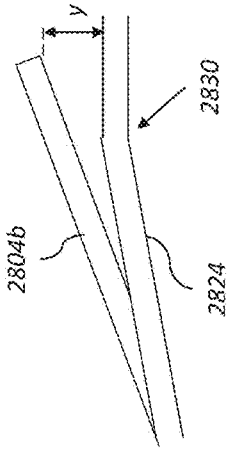
FIG. 28H
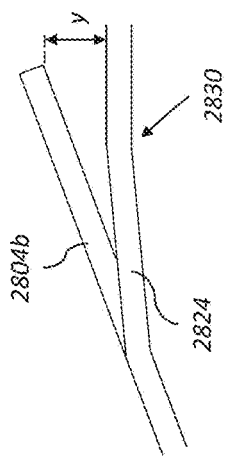
FIG. 28I
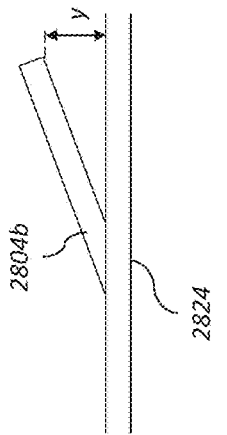
FIG. 28J
FIG. 28K

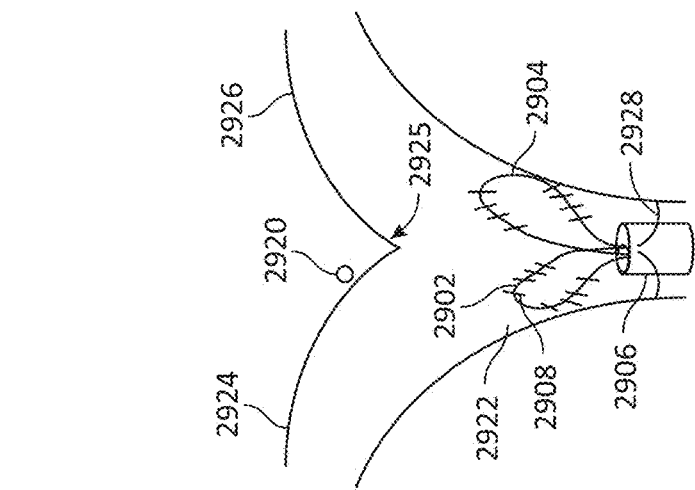
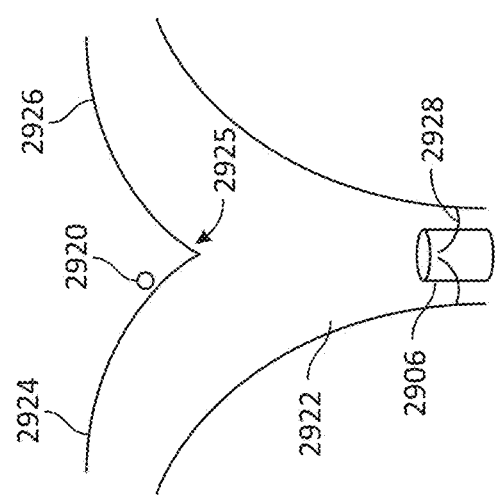
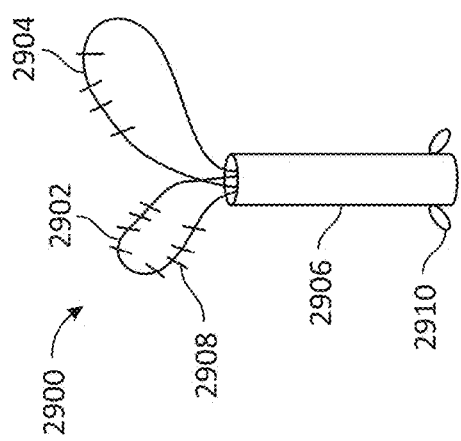
FIG. 29A
FIG. 29B
FIG. 29C

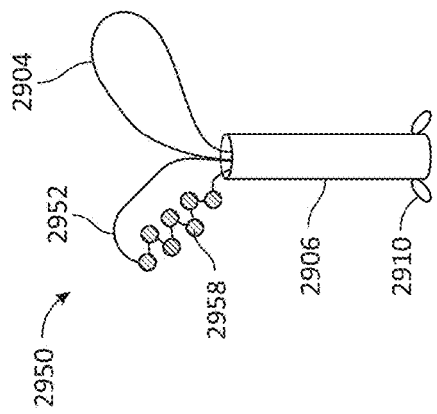
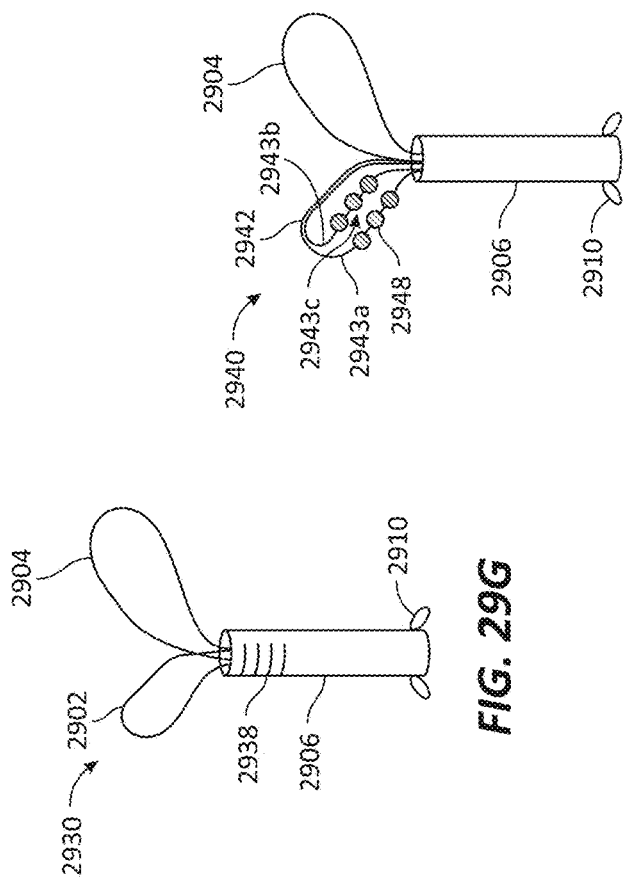

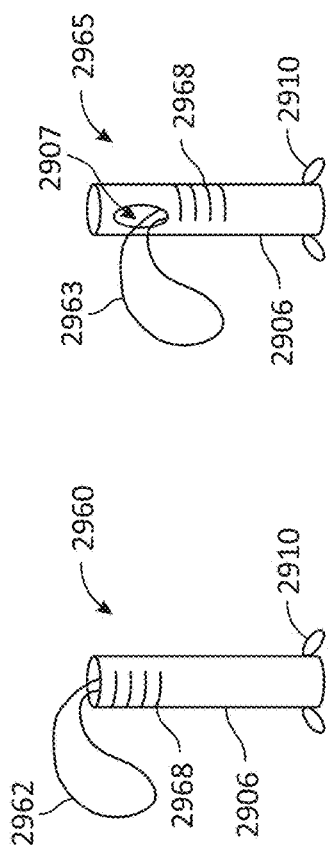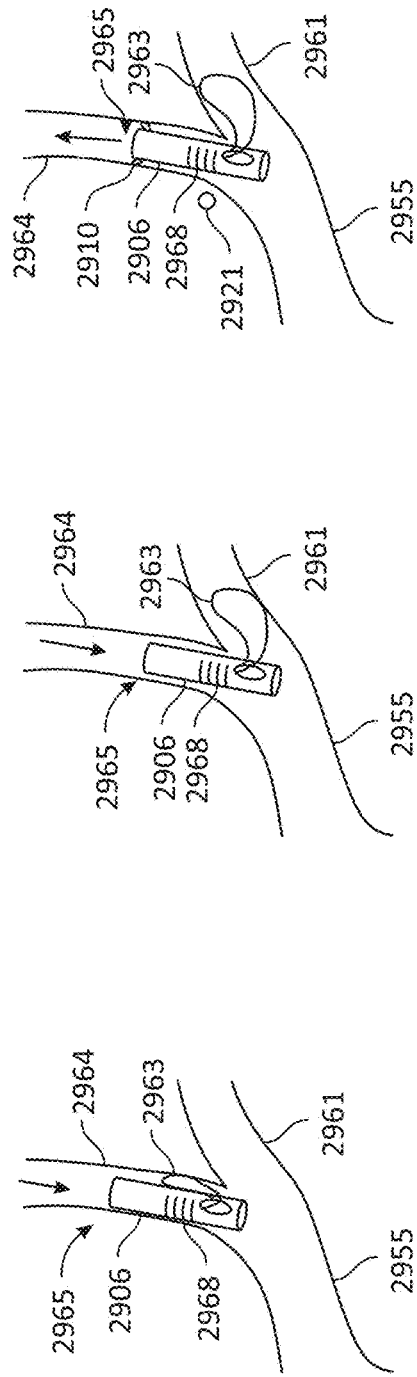

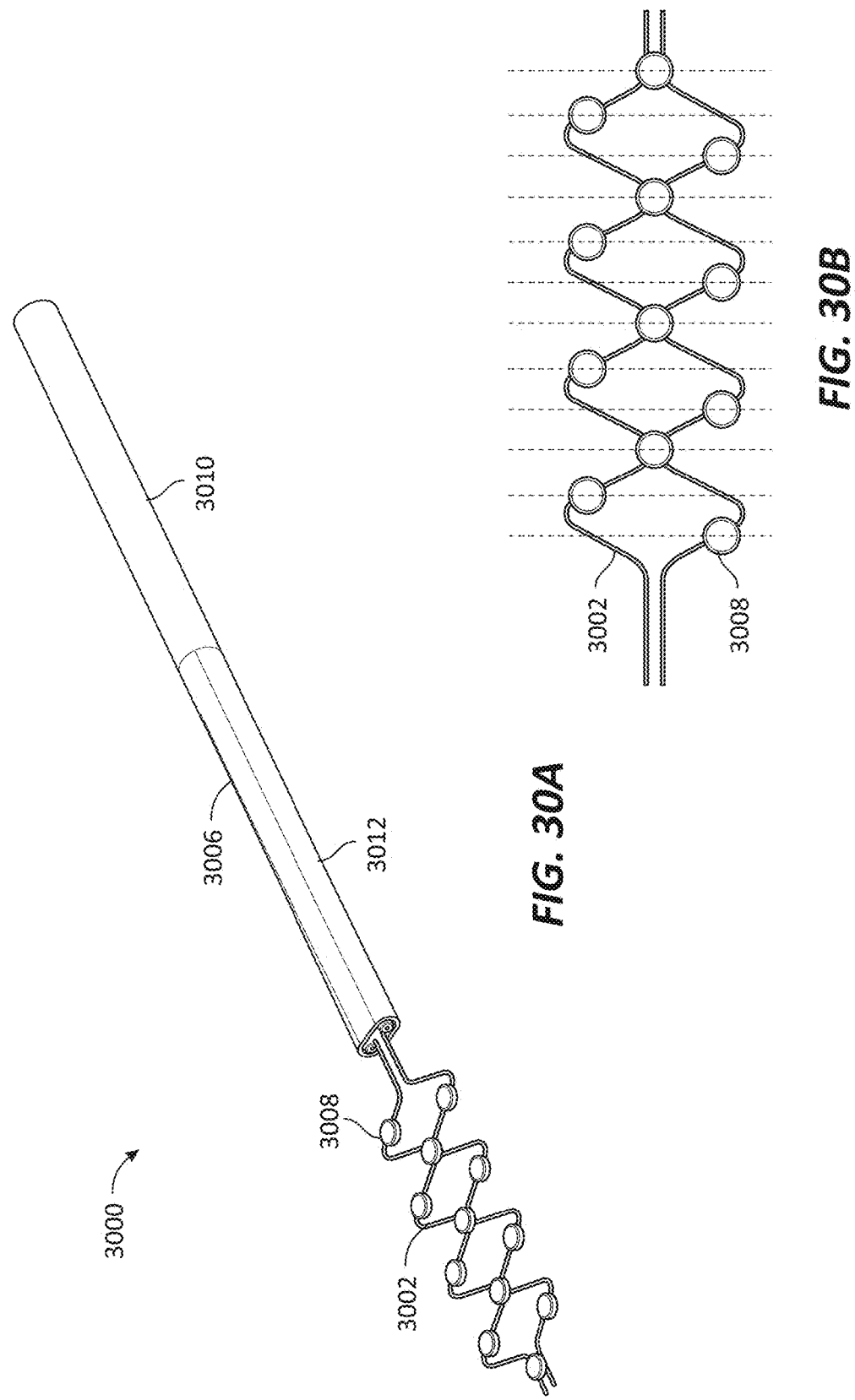

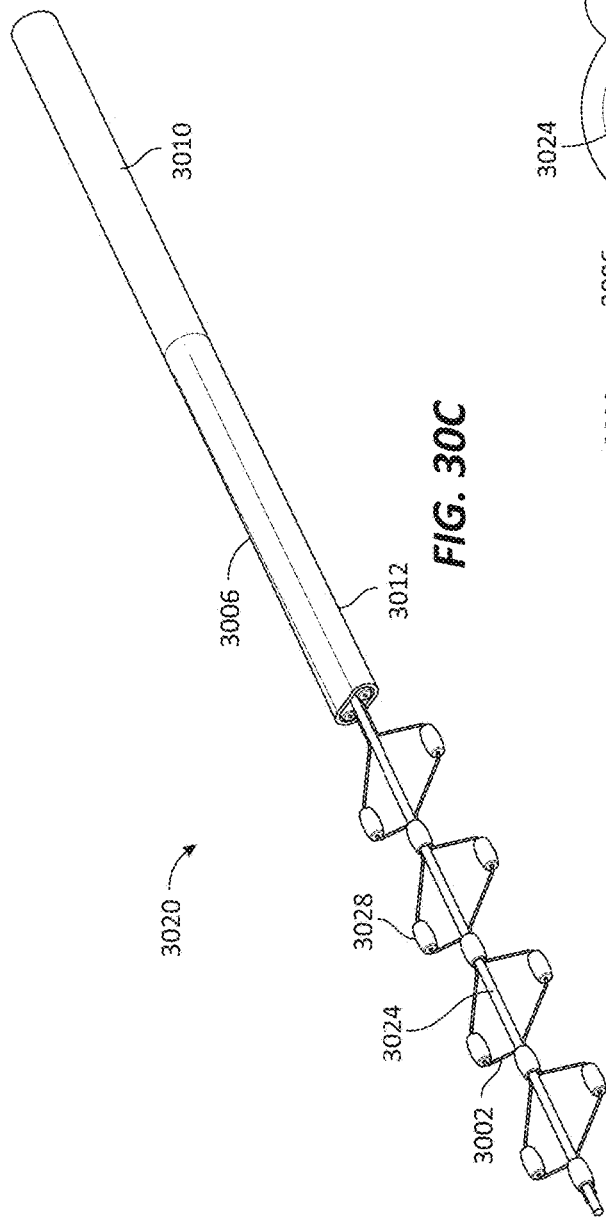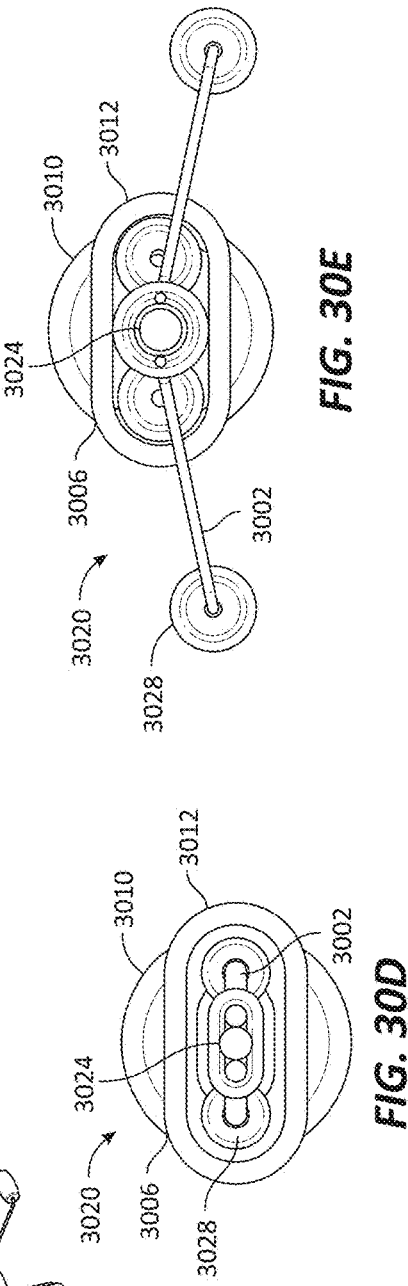

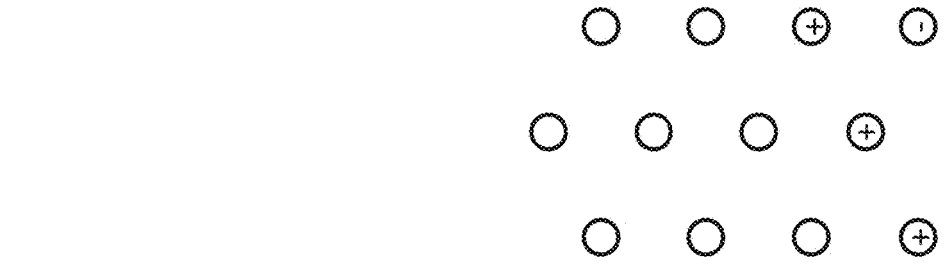
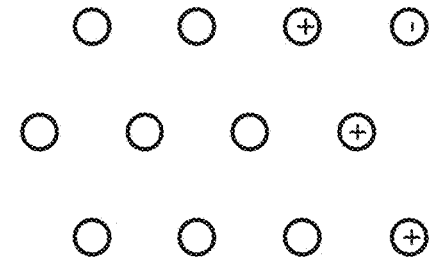
FIG. 32D
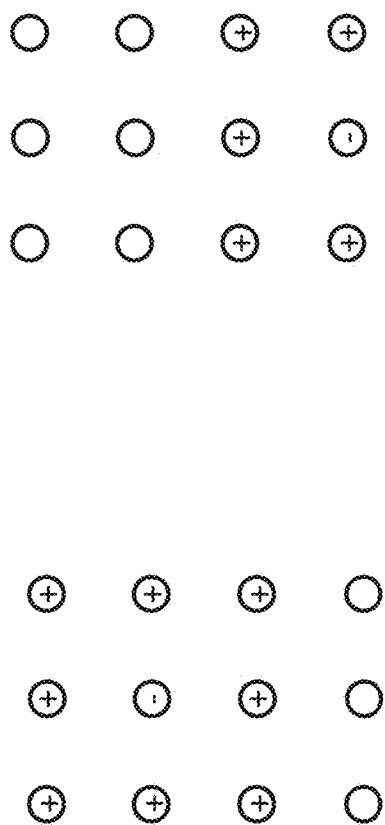
FIG. 32B
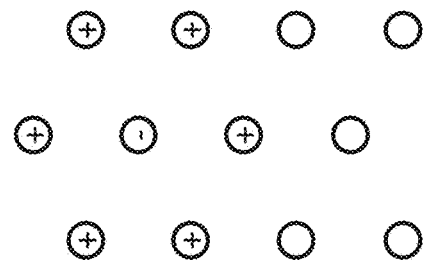
FIG. 32C
FIG. 32A

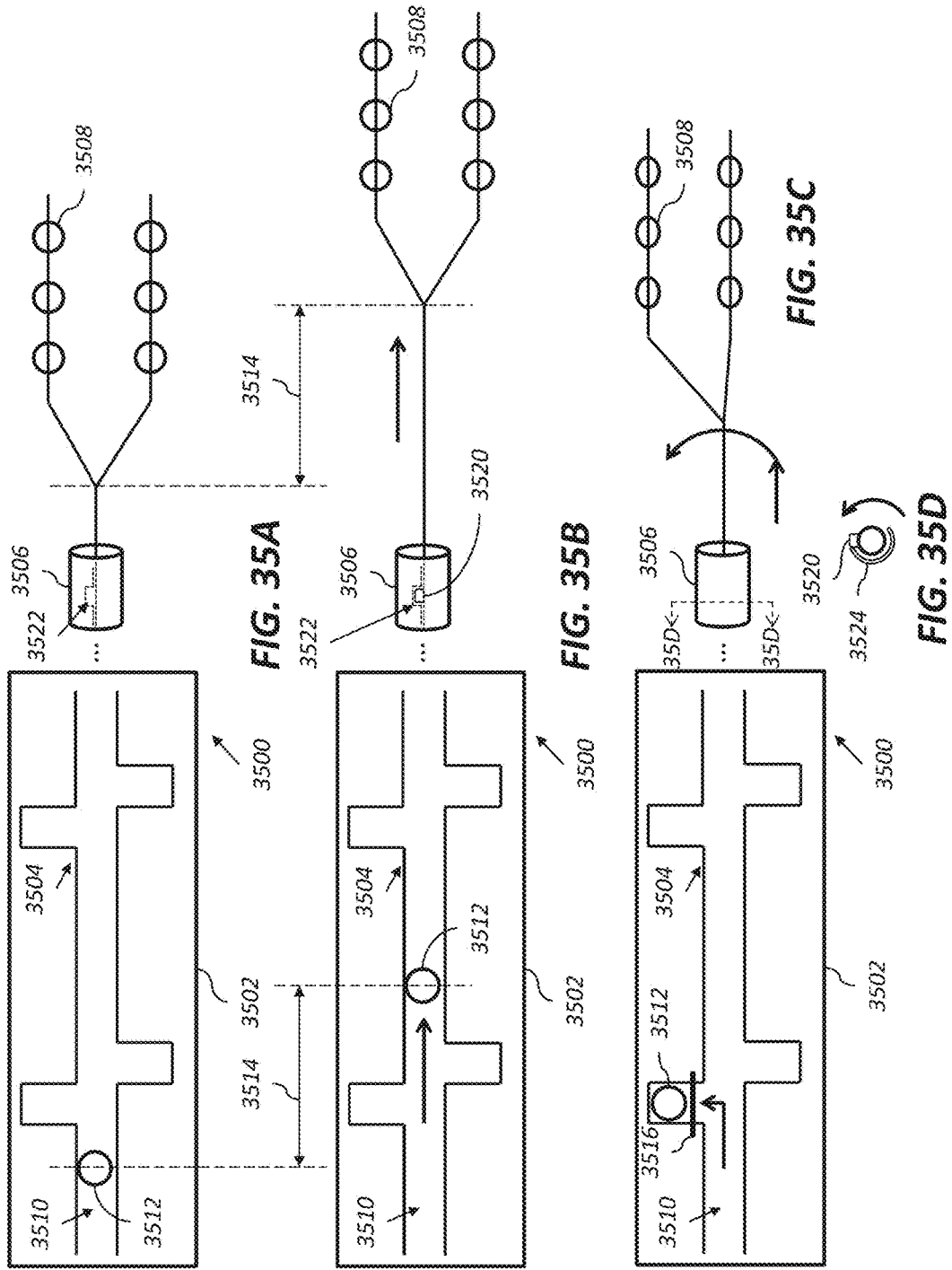

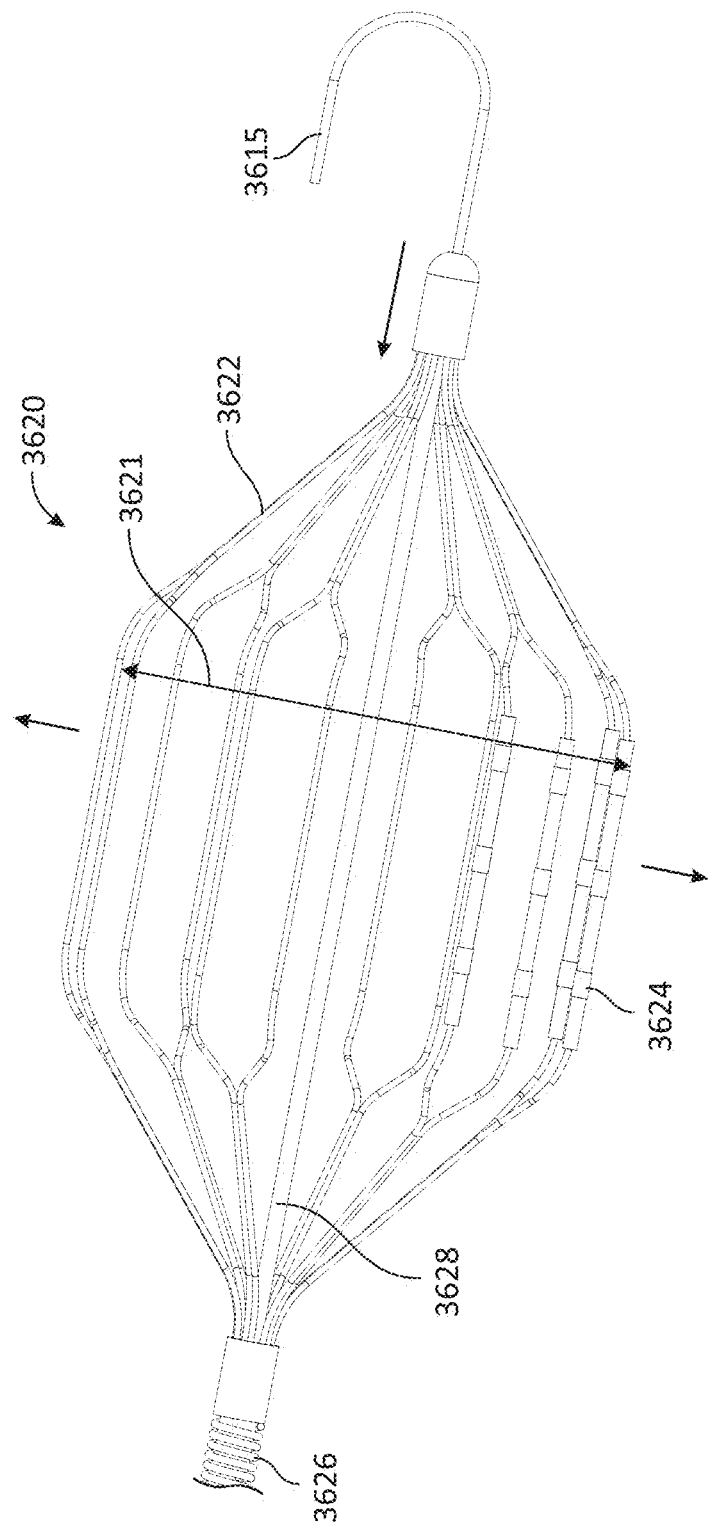

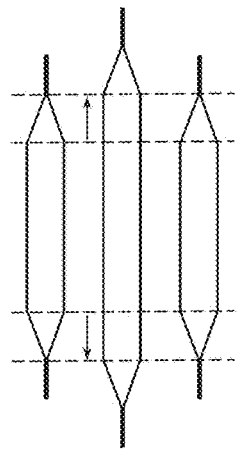
FIG. 36J
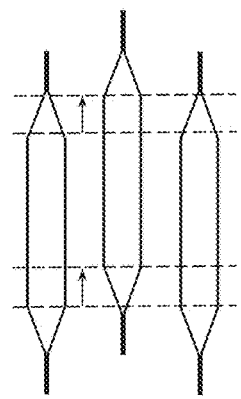
FIG. 36I
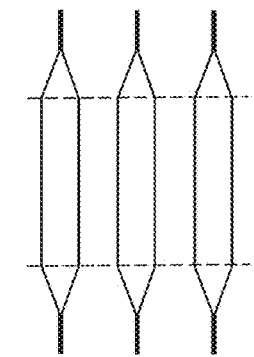
FIG. 36H
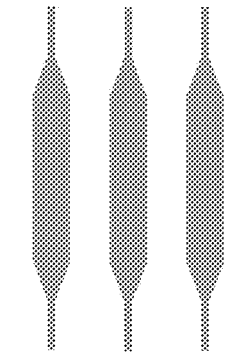
FIG. 36M
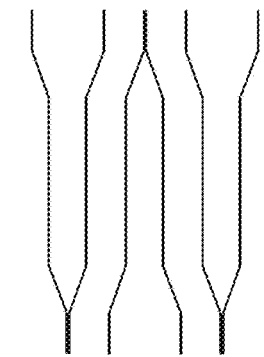
FIG. 36L
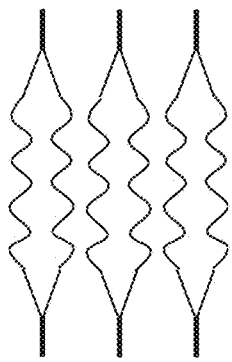
FIG. 36K
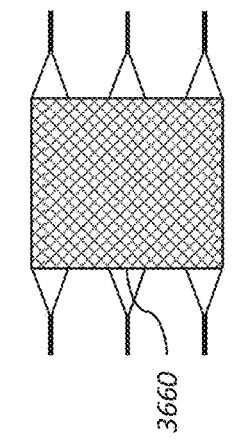
FIG. 36O
FIG. 36N

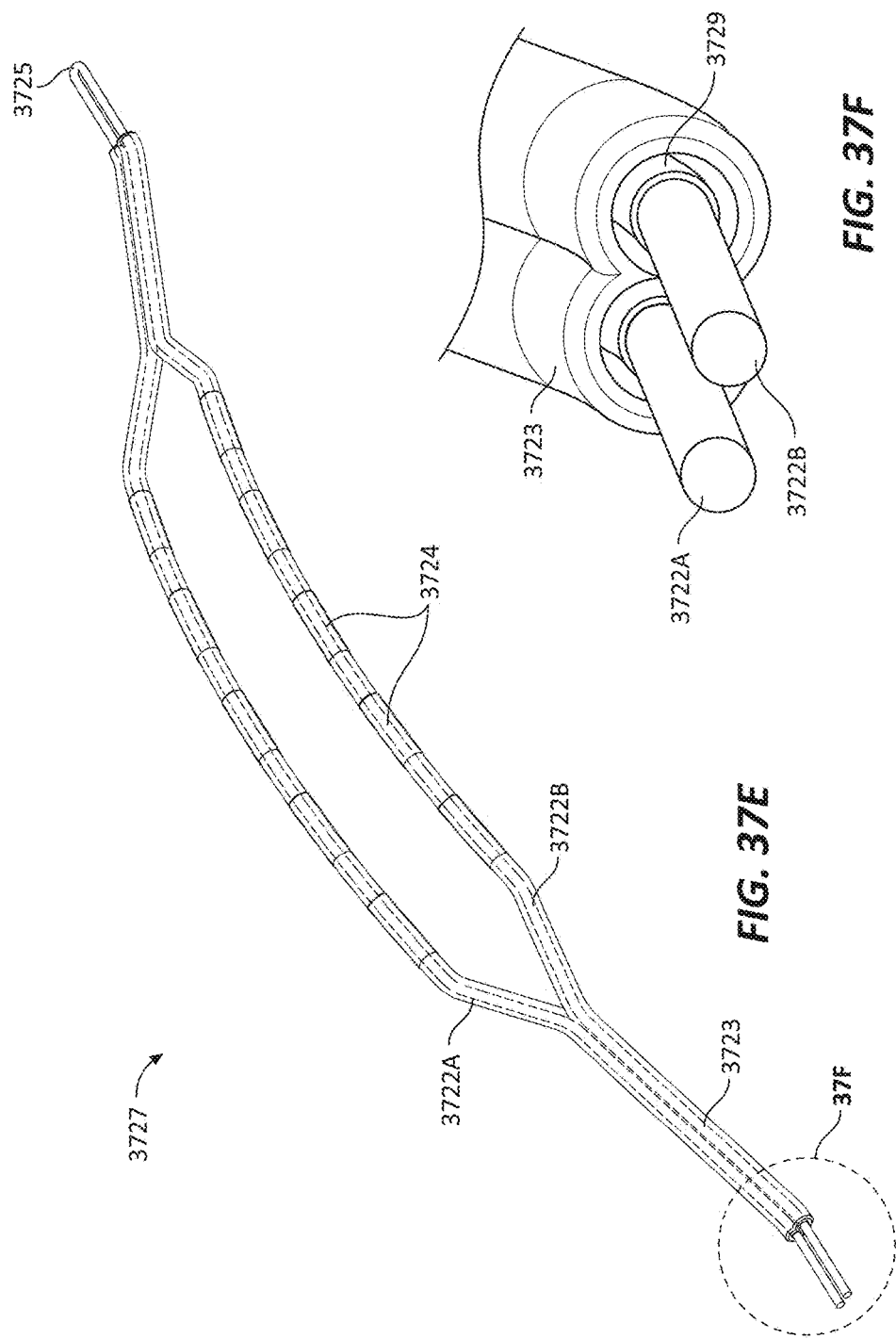

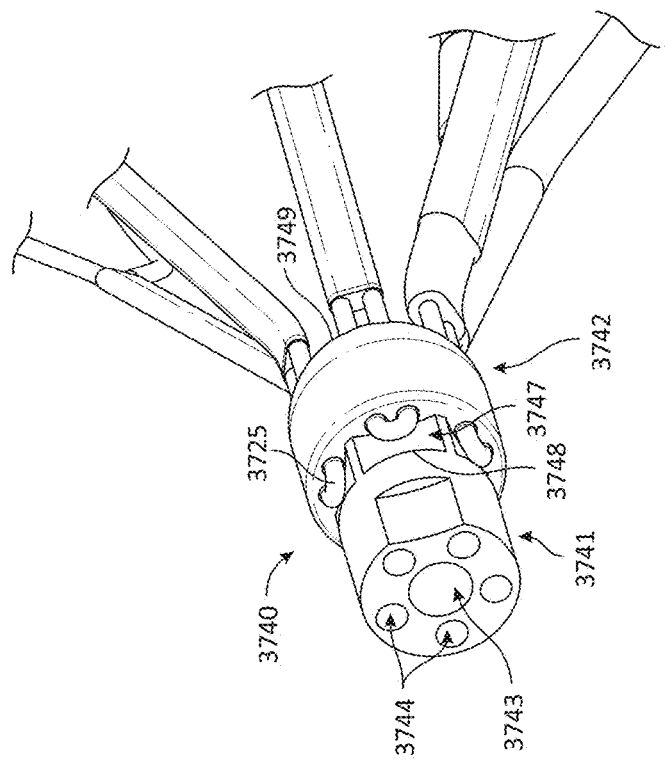
FIG. 37G
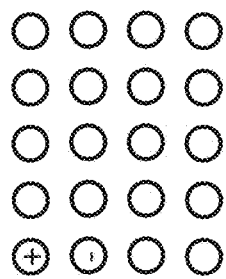
FIG. 37Fi
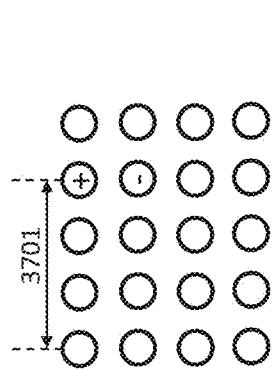
FIG. 37Fii
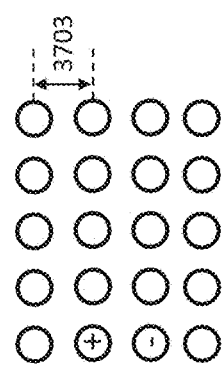
FIG. 37Fiii

FIG. 37Lii

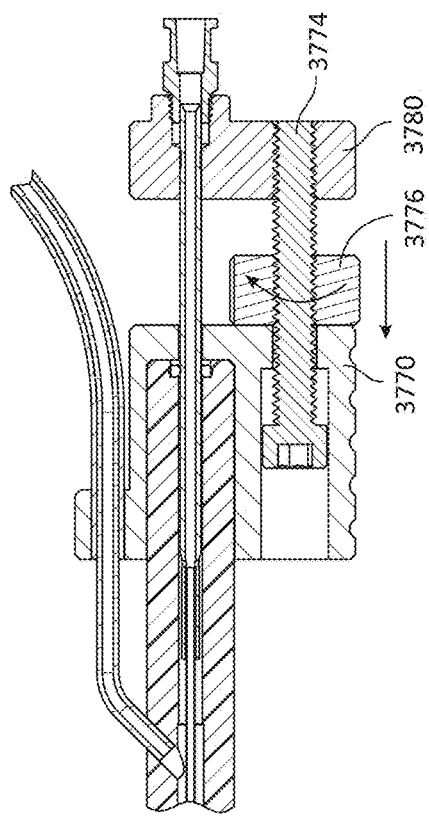
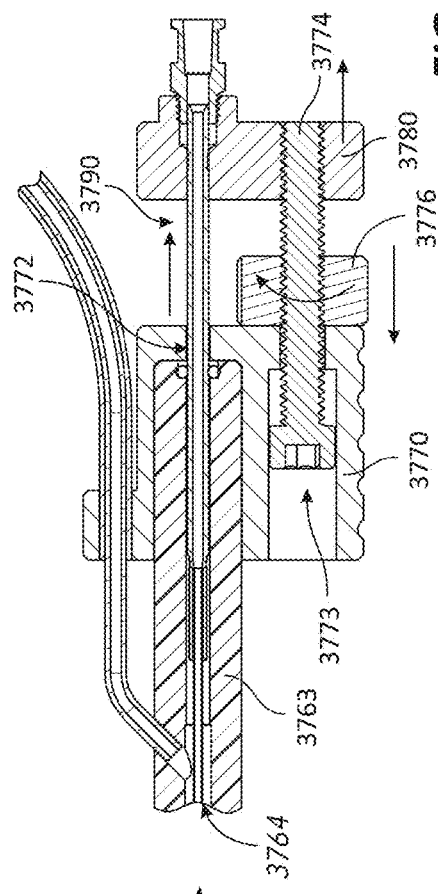
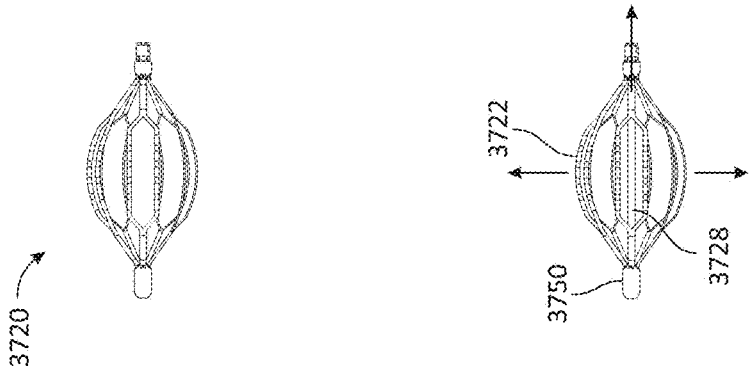
FIG. 37Liii
FIG. 37Liv

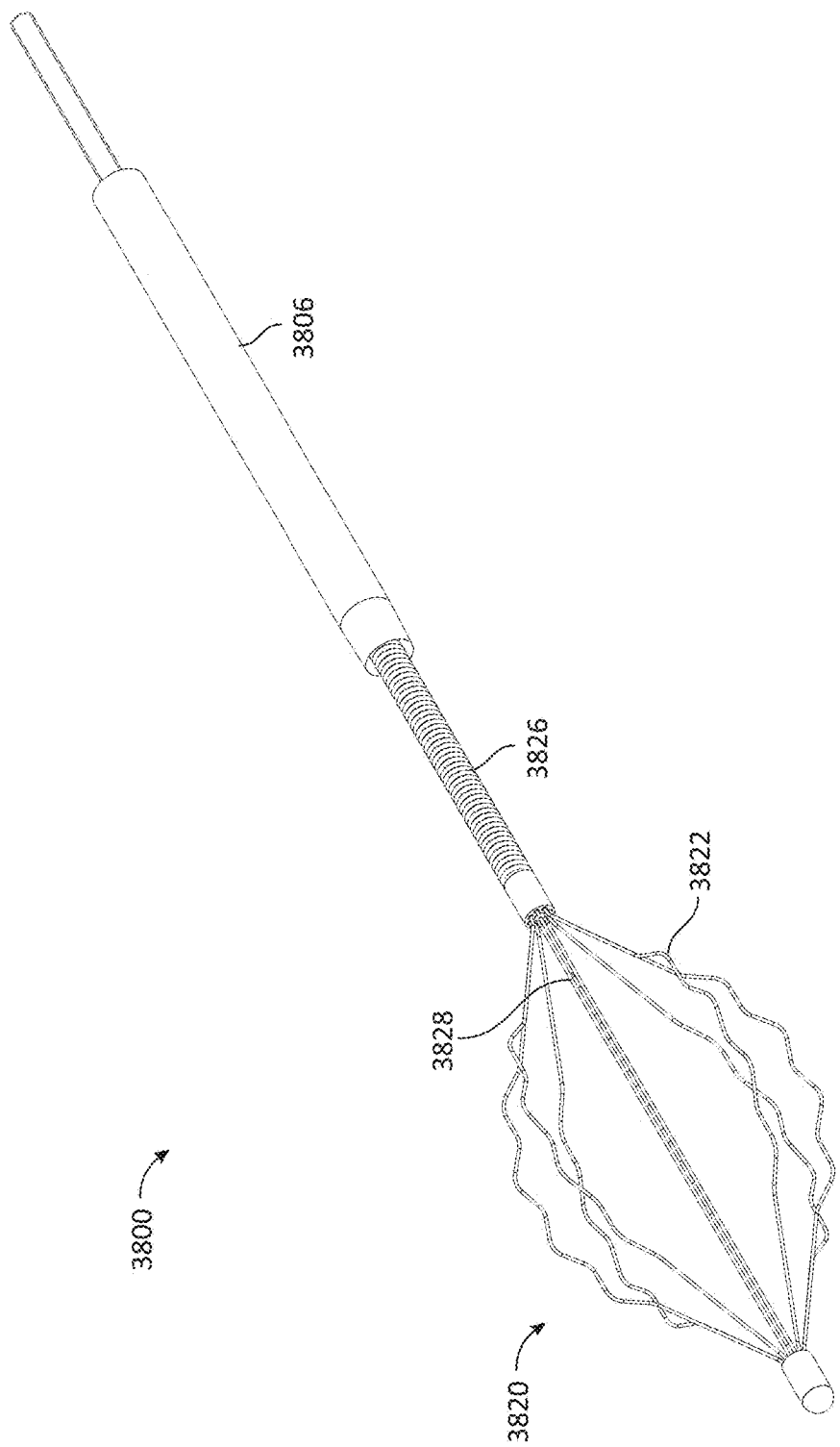

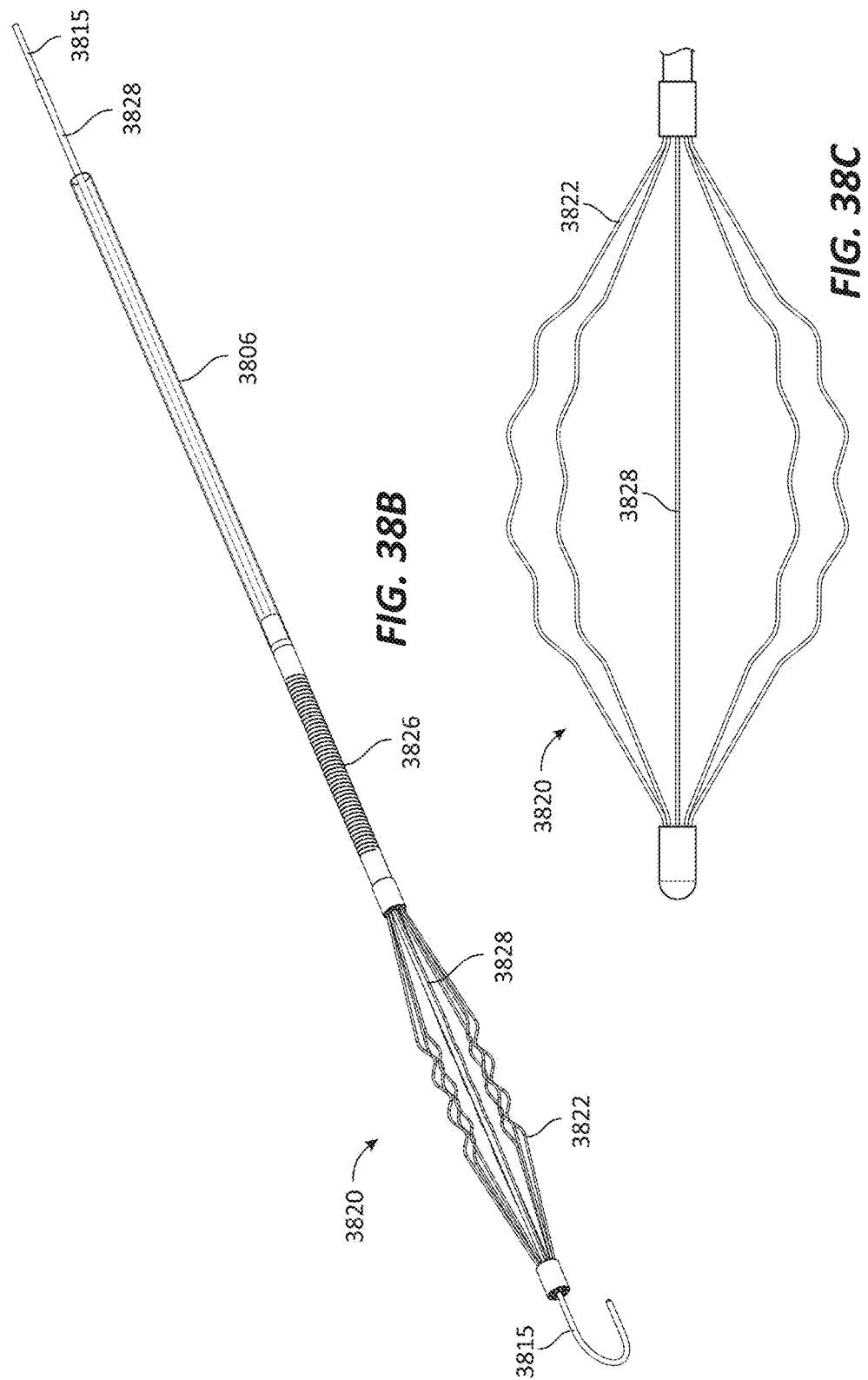

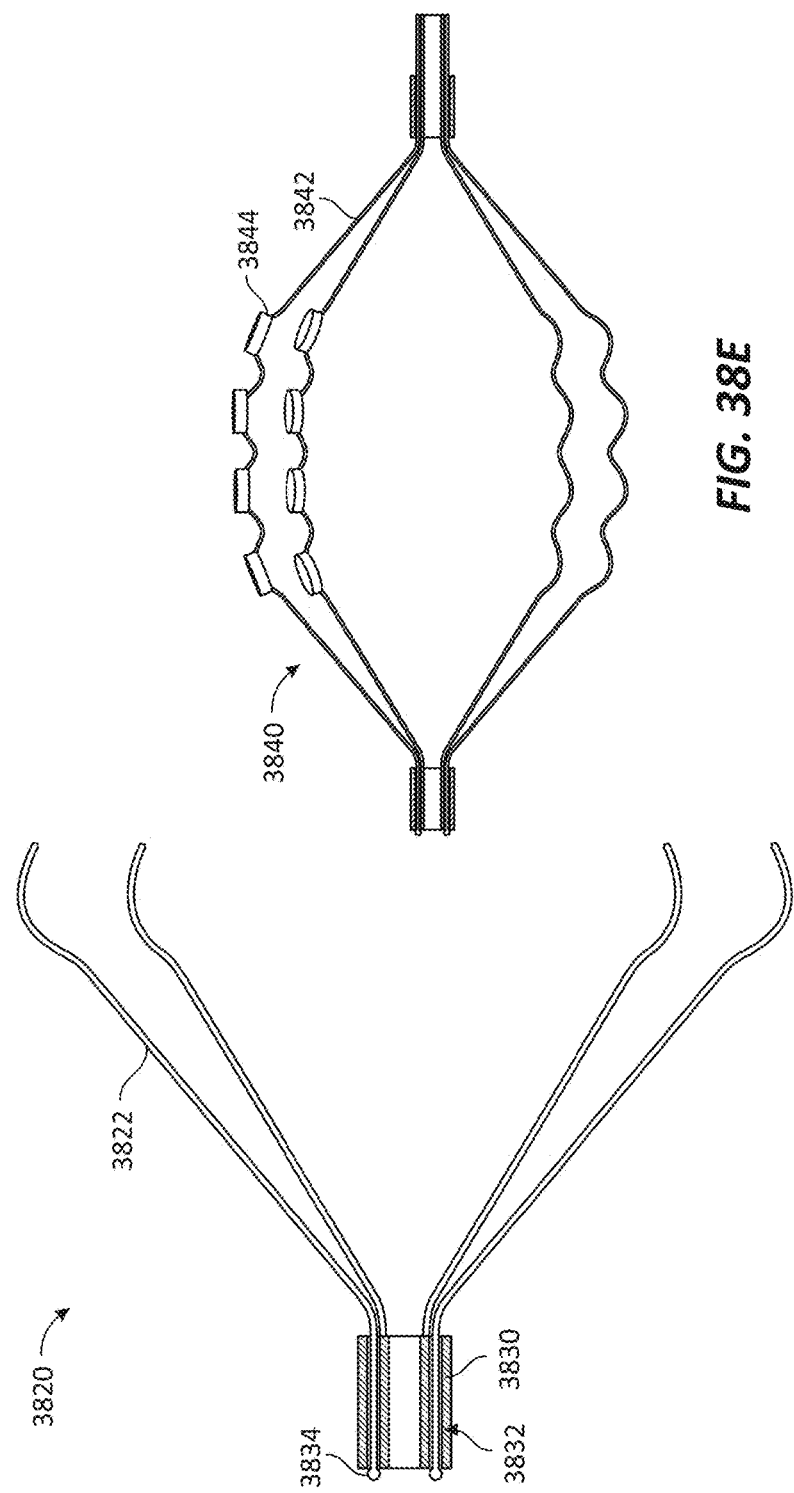

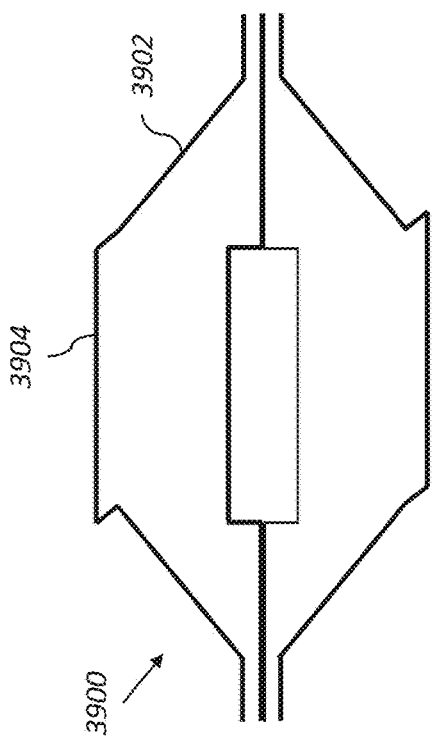
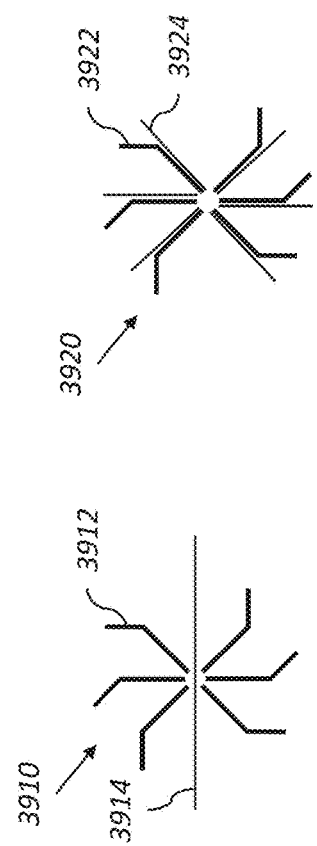
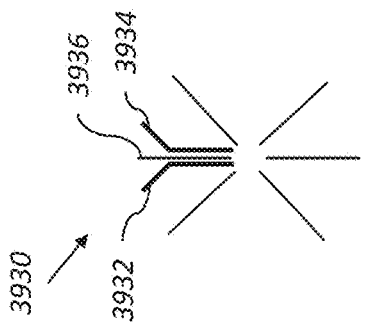
FIG. 39A
FIG. 39B
FIG. 39C
FIG. 39D

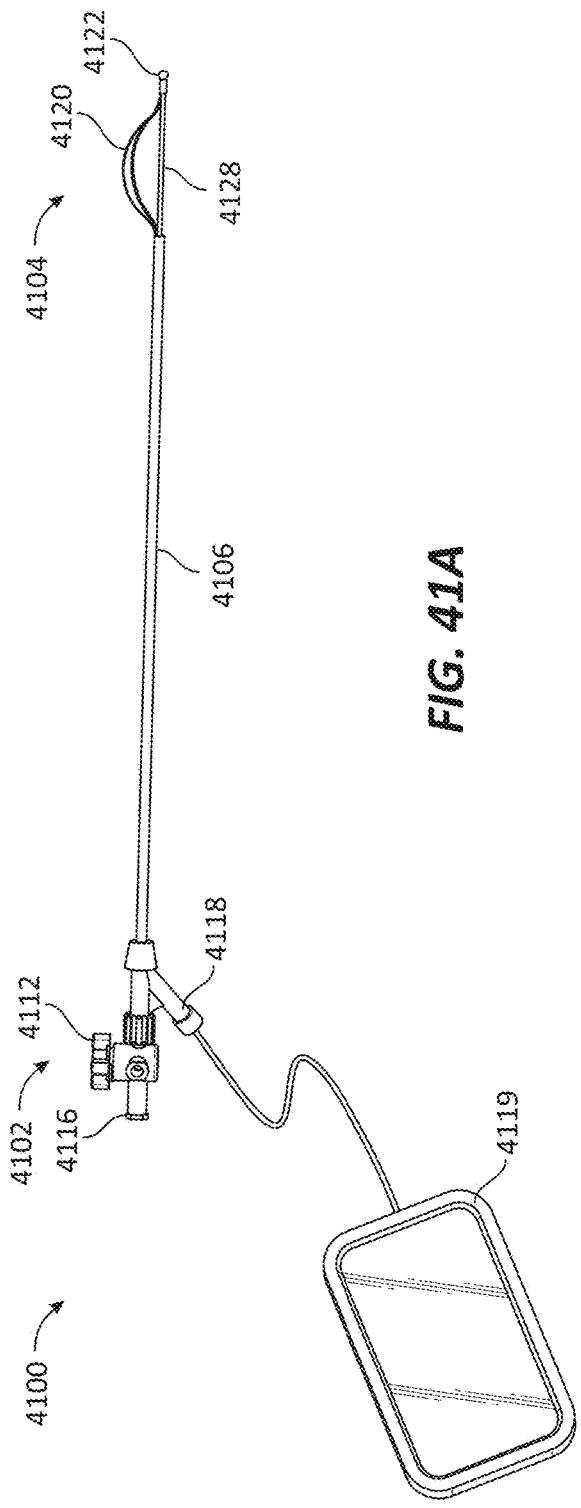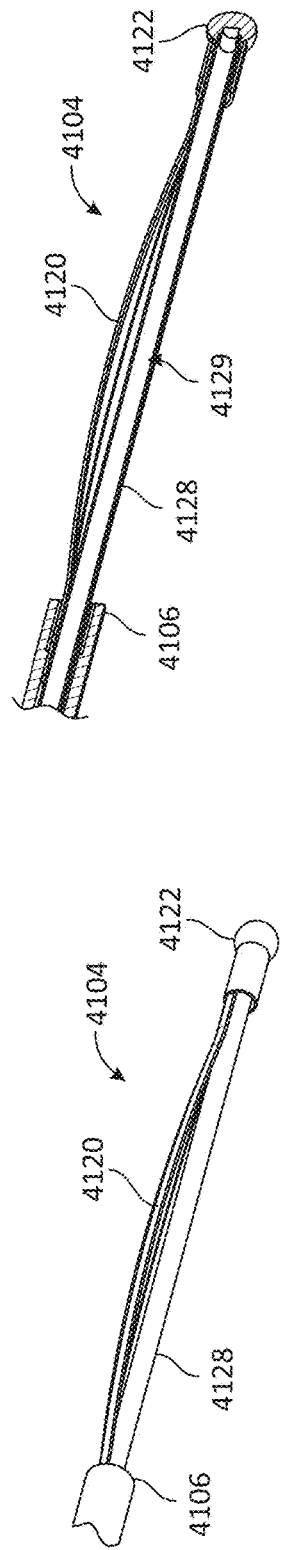

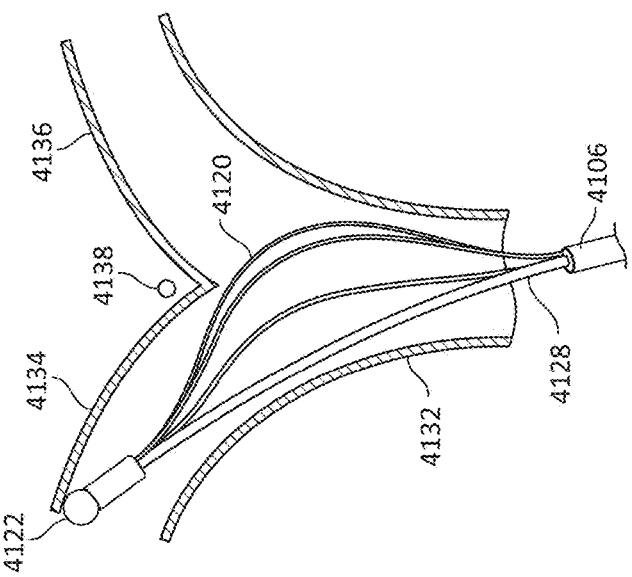
FIG. 41F
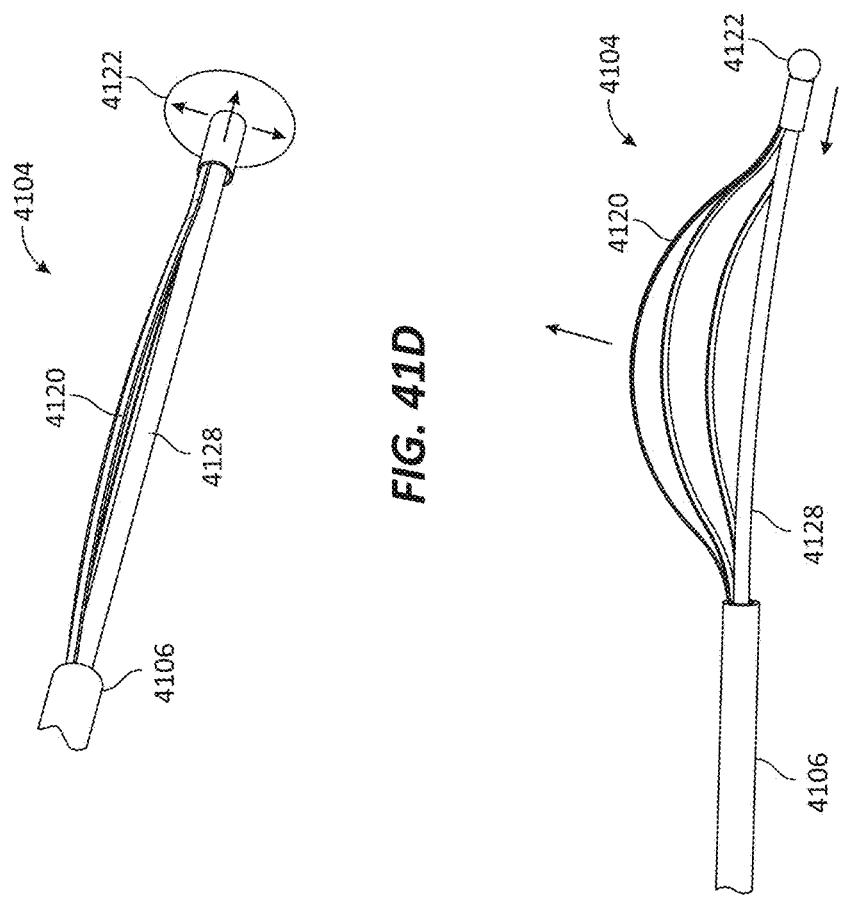
FIG. 41D
FIG. 41E

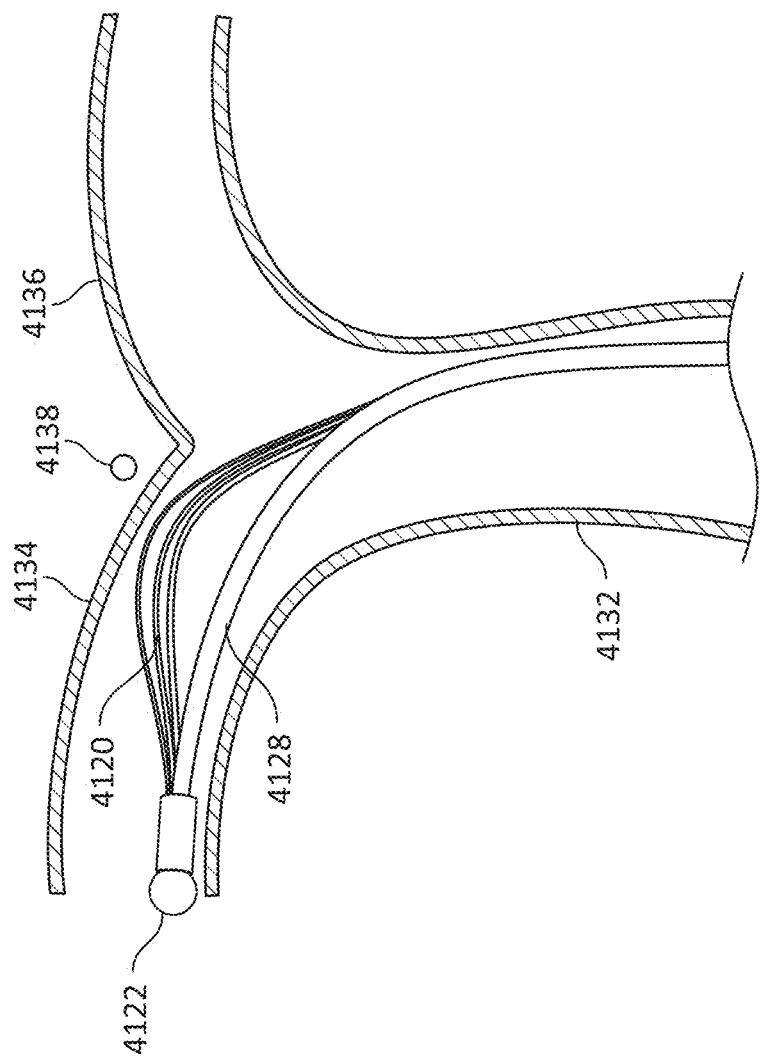

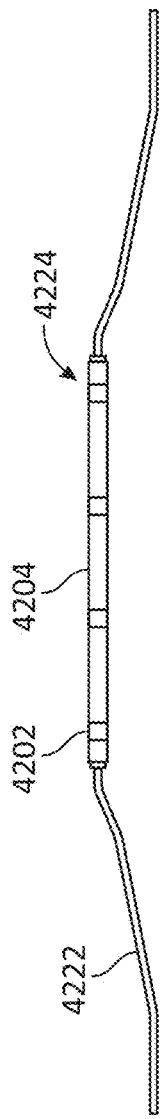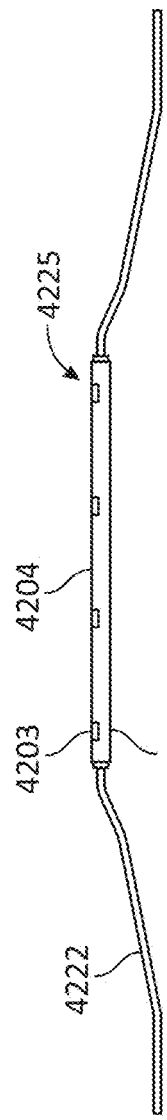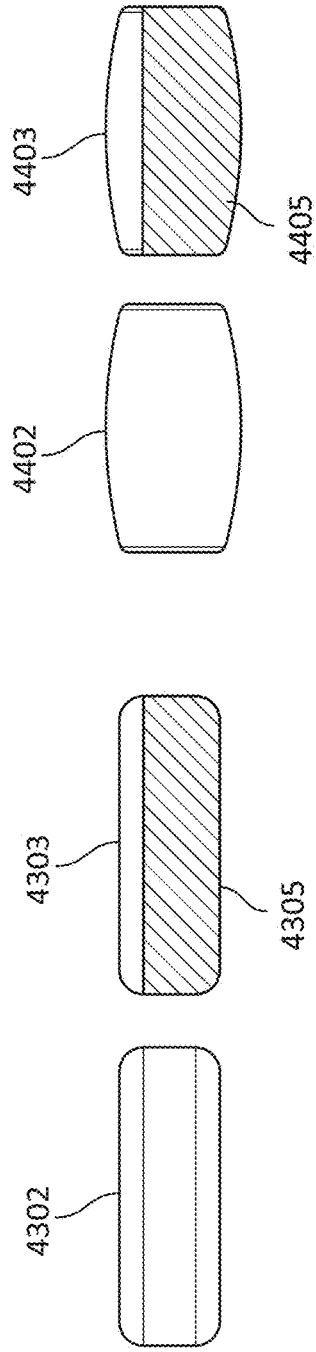

METHODS OF FACILITATING POSITIONING OF ELECTRODES

INCORPORATION BY REFERENCE

This application is a continuation of PCT Application No. PCT/US2017/021214, filed Mar. 7, 2017, which claims priority benefit of U.S. Provisional Patent Application No. 62/305,988, filed Mar. 9, 2016, U.S. Provisional Patent Application No. 62/343,302, filed May 31, 2016, and U.S. Provisional Patent Application No. 62/464,039, filed Feb. 27, 2017, and this application claims the benefit of U.S. Provisional Patent Application No. 62/464,039, filed Feb. 27, 2017, each of which is incorporated herein by reference in its entirety for all purposes. Any and all applications related thereto by way of priority thereto or therefrom are hereby incorporated by reference in their entirety.

BACKGROUND

Field

The present disclosure relates generally to methods and systems for facilitating modulation (e.g., electrical neuromodulation), and more particularly to methods and systems for facilitating therapeutic and calibration electrical neuromodulation of one or more nerves in and around the heart.

Description of the Related Art

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of the patient's congestive state.

SUMMARY

Treatments for acute heart failure include the use of inotropic agents, such as dopamine and dobutamine. These agents, however, have both chronotropic and inotropic effects and characteristically increase heart contractility at the expense of significant increases in oxygen consumption secondary to elevations in heart rate. As a result, although these inotropic agents increase myocardial contractility and improve hemodynamics, clinical trials have consistently demonstrated excess mortality caused by cardiac arrhythmias and increase in myocardium consumption.

As such, there is a need for selectively and locally treating acute heart failure and otherwise achieving hemodynamic control without causing unwanted systemic effects. Accordingly, in some embodiments, no inotropics are used. In other embodiments, reduced dosages of inotropics may be used because, for example, synergistic effects are provided through various embodiments herein. By reducing the dosages, the side effects can also be significantly reduced.

Several embodiments of the present disclosure provide for methods of tissue modulation, such as neuromodulation, for cardiac and other disorders. For example, some embodiments provide methods and devices for neuromodulation of one or more nerves in and around a heart of a patient. Several methods of the present disclosure, for example, may be useful in electrical neuromodulation of patients with cardiac disease, such as patients with acute or chronic cardiac disease. Several methods of the present disclosure encompass, for example, neuromodulation of one or more target sites of the autonomic nervous system of the heart. In some embodiments, sensed non-electrical heart activity properties are used in making adjustments to one or more properties of the electrical neuromodulation delivered to the patient. Non-limiting examples of medical conditions that can be treated according to the present disclosure include cardiovascular medical conditions.

As discussed herein, the configuration of the catheter and electrode systems of the present disclosure may advantageously allow for a portion of the catheter to be positioned within the vasculature of the patient in the main pulmonary artery and/or one or both of the pulmonary arteries (the right pulmonary artery and the left pulmonary artery). Once positioned, the catheter and electrode systems of the present disclosure can provide electrical stimulation energy (e.g., electrical current or electrical pulses) to stimulate the autonomic nerve fibers surrounding the main pulmonary artery and/or one or both of the pulmonary arteries in an effort to provide adjuvant cardiac therapy to the patient.

The catheter can include an elongate body having a first end and a second end. The elongate body can include an elongate radial axis that extends through the first end and the second end of the elongate body, and a first plane extends through the elongate radial axis. At least two elongate stimulation members may extend from the elongate body, where each of the at least two elongate stimulation members curves into a first volume defined at least in part by the first plane. In one embodiment, at least one electrode is on each of the at least two elongate stimulation members, where the at least one electrode form an electrode array in the first volume. Conductive elements may extend through and/or along each of the elongate stimulation members, where the conductive elements conduct electrical current to combinations of two or more of the electrodes in the electrode array.

In one embodiment, the at least two elongate stimulation members can curve only in the first volume defined at least in part by the first plane, and a second volume defined at least in part by the first plane and being opposite the first volume contains no electrodes. A second plane can perpendicularly intersect the first plane along the elongate radial axis of the elongate body to divide the first volume into a first quadrant volume and a second quadrant volume. The at least two elongate stimulation members can include a first elongate stimulation member and a second elongate stimulation member, where the first elongate stimulation member curves into the first quadrant volume and the second elongate stimulation member curves into the second quadrant volume.

Each of the at least two elongate stimulation members can include a stimulation member elongate body and a wire extending longitudinally through the elongate body and the stimulation member elongate body, where pressure applied by the wire against the stimulation member elongate body at or near its distal end causes the wire to deflect, thereby imparting the curve into each of the at least two elongate stimulation members into the first volume defined at least in part by the first plane. The catheter can also include an anchor member that extends from the elongate body into a second volume defined at least in part by the first plane and opposite the first volume, where the anchor member does not include an electrode.

In an additional embodiment, the catheter can also include a structure extending between at least two of the least two elongate stimulation members. An additional electrode can be positioned on the structure, the additional electrode having a conductive element extending from the additional electrode through one of the elongate stimulation members, where the conductive element conducts electrical current to combinations of the additional electrode and at least one of the at least one electrode on each of the at least two elongate stimulation members. An example of such a structure is a mesh structure.

The catheter can also include a positioning gauge that includes an elongate gauge body with a first end and a bumper end distal to the first end. The elongate body of the catheter can include a first lumen that extends from the first end through the second end of the elongate body. The bumper end can have a shape with a surface area no less than a surface area of the distal end of the elongate body taken perpendicularly to the elongate radial axis, and the elongate gauge body can extend through the first lumen of the elongate body to position the bumper end beyond the second end of the elongate body. In one embodiment, the first end of the positioning gauge extends from the first end of the elongate body, the elongate gauge body having a marking that indicates a length between the second end of the elongate body and the bumper end of the positioning gauge.

The present disclosure also includes a catheter system that includes a catheter and a pulmonary artery catheter having a lumen, where the catheter extends through the lumen of the pulmonary artery catheter. The pulmonary artery catheter can include an elongate catheter body with a first end, a second end, a peripheral surface and an interior surface, opposite the peripheral surface, that defines the lumen extending between the first end and the second end of the elongate catheter body. An inflatable balloon can be positioned on the peripheral surface of the elongate catheter body, the inflatable balloon having a balloon wall with an interior surface that, along with a portion of the peripheral surface of the elongate catheter body, defines a fluid tight volume. An inflation lumen extends through the elongate catheter body, the inflation lumen having a first opening into the fluid tight volume of the inflatable balloon and a second opening proximal to the first opening to allow for a fluid to move in and out of the fluid tight volume to inflate and deflate the balloon.

The present disclosure also provides for a catheter that includes an elongate catheter body having a first end, a second end, a peripheral surface and an interior surface defining an inflation lumen that extends at least partially between the first end and the second end of the elongate catheter body; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; a plurality of electrodes positioned along the peripheral surface of the elongate catheter body, the plurality of electrodes located between the inflatable balloon and the first end of the elongate catheter body; conductive elements extending through the elongate catheter body, where the conductive elements conduct electrical current to combinations of two or more of the at least one electrode of the plurality of electrodes; and a first anchor extending laterally from the peripheral surface of the elongate body, the first anchor having struts forming an open framework with a peripheral surface having a largest outer dimension greater than a largest outer dimension of the inflatable balloon.

In one embodiment, the first anchor is positioned between the inflatable balloon and the plurality of electrodes positioned along the peripheral surface of the elongate catheter body. A portion of the elongate catheter body that includes the plurality of electrodes can curve in a predefined radial direction when placed under longitudinal compression. In another embodiment, the first anchor is positioned between the plurality of electrodes positioned along the peripheral surface of the elongate catheter body and the first end of the elongate catheter body.

The elongate catheter body can also include a second interior surface defining a shaping lumen that extends from the first end towards the second end. A shaping wire having a first end and a second end can pass through the shaping lumen with the first end of the shaping wire proximal to the first end of the elongate catheter body and the second end of the shaping wire joined to the elongate catheter body so that the shaping wire imparts a curve into a portion of the elongate catheter body having the plurality of electrodes when tension is applied to the shaping wire.

An embodiment of the catheter can also include an elongate catheter body having a first end, a second end, a peripheral surface and an interior surface defining an inflation lumen that extends at least partially between the first end and the second end of the elongate catheter body; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; a first anchor extending laterally from the peripheral surface of the elongate catheter body the first anchor having struts forming an open framework with a peripheral surface having a diameter larger than a diameter of the inflatable balloon; an electrode catheter having an electrode elongate body and a plurality of electrodes positioned along a peripheral surface of the electrode elongate body; conductive elements extending through the electrode elongate body of the electrode catheter, where the conductive elements conduct electrical current to combinations two or more of the at least one electrode of the plurality of electrodes; and an attachment ring joined to the electrode catheter and positioned around the peripheral surface of the elongate catheter body proximal to both the first anchor and the inflatable balloon.

A catheter system of the present disclosure can also include an elongate catheter body having a first end, a second end, a peripheral surface and an interior surface defining an inflation lumen that extends at least partially between the first end and the second end of the elongate catheter body, where the elongate catheter body includes an elongate radial axis that extends through the first end and the second end of the elongate body, and where a first plane extends through the elongate radial axis; an inflatable balloon on the peripheral surface of the elongate catheter body, the inflatable balloon having a balloon wall with an interior surface that along with a portion of the peripheral surface of the elongate catheter body defines a fluid tight volume, where the inflation lumen has a first opening into the fluid tight volume of the inflatable balloon and a second opening proximal to the first opening to allow for a fluid to move in the volume to inflate and deflate the balloon; an electrode cage having two or more ribs that extend radially away from the peripheral surface of the elongate catheter body towards the inflatable balloon, where the two or more of the ribs of the electrode cage curve into a first volume defined at least in part by the first plane; one or more electrodes on each of the ribs of the electrode cage, where the one or more electrodes on each of the rib form an electrode array in the first volume; conductive elements extending through the two or more of the ribs of the electrode cage and the elongate catheter body, where the conductive elements conduct electrical current to combinations of the one or more electrodes in the electrode array; and an anchoring cage having two or more of the ribs that extend radially away from the peripheral surface of the elongate catheter body towards the inflatable balloon, where the two or more of the ribs of the anchoring cage curve into a second volume defined at least in part by the first plane and being opposite the first volume, where the two or more of the rib of the anchoring cage do not include an electrode.

In one example embodiment, a catheter includes an elongate body having a first end and a second end. The elongate body includes a longitudinal center axis that extends between the first end and the second end. The elongate body further includes three or more surfaces that define a convex polygonal cross-sectional shape taken perpendicularly to the longitudinal center axis. The catheter further includes one or more, but preferably two or more, electrodes on one surface of the three or more surfaces of the elongate body, where conductive elements extend through the elongate body. The conductive elements can conduct electrical current to combinations of the one or more electrodes or in the instance of a single electrode a second electrode is provided elsewhere in the system for flow of current. By way of example, the surfaces defining the convex polygonal cross-sectional shape of the elongate body can be a rectangle. Other shapes are possible. In one embodiment, the one or two or more electrodes are only on the one surface of the three or more surfaces of the elongate body. The one or more electrodes can have an exposed face that is co-planar with the one surface of the three or more surfaces of the elongate body. The one surface of the three or more surfaces of the elongate body can further include anchor structures that extend above the one surface. In addition to the surfaces defining the convex polygonal cross-sectional shape, the elongate body of the catheter can also have a portion with a circular cross-section shape taken perpendicularly to the longitudinal center axis. The catheter of this example embodiment can also include an inflatable balloon on a peripheral surface of the elongate body. The inflatable balloon includes a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon.

In another example embodiment, a catheter includes an elongate body having a peripheral surface and a longitudinal center axis extending between a first end and a second end. The elongate body of this example embodiment has an offset region defined by a series of predefined curves along the longitudinal center axis. The predefined curves include a first portion having a first curve and a second curve in the longitudinal center axis, a second portion following the first portion, where the second portion has a zero curvature (e.g., a straight portion), and a third portion following the second portion, the third portion having a third curve and a fourth curve. An inflatable balloon is positioned on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. One or more electrodes are positioned on the elongate body along the second portion of the offset region of the elongate body. Conductive elements extend through the elongate body, where the conductive elements conduct electrical current to combinations of the one or more electrodes. The portions of the elongate body of this example embodiment of a catheter can have a variety of shapes. For example, the second portion of the elongate body can form a portion of a helix. The elongate body can also have three or more surfaces defining a convex polygonal cross-sectional shape taken perpendicularly to the longitudinal center axis, where the one or more electrodes are on one surface of the three or more surfaces of the elongate body. For this embodiment, the convex polygonal cross-sectional shape can be a rectangle. The one or more electrodes are only on the one surface of the three or more surfaces of the elongate body. The one or more electrodes can have an exposed face that is co-planar with the one surface of the three or more surfaces of the elongate body.

In another example embodiment, a catheter includes an elongate body with a peripheral surface and a longitudinal center axis extending between a first end and a second end. The elongate body includes a surface defining a deflection lumen, where the deflection lumen includes a first opening and a second opening in the elongate body. An inflatable balloon is located on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. One or more electrodes are located on the elongate body, where the second opening of the deflection lumen is opposite the one or more electrodes on the elongate body. Conductive elements extend through the elongate body, where the conductive elements conduct electrical current to combinations of the one or more electrodes. The catheter also includes an elongate deflection member, where the elongate deflection member extends through the second opening of the deflection lumen in a direction opposite the one or more electrodes on one surface of the elongate body.

In another example embodiment, a catheter includes an elongate body having a peripheral surface and a longitudinal center axis extending between a first end and a second end. The elongate body includes a surface defining an electrode lumen, where the electrode lumen includes a first opening in the elongate body. The catheter further includes an inflatable balloon on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. The catheter further includes an elongate electrode member, where the elongate electrode member extends through the first opening of the electrode lumen of the elongate body, where the electrode member includes one or more electrodes and conductive elements extending through the electrode lumen, where the conductive elements conduct electrical current to combinations of the one or more electrodes. The elongate electrode member can form a loop that extends away from the peripheral surface of the elongate body. The elongate electrode member forming the loop can be in a plane that is co-linear with the longitudinal center axis of the elongate body. Alternatively, the elongate electrode member forming the loop is in a plane that is perpendicular to the longitudinal center axis of the elongate body.

According to some methods of the present disclosure and as will be discussed more fully herein, a catheter having an electrode array is inserted into the pulmonary trunk and positioned at a location such that the electrode array is positioned with its electrodes in contact with the posterior surface, the superior surface and/or the inferior surface of the right pulmonary artery. From this location, electrical current can be delivered to or from the electrode array to selectively modulate the autonomic nervous system of the heart. For example, electrical current can be delivered to or from the electrode array to selectively modulate the autonomic cardiopulmonary nerves of the autonomic nervous system, which can modulate heart contractility more than heart rate. Preferably, the electrode array is positioned at a site along the posterior wall and/or superior wall of the right pulmonary artery such that the electrical current delivered to or from the electrode array results in the greatest effect on heart contractility and the least effect on heart rate and/or oxygen consumption compared to electrical current delivered at other sites in the right pulmonary artery and/or left pulmonary artery. In certain embodiments, the effect on heart contractility is to increase heart contractility.

As used herein, the electrical current delivered to or from the electrode array can be in the form of a time variant electrical current. Preferably such a time variant electrical current can be in the form of one or more of a pulse of electrical current (e.g., at least one pulse of electrical current), one or more of waveform, such as a continuous wave of electrical current, or a combination thereof.

As discussed herein, the present disclosure provides for a method for treating a patient having a heart with a pulmonary trunk. Portions of the pulmonary trunk can be defined with a right lateral plane that passes along a right luminal surface of the pulmonary trunk, a left lateral plane parallel with the right lateral plane, where the left lateral plane passes along a left luminal surface of the pulmonary trunk. The right lateral plane and the left lateral plane extend in a direction that generally aligns with the posterior and anterior directions of a subject's (e.g., patient's) body. A branch point is positioned between the right lateral plane and the left lateral plane, where the branch point helps to define the beginning of a left pulmonary artery and a right pulmonary artery of the heart. The method further includes moving a catheter having an electrode array through the pulmonary trunk towards the branch point, where the electrode array includes one or more, preferably two or more, electrodes. The electrode array is positioned in the right pulmonary artery to the right of the left lateral plane, where the one or more electrodes contacts a posterior surface, a superior surface and/or an inferior surface of the right pulmonary artery to the right of the left lateral plane. In an additional embodiment, the electrode array can be positioned in the right pulmonary artery to the right of the right lateral plane, where the one or more electrodes contacts the posterior surface, the superior surface and/or the inferior surface of the right pulmonary artery to the right of the right lateral plane. This example embodiment of a method further includes contacting the one or more electrodes on the posterior surface, the superior surface and/or the inferior surface of the right pulmonary artery at a position superior to (e.g., situated above) the branch point. The at least a portion of the catheter can also be positioned in contact with a portion of the surface defining the branch point. In this embodiment, the portion of the catheter can be provided with a shape that provides an increase in surface area that can help to hold the portion of the catheter against the branch point.

In an additional embodiment, the pulmonary trunk has a diameter taken across a plane perpendicular to both the left lateral plane and the right lateral plane, where the electrode array is positioned in the right pulmonary artery to extend from a point to the right of the left lateral plane to a point about three times the diameter of the pulmonary trunk to the right of the branch point. The right pulmonary artery can also include a branch point that divides the right pulmonary artery into at least two additional arteries that are distal to the branch point helping to define the beginning of the left pulmonary artery and the right pulmonary artery. The electrode array can be positioned in the right pulmonary artery between the branch point helping to define the beginning of the left pulmonary artery and the right pulmonary artery and the branch point that divides the right pulmonary artery into at least two additional arteries. Once in position, electrical current can be provided from or to the one or more electrodes of the electrode array. A value of a cardiac parameter of the patient can be measured in response to the electrical current from or to the one or more electrodes of the electrode array. From the value of the cardiac parameter, changes can be made to which of the electrodes are used to provide the electrical current in response to the value of the cardiac parameter. Changes can also be made to the nature of the electrical current provided in response to the value of the cardiac parameter. Such changes include, but are not limited to, changes in voltage, amperage, waveform, frequency and pulse width, by way of example. In addition, the electrodes of the one or more electrodes on the posterior surface, the superior surface and/or the inferior surface of the right pulmonary artery can be moved in response to the values of the cardiac parameter. The electrical current provided to or from the one or more electrodes of the electrode array can be provided as at least one pulse of electrical current to or from the one or more electrodes of the electrode array. Examples of such a cardiac parameter include, but are not limited to, measuring a pressure parameter, an acoustic parameter, an acceleration parameter and/or an electrical parameter (e.g., ECG) of the heart of the patient as the cardiac parameter.

Several methods of the present disclosure allow for electrical neuromodulation of the heart of the patient, for example including delivering one or more electrical pulses through a catheter positioned in a pulmonary artery of the heart of the patient, sensing from at least a first sensor positioned at a first location within the vasculature of the heart one or more heart activity properties (e.g., a non-electrical heart activity property) in response to the one or more electrical pulses, and adjusting a property of the one or more electrical pulses delivered through the catheter positioned in the pulmonary artery of the heart in response to the one or more heart activity properties. The methods may provide adjuvant cardiac therapy to the patient.

Sensing from at least the first sensor positioned at the first location can include sensing one or more of a pressure property, an acceleration property, an acoustic property, a temperature, and a blood chemistry property from within the vasculature of the heart. Among other locations, the first sensor can be positioned in one of a left pulmonary artery, a right pulmonary artery, a pulmonary artery branch vessel, or a pulmonary trunk of the heart. The one or more electrical pulses can optionally be delivered through the catheter positioned in one of the left pulmonary artery, the right pulmonary artery, or pulmonary trunk of the heart that does not contain the first sensor. The first sensor can also be positioned in a pulmonary trunk of the heart.

Other locations for the first sensor can include in the right ventricle of the heart and in the right atrium of the heart. When positioned in the right atrium of the heart, the first sensor can optionally be positioned on the septal wall of the right atrium of the heart. The first sensor could also be positioned on the septal wall of the right ventricle. The right ventricle and the left ventricle share a septal wall, so a sensor in the right ventricle or on the septal wall of the right ventricle may be preferable for detecting properties indicative of left ventricle contractility or cardiac output. Additional locations for positioning the first sensor include in a superior vena cava of the heart, the inferior vena cava of the heart, and in a coronary sinus of the heart. When positioned in the coronary sinus of the heart, the first sensor can be used to sense at least one of a temperature or a blood oxygen level.

In some embodiments, the first sensor may be positioned in the left atrium (e.g., by forming an aperture in the septal wall between the right atrium and the left atrium, or by using a patent foramen ovale (PFO) or atrial septal defect (ASD)). A sensor in the left atrium may be useful for detecting properties indicative of the left ventricle. If the left atrium has been accessed, in some embodiments, the sensor may be positioned in the left ventricle itself, which may provide the most direct measurement of properties associated with the left ventricle. In some embodiments, the sensor may be positioned downstream of the left ventricle, including the aorta, aortic branch arteries, etc. When the procedure is complete, any aperture that was created or existing may be closed using a closure device such as Amplatzer, Helex, CardioSEAL, or others.

Some methods can include sensing one or more cardiac properties from a skin surface of the patient, and adjusting the property of the one or more electrical pulses delivered through the catheter positioned in the pulmonary artery of the heart in response to the one or more heart activity properties (e.g., non-electrical properties) from the first sensor positioned at a first location within the vasculature of the heart and/or the one or more cardiac properties from the skin surface of the patient. The one or more cardiac properties sensed from the skin surface of the patient can include, for example, an electrocardiogram property.

Some methods can include sensing from at least a second sensor positioned at a second location within the vasculature of the heart one or more heart activity properties (e.g., non-electrical heart activity properties) in response to the one or more electrical pulses, and adjusting the property of the one or more electrical pulses delivered through the catheter positioned in the pulmonary artery of the heart in response to the one or more heart activity properties from the first sensor and/or the one or more heart activity properties from the second sensor.

Adjusting the property of the one or more electrical pulses can include a variety of responses. For example, adjusting the property of the one or more electrical pulses can include changing which of an electrode or plurality of electrodes on the catheter is used to deliver the one or more electrical pulses. For another example, adjusting the property of the one or more electrical pulses can include moving the catheter to reposition one or more electrodes of the catheter in the pulmonary artery of the heart. For yet another example, adjusting the property of the one or more electrical pulses can include changing at least one of an electrode polarity, a pulsing mode, a pulse width, an amplitude, a frequency, a phase, a voltage, a current, a duration, an inter-pulse interval, a duty cycle, a dwell time, a sequence, a wavelength, and/or a waveform of the one or more electrical pulses.

A hierarchy of electrode configurations can be assigned from which to deliver the one or more electrical pulses. The one or more electrical pulses can be delivered based on the hierarchy of electrode configurations, where the one or more heart activity properties sensed in response to the one or more electrical pulses can be analyzed and an electrode configuration can be selected to use for delivering the one or more electrical pulses through the catheter positioned in the pulmonary artery of a heart of a patient based on the analysis. A hierarchy can be assigned to each property of the one or more electrical pulses delivered through the catheter positioned in the pulmonary artery of the heart, where the one or more electrical pulses are delivered based on the hierarchy of each property. The one or more non-electrical heart activity properties sensed in response to the one or more electrical pulses are analyzed and an electrode configuration can be selected to be used for delivering the one or more electrical pulses through the catheter positioned in the pulmonary artery of a heart of a patient based on the analysis. Analyzing the one or more heart activity properties can include analyzing a predetermined number of the one or more heart activity properties.

In some embodiments, a method of facilitating therapeutic neuromodulation of a heart of a patient comprises positioning an electrode in a pulmonary artery of a heart and positioning a sensor in a right ventricle of the heart. The method further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals, and delivering a therapeutic neuromodulation signal to the pulmonary artery using selected electrical parameters. The selected electrical parameters comprise a selected magnitude of the first parameter and a selected magnitude of the second parameter. The selected magnitudes of the first and second parameters are based at least partially on the sensor data. The therapeutic neuromodulation signal increases heart contractility more than heart rate.

The method may further comprise delivering, via the stimulation system, a third series of electrical signals to the electrode. The third series comprises a third plurality of electrical signals. Each of the third plurality of electrical signals comprises the plurality of parameters. Each of the third plurality of electrical signals of the third series only differs from one another by a magnitude of a third parameter of the plurality of parameters. The third parameter is different than the first parameter and the second parameter. The method may further comprise determining, via the sensor, sensor data indicative of the one or more non-electrical heart activity properties in response to delivering the third series of electrical signals. The selected electrical parameters may comprise a selected magnitude of the third parameter. The selected magnitude of the third parameter is based at least partially on the sensor data.

The method may further comprise determining a desired hierarchy between the first series and the second series. The pulmonary artery may comprise a right pulmonary artery. The one or more non-electrical heart activity properties may comprise at least one of a pressure property, an acceleration property, an acoustic property, a temperature, and a blood chemistry property. Determining the sensor data may comprise determining, via a second sensor on a skin surface, sensor data indicative of an electrocardiogram property in response to delivering the first series of electrical signals and the second series of electrical signals.

The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination, and, optionally, the second parameter may be a different one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination. The second parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination. The first parameter may comprise current and the second parameter may comprise a parameter relating to timing (e.g., one of frequency and duty cycle).

In some embodiments, a method of facilitating therapeutic neuromodulation of a heart of a patient comprises positioning an electrode in a pulmonary artery of a heart, positioning a sensor in a right ventricle of the heart, delivering, via a stimulation system, a first electrical signal of a series of electrical signals to the electrode, and, after delivering the first electrical signal, delivering, via the stimulation system, a second electrical signal of the series of electrical signals to the electrode. The second electrical signal differs from the first electrical signal by a magnitude of a first parameter of a plurality of parameters. The method further comprises determining, via the sensor, sensor data indicative of one or more non-electrical heart activity properties in response to the delivery of the series of electrical signals, and delivering a therapeutic neuromodulation signal to the pulmonary artery using selected electrical parameters. The selected electrical parameters comprise a selected magnitude of the first parameter. The selected magnitude of the first parameter is based at least partially on the sensor data. The therapeutic neuromodulation signal increases heart contractility more than heart rate.

The pulmonary artery may comprise a right pulmonary artery. The pulmonary artery may comprise a left pulmonary artery. The pulmonary artery may comprise a pulmonary trunk. The one or more non-electrical heart activity properties may comprise at least one of a pressure property, an acceleration property, an acoustic property, a temperature, and a blood chemistry property. Determining the sensor data may comprise determining, via a second sensor on a skin surface of the patient, sensor data indicative of an electrocardiogram property in response to delivering the series of electrical signals. The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination.

In some embodiments, a method of facilitating therapeutic neuromodulation of a heart of a patient comprises delivering a first series of electrical signals to an electrode in a first anatomical location, and, after delivering the first series of electrical signals to the electrode, delivering a second series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises sensing, via a sensor in a second anatomical location different than the first anatomical location, sensor data indicative of one or more non-electrical heart activity properties in response to delivering the first series of electrical signals and the second series of electrical signals, and providing a therapeutic neuromodulation signal to the first anatomical location using selected electrical parameters. The selected electrical parameters comprise a selected magnitude of the first parameter and a selected magnitude of the second parameter. The selected magnitudes of the first and second parameters are based at least partially on the sensor data. The therapeutic neuromodulation signal increases heart contractility.

The method may further comprise delivering a third series of electrical signals to the electrode. The third series comprises a third plurality of electrical signals. Each of the third plurality of electrical signals comprises the plurality of parameters. Each of the third plurality of electrical signals of the third series only differs from one another by a magnitude of a third parameter of the plurality of parameters. The third parameter is different than the first parameter and the second parameter. The method may further comprise sensing, via the sensor, sensor data indicative of the one or more non-electrical heart activity properties in response to delivering the third series of electrical signals. The selected electrical parameters may comprise a selected magnitude of the third parameter. The selected magnitude of the third parameter is based at least partially on the sensor data.

The method may further comprise determining a desired hierarchy between the first series and the second series. The first anatomical location may comprise a right pulmonary artery. The pulmonary artery may comprise a left pulmonary artery. The pulmonary artery may comprise a pulmonary trunk. The one or more non-electrical heart activity properties may comprise at least one of a pressure property, an acceleration property, an acoustic property, a temperature, and a blood chemistry property. Sensing the sensor data may comprise determining, via a second sensor on a skin surface, sensor data indicative of an electrocardiogram property in response to delivering the first series of electrical signals and the second series of electrical signals.

The first parameter may one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination, and, optionally, the second parameter may be a different one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination. The second parameter may one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination. The first parameter may comprise current and the second parameter may comprise a parameter related to timing (e.g., one of frequency and duty cycle).

In some embodiments, a method of facilitating therapeutic neuromodulation of a heart of a patient comprises delivering a first electrical signal of a series of electrical signals to an electrode in a first anatomical location, and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and providing a therapeutic neuromodulation signal to the first anatomical location using selected electrical parameters. The selected electrical parameters comprise a selected magnitude of the first parameter. The selected magnitude of the first parameter is based at least partially on the sensor data. The therapeutic neuromodulation signal increases heart contractility.

The first anatomical location may comprise a right pulmonary artery. The first anatomical location may comprise a left pulmonary artery. The first anatomical location may comprise a pulmonary trunk. The one or more non-electrical heart activity properties may comprise at least one of a pressure property, an acceleration property, an acoustic property, a temperature, and a blood chemistry property. Sensing the sensor data may comprise sensing, via a second sensor on a skin surface of the patient, sensor data indicative of an electrocardiogram property in response to delivering the series of electrical signals. The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination.

In some embodiments, a neuromodulation system for facilitating delivery of electric signals to a heart of a patient comprises a catheter and a stimulation system. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The catheter further comprises a sensor on the outer surface. The sensor is configured to sense a heart activity property from a location within in vasculature of the patient. The stimulation system comprises a pulse generator configured to deliver a first series of electrical signals and a second series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The stimulation system further comprises a non-transitory computer-readable medium configured to store sensor data indicative of one or more non-electrical heart activity properties in response to delivering the first series of electrical signals and the second series of electrical signals to the electrode, and a processor configured to determine a selected magnitude of the first parameter and a selected magnitude of the second parameter based at least partially on the sensor data. The non-transitory computer readable medium is configured to store selected electrical parameters including the selected magnitude of the first parameter and the selected magnitude of the second parameter. The pulse generator is configured to deliver a therapeutic neuromodulation signal to the electrode using selected electrical parameters.

In some embodiments, a neuromodulation system for facilitating delivery/of electric signals to a heart of a patient comprises a catheter and a stimulation system. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The catheter further comprises a sensor on the outer surface. The sensor is configured to sense a heart activity property from a location within in vasculature of the patient. The stimulation system comprises a pulse generator configured to deliver a series of electrical signals to the electrode. The series comprises a first electrical signal and a second electrical signal. The second electrical signal differs from the first electrical signal by a magnitude of a first parameter of a plurality of parameters. The stimulation system further comprises a non-transitory computer-readable medium configured to store sensor data indicative of one or more non-electrical heart activity properties in response to delivering the series of electrical signals to the electrode, and a processor configured to determine a selected magnitude of the first parameter based at least partially on the sensor data. The non-transitory computer readable medium is configured to store selected electrical parameters including the selected magnitude of the first parameter. The pulse generator is configured to deliver a therapeutic neuromodulation signal to the electrode using selected electrical parameters.

In some embodiments, a neuromodulation system for facilitating delivery of electric signals to a heart of a patient comprises a catheter and a shaping wire. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The shaping wire is configured to be positioned in the lumen of the catheter body. The shaping wire comprises a bent portion. When the shaping wire is inserted in the lumen of the catheter body, the catheter body comprises a curved portion corresponding to the bent portion of the shaping wire.

The heart activity property may comprise a non-electrical hearty activity property. The non-electrical heart activity property may comprise at least one of a pressure property, an acceleration property, an acoustic property, a temperature, and a blood chemistry property. The electrode may be configured to deliver the electrical signal to a right pulmonary artery of the patient. The electrode may be configured to be positioned in a different location than the sensor. The catheter system may comprise a plurality of electrodes including the electrode. The location may be a pulmonary trunk, a right ventricle, a septal wall of a right ventricle, a right atrium, a septal wall of a right atrium, a superior vena cava, a pulmonary branch artery vessel, an inferior vena cava, or a coronary sinus. The neuromodulation system may further comprise a skin sensor configured to sense a cardiac property from a skin surface of the patient. The heart activity property may comprise a non-electrical heart activity property and wherein the cardiac property may comprise an electrical cardiac property. The electrical cardiac property may comprise an electrocardiogram property.

In some embodiments, a method of neuromodulation of a heart of a patient comprises positioning a catheter including an electrode in a pulmonary artery of a heart, positioning a sensor in a location within vasculature of the heart, delivering, via a stimulation system, a first set of one or more electrical pulses to the electrode, the first set of one or more electrical pulses having a first pulse property, and, after delivering the first delivering set of one or more electrical pulses to the electrode, delivering, via the stimulation system, a second set of one or more electrical pulses to the electrode. The second set of one or more electrical pulses has a second pulse property different than the first pulse property. The method further comprises delivering therapeutic electrical pulses to the pulmonary artery using an electrode configuration selected by analyzing one or more heart activity properties sensed, via the sensor, in response to the delivery of the first and second sets of electrical pulses. The electrode configuration comprises the first pulse property or the second pulse property based at least partially on the analysis. The therapeutic neuromodulation signal increases heart contractility more than heart rate.

In some embodiments, a method of modulation (e.g., electrical neuromodulation) of a heart of a patient comprises delivering one or more electrical pulses through a catheter positioned in a pulmonary artery of the heart of the patient, sensing from at least a first sensor positioned at a first location within a vasculature of the heart one or more non-electrical heart activity properties in response to the one or more electrical pulses, and adjusting a property of the one or more electrical pulses delivered through the catheter positioned in the pulmonary artery of the heart in response to the one or more non-electrical heart activity properties.

In some embodiments, sensing from at least the first sensor positioned at the first location may include sensing one or more of a pressure property, an acceleration property, an acoustic property, a temperature, and a blood chemistry property from within the vasculature of the heart.

In one embodiment, a first sensor is placed in one of a left pulmonary artery, a right pulmonary artery, or a pulmonary trunk of the heart. One or more electrical pulses are delivered through the catheter positioned in one of the left pulmonary artery, the right pulmonary artery, or the pulmonary trunk of the heart that does not contain the first sensor.

The first sensor may be positioned in the left pulmonary artery. The first sensor may be positioned in the right pulmonary artery. The first sensor may be positioned in other vessels in and around the heart, including, but not limited to, the pulmonary trunk, a pulmonary artery branch vessel, right ventricle, a septal wall of the right ventricle, a right atrium, the septal wall of the right atrium, a superior vena cava, an inferior vena cava or a coronary sinus The first sensor (e.g., in the coronary sinus) may sense at least one of a temperature or a blood oxygen level.

In several embodiments, the method may include sensing one or more cardiac properties from a skin surface of the patient and adjusting the property of the one or more electrical pulses delivered through the catheter positioned in the pulmonary artery of the heart in response to the one or more non-electrical heart activity properties and the one or more cardiac properties from the skin surface of the patient. The one or more cardiac properties sensed from the skin surface of the patient may include an electrocardiogram property. The may include sensing from at least a second sensor positioned at a second location within the vasculature of the heart one or more non-electrical heart activity properties in response to the one or more electrical pulses and adjusting the property of the one or more electrical pulses delivered through the catheter positioned in the pulmonary artery of the heart in response to the one or more non-electrical heart activity properties received by the first sensor and the second sensor. In several embodiments, adjusting the property of the one or more electrical pulses may include one or more of the following (i) changing which electrode on the catheter is used to deliver the one or more electrical pulses; (ii) moving the catheter to reposition electrodes of the catheter in the pulmonary artery of the heart; (iii) changing at least one of an electrode polarity, a pulsing mode, a pulse width, an amplitude, a frequency, a phase, a voltage, a current, a duration, an inter-pulse interval, a duty cycle, a dwell time, a sequence, a wavelength, a waveform, or an electrode combination of the one or more electrical pulses.

In several embodiments, the method may include assigning a hierarchy of electrode configurations from which to deliver the one or more electrical pulses, delivering the one or more electrical pulses based at least partially on the hierarchy of electrode configurations, analyzing the one or more non-electrical heart activity properties sensed in response to the one or more electrical pulses, and selecting an electrode configuration to use for delivering the one or more electrical pulses through the catheter positioned in the pulmonary artery of a heart of a patient based at least partially on the analysis. The method may include assigning a hierarchy to each property of the one or more electrical pulses delivered through the catheter positioned in the pulmonary artery of the heart, delivering the one or more electrical pulses based at least partially on the hierarchy of each property, analyzing the one or more non-electrical heart activity properties sensed in response to the one or more electrical pulses, and selecting an electrode configuration to use for delivering the one or more electrical pulses through the catheter positioned in the pulmonary artery of a heart of a patient based at least partially on the analysis. Analyzing the one or more non-electrical heart activity properties may include analyzing a predetermined number of the one or more non-electrical heart activity properties.

In several embodiments, therapeutic neuromodulation is not provided. Instead, several embodiments are provided for the purposes of calibrating or optimizing a signal for, e.g., diagnosis or calibration purposes.

In some embodiments, a method of non-therapeutic calibration comprises positioning an electrode in a pulmonary artery of a heart and positioning a sensor in a right ventricle of the heart. The system further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals. The method further comprises determining a therapeutic neuromodulation signal to be delivered to the pulmonary artery using selected electrical parameters. The selected electrical parameters comprise a selected magnitude of the first parameter and a selected magnitude of the second parameter. The selected magnitudes of the first and second parameters are based at least partially on the sensor data.

In some embodiments, a method of non-therapeutic calibration comprises delivering a first electrical signal of a series of electrical signals to an electrode in a first anatomical location and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and determining a therapeutic neuromodulation signal to be delivered to the first anatomical location using selected electrical parameters. The selected electrical parameters comprise a selected magnitude of the first parameter. The selected magnitude of the first parameter is based at least partially on the sensor data.

In some embodiments, a device comprises or consists essentially of a first part and a second part. The first part comprises a first annular portion having a first diameter and a first plurality of splines extending distally from the first annular portion. The second part comprises a second annular portion having a second diameter and a second plurality of splines extending distally and radially outward from the second annular portion. The second diameter is less than the first diameter. The second annular portion is telescopeable in the first annular portion. Each of the first plurality of splines is coupled to one spline of the second plurality of splines. Upon distal longitudinal advancement of the second part relative to the first part, the first part expands from a collapsed state to an expanded state. The first plurality of splines is circumferentially spaced in the expanded state. Upon proximal longitudinal retraction of the second part relative to the first part, the first part collapses from the expanded state to the collapsed state.

A distal end of each of the first plurality of splines may be coupled to one spline of the second plurality of splines.

The distal end of each of the first plurality of splines may be coupled to one spline of the second plurality of splines proximal to a distal end of the one of the second plurality of splines. The distal ends of the second plurality of splines may comprise fixation elements. At least some of the first plurality of splines may comprise electrodes. Each spline of the first plurality of splines may comprise a plurality of electrodes. The plurality of electrodes may at least partially forming an electrode matrix.

The device may further comprise a membrane coupled to the first plurality of splines, the membrane comprising a plurality of electrodes, the plurality of electrodes at least partially forming an electrode matrix. A longitudinal length from a proximal end of a proximal-most electrode of the plurality of electrodes to a distal end of a distal-most electrode the plurality of electrodes may be between 20 mm and 40 mm. A diameter of the first plurality of splines in the expanded state may be between 15 mm and 35 mm.

The device may further comprise a catheter coupled to the first annular portion and an inner member in a lumen of the catheter and coupled to the second annular portion. The inner member may be movable relative to the catheter to distally advance and proximally retract the second part. A proximal end of the first annular portion may be coupled in a distal end of a lumen of the catheter. A proximal end of the second annular portion may be coupled in a distal end of a lumen of the inner member. The inner member may be trackable over a guidewire.

The device may further comprise a gripper coupled to the inner member, a spring engaging the gripper, and a handle element coupled to the inner member. Upon distal advancement of the handle element, the spring may be longitudinally expanded, the inner member may be distally longitudinally advanced, the second part may be distally longitudinally advanced, and the first part may expand from the collapsed state to the expanded state. Upon proximal retraction of the handle element, the spring may be longitudinally compressed, the inner member may be proximally longitudinally retracted, the second part may be proximally longitudinally retracted, and the first part collapses from the expanded state to the collapsed state. The spring may be configured to at least partially proximally retract the handle element.

The device may further comprise a locking mechanism configured to maintain the handle element in a distally advanced state. The locking element may comprise a plurality of arms having an open proximal end. The handle element may be configured to extend through the open proximal end upon distal advancement. The locking element may comprise a plurality of arms having closed proximal end. The handle element may be configured to engage the closed proximal end upon distal advancement. The plurality of arms may comprise leaf springs. The leaf springs may be configured to at least partially proximally retract the handle element.

The first plurality of splines may be not self-expanding. The first plurality of splines may be self-expanding. The first plurality of splines may comprise a non-tapered shape in the expanded state. The first part may comprise a first cut hypotube. The first annular portion may comprise a hypotube and the first plurality of splines may comprise a plurality of wires. The second part may comprise second a cut hypotube.

In some embodiments, a device comprises or consists essentially of a plurality of splines, a structure coupled to at least one spline of the plurality of splines, and an electrode coupled to the structure.

The device may comprise a plurality of electrodes coupled to the structure. The plurality of electrodes may be the electrode. The plurality of electrodes may at least partially form an electrode matrix. The electrode matrix may comprise a 3×4 matrix.

The structure may be coupled to at least two splines of the plurality of splines. The electrode may be circumferentially between two splines of the plurality of splines. The electrode may be circumferentially aligned with a spline of the plurality of splines.

The device may further comprise a second electrode coupled to one of the plurality of splines. The structure may comprise a plurality of flexible strands connected to form a pattern of openings. The structure may comprise a mesh. The structure may comprise a woven or knitted membrane. The structure may comprise shape memory material having an expanded shape when not confined. The structure may comprise insulative material.

In some embodiments, a device comprises or consists essentially of a first sidewall, a second sidewall spaced from the first sidewall, and a third sidewall between the first sidewall and the second sidewall. The first sidewall, the second sidewall, and the third sidewall at least partially define a U-shaped trough. The device further comprises a plurality of conductors in the trough and an electrode electrically connected to one of the plurality of conductors.

The device may comprise a plurality of electrodes including the electrode. The plurality of electrodes may at least partially form an electrode matrix. Each of the plurality of electrodes may be electrically connected to one of the plurality of conductors. The electrode may have a dome shape.

The device may further comprise insulative material between the plurality of conductors and the electrode. The device may further comprise insulative material between the plurality of conductors and the third sidewall. The device may further comprise insulating material extending at least above a bottom of the electrode. The insulating material may comprise a dome shape. The insulating material may comprise a flat upper surface. The insulating material may comprise a crowned surface. The insulating material may cover a sharp edge of the electrode.

The electrode may have no uninsulated sharp edges. The electrode may be configured to be spaced from a vessel wall surface.

In some embodiments, a system comprises a plurality of the devices. The plurality of devices may at least partially form an electrode matrix.

In some embodiments, a device comprises or consists essentially of a catheter comprising a lumen, a fixation structure, and a fixation element. The fixation structure comprises a first side, a second side, and a twist. The fixation element is coupled to the first side of the fixation structure. The first side faces radially inwardly when the fixation structure is inside the lumen of the catheter and faces radially outwardly when the fixation structure is outside the lumen of the catheter.

The lumen may be shaped to correspond to a shape of the fixation structure and the fixation element. The twist may be 180°. The fixation structure may comprise a ribbon. The fixation structure may comprise a strut. The fixation structure may be configured to bend radially outward upon deployment from the catheter. The fixation element may comprise a conical spike.

In some embodiments, a device may comprise or consists essentially of a fixation structure, a fixation mechanism, and an attachment point coupling the fixation structure to the fixation mechanism. The fixation mechanism is configured to turn radially outward upon expansion of the fixation structure. The fixation mechanism is configured to turn radially inward upon collapse of the fixation structure. In an expanded state, the fixation mechanism extends radially outward of the fixation structure.

The fixation mechanism may comprise an aperture. The device may further comprise a radiopaque marker coupled to the fixation mechanism.

The device may further comprise a tether extending proximally from the attachment point. Tether may comprise a bend along a longitudinal length of the fixation mechanism. The bend may be between 30% and 70% of the longitudinal length of the fixation mechanism. The tether may comprise a ramped portion having a wide edge coupled to the attachment point. The tether may comprise a twist proximal to the attachment point.

The device may further comprise a second fixation mechanism extending distally from the fixation structure. The fixation structure, the fixation element, and the attachment point may be monolithically cut from a same hypotube. The fixation structure may comprise an electrode. The fixation structure may comprise a plurality of electrodes including the electrode. The plurality of electrodes may at least partially form an electrode matrix.

In some embodiments, a method of forming a device comprises or consists essentially of cutting a hypotube to form a fixation structure, a fixation mechanism, and an attachment point coupling the fixation structure and the fixation mechanism, and shape setting an expanded shape. The expanded shape includes the fixation mechanism bent radially outward of the fixation structure. After shape setting the expanded shape, the fixation mechanism is configured to turn radially outward upon expansion of the fixation structure and the fixation mechanism is configured to turn radially inward upon collapse of the fixation structure.

Cutting the hypotube may comprise laser cutting the hypotube. Cutting the hypotube may comprise forming a tether extending proximally from the attachment point. Shape setting may comprise bending the tether along a longitudinal length of the fixation mechanism. Bending the tether may be between 30% and 70% of the longitudinal length of the fixation mechanism. Shape setting may comprise bending the tether at a proximal end of the attachment point. Shape setting may comprise forming a twist in the tether proximal to the attachment point.

In some embodiments, a device comprises or consists essentially of a fixation structure, a fixation arm, and a fixation mechanism coupled to the fixation arm. The fixation structure comprises an aperture, a first surface, and a second surface opposite the first surface. The fixation arm is coupled to an inside of the aperture of the fixation structure. The fixation arm does not protrude above the first surface in a first state.

The fixation arm may be configured to flex radially outward when not confined by a catheter. The fixation mechanism may protrude above the first surface when the fixation arm is not confined by the catheter. The fixation arm may be configured to remain stationary when not confined by a catheter. The fixation mechanism may not protrude above the first surface when the fixation arm may be not confined by the catheter.

The fixation structure and the fixation arm may be formed from a same piece of material. The aperture may extend from the first surface to the second surface. The aperture may extends from the first surface to a point above the second surface. The fixation mechanism may comprise a conical spike. The fixation mechanism may comprise a textured surface.

In some embodiments, a device comprises or consists essentially of a catheter comprising a lumen, a first loop longitudinally movable from in the lumen of the catheter to out of the lumen of the catheter, and a second loop longitudinally movable from in the lumen of the catheter to out of the lumen of the catheter. At least one of the catheter, the first loop, and the second loop comprises a first electrode. At least one of the first loop and the second loop may be a pigtail at an end of a finger.

The first loop may comprise a first plurality of electrodes including the first electrode. The first plurality of electrodes may at least partially form a first electrode matrix. The second loop may comprise a second plurality of electrodes. The second plurality of electrodes may at least partially form a second electrode matrix. The second loop may comprise a second electrode.

The first loop may comprise a first portion comprising electrodes of the first plurality of electrodes and a second portion comprising electrodes of the first plurality of electrodes. The second portion may be spaced from the first portion. The second portion may be parallel to the first portion.

The first loop may comprise an undulating segment comprising peaks and troughs. The undulating segment may comprise the first plurality of electrodes. The undulating segment may comprise electrodes of the first plurality of electrodes proximate to the peaks and electrodes of the first plurality of electrodes proximate to the troughs.

The catheter may comprise a plurality of electrodes including the first electrode. The first plurality of electrodes may at least partially form a first electrode matrix.

The first loop and the second loop may be configured to be deployed from the lumen of the catheter at least partially simultaneously. The first loop and the second loop may be configured to be deployed from the lumen of the catheter sequentially.

The device may further comprise a fixation feature extending radially outward from the catheter. The fixation feature may comprise an atraumatic stiff loop.

In some embodiments, a method of using the device may comprise or consist essentially of advancing the catheter distal to a pulmonary valve, advancing the catheter distal to the pulmonary valve, deploying the first loop and the second loop, and after deploying the first loop and the second loop, distally advancing the catheter towards a pulmonary artery bifurcation. The first loop and the second loop are self-orienting so that one of the first loop and the second loop extends into the right pulmonary artery and the other of the first loop and the second loop extends into the left pulmonary artery.

The method may further comprise distally advancing the catheter until advancement may be limited by the pulmonary artery bifurcation. The method may further comprise extending a fixation feature proximate to the pulmonary valve. The method may further comprise attempting to capture a target nerve with the first electrode.

The method may further comprise, if the target nerve may be not captured, withdrawing the first loop and the second loop into the lumen of the catheter, proximally retracting the catheter, rotating the catheter, after rotating the catheter, redeploying the first loop and the second loop, and, after redeploying the first loop and the second loop, distally advancing the catheter towards the pulmonary artery bifurcation. The first loop and the second loop are self-orienting so that one of the first loop and the second loop extends into the right pulmonary artery and the other of the first loop and the second loop extends into the left pulmonary artery in an opposite orientation. The method may further comprise, if the target nerve may be not captured, attempting to capture a target nerve with a second electrode.

In some embodiments, a device comprises, or alternatively consists essentially of, a catheter comprising a lumen and a loop longitudinally movable from in the lumen of the catheter to out of the lumen of the catheter. At least one of the catheter and the loop comprises a first electrode.

The loop may comprise a first plurality of electrodes including the first electrode. The first plurality of electrodes may at least partially form a first electrode matrix.

The loop may comprise a first portion comprising electrodes of the first plurality of electrodes and a second portion comprising electrodes of the first plurality of electrodes. The second portion may be spaced from the first portion. The second portion may be parallel to the first portion.

The loop may comprise an undulating segment comprising peaks and troughs. The undulating segment may comprise the first plurality of electrodes. The undulating segment may comprise electrodes of the first plurality of electrodes proximate to the peaks and electrodes of the first plurality of electrodes proximate to the troughs.

The catheter may comprise a first plurality of electrodes including the first electrode. The first plurality of electrodes may at least partially form a first electrode matrix.

The loop may be configured to be deployed from the lumen of the catheter out of a distal end of the catheter. The loop may be configured to be deployed from the lumen of the catheter out of a side of the catheter.

The device may further comprise a fixation feature extending radially outward from the catheter. The fixation feature may comprise an atraumatic stiff loop.

The loop may be a pigtail at an end of a finger.

A method of using the device may comprise deploying the loop out of the lumen of the catheter; after deploying the loop, advancing the catheter in a first branch vessel towards a primary vessel; allowing the loop to radially expand at a bifurcation comprising the first branch vessel, the primary vessel, and a second branch vessel; and after allowing the loop to radially expand, proximally retracting the catheter until the loop contacts the second branch vessel.

The first branch vessel may comprise the left internal jugular vein, the primary vessel may comprise the left brachiocephalic vein, and the second branch vessel may comprise the left subclavian vein.

The method may further comprise extending a fixation feature.

The method may further comprise attempting to capture a target nerve with the first electrode. The target nerve may comprise a thoracic cardiac branch nerve. The target nerve may comprise a cervical cardiac nerve.

The catheter may comprise a curvature configured to bend towards the target nerve.

In some embodiments, a device comprises or consists essentially of a catheter comprising a lumen, a first sinusoidal wire, a second sinusoidal wire radially spaced from the first sinusoidal wire, and a plurality of electrodes.

Each of the plurality of electrodes may be coupled to at least one the first sinusoidal wire and the second sinusoidal wire.

The device may further comprise a membrane coupled to the first sinusoidal wire and the second sinusoidal wire. Each of the plurality of electrodes may be coupled to the membrane. The membrane may be configured to have a curved shape in an expanded state. The membrane may comprise a flex circuit including conductor wires.

The plurality of electrodes may comprise button electrodes. The plurality of electrodes may comprise barrel electrodes. The plurality of electrodes may comprise cylindrical electrodes. The plurality of electrodes may comprise directional electrodes. Centers the plurality of electrodes may be longitudinally offset.

The catheter may comprise a first segment and a second segment distal to the first segment. The first segment may have a circular cross-section. The second segment may have an oval cross-section. The second segment may be configured to contain the first sinusoidal wire and the second sinusoidal wire.

The first sinusoidal wire and the second sinusoidal wire may be planar in an expanded state. The first sinusoidal wire and the second sinusoidal wire may be at an angle in an expanded state. The first sinusoidal wire and the second sinusoidal wire may comprise shape memory material.

In some embodiments, a device comprises, or alternatively consists essentially of, a handle, a sheath, and an electrode system moveable in and out of the sheath. The handle comprises a repositioning system. The repositioning system comprises a track and a knob slideable within the track. The electrode system is configured to move longitudinally upon longitudinal movement of the knob in the track and to move rotationally upon transverse or rotational movement of the knob in the track.

The track may comprise a longitudinal segment, a first transverse segment extending from the longitudinal segment in a first direction, and a second transverse segment extending from the longitudinal segment in a second direction opposite the first direction. The first transverse segment may be longitudinally offset from the second transverse segment. The first transverse segment may be longitudinally aligned with the second transverse segment.

The electrode system may be configured to move a longitudinal distance upon movement of the knob the same longitudinal distance in the track. The electrode system may be configured to rotate a circumferential angle upon transverse or rotational movement of the knob in the track. The device may further comprise a rotational stop to limit rotation of the electrode system to the circumferential angle.

The device may further comprise a detent and a groove configured to interact with the detent upon movement of the knob. The detent may be configured to produce audible indicia.

The device may further comprise a physical barrier configured to inhibit accidental movement of the knob.

In some embodiments, a device comprises, or alternatively consists essentially of, an expandable structure having a collapsed state and an expanded state. The expandable structure comprises, in the expanded state, a plurality of splines each comprising a proximal segment comprising a first portion, a second portion distal to the first portion, and a third portion distal to the second portion; an intermediate segment distal to the proximal segment; and a distal segment distal to the intermediate segment, the distal segment comprising a fourth portion, a fifth portion distal to the fourth portion, and a sixth portion distal to the fifth portion. The first portion is parallel to a longitudinal axis. The second portion extends radially outward from the first portion. The third portion extends radially outward from the second portion and transverse to the longitudinal axis to the intermediate segment. The fourth portion extends from the intermediate segment radially inward and transverse to the longitudinal axis. The fifth portion extends radially inward from the fourth portion. The sixth portion extends from the fifth portion parallel to a longitudinal axis. At least two of the intermediate segments of the plurality of splines are circumferentially spaced and comprise a plurality of electrodes forming an electrode matrix.

The expandable structure may be self-expanding. The expandable structure may be expandable upon operation of an actuation mechanism.

In the expanded state, the at least two intermediate segments may be parallel to the longitudinal axis. In the expanded state, the at least two intermediate segments may be recessed relative to the longitudinal axis. In the expanded state, the at least two intermediate segments may be crowned relative to the longitudinal axis.

Pairs of the first portions of the plurality of splines may be parallel. Pairs of the sixth portions of the plurality of splines may be parallel. Pairs of the first portions of the plurality of splines may be twisted. Pairs of the sixth portions of the plurality of splines may be twisted.

Proximal ends of the intermediate segments of the plurality of splines may be longitudinally aligned. Proximal ends of the intermediate segments of the plurality of splines may be longitudinally offset. Distal ends of the intermediate segments of the plurality of splines may be longitudinally aligned. Distal ends of the intermediate segments of the plurality of splines may be longitudinally offset.

The plurality of splines may further comprise a spline circumferentially between the at least two intermediate segments.

The plurality of splines may comprise a plurality of wires. The plurality of splines may be formed from a cut hypotube.

The expandable structure may further comprise a membrane coupled to the at least two intermediate segments. The membrane may comprise the electrode matrix.

The device may further comprise a proximal portion and a catheter shaft coupled to the proximal portion and coupled to the expandable structure. The device may further comprise an actuator wire. The proximal portion may comprise an actuator mechanism. The actuator wire may be coupled to the actuator mechanism and coupled to the expandable structure. The expandable structure may be configured to expand upon operation of the actuator mechanism. The proximal portion may comprise a Y-connector comprising a first branch configured to accept a guidewire and a second branch configured to electrically connect the electrode matrix to a stimulation system.

The device may further comprise a strain relief between the catheter shaft and the expandable structure. The strain relief may comprise a spring. The strain relief may comprise a cut hypotube. The cut hypotube may comprise a plurality of helices having the same sense.

The expandable structure may comprise a distal hub comprising a plurality of channels. The distal segments of the plurality of splines may be slideable in the channels of the distal hub. The distal segments may comprise a distal end having a dimension larger than a dimension of the channels.

In some embodiments, a device comprises, or alternatively consists essentially of, an expandable structure having a collapsed state and an expanded state. The expandable structure comprises, in the expanded state, a plurality of arms each comprising a proximal segment, an intermediate segment distal to the proximal segment, and a distal segment distal to the intermediate segment. The intermediate segments of the plurality of arms include an opening. At least two the intermediate segments of the plurality of splines comprise a plurality of electrodes forming an electrode matrix.

The expandable structure may be self-expanding. The expandable structure may be expandable upon operation of an actuation mechanism.

In the expanded state, the at least two intermediate segments may be parallel to the longitudinal axis. In the expanded state, the at least two intermediate segments may be recessed relative to the longitudinal axis. In the expanded state, the at least two intermediate segments may be crowned relative to the longitudinal axis.

Pairs of the first portions of the plurality of splines may be parallel. Pairs of the sixth portions of the plurality of splines may be parallel. Pairs of the first portions of the plurality of splines may be twisted. Pairs of the sixth portions of the plurality of splines may be twisted.

Proximal ends of the intermediate segments of the plurality of splines may be longitudinally aligned. Proximal ends of the intermediate segments of the plurality of splines may be longitudinally offset. Distal ends of the intermediate segments of the plurality of splines may be longitudinally aligned. Distal ends of the intermediate segments of the plurality of splines may be longitudinally offset.

The plurality of splines may further comprise a spline circumferentially between the at least two intermediate segments.

The plurality of splines may comprise a plurality of wires. The plurality of splines may be formed from a cut hypotube.

The expandable structure may further comprise a membrane coupled to the at least two intermediate segments. The membrane may comprise the electrode matrix.

The device may further comprise a proximal portion and a catheter shaft coupled to the proximal portion and coupled to the expandable structure. The device may further comprise an actuator wire. The proximal portion may comprise an actuator mechanism. The actuator wire may be coupled to the actuator mechanism and coupled to the expandable structure. The expandable structure may be configured to expand upon operation of the actuator mechanism. The proximal portion may comprise a Y-connector comprising a first branch configured to accept a guidewire and a second branch configured to electrically connect the electrode matrix to a stimulation system.

The device may further comprise a strain relief between the catheter shaft and the expandable structure. The strain relief may comprise a spring. The strain relief may comprise a cut hypotube. The cut hypotube may comprise a plurality of helices having the same sense.

The expandable structure may comprise a distal hub comprising a plurality of channels. The distal segments of the plurality of splines may be slideable in the channels of the distal hub. The distal segments may comprise a distal end having a dimension larger than a dimension of the channels.

In some embodiments, a device comprises, or alternatively consists essentially of, an expandable structure having a collapsed state and an expanded state. The expandable structure comprises, in the expanded state, a plurality of splines each comprising a proximal segment comprising a first portion, a second portion distal to the first portion, and a third portion distal to the second portion; an intermediate segment distal to the proximal segment; and a distal segment distal to the intermediate segment, the distal segment comprising a fourth portion, a fifth portion distal to the fourth portion, and a sixth portion distal to the fifth portion. The first portion is parallel to a longitudinal axis. The second portion extends radially outward from the first portion. The third portion extends radially outward from the second portion and transverse to the longitudinal axis to the intermediate segment. The fourth portion extends from the intermediate segment radially inward and transverse to the longitudinal axis. The fifth portion extends radially inward from the fourth portion. The sixth portion extends from the fifth portion parallel to a longitudinal axis. The intermediate segments of the plurality of splines have an undulating shape relative to the longitudinal axis. At least two of the intermediate segments of the plurality of splines comprise a plurality of electrodes forming an electrode matrix.

The expandable structure may be self-expanding. The expandable structure may be expandable upon operation of an actuation mechanism.

Pairs of the first portions of the plurality of splines may be parallel. Pairs of the sixth portions of the plurality of splines may be parallel. Pairs of the first portions of the plurality of splines may be twisted. Pairs of the sixth portions of the plurality of splines may be twisted.

Proximal ends of the intermediate segments of the plurality of splines may be longitudinally aligned. Proximal ends of the intermediate segments of the plurality of splines may be longitudinally offset. Distal ends of the intermediate segments of the plurality of splines may be longitudinally aligned. Distal ends of the intermediate segments of the plurality of splines may be longitudinally offset.

The intermediate segments may comprise peaks and troughs. Peaks and troughs of the at least two intermediate segments may be longitudinally aligned. Peaks and troughs of the at least two intermediate segments may be longitudinally offset.

The plurality of splines may comprise a plurality of wires. The plurality of splines may be formed from a cut hypotube.

The expandable structure may further comprise a membrane coupled to the at least two intermediate segments. The membrane may comprise the electrode matrix.

The device may further comprise a proximal portion and a catheter shaft coupled to the proximal portion and coupled to the expandable structure. The device may further comprise an actuator wire. The proximal portion may comprise an actuator mechanism. The actuator wire may be coupled to the actuator mechanism and coupled to the expandable structure. The expandable structure may be configured to expand upon operation of the actuator mechanism. The proximal portion may comprise a Y-connector comprising a first branch configured to accept a guidewire and a second branch configured to electrically connect the electrode matrix to a stimulation system.

The device may further comprise a strain relief between the catheter shaft and the expandable structure. The strain relief may comprise a spring. The strain relief may comprise a cut hypotube. The cut hypotube may comprise a plurality of helices having the same sense.

The expandable structure may comprise a distal hub comprising a plurality of channels. The distal segments of the plurality of splines may be slideable in the channels of the distal hub. The distal segments may comprise a distal end having a dimension larger than a dimension of the channels.

In some embodiments, a device comprises, or alternatively consists essentially of, an expandable structure having a collapsed state and an expanded state. The expandable structure comprises, in the expanded state, a plurality of arms each comprising a proximal segment, an intermediate segment distal to the proximal segment, and a distal segment distal to the intermediate segment. The intermediate segments of the plurality of arms include a sinusoidal shape. At least two the intermediate segments of the plurality of splines comprise a plurality of electrodes forming an electrode matrix.

The expandable structure may be self-expanding. The expandable structure may be expandable upon operation of an actuation mechanism.

Pairs of the first portions of the plurality of splines may be parallel. Pairs of the sixth portions of the plurality of splines may be parallel. Pairs of the first portions of the plurality of splines may be twisted. Pairs of the sixth portions of the plurality of splines may be twisted.

Proximal ends of the intermediate segments of the plurality of splines may be longitudinally aligned. Proximal ends of the intermediate segments of the plurality of splines may be longitudinally offset. Distal ends of the intermediate segments of the plurality of splines may be longitudinally aligned. Distal ends of the intermediate segments of the plurality of splines may be longitudinally offset.

The intermediate segments may comprise peaks and troughs. Peaks and troughs of the at least two intermediate segments may be longitudinally aligned. Peaks and troughs of the at least two intermediate segments may be longitudinally offset.

The plurality of splines may comprise a plurality of wires. The plurality of splines may be formed from a cut hypotube.

The expandable structure may further comprise a membrane coupled to the at least two intermediate segments. The membrane may comprise the electrode matrix.

The device may further comprise a proximal portion and a catheter shaft coupled to the proximal portion and coupled to the expandable structure. The device may further comprise an actuator wire. The proximal portion may comprise an actuator mechanism. The actuator wire may be coupled to the actuator mechanism and coupled to the expandable structure. The expandable structure may be configured to expand upon operation of the actuator mechanism. The proximal portion may comprise a Y-connector comprising a first branch configured to accept a guidewire and a second branch configured to electrically connect the electrode matrix to a stimulation system.

The device may further comprise a strain relief between the catheter shaft and the expandable structure. The strain relief may comprise a spring. The strain relief may comprise a cut hypotube. The cut hypotube may comprise a plurality of helices having the same sense.

The expandable structure may comprise a distal hub comprising a plurality of channels. The distal segments of the plurality of splines may be slideable in the channels of the distal hub. The distal segments may comprise a distal end having a dimension larger than a dimension of the channels.

In some embodiments, a device comprises, or alternatively consists essentially of, a longitudinal axis and a distal portion. The distal portion comprises a first expandable structure and a second expandable structure distal to the first expandable structure. The first expandable structure has a collapsed state and an expanded state. The expandable structure comprises, in the expanded state, a plurality of arms each comprising a proximal segment, an intermediate segment distal to the proximal segment, and a distal segment distal to the intermediate segment. The plurality of arms is on a first side of a plane comprising the longitudinal axis. At least two the intermediate segments of the plurality of splines comprise a plurality of electrodes forming an electrode matrix; and The second expandable structure may comprise a Swan-Ganz balloon. The second expandable structure may be distal to the first expandable structure by between 0.25 cm and 5 cm.

The first expandable structure may be self-expanding. The first expandable structure may be expandable upon operation of an actuation mechanism.

The plurality of splines may comprise a plurality of wires. The plurality of splines may be formed from a cut hypotube.

The first expandable structure may further comprise a membrane coupled to the at least two intermediate segments. The membrane may comprise the electrode matrix.

The device may further comprise a proximal portion and a catheter shaft coupled to the proximal portion and coupled to the expandable structure. The catheter shaft may be configured to appose a wall of a body cavity. The device may further comprise an actuator wire. The proximal portion may comprise an actuator mechanism. The actuator wire may be coupled to the actuator mechanism and coupled to the first expandable structure. The first expandable structure may be configured to expand upon operation of the actuator mechanism. The proximal portion may comprise a Y-connector comprising a first branch configured to accept a guidewire and a second branch configured to electrically connect the electrode matrix to a stimulation system.

The first expandable structure may comprise a distal hub comprising a plurality of channels. Distal segments of the plurality of splines may be slideable in the channels of the distal hub. The distal segments may comprise a distal end having a dimension larger than a dimension of the channels.

The device may further comprise a tubular member extending from the proximal portion to the second expandable structure. The tubular member may comprise a lumen configured to inflate the second expandable structure upon injection of fluid into the lumen. The tubular member may be coupled to the distal segments of the plurality of arms. The first expandable structure may expand upon proximal retraction of the tubular member.

In some embodiments, a method of processing an electrocardiogram signal comprising P waves and S waves comprises, or alternatively consist essentially of, detecting an end of a first S wave, estimating a start of a first P wave, and during a stimulation duration between detecting the end of the first S wave and the estimated start of the first P wave, providing an artificial signal. A non-transitory computer-readable medium may store executable instructions that when executed perform the method.

The artificial signal may comprise a straight line. The straight line may be at a negative value. The straight line may be at a positive value.

In some embodiments, an electrocardiogram signal comprises, or alternatively consist essentially of, a first portion indicative of an electrical activity of a heart during a first duration and a second portion not indicative of the electrical activity of the heart during a second duration after the first duration. The first duration is less than a sinus rhythm. A non-transitory computer-readable medium may be configured to store the signal.

The first portion may comprise a QRS complex. The first portion may comprise a PR interval. The second portion may comprise a ST segment. The second portion may comprise a straight line. The straight line may be at a negative value. The straight line may be at a positive value.

In some embodiments, a method of processing an electrocardiogram signal comprises, or alternatively consist essentially of, detecting a first condition of a first type of wave selected from the group consisting of P waves, Q waves, R waves, S waves, and T waves; after a stimulation duration starting after detecting the first condition of the first type of wave, monitoring for a monitoring duration for second condition of a second type of wave selected from the group consisting of P waves, Q waves, R waves, S waves, and T waves, the second type of wave different than the first type of wave; and if the second condition of the second type of wave may be not detected during the monitoring duration, triggering a physical event. A non-transitory computer-readable medium may store executable instructions that when executed perform the method.

The first condition may comprise a beginning of the first type of wave. The first condition may comprise an end of the first type of wave. The first condition may comprise a peak of the first type of wave. The second condition may comprise a beginning of the second type of wave. The second condition may comprise an end of the second type of wave. The second condition may comprise a peak of the second type of wave. The second condition may comprise a peak of the second type of wave. The first type of wave may comprise a S wave. The second type of wave may comprise a P wave. The second type of wave may comprise a Q wave. The second type of wave may comprise a R wave. The physical event may comprise terminating stimulation. The physical event may comprise sounding an alarm.

In some embodiments, a method of processing an electrocardiogram signal comprises, or alternatively consist essentially of, providing a first portion indicative of electrical activity of a heart during a first duration, the first portion comprising a real P wave, a real Q wave, a real R wave, a real S wave, and a real T wave; and providing a second portion not indicative of the electrical activity of the heart during a second duration after the first duration, stimulation of the heart occurring during the second duration. A non-transitory computer-readable medium may store executable instructions that when executed perform the method.

The portion may comprise a straight line. The straight line may be at zero. The straight line may be at a negative value. The straight line may be at a positive value.

The second portion may comprise a duplication of the first portion.

The second portion may comprise at least a portion of an artificial sinus rhythm. The portion of the artificial sinus rhythm may comprise at least one of an artificial P wave, an artificial Q wave, an artificial R wave, an artificial S wave, and an artificial T wave. The at least one of an artificial P wave, an artificial Q wave, an artificial R wave, an artificial S wave, and an artificial T wave may be shaped like a real wave. The at least one of an artificial P wave, an artificial Q wave, an artificial R wave, an artificial S wave, and an artificial T wave may be shaped like a square wave.

In some embodiments, an electrocardiogram signal comprises, or alternatively consist essentially of, a first portion indicative of electrical activity of a heart during a first duration and a second portion not indicative of the electrical activity of the heart during a second duration after the first duration. The first portion comprises a real P wave, a real Q wave, a real R wave, a real S wave, and a real T wave. Stimulation of the heart occurs during the second duration. A non-transitory computer-readable medium may be configured to store the signal.

The second portion may comprise a straight line. The straight line may be at zero. The straight line may be at a negative value. The straight line may be at a positive value.

The second portion may comprise a duplication of the first portion.

The second portion may comprise at least a portion of an artificial sinus rhythm.

The portion of the artificial sinus rhythm may comprise at least one of an artificial P wave, an artificial Q wave, an artificial R wave, an artificial S wave, and an artificial T wave. The at least one of an artificial P wave, an artificial Q wave, an artificial R wave, an artificial S wave, and an artificial T wave may be shaped like a real wave. The at least one of an artificial P wave, an artificial Q wave, an artificial R wave, an artificial S wave, and an artificial T wave may be shaped like a square wave.

In some embodiments, a device comprises, or alternatively consists essentially of, a handle, an expandable structure, an outer tube, and a shaft. The expandable structure has a collapsed state and a self-expanded state. The expandable structure comprises a plurality of splines extending from a proximal hub to a distal hub. Each of the splines of the plurality of splines comprises a proximal segment, an intermediate segment distal to the proximal segment, a distal segment distal to the intermediate segment, and a first electrode on a first spline of the plurality of splines. The intermediate segment is configured to extend radially outward in the self-expanded state. The outer tube comprises a proximal end coupled to the handle and a distal end coupled to the proximal hub. The shaft comprises a proximal end and a distal end. The shaft extends through the outer tube from the handle to the distal hub. The handle is configured to retract the shaft. The intermediate segments are configured to extend further radially outward upon retraction of the shaft.

At least one spline of the plurality of splines may be devoid of electrodes. The intermediate segment of each spline of the plurality of splines may form a first angle with the proximal segment and/or a second angle with the distal segment. The proximal segment and distal segment of each spline of the plurality of splines may be devoid of electrodes. The first spline may comprise a first plurality of electrodes including the first electrode. The first plurality of electrodes may form an electrode array. The device may further comprise a second electrode on a second spline of the plurality of splines. The first spline may comprise a first plurality of electrodes including the first electrode. The second spline may comprise a second plurality of electrodes including the second electrode. The first plurality of electrodes may comprise five electrodes. The second plurality of electrodes may comprise five electrodes. The first plurality of electrodes and the second plurality of electrodes form an electrode array. The second spline may be circumferentially adjacent to the first spline. The first spline and the second spline may form a first spline pair. The device may further comprise a second spline pair. The second spline pair may comprise a third spline comprising a third plurality of electrodes and a fourth spline comprising a fourth plurality of electrodes. The fourth spline may be circumferentially adjacent to the third spline. The second spline pair may be circumferentially adjacent to the first spline pair. The first plurality of electrodes, the second plurality of electrodes, the third plurality of electrodes, and the fourth plurality of electrodes may form an electrode array. The electrode array may comprise a 4×5 array. At least four circumferentially adjacent splines of the plurality of splines may each comprise a plurality of electrodes. At least one spline of the plurality of splines may be devoid of electrodes. The proximal segment and distal segment of each spline may be straight. The intermediate segment of each spline may be concave. The proximal segment and distal segment of each spline may be straight. The intermediate segment of each spline may be convex. The proximal segment and distal segment of each spline may be straight. The intermediate segment of each spline may be straight. Each spline of the plurality of splines further may comprise a proximal transition segment joining the proximal segment and the intermediate segment and a distal transition segment joining the intermediate segment and the distal segment. The splines may be grouped into circumferentially adjacent spline pairs. Each spline of a spline may be parallel to the other spline of the spline pair along the proximal segment, the intermediate segment, and the distal segment. Each spline of the spline pair may be not parallel to the other spline of the spline pair along the proximal transition segment and the distal transition segment. The intermediate segments of each spline pair may be spaced further apart from each other than the proximal segments and the distal segments. The expandable structure may comprise a longitudinal axis between the proximal hub and the distal hub. The proximal segments of each of the splines of the plurality of splines may radially diverge away from the longitudinal axis and the distal segments of each of the splines of the plurality of splines may radially converge towards the longitudinal axis.

The outer tube may comprise a proximal portion and a distal portion. The proximal portion may have a higher durometer than the distal portion. The outer tube may comprise a plurality of longitudinal portions along a length of the outer tube. Each longitudinal portion the plurality of longitudinal portions may have a higher durometer than the longitudinal portions of the plurality of longitudinal portions distal thereto. At least one longitudinal portion of the plurality of longitudinal portions may be configured with a length and durometer for positioning the at least one longitudinal portion in a specific anatomy. The specific anatomy may comprise a chamber of a heart. The specific anatomy may comprise a blood vessel. The blood vessel may comprise the right pulmonary artery. The outer tube may comprise a first outer diameter at the proximal end of the outer tube and a second outer diameter at the distal end of the outer tube. The first outer diameter may be greater than the second outer diameter. A proximal portion of the outer tube may comprise a first plurality of layers, wherein a distal portion of the outer tube may comprise a second plurality of layers. The first plurality of layers may comprise more layers than the second plurality of layers. The outer tube may comprise a hinge joined to the proximal hub. The hinge may be configured to resist kinking upon bending of the device transverse to a longitudinal axis of the outer tube. The hinge may comprise a coil comprising a proximal end and a distal end, the proximal end of the coil surrounding a portion of the tubing and the distal end of the coil surrounding a portion of the proximal hub. The hinge may comprise a first wire comprising a helical winding, a second wire comprising a helical winding and occupying spaces between helices of the first wire, and a third wire comprising a helical winding and occupying spaces between helices the first wire and between helices of the second wire. The outer tube may comprise tubing. The tubing may comprise an inner diameter configured to mate with an outer diameter of the proximal hub. The tubing may be configured to abut a proximal end of the proximal hub. The tubing may form a fluid seal between the outer tube and the proximal hub.

The spline comprising the electrode may comprise a spline tube, the electrode being on an outer surface of the spline tube. The device may further comprise a spline tube at least partially covering two circumferentially adjacent splines of the plurality of splines. The spline tube may be configured to inhibit the two circumferentially adjacent splines from rotating relative to one another. The spline tube may diverge into two spatially separated tubular channels along the intermediate segments of the two circumferentially adjacent splines. Circumferentially adjacent splines of the plurality of splines may be grouped into spline pairs, each of the spline pairs comprising a proximal tubing at least partially covering the proximal segments and a distal tubing at least partially covering the distal segments. The proximal tubings and the distal tubings may be configured to inhibit the splines of each of the spline pairs from rotating relative to one another. Each of the proximal tubings and the distal tubings may comprise heat-shrink tubing. Circumferentially adjacent splines of the plurality of splines may be grouped into spline pairs, each of the spline pairs comprising a wire bent at a proximal end, and may have wire ends terminating at a distal end.

The proximal hub may comprise a proximal end, a distal end, a central lumen, a plurality of peripheral lumens, and/or a plurality of spline channels. The central lumen may extend from the proximal end of the proximal hub to the distal end of the proximal hub. The shaft may slidably extend through the central lumen of the proximal hub. The plurality of peripheral lumens may be radially outward of the central lumen of the proximal hub. The plurality of peripheral lumens may be configured to transfer fluid flowing through the outer tube to the distal end of the proximal hub. The plurality of spline channels may extend proximally from the distal end of the proximal hub into a distal portion of the proximal hub. One spline of the plurality of splines may be in each spline channel of the plurality of spline channels of the proximal hub. The plurality of spline channels may extend through the distal portion of the proximal hub. Circumferentially adjacent splines of the plurality of splines may be grouped into spline pairs, each of the spline pairs comprising a wire bent at a proximal end. The proximal hub may comprise a plurality of recesses proximal to the distal portion of the proximal hub. The bent proximal ends of the wire of each of the spline pairs may be in a recess of the plurality of recesses. The plurality of recesses may be configured to inhibit movement of the plurality of splines proximal to the recesses. At least one peripheral lumen of the plurality of peripheral lumens may be configured to receive an electrical conductor extending from the handle to the electrode.

The distal hub may comprise a proximal end, a distal end, a central lumen, and/or a plurality of spline channels. The central lumen may extend from the proximal end of the distal hub to the distal end of the distal hub. The shaft may be fixably coupled to the central lumen of the distal hub. A plurality of spline channels may extend distally from the proximal end of the distal hub into the distal hub. One spline of the plurality of splines may be in each spline channel of the plurality of spline channels of the distal hub. Each spline channel of the plurality of spline channels of the distal hub may terminate proximal to the distal end of the distal hub. The proximal end of the distal hub may comprise a tapered surface. The tapered surface of the proximal end of the distal hub may comprise openings to the plurality of spline channels. The tapered surface proximal end of the distal hub may be configured to facilitate bending of the splines in a radially outward direction. The distal end of the distal hub may comprise an atraumatic configuration.

The handle may comprise a handle base and an actuator. The handle base may comprise a proximal end, a distal end, and a lumen extending from the proximal end to the distal end. A proximal end of the outer tube may be coupled to the lumen of the handle base, the shaft slidably extending through the lumen of the handle base. An actuator may be affixed to a proximal end of the shaft, the actuator moveable relative to the handle base in a proximal direction and in a distal direction. The actuator may be configured to expand the expandable structure when moved in a distal direction and to compress the expandable structure when moved in a proximal direction. The handle further may comprise an outer handle, a securing member, and/or a locking member. The outer handle may extend from the handle base. The securing member may comprise a proximal end affixed to the actuator. The locking member may be positioned along the securing member between the outer handle and the actuator. The locking member may be configured to be moved along the longitudinal axis of the securing member and secured at a position along a length of the securing member to inhibit movement of the actuator in a distal direction. The securing member may comprise a threaded shaft and the locking member may comprise a threaded channel. The locking member may be longitudinally moveable along the securing member by rotating the locking member around the threaded shaft.

The handle may comprise a locking member having a locked configuration and an unlocked configuration. The locking member may comprise a main body comprising a proximal end and a distal end, a channel extending from the proximal end to the distal end, and a protrusion extending into the channel of the locking member. The actuator may extend through the channel of the locking member. The protrusion may be configured to inhibit the actuator from moving in at least one of a proximal direction and a distal direction relative to the handle base when the locking member is in the locked configuration. The actuator may be moveable in the proximal direction and in the distal direction when the locking member is in the unlocked configuration. The actuator may comprise an elongate body and a textured surface along a length of the elongate body. The locking member may be moveable between the locked configuration and the unlocked configuration by rotating the locking member around the elongate body of the actuator. The protrusion may be configured to interface with the textured surface in a locked position and configured to not interface with the textured surface in the unlocked position. The locking member may further comprise a tab extending away from the main body, the tab being positionable in a first position relative to the handle base when the locking member is in a locked configuration and being positionable in a second position when the locking member is in an unlocked configuration. The textured surface may comprise a series of ridges, the protrusion of the locking member configured to mate with a notch between the ridges. The channel of the locking member may be oblong. The locking member may be configured to switch between a locked configuration and an unlocked configuration by rotating the locking member approximately a quarter turn. The handle base may further comprise an aperture in a sidewall extending into the lumen of the handle base and proximal to the proximal end of the outer tube. An electrical conductor may extend from an electrical socket into the outer tube through the aperture of the handle base.

The shaft may comprise a lumen. The lumen of the shaft may be configured to receive a guidewire. A proximal end of the shaft may be configured to receive fluid. The proximal end of the shaft may be joined to a fluid valve. The shaft may comprise a sidewall and an aperture in the sidewall, the aperture configured to permit fluid to flow out of the lumen of the shaft and to the proximal hub. The device may be configured to transfer fluid injected into the shaft through the shaft to the distal hub and through the outer tube to the proximal hub. The shaft may comprise a plurality of hypotubes. The plurality of hypotubes may comprise a first hypotube having a proximal end and a distal end and a second hypotube having a proximal end and a distal end. The distal end of the first hypotube may be in the proximal end of the second hypotube. The proximal end of the second hypotube may be in the distal end of the first hypotube. The plurality of hypotubes may include three hypotubes. At least one hypotube of the plurality of hypotubes may comprise a proximal portion having a first outer diameter and a distal portion having a second outer diameter less than the first outer diameter. At least one hypotube of the plurality of hypotubes may comprise a sidewall and an aperture through the sidewall.

In some embodiments, a method of modulating a nerve comprises, or alternatively consists essentially of, inserting a distal portion of a device comprising an expandable structure into vasculature, allowing the expandable member to self-expand, actuating a handle of the device to further expand the expandable structure to anchor the expandable structure in the vasculature, and activating a first electrode of the device to stimulate the nerve. The device comprises a proximal portion comprising the handle and the distal portion comprising the expandable structure. The expandable structure has a collapsed state and a self-expanded state. The expandable structure comprises a plurality of splines extending from a proximal hub to a distal hub. Each of the splines of the plurality of splines comprises a proximal segment, an intermediate segment distal to the proximal segment, and a distal segment distal to the intermediate segment. The intermediate segment is configured to extend radially outward in the self-expanded state. The expandable structure comprises a first electrode on a first spline of the plurality of splines.

The device may comprise an outer tube and a shaft. The outer tube may comprise a proximal end coupled to the handle and a distal end coupled to the proximal hub. The shaft may comprise a proximal end and a distal end and may extend through the outer tube from the handle to the distal hub. The handle may be configured to retract the shaft in a proximal direction relative to the outer tube when the handle is actuated, causing the distal hub and the proximal hub to move closer together.

The method may further comprise accessing the vasculature with a needle and a syringe. The method may further comprise inserting a guidewire into the vasculature. The shaft of the device may comprise a lumen extending from the proximal portion of the device to the distal portion of the device. The insertion of the distal portion of the device into the vasculature may comprise inserting the device over the guidewire such that the guidewire may be slidably received in the lumen of the shaft. The method may further comprise tracking the guidewire to a target location in the vasculature. The method may further comprise inserting a Swan-Ganz catheter into vasculature. The Swan-Ganz catheter may comprise an inflatable balloon at a distal end of the catheter.

The method may further comprise inflating the inflatable balloon, allowing the balloon to be carried by blood flow to the target location, inserting the guidewire through a lumen in the Swan-Ganz catheter to the target location, deflating the inflatable balloon, and retracting the Swan-Ganz catheter from the vasculature. The target location may be the right pulmonary artery.

The method may further comprise inserting an introducer in the vasculature. The insertion of the distal portion of the medical device into the vasculature may comprise inserting the device through a sheath of the introducer. The method may further comprise retracting a distal end of the introducer sheath from the distal portion of the device and/or pushing the distal portion of the device beyond the distal end of the sheath, causing the expandable structure to self-expand. The method may further comprise actuating a locking member on the handle to prevent the expandable structure from being compressed. The method may further comprise positioning the expandable structure in the right pulmonary artery. The nerve may be a cardiopulmonary nerve. The expandable structure may further comprise a second electrode on a second spline of the plurality of splines, the expandable structure being positioned such that the nerve may be positioned along the first spline, along the second spline, or between the first spline and the second spline. The method may further comprise activating the second electrode. The first spline may be circumferentially adjacent the second spline. The first spline may comprise a first plurality of electrodes including the first electrode, and the second spline may comprise a second plurality of electrodes including the second electrode. The first plurality of electrodes may comprise five electrodes and the second plurality of electrodes may comprise five electrodes. The first spline and the second spline may form a first spline pair. The first plurality of electrodes and the second plurality of electrodes may form an electrode array. The expandable structure may further comprise a second spline pair comprising a third spline comprising a third plurality of electrodes and a fourth spline comprising a fourth plurality of electrodes. The first plurality of electrodes, the second plurality of electrodes, the third plurality of electrodes, and the fourth plurality of electrodes may form an electrode array. The electrode array may comprise a 4×5 array. The method may further comprise positioning the expandable structure against tissue in the vasculature so that the nerve may be between at least two electrodes apposed against the tissue. The nerve may be between at least three electrodes apposed against the tissue. The nerve may be between at least four electrodes apposed against the tissue. Activating the first electrode may comprise applying a voltage pulse of a first polarity. The method may further comprise applying a pre-pulse of voltage to tissue surrounding the nerve prior to activating the first electrode, the pre-pulse being a second polarity opposite the first polarity. The method may further comprise measuring the pressure in the right ventricle and approximating the pressure in the left ventricle from the measured pressure in the right ventricle. The method may further comprise positioning a return conductor in the vasculature or on skin, the return conductor configured to conduct current from the activated electrode.

In some embodiments, a device for increasing heart contractility for treating heart failure comprises, or alternatively consists essentially of, a handle, and an expandable structure. The expandable structure has a collapsed state and a self-expanded state. The expandable structure comprises a plurality of splines extending from a proximal hub to a distal hub. The device further comprises a first electrode on a first spline of the plurality of splines, an outer tube extending from the handle to the proximal hub, and a shaft extending through the outer tube from the handle to the distal hub. The handle is configured to retract the shaft. The device is configured for placement in a pulmonary artery and delivery of energy from the first electrode to a target tissue to increase heart contractility for treating heart failure.

At least one spline of the plurality of splines may be devoid of electrodes.

The first spline may comprise a first plurality of electrodes including the first electrode. The first plurality of electrodes may form an electrode array.

The device may further comprise a second electrode on a second spline of the plurality of splines. The first spline may comprise a first plurality of electrodes including the first electrode. The second spline may comprise a second plurality of electrodes including the second electrode. The first plurality of electrodes may comprise five electrodes. The second plurality of electrodes may comprise five electrodes. The first plurality of electrodes and the second plurality of electrodes may form an electrode array. The second spline may be circumferentially adjacent to the first spline. The first spline and the second spline may form a first spline pair. The device may further comprise a second spline pair comprising a third spline comprising a third plurality of electrodes and a fourth spline comprising a fourth plurality of electrodes. The fourth spline may be circumferentially adjacent to the third spline. The second spline pair may be circumferentially adjacent to the first spline pair. The first plurality of electrodes, the second plurality of electrodes, the third plurality of electrodes, and the fourth plurality of electrodes form an electrode array. The electrode array may comprise a 4×5 array. Each of at least four circumferentially adjacent splines of the plurality of splines may comprise a plurality of electrodes.

Each of the splines of the plurality of splines may comprise a proximal segment, an intermediate segment distal to the proximal segment, and a distal segment distal to the intermediate segment. The intermediate segments may be configured to extend radially outward in the self-expanded state. The intermediate segments may be configured to extend further radially outward upon retraction of the shaft. The intermediate segment of each spline of the plurality of splines may form a first angle with the proximal segment and a second angle with the distal segment. The intermediate segment of each spline of the plurality of splines may curve into the proximal segment and the distal segment.

The proximal segment and the distal segment of each spline of the plurality of splines may be devoid of electrodes.

The proximal segment and the distal segment of each spline may be straight. The intermediate segment of each spline may be concave. The intermediate segment of each spline may be convex. The intermediate segment of each spline may be straight. Each of the proximal segment, the distal segment, and intermediate segment of each spline may be arcuate.

Each spline of the plurality of splines may further comprise a proximal transition segment joining the proximal segment and the intermediate segment, and a distal transition segment joining the intermediate segment and the distal segment. Each spline of the spline pair may be not parallel to the other spline of the spline pair along the proximal transition segment and the distal transition segment.

The first spline and a second spline of the plurality of splines may form a first spline pair. The second spline may be circumferentially adjacent to the first spline. The device may further comprise a second spline pair comprising a third spline of the plurality of splines and a fourth spline to the plurality of splines. The fourth spline may be circumferentially adjacent to the third spline. Each spline of a spline pair may be parallel to the other spline of the spline pair along the intermediate segment. Each spline of a spline pair may be parallel to the other spline of the spline pair along the proximal segment and the distal segment. The intermediate segments of each spline pair may be spaced further apart from each other than the proximal segments and the distal segments.

A least one spline of the plurality of splines may be devoid of electrodes.

The expandable structure may comprise a longitudinal axis between the proximal hub and the distal hub. The proximal segments of each of the splines of the plurality of splines may radially diverge away from the longitudinal axis and the distal segments of each of the splines of the plurality of splines may radially converge towards the longitudinal axis.

The plurality of splines may be configured to extend outwardly on one side of a plane crossing a longitudinal axis of the expandable structure. Splines of the plurality of splines comprising electrodes may be configured to extend outwardly on one side of a plane crossing a longitudinal axis of the expandable structure. The splines of the plurality of splines comprising electrodes may circumferentially occupy 100° to 120°. Splines of the plurality of splines not comprising electrodes may be configured to extend outwardly on a second side of the plane crossing the longitudinal axis of the expandable structure. The second side may be opposite the one side.

The outer tube may comprise a proximal portion and a distal portion. The proximal portion may have a higher durometer than the distal portion. The outer tube may comprise a plurality of longitudinal portions along a length of the outer tube. Each longitudinal portion the plurality of longitudinal portions may have a higher durometer than the longitudinal portions of the plurality of longitudinal portions distal thereto. At least one longitudinal portion of the plurality of longitudinal portions may be configured with a length and durometer for positioning the at least one longitudinal portion in a specific anatomy. The specific anatomy may comprise a chamber of a heart. The specific anatomy may comprise a blood vessel. The blood vessel may comprise the right pulmonary artery.

The outer tube may comprise a first outer diameter at the proximal end of the outer tube and a second outer diameter at the distal end of the outer tube. The first outer diameter may be greater than the second outer diameter.

A proximal portion of the outer tube may comprise a first plurality of layers. A distal portion of the outer tube may comprise a second plurality of layers. The first plurality of layers may comprise more layers than the second plurality of layers.

The outer tube may comprise a hinge joined to the proximal hub. The hinge may be configured to resist kinking upon bending of the device transverse to a longitudinal axis of the outer tube. The hinge may comprise a coil comprising a proximal end and a distal end. The proximal end of the coil may surround a portion of the tubing and the distal end of the coil may surround a portion of the proximal hub. The hinge may comprise a first wire comprising a helical winding, a second wire comprising a helical winding and occupying spaces between helices of the first wire, and a third wire comprising a helical winding and occupying spaces between helices the first wire and between helices of the second wire.

The outer tube may comprise tubing. The tubing may comprise an inner diameter configured to mate with an outer diameter of the proximal hub. The tubing may be configured to abut a proximal end of the proximal hub. The tubing may form a fluid seal between the outer tube and the proximal hub.

The first spline may comprise a spline tube. The first electrode may be on an outer surface of the spline tube.

The device may further comprise a spline tube at least partially covering two circumferentially adjacent splines of the plurality of splines. The spline tube may be configured to inhibit the two circumferentially adjacent splines from rotating relative to one another. The spline tube may diverge into two spatially separated tubular channels along the intermediate segments of the two circumferentially adjacent splines.

Circumferentially adjacent splines of the plurality of splines may be grouped into spline pairs. Each of the spline pairs may comprise a proximal tubing at least partially covering the proximal segments and a distal tubing at least partially covering the distal segments. The proximal tubings and the distal tubings may be configured to inhibit the splines of each of the spline pairs from rotating relative to one another. Each of the proximal tubings and the distal tubings may comprise heat-shrink tubing.

Circumferentially adjacent splines of the plurality of splines may be grouped into spline pairs. Each of the spline pairs may comprise a wire bent at a proximal end and having wire ends terminating at a distal end.

The proximal hub may comprise a proximal end, a distal end, and a central lumen extending from the proximal end of the proximal hub to the distal end of the proximal hub. The shaft may slidably extend through the central lumen of the proximal hub. The device may further comprise a plurality of peripheral lumens radially outward of the central lumen of the proximal hub. The plurality of peripheral lumens may be configured to transfer fluid flowing through the outer tube to the distal end of the proximal hub. At least one peripheral lumen of the plurality of peripheral lumens may be configured to receive an electrical conductor extending from the handle to the first electrode. The device may further comprise a plurality of spline channels extending proximally from the distal end of the proximal hub into a distal portion of the proximal hub. One spline of the plurality of splines may be in each spline channel of the plurality of spline channels of the proximal hub. The plurality of spline channels may extend through the distal portion of the proximal hub. Circumferentially adjacent splines of the plurality of splines may be grouped into spline pairs. Each of the spline pairs may comprise a wire bent at a proximal end. The proximal hub may comprise a plurality of recesses proximal to the distal portion of the proximal hub. The bent proximal ends of the wire of each of the spline pairs may be in a recess of the plurality of recesses. The plurality of recesses may be configured to inhibit movement of the plurality of splines proximal to the recesses.

The distal hub may comprise a proximal end, a distal end, and a central lumen extending from the proximal end of the distal hub to the distal end of the distal hub. The shaft may be fixably coupled to the central lumen of the distal hub. The device may further comprise a plurality of spline channels extending distally from the proximal end of the distal hub into the distal hub. One spline of the plurality of splines may be in each spline channel of the plurality of spline channels of the distal hub. Each spline channel of the plurality of spline channels of the distal hub may terminate proximal to the distal end of the distal hub. The proximal end of the distal hub may comprise a tapered surface. The tapered surface of the proximal end of the distal hub may comprise openings to the plurality of spline channels. The tapered surface proximal end of the distal hub may be configured to facilitate bending of the splines in a radially outward direction. The distal end of the distal hub may comprise an atraumatic configuration.

The handle may comprise a handle base comprising a proximal end, a distal end, and a lumen extending from the proximal end to the distal end. The handle may further comprise a proximal end of the outer tube coupled to the lumen of the handle base. The shaft may slidably extend through the lumen of the handle base. The handle may further comprise an actuator affixed to a proximal end of the shaft. The actuator may be moveable relative to the handle base in a proximal direction and in a distal direction. The actuator may be configured to expand the expandable structure when moved in a distal direction and to compress the expandable structure when moved in a proximal direction. The handle may further comprise an outer handle extending from the handle base, a securing member comprising a proximal end affixed to the actuator, and a locking member positioned along the securing member between the outer handle and the actuator. The locking member may be configured to be moved along the longitudinal axis of the securing member and secured at a position along a length of the securing member to inhibit movement of the actuator in a distal direction.

The securing member may comprise a threaded shaft and the locking member may comprise a threaded channel. The locking member may be longitudinally moveable along the securing member by rotating the locking member around the threaded shaft.

The handle may further comprise a locking member having a locked configuration and an unlocked configuration. The locking member may comprise a main body comprising a proximal end and a distal end, a channel extending from the proximal end to the distal end, and a protrusion extending into the channel of the locking member. The actuator may extend through the channel of the locking member. The protrusion may be configured to inhibit the actuator from moving in at least one of a proximal direction and a distal direction relative to the handle base when the locking member may be in the locked configuration. The actuator may be moveable in the proximal direction and in the distal direction when the locking member may be in the unlocked configuration. The actuator may comprise an elongate body, a textured surface along a length of the elongate body of the actuator, and the locking member moveable between the locked configuration and the unlocked configuration by rotating the locking member around the elongate body of the actuator. The protrusion may be configured to interface with the textured surface in a locked position and configured to not interface with the textured surface in the unlocked position.

The locking member may further comprise a tab extending away from the main body. The tab may be positionable in a first position relative to the handle base when the locking member is in a locked configuration. The tab may be positionable in a second position when the locking member is in an unlocked configuration. The textured surface may comprise a series of ridges. The protrusion of the locking member may be configured to mate with a notch between the ridges. The channel of the locking member may be oblong. The locking member may be configured to switch between a locked configuration and an unlocked configuration by rotating the locking member a quarter turn.

The handle base further may comprise an aperture in a sidewall extending into the lumen of the handle base and proximal to the proximal end of the outer tube. An electrical conductor may extend from an electrical socket into the outer tube through the aperture of the handle base.

The shaft may comprise a lumen. The lumen of the shaft may be configured to receive a guidewire. A proximal end of the shaft may be configured to receive fluid. The proximal end of the shaft may be joined to a fluid valve. The shaft may comprise a sidewall and an aperture in the sidewall. The aperture may be configured to permit fluid to flow out of the lumen of the shaft and to the proximal hub.

The device may be configured to transfer fluid injected into the shaft through the shaft to the distal hub and through the outer tube to the proximal hub. The shaft may comprise a plurality of hypotubes. The plurality of hypotubes may comprise a first hypotube having a proximal end and a distal end, and a second hypotube having a proximal end and a distal end. The distal end of the first hypotube may be in the proximal end of the second hypotube. The proximal end of the second hypotube may be in the distal end of the first hypotube. The plurality of hypotubes may include three hypotubes. At least one hypotube of the plurality of hypotubes may comprise a proximal portion having a first outer diameter and a distal portion having a second outer diameter less than the first outer diameter. At least one hypotube of the plurality of hypotubes may comprise a sidewall and an aperture through the sidewall.

The device may further comprise an inflatable member. The device may further comprise an inflation lumen in fluid communication with the inflatable member.

In some embodiments, a device comprises, or alternatively consists essentially of, a handle and an expandable structure. The expandable structure has a collapsed state and a self-expanded state. The expandable structure comprises a plurality of splines extending from a proximal hub to a distal hub. The device further comprises an energy delivery neuromodulator on a first spline of the plurality of splines, an outer tube extending from the handle to the proximal hub, and a shaft extending through the outer tube from the handle to the distal hub, the handle configured to retract the shaft. The energy delivery neuromodulator may comprise an electrode. The neuromodulator may comprise a transducer.

In some embodiments, a device comprises, or alternatively consists essentially of, a handle and an expandable structure. The expandable structure has a collapsed state and a self-expanded state. The expandable structure comprises a plurality of splines extending from a proximal hub to a distal hub. The device further comprises a neuromodulator on a first spline of the plurality of splines, an outer tube extending from the handle to the proximal hub, and a shaft extending through the outer tube from the handle to the distal hub. The handle is configured to retract the shaft. The neuromodulator may comprise a radiofrequency electrode, an ultrasound element, a laser element, a microwave element, a cryogenic element, a thermal delivery device, or a drug delivery device.

Use of the device may be for neuromodulation. Use of the device may be for treatment of a cardiovascular condition. Use of the device may be for treatment of acute heart failure. Use of the device may be for treatment of shock. Use of the device may be for treatment of valvular disease. Use of the device may be for treatment of angina. Use of the device may be for treatment of microvascular ischemia. Use of the device may be for treatment of myocardial contractility disorder. Use of the device may be for treatment of cardiomyopathy. Use of the device may be for treatment of hypertension. Use of the device may be for treatment of pulmonary hypertension. Use of the device may be for treatment of systemic hypertension. Use of the device may be for treatment of orthostatic hypertension. Use of the device may be for treatment of orthopnea. Use of the device may be for treatment of dyspenea. Use of the device may be for treatment of dysautonomia. Use of the device may be for treatment of syncope. Use of the device may be for treatment of vasovagal reflex. Use of the device may be for treatment of carotid sinus hypersensitivity. Use of the device may be for treatment of pericardial effusion. Use of the device may be for treatment of cardiac structural abnormalities.

In some embodiments, a method of modulating a nerve comprises, or alternatively consists essentially of, inserting a distal portion of the device into vasculature, allowing the expandable member to self-expand, actuating the handle to further expand the expandable structure to anchor the expandable structure in the vasculature, and activating the first electrode to stimulate the nerve.

The method may further comprise accessing the vasculature with a needle and a syringe. Accessing the vasculature may be at a jugular vein. Accessing the vasculature may be at a left jugular vein.

The method may further comprise inserting a guidewire into the vasculature. The shaft may comprise a lumen extending from a proximal portion of the device to the distal portion of the device. Inserting the distal portion of the device into the vasculature may comprise tracking the device over the guidewire to position the expandable structure at a target location in the vasculature. The guidewire may slide through the lumen of the shaft.

The method may further comprise inserting a Swan-Ganz catheter comprising a distal end comprising a balloon into vasculature, inflating the balloon, allowing the balloon to be carried by blood flow to the target location, inserting the guidewire through a lumen in the Swan-Ganz catheter, deflating the balloon, and retracting the Swan-Ganz catheter from the vasculature.

The target location may be a pulmonary artery. The target location may be a right pulmonary artery. The target location may be a pulmonary trunk. The target location may be a left pulmonary artery.

The method may further comprise inserting an introducer in the vasculature. Inserting the distal portion of the device into the vasculature may comprise inserting the device through a sheath of the introducer. The method may further comprise at least one of proximally retracting a distal end of the introducer sheath and distally advancing the distal portion of the device, allowing the expandable structure to self-expand. The method may further comprise actuating a locking member on the handle.

The nerve may comprise a cardiopulmonary nerve. The nerve may comprise a right dorsal medial CPN. The nerve may comprise a right dorsal lateral CPN. The nerve may comprise a right stellate CPN. The nerve may comprise a right vagal nerve or vagus. The nerve may comprise a right cranial vagal CPN. The nerve may comprise a right caudal vagal CPN. The nerve may comprise a right coronary cardiac nerve. The nerve may comprise a left coronary cardiac nerve. The nerve may comprise a left lateral cardiac nerve. The nerve may comprise a left recurrent laryngeal nerve. The nerve may comprise a left vagal nerve or vagus. The nerve may comprise a left stellate CPN. The nerve may comprise a left dorsal lateral CPN. The nerve may comprise a left dorsal medial CPN.

The method may comprise positioning the expandable structure against tissue in the vasculature so that the nerve is between the first electrode and a second electrode.

Activating the first electrode may comprise applying a voltage pulse having a first polarity. The method may further comprise, before activating the first electrode, applying a pre-pulse of voltage to tissue surrounding the nerve. The pre-pulse may have a second polarity opposite the first polarity.

The method may further comprise measuring pressure in a right ventricle and approximating pressure in the left ventricle from the pressure measured in the right ventricle.

The method may further comprise positioning a return conductor in the vasculature. The return conductor may be configured to conduct current from an activated electrode.

A current vector from the first electrode to the return electrode may be away from at least one of a heart and a trachea. Positioning the return conductor in the vasculature may comprise positioning the return electrode at least 5 mm away from the first electrode. Positioning the return conductor in the vasculature may comprise positioning the return electrode in a right ventricle. Positioning the return conductor in the vasculature may comprise positioning the return electrode a superior vena cava. Positioning the return conductor in the vasculature may comprise positioning the return electrode a brachiocephalic vein.

The methods summarized above and set forth in further detail below describe certain actions taken by a practitioner; however, it should be understood that they can also include the instruction of those actions by another party. Thus, actions such as "positioning an electrode" include "instructing positioning of an electrode."

For purposes of summarizing the invention and the advantages that may be achieved, certain objects and advantages are described herein. Not necessarily all such objects or advantages need to be achieved in accordance with any particular embodiment. In some embodiments, the invention may be embodied or carried out in a manner that can achieve or optimize one advantage or a group of advantages without necessarily achieving other objects or advantages.

The embodiments disclosed herein are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments. All references cited herein, including patents and patent applications, are incorporated by reference in their entirety.

BRIEF DESCRIPTION OF THE DRAWINGS

FIGS. 2G and 2H are schematic illustrations of vasculature and an electrode matrix.

FIG. 2I is a schematic illustration of heart vasculature and surrounding nerves.

FIG. 3A is a side perspective and partial cross-sectional view of an example of a catheter.

FIG. 3B is a distal end view of the catheter of FIG. 3A as viewed along line 3B-3B in FIG. 3A.

FIG. 4A is a side perspective and partial cross-sectional view of another example of a catheter.

FIG. 4B is a distal end view of the catheter of FIG. 4A as viewed along line 4B-4B in FIG. 4A.

FIGS. 5 and 6 illustrate examples of catheters.

FIGS. 8A and 8B illustrate examples of catheters.

FIG. 8C illustrates the catheter of FIG. 8A positioned within the main pulmonary artery.

FIG. 8D illustrates the catheter of FIG. 8B positioned within the main pulmonary artery.

FIG. 18D illustrates the catheter of FIGS. 18A through 18C positioned in the right pulmonary artery of a heart.

FIG. 19 is partial cross-sectional and perspective view of an example catheter positioned in a heart of a patient.

FIG. 22A is a perspective view of an example of a portion of a catheter.

FIG. 22B is a side elevational view of the portion of FIG. 22A.

FIGS. 22H-22L are side elevational and partial cross-sectional views of examples of catheter deployment systems.

FIG. 23A is a perspective view of an example segment of a strut.

FIG. 23B is a transverse cross-sectional view of an example of a strut.

FIG. 23C is a transverse cross-sectional view of an example of a strut.

FIG. 23H illustrates an example of a strut system.

FIG. 23I shows an example in which a distance between a first strut and a second strut is less than a distance a between a third strut and the second strut.

FIG. 23J shows an example in which a distance between a first strut and a second strut is substantially the same as a distance a between a third strut and the second strut.

FIG. 23K illustrates an example of an electrode on wire system.

FIG. 23L is a cross-sectional view of an electrode spaced from a vessel wall.

FIGS. 23Ni-23Nix illustrate an example method of manufacturing components on a substrate.

FIG. 24A illustrates an example of a fixation system.

FIGS. 24B and 24C illustrate the fixation system of FIG. 24A interacting with a catheter.

FIG. 26A is a side elevational view of an example of a catheter system 2600.

FIGS. 26B-26H illustrate an example method of deploying the catheter system 2600 of FIG. 26A.

FIG. 27G is a perspective view of yet another example of a fixation system.

FIG. 27H is a side view of the fixation system of FIG. 27G.

FIG. 27I is a side view of still another example of a fixation system.

FIG. 28A is a side view of an example of a fixation system.

FIG. 28B is an expanded view of the dashed circle 28B in FIG. 28A.

FIG. 28F is a flattened view of an example of a hypotube cut pattern.

FIG. 28G is an expanded view of the dashed square 28G in FIG. 28F.

FIG. 28H is a side view of the strut of FIG. 28G.

FIG. 28I is a side view of a proximal fixation mechanism being bent radially outward.

FIG. 28J is a side view of a proximal fixation mechanism being bent radially outward and a strut being bent at a bend point.

FIG. 28K is a side view of a strut being bent at a bend point.

FIG. 29A illustrates an example of a catheter system.

FIGS. 29B-29F illustrate an example method of deploying the catheter system of FIG. 29A.

FIG. 29G illustrates an example of a catheter system.

FIG. 29H illustrates another example of a catheter system.

FIG. 29I illustrates yet another example of a catheter system.

FIG. 29J illustrates still another example of a catheter system.

FIG. 29K illustrates yet still another example of a catheter system.

FIGS. 29L-29N illustrate an example method of deploying the catheter system of FIG. 29K.

FIG. 30A is a perspective view of an example of an electrode system.

FIG. 30B is a top plan view of a portion of the electrode system of FIG. 30A.

FIG. 30C is a perspective view of another example of an electrode system.

FIG. 30D is a distal end view of the electrode system of FIG. 30C in a collapsed state.

FIG. 30E is a distal end view of the electrode system of FIG. 30C in an expanded state.

FIGS. 32A-32D show example electrode combinations for twelve electrodes in a 3×4 matrix.

FIG. 35A schematically illustrates a mechanically repositionable electrode catheter system.

FIG. 35B illustrates the catheter system of FIG. 35A after longitudinal advancement.

FIG. 35C illustrates the catheter system of FIG. 35A after longitudinal advancement and rotation.

FIG. 35D is a cross-sectional view taken along the line 35D-35D of FIG. 35C.

FIG. 36C is a side view of a portion of the catheter system of FIG. 36A in an expanded state.

FIG. 36H schematically illustrates an example of an expandable structure pattern.

FIG. 36I schematically illustrates another example of an expandable structure pattern.

FIG. 36J schematically illustrates still another example of an expandable structure pattern.

FIG. 36K schematically illustrates yet another example of an expandable structure pattern.

FIG. 36L schematically illustrates still yet another example of an expandable structure pattern.

FIG. 36M schematically illustrates another example of an expandable structure pattern.

FIG. 36N schematically illustrates an example of an expandable structure.

FIG. 36O schematically illustrates an example of an expandable structure pattern.

FIG. 37A is a perspective view of an example of a catheter system.

FIG. 37B is a side view of an example of an expandable structure.

FIG. 37C is a proximal end view of the expandable structure of FIG. 37B.

FIG. 37D is a perspective view of a wire bent to form a spline pair.

FIG. 37E is a perspective view of a spline pair comprising electrodes.

FIG. 37F is an expanded perspective view of the distal end of the spline pair of FIG. 37E.

FIG. 37Fi-37Fiii illustrate an example of electrical movement of electrodes.

FIG. 37G is a perspective view of an example of a proximal hub of an expandable structure.

Figure 37A:
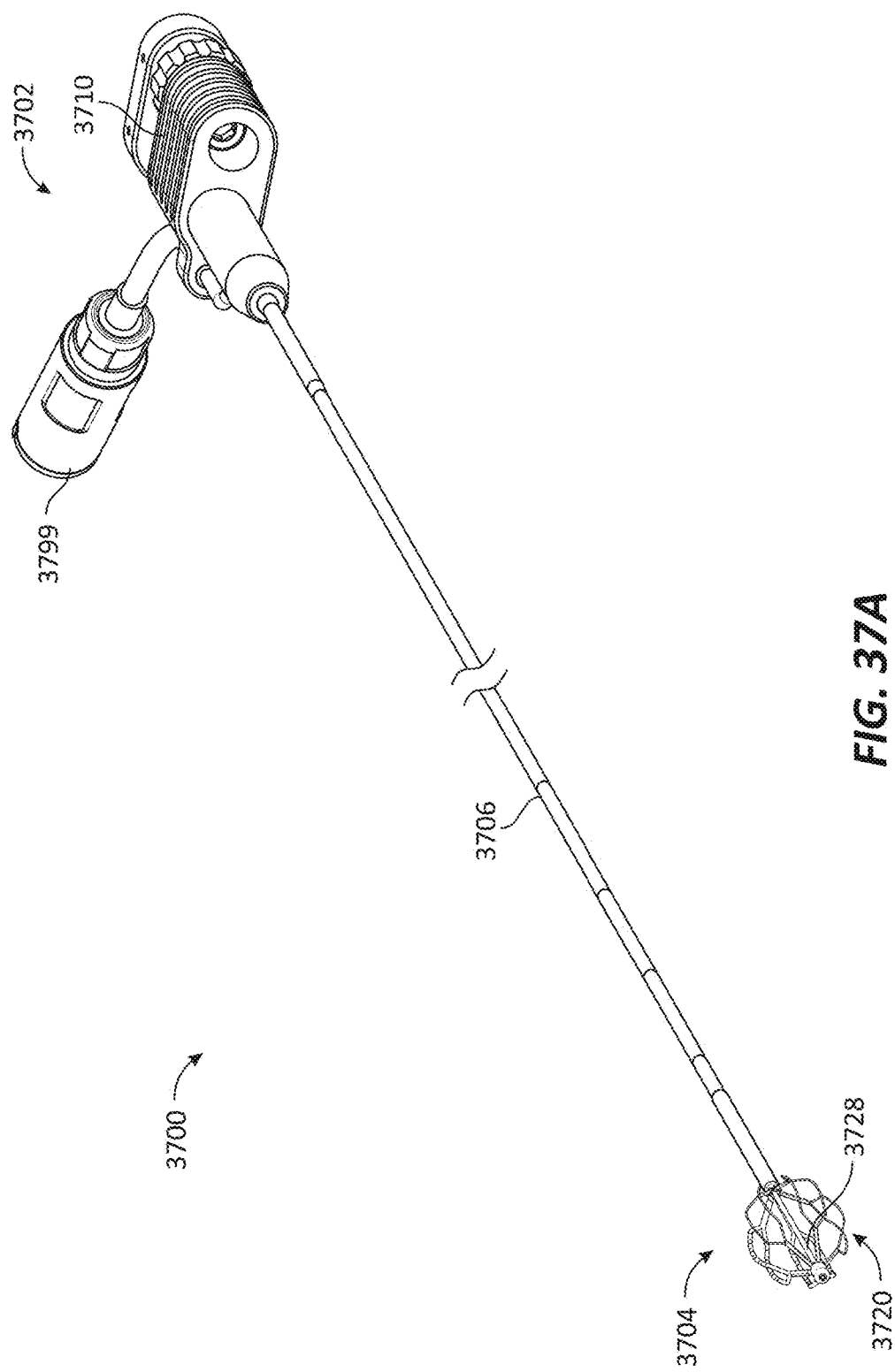
Figure 37B:
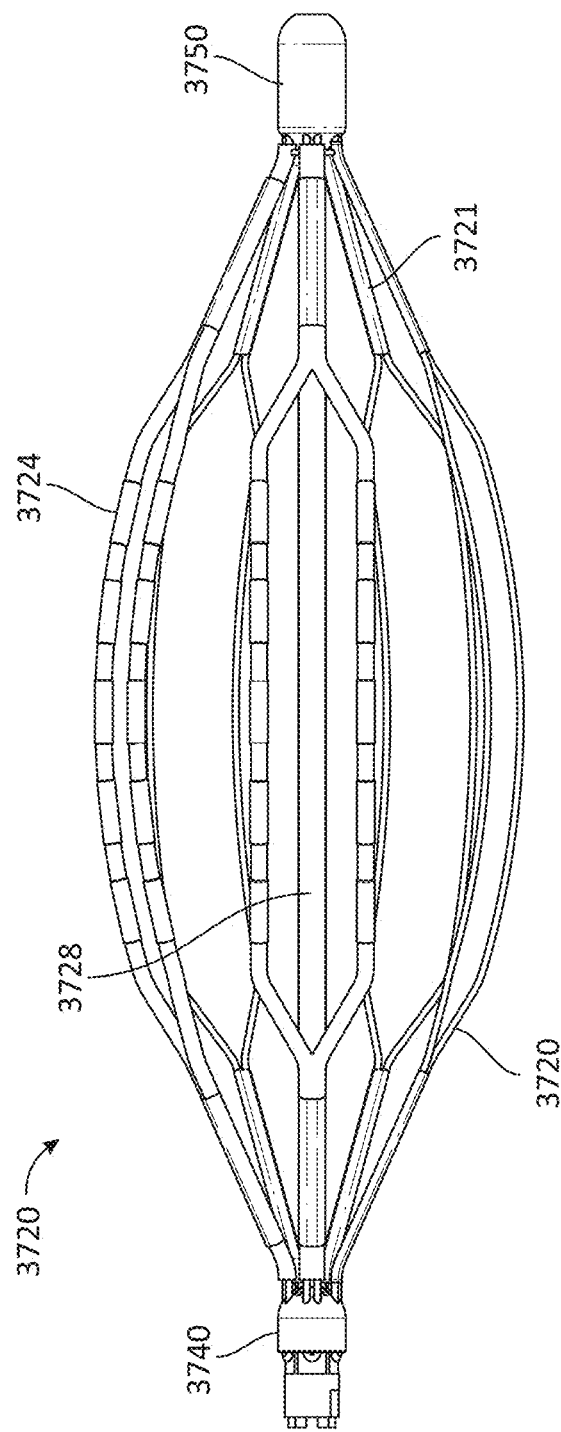
Figure 37C:
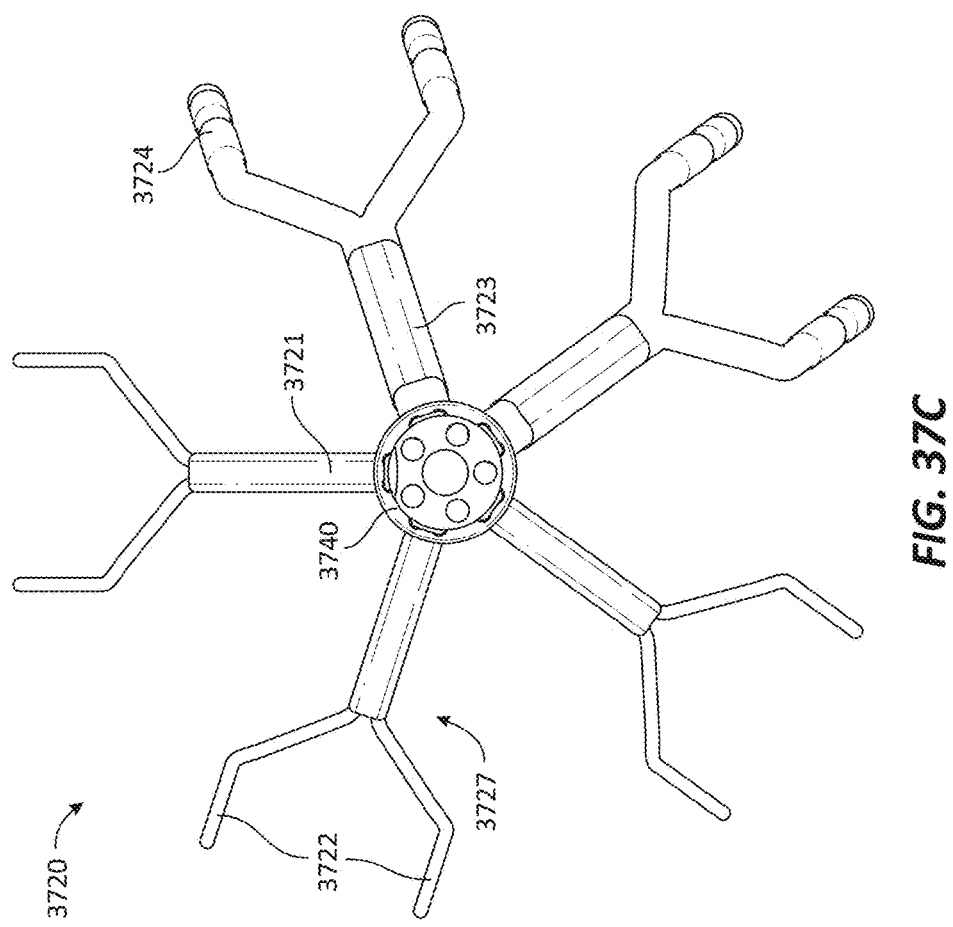
Figure 37D:
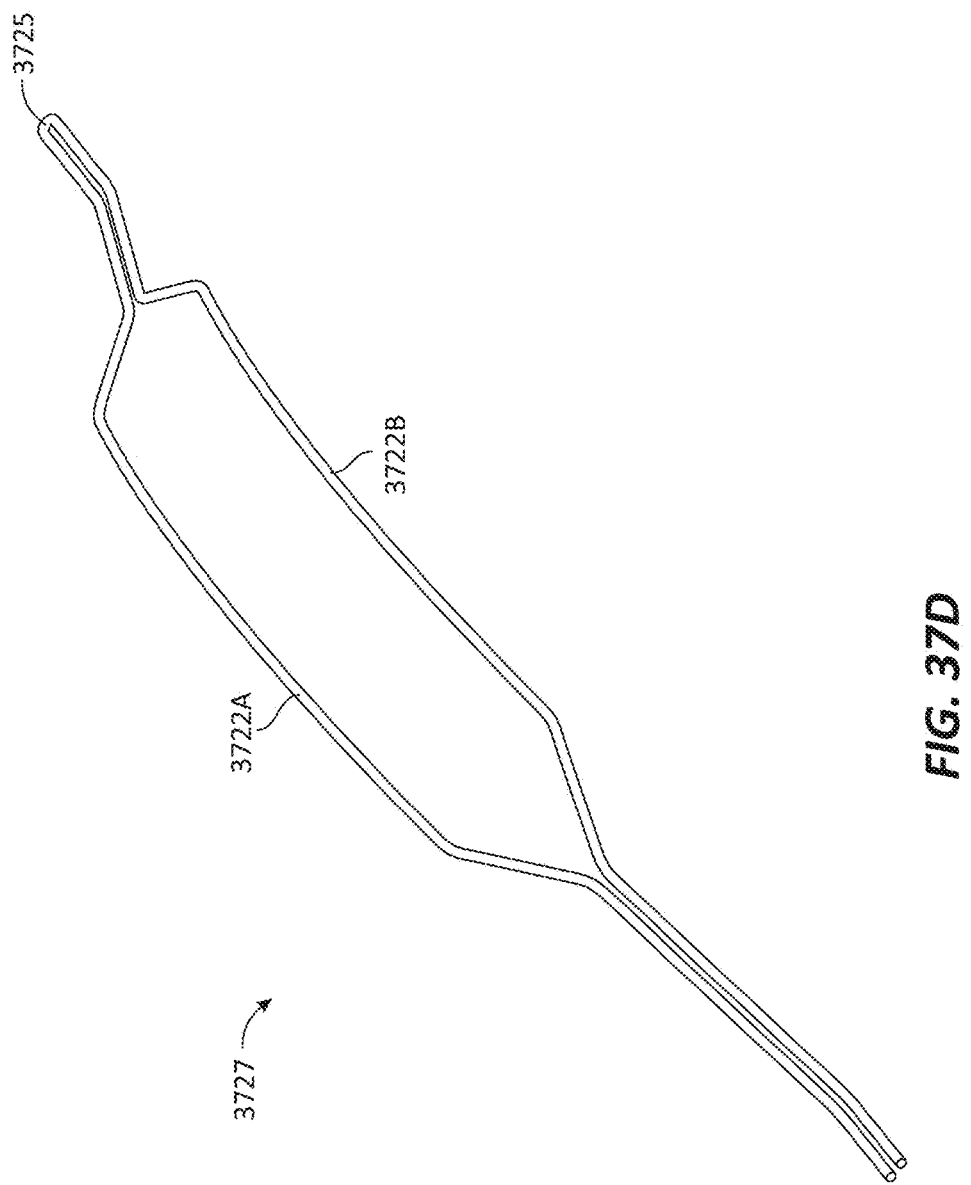
Figure 37H:
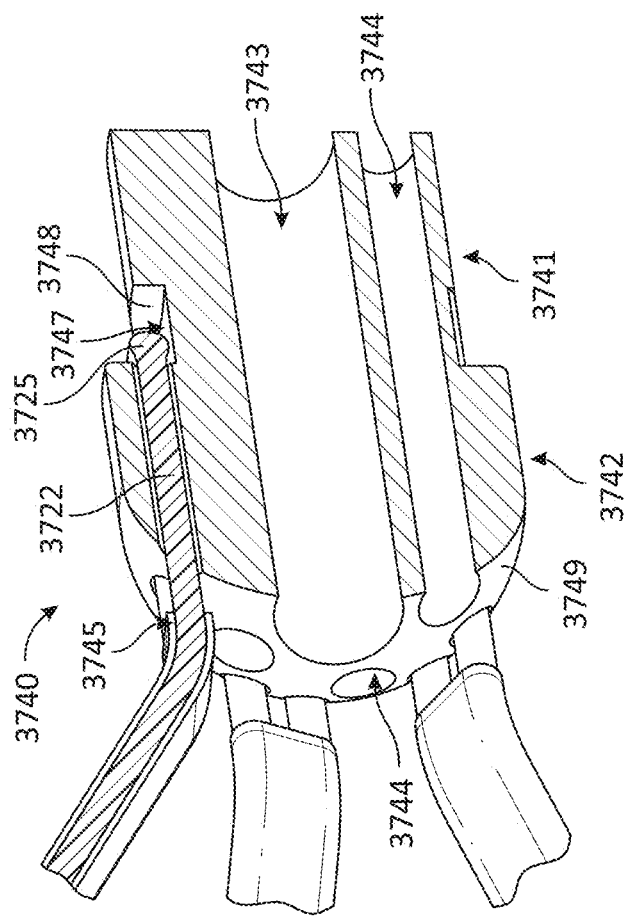

FIG. 37H schematically illustrates a side cross-sectional view of the proximal hub of FIG. 37G.

Figure 37I:
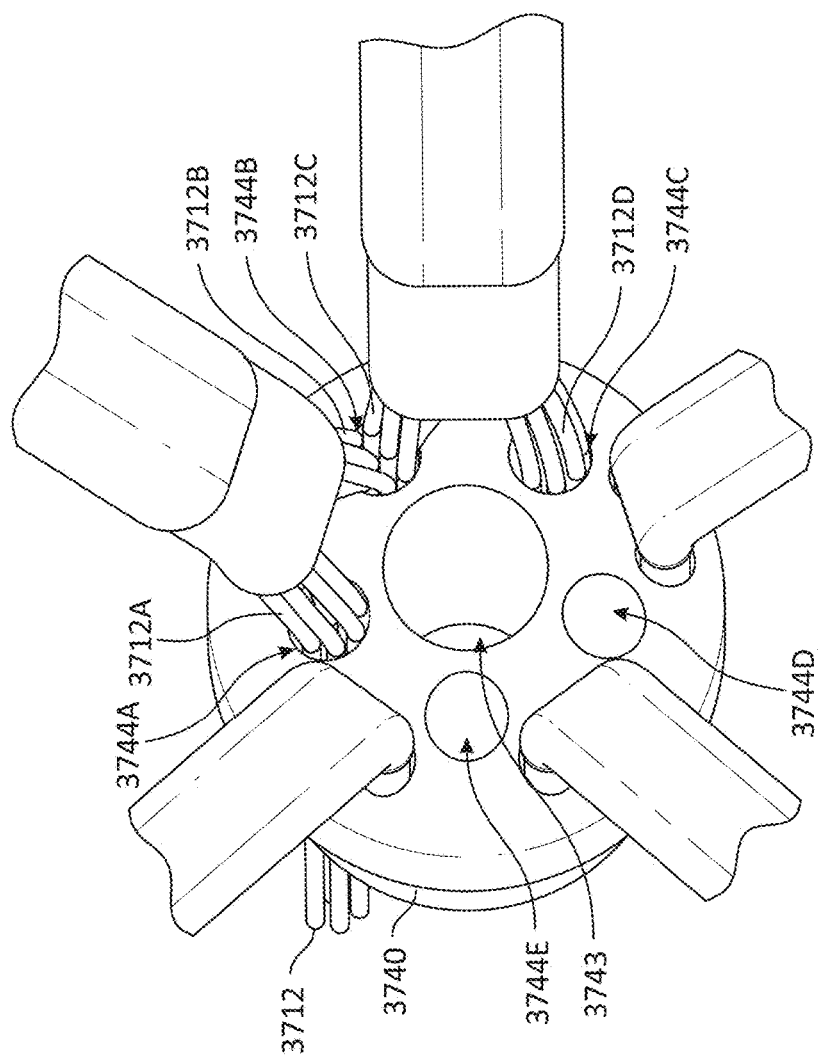

FIG. 37I is a perspective view of a distal end of the proximal hub of FIG. 37G.

Figure 37J:
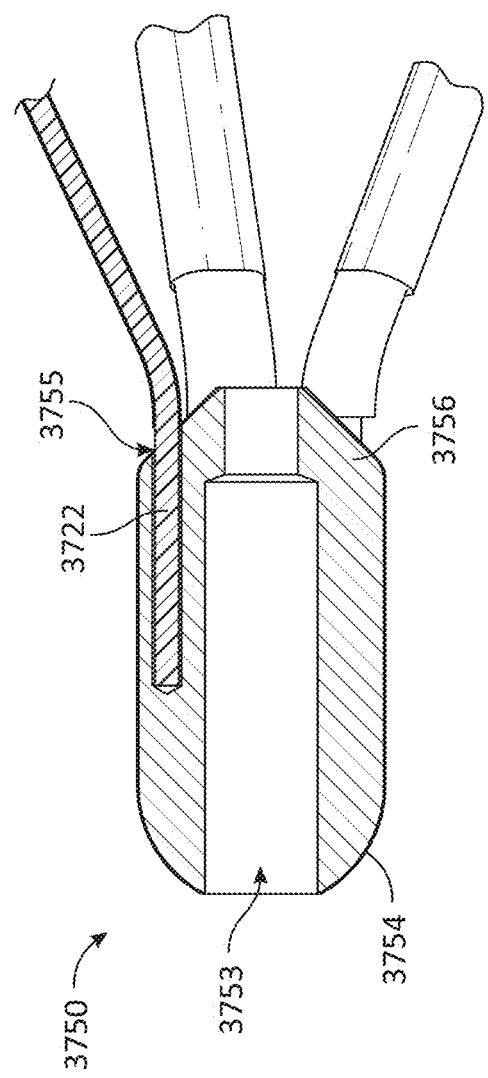

FIG. 37J schematically illustrates a side cross-sectional view of an example of a distal hub of an expandable structure.

Figure 37K:
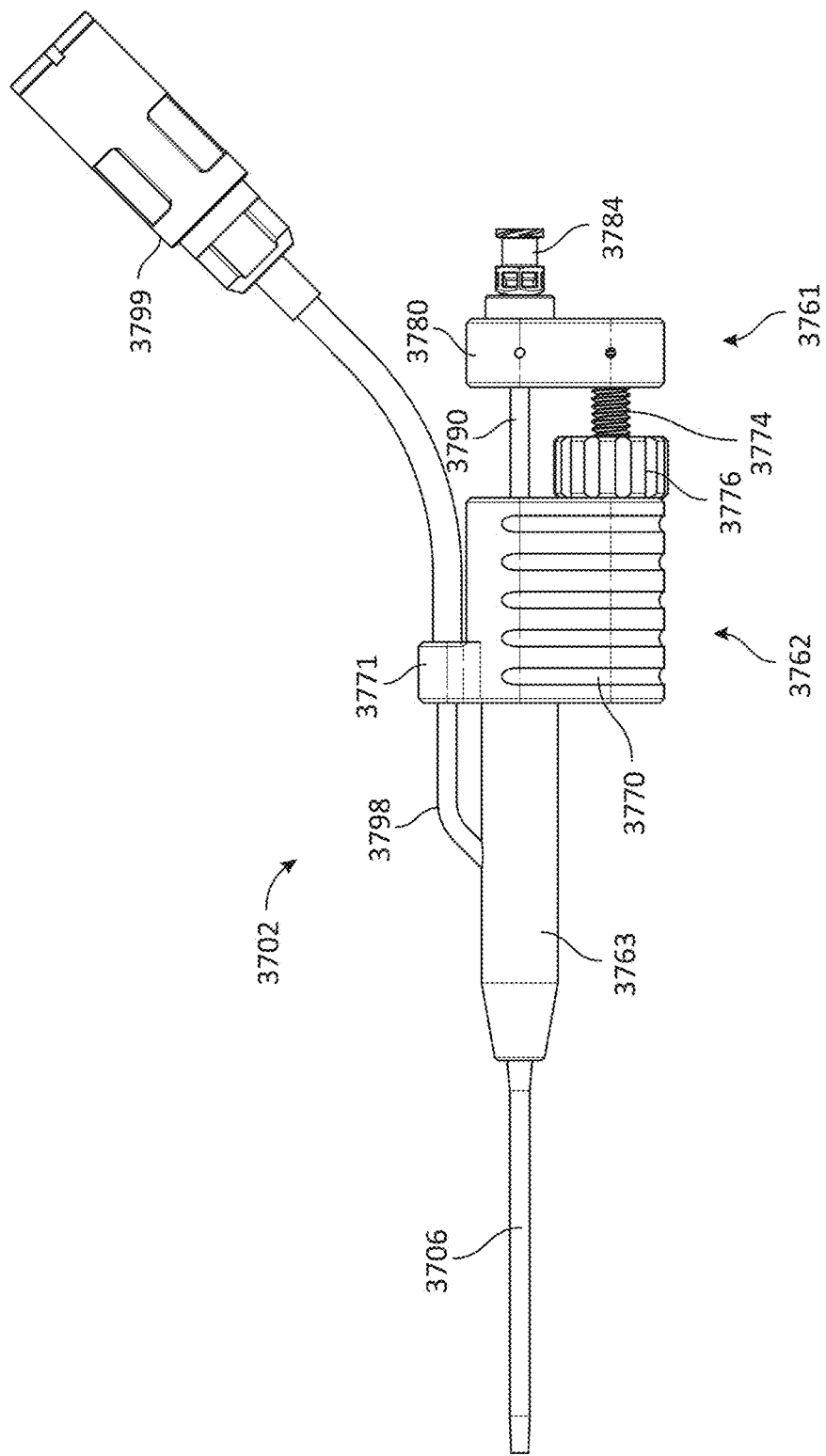

FIG. 37K is a side view of an example of a proximal end of the catheter system of FIG. 37A.

Figure 37L:
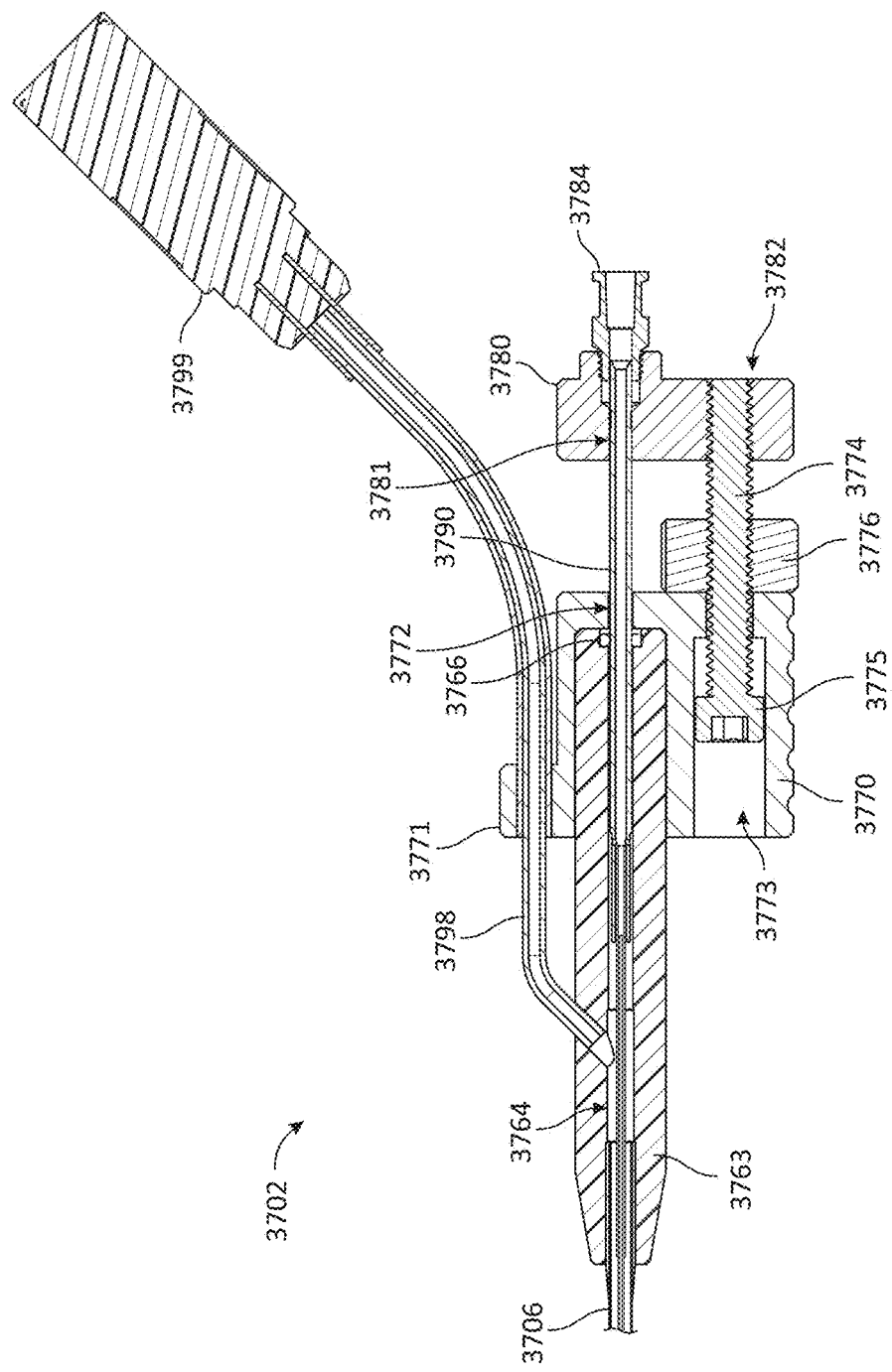
Figure 37L:
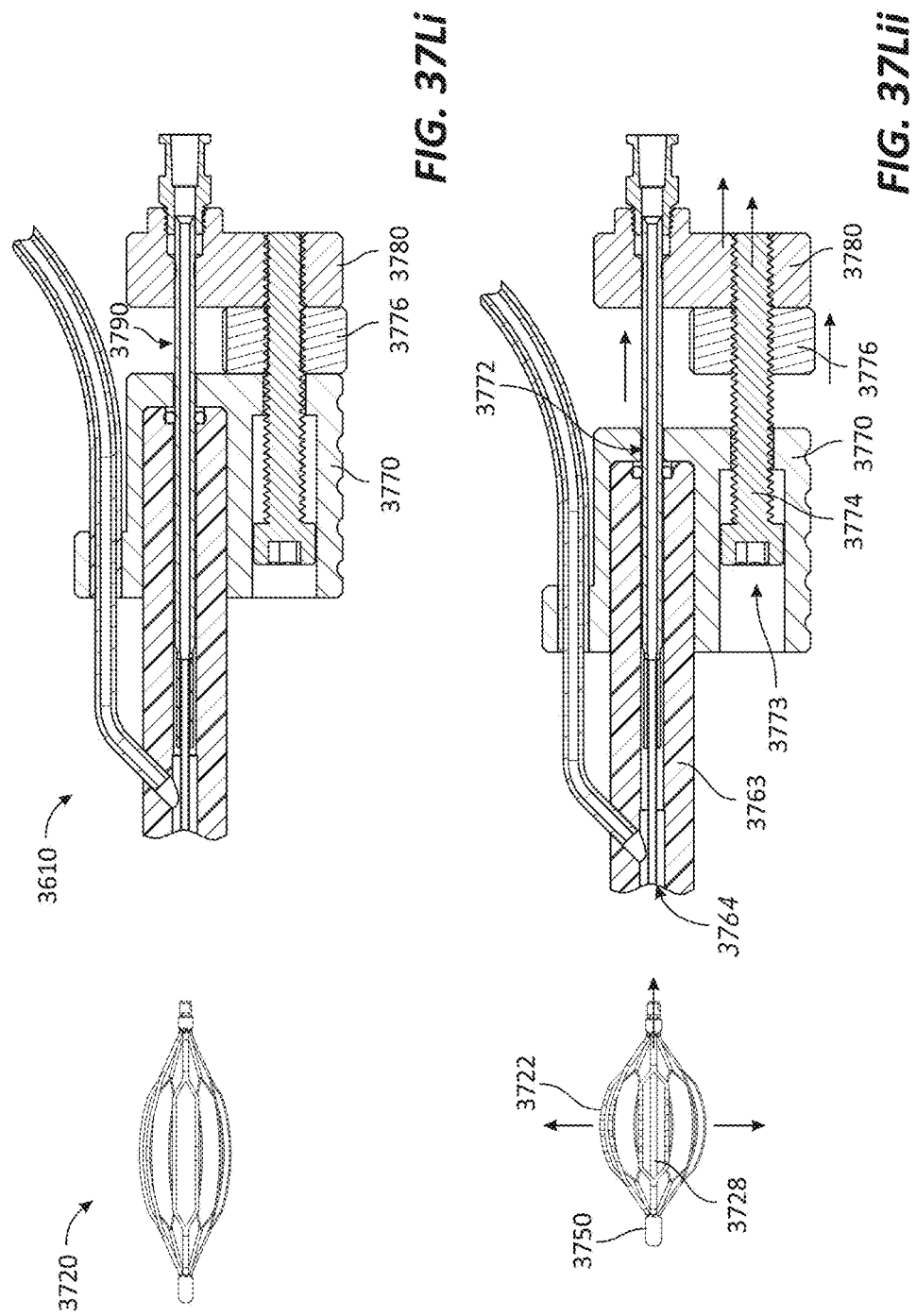

FIG. 37L is a side cross-sectional view of the proximal end of FIG. 37K.

FIGS. 37Li-37Liii show an example method of operating a handle to radially expand an expandable member.

FIGS. 37Li and 37Liv show another example method of operating a handle to radially expand an expandable member.

Figure 37M:
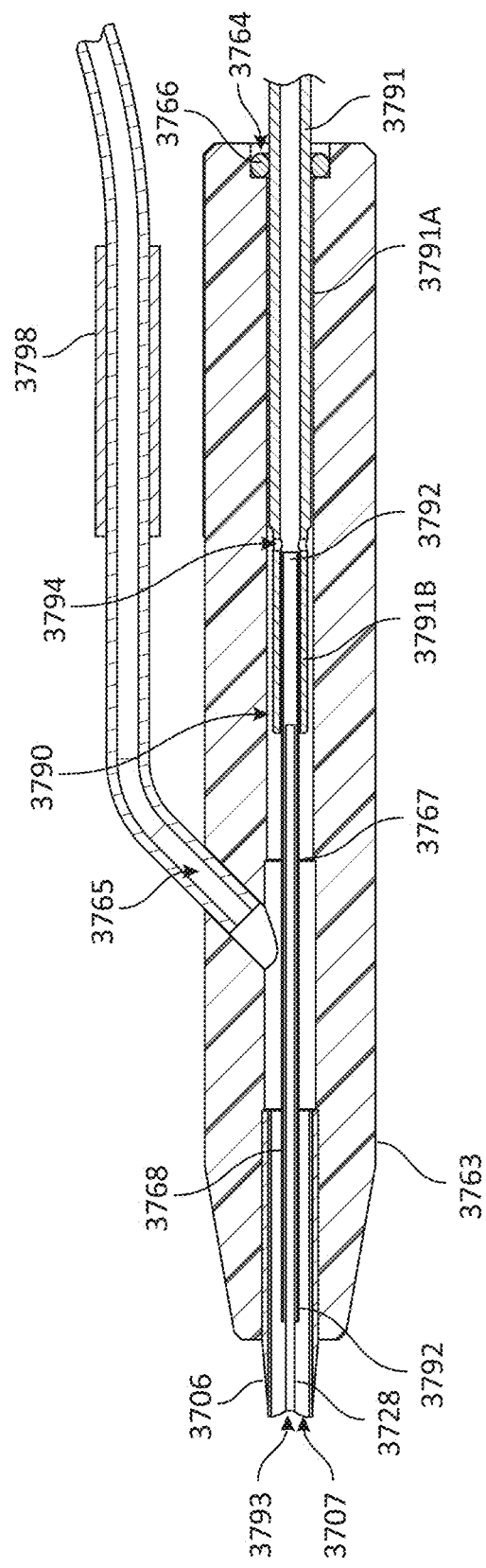

FIG. 37M is a side cross-sectional view of example components of a handle base.

Figure 37N:
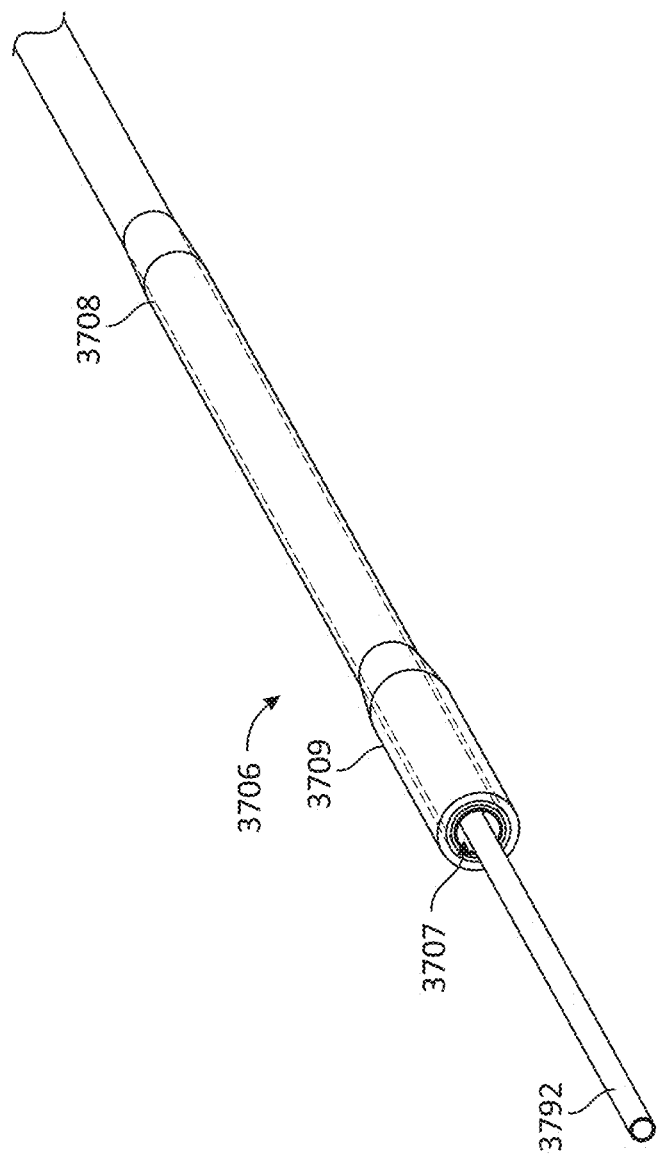

FIG. 37N is a perspective view of a proximal end of an example of a catheter shaft assembly and support tube.

Figure 37P:
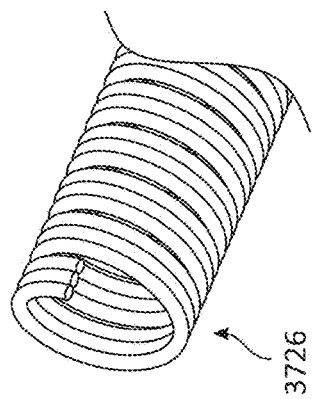
Figure 37O:
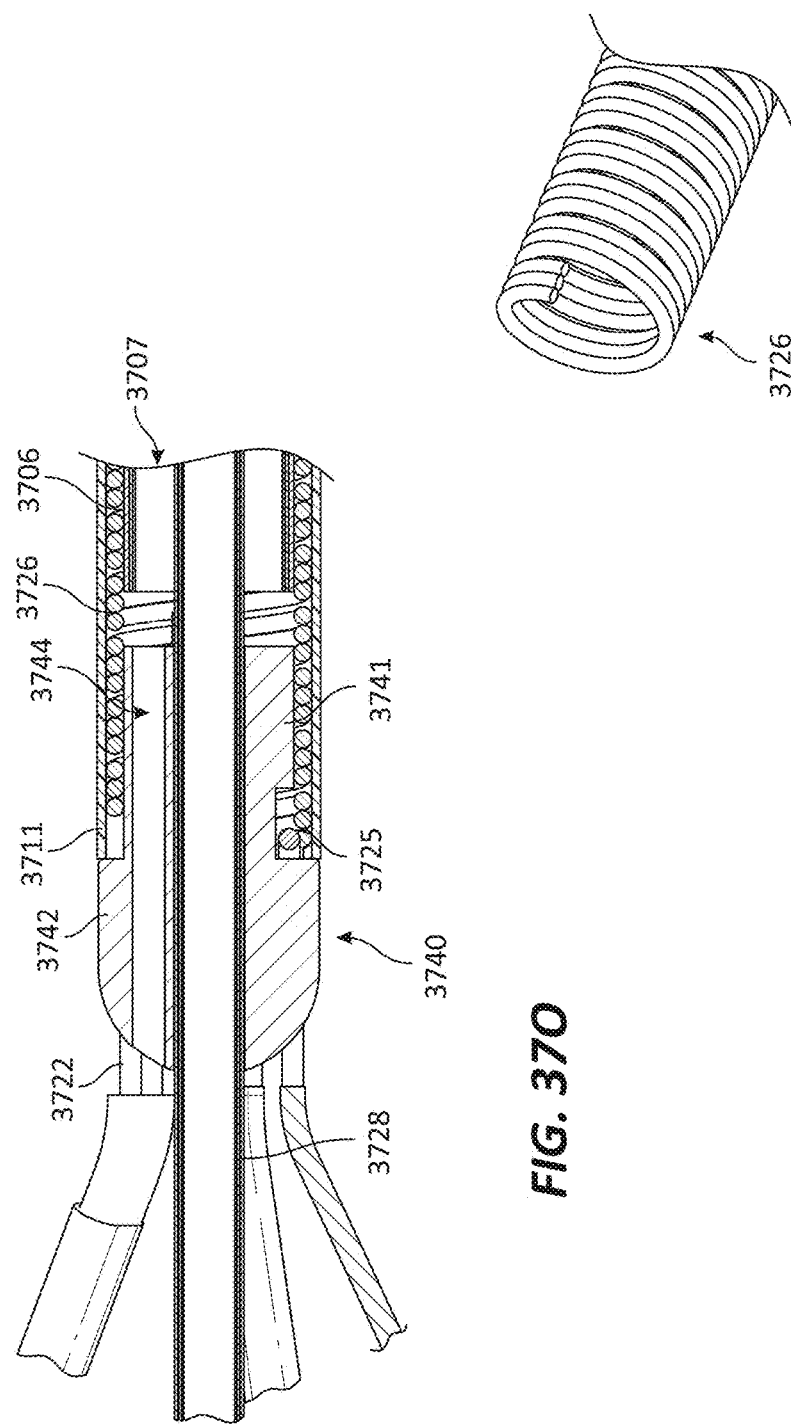

FIG. 37O is a side cross-sectional view of an example connection between a distal end of a catheter shaft assembly and a proximal hub of an expandable structure.

FIG. 37P is a perspective view of an end of an example of a hinge.

Figure 37Q:
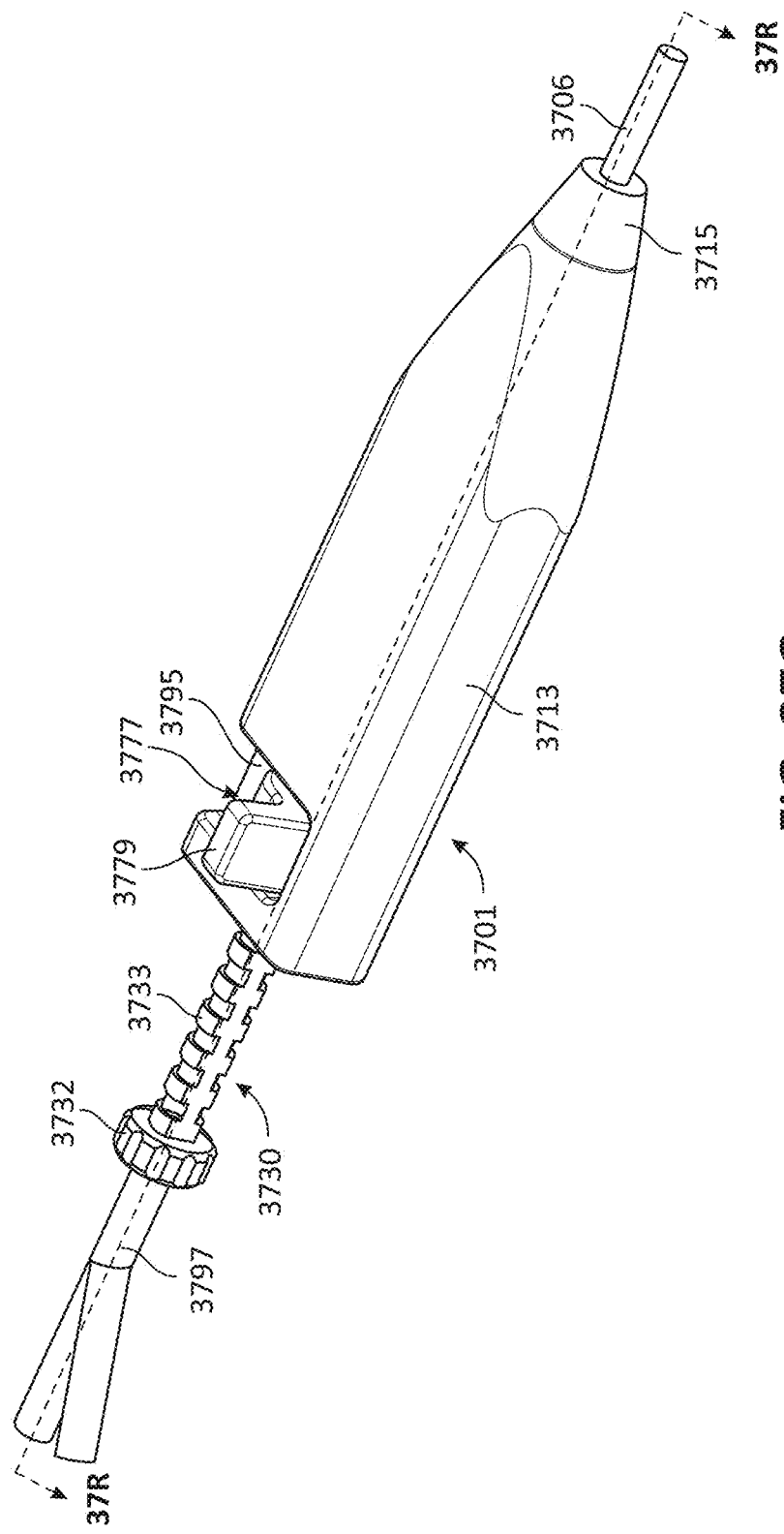

FIG. 37Q is a perspective view of an example handle of a catheter system in an unlocked configuration.

Figure 37R:
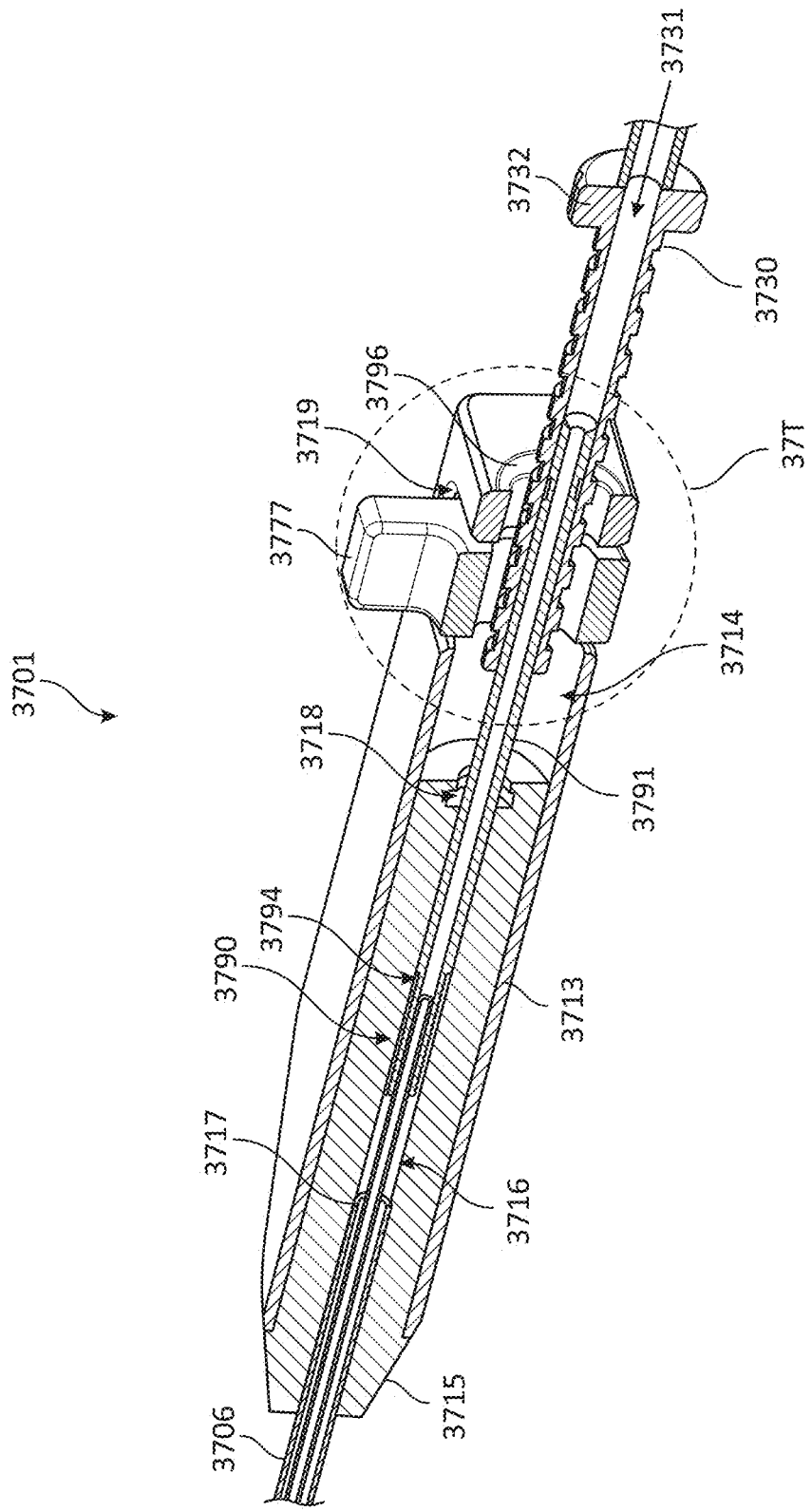

FIG. 37R schematically illustrates a perspective cross-sectional view of the handle of FIG. 37Q along the line 37R-37R.

Figure 37T:
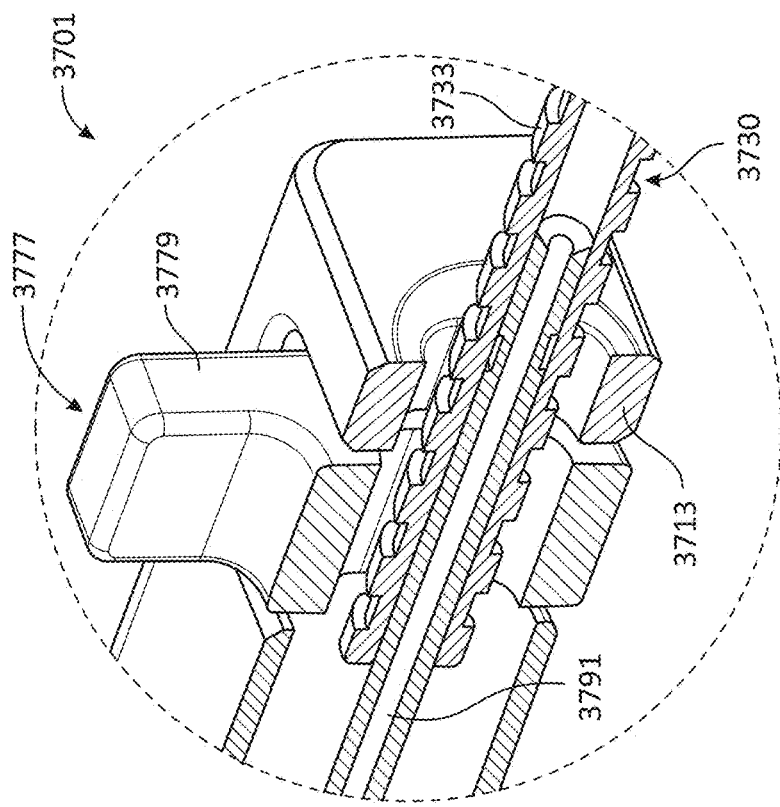
Figure 37S:
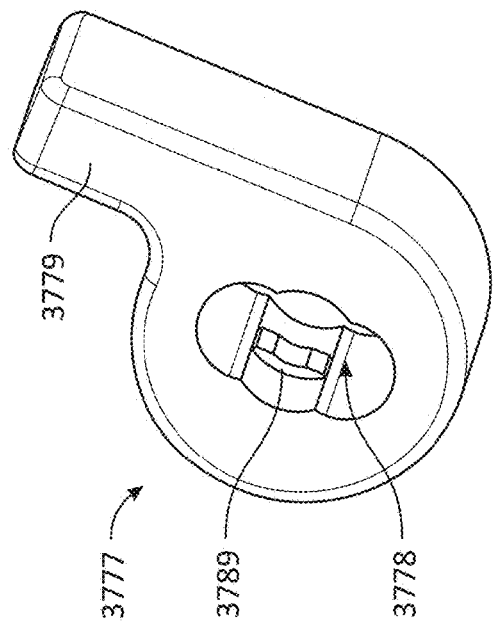

FIG. 37S is a perspective view of an example of a locking member.

FIG. 37T schematically illustrates an expanded perspective cross-sectional view of the handle of FIG. 37Q in an unlocked configuration in the area of the circle 37T of FIG. 37R.

Figure 37U:
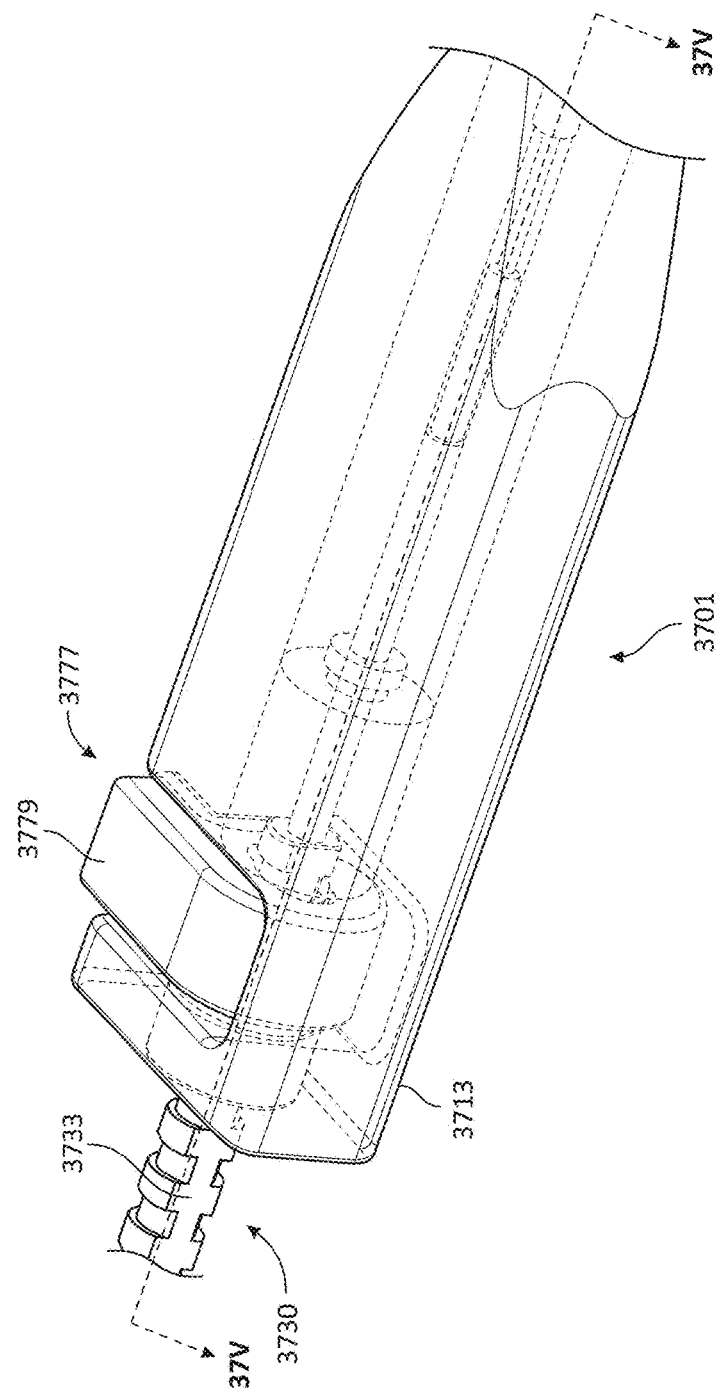

FIG. 37U is a perspective view of the handle of FIG. 37Q in a locked configuration.

Figure 37V:
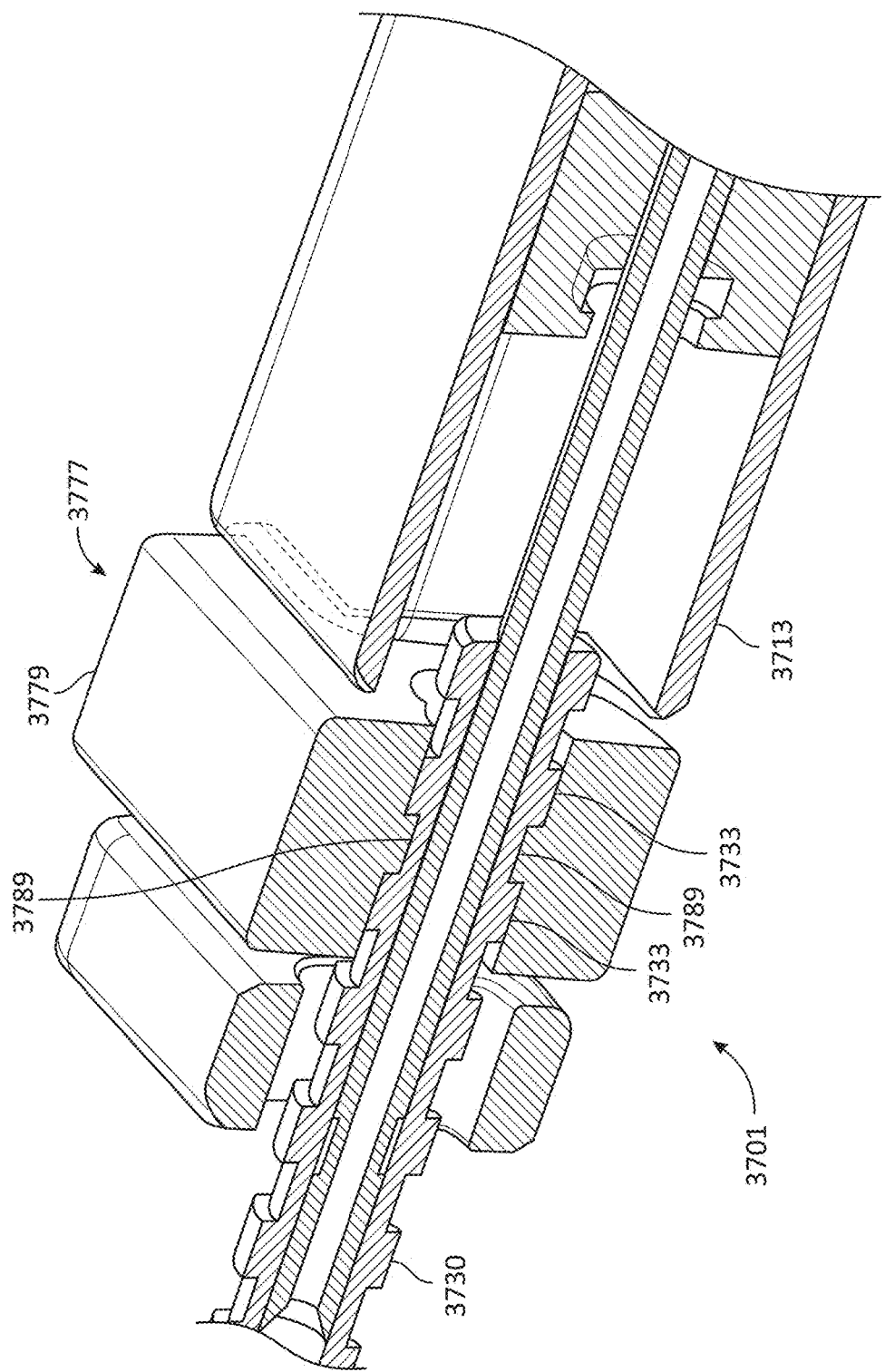

FIG. 37V schematically illustrates a perspective cross-sectional view of the handle of FIG. 37U along the line 37V-37V.

FIG. 38A is a perspective view of an example of a catheter system.

FIG. 38B is a perspective view of a portion of the catheter system of FIG. 38A in a collapsed state.

FIG. 38C is a side view of a portion of the catheter system of FIG. 38A in an expanded state.

FIG. 38D is a partial side cross-sectional view of an expandable structure.

FIG. 38E is a partial side cross-sectional view of an expandable structure.

FIG. 39A is a side view of an example of an expandable structure.

FIG. 39B is an end view of an example of another expandable structure.

FIG. 39C is an end view of an example of yet another expandable structure.

FIG. 39D is an end view of an example of still another expandable structure.

Figure 40B:
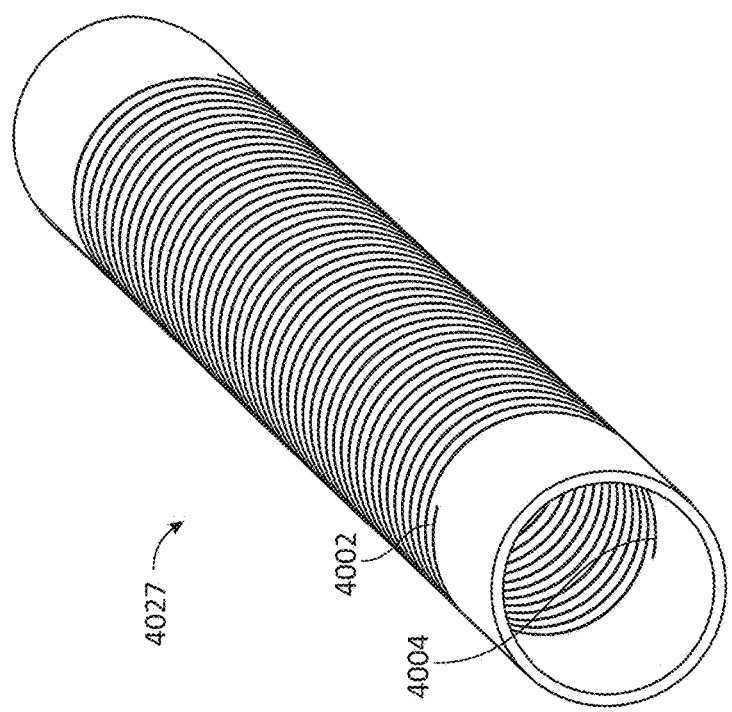
Figure 40A:
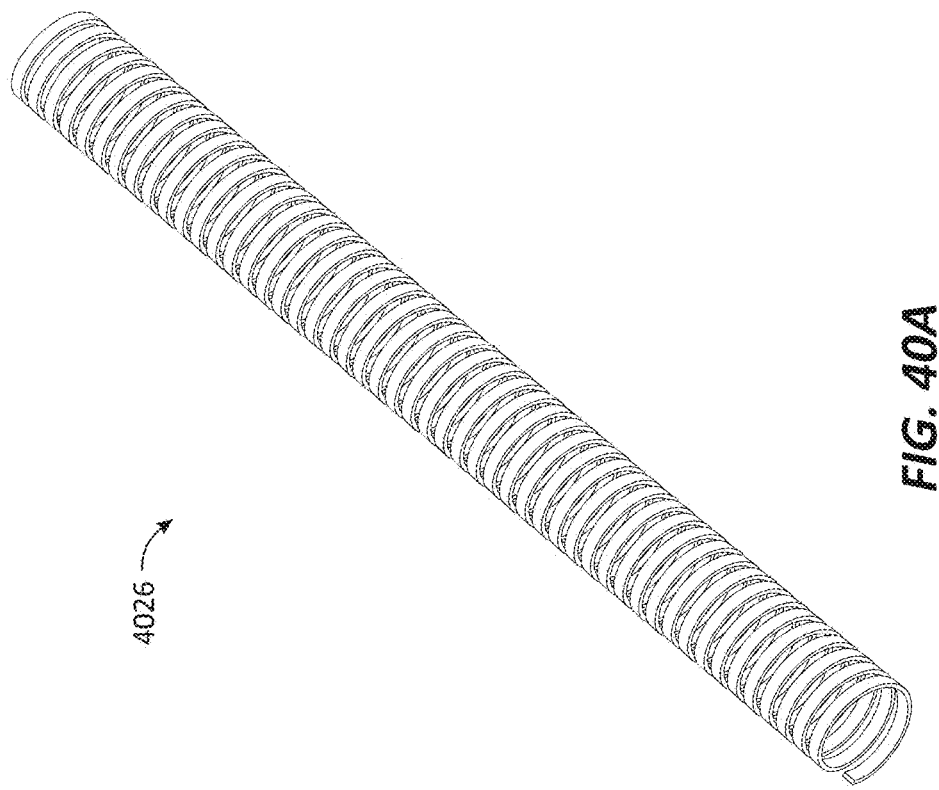

FIG. 40A is a perspective view of an example of a strain relief for a catheter system.

FIG. 40B is a perspective view of another example of a strain relief for a catheter system.

FIG. 41A is a perspective view of an example of a catheter system.

FIG. 41B is a perspective view of a portion of the catheter system of FIG. 41A in a collapsed and deflated state.

FIG. 41C is a transverse cross-sectional side view of the portion of FIG. 41B.

FIG. 41D is a side view of the portion of FIG. 41B in an inflated state.

FIG. 41E is a perspective view of the portion of FIG. 41B in an expanded state.

FIG. 41F schematically illustrates an expandable structure expanded in vasculature.

FIG. 41G schematically illustrates yet another example of an expandable structure expanded in vasculature.

FIG. 42A is a side view of an example of an electrode structure.

FIG. 42B is a side view of another example of an electrode structure.

FIG. 43A is a side view of an example of an electrode.

FIG. 43B is a side view of another example of an electrode.

FIG. 44A is a side view of an example of an electrode.

FIG. 44B is a side view of another example of an electrode.

Figure 45:
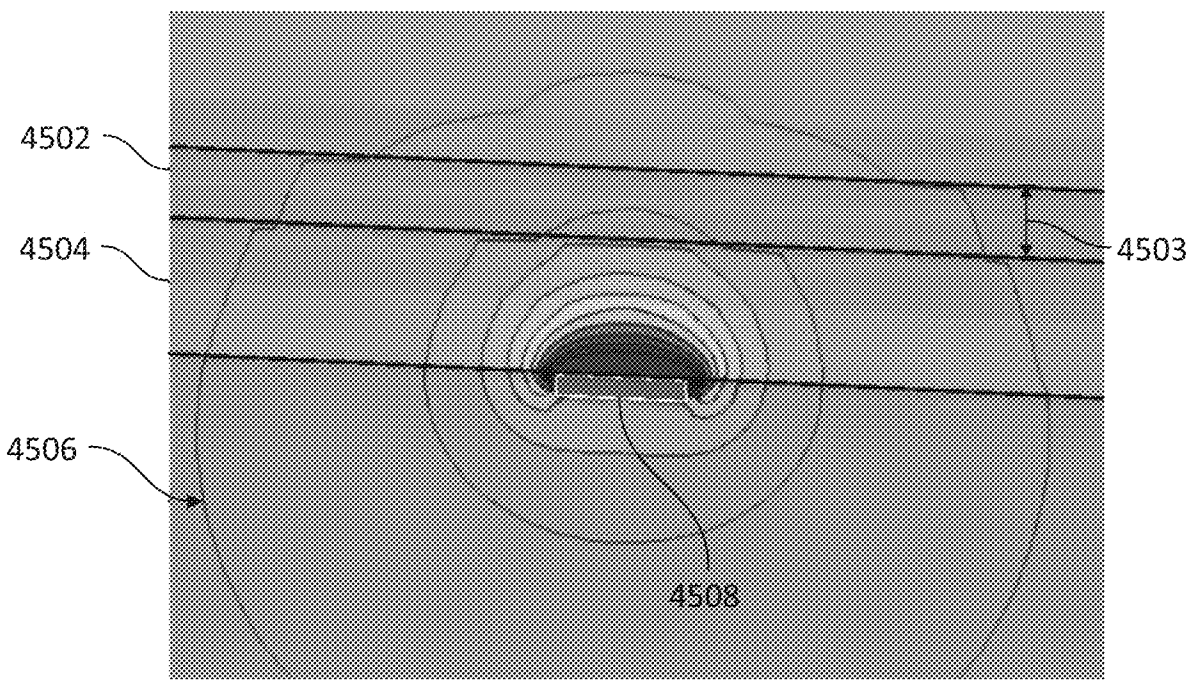

FIG. 45 is a diagram of neurostimulation of a nerve proximate to a vessel wall.

Figure 46A:
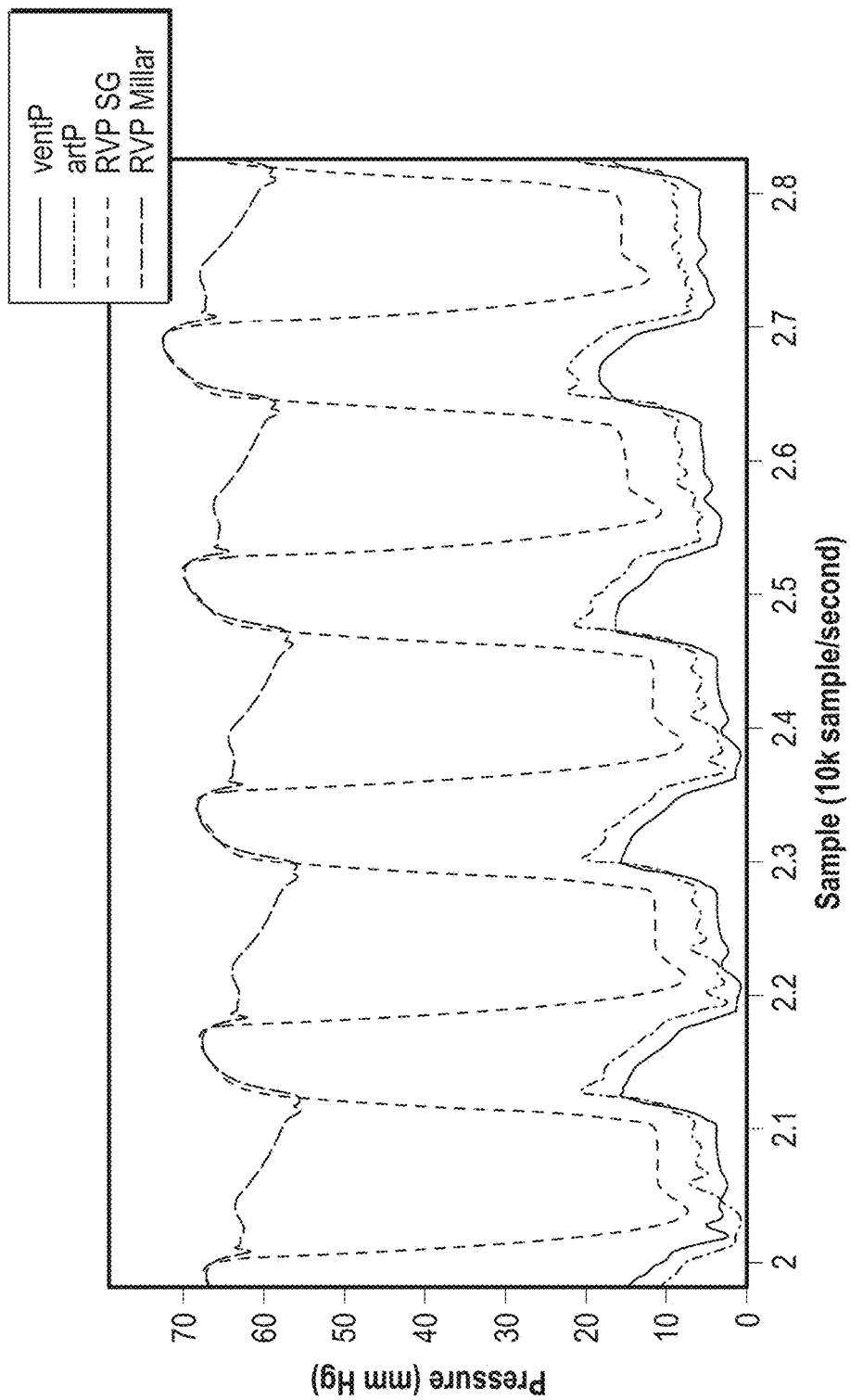

FIG. 46A is a graph showing the monitoring of left ventricle contractility and right ventricle contractility over time.

Figure 46B:
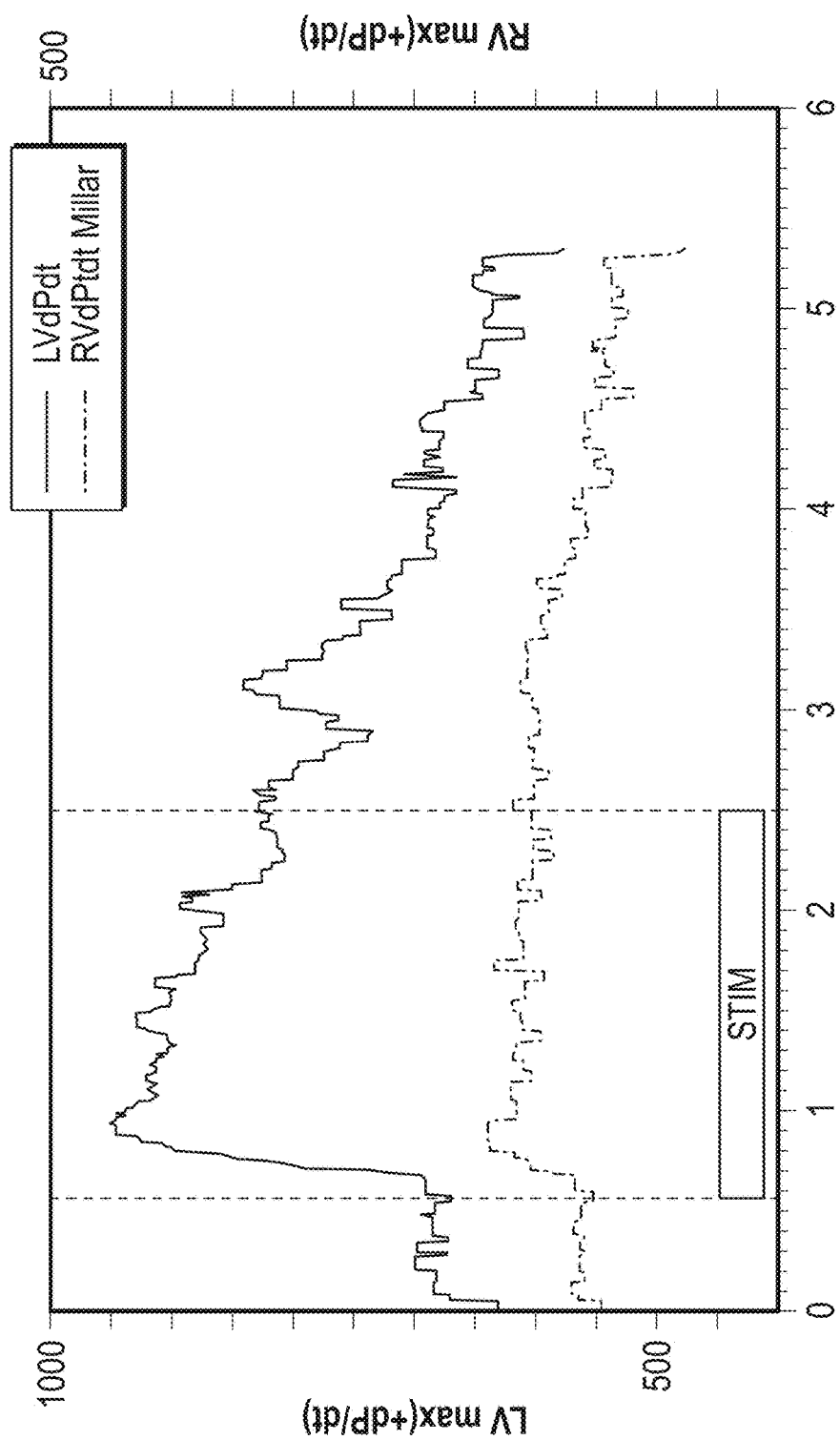

FIG. 46B is another graph showing the monitoring of left ventricle contractility and right ventricle contractility over time.

Figure 47D:
Figure 47E:
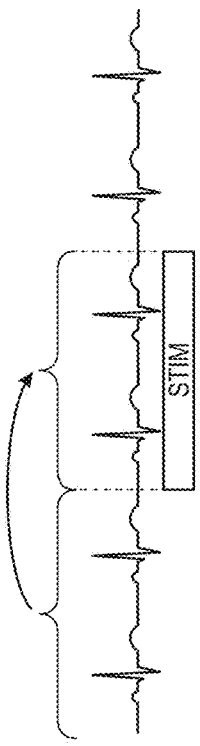
Figure 47F:
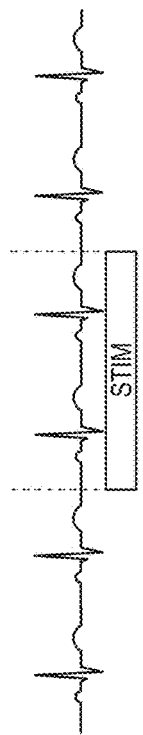
Figure 47G:
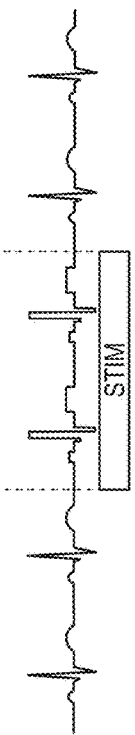
Figure 47A:
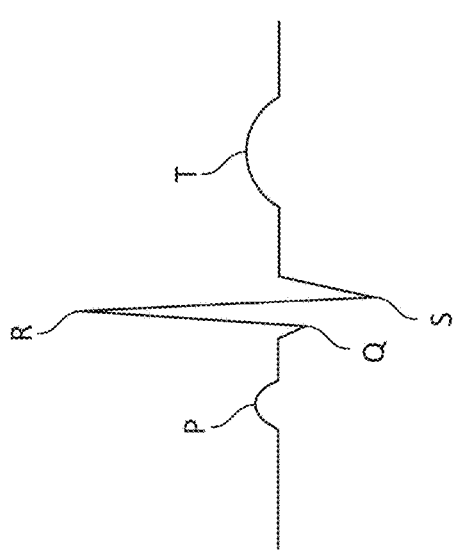

FIG. 47A schematically illustrates an example electrocardiograph.

Figure 47B:
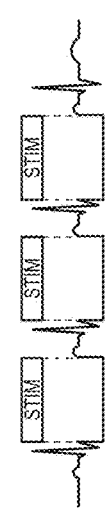

FIG. 47B is an example of a modified electrocardiograph.

Figure 47C:
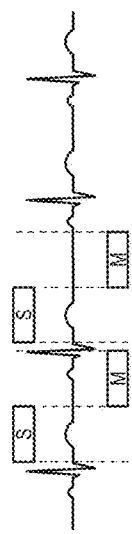

FIG. 47C is an example of a monitored electrocardiograph.

FIG. 47D is an example of a modified electrocardiograph.

FIG. 47E is another example of a modified electrocardiograph.

FIG. 47F is still another example of a modified electrocardiograph.

FIG. 47G is yet another example of a modified electrocardiograph.

Figure 48B:
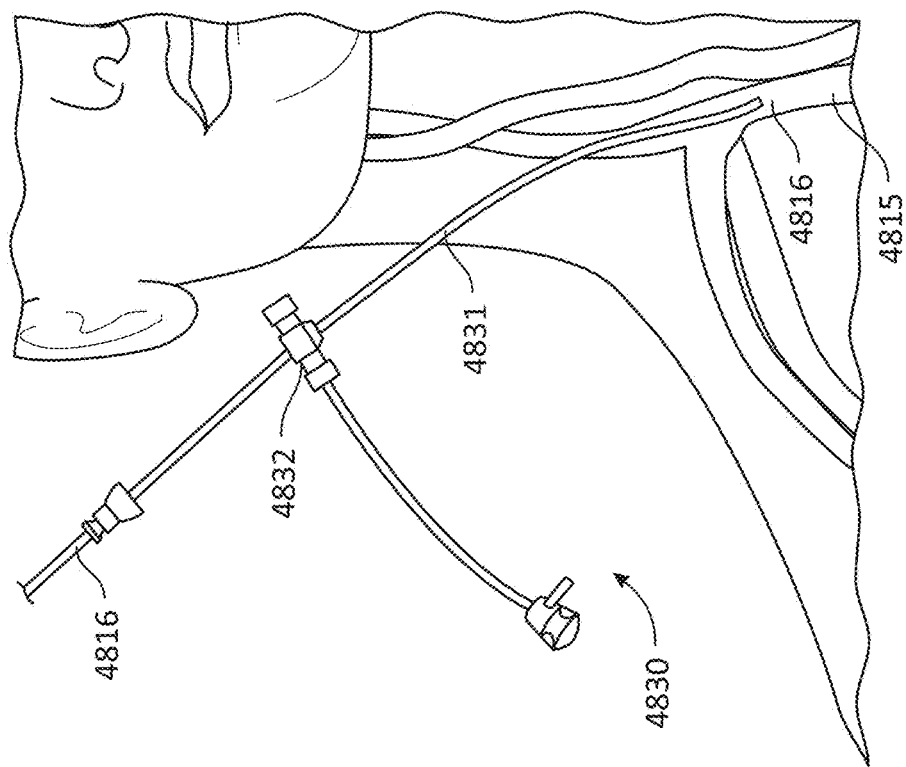
Figure 48A:
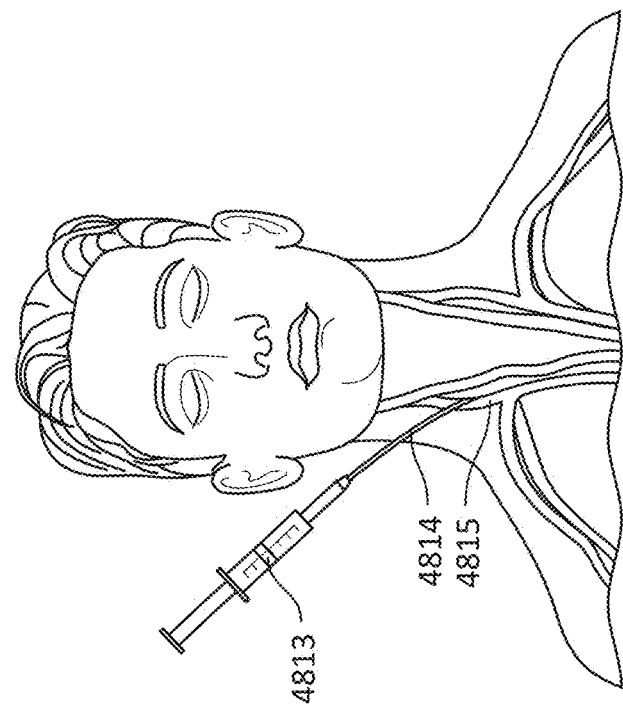

FIG. 48A illustrates insertion of a needle into vasculature.

FIG. 48B illustrates insertion of an introducer and guidewire into vasculature.

Figure 48D:
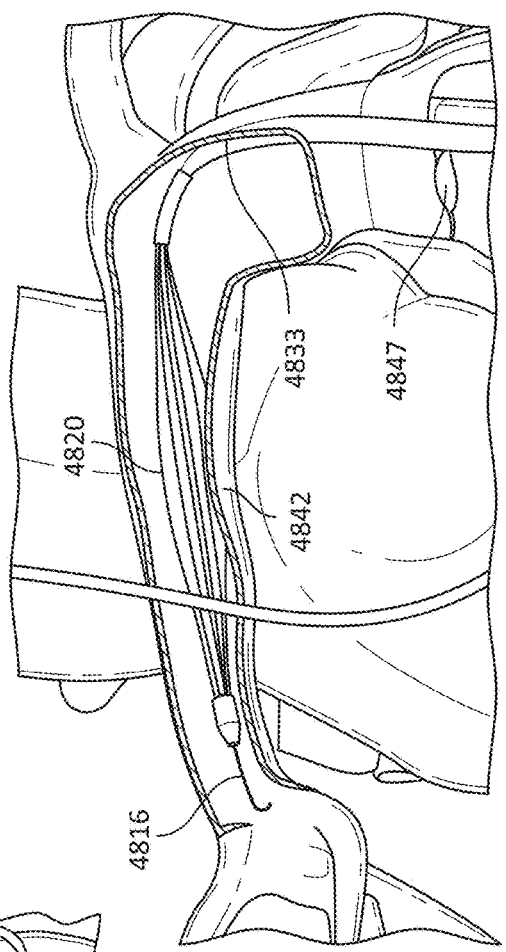
Figure 48C:
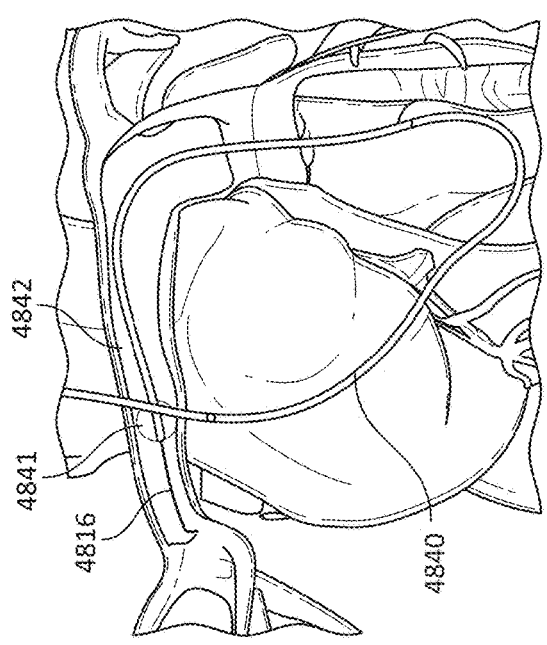

FIG. 48C illustrates a Swan-Ganz catheter and guidewire positioned in the right pulmonary artery.

FIG. 48D illustrates an example catheter system positioned in the right pulmonary artery in an expanded state.

Figure 48E:
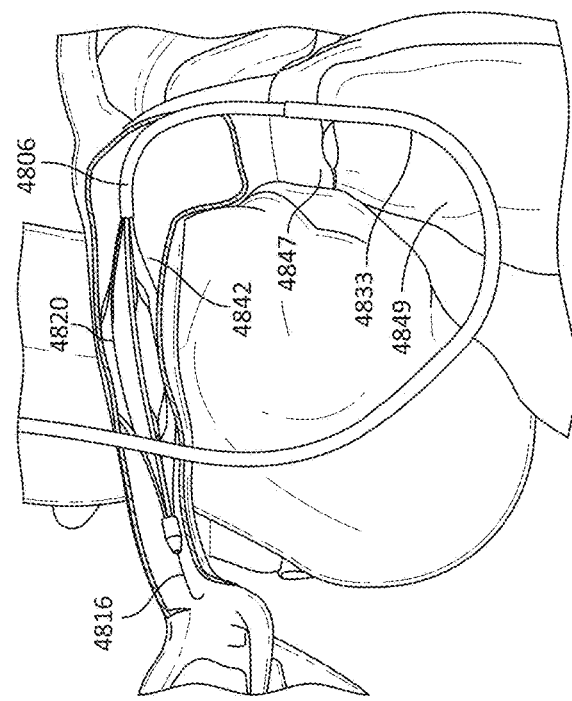

FIG. 48E illustrates the catheter system of FIG. 48D in a further expanded state.

Figure 48F:
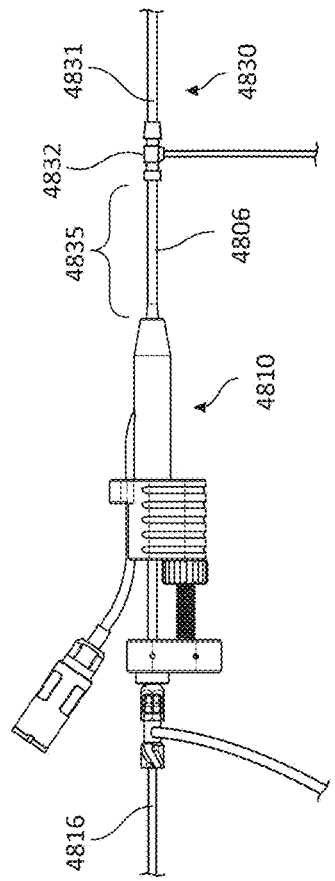

FIG. 48F is a side view of a portion of a catheter system inserted into an introducer.

Figure 48H:
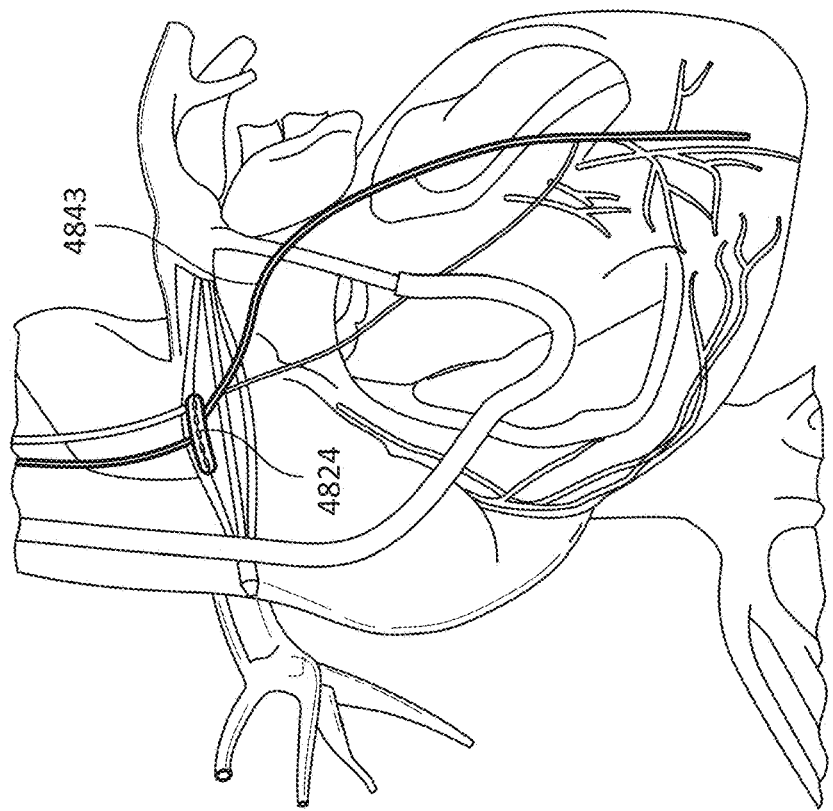
Figure 48G:
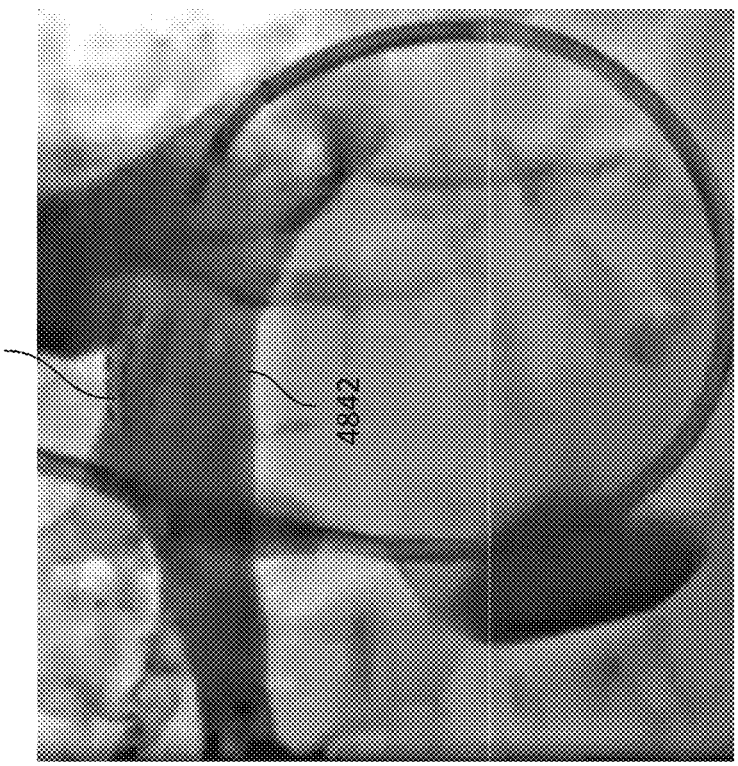

FIG. 48G is a fluoroscopic image of the catheter system positioned in the right pulmonary artery.

FIG. 48H schematically illustrates stimulation of a target nerve by the electrodes of a catheter system positioned in the right pulmonary artery.

DETAILED DESCRIPTION

Several embodiments of the present disclosure provide for methods and devices that can be used to apply electrical neuromodulation to one or more nerves in and around the heart of a subject (e.g., patient). Several embodiments, for example, may be useful in electrical neuromodulation of patients with cardiovascular medical conditions, such as patients with acute or chronic cardiac disease. As discussed herein, several embodiments can allow for a portion of a catheter to be positioned within the vasculature of the patient in at least one of the right pulmonary artery, the left pulmonary artery, and the pulmonary trunk. Once positioned, an electrode system of the catheter can provide electrical energy (e.g., electrical current or electrical pulses) to stimulate the autonomic nervous system surrounding (e.g., proximate to) the pulmonary artery in an effort to provide adjuvant cardiac therapy to the patient. Sensed heart activity properties (e.g., non-electrical heart activity properties) can be used as the basis for making adjustments to one or more properties of the one or more electrical pulses delivered through the catheter positioned in the pulmonary artery of the heart in an effort to provide adjuvant cardiac therapy to the patient.

Certain groups of figures showing similar items follow a numbering convention in which the first digit or digits correspond to the drawing figure number and the remaining digits identify an element or component in the drawing. Similar elements or components between such groups of figures may be identified by the use of similar digits. For example, 336 may reference element "36" in FIG. 3A, and a similar element "36" may be referenced as 436 in FIG. 4A. As will be appreciated, elements shown in the various embodiments herein can be added, exchanged, and/or eliminated so as to provide any number of additional embodiments of the present disclosure. Components or features described in connection with a previous figure may not be described in detail in connection with subsequent figures; however, the embodiments illustrated in the subsequent figures may include any of the components or combinations of components or features of the previous embodiments.

The terms "distal" and "proximal" are used herein with respect to a position or direction relative to the treating clinician taken along the devices of the present disclosure. "Distal" or "distally" are a position distant from or in a direction away from the clinician taken along the catheter. "Proximal" and "proximally" are a position near or in a direction toward the clinician taken along the catheter.

The catheter and electrode systems of the present disclosure can be used to treat a patient with various cardiac conditions. Such cardiac conditions include, but are not limited to, acute heart failure, among others. Several embodiments of the present disclosure provides methods that can be used to treat acute heart failure, also known as decompensated heart failure, by modulating the autonomic nervous system surrounding the pulmonary artery (e.g., the right pulmonary artery, the left pulmonary artery, the pulmonary trunk) in an effort to provide adjuvant cardiac therapy to the patient. The neuromodulation treatment can help by affecting heart contractility more than heart rate. In a preferred embodiment, the autonomic nervous system is modulated so as to collectively affect heart contractility more than heart rate. The autonomic nervous system can be impacted by electrical modulation that includes stimulating and/or inhibiting nerve fibers of the autonomic nervous system.

As discussed herein, the one or more electrodes present on the catheter can be positioned within the main pulmonary artery and/or one or both of the right and left pulmonary arteries. In accordance with several embodiments, the one or more electrodes are positioned in contact the luminal surface of the main pulmonary artery, and/or right or left pulmonary artery (e.g., in physical contact with the surface of the posterior portion of the main pulmonary artery). As will be discussed herein, the one or more electrodes on the catheter and/or catheter system provided herein can be used to provide pulse of electrical energy between the electrodes and/or the reference electrodes. The electrodes of the present disclosure can be used in any one of a unipolar, bi-polar and/or a multi-polar configuration. Once positioned, the catheter and the catheter system of the present disclosure can provide the stimulation electrical energy to stimulate the nerve fibers (e.g., autonomic nerve fibers) surrounding the main pulmonary artery and/or one or both of the right and left pulmonary arteries in an effort to provide adjuvant cardiac therapy to the patient (e.g., electrical cardiac neuromodulation).

In some embodiments, systems other than intravascular catheters may be used in accordance with the methods described herein. For example, electrodes, sensors, and the like may be implanted during open heart surgery or without being routed through vasculature.

Several embodiments, as will be discussed more fully herein, may allow for the electrical neuromodulation of the heart of the patient that includes delivering one or more electrical pulses through a catheter positioned in a pulmonary artery of the heart of the patient, sensing from at least a first sensor positioned at a first location within the vasculature of the heart one or more heart activity properties (e.g., non-electrical heart activity properties) in response to the one or more electrical pulses, and adjusting a property of the one or more electrical pulses delivered through the catheter positioned in the pulmonary artery of the heart in response to the one or more heart activity properties in an effort to provide adjuvant cardiac therapy to the patient.

The catheter can include a plurality of electrodes, which are optionally inserted into the pulmonary trunk, and positioned such that the electrodes are, preferably, in contact with the posterior surface, the superior surface, and/or the inferior surface of the pulmonary artery. From such locations, electrical pulses can be delivered to or from the electrodes to selectively modulate the autonomic nervous system of the heart. For example, electrical pulses can be delivered to or from one or more of the electrodes to selectively modulate the autonomic cardiopulmonary nerves of the autonomic nervous system, which can modulate heart contractility more than heart rate. Preferably, the plurality of electrodes is positioned at a site along the posterior wall and/or superior wall of the pulmonary artery, for example the right or left pulmonary artery. From such a position in the pulmonary artery, one or more electrical pulses can be delivered through the electrodes and one or more heart activity properties (e.g., non-electrical heart activity properties) can be sensed. Based at least in part on these sensed heart activity properties, a property of the one or more electrical pulses delivered to or from the electrodes positioned in the pulmonary artery of the heart can be adjusted in an effort to positively influence heart contractility while reducing or minimizing the effect on heart rate and/or oxygen consumption. In certain embodiments, the effect on heart contractility is to increase heart contractility.

Figure 1:
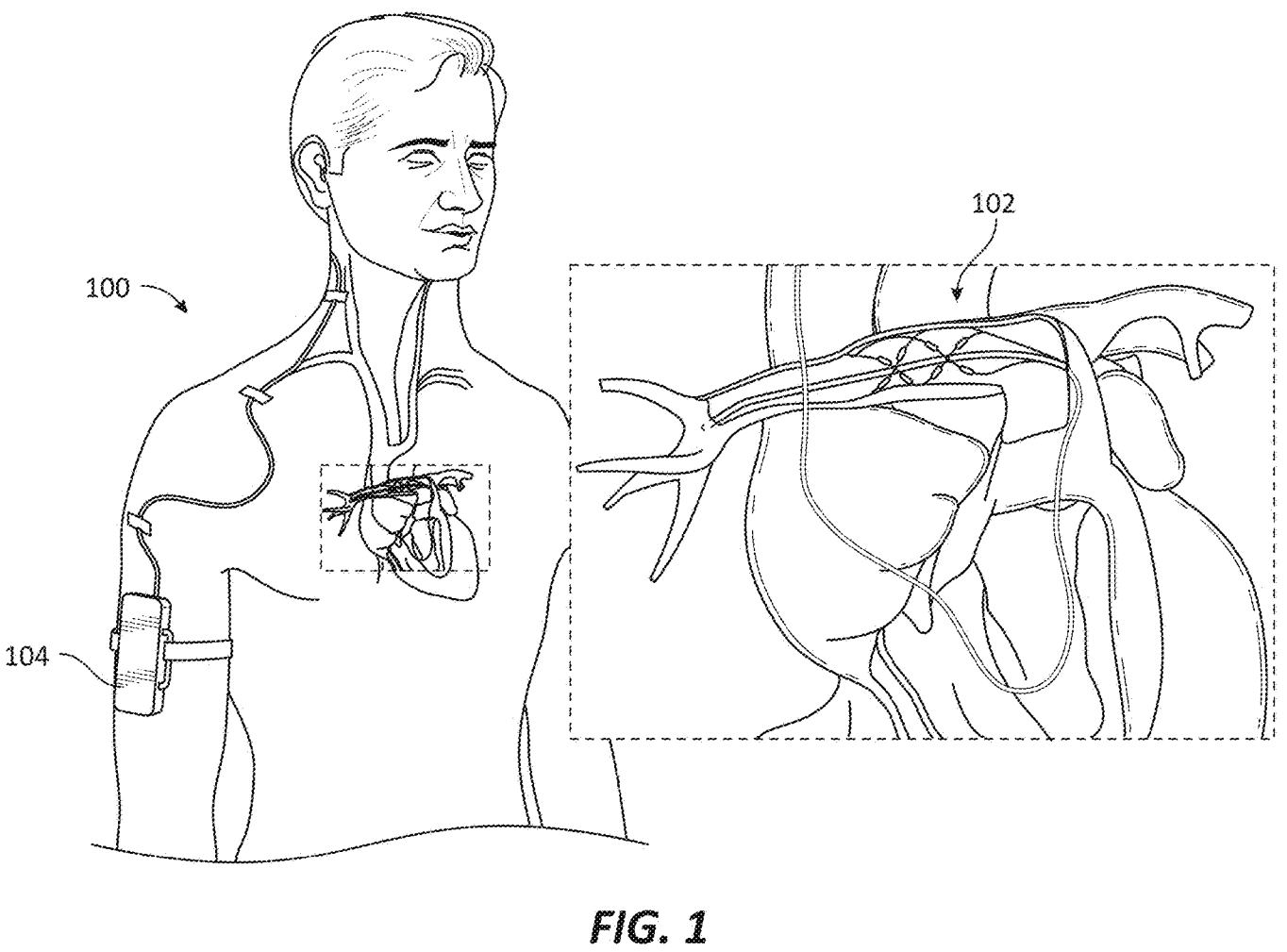
FIG. 1 schematically illustrates a system that can be used to apply electrical neuromodulation to one or more nerves in and around the heart of a subject.

FIG. 1 schematically illustrates a system 100 that can be used to apply electrical neuromodulation to tissue (e.g., including one or more nerves) in and around the heart of a subject. The system 100 comprises a first component 102 and a second component 104. The first component 102 may be positioned in a pulmonary artery (e.g., the right pulmonary artery as shown in FIG. 1, the left pulmonary artery, and/or the pulmonary trunk). The first component 102 may be endovascularly positioned via a minimally invasive, transdermal, percutaneous procedure, for example routed through the vasculature from a remote location such as a jugular vein (e.g., an internal jugular vein, as shown in FIG. 1), an axial subclavian vein, a femoral vein, or other blood vessels. Such an approach can be over-the-wire, using a Swan-Ganz float catheter, combinations thereof, etc. In some embodiments, the first component may be positioned invasively, for example during conventional surgery (e.g., open-heart surgery), placement of another device (e.g., coronary bypass, pacemaker, defibrillator, etc.), or as a stand-alone procedure. As described in further detail herein, the first component comprises a neuromodulator (e.g., electrode, transducer, drug, ablation device, ultrasound, microwave, laser, cryo, combinations thereof, and the like) and may optionally comprise a stent or framework, an anchoring system, and/or other components. The first component 102 may be acutely positioned in the pulmonary artery for 24 to 72 hours. In some embodiments, the first component 102 neuromodulates terminal branches within the cardiac plexus, which can increase left ventricle contractility. The increase in left ventricle contractility may be without an increase in heart rate or may be greater than (e.g., based on a percentage change) than an increase in heart rate. In some embodiments, the first component 102 may be adapted to ablate tissue, including nerves, in addition to or instead of modulating tissue such as nerves.

The first component 102 is electrically coupled to the second component 104 (e.g., via wires or conductive elements routed via a catheter, for example as illustrated in FIG. 1, and/or wirelessly). The second component 104 may be positioned extracorporeally (e.g., strapped to a subject's arm as shown in FIG. 1, strapped to another part of the subject (e.g., leg, neck, chest), placed on a bedside stand, etc.). In some embodiments, the second component 104 may be temporarily implanted in the subject (e.g., in a blood vessel, in another body cavity, in a chest, etc.). The second component 104 includes electronics (e.g., pulse generator) configured to operate the electrode in the first component 102. The second component 104 may include a power supply or may receive power from an external source (e.g., a wall plug, a separate battery, etc.). The second component 104 may include electronics configured to receive sensor data.

The system 100 may comprise a sensor. The sensor may be positioned in one or more of a pulmonary artery (e.g., right pulmonary artery, left pulmonary artery, and/or pulmonary trunk), an atrium (e.g., right and/or left), a ventricle (e.g., right and/or left), a vena cava (e.g., superior vena cava and/or inferior vena cava), and/or other cardiovascular locations. The sensor may be part of the first component 102, part of a catheter, and/or separate from the first component 102 (e.g., electrocardiogram chest monitor, pulse oximeter, etc.). The sensor may be in communication with the second component 104 (e.g., wired and/or wireless). The second component 104 may initiate, adjust, calibrate, cease, etc. neuromodulation based on information from the sensor.

The system 100 may comprise an "all-in-one" system in which the first component 102 is integral or monolithic with the targeting catheter. For example, the first component 102 may be part of a catheter that is inserted into an internal jugular vein, an axial subclavian vein, a femoral vein, etc. and navigated to a target location such as the pulmonary artery. The first component 102 may then be deployed from the catheter. Such a system can reduce the number and/or complexity of procedural steps and catheter exchanges used to position the first component 102. For example, a guidewire may be at least twice as long as a target catheter, which can be difficult to control in a sterile field. Such a system may make repositioning of the first component 102 easier after an initial deployment because positioning systems are already in place.

The system 100 may comprise a telescoping and/or over-the-wire system in which the first component 102 is different than the targeting catheter. For example, a targeting catheter (e.g., a Swan-Ganz catheter) may be inserted into an internal jugular vein, an axial subclavian vein, a femoral vein, etc. and navigated to a target location such as the pulmonary artery (e.g., by floating). A guidewire may be inserted into a proximal hub through the target catheter to the target location (e.g., having a stiffest portion exiting the target catheter distal end) and the first component 102 as part of a separate catheter than the target catheter may be tracked to the target location over the guidewire or using telescoping systems such as other guidewires, guide catheters, etc. The first component 102 may then be deployed from the separate catheter. Such systems are known by interventional cardiologists such that multiple exchanges may be of little issue. Such a system may allow customization of certain specific functions. Such a system may reduce overall catheter diameters, which can increase trackability, and/or allow additional features to be added, for example because not all functions are integrated into one catheter. Such a system may allow use of multiple catheters (e.g., removing a first separate catheter and positioning a second separate catheter without having to reposition the entire system). For example, catheters with different types of sensors may be positioned and removed as desired. The system 100 may be steerable (e.g., comprising a steerable catheter) without a Swan-Ganz tip. Some systems 100 may be compatible with one or more of the described types of systems (e.g., a steerable catheter with an optionally inflatable balloon for Swan-Ganz float, a steerable catheter that can be telescoped over a guidewire and/or through a catheter, etc.).

Figure 2B:
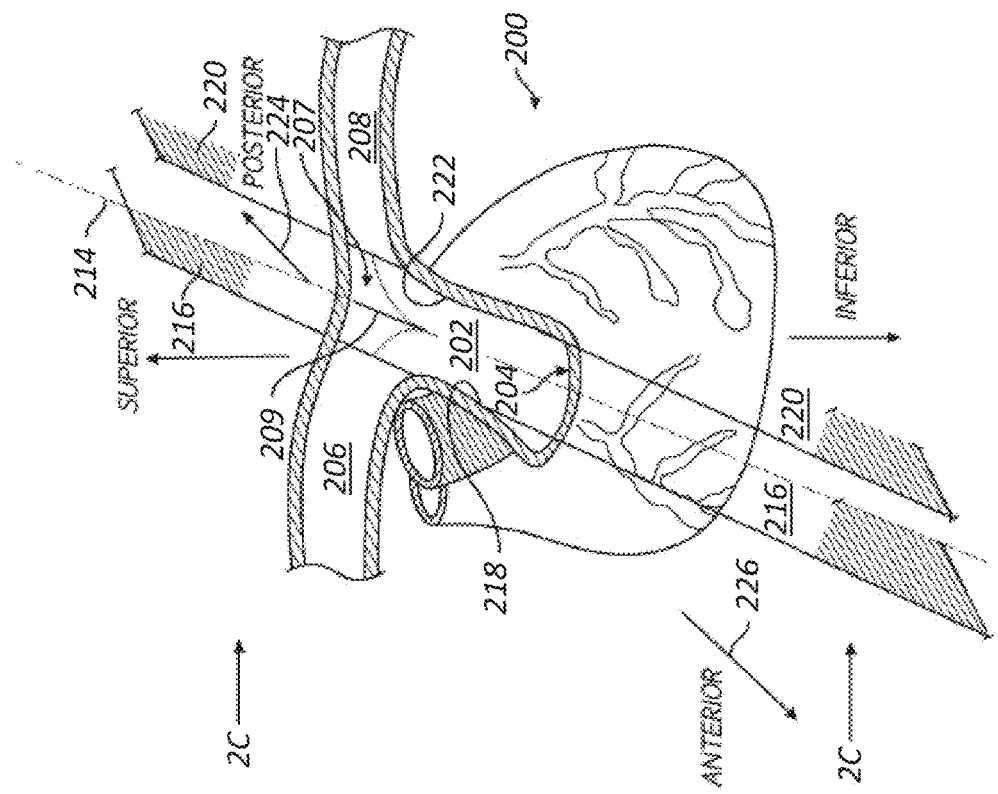
FIGS. 2B-2D are schematic illustrations of a heart and surrounding areas from various perspectives.
Figure 2A:
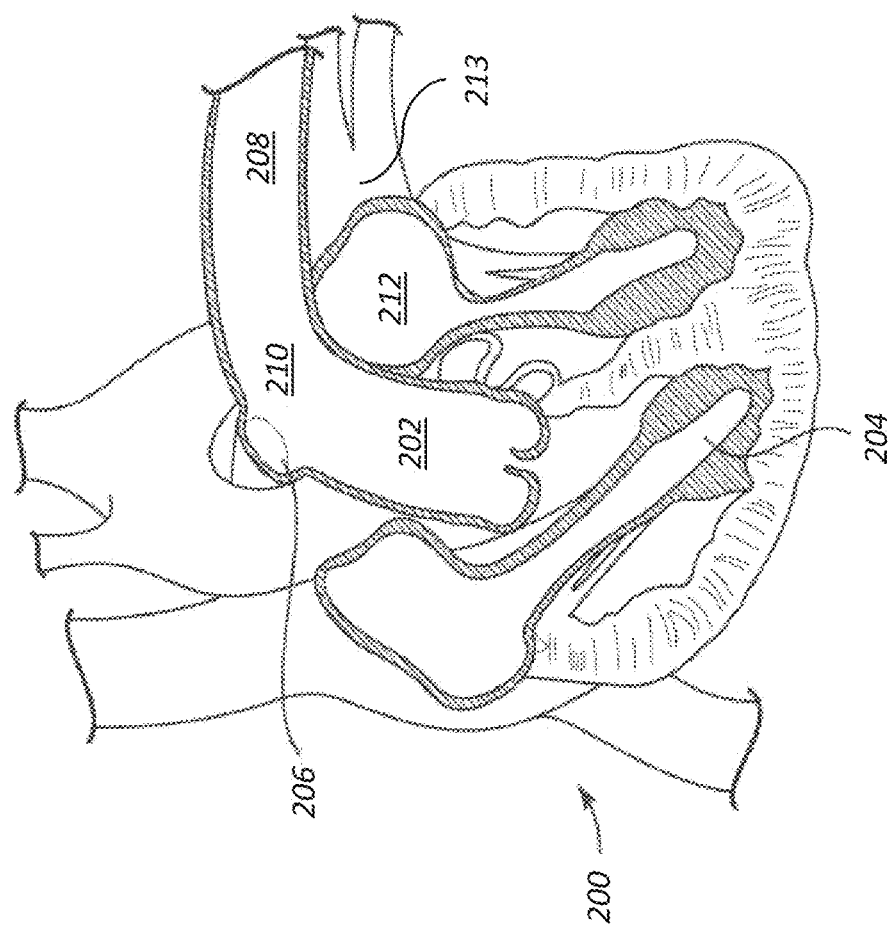
FIG. 2A schematically illustrates a heart and surrounding areas.

FIG. 2A schematically illustrates a heart 200 and surrounding areas. The main pulmonary artery or pulmonary trunk 202 begins at the outlet of the right ventricle 204. In an adult, the pulmonary trunk 202 is a tubular structure having a diameter of about 3 centimeter (cm) (approx. 1.2 inches (in)) and a length of about 5 (approx. 2.0 in). The main pulmonary artery 202 branches into the right pulmonary artery 206 and the left pulmonary artery 208, which deliver deoxygenated blood to the corresponding lung. As illustrated in FIG. 2A, the main pulmonary artery 202 has a posterior surface 210 that arches over the left atrium 212 and is adjacent to the pulmonary vein 213. As discussed herein, a neurostimulator can be positioned at least partially in a pulmonary artery 202, 206, 208, for example with the neurostimulator in contact with the posterior surface 210. In some embodiments, a preferred location for positioning the neurostimulator is the right pulmonary artery 204. PCT Patent App. No. PCT/US2015/047780 and U.S. Provisional Patent App. No. 62/047,313 are incorporated herein by reference in their entirety, and more specifically the descriptions of positioning in the right pulmonary artery disclosed therein are incorporated herein by reference. In some embodiments, a preferred location for positioning the neurostimulator is in contact with the posterior surface 210 of the pulmonary artery 202, 206, 208. From such a location, stimulation electrical energy delivered from an electrode, for example, may be better able to treat and/or provide therapy (including adjuvant therapy) to a subject experiencing a variety of cardiovascular medical conditions, such as acute heart failure. Other locations for the neurostimulator in the pulmonary artery 202, 206, 208 are also possible.

The first component 102 (FIG. 1) can be positioned in the pulmonary artery 202, 206, 208 of the subject, where the neurostimulator of the first component 102 is in contact with the luminal surface of the pulmonary artery 202, 206, 208 (e.g., in physical contact with or proximate to the surface of the posterior portion 210 of the pulmonary artery 202, 206, 208). The neurostimulator of the first component 102 can be used to deliver the stimulation to the autonomic cardiopulmonary fibers surrounding the pulmonary artery 202, 206, 208. The stimulation electrical energy can elicit responses from the autonomic nervous system that may help to modulate a subject's cardiac contractility. The stimulation may affect contractility more than the heart rate, which can improve hemodynamic control while possibly reducing unwanted systemic effects.

In some embodiments, neuromodulation of targeted nerves or tissue as described herein can be used for the treatment of arrhythmia, atrial fibrillation or flutter, diabetes, eating disorders, endocrine diseases, genetic metabolic syndromes, hyperglycemia (including glucose tolerance), hyperlipidemia, hypertension, inflammatory diseases, insulin resistance, metabolic diseases, obesity, ventricular tachycardia, conditions affecting the heart, and/or combinations thereof.

Figure 2D:
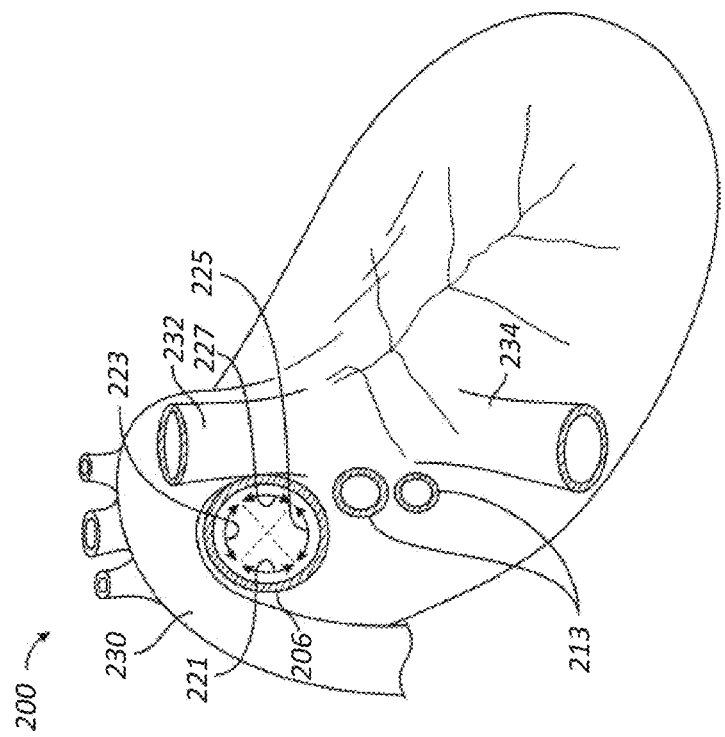
Figure 2C:
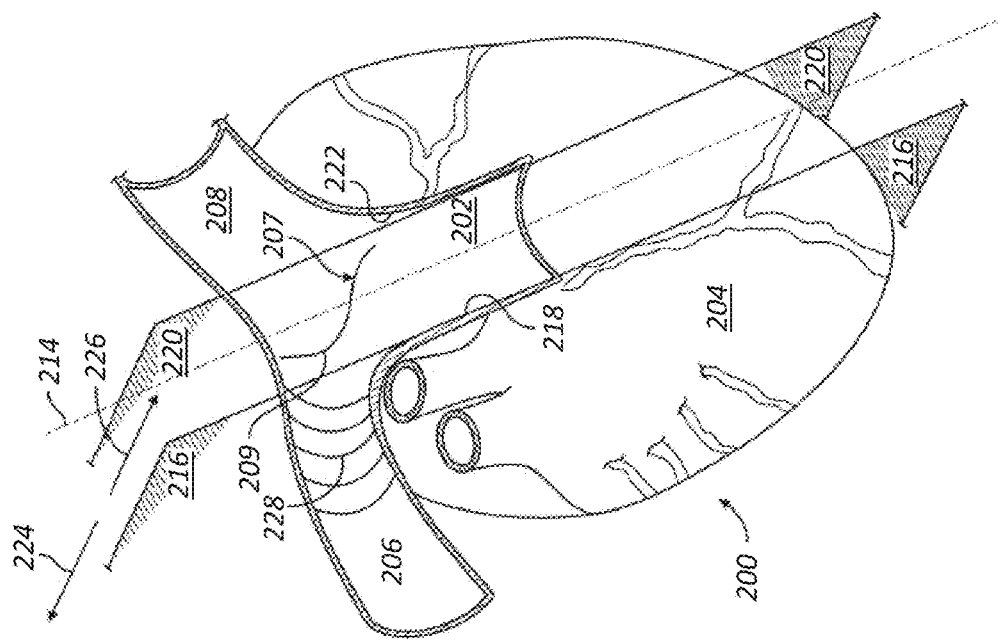

FIGS. 2B-2D are schematic illustrations of a heart 200 and surrounding areas from various perspectives. Portions of the heart 200 (e.g., the aorta, the superior vena cava, among other structures), including a portion of the pulmonary trunk 202, have been removed to allow for the details discussed herein to be shown. FIG. 2B provides a perspective view of the heart 200 as seen from the front of the subject or patient (viewed in an anterior to posterior direction), while FIG. 2C provides a perspective view of the heart 200 as seen from the right side of the subject. As illustrated, the heart 100 includes the pulmonary trunk 102 that begins at the base of the right ventricle 104. In an adult, the pulmonary trunk 102 is a tubular structure approximately 3 centimeters (cm) in diameter and 5 cm in length. The pulmonary trunk 202 branches into the right pulmonary artery 206 and the left pulmonary artery 208 at a branch point or bifurcation 207. The left pulmonary artery 106 and the right pulmonary artery 108 serve to deliver de-oxygenated blood to each corresponding lung.

The branch point 207 includes a ridge 209 that extends from the posterior of the pulmonary trunk 202. As illustrated, the branch point 207, along with the ridge 209, provides a "Y" or "T" shaped structure that helps to define at least a portion of the left pulmonary artery 208 and the right pulmonary artery 206. For example, from the ridge 209, the branch point 207 of the pulmonary trunk 202 slopes in opposite directions. In a first direction, the pulmonary trunk 202 transitions into the left pulmonary artery 208, and in the second direction, opposite the first direction, the pulmonary trunk 202 transitions into the right pulmonary artery 206. The branch point 207 may not necessarily be aligned along a longitudinal center line 214 of the pulmonary trunk 202.

As illustrated in FIG. 2B, portions of the pulmonary artery 202 can be defined with a right lateral plane 216 that passes along a right luminal surface 218 of the pulmonary trunk 202, a left lateral plane 220 parallel with the right lateral plane 216, where the left lateral plane 220 passes along a left luminal surface 222 of the pulmonary trunk 202. The right lateral plane 216 and the left lateral plane 220 extend in both a posterior direction 224 and anterior direction 226. As illustrated, the ridge 209 of the branch point 207 is located between the right lateral plane 216 and the left lateral plane 220. The branch point 207 is positioned between the right lateral plane 216 and the left lateral plane 220, where the branch point 207 can help to at least partially define the beginning of the left pulmonary artery 208 and the right pulmonary artery 206 of the heart 200. The distance between the right lateral plane 216 and the left lateral plane 220 is approximately the diameter of the pulmonary trunk 202 (e.g., about 3 cm).

As discussed herein, the present disclosure includes methods for neuromodulation of the heart 200 of a subject or patient. For example, as discussed herein, a catheter positioned in the pulmonary artery 202 can be used to deliver one or more electrical pulses to the heart 200. A first sensor, for example as discussed herein, positioned at a first location within the vasculature of the heart 200, senses a heart activity property in response to the neurostimulation. Properties of the neurostimulator can be adjusted in response to the sensed heart activity property in an effort to provide adjuvant cardiac therapy to the patient.

FIG. 2D provides an additional illustration the posterior surface 221, the superior surface 223, and the inferior surface 225 of the right pulmonary artery 206. As illustrated, the view of the heart 200 in FIG. 2D is from the right side of the heart 200. As illustrated, the posterior surface 221, the superior surface 223, and the inferior surface 225 account for approximately three quarters of the luminal perimeter of the right pulmonary artery 206, where the anterior surface 227 accounts for the remainder. FIG. 2D also illustrates the aorta 230, pulmonary veins 213, the superior vena cava (SVC) 232, and the inferior vena cava (IVC) 234.

Figure 2E:
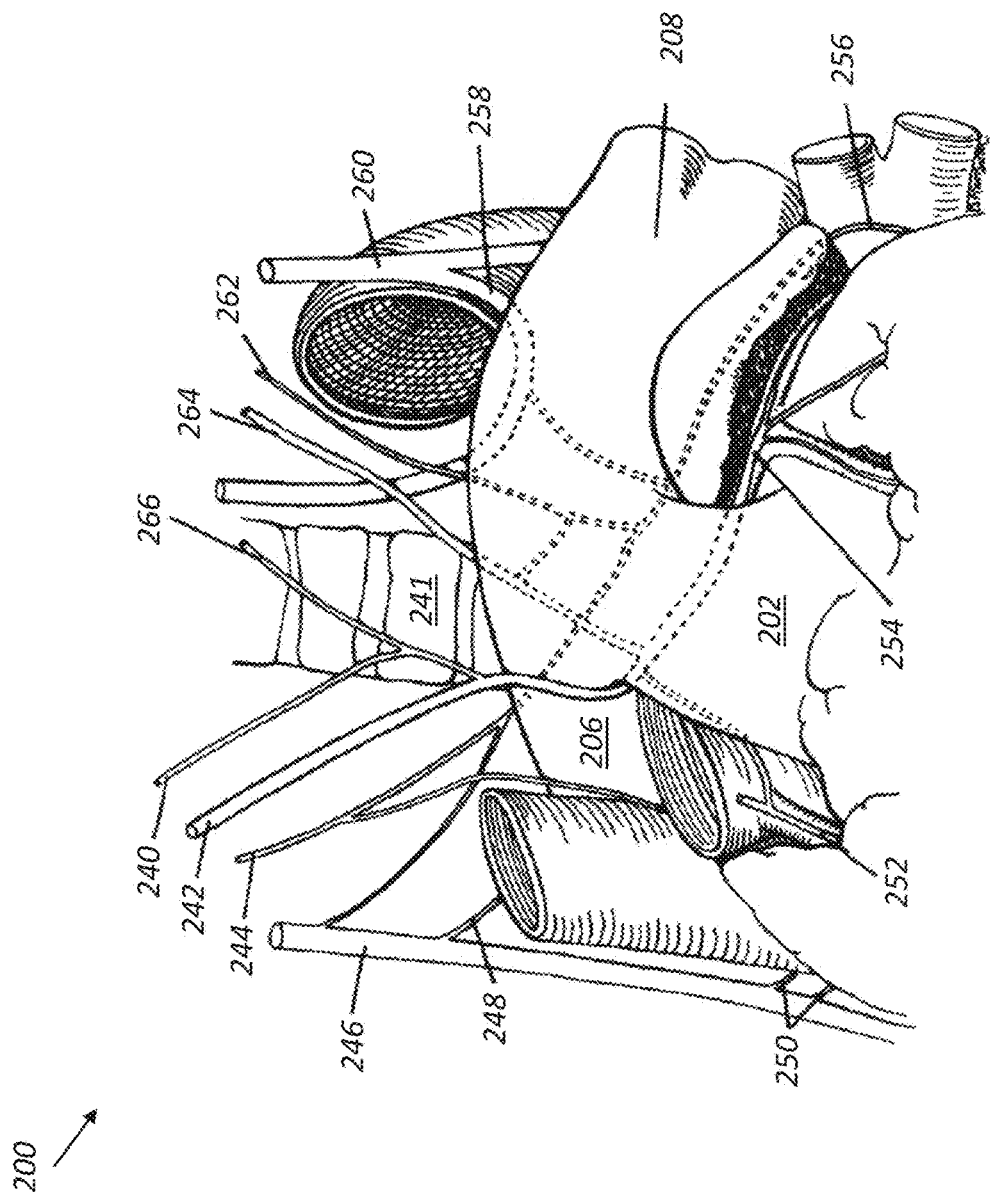
FIGS. 2E and 2F are schematic illustrations of a heart and surrounding nerves.
Figure 2F:
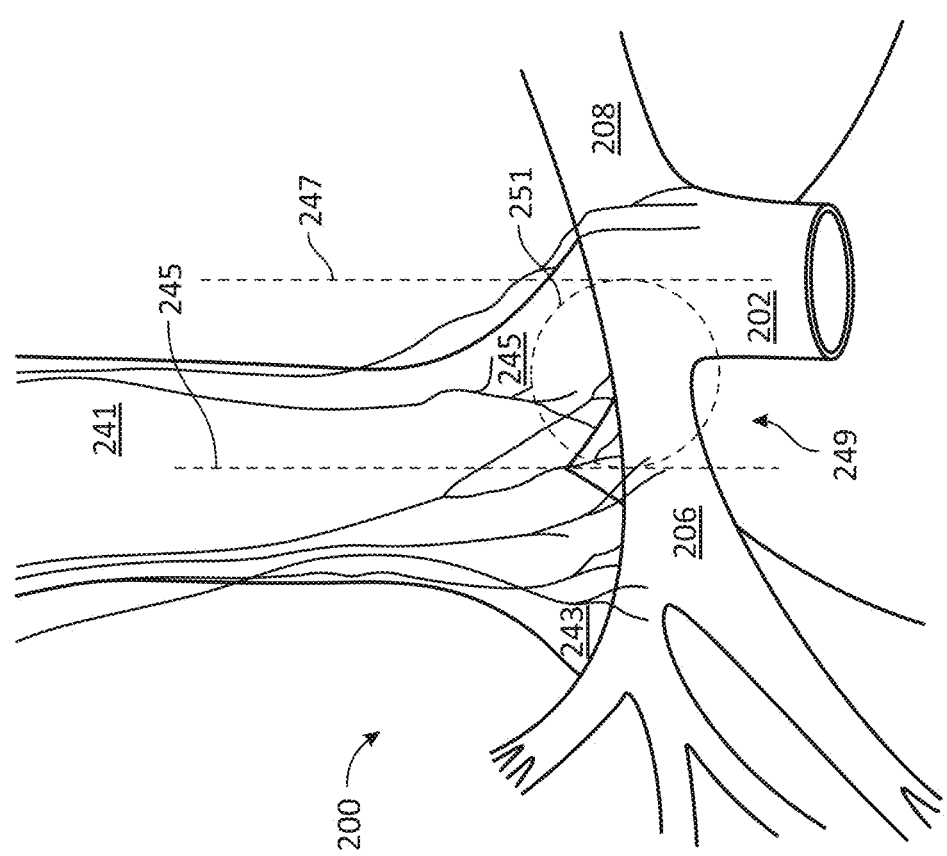

FIGS. 2E and 2F are schematic illustrations of a heart 200 and surrounding nerves. The cardiovascular system is richly innervated with autonomic fibers. Sympathetic fibers originate from stellate and thoracic sympathetic ganglia, and are responsible for increases in the chronotropic (heart rate), lusotropic (relaxation), and inotropic (contractility) state of the heart. Human cadaver anatomical studies show that the fibers responsible for the lusotropic and inotropic state of the ventricles pass along the posterior surface of the right pulmonary artery 206 and the pulmonary trunk 202. FIG. 2E illustrates approximate positions of the right dorsal medial common peroneal nerve (CPN) 240, the right dorsal lateral CPN 242, the right stellate CPN 244, the right vagal nerve or vagus 246, the right cranial vagal CPN 248, the right caudal vagal CPN 250, the right coronary cardiac nerve 252, the left coronary cardiac nerve 254, the left lateral cardiac nerve 256, the left recurrent laryngeal nerve 258, the left vagal nerve or vagus 260, the left stellate CPN 262, the left dorsal lateral CPN 264, and the left dorsal medial CPN 266. These and/or other nerves surrounding (e.g., proximate to) the heart 200 can be targeted for neurostimulation by the systems and methods described herein. In some embodiments, at least one of the right dorsal medial common peroneal nerve 240, the right stellate CPN 244, and the left lateral cardiac nerve 256 is targeted and/or affected for neuromodulation, although other nerves, shown in FIG. 2E or otherwise, may also be targeted and/or affected.

FIGS. 2E and 2F also schematically illustrate the trachea 241. As best seen in FIG. 2F, the trachea 241 bifurcates into the right pulmonary bronchus 243 and the left pulmonary bronchus 241. The bifurcation of the trachea 241 can be considered along a plane 245. The plane 245 is along the right pulmonary artery 206. The bifurcation of the pulmonary artery can be considered along a plane 247, which is spaced from the plane 245 by a gap 249. The gap 249 spans the right pulmonary artery 206. A large number of cardiac nerves cross the right pulmonary artery 206 along the gap 249 as illustrated by the circled area 251, and these nerves may be advantageously targeted by some of the systems and methods described herein. In certain such embodiments, the bifurcation of the trachea 241 and/or the bifurcation of the pulmonary artery 202 may provide a landmark for system and/or component positioning. Stimulation electrodes may be spaced from the trachea 241, for example to reduce cough or other possible respiratory side effects. In some embodiments, stimulation electrodes are spaced from the trachea 241 or the plane 245 by between about 2 mm and about 8 mm (e.g., about 2 mm, about 3 mm, about 4 mm, about 5 mm, about 6 mm, about 7 mm, about 8 mm, ranges between such values, etc.). In some embodiments, stimulation electrodes are spaced from the trachea 241 or the plane 245 by a percentage of a length of the right pulmonary artery 206 between about 10% and about 100% (e.g., about 10%, about 25%, about 30%, about 35%, about 40%, about 45%, about 50%, about 55%, about 75%, about 100%, ranges between such values, etc.).

FIGS. 2G and 2H are schematic illustrations of vasculature and an electrode matrix 201. A majority of the electrode matrix 201 is positioned in the right pulmonary artery 206, although some of the electrode matrix 201 may be considered positioned in the pulmonary trunk 202. The electrode array is shown as a 4×5 matrix of electrodes 203. As described in further detail herein, the electrodes 203 may be positioned on splines, positioned on a membrane or mesh coupled to splines, etc. For example, four splines may each contain five electrodes 203. In some embodiments, the electrodes 203 comprise bipolar electrodes with controllable polarity, allowing configurability of the electrode matrix 201. In some embodiments, edge-to-edge spacing of the electrodes 203 is between about 3 mm and about 7 mm (e.g., about 3 mm, about 4 mm, about 5 mm, about 6 mm, about 7 mm, ranges between such values, etc.). In some embodiments, the electrodes 203 have a surface area between about 0.5 mm$^2$ and about 5 mm$^2$ (e.g., about 0.5 mm$^2$, about 1 mm$^2$, about 1.5 mm$^2$, about 2 mm$^2$, about 2.5 mm$^2$, about 3 mm$^2$, about 3.5 mm$^2$, about 4 mm$^2$, about 4.5 mm$^2$, about 5 mm$^2$, ranges between such values, etc.). The electrodes 203 are generally aligned longitudinally and circumferentially, but offset electrodes 203 are also possible. The coverage of the right pulmonary artery 206 provided by the electrode array 201 is longitudinally between about 25 mm and about 35 mm (e.g., about 25 mm, about 28 mm, about 31 mm, about 35 mm, ranges between such values, etc.) and is circumferentially between about 80° and about 120° (e.g., about 80°, about 90°, about 100°, about 110°, about 120°, ranges between such values, etc.). The electrode array 201 may cover, for example, between about 25% and about 50% (e.g., about 25%, about 30%, about 35%, about 40%, about 45%, about 50%, ranges between such values, etc.) of the circumference of the vessel. In some embodiments, the electrode array 201 comprises a 3×3 matrix, a 3×4 matrix, a 3×5 matrix, a 4×4 matrix, a 4×5 matrix, or a 5×5 matrix. Larger matrices may be more likely to capture the target nerve by at least one combination of electrodes 203, and smaller matrices may be easier to deliver to the target site.

FIG. 2I is a schematic illustration of heart vasculature and surrounding nerves. Similar to FIGS. 2G and 2H, FIG. 2I shows a pulmonary trunk 202, a right pulmonary artery 206, and a left pulmonary artery 208. FIG. 2I also shows traces of the approximate crossing locations of interventricular sulcus nerves 215, 217 along the right pulmonary artery 206 and the pulmonary trunk 202. Stimulation of one or both of the nerves 215, 217 may increase contractility, for example more than heart rate or without affecting heart rate. The electrode matrix 201, including electrodes 203a, 203b, 203c, 203d, 203e, 203f, etc., is shown in phantom in the approximate position of FIGS. 2G and 2H.

In some embodiments, particular electrodes can be selected to target or capture one or more nerves. The electrodes 203a, 203b can be used to target the nerve 215, for example, in a generally transverse manner. The electrodes 203a, 203c can be used to target the nerve 215, for example, in a generally parallel manner. The electrodes 203c, 203d can be used to target the nerve 215 as well as the nerve 217, for example, in a generally transverse manner. The electrodes 203e, 203f can be used to target the nerve 217, for example, in a generally mixed transverse-parallel manner. In some embodiments, the two electrodes can be used in a bipolar manner, with one of the two electrodes being positive and the other of the two electrodes being negative. In some embodiments, more than two electrodes can be used, with two or more electrodes being positive and two or more electrodes being negative.

As described in further detail herein, upon placement of the electrode array, electrode combinations can be stimulated to test their effect. Some combinations may produce a better result but be more likely to result in a side effect, some combinations may produce a better result but be less repeatable, some combinations may affect one nerve but not multiple nerves, etc. In some embodiments, a plurality of electrode combinations or independent outputs can be used in parallel or in series. For example, the electrodes 203a, 203b can be used to target the nerve 215 for a first duration and the electrodes 203e, 203f can be used to target the nerve 217 for a second duration. The second duration may at least partially overlap the first duration, fully overlap the first duration (e.g., starting at the same time, ending at the same time, starting after the first duration starts, ending before the first duration ends, and combinations thereof) or may be temporally spaced from the first duration by a third duration. The third duration may be zero (e.g., the second duration starting as the first duration ends).

In a study of multiple cadavers, the mean diameter 206d of the right pulmonary artery 206 proximate to the branch point 207 was about 26.5 mm with a standard deviation of about 4.6 mm. Assuming a circular vessel, the mean circumference of the right pulmonary artery 206 proximate to the branch point 207 is about 83 mm. If the goal is 30% coverage of the circumference, then an electrode matrix should have a circumferential length of about 25 mm (83 mm×30%). Other electrode matrix dimensions can be estimated or calculated based on other dimensions (e.g., vessel diameter at other points, measured vessel diameter, diameters of other vessels, vessel lengths, etc.), target coverage percentage, nerve location variability, placement accuracy, stimulation parameters, etc.

Figure 2J:
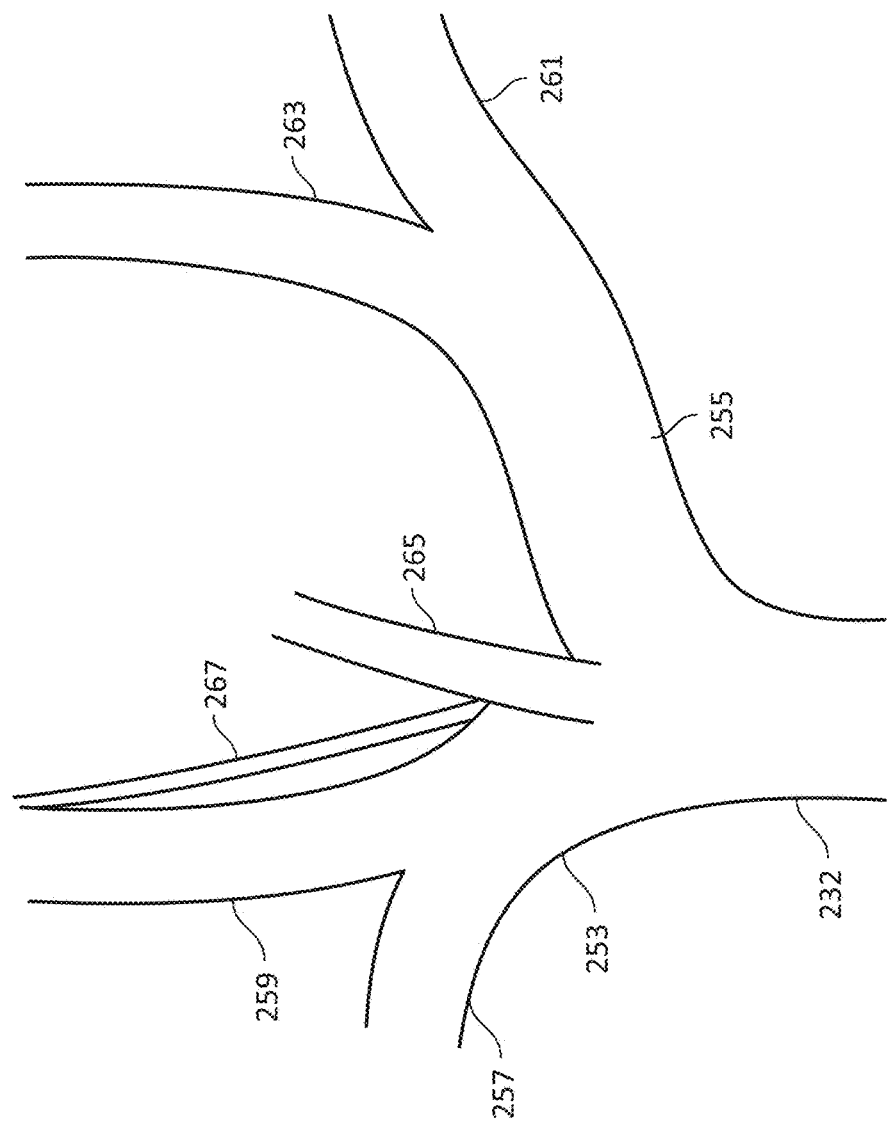
FIG. 2J is a schematic illustration of vasculature and surrounding nerves.

FIG. 2J is a schematic illustration of vasculature and surrounding nerves. The superior vena cava 232, as discussed above, supplies blood to the right atrium of the heart. The vessels supplying blood to the superior vena cava 232 include the right innominate vein or right brachiocephalic vein 253 and the left innominate vein or left brachiocephalic vein 255. The vessels supplying blood to the right brachiocephalic vein 253 include the right subclavian vein 257 and the right internal jugular vein 259. The vessels supplying blood to the left brachiocephalic vein 255 include the left subclavian vein 261 and the left internal jugular vein 263. The inferior thyroid vein 265 also supplies blood to the superior vena cava 232. Although other nerves are present surrounding the vasculature illustrated in FIG. 2F, the right vagus nerve 267 is illustrated as an example. The left vagus nerve runs close to the left internal jugular vein 263 and the common carotid artery, and then crosses the left brachiocephalic vein 255. Thoracic sympathetic cardiac branches also cross the left brachiocephalic vein 255 closer to the crown of the aorta and more medial, generally between the junction of the left subclavian vein and the left internal jugular vein 263 and about half of the length of the left brachiocephalic vein 253. Vasculature that may not typically be characterized as cardiovasculature may also be used in accordance with certain methods and systems described herein.

Figure 2L:
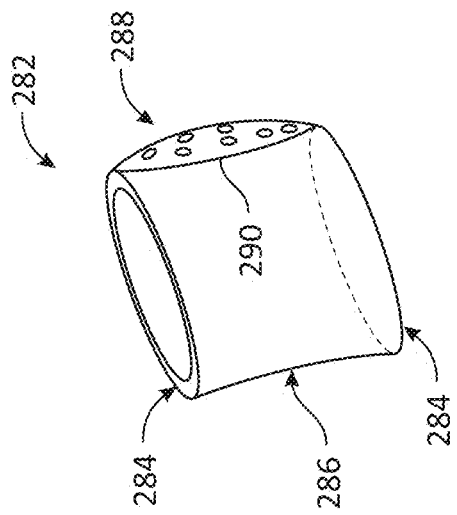
FIG. 2L illustrates an example stimulation device.
Figure 2K:
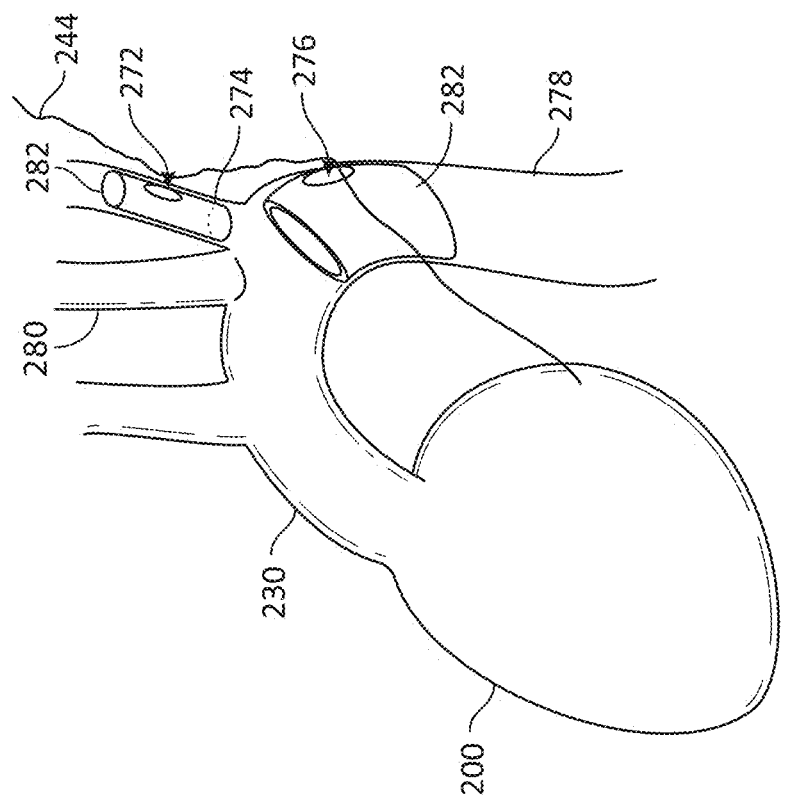
FIG. 2K is another schematic illustration of a heart and surrounding nerves.

FIG. 2K is another schematic illustration of a heart 200 and surrounding nerves. As described in detail herein, nerves affecting contractility (e.g., left ventricle contractility) may be targeted for neuromodulation by positioning a catheter in the pulmonary artery (e.g., right pulmonary artery, pulmonary trunk, left pulmonary artery). In some embodiments, a nerve such as the right stellate CPN 244 may also or alternatively be targeted by positioning a device at a location 272 in the left subclavian artery 274 and/or the location 276 in the descending aorta 278. Positioning in the left common carotid artery 280 is also possible. In FIG. 2K, an example stimulation device 282 is shown at the locations 272, 276. Other stimulation devices are also possible. In embodiments comprising multiple stimulation devices, the stimulation devices may be the same, different, or similar (as a non-limiting example, having a same structure but different dimensions).

FIG. 2L illustrates an example stimulation device 282. The stimulation device 282 may be used, for example, to target stimulation of a right stellate CPN 244 or another nerve. The device 282 comprises a skeletal structure 284, for example a stent, hoops, etc. The skeletal structure 284 may comprise a shape memory material (e.g., nitinol) that is self-expanding. The device 282 further comprise a mesh or membrane 286 attached to the skeletal structure 284. The mesh 286 may comprise, for example, Dacron®. One side of the device 282 comprises an electrode array 288. The electrode array 288 may have an area between about 0.5 cm$^2$ and about 3 cm$^2$ (e.g., about 0.5 cm$^2$, about 1 cm$^2$, about 1.5 cm$^2$, about 2 cm$^2$, about 2.5 cm$^2$, about 3 cm$^2$, ranges between such values, etc.). The electrode array 288 may be powered by implantable electronics 290. The electronics 290 may include, for example, non-volatile memory (e.g., storing electrode combinations and parameters), ASIC stimulation engine and logic, RF engine, battery power, and a sensor (e.g., pressure sensor, contractility sensor, combinations thereof, etc.). The device 282 may be positioned by a catheter routed through vasculature (e.g., from a femoral or radial artery). The device 282 may be positionable until the target nerve is stimulated. In some embodiments, the electrode array 288 may be electronically repositionable (e.g., as described with respect to FIGS. 32A-32D). In some embodiments, an external device (e.g., worn by the subject) can power and/or control the device 282. In embodiments in which the electronics 290 can power and/or control the device 282, the device 282 may be fully implantable. In certain such embodiments, the device 282 may be combined with a pacemaker, defibrillator, or other implantable stimulation device.

FIG. 3A is a side perspective and partial cross-sectional view of an example of a catheter 300. FIG. 3B is a distal end view of the catheter 300 of FIG. 3A as viewed along line 3B-3B in FIG. 3A. The catheter 300 includes an elongate body 302 having a first for proximal end 304 and a second or distal end 306. The second end 306 is distal to the first end 304. The elongate body 302 includes a longitudinal axis 308 that extends through the first end 304 and the second end 306 of the elongate body 302. A first plane 310 extends through the longitudinal axis 308 over the length of the elongate body 302. As used herein, a plane is an imaginary flat surface on which a straight line joining any two points on it would wholly lie, and is used herein to help orientate the relative position of structures on the catheter 300. The first plane 310 is used herein, among other reasons, to help explain the relative position of electrodes. The catheter 300 further includes at least two elongate stimulation members 314 (as illustrated in FIGS. 3A and 3B, 314a and 314b). The stimulation members 314 extend from the elongate body 302. Each of the at least two elongate stimulation members 314a, 314b curves into a first volume 316 defined at least in part by the first plane 310. For example, the at least two elongate stimulation members 314 extend from approximately the second end 306 of the elongate body 302 into the first volume 316.

Each of the at least two elongate stimulation members 314 comprises at least one electrode 318. The at least one electrode 318 on each of the elongate stimulation members 314 form an electrode array in the first volume 316 that is at least partially defined by the first plane 310. The at least one electrode 318 on each of the stimulation members 314 are electrically isolated from one another. In some embodiments, the stimulation members 314 comprise an electrically insulating material.

Each of the at least one electrodes 318 is coupled to a corresponding conductive element 320. The conductive elements 320 are electrically isolated from each other and extend through and/or along the stimulation members 314 from each respective electrode 318 through the first end 304 of the elongate body 302. The conductive elements 320 terminate at a connector port, where each of the conductive elements 320 can be releasably coupled to a stimulation system, for example as discussed herein. In some embodiments, the conductive elements 320 are permanently coupled to the stimulation system (e.g., not releasably coupled). The stimulation system can be used to provide stimulation electrical energy that is conducted through the conductive elements 320 and delivered across combinations of the electrodes 318 in the electrode array.

Each of the at least two elongate stimulation members 314 includes a stimulation member elongate body 322 having a distal end 324. The distal end 324 of the stimulation member elongate body 322 for each of the elongate stimulation members 314 extends from the elongate body 302. Each of the elongate body 302 and the stimulation member elongate body 322 include a surface defining a lumen 328 through which a wire 326 may extend. The wire 326 is joined to its respective stimulation member elongate body 322 at or near the distal end 324 of the stimulation member elongate body 322, where the wire 326 then freely extends through the lumen 328 in the elongate stimulation member 314 past the first end 304 of the elongate body 302. The lumen 328 is dimensioned to allow the wire 326 to be moved longitudinally within the lumen 328. The portion of the wire 326 extending from the first end 304 can be used to apply pressure against the stimulation member elongate body 322 at or near the distal end 324 of the stimulation member elongate body 322, where the wire 326 under such pressure can deflect or bend, which can impart a curve into each of the at least two elongate stimulation members 314 into the first volume 316 defined at least in part by the first plane 310. The at least two elongate stimulation members 314 extend radially away from the elongate body 302 over a range of distances depending upon how much pressure is applied to the wires 326. The curves of the at least two elongate stimulation members 314 can have a radius of curvature that changes along the length of the stimulation member elongate body 322 (e.g., as illustrated in FIG. 3A).

In some embodiments, the at least two elongate stimulation members 314 only curve in the first volume 316 defined at least in part by the first plane 310. A second volume 330 opposite the first volume and defined at least in part by the first plane 310 may contain no electrodes. In some embodiments, the at least two stimulation members 314 include a first elongate stimulation member 314a and a second elongate stimulation member 314b. A second plane 312 perpendicularly intersects the first plane 310 along the longitudinal axis 308 of the elongate body 302. The first plane 310 and the second plane 312 divide the first volume 316 into a first quadrant volume 332 and a second quadrant volume 334. In some embodiments (e.g., as illustrated in FIGS. 3A and 3B), the first elongate stimulation member 314a curves into the first quadrant volume 332 and the second elongate stimulation member 314b curves into the second quadrant volume 334.

The catheter 300 may include an anchor member 336 that extends from the elongate body 302 into the second volume 330. The anchor member 336 may not include or be devoid of an electrode. The anchor member 336 is not occlusive within vasculature and/or does not encourage thrombosis or coagulation of blood within vasculature. The anchor member 336 and the elongate body 302 include surfaces defining a lumen 338 through which wire 340 can pass. The wire 340 is joined to the anchor member 336 at or near a distal end 342 of the member 336, where the wire 340 freely extends through the lumen 338 of the anchor member 336 past the first end 304 of the elongate body 302. The lumen 338 is dimensioned to allow the wire 340 to be moved longitudinally within the lumen 338. The portion of the wire 340 extending from the first end 304 can be used to apply pressure against the anchor member 336 at or near its distal end 342, where the wire 340 under such pressure can deflect or bend, which can impart a curve into the anchor member 336. The anchor member 336 can extend radially away from the elongate body 302 over a range of distances depending upon how much pressure is applied to the wire 340. The anchor member 336 can be used to bring the electrodes 318 into contact with a vascular luminal surface (e.g., a posterior surface of the main pulmonary artery and/or one or both of the pulmonary arteries), for example as described herein, by application of a variety of pressures. Optionally, the anchor member 336 can be configured to include one or more electrodes.

Each of the wires 326 and the wire 340, upon being used to impart the curves in their respective members, can then be releasably locked in place by inhibiting or preventing longitudinal movement of the wire 326, 340 relative the elongate body 302. For example, a clamp or other device can be used to create contact between the wire 326, 340 and the surface of the lumen 328, 338 sufficient to inhibit or prevent the wire 326, 340 from moving relative to the surface of the lumen 328, 338. This clamping action can also function as a hemostasis valve to reduce or minimize blood loss.

FIGS. 3A and 3B also illustrate a pulmonary artery catheter 344 (partially shown to show detail of catheter 300) that can be used with the catheter 300 in a catheter system. The pulmonary artery catheter 344 includes an elongate catheter body 346 having a first or proximal end 348, a second or distal end 350, a peripheral surface 352, and an interior surface 354 opposite the peripheral surface 352. The interior surface 354 at least partially defines a lumen 356 that extends between the first end 348 and the second end 350 of the elongate catheter body 346. The lumen 356 is of a sufficient size and shape to house at least a portion of the catheter 300 inside the lumen 356 during delivery of the catheter 300. For example, the anchor member 336 and the at least two elongate stimulation members 314, along with a least a portion of the elongate body 302, can be positioned at least partially n the lumen 356. The anchor member 336, the at least two elongate stimulation members 314, and at least a portion of the elongate body 302 can be deployed from the distal end 350 of the pulmonary artery catheter 344 during the delivery and implantation of the catheter 300.

The pulmonary artery catheter 344 can further include an inflatable balloon 358 on the peripheral surface 352 of the elongate catheter body 346. The inflatable balloon 358 includes a balloon wall 360 having an interior surface 362 that, along with a portion of the peripheral surface 352 of the elongate catheter body 346, at least partially defines a fluid-tight volume 364. The pulmonary artery catheter 344 further includes an inflation lumen 366 that extends through the elongate catheter body 346. The inflation lumen 366 includes a first opening 368 into the fluid-tight volume 364 of the inflatable balloon 358 and a second opening 370 proximal to the first opening 368 to allow for a fluid to move in and out of the fluid tight volume 364 to inflate and deflate the balloon 358, respectively. A syringe or other such devices containing the fluid (e.g., saline, contrast, gas (e.g., oxygen)) can be used to inflate and deflate the balloon 358. FIG. 3A shows the balloon 358 in an inflated state, while FIG. 3B shows the balloon 358 in a deflated state.

The catheter system can be used to position the catheter 300 in the main pulmonary artery and/or one or both of the pulmonary arteries of the patient, for example as described herein. The pulmonary artery catheter 344, with the catheter 300 positioned within the lumen 356, can be introduced into the vasculature through a percutaneous incision and guided to the right ventricle. For example, the catheter 300 can be inserted into the vasculature via a peripheral vein of the arm (e.g., as with a peripherally inserted central catheter). Changes in a subject's electrocardiography and/or pressure signals from the vasculature can be used to guide and locate the catheter 300 within the subject's heart. Once in the proper location, the balloon 358 can be inflated to allow the pulmonary artery catheter 344 and the catheter 300 to be carried by the flow of blood from the right ventricle to the main pulmonary artery and/or one of the pulmonary arteries. Optionally, various imaging modalities can be used in positioning the catheter 300 and/or catheter system in the main pulmonary artery and/or one of the pulmonary arteries. Such imaging modalities include, but are not limited to, fluoroscopy, ultrasound, electromagnetic, and electropotential modalities.

The catheter system can be advance along the main pulmonary artery until the distal end 350 of the pulmonary artery catheter 344 contacts the top of the main pulmonary artery (e.g., a location distal to the pulmonary valve and adjacent to both of the pulmonary arteries). The advancement can be with the balloon 358 in the inflated or deflated state. Once the distal end 350 of the pulmonary artery catheter 344 reaches the top of the main pulmonary artery, the elongate catheter body 346 can be moved relative the catheter 300 so as to deploy the catheter 300 from the lumen 356 of the pulmonary artery catheter 344.

The peripheral surface of the catheter body 302 may include markings, for example starting and extending from the first end 304 towards the second end 306 of the catheter 300. The distance between the markings can be of units (e.g., millimeters, inches, etc.), which can allow the length between the distal end 350 of the pulmonary artery catheter 344 and the top of the main pulmonary artery to be determined. A marking can also or alternatively be provided on the peripheral surface of the catheter body 302 that indicates when the distal end 350 of the pulmonary artery catheter 344 is clear of the anchor member 336 and the elongate stimulation members 314. In some embodiments, a positioning gauge can be used to locate the catheter 300 within the main pulmonary artery, for example as discussed in further detail herein.

The ability to measure distance from the top of the main pulmonary artery may be helpful in placing the electrodes 318 in a desired location in the main pulmonary artery. In addition or alternative to measuring the distance from which the second end 306 of the elongate body 302 is placed from the top of the main pulmonary artery, the elongate body 302 can also be used to identify or map a position (e.g., a desired or optimal position) for the electrodes 314 within the vasculature. For example, the second end 306 of the elongate body 302 can be positioned at a desired distance from the top of the main pulmonary artery using the markings on the peripheral surface of the catheter body 302. The wires 326 and 340 can then be used to impart the curves into the elongate stimulation members 314 and the anchor member 336. Using the wires 326 and the wire 340, the elongate stimulation members 314 and the anchor member 336 can be imparted with curves of sufficient size to contact a surface of the main pulmonary artery, such as the anterior surface of the main pulmonary artery, which can bring the electrodes 318 into contact with the main pulmonary artery or one of the pulmonary arteries (the left pulmonary artery or the right pulmonary artery). The anchor member 336, as will be appreciated, biases and helps to anchor the electrodes 318 along the vessel surface (e.g., along the posterior surface of the main pulmonary artery or one of the pulmonary arteries (the left pulmonary artery or the right pulmonary artery)).

Due to its adjustable nature (e.g., depending at least partially on how much pressure or longitudinal force is applied to the wire 340), the anchor member 336 can be used to bring the electrodes 318 into contact with the luminal surface of the main pulmonary artery or one of the pulmonary arteries with a variety of pressures. For example, the anchor member 336 can bring the electrodes 318 into contact with the luminal surface of the main pulmonary artery or one of the pulmonary arteries with a first pressure. Using the stimulation system, for example as discussed herein, stimulation electrical energy can be delivered across combinations of two or more of the at least one electrode 318 in the electrode array. It is possible for the subject's cardiac response to the stimulation electrical energy to be monitored and recorded for comparison to other subsequent tests.

For any of the catheters and/or catheter systems discussed herein, any combination of electrodes, including reference electrodes (e.g., as discussed herein), positioned n or on the subject's body, can be used in providing stimulation to and sensing cardiac signals from the subject.

The pressure may be reduced and the elongate body 302 can be rotated in either a clockwise or counter-clockwise direction to reposition the electrodes 318 in contact with the luminal surface of the main pulmonary artery or one of the pulmonary arteries. The stimulation system can be used to deliver stimulation electrical energy across combinations of two or more of the at least one electrode 318 in the electrode array. The subject's cardiac response to this test can then be monitored and recorded for comparison to previous and/or subsequent tests. In this way, a preferred location for the position of the electrodes 318 along the luminal surface of the main pulmonary artery or one of the pulmonary arteries can be identified. Once the preferred location for the position of the electrodes 318 has been identified, the wire 340 can be used to increase the pressure applied by the anchor member 336, which can help to further anchor the catheter 300 in the patient.

FIG. 4A is a side perspective and partial cross-sectional view of another example of a catheter 400. FIG. 4B is a distal end view of the catheter 400 of FIG. 4A as viewed along line 4B-4B in FIG. 4A. The catheter 400 includes at least the structures as discussed herein with respect to the catheter 300, so a detailed discussion of shared or similar elements is not repeated but the element numbers are incremented in the hundreds place in FIGS. 4A and 4B with the understanding that the discussion of these elements is implicit.

Each of the at least two elongate stimulation members 414 comprises a plurality of electrodes 418 (e.g., three electrodes 418 as illustrated in FIGS. 4A and 4B, although other numbers (e.g., one, two, four, five, or more) are also possible). The electrodes 418 on the elongate stimulation members 414 form an electrode array. The electrodes 418 on each of the stimulation members 414 are electrically isolated from one another.

The catheter 400 further includes a structure 472 extending between at least two of the least two elongate stimulation members 414. The structure 472 is flexible such that it can transition between a delivery or low-profile state (radially folded state) that allows the structure 472 to be delivered into the main pulmonary artery and/or one of the pulmonary arteries, and a deployed or expanded state (radially expanded) as illustrated in FIG. 4A. The wires 426 and the least two elongate stimulation members 414 can be used to bring the structure 472 into its deployed or expanded state, for example as described herein. An example of the structure 472 is a mesh structure.

The structure 472 comprises a plurality of flexible strands that are connected to form a pattern of openings between the strands. One or more electrodes 474 can be present at one or more of the connections of the strands. The electrodes 474 can themselves form an electrode array, or together with the electrodes 418 may form an electrode array. In embodiments comprising a plurality of electrodes 474, the electrodes 474 can be aligned (e.g., as illustrated in FIG. 4A), in a two-dimensional pattern, in a three-dimensional pattern (e.g., accounting for the curvature of the stimulation member elongate body 422), or scattered without a specific order. The strands can comprise the same material as the elongate body 402 and/or the elongate stimulation members 414 or material that is different than the elongate body 402 and/or the elongate stimulation members 414. The strands may comprise insulative material. Examples of insulative material for one or more portions of the catheters and structures provided herein can include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high-density polyethylene, low-density polyethylene), and polyimides, among others.

The structure 472 can have a predefined shape that helps to locate and position at least one of the elongate stimulation members 414 and the electrodes 418 thereon. For example, the structure 472 can be used to adjust and/or maintain the distance between electrodes 418 on the adjacent stimulation members 414.

The structure 472 can include one or more additional electrode 474. The additional electrode 474 can either be positioned on the structure 472 or formed as an integral part of the structure 472. Each of the additional electrodes 474 may be electrically isolated from each of the other electrodes 474 and/or the electrodes 418. The additional electrodes 474 each include a conductive element 476. Each of the conductive elements 476 is electrically isolated from each other and can extend through the strands of the structure 472 from each respective additional electrode 474, through the stimulation members 414 and the elongate body 402, to the first end 404. The conductive elements 476 terminate at a connector port, where each of the conductive elements 420 and 476 can be releasably coupled to the stimulation system, for example as discussed herein. In some embodiments, the conductive elements 420 may be non-releasably or permanently coupled to the stimulation system. The stimulation system can be used to provide stimulation electrical energy that is conducted through the conductive elements 420, 476 to combinations of at least one of the additional electrodes 474 and/or at least one of the electrodes 418.

Figure 4C:
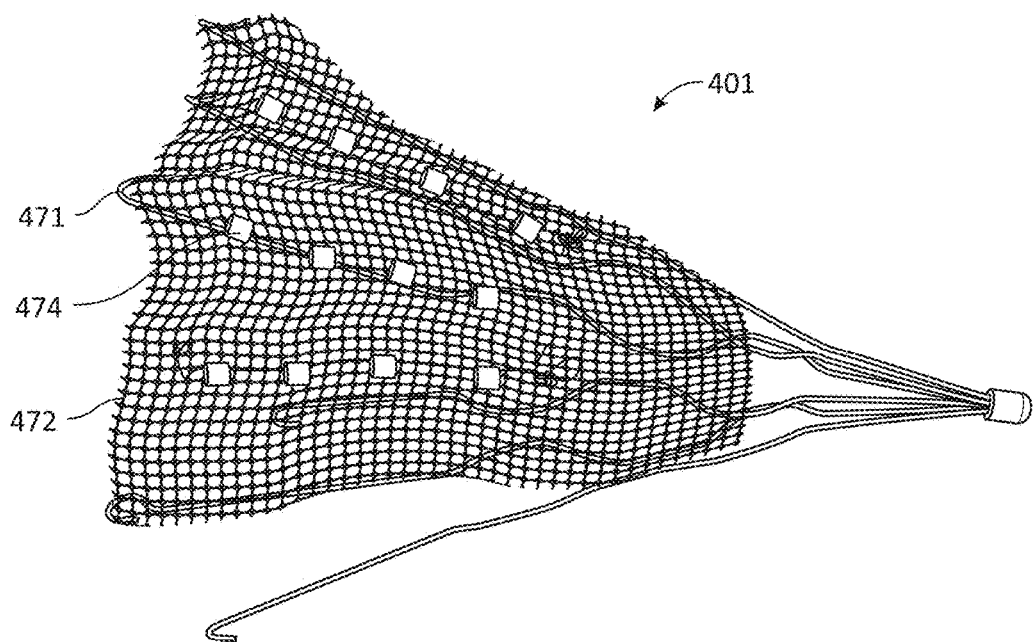
FIG. 4C is a side perspective view of an example of a portion of a catheter.

FIG. 4C is a side perspective view of an example of a portion 401 of a catheter. The portion 401 may be used with the catheter 300, 400, other catheters described herein, and the like. The portion 401 comprises a plurality of elongate splines 471. The splines 471 may comprise resilient or shape memory material configured to form an expanded shape (e.g., the conical shape shown in FIG. 4C or another shape) when not confined, for example in a catheter body. The portion 401 comprises a structure 472 extending between at least two of the elongate splines 471. One or more electrodes 474 can be coupled to the structure 472 (e.g., by adhering, soldering, welding, tying, combinations thereof, and the like). The electrodes 474 may be aligned with the splines 471, between the splines 471, and combinations thereof. For example, in the portion 401, the structure 472 is over three circumferentially-offset splines 471. The middle set of four electrodes 474 is aligned with a middle spline 471 and the outer sets of four electrodes 474 are between the middle spline 471 and the outer splines 471, forming a 3×4 array or matrix of electrodes 474. In embodiments comprising a plurality of electrodes 474, the electrodes 474 can be aligned (e.g., as illustrated in FIG. 4C) in a two-dimensional pattern, in a three-dimensional pattern (e.g., accounting for the curvature of the expanded shape of the splines 471), or scattered without a specific order. The electrodes 474 can themselves form an electrode array, or together with other electrodes (e.g., on the splines 471) may form an electrode array.

The structure 472 can comprise a woven or knitted mesh or membrane. The structure may comprise insulative material, for example medical grade polyurethanes, such as polyester-based polyurethanes, polyether-based polyurethanes, and polycarbonate-based polyurethanes; polyamides, polyamide block copolymers, polyolefins such as polyethylene (e.g., high-density polyethylene, low-density polyethylene), and polyimides, and the like.

In some embodiments, the structure 472 may be slid over the splines 471. For example, lateral edges or medial sections of the structure 472 may include loops configured to be slid over the splines 471. Although illustrated in FIG. 4C as arcuate over part of the circumference of the portion 401, the structure 472 may be arcuate around an entire circumference of the portion 401. In certain such embodiments, the structure 472 can be slid over the splines 471 as a telescoping tube. The structure 472 may be coupled to the splines 471 and/or tethered to a catheter.

In some embodiments, a plurality of structures 472 may be used. For example, a plurality of partially arcuate structures may be positioned around the splines 471 (e.g., in different circumferential positions, in overlapping circumferential positions, and/or in the same circumferential position (e.g., with different electrode 474 patterns)). For another example, a structure 472 may be substantially tubular such that it can be slid over a single spline, and a plurality of such structures 472 can be used on different splines or even the same spline.

Forming electrodes on a structure 472 can aid in manufacturing. For example, the electrodes 474 can be coupled to the structure 472 independent of forming the splines 471 (e.g., as opposed to forming electrodes in or on the splines 471). In some embodiments, the electrodes 474 can be formed on the structure 472, for example like flex circuit manufacturing. The structure 472 may also help to position conductive elements electrically connecting the electrodes 474 to a stimulation system.

The catheter 400 optionally comprises an anchor wire 478 extending longitudinally through the stimulation member elongate body 422. The elongate body 402 and the member elongate body 422 include a surface at least partially defining a lumen having a first opening at the proximal end 404 and a second opening at or adjacent to the distal end 424 of the stimulation member elongate body 422. The anchor wire 478 freely passes through the lumen, with a first end 480 extending from the elongate body 422 at the proximal end 404 of the elongate body 402 and a second end 482 comprising an anchoring structure (e.g., a barb) that extends from the second opening at or adjacent to the distal end 424 of the stimulation member elongate body 422. The anchor wire 478 can be advance through the lumen (e.g., longitudinal force can be applied to the first end 480 of the anchor wire 478) to extend the anchoring structure away from the stimulation member elongate body 414. The anchor member 436 may help to anchor the catheter 400 in the subject, for example as discussed herein. The anchor wire 478 can also or alternatively be used to help secure the catheter 400 in the subject at a desired location. One or more of the anchor wire 478 and the associated structures can also be included with the catheter 300. Optionally, the anchor wire 478 can be configured and used as an electrode with the stimulation system of the present disclosure. For example, the anchor wire 478 can be configured as an anode and one or more of the electrodes 418, 474 can be configured as a cathode and/or an anode, and/or the anchor wire 478 can be configured as a cathode and one or more of the electrodes 418, 474 can be configured as an anode and/or a cathode.

FIG. 4A also illustrates a pulmonary artery catheter 444 (partially shown to show detail of catheter 400), for example similar to the pulmonary artery catheter 344 discussed herein. A catheter system comprising the pulmonary artery catheter 444 can be used to position the catheter 400 in the main pulmonary artery and/or one of the pulmonary arteries of the patient, for example as described herein. The pulmonary artery catheter 444 with the catheter 400 positioned within the lumen 454 is introduced into vasculature through a percutaneous incision and guided to the right ventricle. The balloon 458 is inflated through the inflation lumen 466, allowing the pulmonary artery catheter 444 and the catheter 400 to be carried by the flow of blood from the right ventricle to the main pulmonary artery or one of the pulmonary arteries.

The catheter system shown in FIGS. 4A and 4B comprises an optional positioning gauge 484. The positioning gauge 484 includes an elongate gauge body 486 having a first end 488 and a bumper end 490 distal to the first end 488. The elongate gauge body 486 can be moved longitudinally within a lumen 492 at least partially defined by a surface that extends through the elongate body 402 from its first end 404 through the second end 406. The bumper end 490 can have a shape with an example surface area being no less than a surface area of the distal end 406 of the elongate body 402 taken perpendicularly to the longitudinal axis 408. The elongate gauge body 486 extends through the lumen 492 to position the bumper end 490 distal to the second end 406 of the elongate body 402. The first end 488 of the position gauge 484 extends proximally from the first end 404 of the elongate body 402. The elongate gauge body 486 may include a marking 494 that indicates a length between the second end 406 of the elongate body 402 and the bumper end 490 of the position gauge 484.

During navigating the catheter 400, the bumper end 490 of the positioning gauge 484 may be approximately longitudinally even with the distal end 424 of the stimulation member elongate body 422, the distal end 442 of the anchor member 436, and the distal end 450 of the pulmonary artery catheter 444 (e.g., the elongate body 402, the anchor member 436, and the elongate stimulation members 414 are positioned in the lumen 456 of the pulmonary artery catheter 444). In this configuration, the catheter system can be advance along the main pulmonary artery until the bumper end 490 of the positioning gauge 484 contacts the top of the main pulmonary artery (e.g., a location distal to the pulmonary valve and adjacent to both the pulmonary arteries). The catheter system can be distally advanced when beyond the pulmonary valve with the balloon 458 in the inflated or deflated state.

Once the bumper end 490 contacts the top of the main pulmonary artery, the pulmonary artery catheter 444 (with the catheter 400 positioned in the lumen 456) can be moved relative to the bumper end 490 (e.g., the pulmonary artery catheter 444 and the catheter 400 can be moved away from the bumper end 490). As the pulmonary artery catheter 444 and the catheter 400 move relative to the bumper end 490, the markings 494 on the elongate gauge body 486 can be used to indicate a length between the distal end 224 of the stimulation member elongate body 422, the distal end 442 of the anchor member 436, the distal end 450 of the pulmonary artery catheter 444, and the bumper end 490 of the position gauge 484. The distance between the markings 494 can be in certain units (e.g., millimeters, inches, etc.), which can allow the length the between the distal end 424 of the stimulation member elongate body 422, the distal end 442 of the anchor member 436, and the distal end 450 of the pulmonary artery catheter 444 to be determined. Once a length that is desired is achieved, the pulmonary artery catheter 444 can be moved relative the catheter 400 so as to deploy the anchor member 436 and the elongate stimulation members 414 with the electrodes 418 within the main pulmonary artery or one of the pulmonary arteries.

The ability to measure distance from the top of the main pulmonary artery may be helpful in placing the electrodes 418 in a desired location in the main pulmonary artery or one of the pulmonary arteries. For example, the distal end 424 of the stimulation member elongate body 422 and the distal end 442 of the anchor member 436 can be positioned at the desired distance from the top of the main pulmonary artery using the markings 494 on the peripheral surface of the positioning gauge 484. The wires 426, 440 can be used to impart curves into the elongate stimulation members 414 and the anchor member 436, respectively. Using the wires 426 and the wire 440, the elongate stimulation members 414 and the anchor member 436 can be provided with curves of sufficient size to contact the anterior surface of the main pulmonary artery and bring the electrodes 418 into contact with the luminal surface of the main pulmonary artery. The anchor member 436 can bias and help to anchor the electrodes 418 along the vessel surface (e.g., along the posterior surface of the main pulmonary artery). Optionally, the anchor member 436 can be configured to include one or more electrodes 418, for example as discussed herein.

Due to its adjustable nature (e.g., changing apposition pressure depending on the amount of longitudinal force or pressure is applied to the wire 440), the anchor member 436 can be used to bring the electrodes 418 into contact with the luminal surface of the main pulmonary artery or one of the pulmonary arteries under a variety of pressures. For example, the anchor member 436 can bring the electrodes 418 into contact with the luminal surface of the main pulmonary artery or one of the pulmonary arteries under a first pressure. Using stimulation electrical energy from the stimulation system, electrical energy can be delivered across combinations of two or more of the electrodes 418, 474. The subject's cardiac response to the stimulation electrical energy can then be monitored and recorded for comparison to subsequent tests. If desired, the longitudinal pressure applied to the anchor member 436 can be reduced, and the elongate body 402 can be rotated in either a clockwise or counter-clockwise direction and/or lengthwise relative to the top of the main pulmonary artery or one of the pulmonary arteries to reposition the electrodes 418 in contact with the luminal surface of the main pulmonary artery or one of the pulmonary arteries. The stimulation system can again be used to deliver stimulation electrical energy across combinations of two or more of the electrodes 418, 474. The subject's cardiac response to this subsequent test can then be monitored and recorded for comparison to previous and subsequent tests. In this way, a preferred location for the position of the electrodes 418 along the luminal surface of the main pulmonary artery or one of the pulmonary arteries can be identified. Once identified, the wire 440 can be used to increase the pressure applied by the anchor member 436, thereby helping to better anchor the catheter 400 in the patient.

Referring now to FIG. 5, an embodiment of a catheter 500 is shown, where the catheter 500 may include the structures and features of the other catheters discussed herein. As illustrated, the catheter 500 includes an elongate body 502 having a first end 504 and a second end 506 distal from the first end 504. As illustrated, the elongate body 502 includes an elongate radial axis 508 that extends through the first end 504 and the second end 506 of the elongate body 502. As illustrated, a first plane 510 extends through the elongate radial axis 508 over the length of the elongate body 502. A second plane 512 perpendicularly intersects the first plane 510 along the longitudinal axis 508 of the elongate body 502. The first plane 510 and the second plane 512 divide a first volume 516 into a first quadrant volume 532 and a second quadrant volume 534. The catheter 500 further includes at least two elongate stimulation members 514, as discussed herein, that extend from the elongate body 502. Each of the at least two elongate stimulation members 514-1 and 514-2 curves into a first volume 516 defined at least in part by the first plane 510. For example, the at least two elongate stimulation members 514 may extend from approximately the second end 506 of the elongate body 502 into the first volume 516.

FIG. 5 also illustrates at least one electrode 518 on each of the at least two elongate stimulation members 514. The at least one electrode 518 on each of the elongate stimulation members 514 form an electrode array in the first volume 516. The at least one electrode 518 on each of the elongate stimulation members 514 may be electrically isolated from one another and/or may comprise an electrically insulating material. The catheter 500 also includes conductive elements 520 that extend through and/or along each of the elongate stimulation members 514. As discussed herein, the conductive elements 520 can conduct electrical current to combinations of two or more of the electrodes 518. The conductive elements 520 may be electrically isolated from each other. The conductive elements 520 may terminate at a connector port, where each of the conductive elements 520 can be releasably coupled to a stimulation system, for example as discussed herein. In some embodiments, the conductive elements 520 are permanently coupled to the stimulation system (e.g., not releasably coupled). The stimulation system can be used to provide stimulation electrical energy that is conducted through the conductive elements 520 and delivered across combinations of the electrodes 518 in the electrode array.

Each of the at least two elongate stimulation members 514 includes a stimulation member elongate body 522 having a distal end 524 that can move relative to each other. In other words, the distal ends 524 of each of the stimulation member elongate bodies 522 are free of each other. As illustrated in FIG. 5, the at least two elongate stimulation members 514 curve only in the first volume 516 defined at least in part by the first plane 510. FIG. 5 also illustrates a second volume 530 defined at least in part by the first plane 510 (being opposite the first volume 516) that contains no electrodes. FIG. 5 also illustrates an embodiment in which the at least two elongate stimulation members 514 include a first elongate stimulation member 514-1 and a second elongate stimulation member 514-2, where the first elongate stimulation member 514-1 curves into the first quadrant volume 532 and the second elongate stimulation member 514-2 curves into the second quadrant volume 534, as previously discussed herein. The catheter 500 also includes an anchor member 536 that extends from the elongate body 502 into the second volume 530. As illustrated, the anchor member 536 does not include an electrode. The anchor member 536 includes an elongate body 538 as previously discussed in connection with previous figures. Optionally, the anchor member 536 can be configured to include one or more of the electrodes 518 as discussed herein.

Each of the at least two elongate stimulation members 514 and the anchor member 536 can also include a wire 566 extending longitudinally through the stimulation member elongate body 522 and the elongate body 538, respectively. The wire 566 can provide each of the at least two elongate stimulation members 514 and the anchor member 536 with a predefined shape. For example, the wire 566 in each of the at least two elongate stimulation members 514 and the anchor member 536 can have a coil or helical configuration that imparts a curve to the stimulation member elongate body 522 and the elongate body 538, respectively. The wire 566 can also impart stiffness to the stimulation member elongate body 522 that is sufficient to maintain the predefined shape under the conditions within the vasculature of the patient. So, for example, the wire 566 provides sufficient stiffness and flexibility to the stimulation member elongate body 522 to elastically return the least two elongate stimulation members 514 to their curved configuration when placed in the vasculature of a patient.

The wire 566 can be formed of a variety of metals or metal alloys. Examples of such metals or metal alloys include surgical grade stainless steel, such as austenitic 516 stainless among others, and the nickel and titanium alloy known as Nitinol. Other metals and/or metal alloys can also be used as desired and/or required. The predefined shape may be adapted to conform to a particular anatomical structure (e.g., the right or left pulmonary artery or other portion of a pulmonary trunk).

The at least two elongate stimulation members 514 can also include an anchor wire 544, as discussed herein, extending longitudinally through a lumen in the stimulation member elongate body 522 and the elongate body 502. The anchor wire 544 includes a first end 546 extending from the elongate body 502 and a second end 548 having an anchoring structure (e.g., a barb). The anchor wire 544 can be advanced through the lumen (e.g., longitudinal force can be applied to the first end 546 of the anchor wire 544) to extend the anchoring structure away from the stimulation member elongate body 514. In addition to the use of the anchor member 536 in helping to better anchor the catheter 500 in the patient, as discussed herein, the anchor wire 544 can also be used to help secure the catheter 500 in the patient at the desired location. Optionally, the anchor wire 544 can be configured and used as an electrode with the stimulation system of the present disclosure.

In accordance with several embodiments, the catheter 500 further includes a pulmonary artery catheter 591, as discussed herein. As illustrated, the pulmonary artery catheter 591 (partially shown to show detail of catheter 500) that can be used with catheter 500 to provide for a catheter system. The pulmonary artery catheter 591 includes an elongate catheter body 5100 with a first end 5102, a second end 5104, a peripheral surface 5106 and an interior surface 5108, opposite the peripheral surface 5106. The interior surface 5108 defines a lumen 5110 that extends between the first end 5102 and the second end 5104 of the elongate catheter body 5100. The lumen 5110 is of a sufficient size and shape to house at least a portion of the catheter 500 inside the lumen 5110 during delivery of the catheter 500. For example, the anchor member 536 and the at least two elongate stimulation members 514, along with a least a portion of the elongate body 502, can be positioned within the lumen 5110 during delivery. The anchor member 536, the at least two elongate stimulation members 514 and at least a portion of the elongate body 502 can be deployed from the distal end 5104 of the pulmonary artery catheter 591 during the delivery and implantation of the catheter 500.

The pulmonary artery catheter 591 can further include an inflatable balloon 5112 on the peripheral surface 5106 of the elongate catheter body 5100. The inflatable balloon 5112 includes a balloon wall 5114 with an interior surface 5116 that, along with a portion of the peripheral surface 5106 of the elongate catheter body 5100, defines a fluid tight volume 5118. The pulmonary artery catheter 591 further includes an inflation lumen 5120 that extends through the elongate catheter body 5100, where the inflation lumen 5120 has a first opening 5122 into the fluid tight volume 5118 of the inflatable balloon 5112 and a second opening 5124 proximal to the first opening 5122 to allow for a fluid to move in the fluid tight volume 5118 to inflate and deflate the balloon 5112, as discussed herein. The catheter system shown in FIG. 5 can be used, for example, to position the catheter 500 in the main pulmonary artery 202 and/or one or both of the pulmonary arteries 206, 208 of the patient, for example as described herein. The at least two elongate stimulation members 514 and the anchor member 536 can be repositioned within the lumen 5110 of the pulmonary artery catheter 591 by moving the elongate catheter body 5100 relative to the elongate body 502 back over the at least two elongate stimulation members 514 and the anchor member 536. The catheter system illustrated in FIG. 5 can optionally include the positioning gauge, as discussed in connection with FIGS. 4A and 4B, for example.

Referring now to FIG. 6, another embodiment of a catheter 600 is shown. As illustrated, the catheter 600 includes an elongate body 602 having a first end 604 and a second end 606 distal from the first end 604. As illustrated, the elongate body 602 includes an elongate radial axis 608 that extends through the first end 604 and the second end 606 of the elongate body 602. As illustrated, a first plane 610 extends through the elongate radial axis 608 over the length of the elongate body 602. A second plane 612 perpendicularly intersects the first plane 610 along the longitudinal axis 608 of the elongate body 602. The first plane 610 and the second plane 612 divide a first volume 616 into a first quadrant volume 632 and a second quadrant volume 634. The catheter 600 includes at least two elongate stimulation members 614 that extend from the elongate body 602. Each of the at least two elongate stimulation members 614-1 and 614-2 curves into a first volume 616 defined at least in part by the first plane 610. For example, the at least two elongate stimulation members 614 extend from approximately the second end 606 of the elongate body 602 into the first volume 616.

FIG. 6 also illustrates at least one electrode 618 on each of the at least two elongate stimulation members 614. Multiple electrodes 618 on the elongate stimulation members 614 may form an electrode array in the first volume 616. The catheter 600 also includes conductive elements 620 that extend through and/or along each of the elongate stimulation members 614. As discussed previously, the conductive elements 620 can conduct electrical current to combinations of two or more of the electrodes 618.

Each of the at least two elongate stimulation members 614 includes a stimulation member elongate body 622 each having a distal end 624 that extends from the elongate body 602. In some embodiments (such as illustrated in FIG. 6), the at least two elongate stimulation members 614 curve only in the first volume 616 defined at least in part by the first plane 610. FIG. 6 also illustrates a second volume 630 defined at least in part by the first plane 610 (being opposite the first volume 616) that contains no electrodes. FIG. 6 further illustrates an embodiment in which the at least two elongate stimulation members 614 include a first elongate stimulation member 614-1 and a second elongate stimulation member 614-2, where the first elongate stimulation member 614-1 curves into the first quadrant volume 632 and the second elongate stimulation member 614-2 curves into the second quadrant volume 634, such as previously discussed herein. The catheter 600 also includes an anchor member 636 that extends from the elongate body 602 into the second volume 630. As illustrated, the anchor member 636 does not include an electrode. The anchor member 636 includes an elongate body 638 such as previously discussed. Optionally, the anchor member 636 can be configured to include one or more of the electrodes 618.

Each of the at least two elongate stimulation members 614 and the anchor member 636 can also include a wire 666 extending longitudinally through and/or along the stimulation member elongate body 622 and the elongate body 638, respectively. The wire 666 can provide each of the at least two elongate stimulation members 614 and the anchor member 636 with a predefined shape. For example, the wire 666 in each of the at least two elongate stimulation members 614 and the anchor member 636 can have a coil or helical configuration that imparts a curve to the stimulation member elongate body 622 and the elongate body 638, respectively. The wire 666 can also impart stiffness to the stimulation member elongate body 622 that is sufficient to maintain the predefined shape under the conditions within the vasculature of the patient. So, for example, the wire 666 can provide sufficient stiffness and flexibility to the stimulation member elongate body 622 to elastically return the least two elongate stimulation members 614 to their curved configuration when placed in the vasculature of a patient. The wire 666 can be formed of a variety of metals or metal alloys such as those as discussed herein in connection with other embodiments.

The at least two elongate stimulation members 614 can also include an anchor wire 644 extending longitudinally through and/or along the stimulation member elongate body 622. The anchor wire 644 includes a first end 646 extending from the elongate body 602 and a second end 648 having an anchoring structure (e.g., a barb). Longitudinal force applied to the first end 646 of the anchor wire 644 advances the anchor wire 644 through the stimulation member elongate body 614 to extend the anchoring structure away from the stimulation member elongate body 614. Optionally, the anchor wire 644 can be configured and used as an electrode with the stimulation system of the present disclosure.

The catheter 600 further includes a pulmonary artery catheter 691, as previously discussed herein. As illustrated, the pulmonary artery catheter 691 (partially shown to show detail of catheter 600) can be used with the catheter 600 to provide a catheter system. The pulmonary artery catheter 691 includes an elongate catheter body 670 with a first end 680, a second end 682, a peripheral surface 676 and an interior surface 672, opposite the peripheral surface 676. The interior surface 672 defines a lumen 674 that extends between the first end 680 and the second end 682 of the elongate catheter body 670. The lumen 674 may be of a sufficient size and shape to house at least a portion of the catheter 600 inside the lumen 674 during delivery of the catheter 600. For example, the anchor member 636 and the at least two elongate stimulation members 614, along with a least a portion of the elongate body 602, can be positioned within the lumen 674. The anchor member 636, the at least two elongate stimulation members 614 and at least a portion of the elongate body 602 can be deployed from the distal end 682 of the pulmonary artery catheter 691 during the delivery and implantation of the catheter 600.

The pulmonary artery catheter 691 can further include an inflatable balloon 668 on the peripheral surface 676 of the elongate catheter body 670. The inflatable balloon 668 has a balloon wall 688 with an interior surface 690 that, along with a portion of the peripheral surface 676 of the elongate catheter body 670 defines a fluid tight volume 692. The pulmonary artery catheter 691 further includes an inflation lumen 694 that extends through the elongate catheter body 670, where the inflation lumen 694 has a first opening 696 into the fluid tight volume 692 of the inflatable balloon 668 and a second opening 698 proximal to the first opening 696 to allow for a fluid to move in the fluid tight volume 692 to inflate and deflate the balloon 668, for example as previously discussed herein. The catheter system shown in FIG. 6 can be used to position the catheter 600 in the main pulmonary artery and/or one or both of the pulmonary arteries of the patient, for example as described herein. The at least two elongate stimulation members 614 and the anchor member 636 can be repositioned within the lumen 694 of the pulmonary artery catheter 691 by moving the elongate catheter body 670 relative the elongate body 602 back over the at least two elongate stimulation members 614 and the anchor member 636. The catheter system illustrated in FIG. 6 can optionally include the positioning gauge, as discussed in connection with FIGS. 4A and 4B, for example.

Figure 7A:
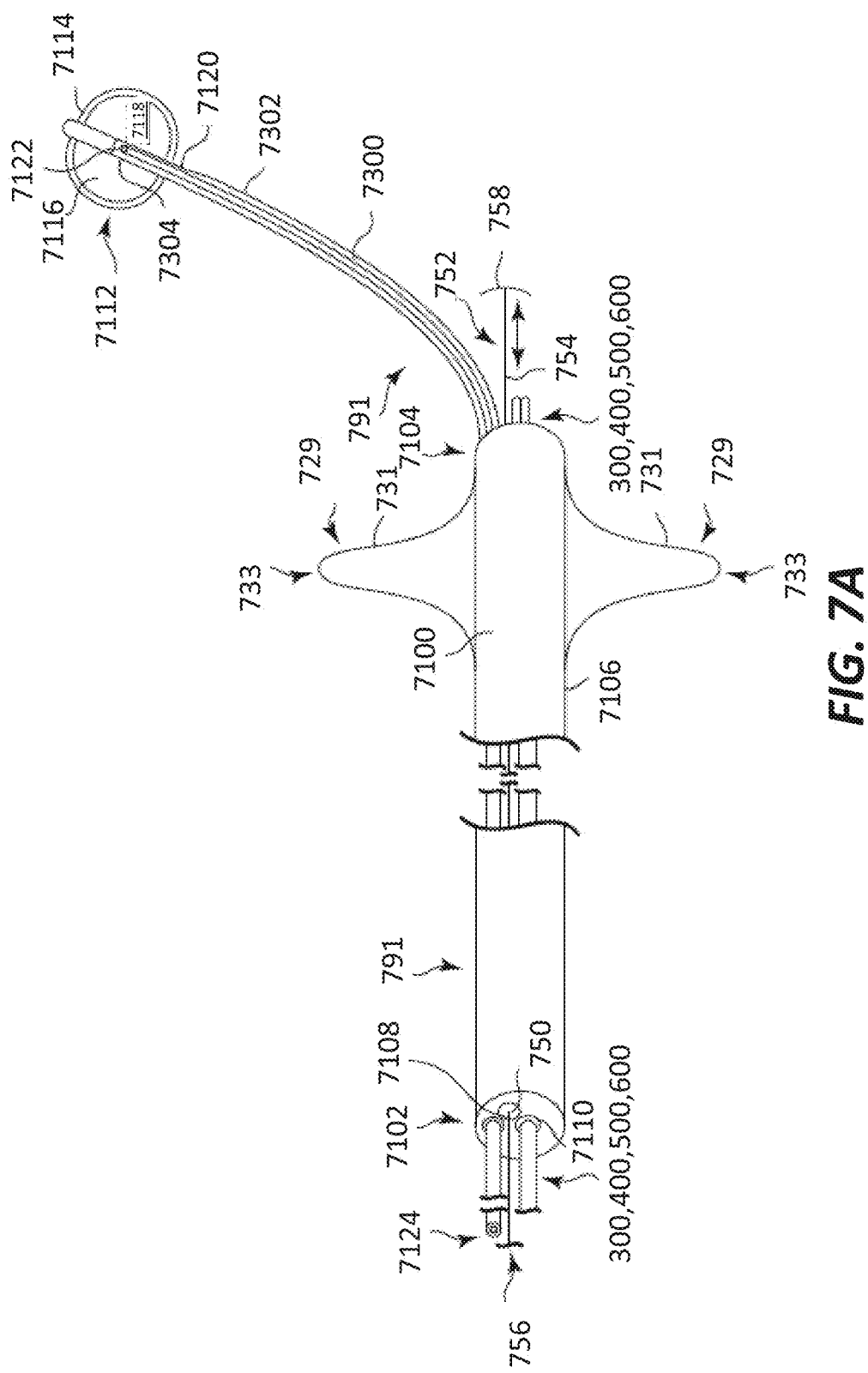
FIGS. 7A and 7B illustrate embodiments of a pulmonary artery catheter that can be used with the catheters according to the present disclosure.
Figure 7B:
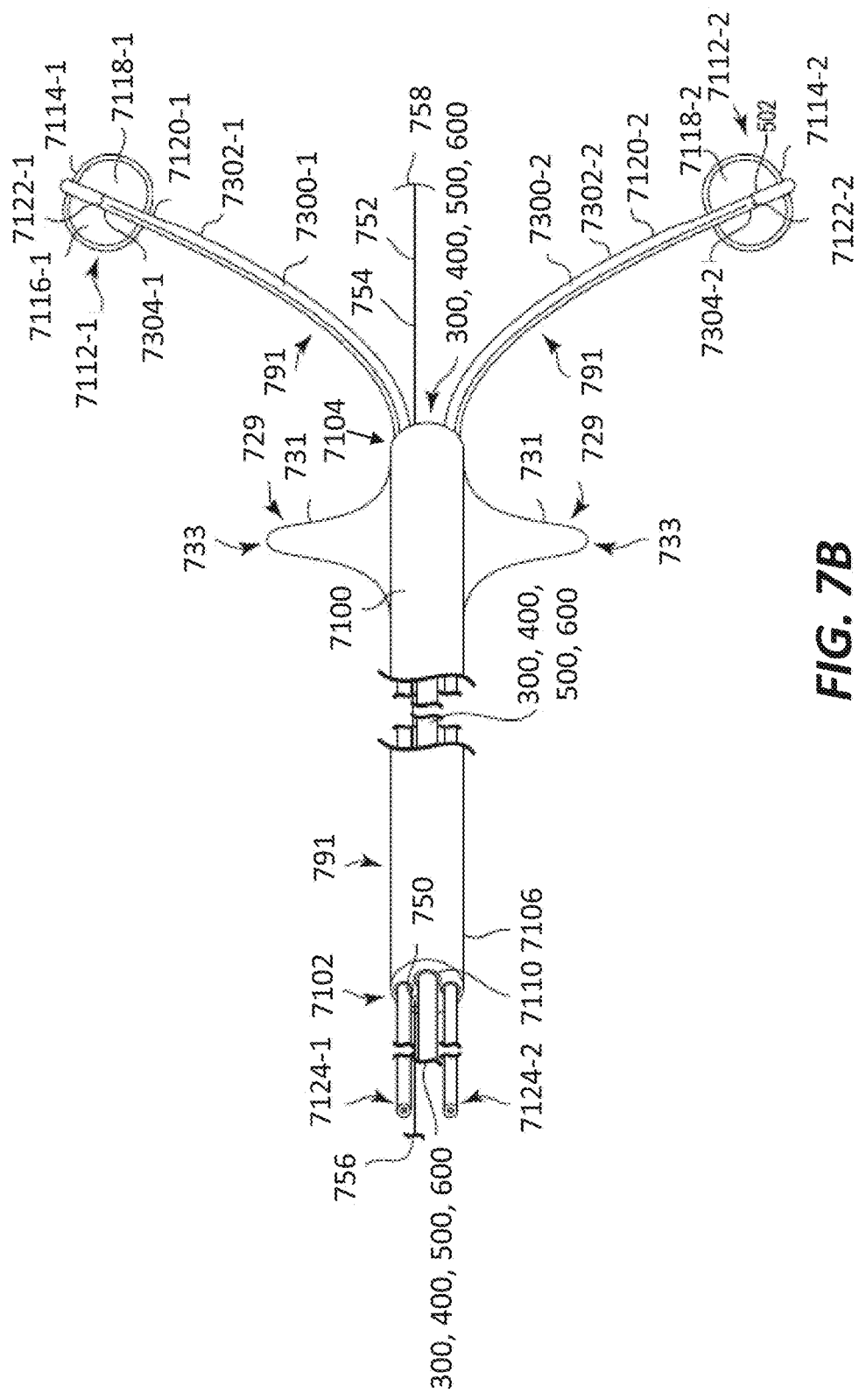

Referring now to FIGS. 7A and 7B, there is shown alternative embodiments of a pulmonary artery catheter 791 that can be used with any of the catheters described herein (e.g., catheter 300, 400, 500 or 600). As illustrated, the pulmonary artery catheter 791 includes an elongate catheter body 7100 with a first end 7102, a second end 7104, a peripheral surface 7106 and an interior surface 7108, opposite the peripheral surface 7106. The interior surface 7108 defines a lumen 7110 that extends between the first end 7102 and the second end 7104 of the elongate catheter body 7100. The lumen 7110 is of a sufficient size and shape to house at least a portion of the catheter (e.g., catheter 300, 400, 500 or 600) inside the lumen 7110 during delivery of the catheter. For example, the anchor member and the at least two elongate stimulation members, along with a least a portion of the elongate body, can be positioned within the lumen 7110. The anchor member, the at least two elongate stimulation members and at least a portion of the elongate body can be deployed from the distal end 7104 of the pulmonary artery catheter 791 during the delivery and implantation of the catheter (e.g., catheter 300, 400, 500 or 600).

The pulmonary artery catheter 791 includes an inflatable balloon 7112. As illustrated, the inflatable balloon 7112 is positioned on an elongate inflation catheter body 7300 that passes through a balloon lumen 7302. The balloon lumen 7302 is defined by lumen surface 7304 that can extend from the first end 7102 through the second end 7104 of the elongate catheter body 7100. The balloon lumen 7302 has a cross-sectional dimension that allows the elongate inflation catheter body 7300 to longitudinally move within the balloon lumen 7302. As such, the inflatable balloon 7112 can be moved relative to the distal end 7104 of the pulmonary artery catheter 791.

The inflatable balloon 7112 has a balloon wall 7114 with an interior surface 7116 that along with a portion of a peripheral surface 7106 of the elongate inflation catheter body 7300 defines a fluid tight volume 7116. The elongate inflation catheter body 7300 further includes an inflation lumen 7120 that extends through the elongate inflation catheter body 7300, where the inflation lumen 7120 has a first opening 7122 into the fluid tight volume 7116 of the inflatable balloon 7112 and a second opening 7124 proximal to the first opening 7122 to allow for a fluid to move in the fluid tight volume 7116 to inflate and deflate the balloon 7112. A syringe, or other known devices, containing the fluid (e.g., saline or a gas (e.g., oxygen)) can be used to inflate and deflate the balloon 7112. The cross-sectional dimension of the balloon lumen 7302 is also sufficient to allow the inflatable balloon 7112 in its fully deflated state to be housed within the lumen 7302. The inflatable balloon 7112 along with at least a portion of the elongate inflation catheter body 7300 can be extended from the second end 7104 when the inflatable balloon 7112 is to be inflated.

FIG. 7B illustrates an alternative embodiment of the pulmonary artery catheter 791 that can be used with any of the catheters (e.g., catheters 300, 400, 500, or 600) according to the present disclosure. As with the pulmonary artery catheter 791 illustrated in FIG. 7A, the pulmonary artery catheter 791 includes an elongate catheter body 7100 with a first end 7102, a second end 7104, a peripheral surface 7106 and an interior surface, opposite the peripheral surface 7106. The interior surface defines the lumen 7110 that extends between the first end 7102 and the second end 7104 of the elongate catheter body 7100. The lumen 7110 is of a sufficient size and shape to house at least a portion of the catheter (e.g., catheter 300, 400, 500, or 600) inside the lumen 7110 during delivery of the catheter. For example, the anchor member and the at least two elongate stimulation members, along with a least a portion of the elongate body, can be positioned within the lumen 7110 (the embodiment illustrated in FIG. 7B has the catheter (e.g., catheter 300, 400, 500, or 600) fully inside the lumen 7110). The anchor member, the at least two elongate stimulation members and at least a portion of the elongate body can be deployed from the distal end 7104 of the pulmonary artery catheter 791 during the delivery and implantation of the catheter (e.g., catheter 300, 400, 500, or 600).

The pulmonary artery catheter 791 illustrated in FIG. 7B includes two inflatable balloons 7112 (shown as 7112-1 and 7112-2 in FIG. 7B). As illustrated, each of the inflatable balloons 7112-1 and 7112-2 are positioned on separate elongate inflation catheter bodies 7300-1 and 7300-2, where each of the elongate inflation catheter bodies 7300-1 and 7300-2 pass through a balloon lumen 7302-1 and 7302-2, respectively. As illustrated, each balloon lumen 7302-1 and 7302-2 is defined by a lumen surface 7304-1 and 7304-2, respectively, which can extend from the first end 7102 through the second end 7104 of the elongate catheter body 7100. The balloon lumens 7302-1 and 7302-2 each have a cross-sectional dimension that allows the elongate inflation catheter body 7300-1 and 7300-2 to longitudinally move within their respective balloon lumen 7302-1 and 7302-2. As such, each of the inflatable balloons 7112-1 and/or 7112-2 can be independently moved relative to the distal end 7104 of the pulmonary artery catheter 791. As with FIG. 7A, the cross-sectional dimension of each balloon lumen 7302-1 and 7302-2 may be sufficient to allow each respective inflatable balloon 7112-1 and 7112-2 in its fully deflated state to be housed within each respective balloon lumen 7302-1 and 7302-2. Each inflatable balloon 7112-1 and 7112-2, along with at least a portion of the elongate inflation catheter body 7300-1 and 7300-2, can independently be extended from the second end 7104 when the inflatable balloon 7112-1 and/or 7112-2 is to be inflated.

Each of the inflatable balloons 7112-1 and 7112-2 has a balloon wall 7114-1 and 7114-2 with an interior surface 7116-1 and 7116-2, respectively, which along with a portion of a peripheral surface 7106 of the elongate inflation catheter body 7300-1 and 7300-2 define a fluid tight volume 7118-1 and 7118-2, respectively. The elongate inflation catheter body 7300 further includes an inflation lumen 7120-1 and 7120-2 that extends through the elongate inflation catheter body 7300-1 and 7300-2, respectively, where the inflation lumen 7120-1, 7120-2 has a first opening 7122-1, 7122-2 into the fluid tight volume 7118-1, 7118-2 of the inflatable balloon 7112-1 and 7112-2 and a second opening 7124-1 and 7124-2 proximal to the first opening 7122-1 and 7122-2 to allow for a fluid (e.g., liquid or gas) to move in and out of the fluid tight volume 7118-1 and 7118-2 to inflate and deflate the balloon 7112-1 and 7112-2. Each of the inflatable balloons 7112-1 and 7112-2 can be independently moved relative to the second end 7104 of the elongate body 7100 as well as independently inflated, as discussed elsewhere herein.

The pulmonary artery catheter 791 further includes a positioning gauge 752. The positioning gauge 752 includes an elongate gauge body 754 with a first end 756 and a bumper end 758 distal to the first end 756. The elongate gauge body 754 can be moved longitudinally within a lumen 750 defined by a surface that extends through the elongate catheter body 7100. The elongate gauge body 754 extends through the lumen 750 of the elongate catheter body 7100 to position the bumper end 758 beyond the second end 7104 of the elongate catheter body 7100. The first end 756 of the position gauge 752 extends from the first end 7102 of the elongate catheter body 7100, where the elongate gauge body 754 includes a marking that indicates a length between the second end 7104 of the elongate catheter body 7100 and the bumper end 758 of the position gauge 752.

The pulmonary artery catheter 791 can also include a first anchor 729 that extends laterally from the peripheral surface 7106 of the elongate catheter body 7100. As illustrated, the first anchor 729 has struts 731 that form an open framework. The struts 731 have a peripheral surface 733 having a largest outer dimension that allows the first anchor 729 (when deployed) to engage a surface of the main pulmonary artery and/or one or both of the pulmonary arteries. A sheath can cover and hold the first anchor 729 in an undeployed state as the pulmonary artery catheter 791 and the catheter (e.g., catheter 300, 400, 500, or 600) are being introduced into the patient.

The catheter system shown in FIGS. 7A and 7B can be used to position a catheter (e.g., catheter 300, 400, 500, and/or 600) in the main pulmonary artery and/or one or both of the right and left pulmonary arteries of the patient, for example as described herein. To accomplish this, the pulmonary artery catheter 791 with the catheter positioned within the lumen 7110 is introduced into the vasculature through a percutaneous incision, and guided to the right ventricle (e.g., using a Swan-Ganz approach through an incision in the neck). For the catheter system of FIG. 7A, the balloon 7112 is inflated, as described, to allow the pulmonary artery catheter 791 and the catheter to be carried by the flow of blood from the right ventricle to the main pulmonary artery or one of the right or left pulmonary arteries. Once the pulmonary artery catheter 791 and the catheter (e.g., catheter 300, 400, 500, and/or 600) have been carried from the right ventricle into the main pulmonary artery or one of the right or left pulmonary arteries the sheath can be retracted, thereby allowing the first anchor 729 to deploy within the main pulmonary artery. The first anchor 729 can be brought back into its undeployed state by positioning the sheath (e.g., advancing the sheath) back over the first anchor 729.

With the first anchor 729 in its deployed position, the positioning gauge 752 can be used to determine a length between the second end 7104 of the elongate catheter body 7100 and the top of the main pulmonary artery (e.g., a location distal to the pulmonary valve and adjacent to both the right and left pulmonary arteries). Knowing this length, the catheter (e.g., catheter 300, 400, 500, 600) can be advanced from the lumen 7110 of the elongate catheter body 7100 to a location between the second end 7104 of the elongate catheter body 7100 and the top of the main pulmonary artery. This location can be determined, for example, using markings (e.g., markings providing a length in, for example, millimeters) on a portion of the elongate body of the catheter that extends proximally from the first end 7102 of the elongate catheter body 7100.

Referring now to FIGS. 8A through 8D, there is shown an additional embodiment of a catheter 800 according to the present disclosure. The catheter 800 includes an elongate catheter body 801 having a first end 803 and a second end 805. The elongate catheter body 801 also includes a peripheral surface 807 and an interior surface 809 defining an inflation lumen 811 (shown with a broken line) that extends at least partially between the first end 803 and the second end 805 of the elongate catheter body 801.

The catheter 800 includes an inflatable balloon 813 on the peripheral surface 807 of the elongate catheter body 801. The inflatable balloon 813 includes a balloon wall 815 with an interior surface 817 that, along with a portion of the peripheral surface 807 of the elongate catheter body 801, defines a fluid tight volume 819. The inflation lumen 811 includes a first opening 821 into the fluid tight volume 819 of the inflatable balloon 813 and a second opening 823 proximal to the first opening 821 to allow for a fluid to move in and out of the volume 819 to inflate and deflate the balloon 813.

The catheter 800 further includes a plurality of electrodes 825 positioned along the peripheral surface 807 of the elongate catheter body 801. The plurality of electrodes 825 is located between the inflatable balloon 813 and the first end 803 of the elongate catheter body 801. Conductive elements 827 extend through the elongate catheter body 801, where the conductive elements 827 conduct electrical current to combinations of two or more of the plurality of electrodes 825.

The catheter 800 further includes a first anchor 829 that extends laterally from the peripheral surface 807 of the elongate body 801, the first anchor 829 having struts 831 forming an open framework. In the illustrated embodiment, the struts 831 have a peripheral surface 833 having a largest outer dimension greater than the largest outer dimension of the inflatable balloon 813 (e.g., its largest diameter). As illustrated, the first anchor 829 has a center point 835 relative to the peripheral surface 833 that is eccentric relative to a center point 837 of the elongate catheter body 801 relative to the peripheral surface 807.

FIGS. 8A and 8B both show the first anchor 829. FIG. 8A shows the first anchor 829 positioned between the inflatable balloon 813 and the plurality of electrodes 825 positioned along the peripheral surface 807 of the elongate catheter body 801. FIG. 8B shows the first anchor 829 positioned between the plurality of electrodes 825 positioned along the peripheral surface 807 of the elongate catheter body 801 and the first end 803 of the elongate catheter body 801.

For the catheter 800 shown in FIG. 8A, a portion 839 of the elongate catheter body 801 that includes the plurality of electrodes 825 may curve in a predefined radial direction when placed under longitudinal compression. To achieve the curving of this portion 839 that includes the plurality of electrodes 825, the elongate catheter body 801 can be pre-stressed and/or the wall can have thicknesses that allow for the elongate catheter body 801 to curve in the predefined radial direction when placed under longitudinal compression. In addition, or alternatively, structures such as coils or a helix of wire having different turns per unit length can be located within the elongate catheter body 801 in the portion 839. One or more of these structures can be used to allow the longitudinal compression to create the curve in the predefined radial direction in the portion 839. To achieve the longitudinal compression, the first anchor 829 can be deployed in the vasculature of the patient (e.g., in the pulmonary artery), where the first anchor 829 provides a location or point of resistance against the longitudinal movement of the elongate body 801. As such, this allows a compressive force to be generated in the elongate catheter body 801 sufficient to cause the portion 839 of the elongate catheter body 801 along which the plurality of electrodes 825 are present to curve in the predefined radial direction.

FIG. 8C provides an illustration of the portion 839 of the elongate catheter body 801 curved in a predefined radial direction when placed under longitudinal compression. The catheter 800 illustrated in FIG. 8C is representative of the catheter shown in FIG. 8A and is described herein. As illustrated, the catheter 800 has been at least partially positioned within the main pulmonary artery 8500 of a patient's heart (the catheter 800 can also be at least partially positioned within the right pulmonary artery 8504 as illustrated), where the balloon 813 and the first anchor 829 are located in the lumen of the left pulmonary artery 8502. From this position, a compressive force applied to the elongate catheter body 801 can cause the portion 839 of the elongate catheter body 801 with the plurality of electrodes 825 to curve in the predefined radial direction, thereby allowing (e.g., causing) the plurality of electrodes 825 to extend towards and/or touch the luminal surface of the main pulmonary artery 8500. In accordance with several embodiments, the plurality of electrodes 825 are brought into position and/or contact with the luminal surface of the main pulmonary artery 8500.

Providing a rotational torque at the first end 803 of the elongate catheter body 801 can help to move the plurality of electrodes 825 relative to the luminal surface, thereby allowing a professional or clinician to "sweep" the plurality of electrodes 825 into different positions along the luminal surface of the main pulmonary artery 8500. As discussed herein, this allows for the patient's cardiac response to the stimulation electrical energy to be monitored and recorded at a variety of locations along the luminal surface of the main pulmonary artery 8500. In this way, a preferred location for the position of the electrodes 825 along the luminal surface of the main pulmonary artery 8500 can be identified. In accordance with other embodiments, the plurality of electrodes 825 may be brought into position and/or contact with the luminal surface of the left pulmonary artery 8502 or the right pulmonary artery 8504 or at other locations, as desired and/or required.

Alternatively, for the catheter 800 shown in FIG. 8B, the elongate catheter body 801 can include a second interior surface 841 defining a shaping lumen 843 that extends from the first end 803 towards the second end 805. The catheter 800 of FIG. 8B can also include a shaping wire 845 having a first end 847 and a second end 849. In one embodiment, the shaping lumen 843 has a size (e.g., a diameter) sufficient to allow the shaping wire 845 to pass through the shaping lumen 843 with the first end 847 of the shaping wire 845 proximal to the first end 803 of the elongate catheter body 801 and the second end 849 of the shaping wire 845 joined to the elongate catheter body 801 so that the shaping wire 845 imparts a curve into the portion 839 of the elongate catheter body 801 having the plurality of electrodes 825 when tension is applied to the shaping wire 845.

FIG. 8D provides an illustration of the portion 839 of the elongate catheter body 801 curved in a predefined radial direction when using the shaping lumen and shaping wire as discussed herein (the catheter 800 illustrated in FIG. 8D is the catheter shown in FIG. 8B and is described herein). As illustrated, the catheter 800 has been at least partially positioned within the main pulmonary artery 8500 of a patient's heart, where the balloon 813 is located in the lumen of the left pulmonary artery 8502 and the first anchor 829 is located in the main pulmonary artery 8500. From this position, the shaping wire 845 can be used to impart the curve into the portion 839 of the elongate catheter body 801 having the plurality of electrodes 825 when tension is applied to the shaping wire 845, thereby allowing (e.g., causing) the plurality of electrodes 825 to extend towards and/or touch the luminal surface of the main pulmonary artery 8500 (the catheter 800 can also be at least partially positioned within the right pulmonary artery 8504 as illustrated). In accordance with several embodiments, the plurality of electrodes 825 are brought into position and/or contact with the luminal surface of the main pulmonary artery. In accordance with other embodiments, the plurality of electrodes 825 may be brought into position and/or contact with the luminal surface of the left pulmonary artery 8502 or the right pulmonary artery 8504 or at other locations, as desired and/or required.

Providing a rotational torque at the first end 803 of the elongate catheter body 801 can help to move the plurality of electrodes 825 relative to the luminal surface of the main pulmonary artery 8500 (and/or the right or left pulmonary artery), thereby allowing a professional or clinician to "sweep" the plurality of electrodes 825 into different positions along the luminal surface of the main pulmonary artery (and/or the right or left pulmonary artery), as discussed herein, so as to identify a preferred location for the position of the electrodes 825 along the luminal surface of the main pulmonary artery (and/or the right or left pulmonary artery).

As illustrated, the catheter 800 of FIGS. 8A and 8B both include an elongate delivery sheath 851 having a lumen 853 that extends over a peripheral surface 807 of the elongate body 801. The elongate delivery sheath 851, in a first position, can have the first anchor 829 positioned within the lumen 853 of the elongate delivery sheath 851. As the elongate delivery sheath 851 moves relative to the peripheral surface 807 of the elongate body 801 the first anchor 829 extends from the peripheral surface 807 of the elongate body 801.

Figure 9:
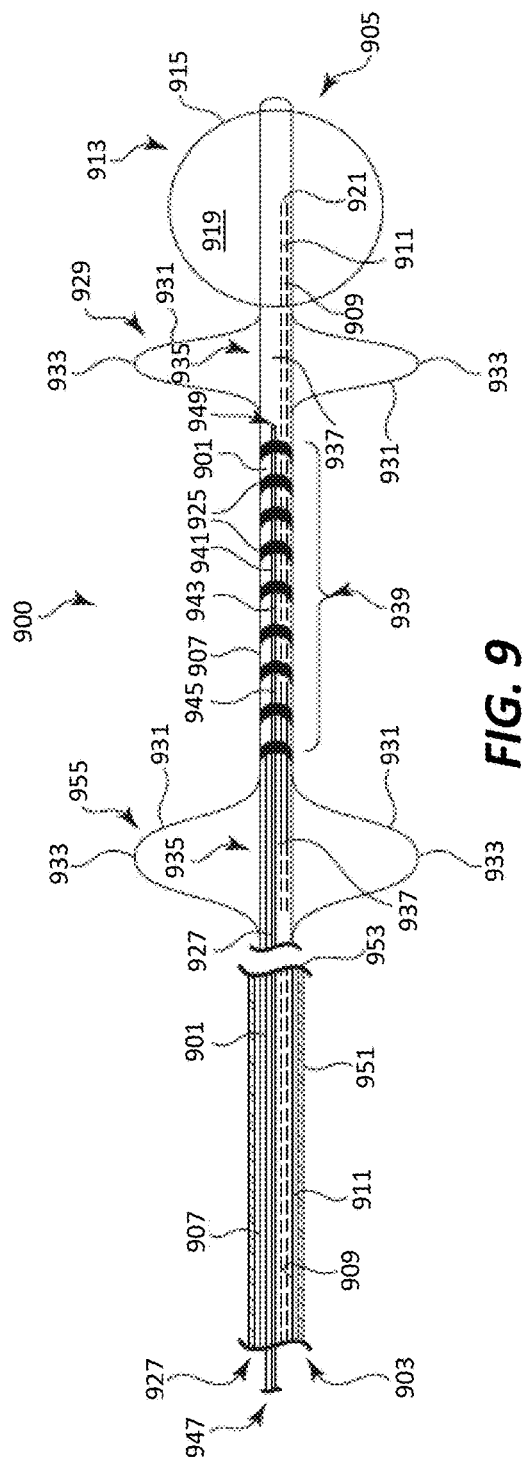
FIGS. 9 and 10 illustrate additional examples of catheters.

Referring now to FIG. 9, there is shown an additional example of a catheter 900. As described for catheter 800, catheter 900 includes an elongate catheter body 901 having a first end 903 and a second end 905, a peripheral surface 907 and an interior surface 909 defining an inflation lumen 911 that extends at least partially between the first end 903 and the second end 905 of the elongate catheter body 901. The catheter 900 includes an inflatable balloon 913 on the peripheral surface 907 of the elongate catheter body 901, the inflatable balloon 913 having a balloon wall 915 with an interior surface 917 that, along with a portion of the peripheral surface 907 of the elongate catheter body 901, defines a fluid tight volume 919. The inflation lumen 911 includes a first opening 921 into the fluid tight volume 919 of the inflatable balloon 913 and a second opening 923 proximal to the first opening 921 to allow for a fluid (e.g., liquid or gas) to move in and out of the volume 919 to inflate and deflate the balloon 913.

The catheter 900 includes a plurality of electrodes 925 positioned along the peripheral surface 907 of the elongate catheter body 901. As shown, the plurality of electrodes 925 is located between the inflatable balloon 913 and the first end 903 of the elongate catheter body 901. Conductive elements 927 extend through the elongate catheter body 901, where the conductive elements 927 conduct electrical current to combinations of one or more of the plurality of electrodes 925.

The catheter 900 further includes a first anchor 929 and a second anchor 955 that both extend laterally from the peripheral surface 907 of the elongate body 901. Both the first anchor 929 and the second anchor 955 have struts 931 that form an open framework for the anchors. The struts 931 have a peripheral surface 933 having a largest outer dimension greater than the largest outer dimension of the inflatable balloon 913 (e.g., its largest diameter). As illustrated, the first anchor 929 has a center point 935 relative to the peripheral surface 933 that is eccentric relative to a center point 937 of the elongate catheter body 901 relative to the peripheral surface 907. In contrast, the second anchor 955 has a center point 935 relative to the peripheral surface 933 that is concentric relative to the center point 937 of the elongate catheter body 901 relative to the peripheral surface 907. In some embodiments, the first anchor 929 may have a center point 935 relative to the peripheral surface 933 that is concentric relative to the center point 937 of the elongate catheter body 901 relative to the peripheral surface 907 and/or the second anchor 955 may have a center point 935 relative to the peripheral surface 933 that is eccentric relative to a center point 937 of the elongate catheter body 901 relative to the peripheral surface 907.

The catheter 900 includes an elongate delivery sheath 951 having a lumen 953 that extends over a peripheral surface 907 of the elongate body 901. The elongate delivery sheath 951, in a first position, can have the first anchor 929 and the second anchor 955 positioned within the lumen 953 of the elongate delivery sheath 951. As the elongate delivery sheath 951 moves relative to the peripheral surface 907 of the elongate body 901 the first anchor 929 extends from the peripheral surface 907 of the elongate body 901. As the elongate delivery sheath 951 moves further away from the inflatable balloon 913 relative to the peripheral surface 907, the second anchor 955 extends from the peripheral surface 907 of the elongate body 901.

As illustrated, the plurality of electrodes 925 are located between the first anchor 929 and the second anchor 955. A portion 939 of the elongate catheter body 901 that includes the plurality of electrodes 925 can be made to curve in a predefined radial direction in a variety of ways. For example, the portion 939 of the elongate catheter body 901 that includes the plurality of electrodes 925 can be made to curve in the predefined radial direction when placed under longitudinal compression (as discussed herein). As with the catheter 800, to cause the portion 939 that includes the plurality of electrodes 925 to curve, the elongate catheter body 901 can be pre-stressed and/or the wall can have thicknesses that allow for the elongate catheter body 901 to curve in the predefined radial direction when placed under longitudinal compression. In addition, or alternatively, structures such as coils of a helix of wire having different turns per unit length can be located within the elongate catheter body 901 in the portion 939. One or more of these structures can be used to allow the longitudinal compression to create the curve in the predefined radial direction in the portion 939.

To achieve the longitudinal compression, the first anchor 929 can be deployed in the vasculature of the patient, as discussed herein, where the first anchor 929 provides a location or point of resistance against the longitudinal movement of the elongate body 901. As discussed herein for example, this can be accomplished by moving the elongate delivery sheath 951 relative to the peripheral surface 907 of the elongate body 901 so as to allow the first anchor 929 to extend from the peripheral surface 907 of the elongate body 901. Once deployed, the first anchor 929 allows a compressive force to be generated in the elongate catheter body 901 sufficient to cause the portion 939 of the elongate catheter body 901 along which the plurality of electrodes 925 are present to curve in the predefined radial direction. Once the curve is formed in the predefined radial direction, the elongate delivery sheath 951 is moved further away from the inflatable balloon 913 relative to the peripheral surface 907 so as to allow the second anchor 955 to extend from the peripheral surface 907 of the elongate body 901.

Alternatively, the elongate catheter body 901 of the catheter 900 can include a second interior surface 941 defining a shaping lumen 943 that extends from the first end 903 towards the second end 905. The catheter 900 can also include a shaping wire 945 having a first end 947 and a second end 949, where the shaping lumen 943 has a size (e.g., a diameter) sufficient to allow the shaping wire 945 to pass through the shaping lumen 943 with the first end 947 of the shaping wire 945 proximal to the first end 903 of the elongate catheter body 901 and the second end 949 of the shaping wire 945 joined to the elongate catheter body 901 so that the shaping wire 945 imparts a curve into the portion 939 of the elongate catheter body 901 having the plurality of electrodes 925 when tension is applied to the shaping wire 945.

Figure 10:
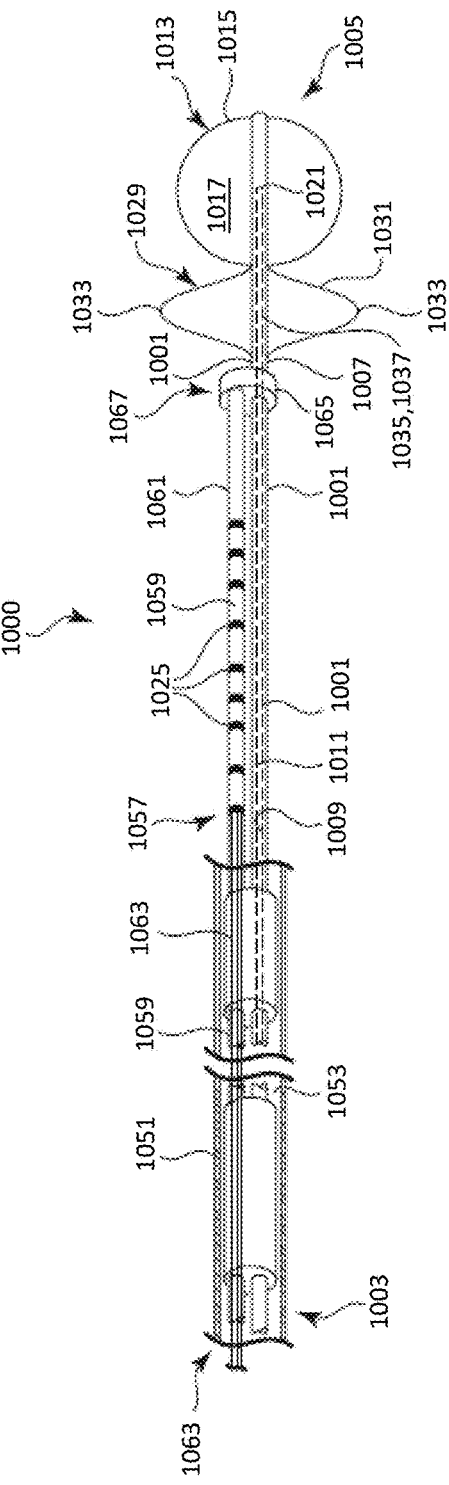

Referring now to FIG. 10, there is shown an additional embodiment of the catheter 1000. As discussed above, catheter 1000 includes an elongate catheter body 1001 having a first end 1003, a second end 1005, a peripheral surface 1007 and an interior surface 1009 defining an inflation lumen 1011 that extends at least partially between the first end 1003 and the second end 1005 of the elongate catheter body 1001. The catheter 1000 also includes an inflatable balloon 1013 on the peripheral surface 1007 of the elongate catheter body 1001, where the inflatable balloon 1013 has the balloon wall 1015 with an interior surface 1017 that, along with a portion of the peripheral surface 1007 of the elongate catheter body 1001, defines a fluid tight volume 1019. The inflation lumen 1011 includes a first opening 1021 into the fluid tight volume 1019 of the inflatable balloon 1015 and a second opening 1023 proximal to the first opening 1021 to allow for a fluid to move in and out of the volume 1019 to inflate and deflate the balloon 1015.

The elongate catheter body 1001 also includes a first anchor 1029 that can extend laterally from the peripheral surface 1007 of the elongate catheter body 1001. As discussed herein, the first anchor 1029 includes struts 1031 forming an open framework with a peripheral surface 1033 having a largest outer dimension greater than the largest outer dimension of the inflatable balloon 1013 (e.g., its largest diameter). As illustrated, the first anchor 1029 has a center point 1035 relative to the peripheral surface 1033 that is eccentric relative to a center point 1037 of the elongate catheter body 1001 relative to the peripheral surface 1007.

The catheter 1000 further includes an electrode catheter 1057 having an electrode elongate body 1059 and a plurality of electrodes 1025 positioned along a peripheral surface 1061 of the electrode elongate body 1059. Conductive elements 1063 extend through and/or along the electrode elongate body 1059 of the electrode catheter 1057, where the conductive elements 1063 conduct electrical current to combinations of one or more of the plurality of electrodes 1025. As illustrated, the first anchor 1029 is positioned between the inflatable balloon 1013 and the plurality of electrodes 1025 positioned along the peripheral surface of the electrode elongate body 1059.

The catheter 1000 further includes an attachment ring 1065 joined to the electrode catheter 1057 and positioned around the peripheral surface 1061 of the electrode catheter body 1001 proximal to both the first anchor 1029 and the inflatable balloon 1013. In one embodiment, the attachment ring 1065 holds a distal end 1067 of the electrode catheter 1057 in a static relationship to the elongate catheter body 1001. From this position, a portion 1039 of the electrode elongate body 1059 that includes the plurality of electrodes 1025 can be made to curve in a predefined radial direction, as previously discussed. The configuration of the portion 1039 of the electrode elongate body 1059 that includes the plurality of electrodes 1025 that curves can have any of the configurations and curvature mechanisms as discussed herein.

FIG. 10 also illustrates an elongate delivery sheath 1051 having a lumen 1053 that extends over the peripheral surface of the elongate catheter body 1001 and the electrode catheter 1057. The elongate delivery sheath 1051, in a first position, can have the first anchor 1029 positioned within the lumen 1053 of the elongate delivery sheath 1051. As the elongate delivery sheath 1051 moves relative to the peripheral surface 1007 of the elongate body 1001 and the peripheral surface 1061 of the electrode catheter 1057, the first anchor 1029 extends from (e.g., away from) the peripheral surface 1007 of the elongate body 1001.

Figure 11:
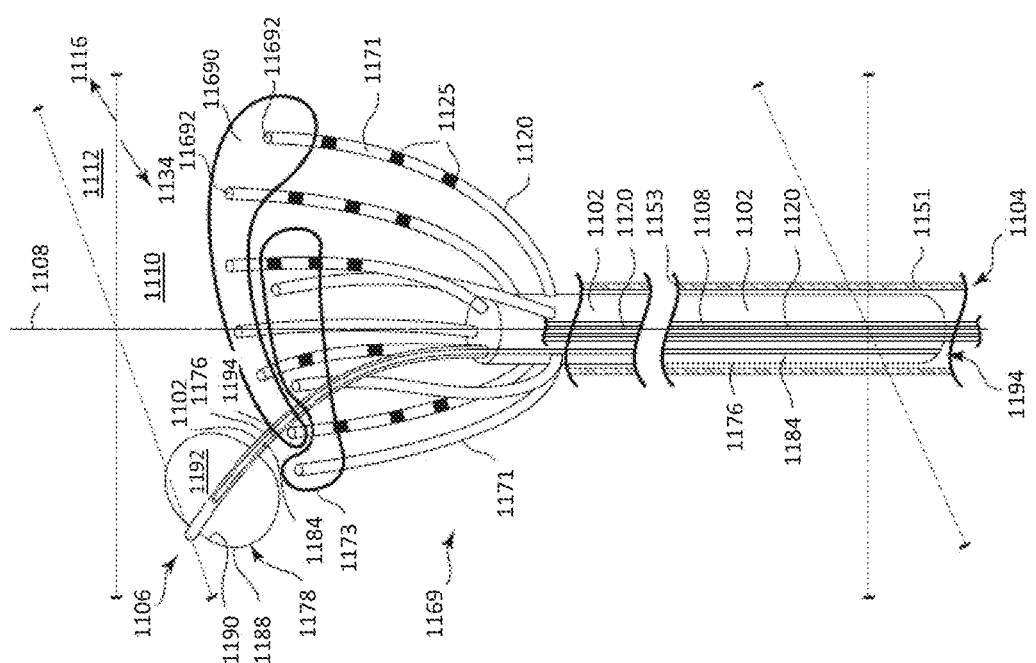
FIG. 11 illustrates an example of a catheter system.

Referring now to FIG. 11, a catheter system 1169 is shown in accordance with an embodiment of the disclosure. The catheter system 1169 includes an elongate catheter body 1102 having a first end 1104, a second end 1106, a peripheral surface 1176 and an interior surface 1184 defining an inflation lumen 1194 that extends at least partially between the first end 1104 and the second end 1106 of the elongate catheter body 1102. The elongate catheter body 1102 includes an elongate radial axis 1108 defined by an intersection of a first plane 1110 and a second plane 1112 perpendicular to the first plane 1110, where the elongate radial axis 1108 extends through the first end 1104 and the second end 1106 of the elongate catheter body 1102.

The catheter system 1169 further includes an inflatable balloon 1178 on the peripheral surface 1176 of the elongate catheter body 1102. The inflatable balloon 1178 has a balloon wall 1188 with an interior surface 1190 that, along with a portion of the peripheral surface 1176 of the elongate catheter body 1102, defines a fluid tight volume 1192. The inflation lumen 1194 includes a first opening 1196 into the fluid tight volume 1192 of the inflatable balloon 1178 and a second opening 1198 proximal to the first opening 1196 to allow for a fluid to move in and out of the volume 1192 to inflate and deflate the balloon 1178.

The catheter system 1169 further includes an electrode cage 11690 having two or more ribs 1171 that extend radially away from the peripheral surface 1176 of the elongate catheter body 1102 towards the inflatable balloon 1178. As illustrated, each of the ribs 1171 of the electrode cage 11690 have a first end 11692 that extends away from the elongate catheter body 1101 towards the inflatable balloon 1178. Each of the first ends 11692 of the ribs 1171 of the electrode cage 11690 is free relative to every other first end of the ribs 1171. In addition, the ribs 1171 of the electrode cage 1169 curve into a first half 1116 of the first plane 1110. Each of the ribs 1171 of the electrode cage 1169 also includes one or more electrodes 1125. The one or more electrodes 1125 on each of the ribs 1171 form an electrode array on the first half 1116 of the first plane 1110. The catheter system 1169 further includes conductive elements 1120 extending through and/or along the ribs 1171 of the electrode cage 1169 and the elongate catheter body 1101, where the conductive elements 1120 conduct electrical current to combinations of one or more electrodes 1125 in the electrode array.

The catheter system 1169 also includes an anchoring cage 1173 having two or more of the ribs 1171 that extend radially away from the peripheral surface 1176 of the elongate catheter body 1101 towards the inflatable balloon 1178. As illustrated, the two or more ribs 1171 of the anchoring cage 1173 curve into the second half 1134 of the first plane 1110. In the illustrated embodiment, the two or more ribs 1171 of the anchoring cage 1173 do not include any electrodes. In some embodiments, one or more of the ribs 1171 of the anchoring cage 1173 include one or more electrodes.

The catheter system 1169 can further include a second inflatable balloon on the peripheral surface 1176 of the elongate catheter body 1101. For example, the elongate catheter body 1101 can further include a third end and a second interior surface defining a second inflation lumen that extends at least partially between the first end and the third end of the elongate catheter body 1101. The second inflatable balloon may be located on the peripheral surface 1176 of the elongate catheter body 1101 adjacent the third end of the elongate catheter body 1101. As with the first inflatable balloon 1178, the second inflatable balloon may include a balloon wall with an interior surface that, along with a portion of the peripheral surface 1176 of the elongate catheter body 1101, defines a fluid tight volume. The second inflation lumen may include a first opening into the fluid tight volume of the second inflatable balloon and a second opening proximal to the first opening to allow for a fluid to move in and out of the volume to inflate and deflate the second balloon.

FIG. 11 also illustrates the elongate delivery sheath 1151 having a lumen 1153 that extends over the peripheral surface of the elongate catheter body 1101 and the ribs 1171 of both the electrode cage 1169 and the anchoring cage 1173. The elongate delivery sheath 1151, in a first position, can have the ribs 1171 of both the electrode cage 1169 and the anchoring cage 1173 within the lumen 1153 of the elongate delivery sheath 1151. As the elongate delivery sheath 1151 moves relative to the peripheral surface 1107 of the elongate body 1101, the ribs 1171 of the electrode cage 1169 extend from the elongate body 1101 to curve into the first half 1116 of the first plane 1110 and the ribs 1171 of the anchoring cage 1173 extend from the elongate body 1101 to curve into the second half 1134 of the first plane 1110.

Figure 12A:
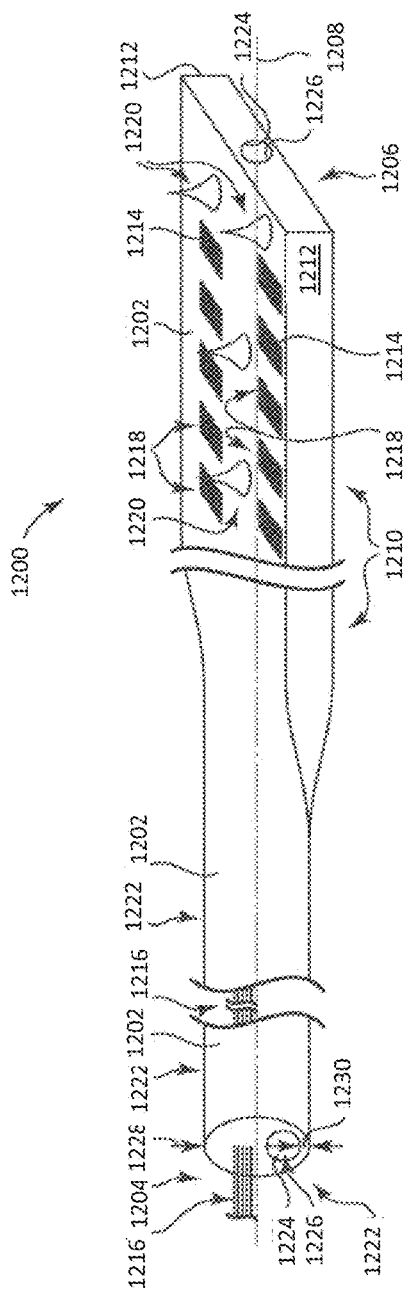
FIG. 12A-12D illustrate various examples of catheters.

Referring now to FIG. 12A, there is shown a perspective view of an embodiment of a catheter 1200. The catheter 1200 includes an elongate body 1202 having a first end 1204 and a second end 1206 distal from the first end 1204. As illustrated, the elongate body 1202 includes a longitudinal center axis 1208 extending between the first end 1204 and the second end 1206 of the elongate body 1202. The elongate body 1202 also includes a portion 1210 that has three or more surfaces 1212 defining a convex polygonal cross-sectional shape taken perpendicularly to the longitudinal center axis 1208.

As used herein, the convex polygonal cross-sectional shape of the elongate body 1202 includes those shapes for which every internal angle is less than 180 degrees and where every line segment between two vertices of the shape remains inside or on the boundary of the shape. Examples of such shapes include, but are not limited to, triangular, rectangular (as illustrated in FIG. 12A), square, pentagon and hexagon, among others.

As illustrated, the catheter 1200 includes one or more (e.g., two or more), electrodes 1214 on one surface of the three or more surfaces 1212 of the elongate body 1202. Conductive elements 1216 extend through and/or along the elongate body 1202, where the conductive elements 1216 can be used, for example as discussed herein, to conduct electrical current to combinations of the one or more electrodes 1214. Each of the one or more electrodes 1214 is coupled to a corresponding conductive element 1216. In some embodiments, the conductive elements 1216 are electrically isolated from each other and extend through and/or along the elongate body 1202 from each respective electrode 1214 through the first end 1204 of the elongate body 1202. The conductive elements 1216 may terminate at a connector port, where each of the conductive elements 1216 can be releasably coupled to a stimulation system, such as the stimulation systems described herein. In some embodiments, the conductive elements 1216 are permanently coupled to the stimulation system (e.g., not releasably coupled). The stimulation system can be used to provide stimulation electrical energy that is conducted through the conductive elements 1216 and delivered across combinations of the one or more electrodes 1214. The one or more electrodes 1214 may be electrically isolated from one another and the elongate body 1202 may be formed of an electrically insulating material as discussed herein. As illustrated, the one or more electrodes 1214 are located only on the one surface of the three or more surfaces 1212 of the elongate body 1202, in accordance with one embodiment.

There can be a variety of the number and the configuration of the one or more electrodes 1214 on the one surface of the three or more surfaces 1212 of the elongate body 1202. For example, as illustrated, the one or more electrodes 1214 can be configured as an array of electrodes, where the number of electrodes and their relative position to each other can vary depending upon the desired implant (e.g., deployment or target) location. As discussed herein, the one or more electrodes 1214 can be configured to allow for electrical current to be delivered from and/or between different combinations of the one or more electrodes 1214. So, for example, the electrodes in the array of electrodes can have a repeating pattern where the electrodes are equally spaced from each other. For example, the electrodes in the array of electrodes can have a column and row configuration (as illustrated in FIG. 12A). Alternatively, the electrodes in the array of electrodes can have a concentric radial pattern, where the electrodes are positioned so as to form concentric rings of the electrodes. Other patterns are possible, where such patterns can either be repeating patterns or random patterns.

As illustrated, the one or more electrodes 1214 have an exposed face 1218. The exposed face 1218 of the electrode 1214 provides the opportunity for the electrode 1214, when implanted (temporarily or for an extended duration of time) in the patient, to be placed into proximity and/or in contact with vascular tissue of the patient (e.g., of the right or left pulmonary artery), as opposed to facing into the volume of blood in the artery or other vessel, lumen or organ. As the one or more electrodes 1214 are located on one surface of the three or more surfaces 1212 of the elongate body 1202, the electrodes 1214 can be placed into direct proximity to and/or in contact with the tissue of any combination of the main pulmonary artery, the left pulmonary artery and/or the right pulmonary artery.

By locating the one or more electrodes 1214 on the one surface of the three or more surfaces 1212, the exposed face 1218 of the electrode can be positioned inside the patient's vasculature to face and/or contact the tissue of the main pulmonary artery, the left pulmonary artery and/or the right pulmonary artery. When the one or more electrodes 1214 are in contact with luminal surface of the patient's vasculature, the one or more electrodes 1214 will be pointing away from the majority of the blood volume of that region of the pulmonary artery, thereby allowing the electrical pulses from the one or more electrodes 1214 to be directed into the tissue adjacent the implant location, instead of being directed into the blood volume.

The exposed face 1218 of the one or more electrodes 1214 can have a variety of shapes. For example, the exposed face 1218 can have a flat planar shape. In this embodiment, the exposed face 1218 of the electrodes 1214 can be co-planar with the one surface of the three or more surfaces 1212 of the elongate body 1202. In an alternative embodiment, the exposed face 1218 of the electrodes 1214 can have a semi-hemispherical shape. Other shapes for the exposed face 1218 of the electrodes 1214 can include semi-cylindrical, wave-shaped, and zig-zag-shaped. The exposed face 1218 of the electrodes 1214 can also include one or more anchor structures. Examples of such anchor structures include hooks that can optionally include a barb. Similarly, the electrodes 1214 can be shaped to also act as anchor structures.

In one embodiment, the one surface of the three or more surfaces 1112 of the elongate body 1102 that includes the exposed face 1218 of the one or more electrodes 1214 can further include anchor structures 1220 that extend above the one surface of the three or more surfaces 1212. As illustrated, the anchor structures 1220 can include portions that can contact the vascular tissue in such a way that the movement of the one or more electrodes 1214 at the location where they contact the vascular tissue is reduced (e.g., minimized). The anchor structures 1220 can have a variety of shapes that may help to achieve this goal. For example, the anchor structures 1220 can have a conical shape, where the vertex of the conical shape can contact the vascular tissue. In one embodiment, the anchor structures 1220 have a hook configuration (with or without a barb). In an additional embodiment, one or more of the anchor structures 1220 can be configured as an electrode.

As illustrated, the elongate body 1202 of the catheter 1200 can also include a portion 1222 with a circular cross-section shape taken perpendicularly to the longitudinal center axis 1208. The elongate body 1202 of catheter 1200 also includes a surface 1224 defining a guide-wire lumen 1226 that extends through the elongate body 1202. The guide-wire lumen 1226 may have a diameter that is sufficiently large to allow the guide wire to freely pass through the guide-wire lumen 1226. The guide-wire lumen 1226 can be positioned concentrically relative to the longitudinal center axis 1208 of the elongate body 1202.

Alternatively, and as illustrated in FIG. 12A, the guide-wire lumen 126 can be positioned eccentrically relative to the longitudinal center axis 1208 of the elongate body 1202. When the guide-wire lumen 1226 is positioned eccentrically relative to the longitudinal center axis 1208, the guide-wire lumen 1226 has a wall thickness 1228 taken perpendicularly to the longitudinal center axis that is greater than a wall thickness 1230 of a remainder of the catheter taken perpendicularly to the longitudinal center axis. For this configuration, the differences in wall thickness 1228 and 1230 help to provide the elongate body 1202 with a preferential direction in which to bend. For example, the wall thickness 1228 of the elongate body 1202 being greater than the wall thickness 1230 causes the side of the elongate body 1102 with the greater wall thickness to preferentially have the larger radius of curvature when the elongate body 1102 bends, in accordance with several embodiments. By positioning the exposed face 1218 of the one or more electrodes 1214 on the side of the elongate body 1202 having the greater wall thickness (e.g., wall thickness 1228), the one or more electrodes 1214 can be more easily and predictably brought into contact with the luminal surface of the vasculature in and around the main pulmonary artery and at least one of the right and left pulmonary arteries.

The catheter 1200 shown in FIG. 12A can be positioned in the main pulmonary artery and/or one or both of the left and right pulmonary arteries of the patient, such as described herein. To accomplish this, a pulmonary artery guide catheter is introduced into the vasculature through a percutaneous incision and guided to the right ventricle using known techniques. For example, the pulmonary artery guide catheter can be inserted into the vasculature via a peripheral vein of the arm (e.g., as with a peripherally inserted central catheter), via a peripheral vein of the neck or chest (e.g., as with a Swan-Ganz catheter approach), or a peripheral vein of the leg (e.g., a femoral vein). Other approaches can include, but are not limited to, an internal jugular approach. Changes in a patient's electrocardiography and/or pressure signals from the vasculature can be used to guide and locate the pulmonary artery guide catheter within the patient's heart. Once in the proper location, a guide wire can be introduced into the patient via the pulmonary artery guide catheter, where the guide wire is advanced into the main pulmonary artery and/or one of the pulmonary arteries (e.g., left and right pulmonary arteries). Using the guide-wire lumen 1226, the catheter 1200 can be advanced over the guide wire so as to position the catheter 1200 in the main pulmonary artery and/or one or both of the left and right pulmonary arteries of the patient, for example as described herein. Various imaging modalities can be used in positioning the guide wire of the present disclosure in the main pulmonary artery and/or one of the left and right pulmonary arteries of the patient. Such imaging modalities include, but are not limited to, fluoroscopy, ultrasound, electromagnetic, and electropotential modalities.

Using a stimulation system, such as the stimulation systems discussed herein, stimulation electrical energy (e.g., electrical current or pulses) can be delivered across combinations of one or more of the electrodes 1214. In accordance with several embodiments described herein, it is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the subject (e.g., patient).

Figure 12B:
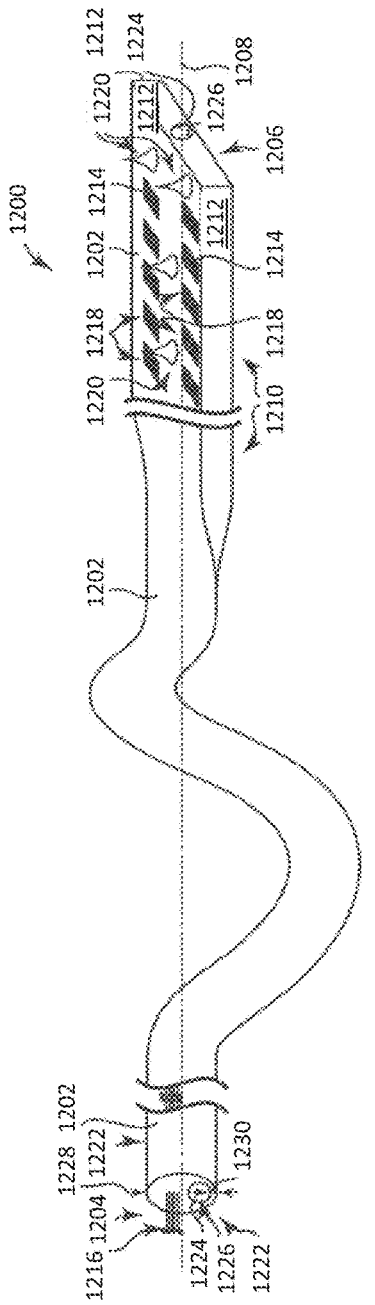

FIG. 12B illustrates another embodiment of the catheter 1200. The catheter 1200 includes the features and components as discussed above, a discussion of which is not repeated but the element numbers are included in FIG. 12B with the understanding that the discussion of these elements is implicit. In addition, the elongate body 1202 of the catheter 1200 includes a serpentine portion 1232 proximal to the one or more electrodes 1214. When implanted (e.g., deployed) in the vasculature of the patient, the serpentine portion 1232 of the elongate body 1202 can act as a "spring" to absorb and isolate the movement of the one or more electrodes 1214 from the remainder of the elongate body 1202 of the catheter 1200. Besides having a serpentine shape, the serpentine portion 1232 can have a coil like configuration. Other shapes that achieve the objective of absorbing and isolating the movement of the one or more electrodes 1214 from the remainder of the elongate body 1202 of the catheter 1200 once implanted may also be used as desired and/or required. During delivery of the catheter 1200, the presence of the guide wire in the guide-wire lumen 1226 can help to temporarily straighten the serpentine portion 1232 of the elongate body 1202.

Figure 12C:
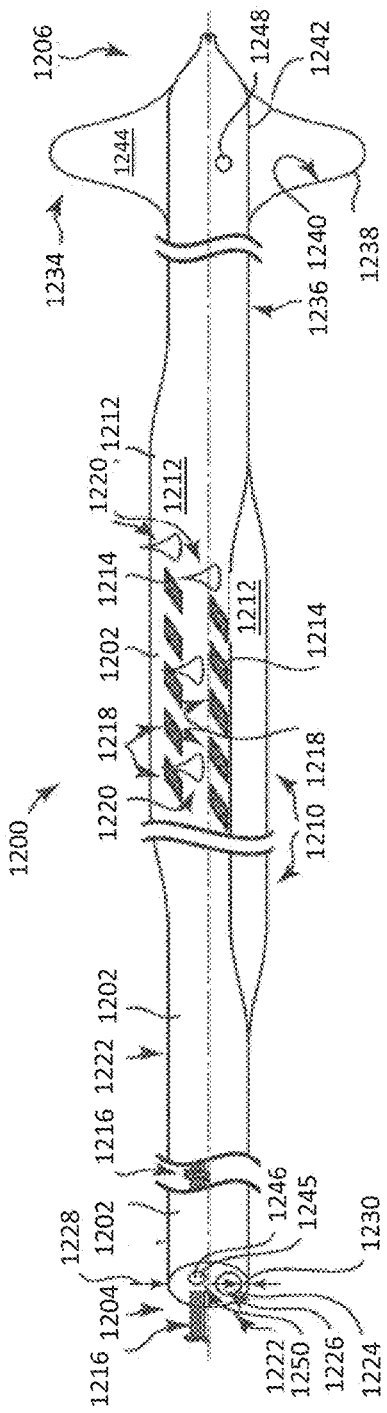

Referring now to FIG. 12C, there is shown an additional embodiment of the catheter 1200 as provided herein. The catheter 1200 can include the features and components as discussed above for the catheters described in connection with FIGS. 12A and 12B, a discussion of which is not repeated but the element numbers are included in FIG. 12C with the understanding that the discussion of these elements is implicit. In addition, the catheter 1200 of the present embodiment includes an inflatable balloon 1234. As illustrated, the elongate body 1202 includes a peripheral surface 1236, where the inflatable balloon 1234 is located on the peripheral surface 1236 of the elongate body 1202. The inflatable balloon 1234 includes a balloon wall 1238 with an interior surface 1240 that, along with a portion 1242 of the peripheral surface 1236 of the elongate body 1202, defines a fluid tight volume 1244.

The elongate body 1202 further includes a surface 1245 that defines an inflation lumen 1246 that extends through the elongate body 1202. The inflation lumen 1246 includes a first opening 1248 into the fluid tight volume 1244 of the inflatable balloon 1234 and a second opening 1250 proximal to the first opening 1248 to allow for a fluid to move in and out of the fluid tight volume 1244 to inflate and deflate the balloon 1234. A syringe, or other known devices, containing the fluid (e.g., saline or a gas (e.g., oxygen)) can be used to inflate and deflate the balloon 334.

The catheter 1200 shown in FIG. 12C can be positioned in the main pulmonary artery and/or one or both of the right and left pulmonary arteries of the patient, for example as described herein. As discussed herein, a pulmonary artery guide catheter is introduced into the vasculature through a percutaneous incision, and guided to the right ventricle. Once in the proper location, the balloon 1234 can be inflated, as described, to allow the catheter 1200 to be carried by the flow of blood from the right ventricle to the main pulmonary artery and/or one of the pulmonary arteries. Additionally, various imaging modalities can be used in positioning the catheter of the present disclosure in the main pulmonary artery and/or one of the pulmonary arteries of the patient. Such imaging modalities include, but are not limited to, fluoroscopy, ultrasound, electromagnetic, and electropotential modalities.

The catheter 1200 can be advanced along the main pulmonary artery until the second end 1206 of the catheter 1200 contacts the top of the main pulmonary artery (e.g., a location distal to the pulmonary valve and adjacent to both the pulmonary arteries). Once the second end 1206 of the catheter 1200 reaches the top of the main pulmonary artery the pulmonary artery guide catheter can be moved relative to the catheter 1200 so as to deploy the catheter 1200 from the pulmonary artery guide catheter.

Markings can be present on the peripheral surface of the catheter body 1202, where the markings start and extend from the first end 1202 towards the second end 1206 of the catheter body 1202. The distance between the markings can be of units (e.g., millimeters, inches, etc.), which can allow the length between the second end 1206 of the catheter 1200 and the top of the main pulmonary artery to be determined.

The ability to measure this distance from the top of the main pulmonary artery may be helpful in placing the one or more electrodes 1214 in a desired location (e.g., at a location within the main pulmonary artery). In addition to measuring the distance from which the second end 1206 of the elongate body 1202 is placed from the top of the main pulmonary artery, the elongate body 1202 can also be used to identify, or map, an optimal position for the one or more electrodes 1214 within the vasculature. For example, the second end 1206 of the elongate body 1202 can be positioned at the desired distance from the top of the main pulmonary artery using the markings on the peripheral surface of the catheter body 1202.

Using the stimulation system, such as the stimulations systems discussed herein, stimulation electrical energy (e.g., electrical current or electrical pulses) can be delivered across combinations of the one or more electrodes 1214. It is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the patient.

Figure 12D:
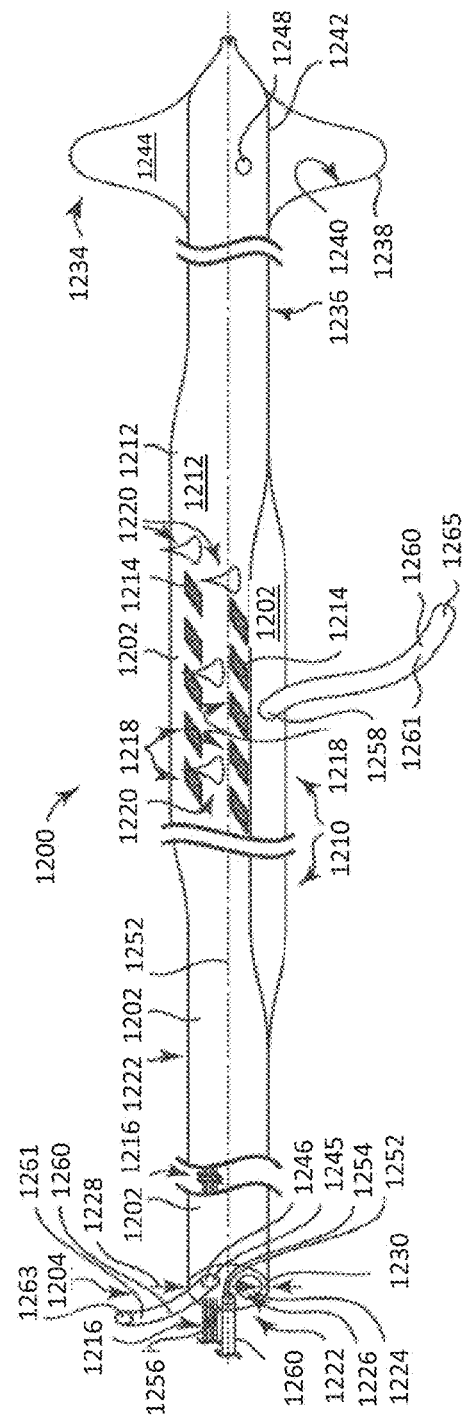

Referring now to FIG. 12D, there is shown an additional embodiment of the catheter 1200. The catheter 1200 can include the features and components as the catheters discussed above in connection with FIGS. 12A-12C, a discussion of which is not repeated but the element numbers are included in FIG. 12D with the understanding that the discussion of these elements is implicit. In addition, the catheter 1200 of the present embodiment includes a surface 1252 defining a deflection lumen 1254. The deflection lumen 1254 includes a first opening 1256 and a second opening 1258 in the elongate body 1202. In one embodiment, the second opening 1258 is opposite the one or more electrodes 1214 on one surface of the three or more surfaces 1212 of the elongate body 1202.

The catheter 1200 further includes an elongate deflection member 1260. The elongate deflection member 1260 includes an elongate body 1261 having a first end 1263 and a second end 1265. The elongate deflection member 1260 extends through the first opening 1256 to the second opening 1258 of the deflection lumen 1254. The deflection lumen 1254 has a size (e.g., a diameter) sufficient to allow the deflection member 1260 to pass through the deflection lumen 1254 with the first end 1263 of the deflection member 1260 proximal to the first end 1204 of the elongate body 1202 and the second end 1265 of the deflection member 1260 extendable from the second opening 1258 of the deflection lumen 1254. Pressure applied from the first end 1263 of the deflection member 1260 can cause the deflection member 1260 to move within the deflection lumen 1254. For example, when pressure is applied to the deflection member 1260 to move the first end 1263 of the deflection member 1260 towards the first opening 1256 of the deflection lumen 1254, the pressure causes the second end 1265 of the deflection member 1260 to extend from the second opening 1258.

As generally illustrated, the elongate deflection member 1260 can be advanced through the deflection lumen 1254 so that elongate deflection member 1260 extends laterally away from the one or more electrodes 1214 on the one surface of the three or more surfaces 1212 of the elongate body 1202. The elongate deflection member 1260 can be of a length and shape that allows the elongate deflection member 1260 to be extended a distance sufficient to bring the one or more electrodes 1214 into contact with the vascular luminal surface (e.g., a posterior surface of the main pulmonary artery and/or one or both of the pulmonary arteries) with a variety of pressures. Optionally, the elongate deflection member 1260 can be configured to include one or more of the electrodes 1214, such as discussed herein.

For the various embodiments, the elongate body 1261 of the deflection member 1260 is formed of a flexible polymeric material. Examples of such flexible polymeric material include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

In one embodiment, the elongate body 1261 of the elongate deflection member 1260 also includes one or more support wires. The support wires can be encased in the flexible polymeric material of the elongate body 1261, where the support wires can help to provide both column strength and a predefined shape to the elongate deflection member 1260. For example, the support wires can have a coil shape that extends longitudinally along the length of the elongate body 1261. In accordance with several embodiments, the coil shape advantageously allows for the longitudinal force applied near or at the first end 1263 of the deflection member 1260 to be transferred through the elongate body 1261 so as to laterally extend the second end 1265 of the deflection member 1260 from the second opening 1258 of the deflection lumen 1254.

The support wires can also provide the deflection member 1260 with a predetermined shape upon laterally extending from the second opening 1258 of the deflection lumen 1254. The predetermined shape can be determined to engage the luminal wall of the pulmonary artery in order to bring the electrodes 1214 into contact with the vascular tissue. The predetermined shape and the support wires can also help to impart stiffness to the deflection member 1260 that is sufficient to maintain the electrodes 1214 on the luminal wall of the pulmonary artery under the conditions within the vasculature of the subject (e.g., patient). The support wires can be formed of a variety of metals or metal alloys. Examples of such metals or metal alloys include surgical grade stainless steel, such as austenitic 316 stainless among others, and the nickel and titanium alloy known as Nitinol. Other metals and/or metal alloys can be used as desired and/or required.

The catheter 1200 shown in FIG. 12D can be positioned in the main pulmonary artery and/or one or both of the left and right pulmonary arteries of the patient, such as described herein. In accordance with several methods, a pulmonary artery guide catheter is introduced into the vasculature through a percutaneous incision, and guided to the right ventricle (e.g., using a Swan-Ganz catheterization approach). Once in the proper location, the balloon 1234 can be inflated, as described, to allow the catheter 1200 to be carried by the flow of blood from the right ventricle to the main pulmonary artery and/or one of the right and left pulmonary arteries. Additionally, various imaging modalities can be used in positioning the catheter in the main pulmonary artery and/or one of the right and left pulmonary arteries of the patient. Such imaging modalities include, but are not limited to, fluoroscopy, ultrasound, electromagnetic, and electropotential modalities.

The catheter 1200 can be advanced along the main pulmonary artery until the second end 1206 of the catheter 1200 contacts the top of the main pulmonary artery (e.g., a location distal to the pulmonary valve and adjacent to both the pulmonary arteries). Once the second end 1206 of the catheter 1200 reaches the top of the main pulmonary artery the pulmonary artery guide catheter can be moved relative to the catheter 1200 so as to deploy the catheter 1200 from the pulmonary artery guide catheter.

Markings, as discussed herein, can be present on the peripheral surface of the catheter body 1202 that can assist in positioning the catheter 1200 within the main pulmonary artery. The ability to measure this distance from the top of the main pulmonary artery may be helpful in placing the one or more electrodes 1214 in a desired location (e.g., a location within the main pulmonary artery). In addition to measuring the distance from which the second end 1206 of the elongate body 1202 is placed from the top of the main pulmonary artery, the elongate body 1202 can also be used to identify, or map, an optimal position for the one or more electrodes 1214 within the vasculature. For example, the second end 1206 of the elongate body 1202 can be positioned at the desired distance from the top of the main pulmonary artery using the markings on the peripheral surface of the catheter body 1202.

When desired, the elongate deflection member 1260 can be extended laterally from the elongate body 1202 to a distance sufficient to cause the one surface of the three or more surfaces 1212 of the elongate body 1202 having the one or more electrodes to contact a surface of the main pulmonary artery, such as the anterior surface of the main pulmonary artery, and thereby bring the one or more electrodes 1214 into contact with the main pulmonary artery or one of the pulmonary arteries (the left pulmonary artery or the right pulmonary artery). The elongate deflection member 1260, as will be appreciated, biases and helps to place the one or more electrodes 1214 along the vessel surface (e.g., along the posterior surface of the main pulmonary artery or one of the pulmonary arteries (the left pulmonary artery or the right pulmonary artery)).

Due to its adjustable nature (e.g., how much pressure is applied to the elongate deflection member 1260), the elongate deflection member 1260 can be used to bring the one or more electrodes 1214 into contact with the luminal surface of the main pulmonary artery or one of the pulmonary arteries with a variety of pressures. So, for example, the elongate deflection member 1260 can bring the one or more electrodes 1214 into contact with the luminal surface of the main pulmonary artery or one of the left and right pulmonary arteries with a first pressure. Using the stimulation system, such as the stimulation systems discussed herein, stimulation electrical energy (e.g., electrical current or electrical pulses) can be delivered across combinations of the one or more electrodes 1214 in the electrode array. It is possible for the patient's cardiac response to the stimulation electrical energy to be monitored and recorded for comparison to other subsequent tests.

It is appreciated that for any of the catheters discussed herein any combination of electrodes, including reference electrodes (as discussed herein) positioned within or on the patient's body, can be used in providing stimulation to and sensing cardiac signals from the patient.

If necessary, the distance the elongate deflection member 1260 extends laterally from the elongate body 1202 can be changed (e.g., made shorter) to allow the elongate body 1202 to be rotated in either a clockwise or counter-clockwise direction, thereby repositioning the one or more electrodes 1214 in contact with the luminal surface of the main pulmonary artery or one of the pulmonary arteries. The stimulation system can again be used to deliver stimulation electrical energy across combinations of one or more of the electrodes 1214 in the electrode array. The patient's cardiac response to this subsequent test can then be monitored and recorded for comparison to previous and subsequent test. In this way, a preferred location for the position of the one or more electrodes 1214 along the luminal surface of the main pulmonary artery or one of the left and right pulmonary arteries can be identified. Once identified, the elongate deflection member 1260 can be used to increase the lateral pressure applied to the one or more electrodes, thereby helping to better anchor the catheter 1200 in the patient.

Figure 13:
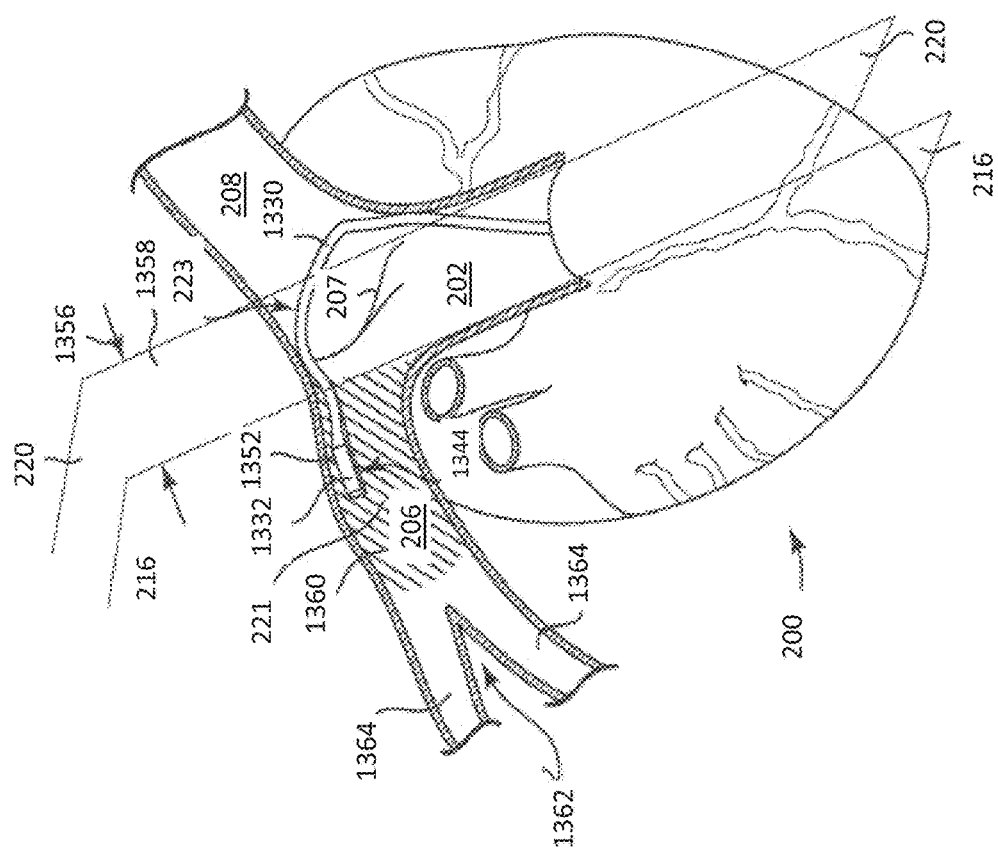
FIG. 13 is a perspective view of a catheter positioned in a heart of a patient.

FIG. 13 provides a perspective view of a catheter 1330 positioned in the heart 200 of the subject (e.g., patient), where one or more of the electrodes 1344 is contacting the posterior surface 221 and/or superior surface 223 of, for example, the right pulmonary artery 206. FIG. 13 also illustrates the one or more of the electrodes 1344 contacting the posterior surface 221 and/or superior surface 223 of the right pulmonary artery 208 at a position that is superior to the branch point 207. FIG. 13 further illustrates that at least a portion of the catheter 1330 is positioned in contact with a portion of the surface defining the branch point 207.

As illustrated, the pulmonary trunk has a diameter 1356 taken across a plane 1358 perpendicular to both the left lateral plane 220 and the right lateral plane 216. In one embodiment, the electrode array of the catheter 1330 is positioned in an area 1360 that extends distally no more than three times the diameter of the pulmonary trunk 202 to the right of the branch point 207. This area 1360 is shown with cross-hatching in FIG. 13.

The right pulmonary artery 206 can also include a branch point 1362 that divides the right pulmonary artery 206 into at least two additional arteries 1364 that are distal to the branch point 207 defining the left pulmonary artery 208 and the right pulmonary artery 206. As illustrated, the electrode array can be positioned between the branch point 207 defining the left pulmonary artery 208 and the right pulmonary artery 206 and the branch point 1362 that divides the right pulmonary artery 206 into at least two additional arteries 1364.

Once in position, electrical current can be provided from or to one or more of the electrodes 1344. Using a first sensor 1352 a value of a non-cardiac parameter of the patient can be measured in response to the electrical current from or to one or more of the electrodes 1344. From the value of the non-cardiac parameter, changes can be made to which of the one or more electrodes are used to provide the electrical current in response to the value of the cardiac parameter. Changes can also be made to the nature of the electrical current provided in response to the value of the non-cardiac parameter. Such changes include, but are not limited to, changes in voltage, amperage, waveform, frequency and pulse width by way of example. It is possible to change combinations of electrodes used and the nature of the electrical current provided by the electrodes. In addition, the electrodes of the one or more electrodes on the posterior surface of the right pulmonary artery 206 can be moved in response to one or more of the values of the non-cardiac parameter. Examples of such a cardiac parameter include, but are not limited to, measuring a pressure parameter, an acoustic parameter, an acceleration parameter and/or an electrical parameter (e.g., ECG) of the heart of the patient as the cardiac parameter. An example of such a pressure parameter can include, but is not limited to, measuring a maximum systolic pressure of the heart of the patient as the pressure parameter. Other suitable cardiac parameters are discussed herein.

Moving the electrodes of the one or more electrodes on the posterior and/or superior surface of the right pulmonary artery 206 in response to one or more of the values of the cardiac parameter can be done by physically moving the one or more electrodes of the catheter 1330 to a different position on the posterior and/or superior surface of the right pulmonary artery 206, electronically moving which electrodes of the one or more electrodes are being used to provide the electrical current from or to the electrode array (while not physically moving the one or more electrodes of the catheter 1330) or a combination of these two actions.

As discussed herein, neuromodulation according to the present disclosure can be accomplished by applying electrical current to the right pulmonary artery 206. Preferably, neuromodulation of the present disclosure includes applying the electrical current to the posterior and/or superior wall of the right pulmonary artery 206. The electrical current is thereby applied to the autonomic cardiopulmonary nerves surrounding the right pulmonary artery 206. These autonomic cardiopulmonary nerves can include the right autonomic cardiopulmonary nerves and the left autonomic cardiopulmonary nerves. The right autonomic cardiopulmonary nerves include the right dorsal medial cardiopulmonary nerve and the right dorsal lateral cardiopulmonary nerve. The left autonomic cardiopulmonary nerves include the left ventral cardiopulmonary nerve, the left dorsal medial cardiopulmonary nerve, the left dorsal lateral cardiopulmonary nerve, and the left stellate cardiopulmonary nerve.

As illustrated and discussed in reference to FIG. 13, the one or more electrodes of the catheter are contacting the posterior surface of the right pulmonary artery 206. From this location, the electrical current delivered through the one or more electrodes may be better able to treat and/or provide therapy (including adjuvant therapy) to the patient experiencing a variety of cardiovascular medical conditions, such as acute heart failure. The electrical current can elicit responses from the autonomic nervous system that may help to modulate a patient's cardiac contractility. The electrical current is intended to affect heart contractility more than the heart rate, thereby helping to improving hemodynamic control while possibly minimizing unwanted systemic effects.

Figure 14A:
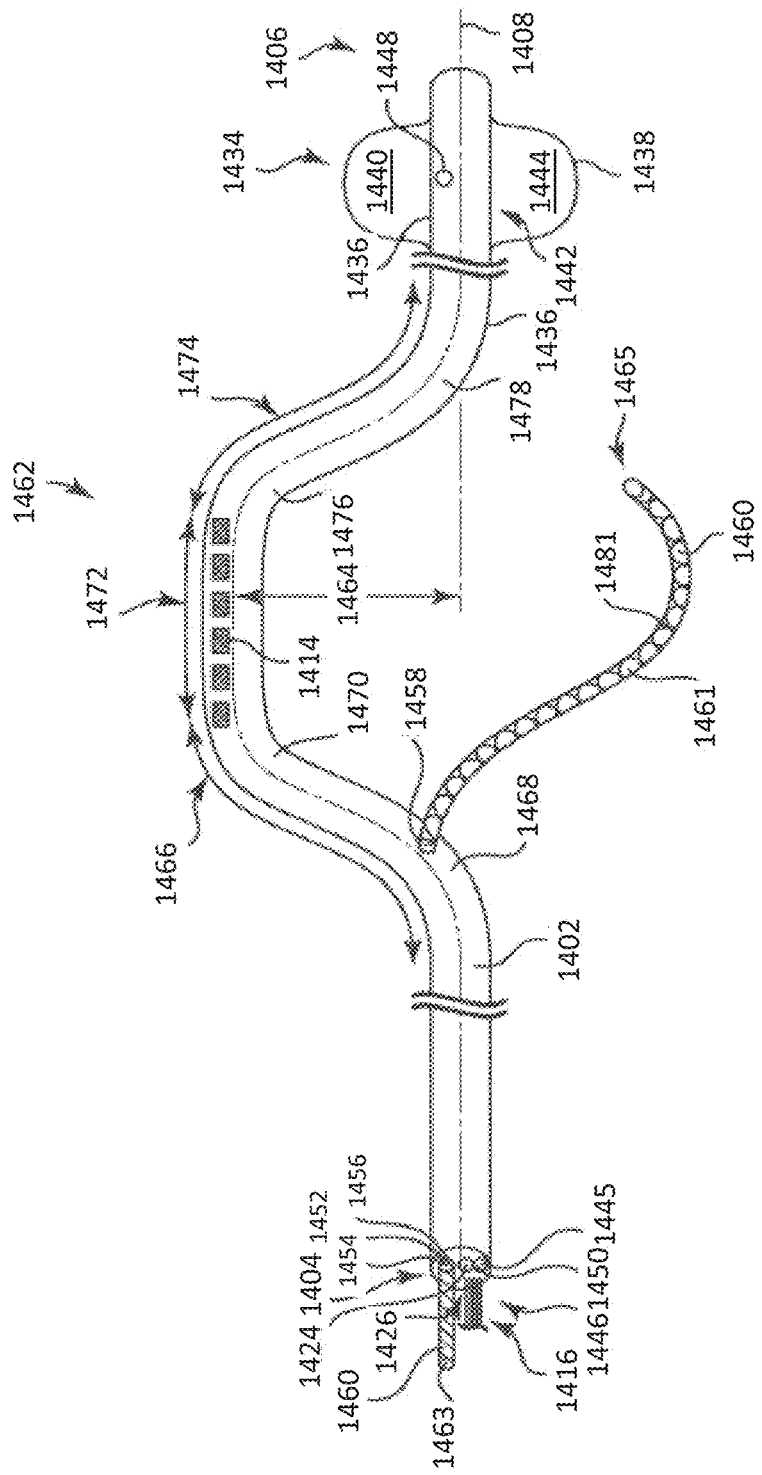
FIGS. 14A, 14B, 15A, 15B, 16 and 17 illustrate examples of catheters.

Referring now to FIG. 14A, there is shown an additional embodiment of a catheter 1462. The catheter 1462 includes an elongate body 1402 having a peripheral surface 1436 and a longitudinal center axis 1408 extending between a first end 1404 and a second end 1406. The catheter 1462 can include the features and components as discussed above for catheters 100, 200, 300 and/or 400, a discussion of which is not repeated but the element numbers are included in FIG. 14A with the understanding that the discussion of these elements is implicit.

The catheter 1462 of the present embodiment includes an inflatable balloon 1434. As illustrated, the elongate body 1402 includes a peripheral surface 1436, where the inflatable balloon 1434 is located on the peripheral surface 1436 of the elongate body 1402. The inflatable balloon 1434 includes a balloon wall 1438 with an interior surface 1440 that along with a portion 1442 of the peripheral surface 1436 of the elongate body 1402 defines a fluid tight volume 1444.

The elongate body 1402 further includes a surface 1445 that defines an inflation lumen 1446 that extends through the elongate body 1402. The inflation lumen 1446 includes a first opening 1448 into the fluid tight volume 1444 of the inflatable balloon 1434 and a second opening 1450 proximal to the first opening 1448 to allow for a fluid to move in the fluid tight volume 1444 to inflate and deflate the balloon 1434. A syringe, or other known devices, containing the fluid (e.g., saline or a gas (e.g., oxygen)) can be used to inflate and deflate the balloon 1434.

The elongate body 1402 further includes an offset region 1464 defined by a series of predefined curves along the longitudinal center axis 1408. As used herein, "predefined curves" are curves formed in the elongate body 1402 during the production of the catheter 1462, where when deformed such curves provide a spring like force to return to their pre-deformation shape (e.g., their original shape). As illustrated, the series of predefined curves includes a first portion 1466 that has a first curve 1468 in the longitudinal center axis 1408 followed by a second curve 1470 in the longitudinal center axis 1408 of the elongate body 1402. The length and degree of each of the first curve 1468 and second curve 1470, along with the distance between such curves, helps to define the height of the offset region 1464. As discussed herein, the height of the offset region 1464 can be determined by the inner diameter of one or more locations along the main pulmonary artery and/or one of the right and left pulmonary arteries.

The first portion 1466 of the elongate body 1402 is followed by a second portion 1472 of the elongate body 1402. The longitudinal center axis 1408 along the second portion 1472 can have a zero curvature (e.g., a straight line), as illustrated in FIG. 14A. The second portion 1472 of the elongate body 1402 is followed by a third portion 1474 of the elongate body 1402. The longitudinal center axis 1408 transitions from the second portion 1472 along a third curve 1476, which then transitions into a fourth curve 1478. As illustrated, after the fourth curve 1478, the longitudinal center axis 1408 is approximately co-linear with the longitudinal center axis 1408 leading up to the first curve 1468. It is noted that the curves of the first portion 1466 and the second portion 1474 can also all be in approximately the same plane. It is, however, possible that the curves of the first portion 1466 and the second portion 1474 are not in the same plane. For example, when the curves of the first portion 1466 and the second portion 1474 are not in the same plane the longitudinal center axis 1408 can include a helical curve through these portions of the elongate body 1402. Other shapes are also possible.

The elongate body 1402 can further include one or more electrodes 1414, for example as discussed herein, along the second portion 1472 of the offset region 1464 of the elongate body 1402. As illustrated, the one or more electrodes 1414 can be on the surface of the elongate body 1402 in the second portion 1472 of the offset region 1464. Conductive elements 1416 extend through and/or along the elongate body 1402, where the conductive elements 1416 can be used, as discussed herein, to conduct electrical current to combinations of the one or more electrodes 1414. Each of the one or more electrodes 1414 is coupled to a corresponding conductive element 1416. The conductive elements 1416 are electrically isolated from each other and extend through and/or along the elongate body 1402 from each respective electrode 1414 through the first end 1404 of the elongate body 1402. The conductive elements 1416 terminate at a connector port, where each of the conductive elements 1416 can be releasably coupled to a stimulation system, for example as discussed herein. It is also possible that the conductive elements 1416 are permanently coupled to the stimulation system (e.g., not releasably coupled). The stimulation system can be used to provide stimulation electrical energy (e.g., electrical current or electrical pulses) that is conducted through the conductive elements 1416 and delivered across combinations of the one or more electrodes 1414. In some embodiments, the one or more electrodes 1414 are electrically isolated from one another, where the elongate body 1402 is formed of an electrically insulating material.

There can be wide variety for the number and configuration of the one or more electrodes 1414 on the one surface of the second portion 1472 of the elongate body 1402. For example, as illustrated, the one or more electrodes 1414 can be configured as an array of electrodes, where the number of electrodes and their relative position to each other can vary depending upon the desired implant location. As discussed herein, the one or more electrodes 1414 can be configured to allow for electrical current to be delivered from and/or between different combinations of the one or more electrodes 1414. The electrodes in the array of electrodes can have a repeating pattern where the electrodes are equally spaced from each other. So, for example, the electrodes in the array of electrodes can have a column and row configuration. Alternatively, the electrodes in the array of electrodes can have a concentric radial pattern, where the electrodes are positioned so as to form concentric rings of the electrodes. Other patterns are possible, where such patterns can either be repeating patterns or random patterns. As discussed herein, the catheter 1462 further includes conductive elements 1416 extending through and/or along the elongate body, where the conductive elements 1416 conduct electrical current to combinations of the one or more electrodes 1414.

As discussed herein, the length and degree of each of the curves, along with the distance between such curves helping to define the first portion 1466 and the third portion 1474 of the longitudinal center axis 1408, helps to define the relative height of the offset region 1464. For the various embodiments, the height of the offset region 1464 can be determined by the inner diameter of one or more locations along the main pulmonary artery and/or one of the right and left pulmonary arteries. In this way, the first portion 1466 and the third portion 1474 can bring the second portion 1472 and the one or more electrodes 1414 on the surface of the elongate body 1402 into contact with the vascular wall of the patient in the main pulmonary artery and/or one of the left or right pulmonary arteries. In other words, the transitions of the first portion 1466 and the third portion 1474 of the elongate body 1402 in the offset region 1464 can act to bias the second portion 1472 and the one or more electrodes 1414 against the vascular wall of the patient in the main pulmonary artery and/or one of the right or left pulmonary arteries.

The elongate body 1402 further includes a surface 1424 defining a guide-wire lumen 1426 that extends through and/or along the elongate body 1402. As provided herein, the guide-wire lumen 1426 can be concentric relative to the longitudinal center axis 1408 of the elongate body 1402 (as illustrated in FIG. 14A). Alternatively, the guide-wire lumen 1426 can be eccentric relative to the longitudinal center axis 1408 of the elongate body 1402. As discussed herein, the guide-wire lumen 1426 can have a wall thickness 1428 that is greater than a wall thickness 1430 of a remainder of the catheter 1462 taken perpendicularly to the longitudinal center axis 1408. In an additional embodiment, a portion of the elongate body 1402 includes a serpentine portion, as discussed and illustrated herein, proximal to the one or more electrodes 1414.

For the present embodiment, a guide-wire used with the catheter 1462 can serve to temporarily "straighten" the offset region 1464 when the guide-wire is present in the guide-wire lumen 1426 that passes along the offset region 1464. Alternatively, the guide-wire can be used to impart the shape of the offset region 1464 to the catheter 1462. In this embodiment, the elongate body 1402 of the catheter 1462 can have a straight shape (e.g., no predefined lateral shape). To impart the offset region 1464 the guide wire is "shaped" (e.g., bent) to the desired configuration of the offset region at point that corresponds to the desired longitudinal location for the offset region on the elongate body 1402. The offset region 1464 of the catheter 1462 can be provided by inserting the guide wire with the predefined lateral shape.

In FIG. 14A, the catheter 1462 of the present embodiment further includes a surface 1452 defining a deflection lumen 1454, as discussed herein. The catheter 1462 further includes an elongate deflection member 1460, also as discussed herein. As generally illustrated, the elongate deflection member 1460 can be advanced through the deflection lumen 1454 so that elongate deflection member 1460 extends laterally away from the one or more electrodes 1414 on the second portion 1472 of the elongate body 1402. The elongate deflection member 1460 can be of a length and shape that allows the elongate deflection member 1460 to be extended a distance sufficient to bring the one or more electrodes 1414 into contact with the vascular luminal surface (e.g., a posterior surface of the main pulmonary artery and/or one or both of the pulmonary arteries) with a variety of pressures.

In one embodiment, the elongate body 1461 of the elongate deflection member 1460 can also include one or more support wires 1481. The support wires 1481 can be encased in the flexible polymeric material of the elongate body 1461, where the support wires 1481 can help to provide both column strength and a predefined shape to the elongate deflection member 1460. For example, the support wires 1481 can have a coil shape that extends longitudinally along the length of the elongate body 1461. In accordance with several embodiments, the coil shape advantageously allows for the longitudinal force applied near or at the first end 1463 of the deflection member 1460 to be transferred through the elongate body 1461 so as to laterally extend the second end 1465 of the deflection member 1460 from the second opening 1458 of the deflection lumen 1454.

The support wires 1481 can also provide the deflection member 1460 with a predetermined shape upon laterally extending from the second opening 1458 of the deflection lumen 1454. The predetermined shape can be determined to engage the luminal wall of the pulmonary artery in order to bring the electrodes 1414 on the second portion 1472 of the offset region 1464 into contact with the vascular tissue. The predetermined shape and the support wires 1481 can also help to impart stiffness to the deflection member 1460 that is sufficient to maintain the electrodes 1414 on the luminal wall of the pulmonary artery under the conditions within the vasculature of the patient.

The support wires 1481 can be formed of a variety of metals or metal alloys. Examples of such metals or metal alloys include surgical grade stainless steel, such as austenitic 316 stainless among others, and the nickel and titanium alloy known as Nitinol. Other metals and/or metal alloys can be used as desired and/or required.

Figure 14B:
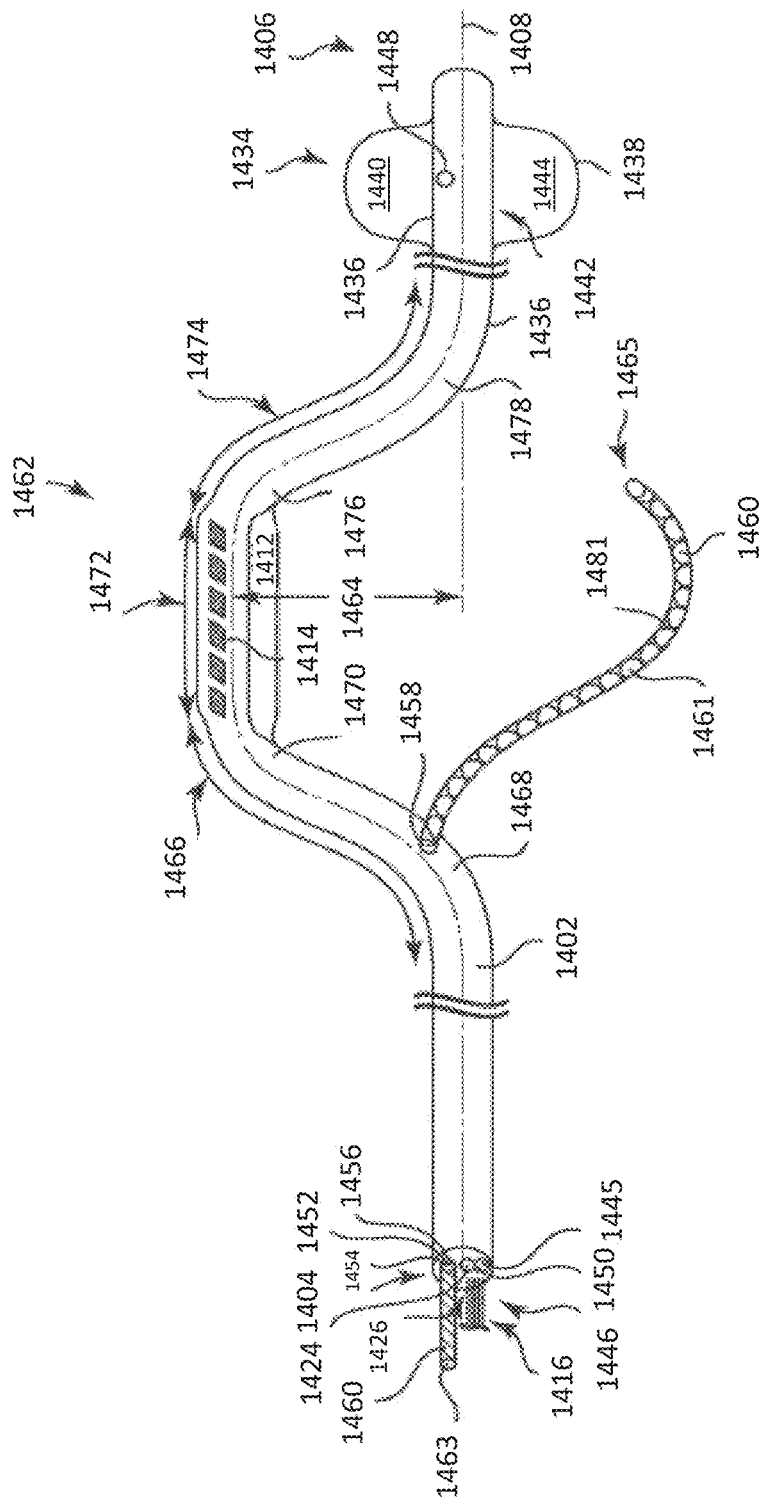

Referring now to FIG. 14B, there is shown an additional embodiment of a catheter 1462. The catheter 1462 can include the features and components of the catheters described above in connection with FIGS. 12A-12D and/or 14A, a discussion of which is not repeated but the element numbers are included in FIG. 14B with the understanding that the discussion of these elements is implicit.

The catheter 1462 seen in FIG. 14B is similar to the catheter 1462 of FIG. 14A, where the elongate body 1402 of catheter 1462 further includes three or more surfaces 1412 defining a convex polygonal cross-sectional shape taken perpendicularly to the longitudinal center axis 1408, as discussed for the catheters 1200 herein. As illustrated, the one or more electrodes 1414 are on one surface of the three or more surfaces 1412 of the elongate body 1402. In the present embodiment, the three or more surfaces 1412 of the elongate body 1402 help to form the second portion 1472 of the elongate body 1402. If desired, the elongate body 1402 can includes a serpentine portion proximal to the one or more electrodes 1414.

Figure 15A:
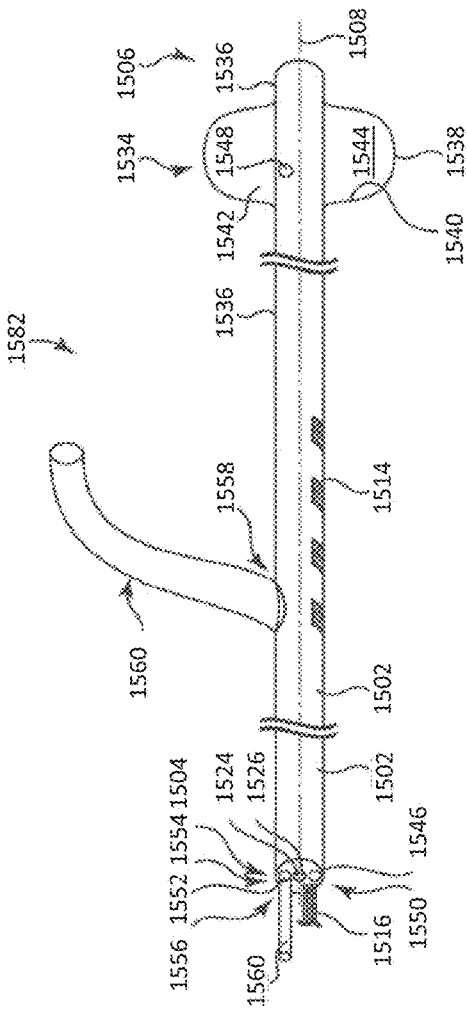

Referring now to FIG. 15A, there is shown an additional embodiment of a catheter 1582 according to the present disclosure. The catheter 1582 can include the features and components of the catheters described above in connection with FIGS. 12A-12D, 14A and/or 14B, a discussion of which is not repeated but the element numbers are included in FIG. 15A with the understanding that the discussion of these elements is implicit.

The catheter 1582 includes an elongate body 1502 having a peripheral surface 1536 and a longitudinal center axis 1508 extending between a first end 1504 and a second end 1506. The elongate body 1502 includes a surface 1552 defining a deflection lumen 1554, where the deflection lumen 1554 includes a first opening 1556 and a second opening 1558 in the elongate body 1502. The catheter 1582 further includes an inflatable balloon 1534 on the peripheral surface 1536 of the elongate body 1502, the inflatable balloon 1534 having a balloon wall 1538 with an interior surface 1540 that along with a portion 1542 of the peripheral surface 1536 of the elongate body 1502 defines a fluid tight volume 1544, such as previously discussed herein. An inflation lumen 1546 extends through the elongate body 1502, where the inflation lumen 1546 has a first opening 1548 into the fluid tight volume 1544 of the inflatable balloon 1534 and a second opening 1550 proximal to the first opening 1548 to allow for a fluid (e.g., liquid or gas) to move in and out of the fluid tight volume 1544 to inflate and deflate the balloon 1534.

One or more electrodes 1514 are on the elongate body 1502, where the second opening 1558 of the deflection lumen 1554 is opposite the one or more electrodes 1514 on the elongate body 1502. The catheter 1582 further includes an elongate deflection member 1560, as discussed herein, where the elongate deflection member 1560 extends through the second opening 1558 of the deflection lumen 1554 in a direction opposite the one or more electrodes 1514 on one surface of the elongate body 1502. The catheter 1582 also includes conductive elements 1516 that extend through and/or along the elongate body 1502, where the conductive elements 1516 conduct electrical current to combinations of the one or more electrodes 1514.

The catheter 1582 further includes a surface 1524 defining a guide-wire lumen 1526 that extends through and/or along the elongate body 1502. As illustrated, the guide-wire lumen 1526 is concentric relative to the longitudinal center axis 1508. As discussed herein, the guide-wire lumen 1526 could also be eccentric relative to longitudinal center axis 1508 of the elongate body 1508. Such embodiments are discussed herein, where the guide-wire lumen 1526 can have a wall thickness taken perpendicularly to the longitudinal center axis 1508 that is greater than a wall thickness of a remainder of the catheter 1582 taken perpendicularly to the longitudinal center axis 1508. The catheter 1582 can also include a serpentine portion of the elongate body 1502 proximal to the one or more electrodes 1514.

Figure 15B:
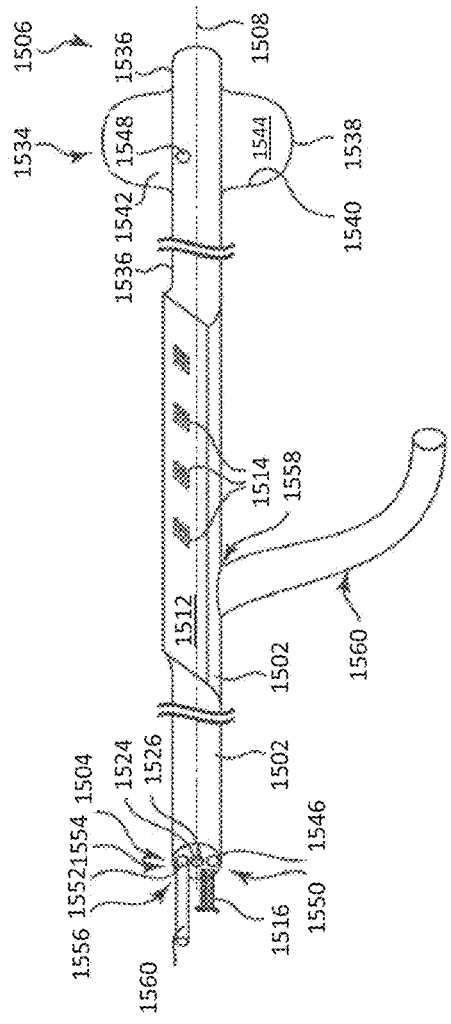

Referring now to FIG. 15B, there is shown an additional embodiment of a catheter 1582. The catheter 1582 can include the features and components described above in connection with FIGS. 12A-12D, 14A, 14B and/or 15A, a discussion of which is not repeated but the element numbers are included in FIG. 15B with the understanding that the discussion of these elements is implicit.

The catheter 1582 includes an elongate body 1502 having a peripheral surface 1536 and a longitudinal center axis 1508 extending between a first end 1504 and a second end 1506. The elongate body 1502 includes a surface 1552 defining a deflection lumen 1554, where the deflection lumen 1554 includes a first opening 1556 and a second opening 1558 in the elongate body 1502. The catheter 1582 further includes an inflatable balloon 1534 on the peripheral surface 1536 of the elongate body 1502, the inflatable balloon 1534 having a balloon wall 1538 with an interior surface 1540 that along with a portion 1542 of the peripheral surface 1536 of the elongate body 1502 defines a fluid tight volume 1544, as discussed herein. An inflation lumen 1546 extends through the elongate body 1502, where the inflation lumen 1546 has a first opening 1548 into the fluid tight volume 1544 of the inflatable balloon 1534 and a second opening 1550 proximal to the first opening 1548 to allow for a fluid (e.g., gas or liquid) to move in and out of the fluid tight volume 1544 to inflate and deflate the balloon 1534.

One or more electrodes 1514 are on the elongate body 1502, where the second opening 1558 of the deflection lumen 1554 is opposite the one or more electrodes 1514 on the elongate body 1502. As illustrated, the elongate body 1502 has three or more surfaces 1512 defining a convex polygonal cross-sectional shape taken perpendicularly to the longitudinal center axis 1508. The one or more electrodes 1514 are on one surface of the three or more surfaces 1512 of the elongate body 1502, such as discussed previously herein.

The catheter 1582 further includes an elongate deflection member 1560, where the elongate deflection member 1560 extends through the second opening 1558 of the deflection lumen 1554 in a direction opposite the one or more electrodes 1514 on one surface of the elongate body 1502. The catheter 1582 also includes conductive elements 1516 that extend through and/or along the elongate body 1502, where the conductive elements 1516 conduct electrical current to combinations of the one or more electrodes 1514.

The catheter 1582 further includes a surface 1524 defining a guide-wire lumen 1526 that extends through and/or along the elongate body 1502. As illustrated, the guide-wire lumen 1526 is concentric relative to the longitudinal center axis 1508. As discussed herein, the guide-wire lumen 1526 could also be eccentric relative to longitudinal center axis 1508 of the elongate body 1502. Such embodiments are discussed herein, where the guide-wire lumen 1526 can have a wall thickness taken perpendicularly to the longitudinal center axis 1508 that is greater than a wall thickness of a remainder of the catheter 1582 taken perpendicularly to the longitudinal center axis 1508. The catheter 1582 can also include a serpentine portion of the elongate body 1502 proximal to the one or more electrodes 1514.

Figure 16:
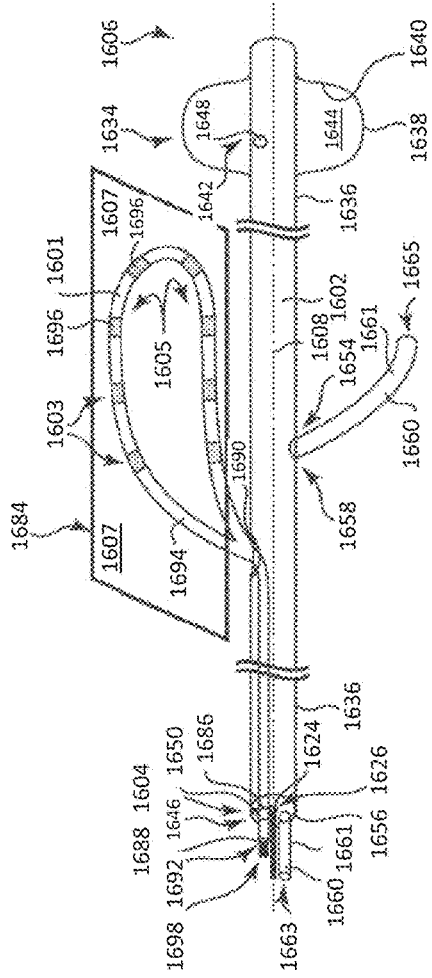

Referring now to FIG. 16, there is shown an additional embodiment of a catheter 1684. The catheter 1684 can include the features and components of the catheters described above in connection with FIGS. 12A-12D, 14A, 14B, 15A and/or 15B, a discussion of which is not repeated but the element numbers are included in FIG. 16 with the understanding that the discussion of these elements is implicit.

The catheter 1684 includes an elongate body 1602 having a peripheral surface 1636 and a longitudinal center axis 1608 extending between a first end 1604 and a second end 1606. The catheter 1684 further includes an inflatable balloon 1634 on the peripheral surface 1636 of the elongate body 1602, the inflatable balloon 1634 having a balloon wall 1638 with an interior surface 1640 that along with a portion 1642 of the peripheral surface 1636 of the elongate body 1602 defines a fluid tight volume 1644, as discussed herein. An inflation lumen 1646 extends through the elongate body 1602, where the inflation lumen 1646 has a first opening 1648 into the fluid tight volume 1644 of the inflatable balloon 1634 and a second opening 1650 proximal to the first opening 1648 to allow for a fluid (e.g., gas or liquid) to move in and out of the fluid tight volume 1644 to inflate and deflate the balloon 1634.

The catheter 1682 includes a surface 1624 defining a guide-wire lumen 1626 that extends through and/or along the elongate body 1602. As illustrated, the guide-wire lumen 1626 is concentric relative to the longitudinal center axis 1608. As discussed herein, the guide-wire lumen 1626 could also be eccentric relative to longitudinal center axis 1608 of the elongate body 1602. Such embodiments are discussed herein, where the guide-wire lumen 1626 can have a wall thickness taken perpendicularly to the longitudinal center axis 1608 that is greater than a wall thickness of a remainder of the catheter 1682 taken perpendicularly to the longitudinal center axis 1608. The catheter 1682 can also include a serpentine portion of the elongate body 1602 proximal to the one or more electrodes 1614.

The elongate body 1602 of the catheter 1684 further includes a surface 1686 defining an electrode lumen 1688. The electrode lumen 1688 includes a first opening 1690 and a second opening 1692 in the elongate body 1602. The catheter 1684 also includes an elongate electrode member 1694, where the elongate electrode member 1694 retractably extends through the first opening 1690 of the electrode lumen 1688 of the elongate body 1602. The electrode lumen 1688 has a size (e.g., a diameter) sufficient to allow the elongate electrode member 1694 to pass through the electrode lumen 1688 to that the elongate electrode member 1694 can retractably extend through the first opening 1690 of the electrode lumen 1688 of the elongate body 1602. The elongate electrode member 1694 can retractably extend through the first opening 1690 of the electrode lumen 1688 of the elongate body 1602 from pressure (e.g., compression or tension) applied by the user (e.g., clinician or professional) through the elongate electrode member 1694 proximal to the second opening 1692 in the elongate body 1608. For the various embodiments, the elongate electrode member 1694 is formed of a flexible polymeric material. Examples of such flexible polymeric material include, but are not limited to, those flexible materials described herein.

The elongate electrode member 1694 includes one or more electrodes 1696 and conductive elements 1698 extending through the electrode lumen 1688. As illustrated, the one or more electrodes 1696 are on the surface 1601 of the elongate electrode member 1694. Conductive elements 1698 extend through the elongate electrode member 1694, where the conductive elements 1698 can be used, such as discussed herein, to conduct electrical current to combinations of the one or more electrodes 1696. Each of the one or more electrodes 1696 is coupled to a corresponding conductive element 1698.

The conductive elements 1698 may be electrically isolated from each other and extend through the elongate electrode member 1694 from each respective electrode 1696 through the second end 1692 of the electrode lumen 1688. The conductive elements 1698 terminate at a connector port, where each of the conductive elements 1698 can be releasably coupled to a stimulation system, as discussed herein. It is also possible that the conductive elements 1698 are permanently coupled to the stimulation system (e.g., not releasably coupled). The stimulation system can be used to conduct electrical current or electrical pulses to combinations of the one or more electrodes 1694 via the conductive elements 1698. The one or more electrodes 1696 are electrically isolated from one another, where the elongate electrode member 1694 is formed of an electrically insulating material.

The number and the configuration of the one or more electrodes 1696 on the elongate electrode member 1694 can vary in different embodiments. For example, as illustrated, the one or more electrodes 1696 can be configured as an array of electrodes, where the number of electrodes and their relative position to each other can vary depending upon the desired implant location. As discussed herein, the one or more electrodes 1696 can be configured to allow for electrical current to be delivered from and/or between different combinations of the one or more electrodes 1696. So, for example, the electrodes in the array of electrodes can have a repeating pattern where the electrodes are equally spaced from each other. Other patterns are possible, where such patterns can either be repeating patterns or random patterns.

As illustrated, the one or more electrodes 1696 have an exposed face 1603. The exposed face 1603 of the electrode 1696 provides the opportunity for the electrode 1696, when implanted (temporarily or for an extended duration of time) in the patient, to be placed into proximity and/or in contact with the vascular tissue of the patient, as opposed to facing into the volume of blood in the artery. To accomplish this, the one or more electrodes 1696 can be located on only one side of the elongate electrode member 1694 (as illustrated in FIG. 16). This allows the one or more electrodes 1696 to be brought into contact with the vascular luminal surface (e.g., a posterior surface of the main pulmonary artery and/or one or both of the pulmonary arteries). As the one or more electrodes 1696 are located on only one side of the elongate electrode member 1694, the electrodes 1696 can be placed into direct proximity to and/or in contact with the tissue of any combination of the main pulmonary artery, the left pulmonary artery and/or the right pulmonary artery.

The exposed face 1603 of the one or more electrodes 1696 can have a variety of shapes, as discussed herein (e.g., a partial ring configuration, where each of the one or more electrodes 1696 is positioned to face away from the elongate body 1602). The exposed face 1603 of the electrodes 1696 can also include one or more anchor structures. Examples of such anchor structures include hooks that can optionally include a barb.

As generally illustrated, the elongate electrode member 1694 can be advanced through the electrode lumen 1688 so that the elongate electrode member 1694 extends laterally away from the elongate body 1608. The elongate electrode member 1694 can be of a length and shape that allows the elongate electrode member 1694 to be extended a distance sufficient from the elongate body 1608 to bring the one or more electrodes 1696 into contact with the vascular luminal surface (e.g., a posterior surface of the main pulmonary artery and/or one or both of the pulmonary arteries).

As illustrated in FIG. 16, the elongate electrode member 1694 forms a loop 1605 that extends away from the peripheral surface 1636 of the elongate body 1602. The loop 1605 can have a variety of configurations relative the longitudinal axis 1608 of the elongate body 1602. For example, as illustrated in FIG. 16, the elongate electrode member 1692 forming the loop 1605 is in a plane 1607 that is co-linear with the longitudinal center axis 1608 of the elongate body 1602.

The catheter 1684 further includes an elongate deflection member 1660, as previously discussed. As discussed herein, pressure is applied to the deflection member 1660 to move the first end 1663 of the deflection member 1660 towards the first opening 1656 of the deflection lumen 1654. The pressure, in addition to moving the first end 1663 of the deflection member 1660 towards the first opening 1656, also causes the second end 1665 of the deflection member 1660 to extend from the second opening 1658. As generally illustrated, the elongate deflection member 1660 can be advanced through the deflection lumen 1654 so that elongate deflection member 1660 extends laterally away from the one or more electrodes 1696 on the elongate electrode member 1694. The elongate deflection member 1660 can be of a length and shape that allows the elongate deflection member 1660 to be extended a distance sufficient to help bring the one or more electrodes 1696 into contact with the vascular luminal surface (e.g., a posterior surface of the main pulmonary artery and/or one or both of the pulmonary arteries) with a variety of pressures. Optionally, the elongate deflection member 1660 can be configured to include one or more of the electrodes.

The catheter 1684 shown in FIG. 16 can be positioned in the main pulmonary artery and/or one or both of the left and right pulmonary arteries of the patient, such as described herein. To accomplish this, a pulmonary artery guide catheter is introduced into the vasculature through a percutaneous incision and guided to the right ventricle (e.g., using a Swan-Ganz catheterization approach). For example, the pulmonary artery guide catheter can be inserted into the vasculature via a peripheral vein of the arm, neck or chest (e.g., as with a peripherally inserted central catheter). Changes in a patient's electrocardiography and/or pressure signals from the vasculature can be used to guide and locate the pulmonary artery guide catheter within the patient's heart. Once in the proper location, a guide wire can be introduced into the patient via the pulmonary artery guide catheter, where the guide wire is advanced into the main pulmonary artery and/or one of the pulmonary arteries. Using the guide-wire lumen 1626, the catheter 1684 can be advanced over the guide wire so as to position the catheter 1684 in the main pulmonary artery and/or one or both of the right and left pulmonary arteries of the patient. Various imaging modalities can be used in positioning the guide wire of the present disclosure in the main pulmonary artery and/or one of the right and left pulmonary arteries of the patient. Such imaging modalities include, but are not limited to, fluoroscopy, ultrasound, electromagnetic, and electropotential modalities.

Using a stimulation system, such as the stimulation systems discussed herein, stimulation electrical energy (e.g., electrical current or electrical pulses) can be delivered across combinations of one or more of the electrodes 1696. It is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the patient.

Figure 17:
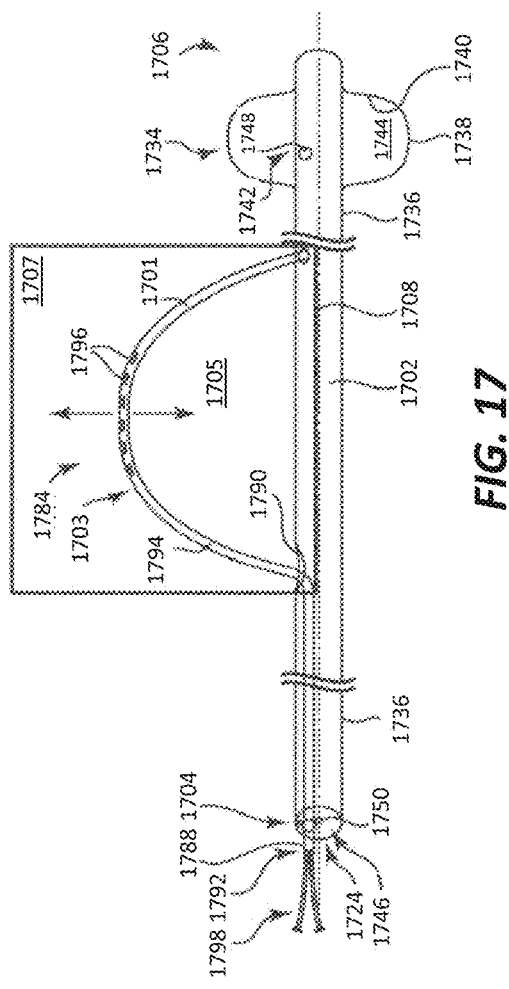

Referring now to FIG. 17, there is shown an additional embodiment of a catheter 1784. The catheter 1784 can include the features and components of the catheters described above in connection with FIGS. 12A-12D, 14A, 14B, 15A, 15B and/or 16, a discussion of which is not repeated but the element numbers are included in FIG. 17 with the understanding that the discussion of these elements is implicit. The catheter 1784 illustrates an embodiment in which the elongate electrode member 1794 forms a loop 1705 in a plane 1707 that is perpendicular to the longitudinal center axis of the elongate body. More than one of the elongate electrode members can be used with a catheter, in accordance with several embodiments.

Figure 18A:
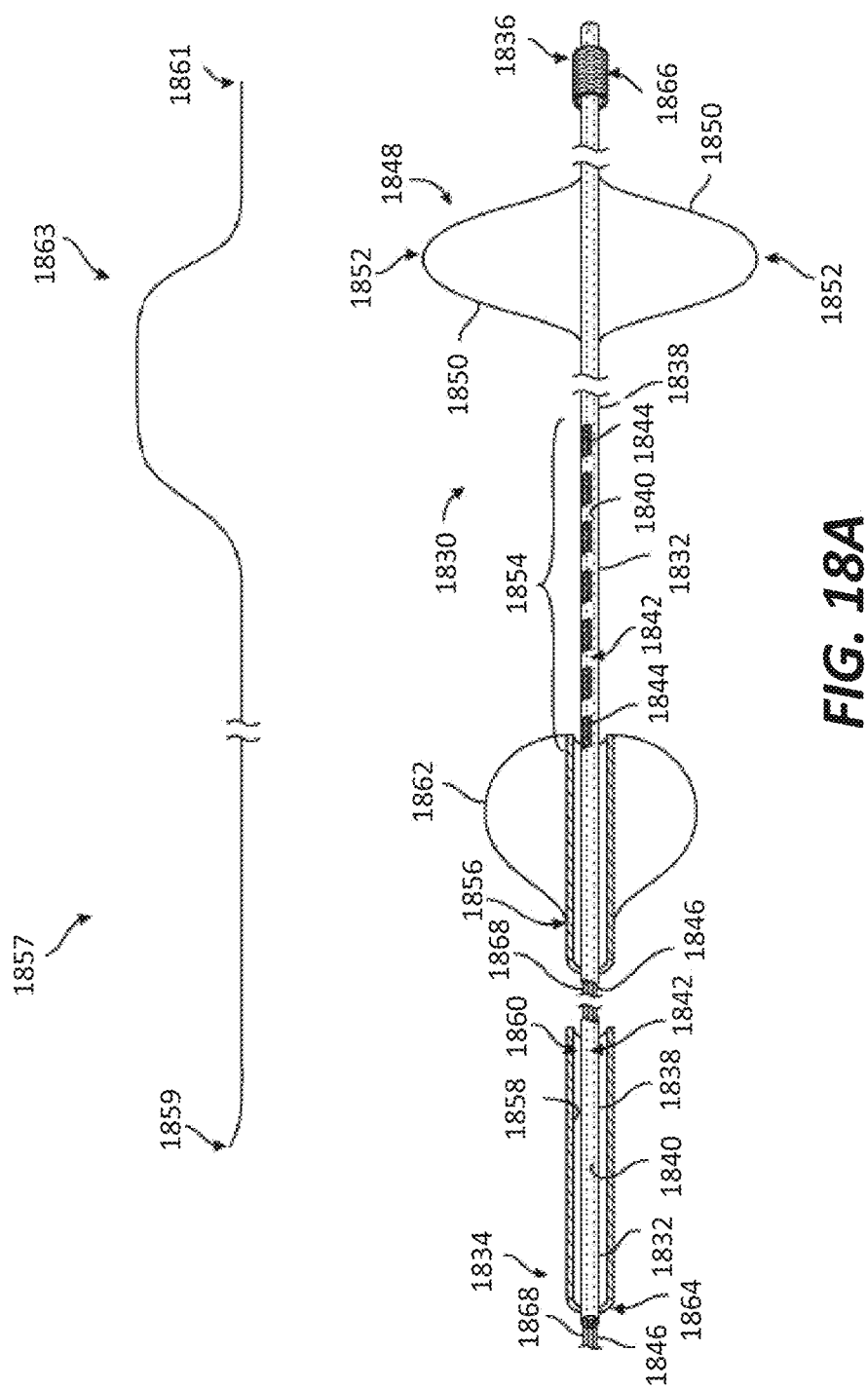
FIGS. 18A through 18C are side partial cross-sectional and perspective views of an example catheter that is suitable for performing the methods of the present disclosure.
Figure 18B:
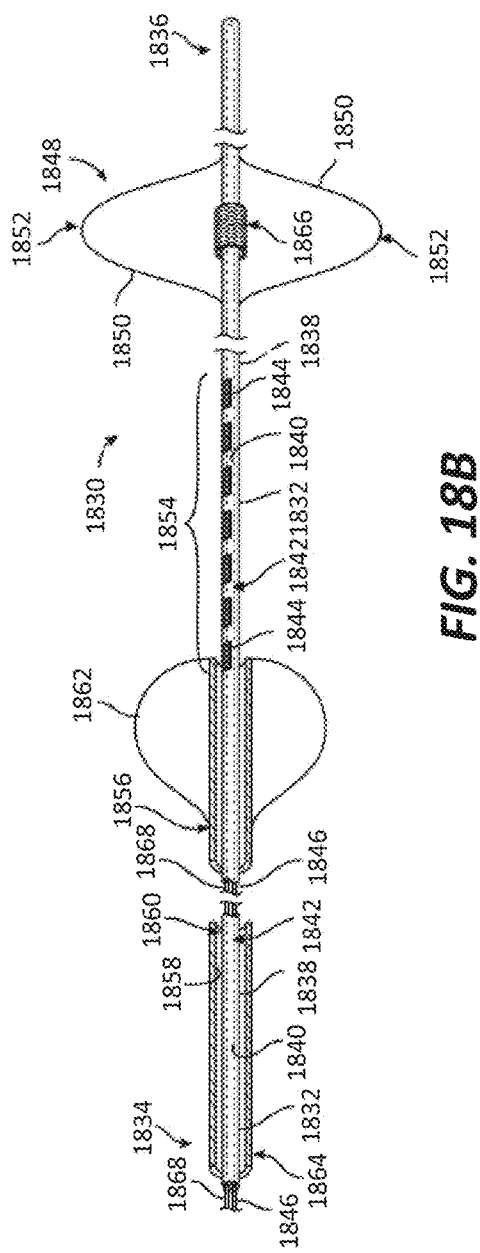
Figure 18C:
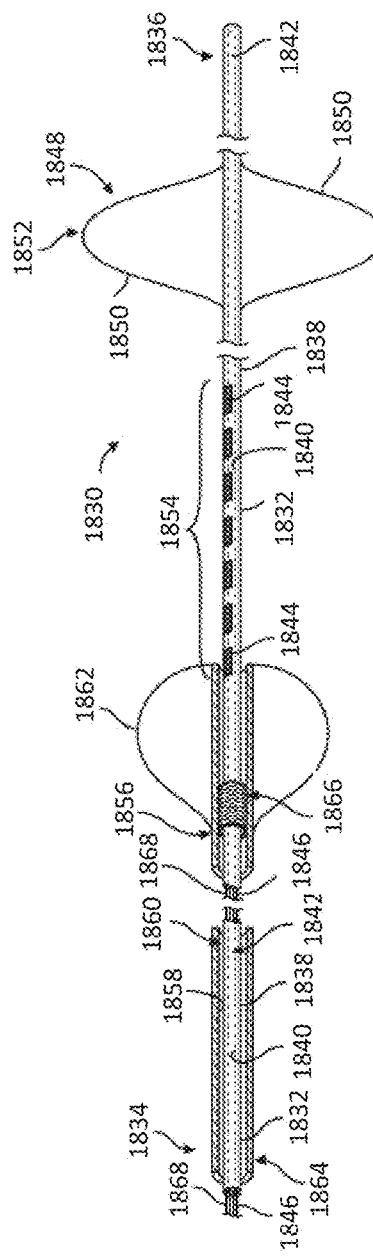

Referring now to FIGS. 18A through 18C, there are shown perspective views of an example catheter 1830 that is suitable for performing certain methods of the present disclosure. The catheter 1830 includes an elongate catheter body 1832 having a proximal or first end 1834 and a distal or second end 1836. The elongate catheter body 1832 also includes an outer or peripheral surface 1838 and an interior surface 1840 defining a lumen 1842 (shown with a broken line) that extends between the first end 1834 and the second end 1836 of the elongate catheter body 1832.

The catheter 1830 further includes a plurality of electrodes 1844 positioned along the peripheral surface 1838 of the elongate catheter body 1832. In some embodiments, the electrodes 1844 are proximate to a distal end 1836 of the catheter 1830. Conductive elements 1846 extend through and/or along the elongate body 1832, where the conductive elements 1846 can be used, as discussed herein, to conduct electrical pulses to combinations of the plurality of electrodes 1844. Each of the plurality of electrodes 1844 is coupled (e.g., electrically coupled) to a corresponding conductive element 1846. The conductive elements 1846 are electrically isolated from each other and extend through the elongate body 1832 from each respective electrode 1844 through the first end 1834 of the elongate body 1832. The conductive elements 1846 terminate at a connector port, where each of the conductive elements 1846 can be releasably coupled to a stimulation system. It is also possible that the conductive elements 1846 are permanently coupled to the stimulation system (e.g., not releasably coupled). As discussed more fully herein, the stimulation system can be used to provide stimulation electrical pulses that are conducted through the conductive elements 1846 and delivered across combinations of the plurality of electrodes 1844. Other positions and configurations of electrodes are also possible. PCT Patent App. Nos. PCT/US2015/031960, PCT/US2015/047770, and PCT/US2015/047780 are incorporated herein by reference in their entirety, and more specifically the electrodes (e.g., electrodes on deployable filaments) and electrode matrices disclosed therein are incorporated herein by reference.

The elongate body 1832 may comprise (e.g., be at least partially formed of) an electrically insulating material. Examples of such insulating material can include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

The catheter 1830 optionally includes an anchor 1848. The anchor 1848 includes struts 1850 that form an open framework, where the struts 1850 extend laterally or radially outwardly from the elongate body 1832 (e.g., from a peripheral surface 1838 of the elongate body 1832) to at least partially define a peripheral surface 1852 configured to engage vascular tissue (e.g., configured to appose sidewalls forming the lumen of the right pulmonary artery and/or the left pulmonary artery). FIGS. 18A through 18C show the anchor 1848 positioned between the second end 1836 and the plurality of electrodes 1844 of the elongate catheter body 1832. It is also possible that the anchor 1848 can be positioned between the plurality of electrodes 1844 and the second end 1836 of the elongate catheter body 1832. In some embodiments, the anchor 1848 can inhibit or prevent at least a portion of the catheter 1830 (e.g., the portion 1854, a portion comprising the electrodes 1844) from extending into vasculature smaller than the expanded struts 1850. For example, with reference to FIG. 19, the plurality of electrodes 1944 can be proximal to the branch point 1976 such that portions of the catheter 1930 proximal to the anchor 1948 do not extend into the two additional arteries 1978. If the sensor 1966 is distal to the anchor 1948, interaction of the anchor 1948 and the branch point 1976 may ensure that the sensor 1966 is in a pulmonary artery branch vessel 1978.

The struts 1850 can have a cross-sectional shape and dimension that allow for the struts 1850 to provide a radial force sufficient to hold the catheter 1830 at the implant location within the pulmonary artery under a variety of situations, as discussed herein. The struts 1850 can be formed of a variety of materials, such as a metal, metal alloy, polymer, etc. Examples of such metals or metal alloys include surgical grade stainless steel, such as austenitic 316 stainless among others, and the nickel and titanium alloy known as Nitinol. Other metals and/or metal alloys, as are known or may be developed, can be used.

A portion 1854 of the elongate catheter body 1832, for example that includes one, some, none, or all the plurality of electrodes 1844, can curve in a predefined radial direction (e.g., anterior, posterior, inferior, superior, and combinations thereof), for example when placed under longitudinal compression. To provide the curve in the portion 1854, the elongate catheter body 1832 can be pre-stressed and/or the wall can have thicknesses that allow for the elongate catheter body 1832 to curve in the predefined radial direction, for example when placed under longitudinal compression. In addition, or alternatively, structures such as coils or a helix of wire having different turns per unit length, a hypotube having varying kerf spacing, etc. can be located in, around, and/or along the elongate catheter body 1832 in the portion 1854. One or more of these structures can be used to allow the longitudinal compression to create the curve in the predefined radial direction in the portion 1854. To achieve the longitudinal compression, the anchor 1848 can be deployed in the vasculature of the patient (e.g., in the pulmonary artery), where the anchor 1848 provides a location or point of resistance against the longitudinal movement of the elongate body 1832. As such, this allows a compressive force to be generated in the elongate catheter body 1832 sufficient to cause the portion 1854 of the elongate catheter body 1832, for example along which the plurality of electrodes 1844 are present, to curve in the predefined radial direction.

FIG. 18D provides an illustration of the portion 1854 of the elongate catheter body 1832 curved in a predefined radial direction when placed under longitudinal compression. The catheter 1830 illustrated in FIG. 18D is similar to the catheter 1830 shown in FIG. 18A and is described herein, although other catheters having similar features can also be used. In the catheter 1830 illustrated in FIG. 18D, a sensor 1866 is proximal to the electrodes 1844. When the electrodes 1844 are in the right pulmonary artery 206, the sensor 1866 can be in the pulmonary trunk 202, for example. If the sensor 1866 is more proximal, the sensor 1866 can be in the right ventricle, the superior vena cava, etc. Positioning the sensor 1866 proximal along the catheter 1830 can allow the sensor 1866 to be in a location different than the location of the electrode 1844 without positioning the sensor 1866 separate from positioning the electrode 1844. As illustrated in FIG. 18D, the catheter 1830 has been at least partially positioned within the main pulmonary artery 202 of a patient's heart 200, where the anchor 1848 is located in the lumen of the right pulmonary artery 206. From this position, a longitudinal compressive force applied to the elongate catheter body 1832 can cause the portion 1854 of the elongate catheter body 1832, along with at least some of the plurality of electrodes 1844 in this embodiment, to curve in the predefined radial direction, superior in this embodiment. The curvature allows (e.g., causes) the plurality of electrodes 1844 to extend towards and/or touch the luminal surface of the main pulmonary artery 202 and/or right pulmonary artery 206. Preferably, the plurality of electrodes 1844 are brought into position and/or contact with the luminal surface of the main pulmonary artery 202 and/or right pulmonary artery 206.

In some embodiments, the elongate catheter body 1832 of the catheter 1830 can use the lumen 1842 that extends from the first end 1834 towards the second end 1836 to provide a curve in a predefined radial direction. For example, the catheter 1830 can include a shaping wire 1857 having a first end 1859 and a second end 1861, as illustrated in FIG. 18A. The shaping wire 1857 can be bent and retain a desired shape that, upon insertion into the lumen 1842, can at least partially provide the catheter 1830 with a curve. The lumen 1842 has a size (e.g., a diameter) sufficient to allow the shaping wire 1857 to pass through the lumen 1842 with the second end 1861 of the shaping wire 1857 proximate to the second end 1836 of the elongate catheter body 1832 so that the bent portion 1863 of the shaping wire 1857 imparts a curve into the portion 1854 of the elongate catheter body 1832, allowing the plurality of electrodes 1844 to extend towards and/or touch the luminal surface of the main pulmonary artery. In some embodiments the shaping wire 1857 can complement the portion 1854. In some embodiments, the shaping wire 1857 can be used in place of the portion 1854 (e.g., if the catheter 1830 does not include the portion 1854 or by not imparting the longitudinal compressive force). In some embodiments, the shaping wire 1857 can be used to impart a curve that is contrary to the curve that the portion 1854 would cause if a compressive force was applied. In some embodiments, the shaping wire 1857 may be inserted into the lumen 1842 in any rotational orientation such that a curve can be imparted in any desired radial direction, for example depending on the position of the anchor 1848. The shaping wire 1857 can allow formation of a curve even if the catheter 1830 does not include an anchor 1848, for example because the catheter body 1832 can conform to the shape of the shaping wire regardless of whether the catheter 1830 is anchored to the vasculature. In some embodiments, insertion of the shaping wire 1857 into the lumen 1842 imparts a curve to the portion 1854 such that at least one of the electrodes 1844 apposes a superior/posterior sidewall of the pulmonary artery.

In some embodiments, a neuromodulation system comprises a catheter 1830 and a shaping wire 1857. The catheter 1830 comprises a catheter body 1832, an electrode 1844, and a sensor 1866. The catheter body 1832 comprises a proximal end 1834, a distal end 1836, a lumen 1842 extending from the proximal end 1834 towards the distal end 1836 (e.g., at least distal to the electrode 1844), and an outer surface 1838. The electrode 1844 is on the outer surface 1838. The electrode 1844 is configured to deliver an electrical signal to a pulmonary artery of a patient (e.g., to provide calibration and/or therapeutic stimulation to a nerve proximate the pulmonary artery).

The shaping wire 1857 comprises a material that is configured to cause the catheter body 1832 to bend. For example, the radial force of the shaping wire 1857 may be greater than the forces that keep the catheter body 1832 in a generally straight configuration. In some embodiments, the shaping wire 1857 comprises a shape memory material (e.g., nitinol, chromium cobalt, copper aluminum nickel, etc.) or a resilient material (e.g., stainless steel, etc.). For example, the shaping wire 1857 may be stressed to a straight wire in a proximal portion of the catheter 1830, but in a portion of the catheter 1830 to be bent, which may be, for example, weaker that the proximal portion of the catheter 1830, the shaping wire 1857 can revert to the unstressed curved shape within the catheter 1830. In some embodiments in which the shaping wire 1857 comprises a shape memory material, the shaping wire 1857 may utilize thermal shape memory. For example, the shaping wire 1857 may be in a substantially straight shape until cold or warm fluid (e.g., saline) causes reversion to the curved shape. In some such embodiments, the entire catheter 1830 may be bendable by the shaping wire 1857, but the temperature change is effected once the shaping wire 1857 is in a desired longitudinal and/or radial position. In some embodiments, the entire catheter 1830 may be bendable by the shaping wire 1857. For example, the curve may propagate along the length of the catheter 1830 until the curve is in a desired position.

The shaping wire 1857 has a diameter or cross-sectional dimension less than the diameter or cross-sectional dimension of the lumen 1842. For example, if the catheter body 1832 is 20 French (Fr) (approx. 6.67 millimeters (mm)), the lumen 1842 may be 18 Fr (approx. 6 mm) and the shaping wire 1857 may be 16 Fr (approx. 5.33 mm). The shaping wire 1857 may be, for example 1 Fr less than the lumen 1842 (e.g., for more radial force than if 2 Fr less) or 2 Fr less than the lumen 1842 (e.g., for less friction during navigation than if 1 Fr less). The shaping wire 1857 may be, for example 2 Fr less than the catheter body 1832 (e.g., if the lumen 1842 is 1 Fr less than the catheter body 1832) or 4 Fr less than the catheter body 1832 (e.g., providing flexibility for the size of the lumen 1842 to be 1 or 2 Fr less than the catheter body). Shaping wire sizes other than on a French catheter scale are also possible (e.g., having a diameter less than a diameter of the lumen 1842 by about 0.05 mm, 0.1 mm, by about 0.2 mm, by about 0.25 mm, by about 0.5 mm, ranges between such values etc.).

The sensor 1866 is on the outer surface 1838. The sensor 1866 is configured to sense a heart activity property (e.g., a non-electrical heart activity property such as a pressure property, an acceleration property, an acoustic property, a temperature, and a blood chemistry property) from a location within in vasculature of the patient. The location may be different than the pulmonary artery in which the electrode 1844 is positioned. For example, if the electrode 1844 is in the right pulmonary artery, the location of the sensor 1866 may be in the pulmonary trunk, a pulmonary artery branch vessel, the right ventricle, the ventricular septal wall, the right atrium, the septal wall of the right atrium, the superior vena cava, the inferior vena cava, the left pulmonary artery, the coronary sinus, etc. The shaping wire 1857 is configured to be positioned in the lumen 1842 of the catheter body 1832. The shaping wire comprising a bent portion 1863. For example, from a proximal end 1859 to a distal end 1861, the shaping wire 1857 may be substantially straight in a substantially straight portion, then have a bent portion 1863 extending away from a longitudinal axis of the straight portion. The bent portion 1863 may include one bend or a plurality of bends (e.g., two bends (as illustrated in FIG. 18A), three bends, or more bends). The shaping wire 1857 may optionally comprise another substantially straight portion after the bent portion, which may have a longitudinal axis that is substantially aligned with the longitudinal axis of the proximal straight portion. When the shaping wire 1857 is inserted in the lumen 1842 of the catheter body 1832, the catheter body 1832 comprises a curved portion 1854 corresponding to the bent portion 1863 of the shaping wire 1857. For example, the catheter body 1832, or the portion 1854, may comprise a material that can be bent due to pressure or stress applied to the lumen 1842 or interior surface 1840 of the catheter body 1832. In some embodiments, insertion of the shaping wire 1857 into the lumen 1842 imparts a curve to the portion 1854 such that at least one of the electrodes 1844 apposes a superior/posterior sidewall of the pulmonary artery.

FIGS. 18A through 18C further illustrate an example delivery catheter 1856 that can be used in conjunction with the catheter 1830. The delivery catheter 1856 can be a Swan-Ganz type pulmonary artery catheter, as are known, that includes a surface 1858 defining a lumen 1860 sized sufficiently to receive, store, and deploy the catheter 1830. As illustrated, the delivery catheter 1856 includes a reversibly inflatable balloon 1862 in fluid communication with a balloon inflation lumen that extends from a proximal or first end 1864 of the delivery catheter 1856 (e.g., where the inflation lumen can be to an inflation fluid source) to the interior volume of the reversibly inflatable balloon 1862.

The catheter 1830 also includes a first sensor 1866. As illustrated in FIGS. 18A through 18C, the first sensor 1866 can be positioned at a number of different locations along the catheter 1830. In FIG. 18A, the first sensor 1866 is positioned on the elongate catheter body 1832 distal to the anchor 1848. A sensor 1866 that is proximate to the distal end 1836 of the catheter 1830 may also or alternatively be useful for navigation of the catheter 1830, for example to determine an anatomical location during floating a balloon such as with a Swan-Ganz catheter. In FIG. 18B, the first sensor 1866 is positioned on or between one of the struts 1850 of the anchor. In FIG. 18C, the first sensor 1866 is positioned proximal to both the anchor 1848 and the plurality of electrodes 1844. In FIG. 18D, the first sensor 1866 is positioned proximal enough that the first sensor 1866 can be in a location of the vasculature different than the electrodes 1844. In some embodiments, the catheter 1830 comprises a plurality of sensors 1866 at more than one of the positions illustrated in FIGS. 18A through 18C and/or other positions.

The catheter 1830 further includes a sensor conductor 1868. The first sensor 1866 is coupled to the sensor conductor 1868 and is isolated from the conductive elements 1846 and electrodes 1844. The coupling may be electrical, optical, pressure, etc. The sensor conductor 1868 extends through the elongate body 1832 from the first sensor 1866 through the first end 1834 of the elongate body 1832. The sensor conductor 1868 terminates at a connector port that can be used, for example, to releasably couple the first sensor 1866 to the stimulation system, as discussed herein.

The first sensor 1866 can be used to sense one or more activity property (e.g., electrical and/or non-electrical heart activity properties). In some embodiments, the property can be measured in response to one or more electrical pulses delivered using the plurality of electrodes 1844. Examples of non-electrical heart activity properties include, but are not limited to, one or more of a pressure property, an acceleration property, an acoustic property, a temperature, and a blood chemistry property measured from within the vasculature of the heart. As appreciated, two or more of the non-electrical heart activity properties can be measured by using more than one sensor on the catheter 1830.

For use in detecting a pressure property, the first sensor 1866 can be a pressure sensing transducer, for example such as disclosed in U.S. Pat. No. 5,564,434 (e.g., configured to detect changes in blood pressure, atmospheric pressure, and/or blood temperature and to provide modulated pressure and/or temperature related signals), incorporated by reference herein in its entirety. For use in detecting an acceleration property, the first sensor 1866 can be an acceleration sensor, for example such as disclosed in U.S. Patent Pub. No. 2004/0172079 to Chinchoy (e.g., configured to generate a signal proportional to acceleration of a heart muscle or wall such as a coronary sinus wall, septal wall, or ventricle wall) or U.S. Pat. No. 7,092,759 to Nehls et al. (e.g., configured to generate a signal proportional to acceleration, velocity, and/or displacement of a heart muscle or wall such as a coronary sinus wall, septal wall, or ventricle wall), each of which is incorporated by reference herein in its entirety. For use in detecting an acoustic property, the first sensor 1866 can be a piezoelectric transducer (e.g., a microphone) or a blood flow sensor, for example such as disclosed in U.S. Pat. No. 6,754,532 (e.g., configured to measure a velocity of blood to estimate blood flow volume), which is incorporated by reference herein in its entirety. For use in detecting a temperature, the first sensor 1866 can be a temperature sensor, for example such as disclosed in U.S. Pat. No. 5,336,244 (e.g., configured to detect variations in blood temperature and/or oxygen concentration indicative of the mechanical pumping action of the heart) and/or U.S. Patent Pub. No. 2011/0160790 (e.g., configured to sense temperature and to produce a temperature signal), each of which is incorporated by reference herein in its entirety. For use in detecting a blood chemistry properties, the first sensor 1866 can be an oxygen sensor or a glucose sensor, for example such as disclosed in U.S. Pat. No. 5,213,098 (e.g., configured to sense blood oxygen saturation levels that vary with cardiac muscle oxygen uptake) and/or U.S. Patent Pub. No. 2011/0160790 (e.g., configured to measure oxygen and/or glucose concentration in blood and to produce an oxygen and/or glucose signal), each of which is incorporated by reference herein in its entirety. Other types of sensors can also be used for the first sensor 1866, other sensors described herein, and the like.

The catheter 1830 shown in FIGS. 18A through 18C can be positioned in the right pulmonary artery, the left pulmonary artery, or the pulmonary trunk of the patient, for example as described herein. To accomplish this, the delivery catheter 1856 with the catheter 1830 housed therein can be introduced into the vasculature through a percutaneous incision, and guided to the right ventricle. For example, the delivery catheter 1856 can be inserted into the vasculature via a peripheral vein of the neck or chest (e.g., as with a Swan-Ganz catheter). Changes in a patient's electrocardiography and/or pressure signals from the vasculature can be used to guide and locate the pulmonary artery catheter within the patient's heart. Once in the proper location, a guide wire can be introduced into the patient via the pulmonary artery guide catheter, where the guide wire is advanced into the desired pulmonary artery (e.g., the right pulmonary artery). The delivery catheter 1856 with the catheter 1830 housed therein can be advanced over the guide wire so as to position the catheter 1830 in the desired pulmonary artery of the patient (e.g., the right pulmonary artery or the left pulmonary artery), for example as described herein. Various imaging modalities can be used in positioning the guide wire of the present disclosure in the pulmonary artery of the patient. Such imaging modalities include, but are not limited to, fluoroscopy, ultrasound, electromagnetic, and electropotential modalities.

When the catheter 1830 is positioned in the right pulmonary artery or the left pulmonary artery and the sensor 1866 is configured to be proximal to the electrodes 1844, a distance between the electrodes 1844 (e.g., from the proximal-most electrode 1844) and the sensor 1866 may be between about 1 cm and about 5 cm (e.g., about 1 cm, about 2 cm, about 3 cm, about 4 cm, about 5 cm, ranges between such values, etc.), in which case the sensor 1866 can reside in the pulmonary trunk, between about 8 cm and about 20 cm (e.g., about 8 cm, about 9 cm, about 10 cm, about 11 cm, about 12 cm, about 13 cm, about 14 cm, about 16 cm, about 18 cm, about 20 cm, ranges between such values, etc.), in which case the sensor 1866 can reside in the right ventricle, between about 16 cm and about 27 cm (e.g., about 16 cm, about 17 cm, about 18 cm, about 19 cm, about 20 cm, about 21 cm, about 22 cm, about 23 cm, about 25 cm, about 27 cm, ranges between such values, etc.), in which case the sensor 1866 can reside in the right atrium, or between about 21 cm and about 33 cm (e.g., about 21 cm, about 23 cm, about 25 cm, about 26 cm, about 27 cm, about 28 cm, about 29 cm, about 30 cm, about 31 cm, about 32 cm, about 33 cm, ranges between such values, etc.), in which case the sensor 1866 can reside in the superior vena cava.

When the catheter 1830 is positioned in the pulmonary trunk and the sensor 1866 is configured to be distal to the electrodes 1844, a distance between the electrodes 1844 (e.g., from the distal-most electrode 1844) and the sensor 1866 may be between about 1 cm and about 5 cm (e.g., about 1 cm, about 2 cm, about 3 cm, about 4 cm, about 5 cm, ranges between such values, etc.), in which case the sensor 1866 can reside in the right pulmonary artery or the left pulmonary artery. When the catheter 1830 is positioned in the pulmonary trunk and the sensor 1866 is configured to be proximal to the electrodes 1844, a distance between the electrodes 1844 (e.g., from the proximal-most electrode 1844) and the sensor 1866 may be between about 3 cm and about 19 cm (e.g., about 3 cm, about 5 cm, about 6 cm, about 7 cm, about 8 cm, about 9 cm, about 10 cm, about 12 cm, about 15 cm, about 19 cm, ranges between such values, etc.), in which case the sensor 1866 can reside in the right ventricle, between about 11 cm and about 26 cm (e.g., about 11 cm, about 13 cm, about 15 cm, about 16 cm, about 17 cm, about 18 cm, about 19 cm, about 20 cm, about 22 cm, about 24 cm, about 26 cm, ranges between such values, etc.), in which case the sensor 1866 can reside in the right atrium, or between about 16 cm and about 32 cm (e.g., about 16 cm, about 18 cm, about 20 cm, about 22 cm, about 24 cm, about 25 cm, about 26 cm, about 27 cm, about 28 cm, about 30 cm, about 32 cm, ranges between such values, etc.), in which case the sensor 1866 can reside in the superior vena cava.

FIG. 19 provides a perspective view of a catheter 1930 positioned in the heart 200 of a subject (e.g., patient), where one or more of a plurality of electrodes 1944 are contacting the posterior 221 and/or superior surface 223 of the right pulmonary artery 206 (e.g., at a position that is superior to the branch point 207). FIG. 19 further illustrates the embodiment in which the first sensor 1966 is positioned distal from the anchor 1948. As illustrated, the pulmonary trunk 202 has a diameter 1970 taken across a plane 1972 substantially perpendicular to both the left lateral plane 220 and the right lateral plane 216. In a preferred embodiment, the plurality of electrodes 1944 of the catheter 1930 is positioned in an area 1974 that extends distally no more than about three times the diameter 1970 of the pulmonary trunk 202 to the right of the branch point 207. This area 1974 is shown with cross-hatching in FIG. 19.

The right pulmonary artery 206 can also include a branch point 1976 that divides the right pulmonary artery 206 into at least two additional arteries 1978 that are distal to the branch point 207 defining the left pulmonary artery 208 and the right pulmonary artery 206. As illustrated in FIG. 19, the plurality of electrodes 1944 can be positioned between the branch point 207 defining the left pulmonary artery 208 and the right pulmonary artery 206 and the branch point 1976 that divides the right pulmonary artery 206 into at least two additional arteries 1978. In other words, the plurality of electrodes 1944 of the catheter 1930 could be positioned so as to contact the posterior 221 and/or superior surface 223 of the right pulmonary artery 206 up to an including the branch point 1976.

Once positioned in a pulmonary artery of the heart of the patient (e.g., the right pulmonary artery 206 as illustrated in FIG. 19, the left pulmonary artery 208, and/or the pulmonary trunk 202), one or more therapeutic and/or calibrating electrical pulses can be delivered through the plurality of electrodes 1944 of the catheter 1930. One or more heart activity properties in response to the one or more electrical pulses are sensed from at least the first sensor 1966 positioned at a first location within the vasculature of the heart 200.

The catheter 1830, 1930 may be permanently or reversibly implantable into the vasculature. For example, the catheter 1830, 1930 may be retracted from the vasculature (e.g., after removing the anchor 1848, 1948) after a duration. The duration may be determined based at least partially on a set duration (e.g., a certain number of hours or days (e.g., 12 hours, 18 hours, 24 hours, 2 days, 3 days, 4 days, 5 days, 6 days, etc.)). The duration may be determined based at least partially on a response of a patient (e.g., retracted when the patient has improved in an aspect by a certain amount or is deemed ready to have the catheter 1830, 1930 removed).

Figure 20:
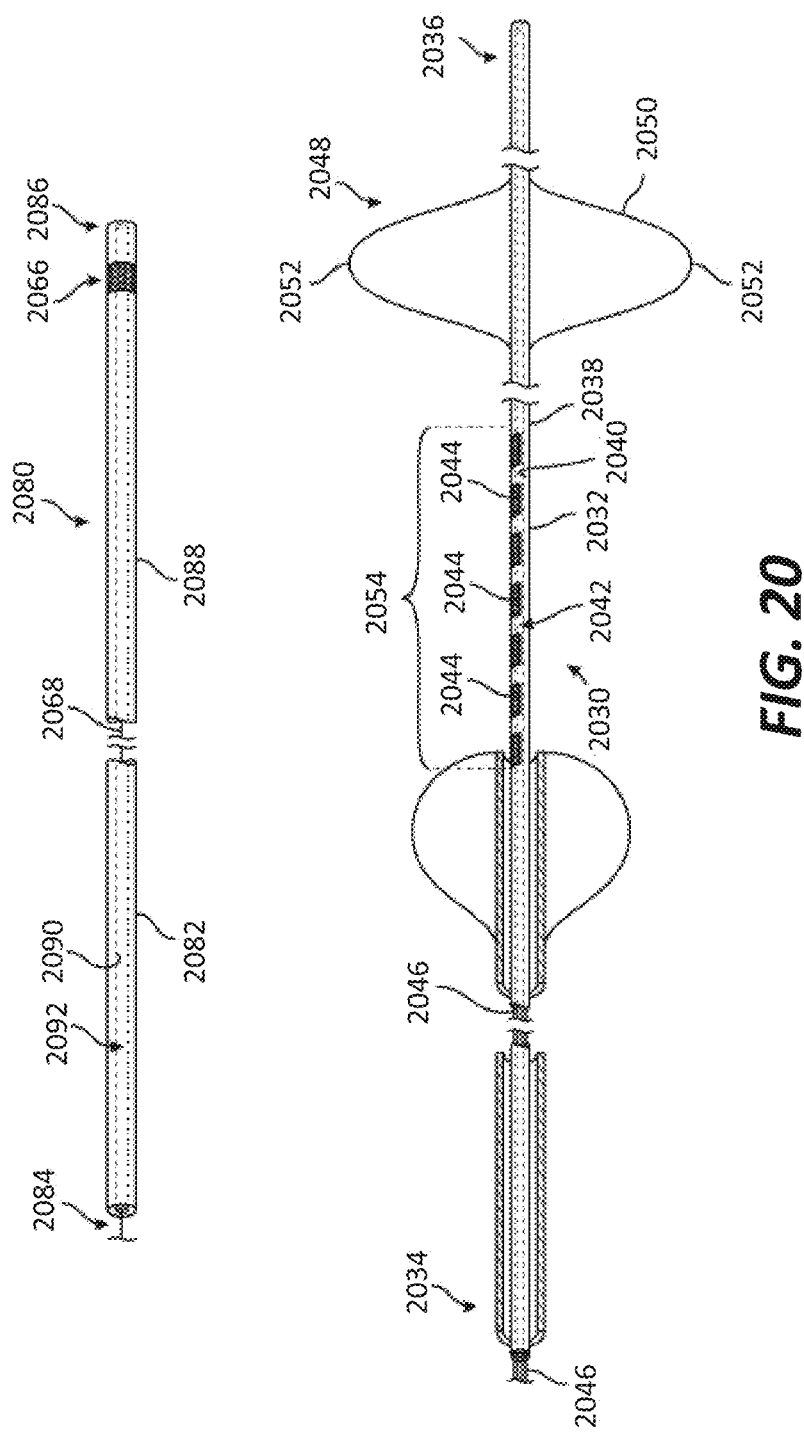
FIG. 20 is a side partial cross-sectional and perspective view of an example first catheter and an example second catheter that are suitable for performing the methods of the present disclosure.

FIG. 20 illustrates an example catheter 2030 and a separate first sensor 2066 useful for the methods of the present disclosure. Similar to the catheter 1830, the catheter 2030 includes an elongate catheter body 2032 having a proximal or first end 2034 and a distal or second end 2036, a peripheral surface 2038 and an interior surface 2040 defining a lumen 2042 (shown with a broken line) that extends between the first end 2034 and the second end 2036 of the elongate catheter body 2032. The catheter 2030 further includes a plurality of electrodes 2044 positioned along the peripheral surface 2038 of the elongate catheter body 2032, and conductive elements 2046 extending through the elongate body 2032 between the plurality of electrodes 2044 and the first end 2034, as discussed herein. The catheter 2030 further includes an anchor 2048 comprising struts 2050 that provide a peripheral surface 2052 that can engage vascular tissue (e.g., the lumen of either the right pulmonary artery or the left pulmonary artery).

The catheter 2030 further includes a portion 2054 of the elongate catheter body 2032, for example including the plurality of electrodes 2044, where the portion 2054 can curve in a predefined radial direction when placed under longitudinal compression, as discussed herein. The elongate catheter body 2032 of the catheter 2030 can also or alternatively include a lumen 2042 that can receive a shaping wire, as discussed herein.

In contrast to the catheter illustrated in FIGS. 18A through 18D, however, the catheter 2030 does not include a first sensor. Rather, a second catheter 2080 includes a first sensor 2066. As illustrated in FIG. 20, the second catheter 2080 includes an elongate catheter body 2082 having a first end 2084 and a second end 2086, a peripheral surface 2088 and an interior surface 2090 defining a lumen 2092 (shown with a broken line) that extends between the first end 2084 and the second end 2086 of the elongate catheter body 2082, where the lumen 2092 can receive a guide wire for help in positioning the second catheter 2080 in the vasculature of the heart. The second catheter 2080 further includes a first sensor 2066, as discussed herein, on the elongate catheter body 2082 and a sensor conductor 2068 that extends through the elongate catheter body 2082 to terminate at a connector port that can be used, for example, to releasably couple the first sensor 2066 to the stimulation system, as discussed herein.

As the first sensor 2066 is included on the second catheter 2080, the first sensor 2066 can be positioned in a location within the vasculature of the patient that is different than the first location in which the catheter 2030 is positioned. For example, the catheter 2030 can be positioned with the plurality of electrodes 2044 positioned in the right pulmonary artery, as discussed herein, while the first sensor 2066 is positioned in the left pulmonary artery. In this way, one or more electrical pulses can be delivered through the catheter 2030 positioned in the right pulmonary artery of the heart that does not contain the first sensor 2066. In some embodiments, when the catheter 2030 is positioned with the plurality of electrodes 2044 positioned in the left pulmonary artery, the first sensor 2066 can be positioned in the right pulmonary artery. In this way, one or more electrical pulses can be delivered through the catheter 2030 positioned in the left pulmonary artery of the heart that does not contain the first sensor 2066.

In some embodiments, the catheter 2030 can be positioned with the plurality of electrodes 2044 positioned in either one of the left pulmonary artery or the right pulmonary artery, and the first sensor 2066 on the second catheter 2080 can be positioned in the right ventricle of the heart. The first sensor 2066 on the second catheter 2080 can also be positioned in the right atrium of the heart.

In some embodiments, the first sensor 2066 on the second catheter 2080 can also be positioned on the septal wall of the right atrium or the ventricular septal wall of the heart. The elongate catheter body 2082 of the second catheter 2080 can include a positive fixation structure (e.g., a helical screw) that helps to secure the elongate catheter body 2082 and the first sensor 2066 to the septal wall of the right atrium of the heart.

In some embodiments the first sensor 2066 on the second catheter 2080 can be positioned in a superior vena cava of the heart. In some embodiments, the first sensor 2066 on the second catheter 2080 can be positioned in an inferior vena cava of the heart. In some embodiments, the first sensor 2066 on the second catheter 2080 can be positioned in a coronary sinus of the heart. In a preferred embodiment, when the first sensor 2066 is positioned in the coronary sinus of the heart, the first sensor 2066 is used to sense at least one of a temperature and a blood oxygen level.

One or more cardiac properties can also or alternatively be sensed from a skin surface of the patient. An example of such a cardiac property includes an electrocardiogram property, where the electrical activity of the heart can be sensed using electrodes, as are known, attached to the surface of the patient's skin. Another example of such a cardiac property can include a Doppler echocardiogram, which can be used to determine the speed and direction of the blood flow. Acoustic signals sensed from the skin surface of the patient may also be used as the cardiac property. The properties of the one or more electrical pulses delivered through the catheter positioned in the pulmonary artery of the heart can then be adjusted, as discussed herein, in response to the one or more heart activity properties measured intravascularly and/or the one or more cardiac properties from the skin surface of the patient.

In some embodiments, a second sensor located at a second location within the vasculature of the heart can be used, in addition to the first sensor, to sense one or more heart activity properties, as discussed herein, for example in response to the one or more electrical pulses. The second location is different than the first location. For example, the first location may be the left pulmonary artery and the second location may be the right pulmonary artery; the first location may be the left pulmonary artery and the second location may be the pulmonary trunk; the first location may be the left pulmonary artery and the second location may be the right ventricle; the first location may be the left pulmonary artery and the second location may be the right atrium; the first location may be the left pulmonary artery and the second location may be the septal wall of the right atrium; the first location may be the left pulmonary artery and the second location may be the ventricular septal wall; the first location may be the left pulmonary artery and the second location may be the superior vena cava; the first location may be the left pulmonary artery and the second location may be the inferior vena cava; the first location may be the left pulmonary artery and the second location may be the coronary sinus; and other permutations of these locations.

In some embodiments, the second sensor is the sensor 2066 of the second catheter 2080, and the first sensor is the sensor 266 of the catheter 230. In some embodiments the first sensor and the second sensor can be located on the same catheter (e.g., the catheter 230, the catheter 2080). For example, both the first sensor and the second sensor can be located on the second catheter 2080 for sensing at least two different heart activity properties. For another example, both the first sensor and the second sensor can be located on the catheter 230 for sensing at least two different heart activity properties. The properties of the one or more electrical pulses delivered through the catheter positioned in the pulmonary artery of the heart can be adjusted, as discussed herein, in response to the one or more heart activity properties received from the first sensor and the second sensor.

Neuromodulation of the heart according to the present disclosure can be accomplished by applying electrical pulses in and/or around the region of the pulmonary artery. For example, the neuromodulation of the present disclosure can apply the electrical pulses to the posterior, superior wall, and/or the inferior wall of the right pulmonary artery. Preferably, neuromodulation of the present disclosure includes applying the electrical pulses to the posterior and/or superior wall of the right pulmonary artery, although other positions in the right pulmonary artery, the left pulmonary artery, and the pulmonary trunk are also possible. The electrical pulses are thereby applied to the autonomic cardiopulmonary nerves surrounding the right pulmonary artery. These autonomic cardiopulmonary nerves can include the right autonomic cardiopulmonary nerves and the left autonomic cardiopulmonary nerves. The right autonomic cardiopulmonary nerves include the right dorsal medial cardiopulmonary nerve and the right dorsal lateral cardiopulmonary nerve. The left autonomic cardiopulmonary nerves include the left ventral cardiopulmonary nerve, the left dorsal medial cardiopulmonary nerve, the left dorsal lateral cardiopulmonary nerve, and the left stellate cardiopulmonary nerve. Stimulation of other nerves proximate to the right pulmonary artery is also possible.

With reference to FIG. 19, one or more of the plurality of electrodes 1944 of the catheter 1930 can be contacting the posterior surface 221 of the right pulmonary artery 206. From this location, the electrical pulses delivered through one or more of the plurality of electrodes 1944 may be better able to treat and/or provide therapy (including adjuvant therapy) to the patient experiencing a variety of cardiovascular medical conditions, such as acute heart failure. The electrical pulses can elicit responses from the autonomic nervous system that may help to modulate a patient's cardiac contractility. The electrical pulses applied by the methods described herein preferably affect heart contractility more than the heart rate, which can help to improve hemodynamic control while possibly and/or reducing or minimizing unwanted systemic effects.

In accordance with several embodiments, a stimulation system is electrically coupled to the plurality of electrodes of the catheters described herein (e.g., via the conductive elements extending through the catheter). The stimulation system can be used to deliver the stimulation energy (e.g., electrical current or electrical pulses) to the autonomic cardiopulmonary fibers surrounding a pulmonary artery (e.g., the right or left pulmonary artery or the main pulmonary artery or trunk). The stimulation system is used to operate and supply the stimulation energy (e.g., electrical current or electrical pulses) to the plurality of electrodes of the catheter. The stimulation system controls the various properties of the stimulation energy (e.g., electrical current or electrical pulses) delivered across the plurality of electrodes. Such properties include control of polarity (e.g., used as a cathode or an anode), pulsing mode (e.g., unipolar, bi-polar, biphasic, and/or multi-polar), a pulse width, an amplitude, a frequency, a phase, a voltage, a current, a duration, an inter-pulse interval, a dwell time, a sequence, a wavelength, and/or a waveform associated with the stimulation energy (e.g., electrical current or electrical pulses). The stimulation system may operate and supply the stimulation energy (e.g., electrical current or electrical pulses) to different combinations and numbers of the one or more electrodes, including one or more reference electrodes. The stimulation system can be external to the patient's body or internal to the patient's body. When located outside the body, a professional can program the stimulation system and monitor its performance. When located within the patient, the housing of the stimulation system or an electrode incorporated in the housing can be used as a reference electrode for both sensing and unipolar pulsing mode.

Examples of non-electrical heart activity properties include, but are not limited to, a pressure property, an acceleration property, an acoustic property, a temperature, or a blood chemistry property. The non-electrical heart activity properties may be sensed by at least a first sensor positioned at a first location within the vasculature of the heart. In response to the one or more non-electrical heart activity properties, a property of the one or more electrical pulses delivered through the catheter positioned in the pulmonary artery of the heart can be adjusted. Examples of such adjustments include, but are not limited to, changing which electrode or electrodes of the plurality of electrodes on the catheter is/are used to deliver one or more electrical pulses. Adjustments can also be made to the properties of the electrical pulses, for example by changing at least one of an electrode polarity, a pulsing mode, a pulse width, an amplitude, a frequency, a phase, a voltage, a current, a duration, an inter-pulse interval, a duty cycle, a dwell time, a sequence, a wavelength, a waveform, and/or an electrode combination of the one or more electrical pulses. It is possible to adjust combinations of electrodes used and the properties of the electrical pulses provided by the electrodes. Adjusting a property of the one or more electrical pulses can include moving the catheter to reposition electrodes of the catheter in the pulmonary artery of the heart. Combinations of these adjustments are also possible.

By way of example, the stimulation energy (e.g., electrical current or electrical pulses) can have a voltage between about 0.1 microvolts (mV) and about 75 volts (V) (e.g., about 0.1 mV, about 0.5 mV, about 1 mV, about 10 mV, about 100 mV or about 0.1 V, about 1 V, about 10 V, about 20 V, about 30 V, about 40 V, about 50 V, about 60 V, about 75 V, between 1 V and 50 V, between 0.1V and 10V, ranges between such values, etc.). The stimulation energy (e.g., electrical current or electrical pulses) can also have an amplitude between about 1 milliamps (mA) to about 40 mA (e.g., about 1 mA, about 2 mA, about 3 mA, about 4 mA, about 5 mA, about 10 mA, about 15 mA, about 20 mA, about 25 mA, about 30 mA, about 35 mA, about 40 mA, ranges between such values, etc.). The stimulation energy (e.g., electrical current or electrical pulses) can be delivered at a frequency of between 1 Hertz (Hz) and about 100,000 Hz or 100 kilohertz (kHz) (e.g., between 1 Hz and 10 kHz, between 2 Hz and 200 Hz, about 1 Hz, about 2 Hz, about 10 Hz, about 25 Hz, about 50 Hz, about 75 Hz, about 100 Hz, about 150 Hz, about 200 Hz, about 250 Hz, about 500 Hz, about 1,000 Hz or 1 kHz, about 10 kHz, ranges between such values, etc.). The electrical pulses can have a pulse width between about 100 microseconds (μs) and about 100 milliseconds (ms) (e.g., about 100 μs, about 200 μs, about 500 μs, about 1,000 μs or 1 ms, about 10 ms, about 50 ms, about 100 ms, ranges between such values, etc.). For variation of duty cycle, or the duration that the electrical pulses are delivered versus the duration that electrical pulses are not delivered, the electrical pulses may be delivered for between about 250 ms and about 1 second (e.g., about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, about 950 ms, ranges between such values, etc.), and thereafter not delivered for between about 1 second and about 10 minutes (e.g., about 1 second, about 5 seconds, about 10 seconds, about 15 seconds, about 30 seconds, about 45 seconds, about 1 minute, about 2 minutes, about 3 minutes, about 5 minutes, about 10 minutes, ranges between such values, etc.). An optimized duty cycle may, for example, reduce response time, increase battery life, patient comfort (reduce pain, cough, etc.), etc. The stimulation energy (e.g., electrical current or electrical pulses) can also have a variety of waveforms, such as: square wave, biphasic square wave, sine wave, arbitrary defined waveforms that are electrically safe, efficacious, and feasible, and combinations thereof. The stimulation energy (e.g., electrical current or electrical pulses) may be applied to multiple target sites via multiple electrodes at least partially simultaneously and/or sequentially.

In some embodiments, the waveform of a stimulation signal is a charge balanced, constant current cathodic first biphasic waveform with a low impedance closed switch second phase electrode discharge. Pulse train characteristics can include, for example, a pulse amplitude between about 8 mA and about 20 mA, a pulse width between about 2 ms and about 8 ms, and a pulse frequency of about 20 Hz. Pulse amplitude and/or pulse width may be lower based on certain electrode designs.

The methods of the present disclosure can include assigning a hierarchy of electrode configurations from which to deliver the one or more electrical pulses. The hierarchy can include two or more predetermined patterns and/or combinations of the plurality of electrodes to use in delivering the one or more electrical pulses. For example, the one or more electrical pulses can be delivered using the hierarchy of electrode configurations. A heart activity property sensed in response to the one or more electrical pulses delivered using the hierarchy of electrode configurations can be analyzed. Such an analysis can include, for example, determining which of the hierarchy of electrode configurations provide the highest contractility or relative contractility of the patient's heart. Based on this analysis, an electrode configuration can be selected to use for delivering the one or more electrical pulses through the catheter positioned in the pulmonary artery of the patient's heart.

In some embodiments, a method can include assigning a hierarchy to one or more properties of the one or more electrical pulses delivered through the catheter positioned in the pulmonary artery of the heart. The hierarchy can include providing an order of which property (e.g., electrode polarity, pulsing mode, pulse width, amplitude, frequency, phase, voltage, current, duration, inter-pulse interval, duty cycle, dwell time, sequence, wavelength, or waveform of the one or more electrical pulses) is to be changed and by how much, and for a predetermined number of electrical pulses delivered to the patient's heart. The predetermined number of electrical pulses can be, for example, 10 to 100 electrical pulses at a given property of the hierarchy. The one or more heart activity properties can be recorded for the predetermined number of the one or more electrical pulses delivered to the patient's heart for a given property of the one or more electrical pulses. The one or more heart activity properties sensed in response to the one or more electrical pulses can then be analyzed. For example, the recorded properties for each set of predetermined numbers of pulses can be analyzed against other sets of recorded properties and/or against predetermined standards for a given heart activity properties and/or cardiac property (e.g., contractility). Based on this analysis, an electrode configuration can be selected to use for delivering the one or more electrical pulses through the catheter positioned in the pulmonary artery of the patient's heart. As a non-limiting example, a current of 1 mA can be applied to an electrode for 50 electrical pulses, followed by the application of a current of 10 mA to the electrode for 50 electrical pulses. The responses at 1 mA and 10 mA can be compared. If 10 mA works better, a current of 20 mA can be applied to the electrode for 50 electrical pulses, and the responses at 10 mA and 20 mA can be compared. If 10 mA works better, 10 mA may be selected as the current for the method. A wide variety of selection processes may be used, including but not limited to iterative methods (e.g., comprising making comparisons until a limit is found at which a difference is negligible) and brute force methods (e.g., measuring responses and selecting one magnitude after completion of all responses or until a certain value is achieved). This can be repeated for one or more additional properties according to the hierarchy (e.g., current followed by frequency). The selection process may be the same or different for each member of the hierarchy.

In some embodiments, a first electrical signal of a series of electrical signals is delivered (e.g., via a stimulation system such as the stimulation system 2101) to an electrode in the pulmonary artery (e.g., the right pulmonary artery, the left pulmonary artery, the pulmonary trunk). After delivering the first electrical signal, a second electrical signal of the series of electrical signals is delivered (e.g., via the stimulation system) to the electrode. The second electrical signal differs from the first electrical signal by a magnitude of a first parameter of a plurality of parameters. For example, if the first parameter is current, the first electrical signal may have a voltage such as 1 mA and the second electrical signal may have a different voltage such as 2 mA, while each of the other parameters (e.g., polarity, pulse width, amplitude, frequency, voltage, duration, inter-pulse interval, dwell time, sequence, wavelength, waveform, and/or an electrode combination) are the same.

Sensor data indicative of one or more non-electrical heart activity properties may be determined in response to delivering the series of electrical signals (e.g., via a sensor in the vasculature (e.g., as part of a same catheter that comprises the electrode, as part of a different catheter), via a sensor on a skin surface, combinations thereof, and the like)). Electrical parameters to use for therapeutic modulation may be selected based at least partially on the sensor data. For example, the selected electrical parameters may comprise a selected magnitude of the first parameter. A therapeutic neuromodulation signal may be delivered to the pulmonary artery using selected electrical parameters. The therapeutic neuromodulation signal may increase heart contractility (e.g., more than heart rate).

In some embodiments, a first series of electrical signals is delivered (e.g., via a stimulation system such as the stimulation system 501) to an electrode in the pulmonary artery (e.g., the right pulmonary artery, the left pulmonary artery, the pulmonary trunk). The first series comprises a first plurality of electrical signals. Each of the first plurality of electrical signals comprises a plurality of parameters (e.g., polarity, pulsing mode, pulse width, amplitude, frequency, phase, voltage, current, duration, inter-pulse interval, duty cycle, dwell time, sequence, wavelength, waveform, electrode combination, subsets thereof, or the like). Each of the first plurality of electrical signals of the first series only differs from one another by a magnitude of a first parameter of the plurality of parameters (e.g., one of polarity, pulsing mode, pulse width, amplitude, frequency, phase, voltage, current, duration, inter-pulse interval, duty cycle, dwell time, sequence, wavelength, and waveform changes in each of the first plurality of electrical signals). For example, if the first parameter is current, the first plurality of electrical signals of the first series may differ by having different currents such as 1 mA, 2 mA, 3 mA, 4 mA, etc., while each of the other parameters (e.g., polarity, pulsing mode, pulse width, amplitude, frequency, phase, voltage, duration, inter-pulse interval, duty cycle, dwell time, sequence, wavelength, and waveform) are the same.

After the first series of electrical signals is delivered to the electrode, a second series of electrical signals can be delivered (e.g., via the stimulation system) to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters different than the first parameter (e.g., a different one of polarity, pulsing mode, pulse width, amplitude, frequency, phase, voltage, current, duration, inter-pulse interval, duty cycle, dwell time, sequence, wavelength, and waveform changes in each of the second plurality of electrical signals). For example, if the first parameter is current, the second parameter may be related to timing such as frequency or duty cycle. For example, in the case of frequency, the second plurality of electrical signals of the second series may differ by having different frequencies such as 1 Hz, 2 Hz, 3 Hz, 4 Hz, etc., while each of the other parameters (e.g., current, polarity, pulsing mode, pulse width, amplitude, phase, voltage, duration, inter-pulse interval, duty cycle, dwell time, sequence, wavelength, and waveform) are the same.

Sensor data indicative of one or more non-electrical heart activity properties may be determined in response to delivering the first series of electrical signals and the second series of electrical signals (e.g., via a sensor in the vasculature (e.g., as part of a same catheter that comprises the electrode, as part of a different catheter), via a sensor on a skin surface, combinations thereof, and the like)). Electrical parameters to use for therapeutic modulation may be selected based at least partially on the sensor data. For example, the selected electrical parameters may comprise a selected magnitude of the first parameter and a selected magnitude of the second parameter. A therapeutic neuromodulation signal may be delivered to the pulmonary artery using selected electrical parameters. The therapeutic neuromodulation signal may increase heart contractility (e.g., more than heart rate).

Other series of electrical signals may be delivered to the electrode, for example only differing from one another by a magnitude of a different parameter of the plurality of parameters than the first parameter and the second parameter. As many parameters as may be desired to have a selected value may be calibrated or optimized. An order of the parameters may be based on a hierarchy (e.g., first select a current, then select a frequency, etc.).

A calibration or optimization process may be performed once (e.g., when a catheter 1830, 1930 is initially positioned) or a plurality of times. For example, the process may be repeated periodically or after a certain duration (e.g., once per hour, per 2 hours, per 4 hours, per 6 hours, per 8 hours, per 12 hours, per 18 hours, per 24 hours, per 36 hours, per 2 days, per 60 hours, per 3 hours, etc.). In some implementations the process may be repeated upon detection of a change (e.g., by the sensor 266, 366, 466). For example, if a heart activity property changes by more than a certain percentage in a certain duration (e.g., ±10%, ±25%, ±50%, etc. in ≤1 minute, ≤2 minutes, ≤5 minutes, etc.), that may be indicative that the catheter and/or sensor changed position or that something else in the system or patient may have changed (e.g., patient condition, physiological status, other therapy regiments, etc.).

Figure 21:
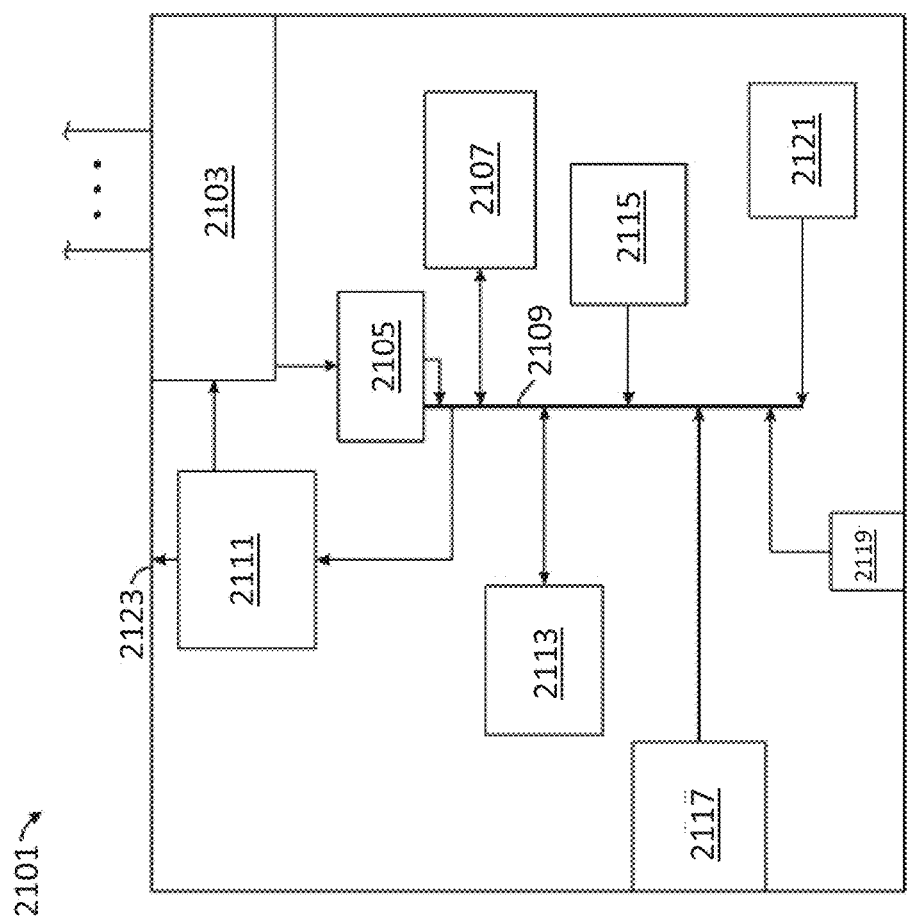
FIG. 21 illustrates an embodiment of a stimulation system for use with the catheters or catheter systems of the present disclosure.

For example, FIG. 21 illustrates an embodiment of a stimulation system 2101. U.S. Provisional Patent App. No. 62/001,729, filed May 22, 2014, is incorporated herein by reference in its entirety, and more specifically the stimulation system 11600 disclosed in FIG. 11 and page 41, line 5 to page 42, line 19 are incorporated herein by reference. As shown in FIG. 21, the stimulation system 2101 includes an input/output connector 2103 that can releasably join the conductive elements of the catheter, conductive elements of a second catheter, and/or sensors for sensing the one or more cardiac properties from the skin surface of the patient, as discussed herein. An input from the sensor can also be releasably coupled to the input/output connector 11602 so as to receive the sensor signal(s) discussed herein. The conductive elements and/or sensors may be permanently coupled to the stimulation system (e.g., not releasably coupled).

The input/output connector 2103 is connected to an analog to digital converter 2105. The output of the analog to digital converter 2105 is connected to a microprocessor 2107 through a peripheral bus 2109 including, for example, address, data, and control lines. The microprocessor 2107 can process the sensor data, when present, in different ways depending on the type of sensor in use. The microprocessor 2107 can also control, as discussed herein, the pulse control output generator 2111 that delivers the stimulation electrical energy (e.g., electrical pulses) to the one or more electrodes via the input/output connector 2103 and/or housing 2123.

The parameters of the stimulation electrical energy (e.g., properties of the electrical pulses) can be controlled and adjusted, if desired, by instructions programmed in a memory 2113 and executed by a programmable pulse generator 2115. The memory 2113 may comprise a non-transitory computer-readable medium. The memory 2113 may include one or more memory devices capable of storing data and allowing any storage location to be directly accessed by the microprocessor 2107, such as random access memory (RAM), flash memory (e.g., non-volatile flash memory), and the like. The stimulation system 2101 may comprise a storage device, such as one or more hard disk drives or redundant arrays of independent disks (RAID), for storing an operating system and other related software, and for storing application software programs, which may be the memory 2113 or a different memory. The instructions in memory 2113 for the programmable pulse generator 2115 can be set and/or modified based on input from the sensors and the analysis of the one or more heart activity properties via the microprocessor 2107. The instructions in memory 2113 for the programmable pulse generator 2115 can also be set and/or modified through inputs from a professional via an input 2117 connected through the peripheral bus 2109. Examples of such an input include a keyboard and/or a mouse (e.g., in conjunction with a display screen), a touch screen, etc. A wide variety of input/output (I/O) devices may be used with the stimulation system 2101. Input devices include, for example, keyboards, mice, trackpads, trackballs, microphones, and drawing tablets. Output devices include, for example, video displays, speakers, and printers. The I/O devices may be controlled by an I/O controller. The I/O controller may control one or more I/O devices. An I/O device may provide storage and/or an installation medium for the stimulation system 2101. The stimulation system 2101 may provide USB connections to receive handheld USB storage devices. The stimulation system 2101 optionally includes a communications port 2119 that connects to the peripheral bus 2109, where data and/or programming instructions can be received by the microprocessor 2107 and/or the memory 2113.

Input from the input 2117 (e.g., from a professional), the communications port 2119, and/or from the one or more heart activity properties via the microprocessor 2107 can be used to change (e.g., adjust) the parameters of the stimulation electrical energy (e.g., properties of the electrical pulses). The stimulation system 2101 optionally includes a power source 2121. The power source 2121 can be a battery or a power source supplied from an external power supply (e.g., an AC/DC power converter coupled to an AC source). The stimulation system 2101 optionally includes a housing 2123.

The microprocessor 2107 can execute one or more algorithms in order to provide stimulation. The microprocessor 2107 can also be controlled by a professional via the input 2117 to initiate, terminate, and/or change (e.g., adjust) the properties of the electrical pulses. The microprocessor 2107 can execute one or more algorithms to conduct the analysis of the one or more heart activity properties sensed in response to the one or more electrical pulses delivered using the hierarchy of electrode configurations and/or the hierarchy of each property of the one or more electrical pulses, for example to help identify an electrode configuration and/or the property of the one or more electrical pulses delivered to the patient's heart. Such analysis and adjustments can be made using process control logic (e.g., fuzzy logic, negative feedback, etc.) so as to maintain control of the pulse control output generator 2111.

In some embodiments, the stimulation is operated with closed loop feedback control. In some embodiments, input is received from a closed-looped feedback system via the microprocessor 2107. The closed loop feedback control can be used to help maintain one or more of a patient's cardiac parameters at or within a threshold value or range programmed into memory 2113. For example, under closed loop feedback control measured cardiac parameter value(s) can be compared and then it can be determine whether or not the measured value(s) lies outside a threshold value or a pre-determined range of values. If the measured cardiac parameter value(s) do not fall outside of the threshold value or the pre-determined range of values, the closed loop feedback control continues to monitor the cardiac parameter value(s) and repeats the comparison on a regular interval. If, however, the cardiac parameter value(s) from a sensor indicate that one or more cardiac parameters are outside of the threshold value or the pre-determined range of values one or more of the parameters of the stimulation electrical energy will be adjusted by the microprocessor 2107.

The stimulation system 2101 may comprise one or more additional components, for example a display device, a cache memory (e.g., in communication with the microprocessor 2107), logic circuitry, signal filters, a secondary or backside bus, local buses, local interconnect buses, and the like. The stimulation system 2101 may support any suitable installation device, such as a CD-ROM drive, a CD-R/RW drive, a DVD-ROM drive, tape drives of various formats, USB device, hard-drive, communication device to a connect to a server, or any other device suitable for installing software and programs. The stimulation system 2101 may include a network interface to interface to a Local Area Network (LAN), Wide Area Network (WAN), or the Internet through a variety of connections including, but not limited to, standard telephone lines, LAN or WAN links, broadband connections, wireless connections (e.g., Bluetooth, WiFi), combinations thereof, and the like. The network interface may comprise a built-in network adapter, network interface card, wireless network adapter, USB network adapter, modem, or any other device suitable for interfacing the stimulation system 2101 to any type of network capable of communication and performing the operations described herein. In some embodiments, the stimulation system 2101 may comprise or be connected to multiple display devices, which may be of the same or different in type and/or form. As such, any of the I/O devices and/or the I/O controller may comprise any type and/or form of suitable hardware, software, or combination of hardware and software to support, enable, or provide for the connection and use of multiple display devices by the stimulation system 2101. The stimulation system can interface with any workstation, desktop computer, laptop or notebook computer, server, handheld computer, mobile telephone, any other computer, or other form of computing or telecommunications device that is capable of communication and that has sufficient processor power and memory capacity to perform the operations described herein and/or to communication with the stimulation system 2101. The arrows shown in FIG. 21 generally depict the flow of current and/or information, but current and/or information may also flow in the opposite direction depending on the hardware.

Analysis, determining, adjusting, and the like described herein may be closed loop control or open loop control. For example, in closed loop control, a stimulation system may analyze a heart activity property and adjust an electrical signal property without input from a user. For another example, in open loop control, a stimulation system may analyze a heart activity property and prompt action by a user to adjust an electrical signal property, for example providing suggested adjustments or a number of adjustment options.

In some embodiments, a method of non-therapeutic calibration comprises positioning an electrode in a pulmonary artery of a heart and positioning a sensor in a right ventricle of the heart. The system further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals. The method further comprises determining a therapeutic neuromodulation signal to be delivered to the pulmonary artery using selected electrical parameters. The selected electrical parameters comprise a selected magnitude of the first parameter and a selected magnitude of the second parameter. The selected magnitudes of the first and second parameters are based at least partially on the sensor data.

In some embodiments, a method of non-therapeutic calibration comprises delivering a first electrical signal of a series of electrical signals to an electrode in a first anatomical location and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and determining a therapeutic neuromodulation signal to be delivered to the first anatomical location using selected electrical parameters. The selected electrical parameters comprise a selected magnitude of the first parameter. The selected magnitude of the first parameter is based at least partially on the sensor data.

In some embodiments, the stimulation system can be used to help identify a preferred location for the position of the one or more electrodes along the posterior, superior and/or inferior surfaces of the main pulmonary artery, left pulmonary artery, and/or right pulmonary artery. To this end, the one or more electrodes of the catheter or catheter system are introduced into the patient and tests of various locations along the posterior, superior and/or inferior surfaces of the vasculature using the stimulation system are conducted so as to identify a preferred location for the electrodes. During such a test, the stimulation system can be used to initiate and adjust the parameters of the stimulation electrical energy (e.g., electrical current or electrical pulses). Such parameters include, but are not limited to, terminating, increasing, decreasing, or changing the rate or pattern of the stimulation electrical energy (e.g., electrical current or electrical pulses). The stimulation system can also deliver stimulation electrical energy (e.g., electrical current or electrical pulses) that is episodic, continuous, phasic, in clusters, intermittent, upon demand by the patient or medical personnel, or preprogrammed to respond to a signal, or portion of a signal, sensed from the patient.

An open-loop or closed-loop feedback mechanism may be used in conjunction with the present disclosure. For the open-loop feedback mechanism, a professional can monitor cardiac parameters and changes to the cardiac parameters of the patient. Based on the cardiac parameters the professional can adjust the parameters of the electrical current applied to autonomic cardiopulmonary fibers. Non-limiting examples of cardiac parameters monitored include arterial blood pressure, central venous pressure, capillary pressure, systolic pressure variation, blood gases, cardiac output, systemic vascular resistance, pulmonary artery wedge pressure, gas composition of the patient's exhaled breath and/or mixed venous oxygen saturation. Cardiac parameters can be monitored by an electrocardiogram, invasive hemodynamics, an echocardiogram, or blood pressure measurement or other devices known in the art to measure cardiac function. Other parameters such as body temperature and respiratory rate can also be monitored and processed as part of the feedback mechanism.

In a closed-loop feedback mechanism, the cardiac parameters of the patient are received and processed by the stimulation system, where the parameters of the electrical current are adjusted based at least in part on the cardiac parameters. As discussed herein, a sensor is used to detect a cardiac parameter and generate a sensor signal. The sensor signal is processed by a sensor signal processor, which provides a control signal to a signal generator. The signal generator, in turn, can generate a response to the control signal by activating or adjusting one or more of the parameters of the electrical current applied by the catheter to the patient. The control signal can initiate, terminate, increase, decrease or change the parameters of the electrical current. It is possible for the one or more electrodes of the catheter to be used as a sensor a recording electrode. When necessary these sensing or recording electrodes may deliver stimulation electrical energy (e.g., electrical current or electrical pulses) as discussed herein.

The stimulation system can also monitor to determine if the one or more electrodes have dislodged from their position within the right pulmonary artery. For example, impedance values can be used to determine whether the one or more electrodes have dislodged from their position within the right pulmonary artery. If changes in the impedance values indicate that the one or more electrodes have dislodged from their position within the right pulmonary artery, a warning signal is produced by the stimulation system and the electrical current is stopped.

In several embodiments, the catheters provided herein include a plurality of electrodes, which includes two or more electrodes. It is understood that the phrase "a plurality of electrodes" can be replaced herein with two or more electrodes if desired. For the various embodiments of catheters and systems disclosed herein, the electrodes can have a variety of configurations and sizes. For example, the electrodes discussed herein can be ring-electrodes that fully encircle the body on which they are located. The electrodes discussed herein can also be a partial ring, where the electrode only partially encircles the body on which they are located. For example, the electrodes can be partial ring electrodes that preferably only contact the luminal surface of the main pulmonary artery and/or pulmonary arteries, as discussed herein. This configuration may help to localize the stimulation electrical energy, as discussed herein, into the vascular and adjacent tissue structures (e.g., autonomic fibers) and away from the blood. The electrodes and conductive elements provided herein can be formed of a conductive biocompatible metal or metal alloy. Examples of such conductive biocompatible metal or metal alloys include, but are not limited to, titanium, platinum or alloys thereof. Other biocompatible metal or metal alloys are known.

For the various embodiments, the elongate body of the catheters provided herein can be formed of a flexible polymeric material. Examples of such flexible polymeric material include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

Each of the catheters and/or catheter systems discussed herein can further include one or more reference electrodes positioned proximal to the one or more electrodes present on the elongate body. These one or more reference electrodes can each include insulated conductive leads that extend from the catheter and/or catheter system so as to allow the one or more reference electrodes to be used as common or return electrodes for electrical current that is delivered through one or more of the one or more electrodes on the elongate body of the catheter and/or catheter system.

With respect to treating cardiovascular medical conditions, such medical conditions can involve medical conditions related to the components of the cardiovascular system such as, for example, the heart and aorta. Non-limiting examples of cardiovascular conditions include post-infarction rehabilitation, shock (hypovolemic, septic, neurogenic), valvular disease, heart failure including acute heart failure, angina, microvascular ischemia, myocardial contractility disorder, cardiomyopathy, hypertension including pulmonary hypertension and systemic hypertension, orthopnea, dyspenea, orthostatic hypotension, dysautonomia, syncope, vasovagal reflex, carotid sinus hypersensitivity, pericardial effusion, and cardiac structural abnormalities such as septal defects and wall aneurysms.

In some embodiments, a catheter, for example as discussed herein, can be used in conjunction with a pulmonary artery catheter, such as a Swan-Ganz type pulmonary artery catheter, to deliver transvascular neuromodulation via the pulmonary artery to an autonomic target site to treat a cardiovascular condition. In certain such embodiments, the catheter (or catheters) is housed within one of the multiple lumens of a pulmonary artery catheter.

In addition to the catheter and catheter system of the present disclosure, one or more sensing electrodes can be located on or within the patent. Among other things, the sensing electrodes can be used to detect signals indicting changes in various cardiac parameters, where these changes can be the result of the pulse of stimulation electrical energy delivered to stimulate the nerve fibers (e.g., autonomic nerve fibers) surrounding the main pulmonary artery and/or one or both of the pulmonary arteries. Such parameters include, but are not limited to, the patient's heart rate (e.g., pulse), among other parameters. The sensing electrodes can also provide signals indicting changes in one or more electrical parameter of vasculature (electrical activity of the cardiac cycle). Such signals can be collected and displayed, as are known, using known devices (e.g., electrocardiography (ECG) monitor) or a stimulation system, as discussed herein, which receives the detected signals and provides information about the patient.

Other sensors can also be used with the patient to detect and measure a variety of other signals indicting changes in various cardiac parameters. Such parameters can include, but are not limited to, blood pressure, blood oxygen level and/or gas composition of the patient's exhaled breath. For example, catheter and catheter system of the present disclosure can further include a pressure sensor positioned within or in-line with the inflation lumen for the inflatable balloon. Signals from the pressure sensor can be used to both detect and measure the blood pressure of the patient. Alternatively, the catheter and catheter system of the present disclosure can include an integrated circuit for sensing and measuring blood pressure and/or a blood oxygen level. Such an integrated circuit can be implemented using 0.18 µm CMOS technology. The oxygen sensor can be measured with optical or electrochemical techniques as are known. Examples of such oxygen sensors include reflectance or transmissive pulse oximetry those that use changes in absorbance in measured wavelengths optical sensor to help determined a blood oxygen level. For these various embodiments, the elongate body of the catheter can include the sensor (e.g., a blood oxygen sensor and/or a pressure sensor) and a conductive element, or elements, extending through each of the elongate body, where the conductive element conducts electrical signals from the blood oxygen sensor and/or the pressure sensor.

The detected signals can also be used by the stimulation system to provide stimulation electrical energy in response to the detected signals. For example, one or more of these signals can be used by the stimulation system to deliver the stimulation electrical energy to the one or more electrodes of the catheter or catheter system. So, for example, detected signals from the patent's cardiac cycle (e.g., ECG waves, wave segments, wave intervals or complexes of the ECG waves) can be sensed using the sensing electrodes and/or timing parameter of the subject's blood pressure. The stimulation system can receive these detected signals and based on the features of the signal(s) generate and deliver the stimulation electrical energy to the one or more electrode of the catheter or catheter system. As discussed herein, the stimulation electrical energy is of sufficient current and potential along with a sufficient duration to stimulate one or more of the nerve fibers surrounding the main pulmonary artery and/or one or both of the pulmonary arteries so as to provide neuromodulation to the patient.

Figure 22D:
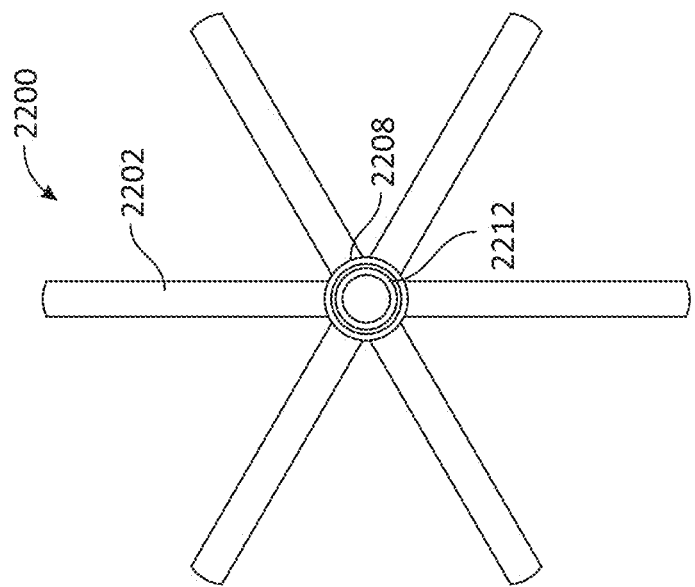
FIG. 22D is a proximal end view of the portion of FIG. 22A.
Figure 22C:
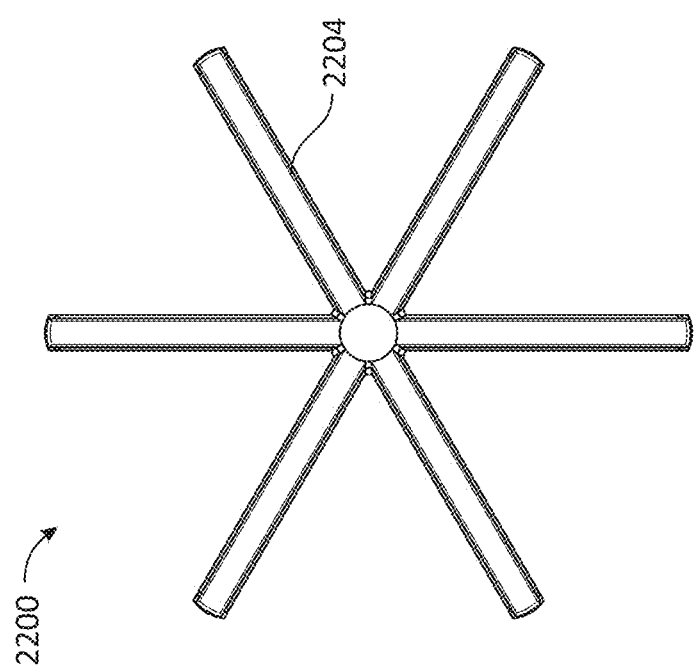
FIG. 22C is a distal end view of the portion of FIG. 22A.

FIG. 22A is a perspective view of an example of a portion 2200 of a catheter. FIG. 22B is a side elevational view of the portion 2200 of FIG. 22A. FIG. 22C is a distal end view of the portion 2200 of FIG. 22A. FIG. 22D is a proximal end view of the portion 2200 of FIG. 22A. The portion 2200 may be coupled to or form part of a catheter (e.g., an all-in-one catheter or a telescoping catheter), for example as described herein.

The portion 2200 comprises a first cut hypotube 2202 and a second cut hypotube 2204 coupled at points 2206. As may be appropriate for any of the cut hypotubes described herein, a sheet may be cut and rolled into a hypotube with an intermediate shape setting into a tube or directly into a final shape. The first cut hypotube 2202 comprises a cylindrical (e.g., uncut) portion 2208 and a plurality of splines 2210. The second cut hypotube 2204 comprises a cylindrical (e.g., uncut) portion 2212 and a plurality of splines 2214. As may be best seen in FIG. 22B, the splines 2210 are convex and the splines 2214 are concave.

In the embodiment illustrated in FIGS. 22A and 22B, the distal ends of the splines 2210 are coupled radially inward of, but proximate to, the distal ends of the splines 2214 at the points 2206. In some embodiments, the distal ends of the splines 2210 may be coupled to the splines 2214 even further radially inward. In some embodiments, the distal ends of the splines 2214 may be coupled radially inward of the distal ends of the splines 2210. The points 2206 may be proximate to the distal ends of the splines 2210 and the distal ends of the splines 2214 (e.g., as shown in FIGS. 22A and 22B), between the distal ends of the splines 2214 and points along the splines 2210 (e.g., an approximate longitudinal midpoint, about 75% of the length closer to the distal end, etc.), or between the distal ends of the splines 2210 and points along the splines 2214 (e.g., including embodiments in which the splines 2214 are configured to be convex distal to the points 2206).

As shown in FIGS. 22C and 22D, the cylindrical portion 2212 telescopes radially inward of the cylindrical portion 2208. The cylindrical portion 2212 has a lower diameter than the cylindrical portion 2208. As the cylindrical portion 2208 and the cylindrical portion 2212 move relatively away from each other (e.g., by distal advancement of the second cut hypotube 2204 and/or proximal retraction of the first cut hypotube 2202), the splines 2204 push the splines 2210 radially outward.

FIGS. 22A-22D illustrate six splines 2210 and six splines 2214. Other numbers of splines 2210, 2214 are also possible (e.g., between 2 and 12 (e.g., about 2, 3, 4, 5, 6, 7, 8, 9, 10, 11, 12, ranges between such values, etc.)). The splines 2210, 2214 may be uniformly circumferentially spaced, or some splines 2210, 2214 may be closer circumferentially. The splines 2210, 2214 may provide a circumferential coverage between about 60° and 360° (e.g., about 60°, about 90°, about 120°, about 180°, about 210°, about 240°, about 270°, about 300°, 360°, ranges between such values, etc.). If the portion 2200 is rotatable to find a target nerve, the circumferential coverage may optionally be at the lower end of the range. As described with respect to FIG. 22E, at least some of the splines 2210 may comprise electrodes. Others of the splines 2210 may be free of electrodes or include electrodes that are not used, but may act as apposition arms (e.g., in cases when the splines 2210 are not pushed to a side of a vessel due to rigidity and a natural course of a navigation path), which can help push the electrodes against or close to the tissue.

Figure 22E:
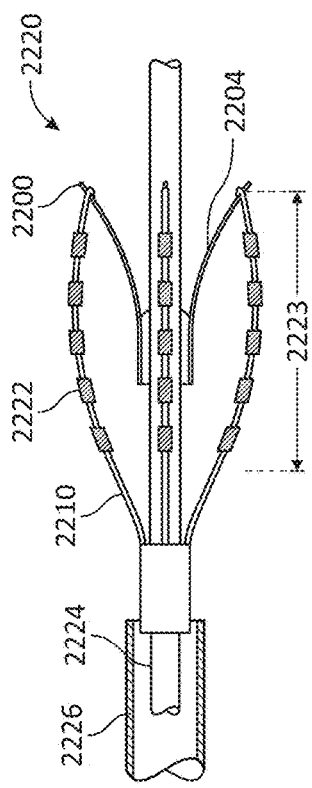
FIGS. 22E-22G are side partial cross-sectional views of an example of a catheter including the portion of FIG. 22A.
Figure 22F:
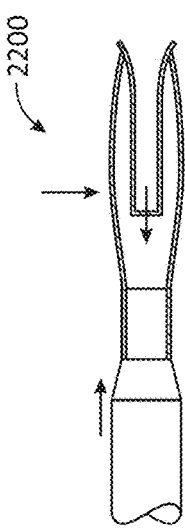
Figure 22G:
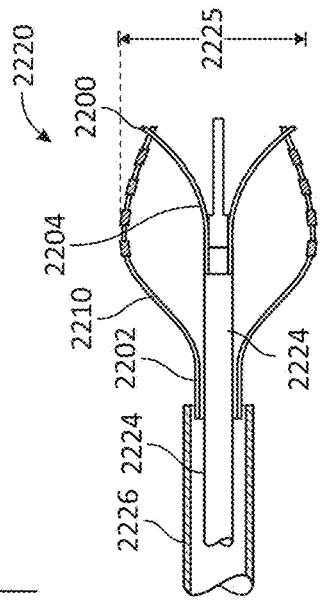

FIGS. 22E-22G are side partial cross-sectional views of an example of a catheter 2220 including the portion 2200 of FIG. 22A. The splines 2210 comprise electrodes 2222, for example on an exterior surface, annularly around, in U-shaped channels (e.g., as described herein), as part of a mesh covering (e.g., as described with respect to FIG. 4C), etc. In some embodiments, the length 2223 of the parts of the splines 2210 comprising electrodes is between about 20 mm and about 40 mm (e.g., about 20 mm, about 25 mm, about 30 mm, about 35 mm, about 40 mm, ranges between such values, etc.). The first cut hypotube 2202 is coupled to a cannula or sheath 2226. The first cut hypotube 2202 may be coupled in a lumen of the cannula 2226 (e.g., as shown in FIGS. 22E and 22G), on an outside of the cannula 2226, end-to-end, by tethers, etc. The cannula 2226 may have a diameter between about 7 Fr and about 11 Fr (e.g., about 7 Fr, about 8 Fr, about 9 Fr, about 10 Fr, about 11 Fr, ranges between such values, etc.). The second cut hypotube 2204 is coupled to an inner member 2224. The second cut hypotube 2204 may be coupled in a lumen of the inner member 2224 (e.g., as shown in FIG. 22G), on an outside of the inner member 2224, end-to-end, by tethers, etc. FIG. 22G shows the first cut hypotube 2202 in cross-section to show the coupling between the second cut hypotube 2204 and the inner member 2224. Relative movement between the inner member 2224 (and thus the second cut hypotube 2204) and the cannula 2226 (and thus the first cut hypotube 2202) can cause the splines 2210 to flex radially (e.g., proximal retraction of the cannula 2226 and/or distal advancement of the inner member 2224 can cause the splines 2210 to flex radially outward, proximal retraction of the inner member 2210 and/or distal advancement of the cannula 2226 can cause the splines 2210 to flex radially inward), as shown in FIG. 22F. Since the splines 2214 can push the splines 2210 radially outward, the splines 2210 can be free of a taper, which can reduce the profile and length of the catheter 2220 and the throw distance. In some embodiments, the diameter 2225 of the splines 2210 in the expanded state is between about 15 mm and about 35 mm (e.g., about 15 mm, about 20 mm, about 25 mm, about 30 mm, about 35 mm, ranges between such values, etc.).

A potential advantage of a catheter 2220 in which the splines 2210 are in a collapsed position (FIG. 22F) is that in the event of a failure (e.g., proximal breakage), the splines 2210 collapse inwardly instead of expanding. That is, the collapsed state is the default state, which may be safer than an expanded state being a default state, for example when the catheter 2220 passes by valves, chordae tendinae, etc. A potential advantage of not using shape memory material, which is possible when expansion is due to longitudinal movement, is reduced costs.

In some embodiments, the splines 2210 may be self-expanding, for example able to expand upon removal of a force from the inner member 2224. Reduced length can be useful when a target vessel is short, for example a pulmonary artery. Relative movement may be manual or, for example as described herein, spring assisted.

In some embodiments, the catheter 2220 may comprise a fixation system separate from the portion 2200. For example, the fixation system may extend through the lumen of the second cut hypotube 2204. The fixation system may be axially and rotationally movable relative to the portion 2200, which can be useful to provide appropriate fixation and nerve targeting. Once a user is satisfied with the positions of the portion 2200 and the fixation system, the portion 2200 and the fixation system may be coupled (e.g., at a handle outside the subject). Even once coupled, the portion 2200 and the fixation system may be able to rotate (e.g., ±20°) and/or move longitudinally, (e.g., ±1 cm, ±2 cm) relative to each other. The portion 2200 may be moved to improve nerve targeting even while the fixation mechanism does not move, which can reduce tissue disturbance. In some embodiments, distal ends of the splines 2214 may provide alternate or additional fixation.

In some embodiments, the splines 2210, the splines 2204, or another part of the portion 2200 or the catheter 2220 comprises a sensor (e.g., a pressure sensor, a contractility sensor, etc.).

In some embodiments, rotation of a proximal handle may impart longitudinal movement and/or rotational movement that is not 1:1 at the distal end of the catheter 2220, for example due to catheter shape, bending, or other factors.

FIGS. 22H-22L are side elevational and partial cross-sectional views of examples of catheter deployment systems 2230, 2240. In FIGS. 22H-22J, the proximal end or handle of the catheter deployment systems are illustrated. In FIGS. 22K and 22L, the proximal end or handle of the catheter deployment systems are illustrated. The catheter deployment systems 2230, 2240 may be used, for example, with the catheter 2220.

The system 2230 comprises a spring 2232. The spring abuts a gripper 2234, which is coupled to the inner member 2224. The spring 2232 has a negative spring constant (restoring force is inwards), but a spring having a positive spring constant (restoring force outwards) is also possible by rearrangement of other features. To expand the splines 2210, a handle element 2236 such as a knob is pushed distally relative to the cannula 2226, against the force of the spring 2232. The system 2230 may comprise a locking mechanism 2238 configured to hold the handle element 2236 in a distal position. In the system 2230, in the event of a break in the system 2230 (e.g., failure of the locking mechanism 2238), the spring 2232 retracts the inner element 2224, collapsing the splines 2210, which can allow for easy recovery of the catheter 2220. The spring 2232 may provide a range of deployment options compared to a solely manual structure, for example due to forces provided by the spring 2232.

FIG. 22I shows an example of the locking mechanism 2238 comprising a plurality of arms that can resiliently hold the handle element 2236 in a distal position. The arms may be open at a proximal end, and the handle element 2236 (e.g., the entire handle element 2236) may be captured in the arms. When the splines 2210 are to be collapsed, the arms may be opened, allowing the spring 2232 to force the handle element 2236 proximally, retracting the inner element 2224 and collapsing the splines 2210.

FIG. 22J shows another example of the locking mechanism 2238 comprising a plurality of arms that can resiliently hold the handle element 2236 in a distal position. The arms may be closed at a proximal end. The arms may be biased radially outward to promote radial expansion. The arms may act as secondary leaf springs. In some embodiments, the handle element 2236 and the closed proximal end of the locking mechanism 2238 comprise Velcro®, magnets, threads, or other features to hold the handle element 2236 in a distal position. When the splines 2210 are to be collapsed, the handle element 2236 may be disengaged, allowing the spring 2232 (and the arms) to force the handle element 2236 proximally, retracting the inner element 2224 and collapsing the splines 2210. In some embodiments, compressing the arms can cause the handle element 2236 to be disengaged.

The system 2240 comprises a spring 2242. The spring abuts a gripper 2244, which is coupled to the inner member 2224. The spring 2242 has a positive spring constant (restoring force is inwards), but a spring having a positive spring constant (restoring force outwards) is also possible by rearrangement of other features.

In FIG. 22K, to expand the splines 2210, a handle element coupled to the inner member 2224 is pulled proximally relative to the cannula 2226, against the force of the spring 2242. The pulling element 2246 is coupled to the inner member 2224. The pulling element 2246 is coupled to splines 2247 (e.g., similar to the splines 2214 but opposite in orientation such that the splines 2247 extend distally in a collapsed state). As the pulling element 2246 is pulled proximally, the splines 2247 expand radially outward, pushing the splines 2210 radially outward to an expanded state.

In FIG. 22L, the splines 2210 have a slightly tapered shapes so that a pulling element 2246 can rest between the splines 2210 in a collapsed state and interact with the splines 2210 during retraction. To expand the splines 2210, a handle element coupled to the inner member 2224 is pulled proximally relative to the cannula 2226, against the force of the spring 2242. The pulling element 2246 is coupled to the inner member 2224. As the pulling element 2246 is pulled proximally, the proximal end of the pulling element 2246 bears against the inside surfaces of the splines 2210, pushing the splines 2210 radially outward to an expanded state.

In the system 2240 of FIGS. 22K and 22L, in the event of a break in the system 2240, the spring 2242 advances the inner element 2224, collapsing the splines 2210, which can allow for easy recovery of the catheter 2220. The spring 2242 may provide a range of deployment options compared to a solely manual structure, for example due to forces provided by the spring 2242.

Figure 22M:
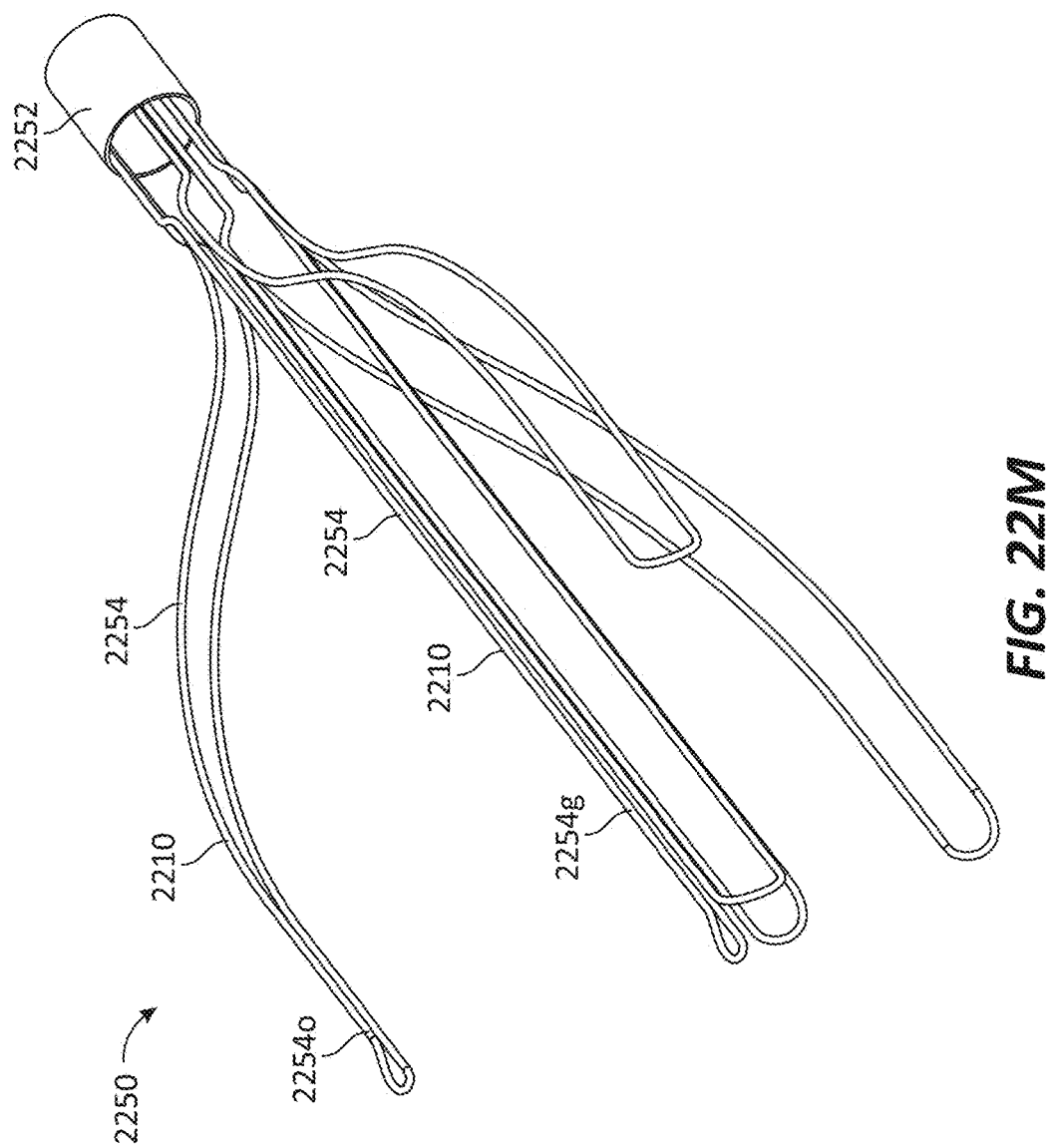
FIG. 22M illustrates an example part of the portion of FIG. 22A.

FIG. 22M illustrates an example part 2250 of the portion 2200 of FIG. 22A. Rather than a first cut hypotube 2202, the part 2250 comprises a hypotube 2252 coupled to a plurality of wires 2254 shaped into splines 2210. The orange wires 2254o show the shapes of the splines 2210 in an open or expanded state, and the grey wires 2254g show the shapes of the splines 2210 in a closed or collapsed state. As with the splines 2210 of the first cut hypotube 2202, the wires 2254 may comprise shape memory material (e.g., nitinol) and/or may be moved to an expanded position by a second cut hypotube 2204 or similar device. Referring to FIGS. 22E and 4C, the part 2250 may comprise electrodes on the wires 2254, on a mesh attached to the wires 2254, combinations thereof, and the like.

FIG. 23A is a perspective view of an example segment 2300 of a strut. The segment 2300 generally has a U-shape. The segment 2300 comprises walls 2302 at least partially defining a channel or trough 2304. The walls 2302 and trough 2304 may be formed in a variety of ways. In some embodiments, a wire may be extruded in the U-shape. In some embodiments, a hypotube may be cut to form generally rectangular struts, and the trough 204 may be formed by removing material from the struts (e.g., by milling). In some embodiments, sides of a flat wire may be bent upwards. In some embodiments, the U-shape may comprise plastic (e.g., extruded, molded, etc.). The trough 2304 may be lined with insulative material. In some embodiments, the insulative material comprises epoxy. In some embodiments, a trough 2304 lined with insulative material can help to make electrodes directional, which can help to aim energy at a vessel wall and at a nerve. A plurality of wires or leads or conductors 2306 may lie in the trough 2304. Positioning the wires 2306 in the trough 2304 can aid in manufacturing (positioning of the wires 2306), may reduce the risk that the conductors may cross-talk, and/or may protect the wires 2306 from breaking. The wires 2306 are electrically connected to electrodes, transducers, and the like that can be used to provide neuromodulation. FIGS. 23B-23F show examples of configurations that may be used to position wires 2306, insulator, and an electrode 2308 at least partially in a U-shaped segment of a strut. In some embodiments, a U-shaped segment may be coupled to a strut (e.g., adhered, welded, soldered, interference fit, etc.).

The trough 2304 may have a depth 2370 between about 0.003 inches and about 0.02 inches (e.g., about 0.003 inches, about 0.005 inches, about 0.01 inches, about 0.015 inches, about 0.02 inches, ranges between such values, and the like). The trough 2306 may have a width 2372 between about 0.15 inches and about 0.1 inches (e.g., about 0.015 inches, about 0.02 inches, about 0.025 inches, about 0.05 inches, about 0.06 inches, about 0.08 inches, about 0.1 inches, ranges between such values, and the like).

FIG. 23B is a transverse cross-sectional view of an example of a strut 2320. The strut 2320 includes walls 2302 at least partially defining a trough. In some embodiments, the walls 2302 form a depth 2370 configured to at least partially laterally cover an electrode 2308. A plurality of wires 2306 lies in the trough. The wires 2306 are covered by an insulating sheet or insert 2310. Each of the wires 2306 may be coated with insulative material and/or the insulating sheet 2310 may provide insulation for the wires 2306. Insulation at welds and at junctions between wires 2306 and electrodes 2308 can inhibit or prevent damage from body fluids and corrosion. An electrode 2308 is electrically connected to one of the wires 2306 through the insulating sheet 2310. The electrode 2308 illustrated in FIG. 23B has a rectangular cross-section. FIG. 23C illustrates a transverse cross-sectional view of an example of a strut 2325 in which the electrode 2308 has a rounded cross-section (e.g., shaped as a dome), which can help to reduce edge effects and hot spots due to sharp edges. In some embodiments in which the electrode 2308 includes sharp edges, insulating material can at least partially cover the sharp edges, which can help reduce edge effects. The electrode 2308 may be sunk in a well of insulative material such that only a top surface is exposed, which can help the electrode 2308 to be directional. The electrode 2308, as with all electrodes described herein, may lack sharp edges and/or lack sharp edges that are not covered with insulative material.

Figure 23G:
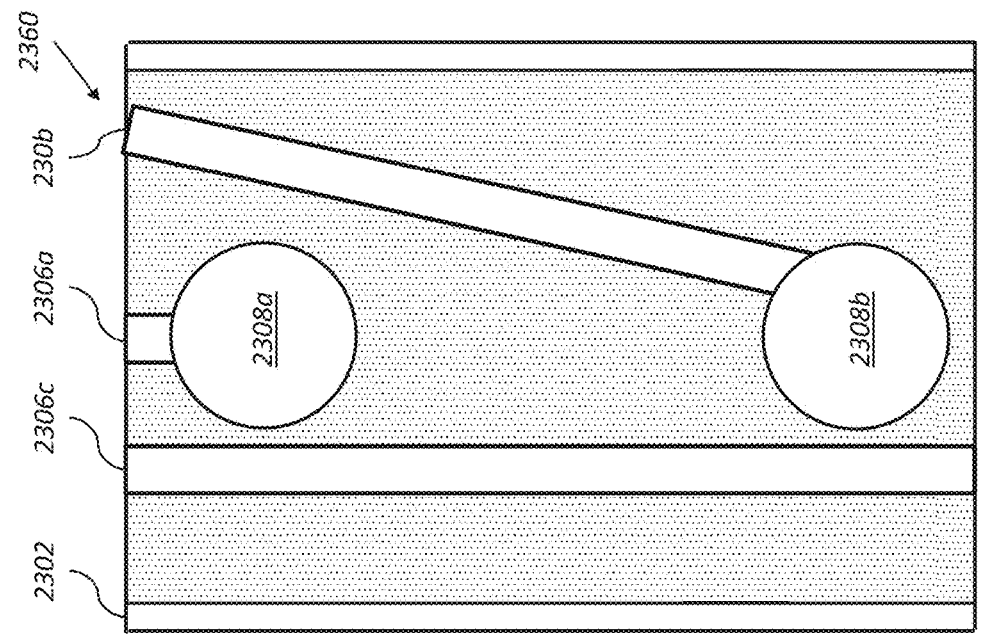
FIG. 23G is a top partial cross-sectional view of an example segment of a strut.
Figure 23D:
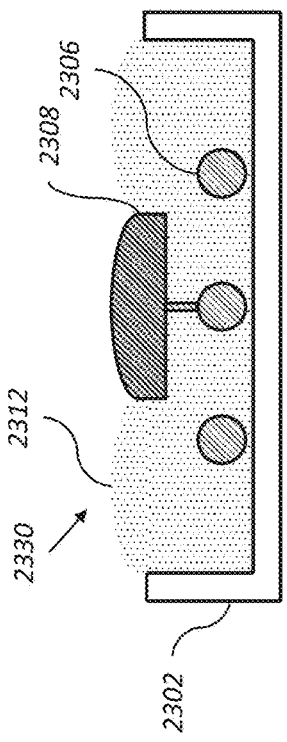
FIG. 23D is a transverse cross-sectional view of another example of a strut.

FIG. 23D is a cross-sectional view of another example of a strut 2330. The strut 2330 includes walls 2302 at least partially defining a trough. A plurality of wires 2306 lies in the trough. The wires 2306 are covered by an insulating layer 2312. The insulating layer 2312 may comprise, for example, silicone or any suitable insulating, flexible material. Each of the wires 2306 may be coated with insulative material and/or the insulating layer 2312 may provide insulation for the wires 2306. An electrode 2308 is electrically connected to one of the wires 2306 through the insulating layer 2312. The electrode 2308 may be the same height as the insulating layer 2312. The insulating layer 2312 may include dome shapes.

Figure 23E:
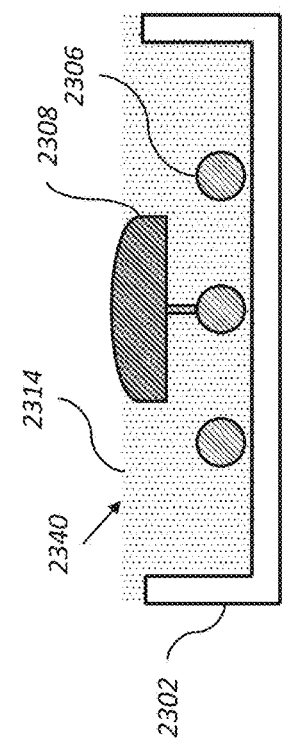
FIG. 23E is a transverse cross-sectional view of yet another example of a strut.

FIG. 23E is a transverse cross-sectional view of yet another example of a strut 2340. The strut 2340 includes walls 2302 at least partially defining a trough. A plurality of wires 2306 lies in the trough. The wires 2306 are covered by an insulating layer 2314. The insulating layer 2314 may comprise, for example, silicone or any suitable insulating, flexible material. Each of the wires 2306 may be coated with insulative material and/or the insulating layer 2314 may provide insulation for the wires 2306. An electrode 2308 is electrically connected to one of the wires 2306 through the insulating layer 2314. The electrode 2308 may be the same height as the insulating layer 2314. The insulating layer 2312 may include a generally flat or planar upper surface.

Figure 23F:
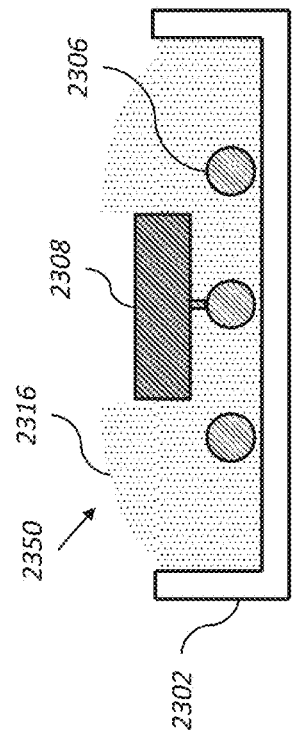
FIG. 23F is a transverse cross-sectional view of still another example of a strut.

FIG. 23F is a transverse cross-sectional view of still another example of a strut 2350. The strut 2350 includes walls 2302 at least partially defining a trough. A plurality of wires 2306 lies in the trough. The wires 2306 are covered by an insulating layer 2316. The insulating layer 2316 may comprise, for example, silicone or any suitable insulating, flexible material. Each of the wires 2306 may be coated with insulative material and/or the insulating layer 2316 may provide insulation for the wires 2306. An electrode 2308 is electrically connected to one of the wires 2306 through the insulating layer 2316. The insulating layer 2316 may include a generally crowned surface. The electrode 2308 may be the sunken into the insulating layer 2316, which can help to reduce edge effects. Reducing edge effects can increase uniformity of an electric field emanating from the electrode 2308. An electrode 2308 that is below an upper surface of the insulating layer 2316 may be spaced from tissue, which can allow blood flow across the electrode 2308.

The insulating layer 2312, 2314, 2316 may maintain positions of the wires 2306 in the U-shaped trough, for example inhibiting tangling and/or maintaining a spatial separation. The insulating layer 2312, 2314, 2316 may protect the wires 2306, for example from body fluids and external forces.

The insulating layer 2312, 2314, 2316 may be deposited over the wires 2306 in the trough. The insulating layer 2312, 2314, 2316 may be cured and then ablated (e.g., laser ablated, milled) to allow the positioning of the electrode 2308 and a connector thereto. In some embodiments, a plug (e.g., comprising a material that doesn't stick to the material of the insulating layer 2312, 2314, 2316, such as PTFE) may be positioned in the insulating layer 2312, 2314, 2316 and then removed after curing to allow the positioning of the electrode 2308 and a connector thereto.

FIG. 23G is a top partial cross-sectional view of an example segment 2360 of a strut. As illustrated, the wires 2306 are spatially separated. In embodiments in which the wires 2306 are not individually insulated, the insulating material can inhibit or prevent electrical communication between the wires 2306. A first wire 2306a is connected to a first electrode 2308a. A second wire 2306b is connected to a second electrode 2308b. A third wire 2306c is connected to a third electrode (not shown).

FIG. 23H illustrates an example of a strut system 2380 comprising a plurality of struts or splines 2382 each having a generally U-shaped trough. The U-shaped troughs can help to align or maintain the spacing or separation distance between the struts 2382. FIG. 23I shows an example in which a distance b between a first strut 2382a and a second strut 2382b is less than a distance a between a third strut 2382c and the second strut 2382b. FIG. 23J shows an example in which a distance 2374 between a first strut 2382a and a second strut 2382b is substantially the same as a distance a between a third strut 2382c and the second strut 2382b. In some embodiments, the distance b or 2374 between struts or strut-to-strut spacing may be between about 10 mm and about 15 mm (e.g., about 10 mm, about 11 mm, about 12 mm, about 13 mm, about 14 mm, about 15 mm, ranges between such values, etc.). With the U-shape, the splines 2382 may flex less in a radial configuration than a round-wire spline system, which can help to keep spacing between the splines more consistent, whether the spacing is meant to be consistent or varying. The U-shape may reduce the likelihood that the splines 2382 slide relative to each other and that the electrodes 2308 in each of the splines 2382 slide relative to each other, which can maintain spacing of the electrodes.

FIG. 23K illustrates an example of an electrode on wire system 2390. The system 2390 comprises a wire 2392 and an electrode 2394 over (e.g., radially outward of, annularly or arcuately around) the wire 2392. The wire 2392 may comprise a shape memory material (e.g., nitinol). The electrode 2394 may comprise, for example, a platinum-iridium electrode. Other materials for the wire 2392 and the electrode 2394 are also possible. The system 2390 may comprise an insulator 2396 between the wire 2392 and the electrode 2394. The electrode 2394 may be electrically coupled to a conductor wire 2398. In some embodiments, a single wire 2392 may comprise a plurality of electrodes 2394, for example forming an array.

FIG. 23L is a cross-sectional view of an electrode 2308 spaced from a vessel wall 2397. The blood vessel is spaced from a nerve 2399. The electrode 2308 may be positioned as close to the vessel wall 2397 as possible so that the electrode 2308 is as close to the nerve 2399 as possible. In some embodiments, the electrode 2308 may be intentionally spaced from the vessel wall 2397 a distance d, which can allow blood to flow both under and over the electrode 2308, for example as shown by the thick arrows. In some embodiments, the distance d is between about 0.1 mm and about 1 mm (e.g., about 0.1 mm, about 0.2 mm, about 0.3 mm, about 0.5 mm, about 0.7 mm, about 0.9 mm, about 1 mm, ranges between such values, etc.). Referring again to FIG. 23F, the insulating material 2316, for example, may act as a spacer. Allowing blood to flow over the electrode 2308 may inhibit corrosion of the electrode 2308. Allowing blood to flow over the electrode 2308 may allow blood to contact the vessel wall 2397 in the area of the electrode 2308 such that cells may be replenished. In some embodiments, the electrode may comprise longitudinal channels, a bumpy surface, etc. to allow blood to flow radially outward of the electrode 2308 but to still be closer to the nerve 2399. In certain such embodiments, surface area of the electrode 2308 may be advantageously increased.

FIGS. 23Ni-23Nix illustrate an example method of manufacturing components on a substrate 2301. The substrate 2301 may comprise, for example, a shape-memory alloy such as nitinol forming a spline of an electrode system. Flex-circuit processing can be used to pattern electrodes, conductors, insulators, and other components (e.g., resistors) on a spline. In FIG. 23Ni, an insulating layer 2303 comprising insulative material (e.g., oxide, polyimide) is deposited over the substrate 2301. If the substrate 2301 is insulating, the layer 2303 may be omitted. As used with respect to FIG. 23Ni-23Nix, the term "over" could mean on or directly on as viewed from a certain orientation, and is not intended to limit intervening layers, and the term "layer" could mean a plurality of layers (e.g., including adhesive layers). In FIG. 23Nii, a conductive layer 2305 comprising conductive material (e.g., aluminum, copper, doped silicon) is deposited over the insulating layer 2303. In FIG. 23Niii, the conductive layer 2305 is patterned into conductor wires 2306 (e.g., using photolithography, lift-off lithography, etc.). In some embodiments, the conductor wires 2306 may be formed directly (e.g., using screen printing, inkjet printing). In FIG. 23Niv, an insulating layer 2307 insulative material (e.g., oxide, polyimide) is deposited over the conductor wires 2306 and the insulating layer 2303. The insulative material of the insulating layers 2303, 2307 may be the same or different. In FIG. 23Nv, a via 2311 is formed (e.g., via etching, milling) in the insulating layer 2307, exposing a portion of the middle conductor wire 2306. In FIG. 23Nvi, a conductive layer 2309 comprising conductive material (e.g., aluminum, copper, doped silicon) is formed over the insulating layer 2307 and filling the via 2311. The conductive material of the conductive layers 2305, 2309 may be the same or different. In FIG. 23Nvii, the conductive layer 2309 is patterned into electrodes 2308. Wet etching, for example, may help to form a domed shape of the electrode 2308. Although not illustrated, vias 2311 may be formed to connect each conductor wire 2306 to a different electrode 2308. In FIG. 23Nviii, an insulating layer 2313 (e.g., comprising oxide, polyimide) is formed over the electrode 2308 and the insulating layer 2307. The insulative material of the insulating layers 2303, 2307, 2313 may be the same or different. In FIG. 23Nix, the insulating layer 2313 has been patterned to reveal the electrode 2308 and to form an insulating layer 2316 including a generally crowned surface. The electrode 2308 being sunken into the insulating layer 2316 can help to reduce edge effects, which can increase uniformity of an electric field emanating from the electrode 2308. The electrode 2308 can also be spaced from tissue by an upper surface of the insulating layer 2316, which can allow blood flow across the electrode 2308. In some embodiments, the insulating layer 2316 may be omitted. In some embodiments, a dual damascene structure can be formed in the insulating layer 2307 and the electrode 2308 can be formed in the insulating layer 2307, which can be shaped to have a crowned surface. A wide variety of layers, patterns, and processes can be used to form the described components and other components. For example, a resistor layer may be patterned proximate to the substrate 2301, which can provide localized heating, which can cause a shape-memory substrate to locally deform to an austenitic state.

Although not meant to be limiting, the following electrode dimensions may be adequate to generate a hemodynamic response due to neurostimulation. About half of the electrodes can be assumed to contact the vessel and about half of the electrodes can be assumed to be exposed to low impedance blood flow. Referring again to the elevational view of FIG. 23G as an example, the length of an electrode 2806 may be between about 1 mm and about 3 mm (e.g., about 1 mm, about 1.5 mm, about 2 mm, about 2.5 mm, about 2 mm, ranges between such values, etc.); the width of an electrode 2806 may be between about 1 mm and about 4 mm (e.g., about 1 mm, about 2 mm, about 3 mm, about 4 mm, ranges between such values, etc.); and the spacing between electrodes 2806 may be between about 2 mm and about 8 mm (e.g., about 2 mm, about 3 mm, about 4 mm, about 5 mm, about 6 mm, about 7 mm, about 8 mm, ranges between such values, etc.). The spacing between electrodes may refer to the distance between a distal end of a proximal electrode and the proximal end of a distal electrode, the distance between the center of one electrode and the center of another electrode, and/or the distance between circumferentially or laterally spaced electrodes. The electrode 2308 may be configured to maintain a charge density at an electrochemically stable level less than about 400 μC/cm² for Pt/Ir[1,2,3]. Referring again to FIG. 23G as an example of an annular electrode, the electrodes 2394 may have a diameter of about 7 Fr (approx. 2.3 mm), have a length of about 1.5 mm, and be spaced by about 8 mm. In some embodiments, the electrodes 2394 may have a length between about 1 mm and about 3 mm (e.g., about 1 mm, about 1.5 mm, about 2 mm, about 2.5 mm, about 2 mm, ranges between such values, etc.), a diameter between about 0.5 mm and about 1.5 mm (e.g., about 0.5 mm, about 0.75 mm, about 1 mm, about 1.25 mm, about 1.5 mm, ranges between such values, etc.), and spacing between about 1 mm and about 3 mm (e.g., about 1 mm, about 1.5 mm, about 2 mm, about 2.5 mm, about 2 mm, ranges between such values, etc.).

The target nerve may be a very small target to capture via neurostimulation. Electrodes, most likely the cathode, may need to be very close to the nerve, if not by depth than by lateral positioning. One option to provide close lateral positioning is to have an effectively infinite number of electrodes, or at least an electrode matrix that can cover all possible areas of the nerve with respect to the target vessel. Another option to provide close lateral positioning is to provide repositionable electrodes, for example electrodes in a matrix that can be extended, retracted, and/or rotated.

Figure 23M:
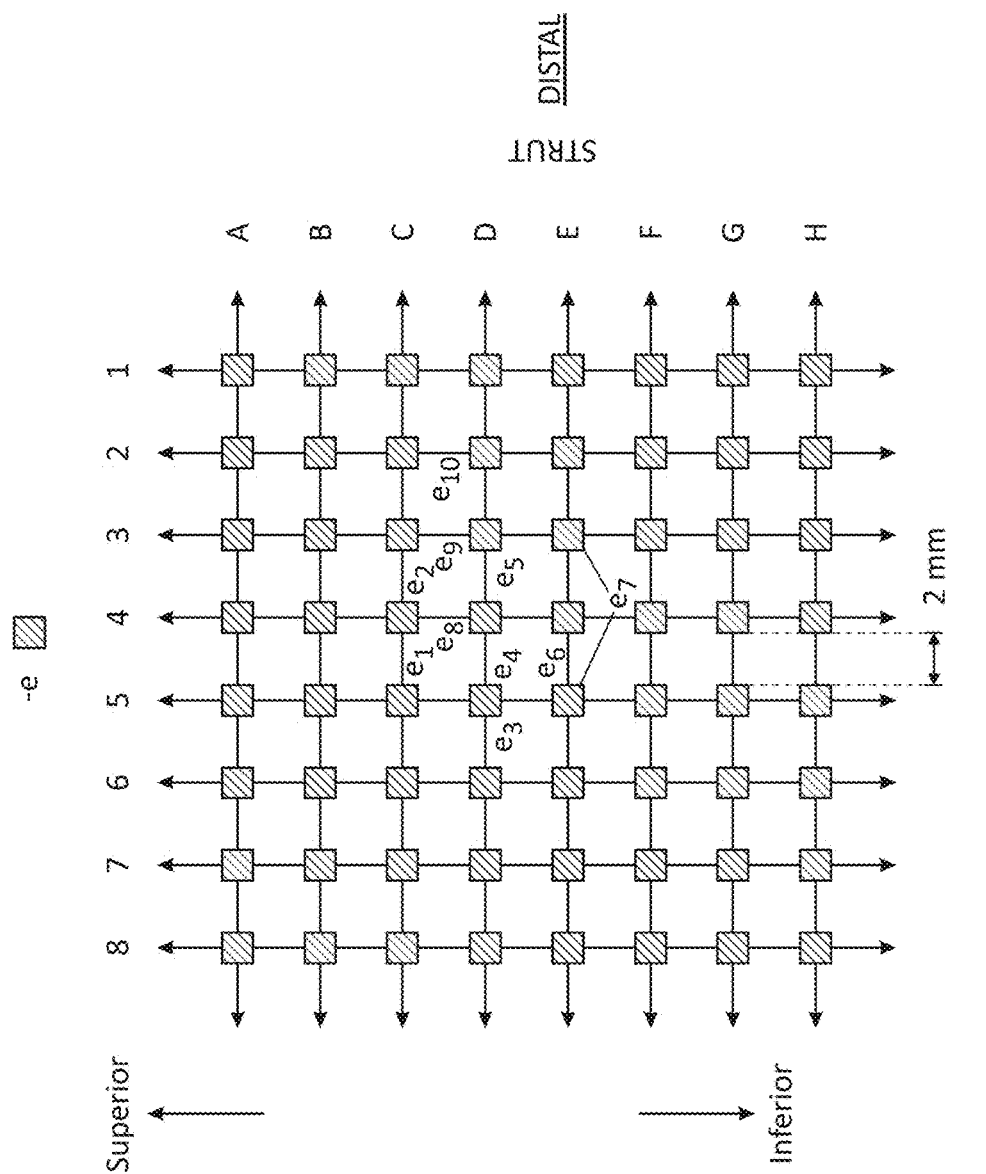
FIG. 23M shows an example electrode matrix.

FIG. 23M shows an example electrode matrix. The electrodes are spaced edge-to-edge by about 2 mm proximal-distal and superior-inferior. The initial target area estimate may be as large as 15 mm superior-inferior and 19 mm laterally. In some embodiments, for example as illustrated in FIG. 23M, an electrode matrix has these dimensions, which may effectively behave as an infinite number of electrodes in view of the size of the target area. In some embodiments, an electrode matrix may have smaller dimensions and may be rotated and/or longitudinally moved. Although illustrated in two dimensions in FIG. 23N, in some embodiments, the electrode matrix may take a three-dimensional shape (e.g., conforming to an inside wall of a blood vessel). In certain such embodiments, the electrode matrix may cover between about 15° and about 360° of the circumference of the vessel wall (e.g., about 15°, about 30°, about 45°, about 60°, about 75°, about 90°, about 105°, about 120°, about 180°, about 210°, about 270°, about 300°, about 360°, ranges between such values, etc.). The e values indicate the percent above baseline hemodynamic response. The value of $e_1$ between electrodes C5 and C4 was 3.0%. The value of $e_2$ between electrodes C4 and C3 was 12.1%. The value of $e_3$ between electrodes D6 and D5 was 18.5%. The value of $e_4$ between electrodes D5 and D4 was 40.2%. The value of $e_5$ between electrodes D4 and D3 was 23.7%. The value of $e_6$ between electrodes E5 and E4 was 0%. The value of $e_7$ between electrodes E5 and E3 was 0.3%. The value of $e_8$ between electrodes C4 and D4 was 28.9%. The value of $e_9$ between electrodes C3 and D3 was 21.3%. The value of $e_{10}$ between electrodes C2 and D2 was 7.1%.

Hemodynamic response decreases by approximately half as the excitation is moved from one pair of electrodes to the adjacent space pair. When center-to-center spacing is 3.5 mm, this would suggest that once an optimum target has been determined, a movement of the electrode matrix on the order of 3.5 mm would significantly decrease the hemodynamic response. Certain fixation systems described herein can limit electrode movement to less than an order of magnitude of this variation (e.g., about 0.035 mm total electrode migration), over the therapy application period. In some embodiments, a fixation system can inhibit electrode migration to be less than about 1 mm, less than about 0.5 mm, less than about 0.25 mm, less than about 0.1 mm, less than about 0.075 mm, less than about 0.05 mm, less than about 0.035 mm, less than about 0.025 mm, or less than about 0.015 mm, with the lower limit of such "less than" ranges being 0 mm.

In some embodiments, an electrode matrix (e.g., including a portion of an electrode utilized for calibration stimulation and/or therapeutic stimulation) may have an area between about 10 mm$^2$ and about 15 mm$^2$ (e.g., about 10 mm$^2$, about 11 mm$^2$, about 12 mm$^2$, about 13 mm$^2$, about 14 mm$^2$, about 15 mm$^2$, ranges between such values, etc.). In some embodiments, an electrode matrix may have an area between about 10 mm$^2$ and about 300 mm$^2$ (e.g., about 10 mm$^2$, about 50 mm$^2$, about 100 mm$^2$, about 150 mm$^2$, about 200 mm$^2$, about 250 mm$^2$, about 300 mm$^2$, ranges between such values, etc.).

FIG. 24A illustrates an example of a fixation system 2400. The fixation system 2400 comprises a fixation structure 2402 and fixation mechanisms 2404. The fixation structure 2402 may comprise, for example, a hypotube that has been cut and shape set into a plurality of arms, wires that have been shape set into a plurality of arms, and the like. The arms may be the same or different (e.g., as illustrated in FIG. 24A, one arm may flex upward). The fixation mechanisms 2404 may comprise, for example, points or barbs pointing radially outward from the fixation structure 2402. The fixation mechanisms 2404 may be integral with the fixation structure 2402 or coupled to the fixation structure 2402.

FIGS. 24B and 24C illustrate the fixation system 2400 of FIG. 24A interacting with a catheter 2406. As the fixation structure 2402 and the catheter 2406 are moved longitudinally to each other (e.g., retracting the fixation structure 2402 and/or advancing the catheter 2406), the arms of the fixation structure 2402 move radially inward. The fixation mechanisms 2402 may injure tissue during this interaction. The fixation mechanisms 2402 may catch on the catheter 2406 (e.g., starting at the end of the catheter 2406) and may dig into the catheter 2406 to form trenches 2408, which may release catheter residue, use more longitudinal interaction force, etc. In some embodiments, the catheter 2406 may include grooves or channels configured to accommodate the fixation mechanisms, although radial outward force provided by the fixation structure 2402 may still tissue injury and/or trenches 2408.

Figure 25D:
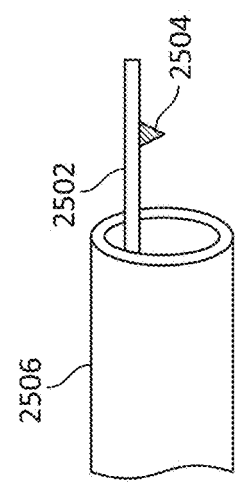
FIGS. 25D and 25E illustrate the fixation system of FIG. 25A interacting with a catheter.
Figure 25E:
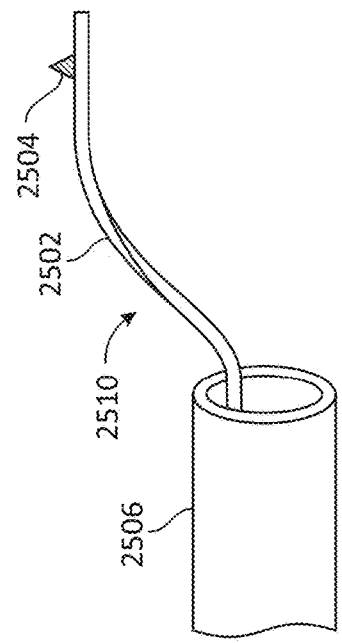
Figure 25A:
FIG. 25A is a perspective view of another example of a fixation system.
Figure 25B:
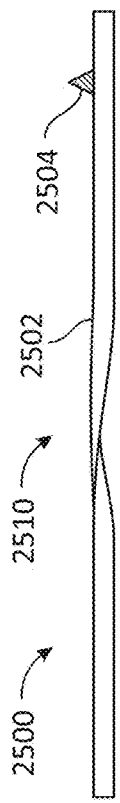
FIG. 25B is a side elevational view of the fixation system of FIG. 25A.
Figure 25C:
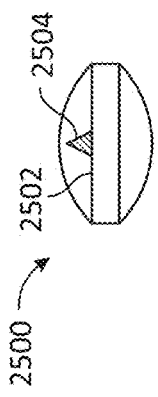
FIG. 25C is an end view of the fixation system of FIG. 25A.

FIG. 25A is a perspective view of another example of a fixation system 2500. FIG. 25B is a side elevational view of the fixation system 2500 of FIG. 25A. FIG. 25C is an end view of the fixation system 2500 of FIG. 25A. The fixation system 2500 comprises a fixation structure 2502 and a fixation mechanism 2504. The fixation structure 2502 may comprise, for example, a hypotube that has been cut and shape set, a ribbon that has been shape set, and the like. The fixation mechanisms 2504 may comprise, for example, points or barbs pointing radially outwardly in a deployed position or state and pointing radially inwardly in a constrained position or state due to the fixation structure 2502 comprising a rotation or twist 2510. The rotation 2510 may be between about 60° and about 300° (e.g., about 60°, about 90°, about 120°, about 150°, about 180° (e.g., as illustrated in FIGS. 25A-25C), about 210°, about 240°, about 270°, about 300°, ranges between such values, and the like). In some embodiments, the fixation structure 2502 comprises a shape memory material and the rotation 2510 is imparted as at least part of a shape set. The fixation mechanism 2504 may be integral with the fixation structure 2502 or coupled to the fixation structure 2502.

FIGS. 25D and 25E illustrate the fixation system 2500 of FIG. 25A interacting with a catheter 2506. As the fixation system 2500 is moved longitudinally relative to the catheter 2506, the fixation structure 2502 rotates relative to the longitudinal axis. The fixation mechanism 2502, which faces radially inward in the catheter 2506, rotates to face radially outward upon extension out of the catheter 2506. Conversely, the fixation mechanism 2502, which faces radially outward out of the catheter 2506, rotates to face radially inward upon retraction into the catheter 2506. The fixation structure 2502 may be radially outwardly biased to push against the lumen of the catheter 2506.

Figure 25F:
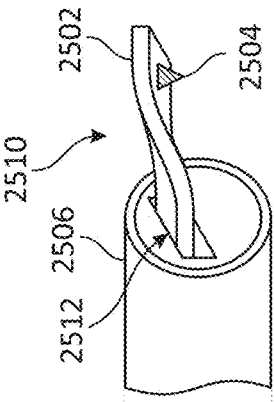
FIG. 25F illustrates an example of a catheter comprising a shaped lumen.

FIG. 25F illustrates an example of a catheter 2506 comprising a lumen 2512 having a shape configured to accommodate the fixation structure 2502 and the fixation mechanism 2504. The lumen 2512 may, for example, comprise a pentagon configured to interact with three sides of a rectangular fixation structure 2502 and a pointed fixation mechanism 2504 extending from the other side of the fixation structure 2502. Other shapes of the lumen 2512 are also possible. For example, referring again to FIG. 25C, the lumen 2512 may comprise a generally arcuate shape configured to interact with two sides of a rectangular fixation structure 2502.

Figure 25G:
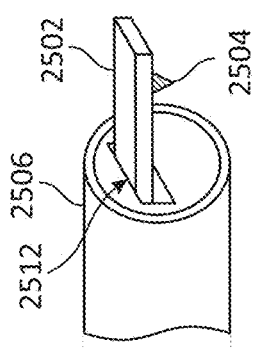
FIGS. 25G-25J illustrate an example deployment out of the lumen of the catheter of FIG. 25F.
Figure 25H:
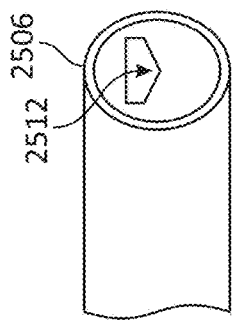
Figure 25I:
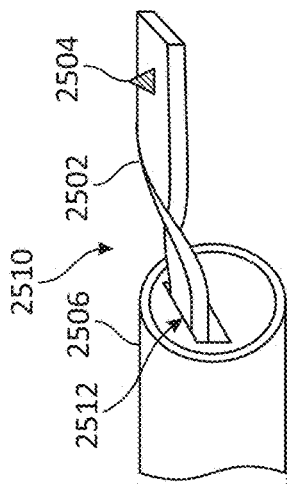
Figure 25J:
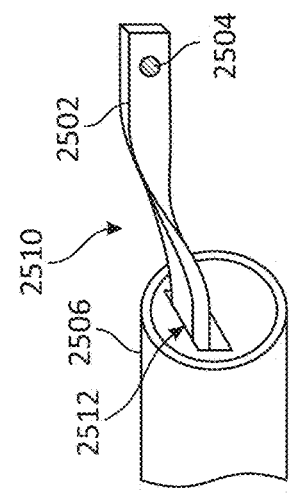

FIGS. 25G-25J illustrate an example deployment of the fixation structure 2502 and the fixation mechanism 2504 out of the lumen 2512 of the catheter 2506 of FIG. 25F. As shown in FIG. 25G, as the fixation structure 2502 and fixation mechanism 2504 is initially deployed out of the lumen 2512 of the catheter 2510, with the twist 2510 still in the lumen 2512, the fixation mechanism 2504 faces radially inwardly. As shown in FIG. 25H, when the twist 2510 is out of the lumen 2512, the fixation mechanism 2504 can start to turn radially outward. FIG. 25I shows the fixation mechanism 2504 continuing to turn radially outward as the twist 2510 is further from the lumen 2512, which allows the shape of the fixation structure 2502 to rotate. FIG. 25J shows the fixation mechanism 2504 facing radially outward or standing proud. In some embodiments, the fixation structure 2502 and fixation mechanism 2504 may be deployed out of an end of the catheter 2506. In some embodiments, the fixation structure 2502 and fixation mechanism 2504 may be deployed out of a side of the catheter.

FIG. 26A is a side elevational view of an example of a catheter system 2600. The catheter system 2600 comprises a fixation system 2602 and an electrode system 2604. The fixation system 2602 may comprise radially outwardly extending features, for example as described herein. The electrode system 2604 may comprise a scaffold and electrodes, for example as described herein. In the embodiment illustrated in FIG. 26A, the electrode system 2604 includes tethers 2605, which can help with positioning in and out of a sheath 2606. The fixation system 2602 is distal to the electrode system 2604.

FIGS. 26B-26H illustrate an example method of deploying the catheter system 2600 of FIG. 26A. This is an example of an over-the-wire or stepwise placement method in which a balloon is used to place a guidewire, which provides a rail to guide components to a target location.

In FIG. 26A, a Swan-Ganz catheter 2612 comprising a distal balloon 2614 is floated to a target area. For example, a Swan-Ganz catheter 2612 may be inserted into an access point of an internal jugular vein (left or right) in an uninflated state, then inflated, after which it can be carried by blood flow to a target site such as a pulmonary artery (left, right, or trunk). In some embodiments, the Swan-Ganz catheter 2612 is a 8 Fr Swan-Ganz catheter having a 1.5 cm$^3$ balloon, for example as is available from Edwards Lifesciences Corp. In FIG. 26C, a guidewire 2616 is routed through a lumen of the Swan-Ganz catheter 2612 until the distal end of the guidewire 2614 protrudes from the distal end of the Swan-Ganz catheter 2612. In FIG. 26D, the Swan-Ganz catheter 2612 is withdrawn, leaving the guidewire 2616.

In FIG. 26E, a fixation catheter 2620 including the fixation system 2602 at the distal end of a tether 2622 is advanced over the guidewire 2616 and the fixation system 2602 is deployed. In some embodiments, the fixation catheter 2620 is 8 Fr or 9 Fr. In FIG. 26F, the guidewire 2616 and the fixation catheter 2620 are withdrawn, leaving the fixation system 2602 and the tether 2622 in place. In FIG. 26G, the sheath 2606 including the electrode system 2604 is advanced over the tether 2622. In some embodiments, the distance between the fixation system 2602 and the distal end of the sheath 2606 may be known, for example, from proximal markings. In FIG. 26H, the sheath 2606 is proximally retracted to deploy the electrode system 2604. In some embodiments, the electrode system 2604 has a diameter of about 25 mm in the expanded state. The fixation system 2602 and the electrode system 2604 may be coupled, for example at a proximal end. In some embodiments, the electrode system 2604 is able to move relative to the fixation system 2602. Deploying catheters in a serial fashion (target location, then fixation system, then electrodes system) can allow the catheter diameters to be small and flexible (e.g., compared to an all-in-one or combination systems).

To withdraw the system, the steps may be reversed with some access steps omitted. For example, the sheath 2606 may be distally advanced to capture the electrode system 2604, for example due to the tethers 2605 helping to pull the electrode system 2604 into the sheath 2606. The sheath 2606 including the electrode system 2604 may then be withdrawn. The fixation catheter 2620 may be advanced over the tether 2622 to capture the fixation system 2602, and the fixation catheter 2620 including the fixation system 2602 may be withdrawn. The dimensions in this example method are not meant to be limiting to any particular embodiment (see, for example, other dimensions provided herein for these types of elements).

In some embodiments, a single catheter could include the fixation system 2602 and the electrode system 2604 (e.g., allowing integration of FIGS. 26E-26H). In some embodiments, the fixation system 2602 may be proximal to the electrode system.

In some embodiments, the fixation system 2602 can be anchored in the distal right pulmonary artery (e.g., delivering the fixation catheter 2620 as far as it can extend before deploying the fixation system 2602), and the electrode system 2604 can be deployed in a more proximal position. Fixation in the distal right pulmonary artery may be more stable and/or repeatable. The electrode system 2604 could be repositionable (e.g., able to slide, rotate) to map without modifying the position of the fixation system 2602. A proximal hub could comprise a locking mechanism to hold the electrode system 2604 in a set position and/or an apposition device could secure the electrode system 2604.

Figure 27B:
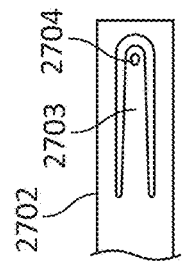
FIG. 27B is an elevational view of a portion of the fixation system of FIG. 27A.
Figure 27D:
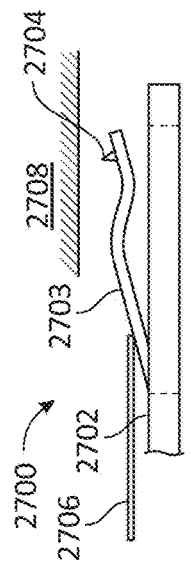
FIGS. 27C-27F illustrate the fixation system of FIG. 27A being retracted after engagement with tissue.
Figure 27F:
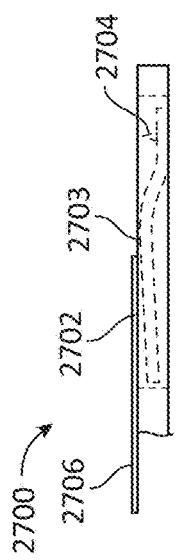
Figure 27A:
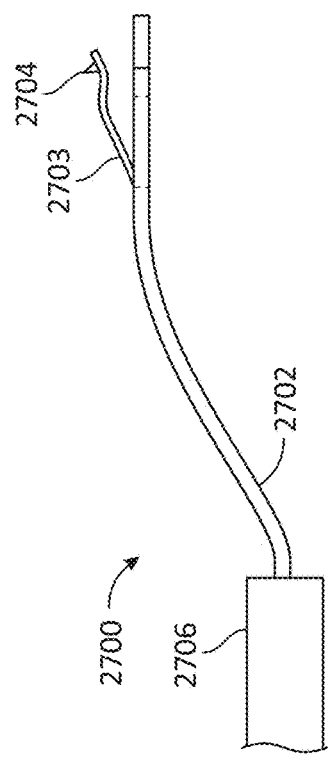
FIG. 27A is a perspective view of another example of a fixation system.
Figure 27C:
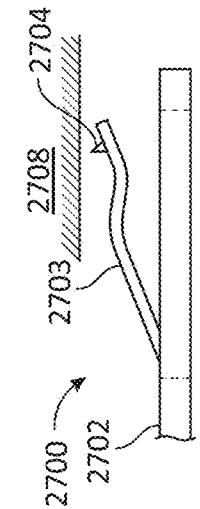

FIG. 27A is a perspective view of another example of a fixation system 2700. FIG. 27B is an elevational view of a portion of the fixation system 2700 of FIG. 27A. The fixation system 2700 comprises a fixation structure 2702 and a fixation mechanism 2504. The fixation structure 2702 may comprise, for example, a hypotube that has been cut and shape set, a ribbon that has been shape set, and the like. The fixation structure 2702 may be shape set, for example to flare radially outward when not constrained by a catheter 2706. The fixation mechanism 2704 is illustrated as comprising a conical structure, but may comprise other shapes, for example, points or barbs. The fixation mechanism 2704 is coupled to the fixation structure 2702 by a fixation arm 2703. In some embodiments, the fixation arm 2703 may be integral or monolithic with the fixation structure 2702, for example being milled from the fixation structure 2702. In some embodiments, the fixation arm 2703 is the same thickness as the fixation structure 2702. In some embodiments, the fixation arm 2703 a different thickness than the fixation structure 2702, for example to provide different collapsing characteristics. In some embodiments, the fixation arm 2703 may formed separately and then coupled to the fixation structure 2702, for example by welding, soldering, etc. to the fixation structure 2702 in a hole or aperture that has been milled in the fixation structure 2702. In some embodiments, the fixation arm 2703 may be integral or monolithic with the fixation mechanism 2704, for example both being milled from a same piece of material (e.g., the fixation structure 2702). In some embodiments, the fixation arm 2703 may formed separately and then coupled to the fixation mechanism 2704, for example by welding, soldering, etc. The fixation arm 2703 is configured to flare radially outward of the fixation structure 2702 when not constrained. The fixation arm 2703 comprises a curved shape such that, when the fixation arm 2703 is constrained, for example by a catheter 2706, the fixation mechanism 2704 is radially inward of or below the outer surface of the fixation structure 2702.

Figure 27E:
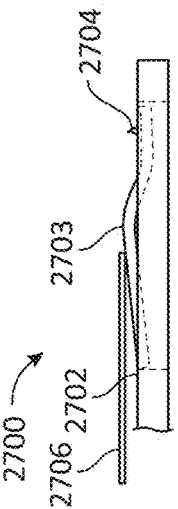

FIGS. 27C-27F illustrate the fixation system 2700 of FIG. 27A being retracted after engagement with tissue 2708. Prior to the state illustrated in FIG. 27C, the system 2700 was advanced to a fixation site. The system 2700 was advanced out of the catheter 2706, for example out of the side or out of the end of the catheter 2706. When not constrained by the catheter 2706, the fixation structure 2702 may flare radially outwardly. When not constrained by the catheter 2706, the fixation arm 2703 may flare radially outwardly from the fixation structure 2702 and engage the tissue 2708. For example, the fixation arm 2703 may pivot or rotate at the point where the fixation arm 2703 contacts the fixation structure 2702. In FIGS. 27D-27F, a catheter 2706 advancing over the fixation arm 2703 causes the fixation arm 2703 to flex radially inwardly until, as shown in FIG. 27F, the fixation mechanism 2704 is radially inward of or below the outer surface of the fixation structure 2702. In FIG. 27D, the fixation structure 2704 is pulled out of the tissue 2708 in the same direction as the initial interaction with the tissue 2708, which can be gentle on the tissue 2708 (e.g., reducing or preventing endothelial damage such as snagging, tearing, scratching, etc.).

FIG. 27G is an elevational view of yet another example of a fixation system 2750. The fixation system 2750 is similar to the fixation system 2700, comprising a fixation structure 2752, a fixation mechanism 2754, and a fixation arm 2753, but the fixation arm 2753 is not configured to move relative to the fixation structure 2752. FIG. 27G also illustrates the fixation arm 2753 having an end shape configured to correspond to a shape of the base of the fixation mechanism 2754 (e.g., annular for a conical fixation mechanism 2754). FIG. 27H is a side view of the fixation system 2750 of FIG. 27G. The fixation arm 2753 is spaced radially inward from the outer surface of the fixation structure 2752 by a first cavity 2755. The fixation arm 2753 is spaced radially outward from the inner surface of the fixation structure 2752 by a second cavity 2757. When the fixation system 2750 is pressed against tissue, some of the tissue may enter the cavity 2755 and interact with the fixation mechanism 2754. The second cavity 2757 may allow the fixation arm 2753 to bend or flex radially inward. When the fixation system 2750 is pried away from tissue, for example by retracting the fixation structure 2752 into a catheter, the tissue may exit the cavity 2755 and stop interacting with the tissue.

FIG. 27I is a side view of still another example of a fixation system 2760. The fixation system 2760 is similar to the fixation system 2750, comprising a fixation structure 2762, a fixation mechanism 2764, and a fixation arm 2763, but the fixation arm 2763 is not configured to flex. The fixation arm 2763 is spaced radially inward from the outer surface of the fixation structure 2762 by a first cavity 2755, but is not spaced radially outward from the inner surface of the fixation structure 2762 by a second cavity. When the fixation system 2760 is pressed against tissue, some of the tissue may enter the cavity 2765 and interact with the fixation mechanism 2764. The lack of a second cavity may allow the fixation arm 2763 to remain solid, which may increase likelihood of tissue engagement. When the fixation system 2760 is pried away from tissue, for example by retracting the fixation structure 2762 into a catheter, the tissue may exit the cavity 2765 and stop interacting with the tissue.

FIG. 28A is a side view of an example of a fixation system 2800. The fixation system 2800 comprises a fixation structure 2802, distal fixation mechanisms 2804a, and proximal fixation mechanisms 2804b. The distal fixation mechanisms 2804a extend distally from the distal end of the fixation structure 2802 (e.g., distal ends of cells formed by struts of the fixation structure 2802). The distal fixation mechanisms 2804a flare radially outward in an expanded position. Upon retraction of the fixation structure 2802, for example into a catheter, the distal fixation mechanisms 2804a flex radially inwardly from proximal to distal. The proximal fixation mechanisms 2804b extend proximally from an intermediate portion of the fixation structure 2802 (e.g., proximal ends of cells formed by struts of the fixation structure 2802). The proximal fixation mechanisms 2804b flare radially outward in an expanded position. Upon retraction of the fixation structure 2802, for example into a catheter, the proximal fixation mechanisms 2804b flex radially inwardly as described in further detail herein. FIG. 28B is an expanded view of the circle 28B in FIG. 28A, which better illustrates the radially outward flexing of the proximal fixation mechanism 2804b (e.g., versus the other contours of the fixation system 2800). The fixation mechanisms 2804 are shape-set to protrude outside the wall of the fixation structure 2802.

Figure 28D:
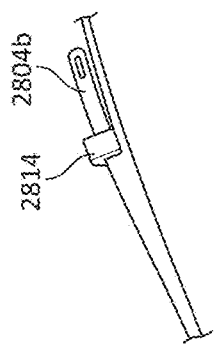
FIG. 28D shows an example of a radiopaque marker coupled to a proximal fixation mechanism.
Figure 28E:
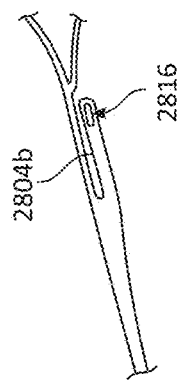
FIG. 28E shows an example of a hole in a proximal fixation mechanism.
Figure 28C:
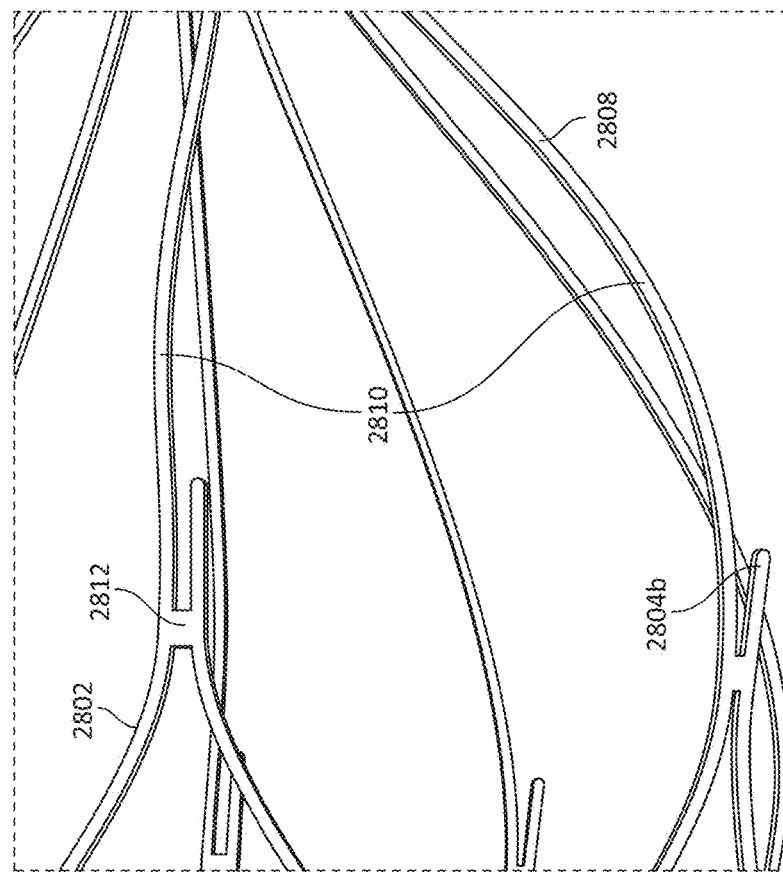
FIG. 28C is an expanded view of the dotted square 28C in FIG. 28A.

FIG. 28C is a partial elevational view of the fixation system 2800 of FIG. 28A. The proximal fixation mechanisms 2804b are coupled to the fixation structure 2802 at attachment points 2812. The proximal fixation mechanisms 2804b may be integral or monolithic with the fixation structure 2802 (e.g., cut from the same hypotube, for example as described with respect to FIG. 28F). The strands proximal to the attachment points 2812 are tethers 2808 comprising twists or bends 2810. When a hypotube is cut to form an attachment point 2812, a proximal fixation mechanism 2804b, a tether 2808, cell struts, etc., the attachment point 2812 naturally becomes radially offset (e.g., because a large mass naturally wants to remain straight) such that the proximal fixation mechanism 2804b is slightly radially inward of the cell struts and the tether 2808. A similar phenomenon occurs at the connecting struts 2817 (FIG. 28A) between cells. The cut hypotube may be shape set including, without limitation, flaring the fixation structure 2802 radially outward from proximal to distal, flaring the fixation mechanisms 2804a, 2804b radially outward from the fixation structure 2802 (e.g., so the fixation mechanisms 2804a, 2804b stand proud compared to the fixation structure 2802), and twisting the tethers 2808.

FIG. 28D shows an example of a radiopaque marker 2814 coupled to a proximal fixation mechanism 2804b. The radiopaque marker 2814 may comprise a band, an identifiable shape (e.g., a rectangle, circle, etc.). In some embodiments, the radiopaque member 2814 protrudes outward from the proximal fixation mechanism 2804b. In some embodiments, the radiopaque member 2814 is flush with the proximal fixation mechanism 2804b. Other portions of the fixation system 2800 may comprise a radiopaque marker (e.g., other proximal fixation mechanisms 2804b, distal fixation mechanisms 2804a, fixation structure 2802, tethers 2810, etc.)

FIG. 28E shows an example of a hole or opening or aperture 2816 in a proximal fixation mechanism 2804b. In some embodiments, the hole 2816 may be used to attach other components (e.g., radiopaque markers, fixation elements such as conical members, barbs, fixation arms, etc.), such as by crimping, welding, etc. Attaching certain structures may provide better control of certain properties, for example shape-setting. In some embodiments, the hole 2816 may help to capture tissue, for example the edges of the hole 2816 apposing tissue penetrating the hole 2816.

FIG. 28F is a flattened view of an example of a hypotube cut pattern 2820. The cut pattern 2820 includes tethers 2808, attachment points 2812, proximal fixation mechanisms 2804b including holes 2816, fixation structure 2802, and distal fixation mechanisms 2804a. The cut pattern also shows ramped or tapered areas 2822. The tapered areas 2822 can engage the distal end of a catheter during retraction, and may help with turning the proximal fixation mechanisms 2804b. In some embodiments, it may be possible to cut a sheet and roll the sheet into a tube (e.g., initially shape setting into a cylinder and then shape setting, or directly shape setting). The cut hypotube may be shape set, for example into the shape shown in FIG. 28A.

FIG. 28G is an expanded view of the dashed square 28G in FIG. 28F. In addition to the other manners of shape setting described herein, a strut 2824 adjacent to the proximal fixation mechanism 2804b may be bent at an angle. FIG. 28H is a side view of the strut 2824 of FIG. 28G. The proximal end 2826 of the proximal fixation mechanism 2804b and the distal end 2828 of the proximal fixation mechanism 2804b are shown in dotted lines behind the strut 2824. FIG. 28I is a side view of the proximal fixation mechanism 2804b being bent radially outward. FIG. 28J is a side view of the proximal fixation mechanism 2804b being bent radially outward and the strut 2824 being bent at a bend point 2830. Referring again to FIG. 28H, the length x of the proximal fixation mechanism 2804b is shown. In some embodiments, the bend point 2830 is about 50% of x ±20% (e.g., measured from the proximal end 2826 or the distal end 2828, about 20% of x, about 30% of x, about 40% of x, about 50% of x, about 60% of x, about 70% of x, ranges between such values, etc.). The more proximal the bend point 2830, the more the proximal fixation mechanism 2804b protrudes radially outward. The more distal the bend point 2830, the less the proximal fixation mechanism 2804b protrudes radially outward. The angle of the portion of the strut 2824 proximal to the bend point 2830 relative to the portion of the strut 2824 distal to the bend point 2830 is between about 20° and about 50° (e.g., about 20°, about 30°, about 40°, about 50°, ranges between such values, etc.). In some embodiments, the distance y between the distal end of the proximal fixation mechanism 2804*b* and the portion of the strut 2824 distal to the bend point (or, in FIG. 28I, the unbent strut 2824) in an unconstrained state is between about 0.02 inches and about 0.06 inches (e.g., about 0.02 inches, about 0.03 inches, about 0.04 inches, about 0.05 inches, about 0.06 inches, ranges between such values, etc.), although factors such as vessel diameter, the length x, etc. may influence the distance y.

FIG. 28K is a side view of the strut 2824 being bent at the bend point 2830. In contrast to FIG. 28J, the proximal fixation mechanism 2804*b* is not bent, although other parameters (e.g., bend angle, location of the bend point 2830, the distance y, etc.) may remain the same.

Figure 28L:
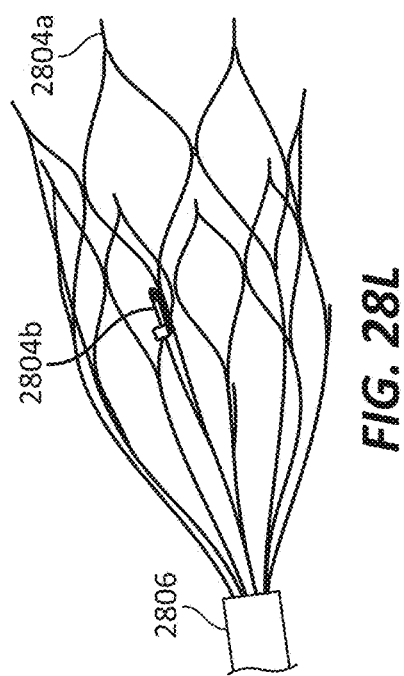
FIGS. 28L-28O show proximal fixation mechanisms rotating inwardly during retrieval into a catheter.
Figure 28M:
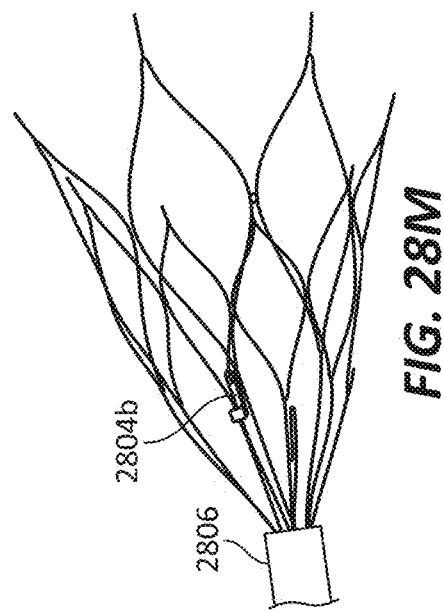
Figure 28N:
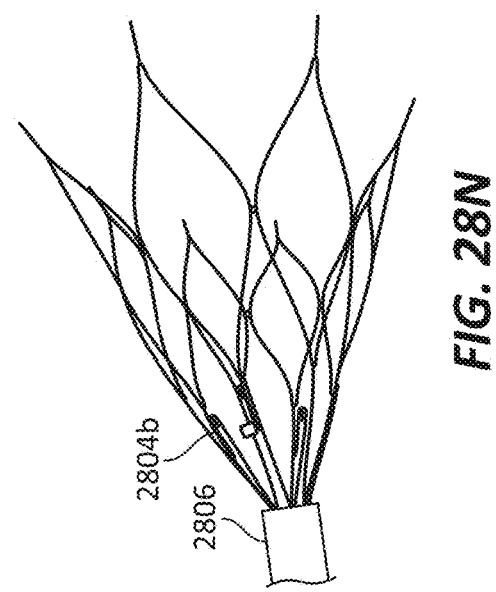
Figure 28O:
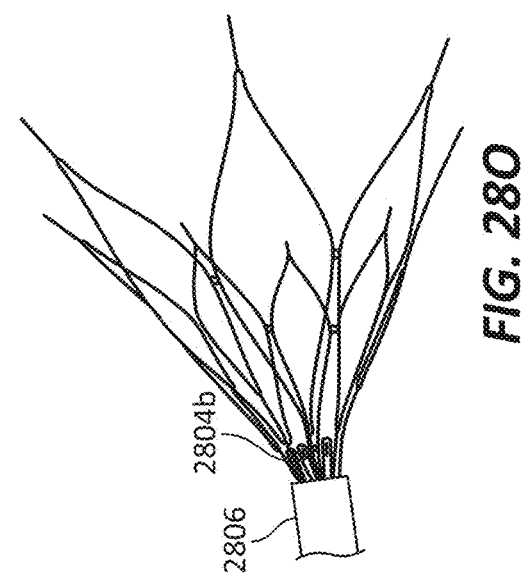

FIGS. 28L-28O show the proximal fixation mechanisms 2804*b* rotating inwardly during retrieval into a catheter 2806. In FIG. 28L, the fixation system 2800 is fully deployed. The proximal fixation mechanisms 2804*b* stand proud. The distal fixation mechanisms 2804*a* also stand proud, providing bidirectional fixation. In FIG. 28M, the fixation system 2800 is starting to be withdrawn into the catheter 2806. The proximal fixation mechanisms 2804*b* still stand proud. In FIG. 28N, the fixation system 2800 is further withdrawn into the catheter 2806. The proximal fixation mechanisms 2804*b* still rotate inwardly as the distal end of the catheter 2806 interacts with the tapered portions 2822. In FIG. 28O, the fixation system 2800 is further withdrawn into the catheter 2806. The proximal fixation mechanisms 2804*b* except for the distal ends are in the catheter 2806. No snagging, scratching, etc. occurred during retraction. Further retraction of the fixation system 2800 would place the remainder of the fixation structure 2802 and the distal fixation mechanisms 2804*a* in the catheter 2806.

Having the proximal fixation mechanisms 2804*b* pointed distally can allow for improved performance during retrieval of the fixation system 2800 (e.g., lower probability of the proximal fixation mechanisms 2804*b* or any other part of the fixation system 2800 getting snagged by the distal end of the catheter 2806). Since the proximal fixation mechanisms 2804*b* articulate radially inwards upon retrieval, the proximal fixation mechanisms 2804*b* can be included with little concern of scratching and/or engaging the inner surface of the catheter 2806 during deployment or retrieval. The degree of inward flex of the proximal fixation mechanisms 2804*b* during retrieval can be controlled by, for example, the location of the bend point 2830, the attachment point 2812, and/or bending of the proximal fixation mechanisms 2804*b*. The distal end can comprise distal fixation mechanisms 2804*a*, which can provide resistance to distal motion.

In some embodiments, the fixation mechanisms described herein may take the form of a textured surface. For example, material may be added to and/or removed from a fixation arm or a fixation structure to form a stippled, striped, rough, etc. surface. The texture may increase the surface area, which can increase the amount of tissue that is engaged.

FIG. 29A illustrates an example of a catheter system 2900. The catheter system 2900 comprises a sheath 2906, a first loop 2902 extending from a distal end of the sheath 2906, and a second loop 2904 extending from the distal end of the sheath 2906. At least one of the first loop 2902 and the second loop 2904 comprises a plurality of electrodes 2908. In some embodiments, the catheter system 2900 comprises fixation features 2910 (e.g., comprising atraumatic stiff loops).

Figure 29D:
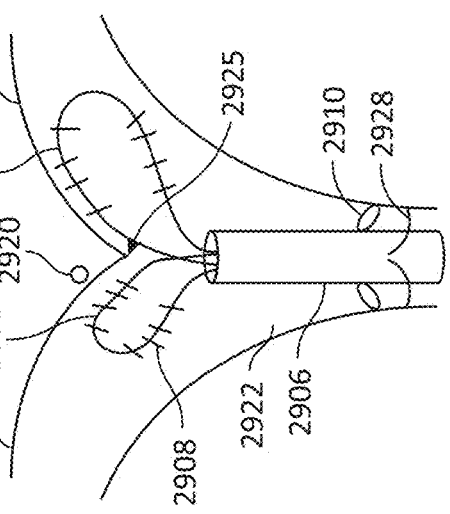

FIGS. 29B-29F illustrate an example method of deploying the catheter system 2900 of FIG. 29A. In FIG. 29B, the sheath 2906 has been advanced past the pulmonary valve 2928 into the pulmonary trunk 2922. The pulmonary valve 2928 is a tricuspid valve. In some embodiments, the sheath 2906 may have a shape configured to interact with the cuspids of the pulmonary valve 2928. The sheath 2902 may comprise a pressure sensor proximate to a distal end to help a user determine when the distal end of the sheath 2906 is distal to the pulmonary valve 2928. FIG. 29A also illustrates the right pulmonary artery 2924, the left pulmonary artery 2926, the bifurcation 2925 between the right pulmonary artery 2924 and the left pulmonary artery 2926, and a target nerve 2920 (e.g., the right stellate CPN).

In FIG. 29C, the loops 2902, 2904 are deployed from the distal end of the sheath 2906. In some embodiments, the loops 2902, 2904 are deployed substantially simultaneously, which can reduce delivery complexity, for example using a single actuation mechanism having a short delivery throw. In some embodiments, the loops 2902, 2904 may be deployed sequentially or serially or staggered with either loop being deployed first, which can reduce the profile of the catheter system 2900. The loops 2902, 2904 may be in any rotational orientation.

In FIG. 29D, the sheath 2906, with the loops 2902, 2904 deployed, is advanced towards the bifurcation 2925. The loops 2902, 2904 self-orient into the right pulmonary artery 2904 and left pulmonary artery 2906, regardless of the original rotational orientation of the loops 2902, 2904. For example, the catheter system 2900 may rotate during distal advancement in response to the loops 2902, 2904 interacting with the anatomy.

Figure 29E:
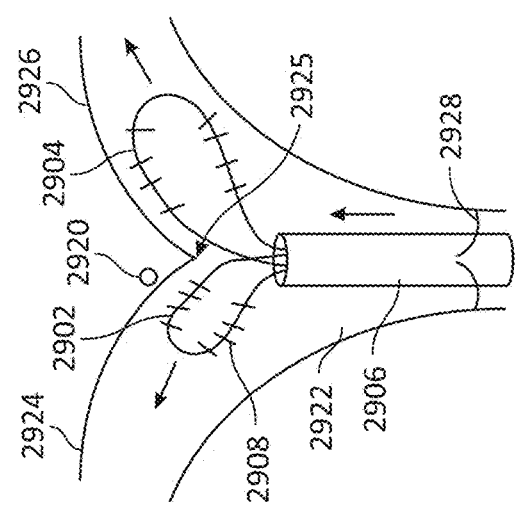
Figure 29F:
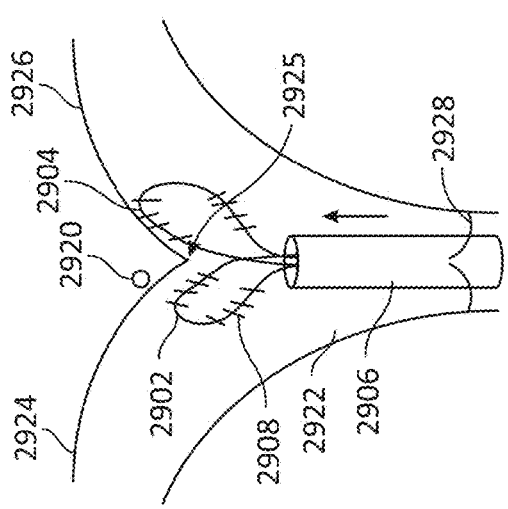

In FIG. 29E, the sheath 2906 is further distally advanced towards the bifurcation 2925. The loops 2902, 2904 may advance further into the right pulmonary artery 2924 and the left pulmonary artery 2926, respectively, but advancement is limited by the bifurcation 2925. In FIG. 29F, fixation features 2910 may optionally be deployed from the sheath 2906, for example proximate to the pulmonary valve 2928. The fixation features 2910 may bias the sheath 2906 distally towards the bifurcation 2925, which can limit distal advancement. In some embodiments, the fixation features 2910 comprise a shape memory material such as nitinol. Blood flow is in the distal direction, which can help to maintain the positions of the loops 2906. In some embodiments, the sheath 2906 may comprise features to interact with the blood flow (e.g., fins, a balloon, etc.).

The electrodes 2908 of the first loop 2902 and the electrodes 2908 of the second loop 2904 may be activated according to a predetermined or logical sequence to determine which loop 2902, 2904 can modulate the target nerve 2910. The electrodes 2908 of the selected loop may be used for neuromodulation and the electrodes 2908 of the other loop may be deactivated.

In some embodiments, only the first loop 2902 comprises electrodes 2908. The second loop 2904 may still provide self-orientation and interaction with the bifurcation 2925. The electrodes 2908 of the first loop 2902 may be activated according to a predetermined or logical sequence to determine if the first loop 2902 can modulate the target nerve 2910. If the first loop 2902 is determined to not be able to modulate the target nerve 2910, the catheter system 2900 may be repositioned (e.g., including rotating, for example) 180° so that the first loop 2902 is in the other of the right pulmonary artery 2924 and the left pulmonary artery 2926.

In some embodiments, rather than loops 2902, 2904, a catheter system comprises two fingers having pigtail ends. The pigtail ends may provide the same benefits, for example bifurcation interaction, as the loops 2902, 2904, and reduce potential issues such as poking the vasculature, bending, etc.

In some embodiments, neither of the loops 2902, 2904 comprises electrodes 2938. In certain such embodiments, the electrodes 2938 may be disposed on the sheath 2906. FIG. 29G illustrates an example of a catheter system 2930. The catheter system 2930 comprises a sheath 2906, a first loop 2902 extending from a distal end of the sheath 2906, and a second loop 2904 extending from the distal end of the sheath 2906. The sheath 2906 comprises a plurality of electrodes 2938. In some embodiments, the catheter system 2930 comprises fixation features 2910 (e.g., comprising atraumatic stiff loops). The loops 2902, 2904 may inhibit or prevent distal migration and/or the fixation features 2910 may inhibit or prevent proximal migration. The catheter system 2930 may be positioned as described with respect to the catheter system 2900, for example passing distal to the pulmonary valve, deploying the loops 2902, 2904, and advancing towards a bifurcation where one loop 2902 extends into one branch vessel and the other loop 2904 extends into the other branch vessel.

The electrodes 2938 may be annular, partially annular, points, etc. In some embodiments, for example in which the electrodes 2938 are on one side of the sheath 2906, the electrodes 2938 may be activated according to a predetermined or logical sequence to determine if the target nerve is captured. If the target nerve is not captured, the catheter system 2930 may be repositioned (e.g., including rotating, for example 180°) so that the first loop 2902 is in the other of the right pulmonary artery 2924 and the left pulmonary artery 2926. In some embodiments in which one or both of the loops 2902, 2904 comprise electrodes 2908, the sheath 2908 may comprise electrodes 2938.

In some embodiments, electrodes that are separate from the loops 2902, 2904 may be deployed from the catheter 2906. For example, catheter systems described herein provide electrode matrices that can be deployed from a side of a catheter and/or an end of a catheter. In certain such embodiments, the loops 2902, 2904 can be used to orient and position the catheter 2906 at a target site, and then an electrode matrix can be deployed from the catheter 2906 at the target site.

In some embodiments, rather than being a plain loop, at least one of the loops 2902, 2904 may be modified, for example as described herein with respect to other catheter systems. In some embodiments, each of the loops 2902, 2904 may be modified differently.

FIG. 29H illustrates an example of a catheter system 2940. The catheter system 2940 comprises a sheath 2906, a first loop 2942 extending from a distal end of the sheath 2906, and a second loop 2904 extending from the distal end of the sheath 2906. The first loop 2942 comprises a first wire 2943a and a second wire 2943b. Each of the wires 2943a, 2943b comprises electrodes 2948, forming an electrode matrix. Distal to the distal end of the sheath 2906, the first wire 2943a and the second wire 2943b are spaced to form a gap 2943c that spaces the electrodes 2948 on the wire 2943a from the electrodes 2948 on the wire 2943b. More wires and electrodes are also possible. For example, a third wire may extend between the first wire 2943a and the second wire 2943b. The electrodes 2948 are shown as button electrodes, but other types of electrodes are also possible (e.g., barrel, within a U-channel, etc.).

In some embodiments, the catheter system 2940 comprises fixation features 2910 (e.g., comprising atraumatic stiff loops). The catheter system 2940 may be positioned as described with respect to the catheter system 2900, for example passing distal to the pulmonary valve, deploying the loops 2942, 2904, and advancing towards a bifurcation where one loop 2942 extends into one branch vessel and the other loop 2904 extends into the other branch vessel.

FIG. 29I illustrates an example of a catheter system 2950. The catheter system 2950 comprises a sheath 2906, a first loop 2952 extending from a distal end of the sheath 2906, and a second loop 2904 extending from the distal end of the sheath 2906. The first loop 2952 comprises a wire having an undulating or zig-zag or sinusoidal or wave shape. The first loop 2952 comprises electrodes 2958 at peaks and valleys, forming an electrode matrix. The electrodes 2958 may also or alternatively be positioned between peaks and valleys. The first loop 2952 may comprise additional wires and/or electrodes. For example, a second wire, which may be straight, sinusoidal, or another shape, may extend along the first wire. The electrodes 2958 are shown as button electrodes, but other types of electrodes are also possible (e.g., barrel, within a U-channel, etc.). In some embodiments, a sinusoidal shape may be in a plane configured to transversely appose a vessel wall. In certain such embodiments, electrodes are at sinusoidal peaks, which can provide increased or optimum vessel wall contact. In some embodiments, a sinusoidal shape can increase rigidity, which can improve wall apposition, for example compared to a straight shape.

In some embodiments, the catheter system 2950 comprises fixation features 2910 (e.g., comprising atraumatic stiff loops). The catheter system 2950 may be positioned as described with respect to the catheter system 2900, for example passing distal to the pulmonary valve, deploying the loops 2952, 2904, and advancing towards a bifurcation where one loop 2952 extends into one branch vessel and the other loop 2904 extends into the other branch vessel.

Several processes described herein are provided with respect to entering the pulmonary trunk and then advancing into the right pulmonary artery and/or the left pulmonary artery, or more generically entering a main or afferent vessel and advancing into one or more efferent or branch vessels. In some embodiments, a catheter system may enter from a branch vessel and be advanced towards a main vessel and/or another branch vessel. For example, a catheter system may be inserted into the right internal jugular vein and advanced towards a superior vena cava. For another example, a catheter system may be inserted into the left internal jugular vein and advanced towards a left brachiocephalic vein.

FIG. 29J illustrates another example of a catheter system 2960. The catheter system 2960 comprises a sheath 2906 and a loop 2962. The loop 2962 is configured to extend from a distal end of the sheath 2906 and to bend proximally back towards the sheath 2906. In some embodiments, for example as described with respect to the catheter system 2900, the loop 2962 may comprise electrodes. In some embodiments, the catheter system 2960 comprises fixation features 2910 (e.g., comprising atraumatic stiff loops). For example as described with respect to the catheter system 2930, the sheath 2906 comprises electrodes 2968. In some embodiments, the catheter system 2960 comprises sheath electrodes 2968 and the electrodes on the loop 2962.

FIG. 29K illustrates another example of a catheter system 2965. The catheter system 2965 is similar to the catheter system 2960 except that the loop 2963 is configured to extend from a side of the sheath 2906, through an aperture 2907, and to bend proximally. In some embodiments, the aperture 2907 may comprise turning features such as a ramp.

FIGS. 29L-29N illustrate an example method of deploying the catheter system 2965 of FIG. 29K. The example method may also or alternatively be used to deploy the catheter system 2960 of FIG. 29J or other catheter systems.

The vasculature illustrated in FIGS. 29L-29N includes the left innominate vein or left brachiocephalic vein 2955, the left subclavian vein 2961, and the left internal jugular vein 2964, described in further detail herein with respect to FIG. 21, although other the method may also be appropriate for use at other vascular or other lumen bifurcations. The catheter systems can be adjusted to better interact with a Y-shaped bifurcation, a T-shaped bifurcation, from an afferent vessel, from an efferent vessel, depending on the relative sizes of the vessels, etc. In some embodiments, such catheter systems can advantageously positively locate the catheter at anatomical junctions. Certain such anatomical junctions may have known passing nerves, which can allow the user to locate electrodes in a precise location with reduced or minimal or no visualization (e.g., fluoroscopy) and/or guidance (e.g., use of a guidewire and/or guide catheter). In some embodiments, the Y-shaped or T-shaped anatomy may help ensure that the catheter and electrodes remain fixed in place.

In FIG. 29L, the catheter system 2965 is in the left internal jugular vein 2964, which may the point at which the vasculature is accessed by an introducer. The catheter system 2965 is advanced towards the left brachiocephalic vein 2955. At least during advancing past the junction of the left subclavian vein 2961 and the left internal jugular vein 2964, the loop 2963 is deployed out of the sheath 2906. As the sheath 2906 is advanced in the left internal jugular vein 2964, the loop 2963 is inwardly compressed slides along the wall of the left internal jugular vein 2964.

In FIG. 29M, the catheter system 2965 is advanced far enough that the loop 2963 is unconstrained and able to outwardly expand to a set shape. In FIG. 29N, the catheter system 2965 is retracted until the loop 2963 contacts the left subclavian vein 2961. The catheter system 2965 can be repeatably placed at the junction between the left subclavian vein 2961 and the left internal jugular vein 2964. In some embodiments, placement can be without fluoroscopy, for example using distance and/or tactile changes to determine that the catheter system 2965 is properly positioned. Fixation features 2910 may optionally be deployed from the sheath 2906, for example proximate to the junction in the left internal jugular vein 2964. The electrodes 2968 can be positioned along the sheath 2906 to capture a target nerve 2921. The target nerve 2921 may comprise, for example, a thoracic cardiac branch nerve. In some embodiments, the target nerve 2921 is a cervical cardiac nerve. Cervical cardiac nerves may also or alternatively be targeted from the left internal jugular vein 2964. In some embodiments, the catheter system 2965 comprises features that may help to capture a target nerve. For example, the sheath 2906 may comprise a curvature to bend towards the position 2921, the catheter system 2965 may comprise a second loop comprising electrodes and configured to be deployed out of the distal end or the side of the sheath 2906 in a direction opposite the loop 2963, and/or the electrodes 2968 may be longitudinally aligned with and/or distal to the aperture 2907.

FIG. 30A is a perspective view an example of an electrode system 3000. The system 3000 comprises a catheter 3006, a framework 3002, and a plurality of electrodes 3008. FIG. 30B is a top plan view of a portion of the electrode system 3000 of FIG. 30A. The catheter 3006 comprises a proximal segment 3010 having a generally circular cross-section and a distal segment 3012 having a generally oval cross-section. The round shape of the proximal segment 3010 can be useful, for example, to couple to round proximal components such as luer fittings, other round catheters, etc. The oval shape of the distal segment 3012 can be useful, for example, to preferentially align near the target zone, which can reduce or minimize distance from the sheath 3006 to the target zone. The oval shape of the distal segment 3012 can be useful, for example, to resist torque and rotation. The framework 3002 may comprise, for example, two shape memory (e.g., nitinol) wires forming a zig-zag or undulating or sinusoidal pattern or serpentine to create a wave frame or accordion shape. The framework 3002 can be substantially level or planar, or can comprise a curve, for example to bias or conform to a vessel wall. Leads or conductor wires coupling the electrodes 3008 to a modulation system can run along and/or through the framework 3002.

The electrodes 3008 comprise buttons coupled to the framework 3002. In some embodiments, the electrodes 3008 have a diameter between about 1 mm and about 3 mm (e.g., about 1 mm, about 1.5 mm, about 2 mm, about 2.5 mm, about 3 mm, ranges between such values, etc.). The electrodes 3008 are longitudinally offset, as shown by the dashed lines in FIG. 30B, to sequentially nest in catheter 3006 the before deployment and/or upon retraction, which can reduce the profile of the catheter. In some embodiments, at least some of the electrodes 3008 may be side-by-side. In some embodiments, one side of the electrodes 3008 is insulated, which can provide directional electrodes 3008. The electrodes 3008 may be coupled to the framework 3002 to inhibit rotation of the electrodes 3008, for example keeping the surfaces of the electrodes 3008 generally level or planar. Interaction with tissue such as a vessel wall may induce the framework 3002 to bend before inducing the electrodes 3008 to rotate.

FIG. 30C is a perspective view of another example of an electrode system 3020. Similar to the system 3000, the system 3020 comprises a catheter 3006, a framework 3002, and a plurality of electrodes 3028. FIG. 30D is a distal end view of the electrode system 3020 of FIG. 30C in a collapsed state. FIG. 30E is a distal end view of the electrode system 3020 of FIG. 30C in an expanded state. The expanded state shown in FIGS. 30C and 30E is partially expanded, as some electrodes 3028 remain in the catheter 3006. A selected number of electrodes 3028 may be deployed as determined by the user (e.g., based on the subject's anatomy, the indication, etc.).

The electrodes 3028 comprise barrel-shapes coupled to the framework 3002. The framework 3002 may include longitudinal segments rather than peaks to accommodate the lengths of the electrodes 3008, and the bends in the framework 3002 can maintain longitudinal positioning of the electrodes 3028. In some embodiments, the electrodes 3028 have a diameter between about 0.01 in and about 0.1 in (e.g., about 0.01 in, about 0.02 in, about 0.03 in, about 0.04 in, about 0.05 in, about 0.06 in, about 0.08 in, about 0.1 in, ranges between such values, etc.). In some embodiments, the electrodes 3028 have a length between about 0.02 in and about 0.2 in (e.g., about 0.02 in, about 0.03 in, about 0.04 in, about 0.05 in, about 0.06 in, about 0.07 in, about 0.08 in, about 0.09 in, about 0.1 in, about 0.12 in, about 0.15 in, 0.2 in, ranges between such values, etc.). The edge electrodes 3028 are laterally side-by-side, which can provide certain electrode combination patterns (e.g., as discussed with respect to FIGS. 32A-32D). In some embodiments, a central electrode 3028 can be a cathode and the four closest lateral electrodes 3028 can be anodes. In some embodiments, the electrodes 3028 may be laterally offset (e.g., like the electrodes 3008). In some embodiments, a circumferential arc of the electrodes 3028 is insulated, which can provide directional electrodes 3028. The electrodes 3028 may be coupled to the framework 3002 to inhibit rotation of the electrodes 3028, for example maintaining uninsulated surfaces of the electrodes 3028 facing a certain direction. Other shapes of the electrodes 3028 are also possible (e.g., cylindrical, spherical).

The system 3020 comprises an optional core element 3024. The core element may, for example, help to carry conductor wires and/or to maintain a shape of the framework 3002. In some embodiments, the core element 3024 comprises a round tube (e.g., a hypotube). In some embodiments, the core element 3024 is flat or ribbon shaped, rectangular, oval, or other shapes. In some embodiments, the core element 3024 is laterally offset from a center of the framework 3002.

Figure 30F:
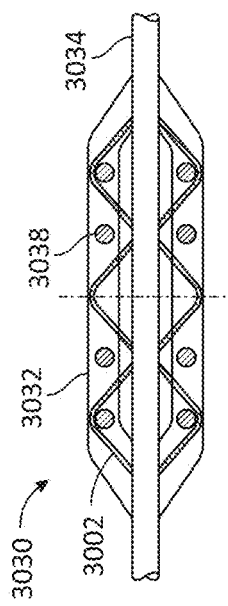
FIG. 30F is a plan view of yet another example of an electrode system.

FIG. 30F is a plan view of yet another example of an electrode system 3030. Similar to the system 3000, the system 3030 comprises a framework 3002 and a plurality of electrodes 3038. The system 3030 comprises a sheet or membrane or mesh 3032. In contrast to the systems 3000, 3020, the electrodes 3038 of the system 3030 are on the sheet 3032 comprising a flexible material (e.g., polyimide, silicone). The sheet 3032 may comprise, for example, a flex circuit including patterned conductor wires. The sheet 3032 may comprise, for example, a mesh such as described with respect to FIG. 4C. The sheet 3032 holding the electrodes 3038 can provide control of the relative positions and spacing of the electrodes 3038.

Figure 30G:
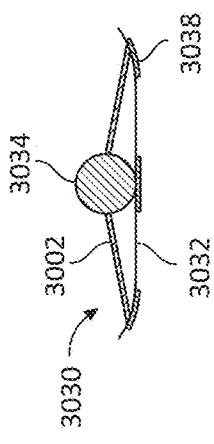
FIG. 30G is a distal end view of the electrode system of FIG. 30F.

The system 3030 optionally comprises a core element 3034. The framework 3032 may be coupled to the core element 3034, for example as individual V-shaped segments. The sheet 3032 is coupled to the framework 3002, and optionally to the core element 3034. In some embodiments, the framework 3002 and the sheet 3034 wrap around the core element 3034 in a collapsed state. The system 3030 can be delivered in a collapsed state without a catheter (e.g., tracking the core element 3034 over a guidewire or tether), for example if the sheet 3032 at least partially thermally insulates the framework 3002 such that thermal shape memory is slow to take effect. FIG. 30G is a distal end view of the electrode system 3030 of FIG. 30F. In the deployed state, as best seen in FIG. 30G, the sheet 3032 has a curved shape, which can help to hold the electrodes 3038 against a vessel wall.

Figure 31A:
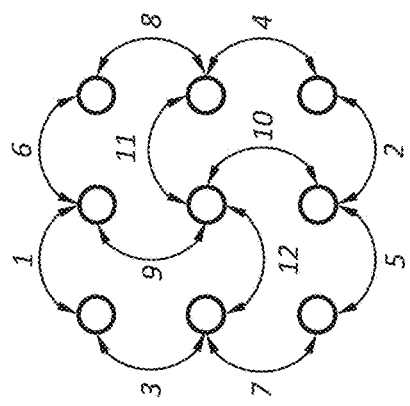
FIGS. 31A and 31B show example electrode combinations for nine electrodes in a 3×3 matrix.
Figure 31B:
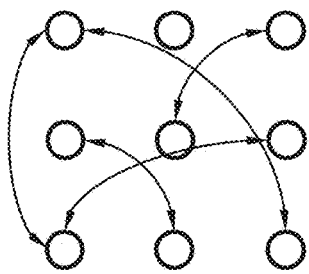

FIGS. 31A and 31B show example electrode combinations for nine electrodes in a 3×3 matrix. Other numbers of electrodes and patterns of matrices can be used, and the 3×3 matrix is shown only for the sake of discussion. In embodiments in which a power supply is external to the subject, energy budget may be of less concern than accurate tissue nerve targeting. A sequence of combinations in which a first electrode is cathodic and a second electrode is anodic can be tested to see which combinations provide certain effects (e.g., effecting contractility and/or not affecting heart rate). A subject could provide input regarding pain, cough, general discomfort, tingling, and/or other sensations during the process to give the system feedback about which electrode combinations cause those effects. The contractility response could be measured, for example via a pressure sensor, accelerometer, or other contractility measurement, including external tools such as echo ultrasound.

FIG. 31A shows an example sequence of twelve combinations in which one electrode is anodic and one electrode is cathodic. Each combination may be operated, for example, 4 ms, followed substantially immediately by the next combination in the sequence. The sequence may be repeated if the initial run was successful, for example about 50 ms (20 Hz) later. After running the sequence of tests 1-12, combinations of electrodes that have an effect above or below a certain threshold may be identified for use and/or non-use in calibration stimulation and/or therapeutic stimulation. This can automate the mapping of the nerve location and increase or optimize stimulus response for efficacy and tolerance. FIG. 32A shows that other combinations of these same electrodes are also possible, for example, with an electrode in the middle, diagonal, etc. The same sequence or a shorter sequence (e.g., comprising tests 1, 2, 7, and 8) may be used to verify positioning on a macro level (e.g., that some combination of electrodes in that matrix position provides stimulation), for example upon initial positioning, repositioning, and/or periodically to check for matrix migration.

In some embodiments, a monopolar mode in which one electrode in the matrix is made cathodic with an anodic body patch (or vice versa) on the subject's chest, back, or arm can be used before bipolar combinations of electrodes to find nerve faster, and then bipolar or guarded bipolar or bullseye (e.g., as discussed herein) combinations can be used to more selectively capture the nerve.

In some embodiments, a plurality of sequences may be available (e.g., having at least one electrical parameter or electrode combination sequence that is different). For example if a first sequence causes more than a threshold number of undesired responses, a second sequence may start, and so on. The system may return to an initial sequence based on results of other sequences.

Sequences of combinations in which a plurality of electrodes are cathodic and one electrode is cathodic, in which one electrode is anodic and a plurality of electrodes are cathodic, and in which a plurality of electrodes are anodic and a plurality of electrodes are cathodic are also possible.

FIGS. 32A-32D show example electrode combinations for twelve electrodes in a 3×4 matrix. The 3×4 matrix is an example, and other matrices are also possible (for example, but not limited to, 2×2, 2×3, 2×4, 2×5, 3×3, 3×5, 4×4, 5×5, reversals (e.g., 3×2 being a reversal of 2×3), etc.). In some embodiments, the matrix may be irregularly shaped, for example, being 2×2 and then 3×3. In FIGS. 32C and 32D, the middle column is offset relative to the left and right columns. The electrode combinations of FIGS. 32A-32D may be called "guarded bipolar" combinations because the cathode is completely surrounded by anodes, or is at least not adjacent to a non-anodic cathode. In FIG. 32A, the cathodic electrode in row 2, column 2 is surrounded by anodic electrodes in row 1, row 3, and row 2, columns 1 and 3. In FIG. 32B, the cathodic electrode in row 4, column 2 is surrounded by anodic electrodes in row 3, and row 4, columns 1 and 3. In FIG. 32C, the cathodic electrode column 2, second from the top is surrounded by anodic electrodes in column 1, first two from the top, column 3, first two from the top, and column 2, first and third from the top. In FIG. 32D, the cathodic electrode column 2, first from the bottom is surrounded by anodic electrodes in column 3, first from the bottom, column 2, first from the bottom, and column 3, second from the bottom. Guarded cathodes (using two or more anodes) can allow for controlling the spread of the electric field, which can provide a more efficient stimulation to the target nerve, and/or which can reduce spillover of the electric field to non-target nerves, which could cause unintended side-effects.

In some embodiments, an electrode matrix can be used to electronically reposition the electrodes. For example, referring to FIG. 32A, if all of the anodes and cathodes are shifted down one row such that the cathodic electrode in row 3, column 2 is surrounded by anodic electrodes in row 2, row 4, and row 3, columns 1 and 3. Referring again to FIG. 31A, changing from test 3 to test 9, from test 1 to test 11, etc.

could be considered electronic repositioning. Electrodes may thereby be electronically repositioned in multiple directions. In electronic repositioning, the electrode matrix itself does not move or migrate. Electronic repositioning may be used to counter unintended movement or migration of the electrode matrix.

In some embodiments, the stimulation comprises an active biphasic waveform in which area under a curve is actively managed to be zero by forcing a pulse in opposite charge over a longer duration by measuring charge. In some embodiments, the stimulation comprises a passive biphasic waveform in which area under a curve is zero by allowing the charge to dissipate from the tissue.

In some embodiments, the stimulation comprises an amplitude between about 1 mA and about 20 mA (e.g., about 1 mA, about 2 mA, about 3 mA, about 4 mA, about 5 mA, about 6 mA, about 7 mA, about 8 mA, about 9 mA, about 10 mA, about 15 mA, about 20 mA, ranges between such values, etc.). Lower amplitudes may advantageously have less penetration depth, which can inhibit or avoid stimulation of nerves or other tissue that is not targeted. Higher amplitudes may advantageously be more likely to have a therapeutic effect. In some embodiments, the stimulation comprises a pulse width between about 0.5 ms and about 4 ms (e.g., about 0.5 ms, about 0.75 ms, about 1 ms, about 1.25 ms, about 1.5 ms, about 1.75 ms, about 2 ms, about 2.25 ms, about 3 ms, about 4 ms, ranges between such values, etc.). In some embodiments, lower amplitude (e.g., less than about 10 mA) can be used in combination with a pulse width according to a strength-duration curve to provide the desired effect. Lower amplitudes may advantageously have less penetration depth, which can inhibit or avoid stimulation of nerves or other tissue that is not targeted. Higher amplitudes may advantageously be more likely to have a therapeutic effect. In some embodiments, a lower amplitude (e.g., less than about 10 mA) can be used in combination with a pulse width according to a strength-duration curve to provide the desired effect.

In some embodiments, the stimulation comprises a frequency between about 2 Hz and about 40 Hz (e.g., about 2 Hz, about 5 Hz, about 10 Hz, about 15 Hz, about 20 Hz, about 25 Hz, about 30 Hz, about 40 Hz, ranges between such values, etc.). Lower frequencies (e.g., less than about 10 Hz) may advantageously have negligible effect on pain receptors that generally respond to much higher frequencies such that a subject is more tolerant of the therapy.

In some embodiments, the stimulation is ramped at a beginning and/or an end of the stimulation duration. For example, if stimulation duration is 10 seconds, the initial stimulation burst may be about 50% based on at least one parameter (e.g., ON duration, amplitude, pulse width, frequency, etc.), then increased or ramped up to 60%, 70%, etc. over the course of 2 seconds until reaching 100%. After 6 seconds at 100%, the stimulation may be decreased or ramped down to 95%, 90%, etc. over the course of 2 seconds until reaching 50%, after which the stimulation may be turned off. Ramping up and/or down may reduce side effects, increase subject tolerance, and/or avoid shocks to the system that may occur with an initial full burst. The duration of the ramp(s) may be based on a percentage of stimulation duration (e.g., 20% ramp up, 20% ramp down), absolute durations (e.g., 2 seconds ramp regardless of stimulation duration), or other factors. The ramp may be linear or take some other function (e.g., decreasing steps for a ramp up, increasing steps for a ramp down). In embodiments in which a ramp up and a ramp down are used, the ramp up may be different than the ramp down (e.g., starting percentage may be different than end percentage, ramp up duration may be different than ramp down duration, ramp up function may be different than ramp down duration, etc.).

Figure 33A:
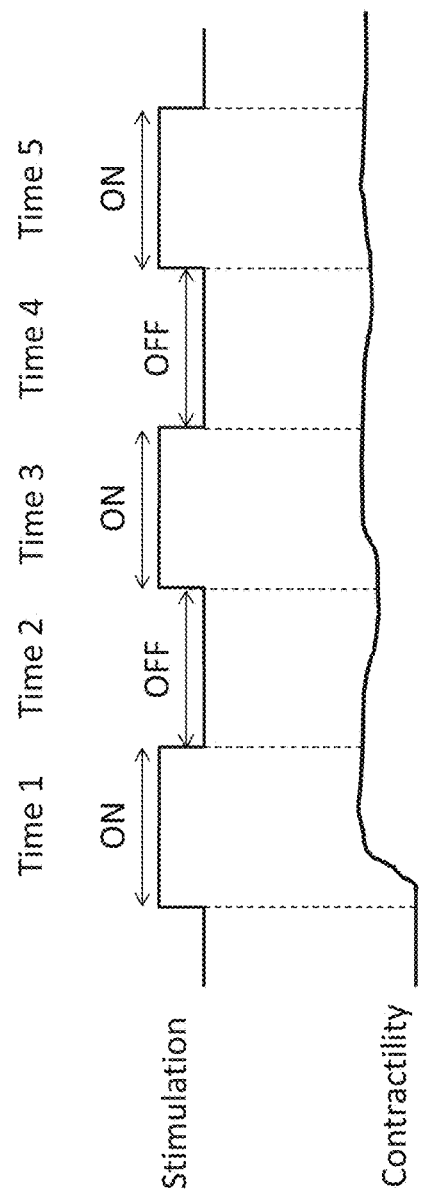
FIG. 33A is a plot of contractility versus stimulation.

FIG. 33A is a plot of contractility versus stimulation. Starting from a baseline contractility, the stimulation is turned ON for Time 1. There is some time delay for the stimulation to result in a change in contractility (e.g., about 10 to 20 seconds), after which contractility steadily climbs until reaching a fairly steady state. When contractility is turned OFF in time 2, there is some time delay before the contractility begins to decay. The decay delay when stimulation is OFF is longer than the delay when stimulation is ON. The time to ramp up to a baseline level during the decay is also less than from a baseline. The decay may also be reduced over time. Accordingly, the stimulation ON and OFF do not perfectly correlate to the durations when contractility changes.

In some embodiments, stimulation is turned ON for 5 seconds, followed by stimulation being turned OFF for 10 seconds. In some embodiments, stimulation is turned ON for 2 seconds, followed by stimulation being turned OFF for 5 seconds. In some embodiments, stimulation is turned ON for 10 seconds, followed by stimulation being turned OFF for 30 seconds. In some embodiments, stimulation is turned ON until a substantially steady state is achieved, followed by stimulation being turned OFF until a certain contractility is reached, at which point the stimulation is turned ON until the substantially steady state is again achieved, etc. Such an approach can reduce or minimize an effective dose. A duty cycle approach in view of this discovery can reduce the amount of time that stimulation is ON, which can reduce energy usage, maintain therapeutic effect, and/or reduce side effects, which can increase patient comfort and tolerability.

In some embodiments, a ramping feature could be used to slowly ramp the intensity of the stimulation ON and OFF, or to shut the stimulation OFF quickly. A ramping feature can allow the patient to adapt to stimulation and reduce sudden transitions. For example, at least one parameter (e.g., ON duration, amplitude, pulse width, frequency, etc.) could be slowly increased and/or decreased over time until building towards a final value.

In some embodiments, for example for short term treatment, a duty cycle may comprise alternating ON for 5 seconds and OFF for 5 seconds for 1 hour. In some embodiments, for example for short term treatment, a duty cycle may comprise alternating ON for 5 seconds and OFF for 10 seconds for 1 hour. In some embodiments, for example for short term treatment, a duty cycle may comprise alternating ON for 10 minutes and OFF for 50 minutes for 1 hour. In some embodiments, for example for long term treatment, a duty cycle may comprise alternating ON for 1 hour and OFF for 1 hour for 1 day. In some embodiments, for example for long term treatment, a duty cycle may comprise alternating ON for 1 hour and OFF for 1 hour for 1 day. In some embodiments, for example for long term treatment, a duty cycle may comprise alternating ON for 1 hour and OFF for 23 hours for 1 day. The ON durations in long term treatment may include the cycling of the short term treatments. For example, if alternating ON for 1 hour and OFF for 1 hour for 1 day, the durations in which stimulation is ON for 1 hour may comprise alternating ON for 5 seconds and OFF for 5 seconds for that 1 hour. In some embodiments, a plurality of different ON/OFF cycles may be used during a long term ON duration, for example 10 seconds ON and 10 seconds OFF for 1 minute, then 1 minute ON and 5 minutes OFF for 10 minutes, then 10 minutes ON and 50 minutes OFF for 4 hours, for a long term ON duration of 4 hours and 11 minutes. Short term and/or long term ON/OFF cycles may be at least partially based on a patient state (e.g., awake or sleeping, laying down or upright, time since initial stimulation, etc.).

Figure 33B:
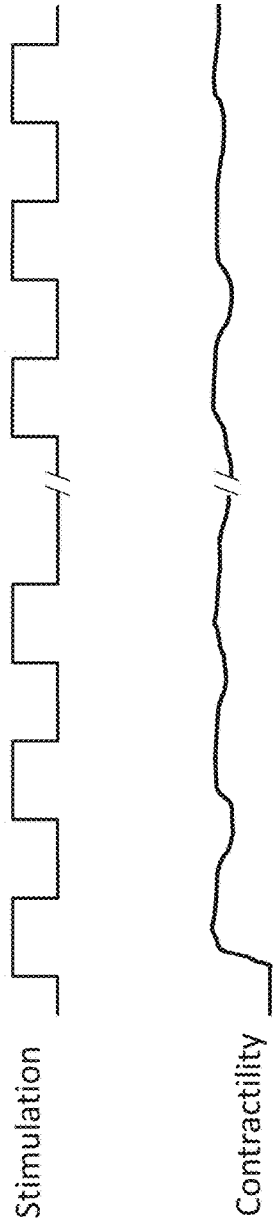
FIG. 33B is another plot of contractility versus stimulation.

FIG. 33B is a plot of contractility versus stimulation using a threshold-based approach and an optimized duty cycle. Stimulation is turned ON and OFF for some duration. As noted above, the decay of contractility after the duration is reduced such that contractility remains above a threshold for a certain duration. This duration may be known or determined, for example by sensing contractility. The broken line in FIG. 33B shows a time when the determination is made to restart the stimulation cycle for another duration. This process may be repeated for the time that the subject is being treated, until a recalibration, etc.

Figure 34:
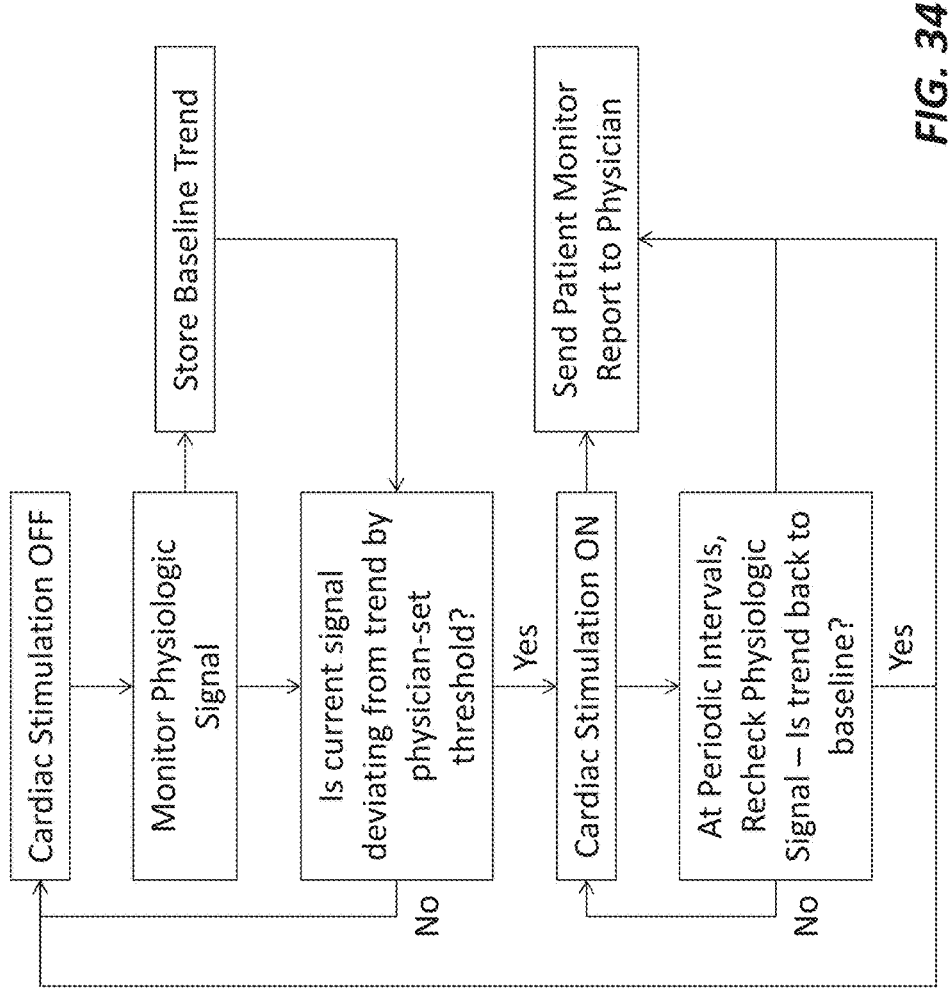
FIG. 34 is an example process flow that can be used to implement a duty cycle method.

FIG. 34 is an example process flow that can be used to implement a duty cycle method, for example as described with respect to FIGS. 33A and 33B. Stimulation is turned ON for 5 seconds, then OFF for 5 seconds, then repeated for 10 minutes, after which stimulation is turned OFF for one hour. The process flow of FIG. 34 then begins. Starting with cardiac stimulation OFF, a physiologic signal is monitored. A baseline trend is stored. The current signal is checked for deviation from the trend by a physician-set threshold (e.g., less than or greater than a certain quantity, percentage, etc.). If the current signal has not deviated, the cardiac stimulation remains OFF and the physiologic signal continues to be monitored and the baseline trend stored until the current deviates. When the current deviates from the trend, cardiac stimulation is turned ON. A patient monitor report is sent to the physician. At periodic intervals, the physiologic signal is rechecked to see if the trend is back to baseline. If the trend is not back to baseline, the cardiac stimulation remains ON. If the trend is back to baseline, the cardiac stimulation is turned OFF and the process starts all over.

In some embodiments, the system comprises one or more of the following: means for modulation (e.g., an electrode or other type of stimulation catheter or delivery device), means for fixation (e.g., barbs, prongs, anchors, conical structures, or other types of fixation mechanisms), means for sensation (e.g., a sensor integral with a catheter, on a separate catheter, external to a subject), and means for calibration (e.g., predetermined or logical sequences of determining stimulation parameters).

Several embodiments of the invention are particularly advantageous because they include one, several, or all of the following benefits: (i) increasing contractility (e.g., left ventricle), (ii) not affecting heart rate or affecting heart rate less than contractility, (iii) providing an anchoring or fixation system to resist movement, (iv), and/or (x)

FIG. 35A schematically illustrates a mechanically repositionable electrode catheter system 3500. The system 3500 comprises a proximal portion a handle or hub 3502. The handle 3502 includes a mechanical repositioning system 3504 including a track or channel or groove 3510 and a knob 3512 slideable within the groove 3510. The system 3500 further comprises a sheath 3506 and an electrode system 3508. The electrode system 3508 may be movable in and out of the sheath 3506. FIG. 35A shows the electrode system 3508 already expanded out of the sheath 3506. The knob 3512 is coupled to the electrode system 3508 such that longitudinal and/or rotational movement of the knob 3512 results in corresponding longitudinal and/or rotational movement of the electrode system 3508. The sheath 3506 may be separately anchored in the vasculature, for example as described herein, such that only the electrode system 3508 moves upon movement of the knob 3512.

In some embodiments, longitudinal movement of the knob 3512 results in the same or 1:1 longitudinal movement of the electrode system 3508. In some embodiments, gears or other mechanical devices can be used to make the movement ratio more than 1:1 or less than 1:1. Pulleys and other mechanical devices can be used to reverse movement of the knob 3512. FIG. 35A shows a detent groove 3522 in the sheath 3506, which can interact with a detent coupled to the electrode system 3508 and/or the knob 3512, for example as described with respect to FIG. 35B. In FIG. 35A, the knob 3512 has already been longitudinally advanced enough, from a proximal position, that the electrode system 3508 is deployed out of the sheath 3506.

In some embodiments, the electrodes of the electrode system 3508 may be stimulated to test the effect of certain pairs of electrodes. If none of the electrodes pairs has an effect, the electrode system 3508 may be moved using the repositioning system 3504 and the test rerun. In some embodiments, a distal-most electrode pair may have the most effect, but not as large an effect as may have been expected. The electrode system 3508 may be advanced distally to better test the effects of the electrodes distal to the original site.

FIG. 35B illustrates the catheter system 3500 of FIG. 35A after longitudinal advancement. Compared to FIG. 35A, the knob 3512 has longitudinally advanced a distance 3514. Movement of the knob 3512 can be manual, electronic, mechanical, combinations thereof, and the like. The electrode system 3508 has also longitudinally advanced a distance 3514. The electrode system 3508 is coupled to a detent 3520. For example, the detent 3520 may be coupled to a hypotube, a wire, etc. When the detent 3520 reaches a certain longitudinal position, the detent 3520 may extend into the detent groove 3522 in the sheath 3506. The extension may produce an audible click or other identifiable sound. In some embodiments, a number of audible clicks (e.g., 1, 2, 3, or more) can inform the user that the electrode system 3508 is fully deployed. In some embodiments, the detent interaction may be indicative that an event has occurred to provide deterministic position, for example longitudinal advancement of a certain distance (e.g., a cm, an inch, etc.), longitudinal advancement enough to fully deploy the electrode system 3508, longitudinal advancement to a rotational movement track, etc. The system 3500 may comprise multiple detents 3520 and/or multiple detent grooves 3522. In some embodiments, a detent system can inhibit undesired or accidental movement of the electrode system 3508.

In some embodiments, rotational movement of the knob 3512 or movement of the knob 3512 transverse to longitudinal movement can result in rotational movement of the electrode system 3508 in the same rotational or transverse direction. Twisting and turning of the sheath 3506 may result in a movement ratio that is not 1:1. The catheter system 3500 may comprise a rotational hard stop to limit rotational movement of the electrode system 3508, for example as described with respect to FIGS. 35C and 35D.

FIG. 35C illustrates the catheter system 3500 of FIG. 35A after longitudinal advancement and rotation. FIG. 35D is a cross-sectional view taken along the line 35D-35D of FIG. 35C. Compared to FIG. 35A, the knob 3512 has longitudinally advanced and rotated. The electrode system 3508 has also longitudinally advanced and rotated. The rotation of the knob 3512 may be greater than the rotation of the electrode system 3508. In some embodiments, the system 3500 comprises a rotational hard stop 3524, for example in the sheath 3506. Even if the knob 3512 was able to rotate further in the track groove 3510, the hard stop 3524 would inhibit or prevent further rotation of the electrode system 3508. Such a system can provide a predictable amount of rotational repositioning. The system 3500 may comprise a stop 3516 (e.g., comprising a physical barrier) or other means for inhibiting or preventing accidental or unwanted movement of the knob 3512 and/or movement of the electrode system 3508.

Figure 36A:
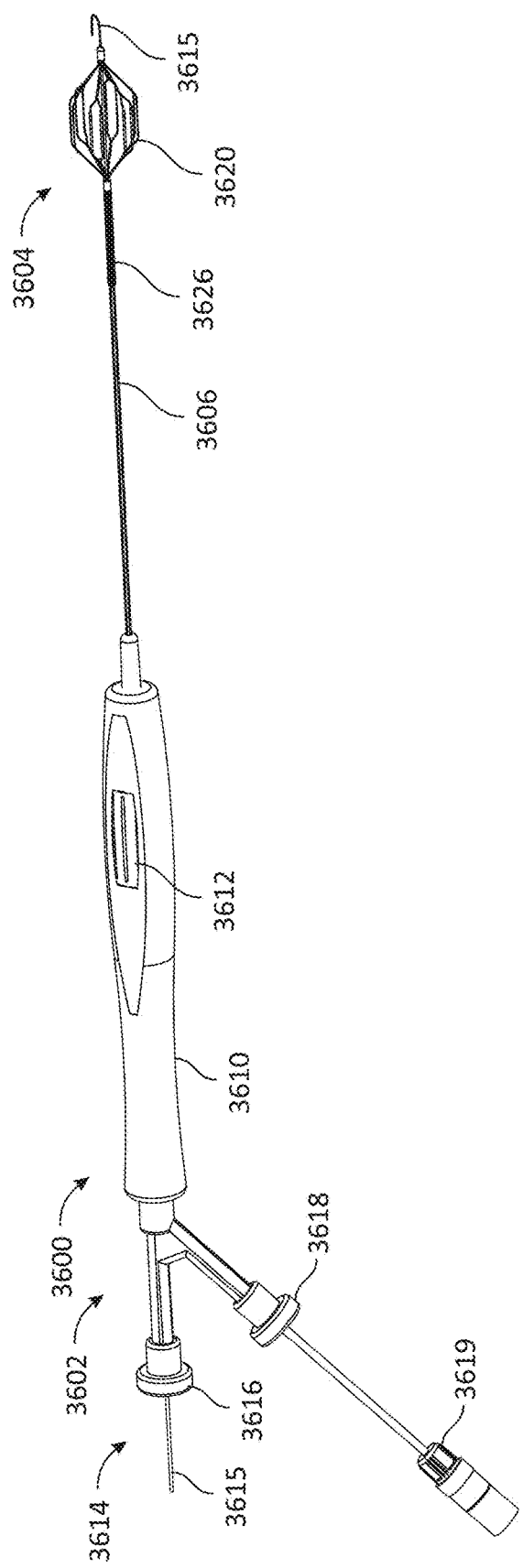
FIG. 36A is a perspective view of an example of a catheter system.

FIG. 36A is a perspective view of an example of a catheter system 3600. The system 3600 comprises a proximal portion 3602 configured to remain out of the body of a subject and a distal portion 3604 configured to be inserted into vasculature of a subject. The distal portion 3604 comprises an expandable structure 3620. The proximal portion comprises a handle 3610 and an actuation mechanism 3612. The proximal portion 3602 is coupled to the distal portion 3604 by a catheter shaft 3606. In some embodiments, the system 3600 comprises a strain relief 3626 between the catheter shaft 3606 and the expandable structure 3620. The proximal portion 3602 may comprise an adapter comprising a plurality of ports, for example the Y-adapter comprising a first Y-adapter port 3616 and a second Y-adapter port 3618. The first Y-adapter port 3616 may be in communication with a lumen configured to allow insertion of a guidewire 3615 through the system 3600. The second Y-adapter port 3618 may comprise an electronics connector 3619, which can be used to couple an electrode matrix of the system 3600 to a stimulator system.

Figure 36B:
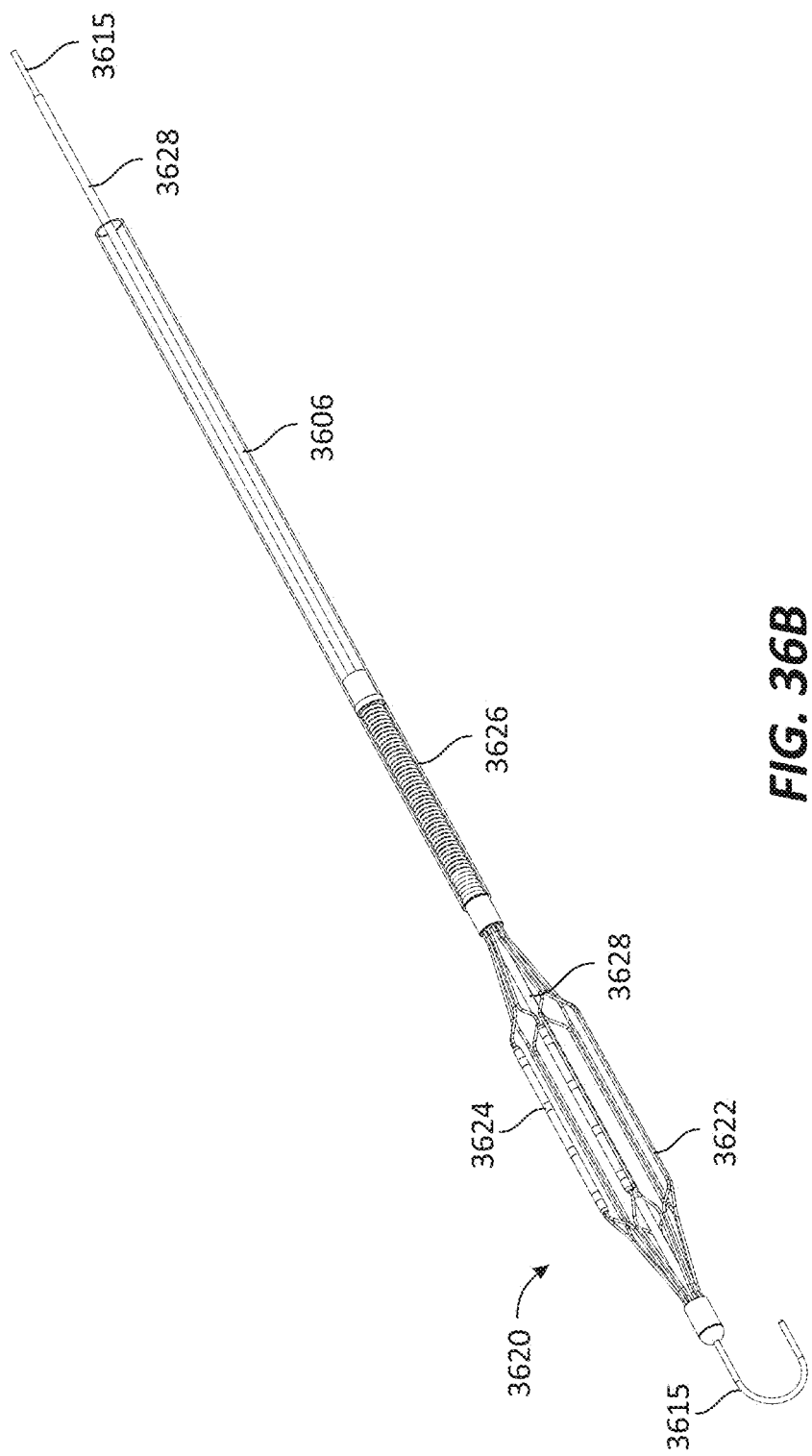
FIG. 36B is a perspective view of a portion of the catheter system of FIG. 36A in a collapsed state.

FIG. 36B is a perspective view of a portion of the catheter system 3600 of FIG. 36A in a collapsed state. The illustrated portion includes part of the catheter shaft 3606, the strain relief 3626, and the expandable structure 3620. The strain relief 3626 may be at least partially in a lumen of the catheter shaft 3606. The expandable structure 3620 includes a plurality of splines 3622. Four of the splines 3622 comprise an electrode array 3624 comprising four electrodes to form a 4×4 electrode matrix. The number of electrodes in the electrode matrix, electrode sizing, electrode spacing, etc. may be in accordance with other systems described herein. For example, in some embodiments, the expandable structure 3620 comprises a mesh or membrane comprising electrodes that is stretched across two or more of the splines 3622. The illustrated portion also includes an actuator wire 3628, which can be coupled to the actuator mechanism 3612 to cause expansion or retraction of the expandable structure 3620. The actuator wire 3628 may be in a lumen of the catheter shaft 3606. A guidewire 3615 is also shown in the lumen of the actuator wire 3628. In some embodiments, the actuator wire 3628 comprises a lumen capable of receiving a 0.018 inch guidewire 3615.

FIG. 36C is a side view of a portion of the catheter system 3600 of FIG. 36A in an expanded state. Operation of the actuation mechanism 3612 can cause the expandable structure 3620 to expand and contract. For example, rotation and/or longitudinal movement of the actuation mechanism 3612 can cause the actuator wire 3628 to proximally retract, which can push the splines 3622 radially outward. In some embodiments, the distal ends of the splines 3622 are coupled to a distal hub that is coupled to the actuator wire 3628, and the proximal ends of the splines 3622 are coupled to a proximal hub that is coupled to the catheter shaft 3606. In the expanded state, the expandable structure 3620 comprises splines 3622 that are spaced from each other generally parallel to a longitudinal axis at a radially outward position of the splines 3622. The parallel orientation of the splines 3622 can provide circumferential spacing of the splines 3622, for example in contrast to singular splines or wires that may circumferentially bunch. In some embodiments, the splines 3622 comprise wires having a diameter between about 0.006 inches (approx. 0.15 mm) and about 0.015 inches (approx. 0.38 mm) (e.g., about 0.006 inches (approx. 0.15 mm), about 0.008 inches (approx. 0.2 mm), about 0.01 inches (approx. 0.25 mm), about 0.012 inches (approx. 0.3 mm), about 0.015 inches (approx. 0.38 mm), ranges between such values, etc.). A frame comprising openings between arms or splines can help with fixation of the expandable structure 3620. For example, vessel tissue can deform such that some vessel tissue enters into the openings, which can provides a good fixation.

In some embodiments, the diameter 3621 of the expandable structure 3620 in the expanded state is between about 15 mm and about 30 mm (e.g., about 15 mm, about 20 mm, about 22 mm, about 24 mm, about 26 mm, about 28 mm, about 30 mm, ranges between such values, etc.). In some embodiments, the splines 3622 may be self-expanding such that the actuation mechanism 3612 or another mechanism (e.g., retraction of a sheath over the splines 3622) allows the splines to self-expand from a compressed state for navigation to a target site to an expanded state for treatment at the target site. In certain such embodiments, the diameter of the expandable structure 3620 in the expanded state may be oversized to most the intended vasculature of most subjects to ensure vessel wall apposition. In some embodiments, the splines 3622 may be non-self-expanding such that the splines only expand upon operation of the actuation mechanism 3612. In some embodiments, the splines 3622 may be self-expanding, and the actuation mechanism 3612 may further expand the splines 3622, which may provide an adjustable expandable structure 3620 diameter usable for a range of vessel sizes, wall apposition forces, etc. Embodiments in which the expandable structure 3620 does not appose the wall in the event of an error could be advantageous for safety, for example as described with respect to the system 2200. In some embodiments, the wires are not fixed distally (e.g., to a distal hub), which can allow each wire to move independently, which may accommodate curvature at a deployment site. Upon expansion of the expandable structure 3620, the electrodes of the electrode matrix may be selectively activated for testing nerve capture, calibration, and/or therapy, for example as described herein.

Figure 36E:
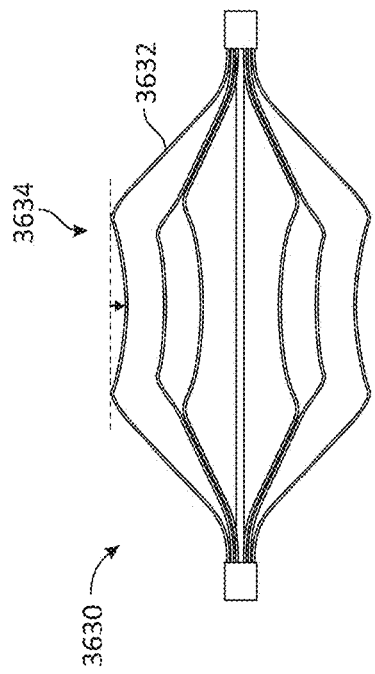
FIG. 36E schematically illustrates a side view of another example of an expandable structure.
Figure 36G:
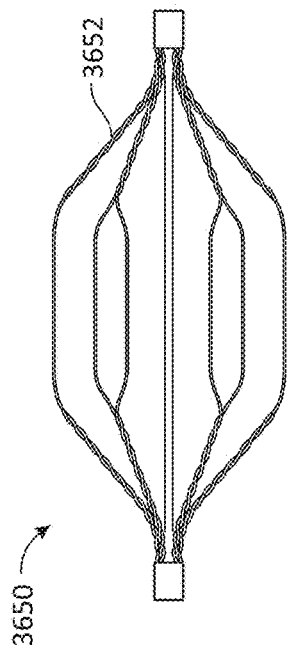
FIG. 36G schematically illustrates a perspective view of yet another example of an expandable structure.
Figure 36D:
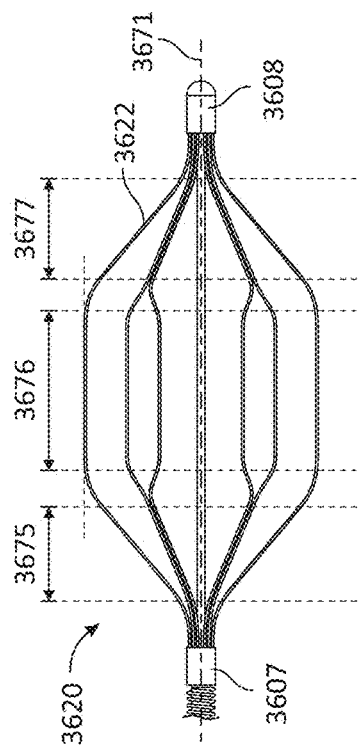
FIG. 36D schematically illustrates a side view of an example of an expandable structure.

FIG. 36D schematically illustrates a side view of an example of an expandable structure 3620. The expandable structure 3620 comprises eight splines 3622 extending from a proximal hub 3607 to a distal hub 3608. The splines 3622 are grouped in pairs that run generally parallel to each other. Pairs of the splines 3622 may be different wires or the same wire (e.g., bent at the proximal end or the distal end), for example as described herein. The splines 3622 extend laterally and only outwardly from the proximal hub 3607 at a first angle to the longitudinal axis 3671, or parallel to the longitudinal axis 3671 and then bend to form the first angle after a short length. The splines 3622 continue at that angle for a first length 3675. In some embodiments, an angle between the longitudinal axis 3671 and the first length 3675 is between about 10° and about 60° (e.g., about 10°, about 20°, about 30°, about 40°, about 50°, about 60°, ranges between such values, etc.).

After the first length 3675, the splines 3622 of each pair of parallel splines circumferentially diverge at second angles from an axis aligned with the splines along the first length 3675, coming out of plane with the longitudinal axis 3671. The second angles may be the same or different. After a short length, the splines 3622 bend again at third angles relative to the axis of the first length 3675 to return the splines 3622 to being parallel with each other. The third angles may be the same or different. In some embodiments, a difference between the second angles and a difference between the third angles are complementary. The splines 3622 are parallel for a second length 3676 at a fourth angle with the longitudinal axis 3671, the fourth angle being about 0°. In some embodiments, an angle between the first length 3675 and the second length 3676 is between about 120° and about 170° (e.g., about 120°, about 130°, about 140°, about 150°, about 160°, about 170°, ranges between such values, etc.).

After the second length 3676, the splines 3622 bend at fifth angles coming out of plane with the longitudinal axis 3671 for a short distance until the splines 3622 converge. The fifth angles may be the same or different. In some embodiments, one or both of the fifth angles is the same as one or both of the third angles. After the splines 3622 converge, the splines 3622 bend at seventh angles, which return the splines 3622 to being parallel with each other and coming into plane with the longitudinal axis 3671 for a third length 3677, still at the fifth angle with respect to the longitudinal axis 3671. In some embodiments, an angle between the longitudinal axis 3671 and the third length 3677 is between about 10° and about 60° (e.g., about 10°, about 20°, about 30°, about 40°, about 50°, about 60°, ranges between such values, etc.). In some embodiments, an angle between the third length 3677 and the second length 3676 is between about 120° and about 170° (e.g., about 120°, about 130°, about 140°, about 150°, about 160°, about 170°, ranges between such values, etc.). The first length 3665 may be the same as or different from the third length 3667. After the third length 3677, the splines 3622 bend into the distal hub 3608 at the fifth angle or bend to extend into the distal hub 3608 parallel to the longitudinal axis 3671.

The angles described herein may refer to the shape of the expandable structure 3620 in the absence of forces. Forces applied by a sheath and/or actuator wire 3628 may increase or decrease the angles. For example, restraint of the expandable structure 3620 in a sheath may reduce the angles of the first length 3675 and the third length 3677 relative to the longitudinal axis 3671. For another example, longitudinal extension of the distal hub 3608 relative to the proximal hub 3607 (e.g., by distally advancing the actuator wire 3628) may reduce the angles of the first length 3675 and the third length 3677 relative to the longitudinal axis 3671. For yet another example, longitudinal retraction of the distal hub 3608 relative to the proximal hub 3607 (e.g., by proximally retracting the actuator wire 3628) may increase the angles of the first length 3675 and the third length 3677 relative to the longitudinal axis 3671.

The area created by the pairs of splines 3622 diverging, being parallel, and then converging, may be a cell. The splines 3622 may comprise electrodes along at least the second length 3672. This pattern may be produced using any number of splines 3622. Other bend patterns are also possible. For example, the splines 3622 may bend to become parallel with the longitudinal axis 3671 before diverging and/or remain parallel with the longitudinal axis 3671 until converging and/or may converge and/or diverge at a non-parallel angle to the first length 3675 and the second length 3677. For another example, the splines 3622 may diverge along the first length 3675 and/or converge along the third length 3677. For yet another example, a single wire may be bent back and forth to form the splines 3622. For still another example, the bends may be more gently curved than angular. The elongated contact between the splines 3622 along the second length 3676 and the vessel walls can inhibit or prevent wobble of the longitudinal axis 3671 of the expandable structure 3620. In some embodiments, the expandable structure 3620 comprises parallel portions for splines 3622 that comprise electrodes, but splines 3622 that do not comprise electrodes, for example splines 3622 that are used for vessel wall apposition, may comprise parallel wires, non-parallel wires, wires with other shapes, wires with different diameters, different numbers of wires (e.g., more or fewer), etc. In certain such embodiments, the expandable structure 3620 may be radially and/or circumferentially asymmetrical.

FIG. 36E schematically illustrates a side view of another example of an expandable structure 3630. The portions of the splines 3632 of the expandable structure 3630 comprising electrodes (e.g., as shown in FIG. 36C) are radially inward from an outer diameter in the expanded state. The intersection of the recessed portions and the outer diameter can create anchor points 3634, which can help to secure the position of the expandable structure 3630. In some embodiments, an expandable structure 3620 may take the shape of the expandable structure 3630.

Figure 36F:
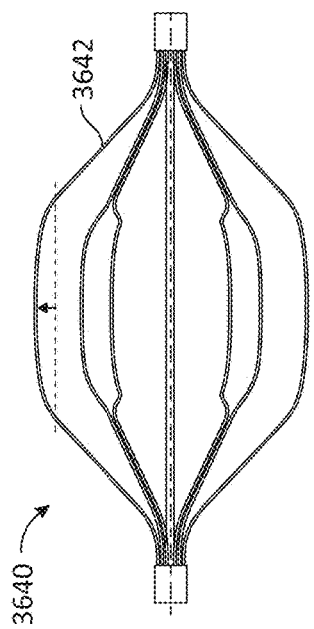
FIG. 36F schematically illustrates a side view of still another example of an expandable structure.

FIG. 36F schematically illustrates a side view of still another example of an expandable structure 3640. The portions of the splines 3642 of the expandable structure 3640 comprising electrodes (e.g., as shown in FIG. 36C) protrude radially outward or are crowned in the expanded state. In some embodiments, an expandable structure 3640 may take the shape of the expandable structure 3620, for example because the generally straight vessel wall may straighten the portions of the splines 3642. A crowned expandable structure 3640 may counteract forces on an expandable structure 3620 that may result in the shape of the expandable structure 3630 in a vessel, which may increase apposition area and/or reduce longitudinal wobble.

FIG. 36G schematically illustrates a perspective view of yet another example of an expandable structure 3650. The expandable structures 3620, 3630, 3640 are illustrated as having splines 3622, 3632, 3642 that are parallel until diverging to form the parallel portions. The expandable structure 3650 comprises twisted wires 3652 rather than parallel wires, which can make the expandable structure 3650 stiffer while still providing some amount of movement as the wires are able to slightly slide along and around each other. A stiffer expandable structure 3650 may help with circumferential spacing of the parallel portions and electrodes of the electrode matrix. In some embodiments, wires of the expandable structure 3650 or the expandable structures 3620, 3630, 3640 can be coupled (e.g., using a coupling structure), crimped, welded, soldered, adhered, combinations thereof, and the like, which can also or alternatively increase stiffness.

FIG. 36H schematically illustrates an example of an expandable structure pattern. The pattern is also illustrated in the expandable structures 3620, 3630, 3640, and includes parallel portions having proximal starting and distal ending points that are generally circumferentially aligned. Circumferential alignment may reduce manufacturing complexity, for example because the expandable structure 3620 is symmetrical so the same tooling and setup may be used to shape each wire. Circumferential alignment may provide electrode matrix flexibility, for example if each of the splines comprises the same electrode array such that any rotational position is acceptable.

FIG. 36I schematically illustrates another example of an expandable structure pattern. The middle parallel portions have proximal starting and distal ending points that are shifted distally from the proximal starting and distal ending points, respectively, of the top and bottom parallel portions.

Staggering the starting and/or ending points can allow the splines to nest in a collapsed state, which can reduce system diameter. Staggering the starting and/or ending points can reduce the chances that an electrode may snag during expansion and/or collapse of the expandable structure.

FIG. 36J schematically illustrates another example of an expandable structure pattern. The middle parallel portions have proximal starting points that are shifted proximally and distal ending points that are shifted distally from the proximal starting and distal ending points, respectively, of the top and bottom parallel portions. Staggering the starting and/or ending points can allow the splines to nest in a collapsed state, which can reduce system diameter. Staggering the starting and/or ending points can reduce the chances that an electrode may snag during expansion and/or collapse of the expandable structure.

FIG. 36K schematically illustrates another example of an expandable structure pattern. The wires includes parallel portions as in the expandable structures 3620, 3630, 3640, and the portions of the wires proximal and distal to the parallel portions do not circumferentially converge for each set of parallel portions. Wires that do not converge or wires that converge less or partially (e.g., at one end of each set of parallel portions) can reduce forces (e.g., rotational or twisting forces) that may otherwise cause uneven spacing of the parallel portions in an expanded state.

FIG. 36L schematically illustrates another example of an expandable structure pattern. The parallel portions comprise a third non-diverging spline between the diverging parallel portions. In embodiments in which each of the splines includes electrodes, a third spline can increase the number of rows in an electrode matrix and/or provide more flexibility in electrode positioning. More or fewer wires or splines are also possible. Some or all of the wires or splines may include electrodes and/or may be coupled to a membrane or mesh comprising electrodes.

FIG. 36M schematically illustrates another example of an expandable structure pattern. As opposed to comprising a plurality of wires, the splines comprise flat surfaces of a cut hypotube. In some embodiments, a plurality of electrodes is positioned on an outer side of one or more splines. A wide variety of cut patterns are possible. For example, splines comprising electrodes may be shaped to correspond to the electrode shapes and/or pattern. In some embodiments, the splines may comprise flat wires (e.g., having a rectangular cross-section). In some embodiments, the splines may comprise U-shaped wires (e.g., as described herein).

FIG. 36N schematically illustrates an example of an expandable structure. The expandable structure comprises a mesh 3660 coupled to the splines. The mesh 3660 may comprise an electrode matrix in accordance with the disclosure herein. In some embodiments, a first circumferential edge of the mesh 3660 may be coupled to a first spline and a second circumferential edge of the mesh 3660 may be coupled to a second spline such that the remainder of the mesh can slide with respect to other splines.

FIG. 36O schematically illustrates an example of an expandable structure pattern. The splines comprise a sinusoidal or wave or undulating or zig-sag shape. The undulating wires may provide more flexibility in electrode positioning. For example, electrodes may be placed at peaks, troughs, and/or rising or falling portions. The undulating wires may provide better wall apposition than parallel portions due to more surface area contact with the vessel wall.

Figures 36P, 36Q:
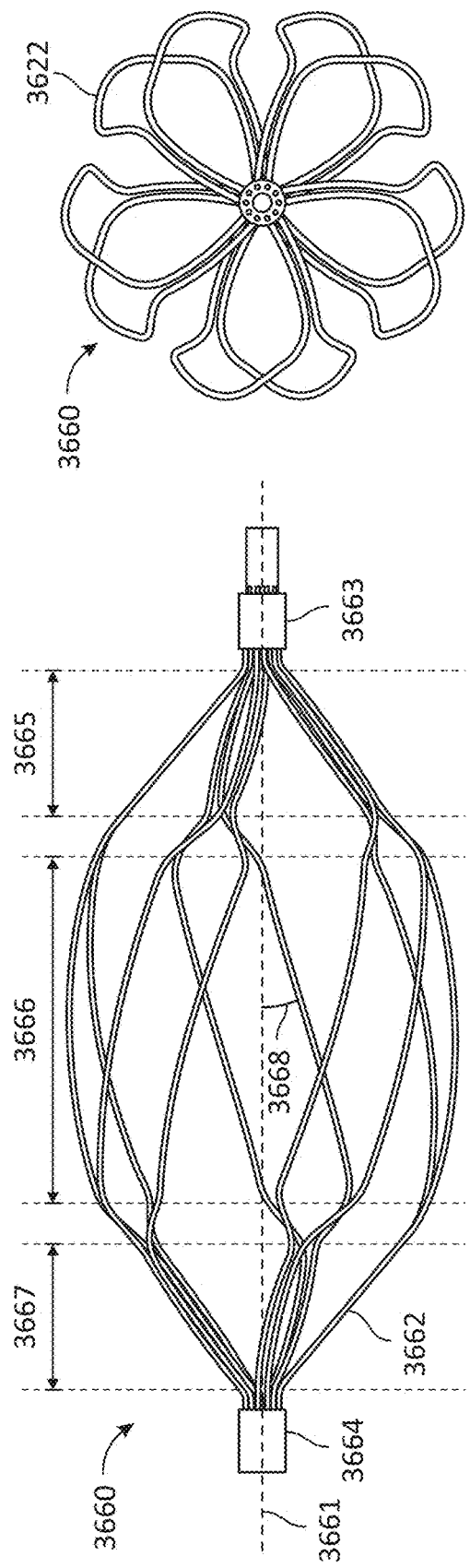
FIG. 36P schematically illustrates a side view of an example of an expandable structure.
FIG. 36Q is a proximal end view of the expandable structure of FIG. 36P.

FIG. 36P schematically illustrates a side view of an example of an expandable structure 3660. FIG. 36Q is a proximal end view of the expandable structure 3660 of FIG. 36P. The expandable structure 3660 comprises ten splines 3662 extending from a proximal hub 3663 to a distal hub 3664. The splines 3662 are grouped in pairs that run generally parallel to each other. Pairs of the splines 3662 may be different wires or the same wire (e.g., bent at the proximal end or the distal end), for example as described herein. The splines 3622 may each have a proximal starting point and distal ending point that are not circumferentially aligned. The splines 3662 extend from the proximal hub 3663 at a first angle to the longitudinal axis 3661, or straight and then bend to the first angle after a short length. The splines simultaneously extend in a circumferential direction at a second angle relative to a circumferential origin. The splines 3662 continue at those angles for a first length 3665. After the first length 3665, half of the splines 3662, one from each pair of parallel splines 3662, bends in a circumferential direction at a third angle greater than the second angle, and the other half of the splines 3662, the other from each pair of parallel splines 3662, bends at a fourth angle opposite the second angle. These bends cause the pairs of splines 3662 to circumferentially diverge.

After a short length, the splines 3622 bend again, at a fifth angle and a sixth angle, so that the pairs of splines 3662 are parallel to each other, at a seventh angle 3668 relative to the longitudinal axis 3661, for a second length 3666. The second length 3666 may be the same as or different than (e.g., greater than) the first length 3665. The seventh angle 3668 may be the same as or different than the first angle. The seventh angle 3668 may be between about 5° and about 60° (e.g., about 5°, about 10°, about 15°, about 20°, about 25°, about 30°, about 35°, about 40°, about 45°, about 50°, about 55°, about 60°, ranges between such values, etc.). After the second length 3666, the splines 3662 again bend in opposite circumferential directions, at an eight angle and an ninth angle opposite to the seventh angle, to circumferentially converge at a tenth angle relative to the longitudinal axis 3661. The areas created by the pairs of splines 3662 diverging, being parallel, and then converging, may be a cell. The splines 3662 may comprise electrodes along at least the second length 3666. The tenth angle may be the same or different as the first angle. After a short length, the splines 3662 bend again, at an eleventh angle and a twelfth angle, so that the pairs of splines 3662 are again parallel to each other, at the tenth angle relative to the longitudinal axis 3661 and a thirteenth angle relative to the circumferential origin, for a third length 3667. The third length 3667 may be the same as or different than the first length 3665. The second length 3666 may be the same as or different than (e.g., less than) the second length 3666. In the embodiment illustrated in FIG. 36P, the first length 3665 is about the same as the third length 3667, and the second length 3666 is greater than each of the first length 3665 and the third length 3667. The thirteenth angle may be the same as or different than the seventh angle. The thirteenth angle may be the same as or different than the second angle. The splines 3662 extend into distal hub 3664 at the tenth angle relative to the longitudinal axis 3661 and the thirteenth angle relative to the circumferential origin, or bend to extend straight into the distal hub 3664.

The starting proximal point and distal ending point for each spline 3622 may be circumferentially offset, for example depending on the bend angles and lengths. This pattern may be produced using any number of splines 3662. Splines 3662 at an angle to the longitudinal axis 3661 may provide better wall apposition than splines that extend parallel to the longitudinal axis, for example due to increased surface area contact with the vessel wall. Although the expandable structure 3660 may be considered an angled, 5-pair version of the expandable structure 3620, for example, any of the expandable structures described herein may be angled as appropriate. In some embodiments, the splines 3662 may be shape set to be angled. In some embodiments, the splines 3662 may be angled during use, for example by rotating the distal hub 3664 relative to the proximal hub 3663.

Combinations of the expandable structure patterns described herein and other expandable structure patterns are also possible. For example, an expandable structure may comprise longitudinal offset and three wires. For another example, an expandable structure may comprise longitudinal offset and undulating wires. In some embodiments, an anchor (e.g., barb) may be integrated with splines of an expandable structure.

FIG. 37A is a perspective view of an example of catheter system 3700. The catheter system 3700 may share at least some similar features with the catheter system 3600 and/or other catheter systems described herein. The system 3700 comprises a proximal portion 3702 configured to remain out of the body of a subject and a distal portion 3704 configured to be inserted into vasculature of a subject. The distal portion 3704 comprises an expandable structure 3720. The proximal portion comprises a handle 3710. A catheter shaft assembly 3706 extends from the handle 3710 to the proximal end of the expandable structure 3720. An actuation tube 3728 extends from the handle 3710 through the catheter shaft assembly 3706 to the distal end of the expandable structure 3720. The proximal end 3702 further comprises an electrical socket 3799, which is configured to connect to an electrical plug of a neurostimulator (e.g., radiofrequency generator or other appropriate source depending on the stimulation or ablation modality).

FIG. 37B schematically illustrates a side view of expandable structure 3720 and FIG. 37C shows a proximal end view of expandable structure 3720. The expandable structure 3720 includes a plurality of splines 3722 extending from a proximal hub 3740 to a distal hub 3750. Some splines 3722 of the expandable structure 3720 may include electrodes 3724 configured to stimulate a target nerve. Some of the splines 3722 may be devoid of, free from, or not include electrodes 3724. In some embodiments, the expandable structure 3720 includes ten splines 3722, of which four circumferentially adjacent splines 3722 each comprise five electrodes 3724. The splines 3722 may comprise proximal segments, intermediate segments, and distal segments. The intermediate segments may be configured to extend radially outward when the expandable structure 3720 is in a self-expanded state. The proximal segment of a spline 3722 may form a first angle with the intermediate segment and the distal segment may form a second angle with the intermediate segment. In some embodiments, the proximal segment and distal segment may be straight and the intermediate segment may be convex, bending radially outward. In some embodiments, the proximal segment and distal segment may be straight and the intermediate segment may be concave, bending radially inward. In some embodiments, the proximal segment, intermediate segment, and distal segment may all be straight. Splines 3722 which comprise electrodes 3724 may comprise proximal segments and distal segments devoid of electrodes 3724. The splines 3722 may further comprise proximal transitional segments, joining the proximal segments and intermediate segments, and distal transitional segments, joining the intermediate segments and distal segments.

The splines 3722 comprising electrodes 3724 may be configured to extend outwardly on one side of a plane crossing a longitudinal axis of the expandable structure 3720. The splines 3722 not comprising electrodes 3724 may be configured to extend outwardly on a second side of the plane opposite the one side. For example, the splines 3722 not comprising electrodes 3724 illustrated in FIG. 37C could be less circumferentially spaced to be on the same side of a plane crossing the longitudinal axis at the center of the expandable structure 3720. The splines 3722 comprising electrodes 3724 may circumferentially occupy less than 180° on the one side. For example, the splines 3722 comprising electrodes 3724 may circumferentially occupy about 30° to about 170° (e.g., about 30°, about 45°, about 60°, about 90°, about 100°, about 110°, about 120°, about 150°, about 170°, ranges between such values, etc.). The four splines 3722 comprising electrodes 3724 illustrated in FIG. 37C circumferentially occupy about 110°.

Other numbers of splines 3722 comprising electrodes 3724 are also possible. For example, all of the splines 3722 or a subset of the splines 3722 (e.g., 1, 2, 3, 4, 5, 6, 7, 8, 9, or 10 of the splines 3722) may comprise an electrode 3724. In embodiments comprising more than 10 splines, more than 10 splines may comprise an electrode. All of the splines 3722 or a percentage of the splines 3722 (e.g., 10%, 20%, 30%, 40%, 50%, 60%, 70%, 80%, 90%, or 100% of the splines 3722) may comprise an electrode 3724. The splines 3722 that comprise an electrode 3724 may be circumferentially adjacent or have one or more non-electrode splines 3722 therebetween.

The splines 3722 may comprise between one electrode 3724 and twenty electrodes 3724 (e.g., 1 electrode, 2 electrodes, 3 electrodes, 4 electrodes, 5 electrodes, 6 electrodes, 7 electrodes, 8 electrodes, 9 electrodes, 10 electrodes, 15 electrodes, 20 electrodes, ranges between such values, etc.). More electrodes 3724 can provide more stimulation options and/or more targeted nerve capture. Fewer electrodes 3724 can reduce the number of electrical connectors, which can reduce device profile and/or reduce valuable device volume taken by electrical connectors.

FIG. 37D is a perspective view of a wire bent to form a spline pair 3727. A single wire may be bent at a bend 3725 to form a spline pair 3727 comprising a first spline 3722A from a first portion of the wire and a second spline 3722B from a second portion of the wire. The bend 3725 may be positioned at the proximal end of the spline pair 3727, such that a proximal-facing end of the spline pair 3727 is an atraumatic bend as opposed to possibly traumatic wire ends. The bend 3725 may be positioned at the distal end of the spline pair 3727. The spline pair 3727 may be formed with two or more individual wires positioned in the same configuration, for example coupled by welding, soldering, etc. The splines 3722A, 3722B may each comprise a different wire. The wires may be coupled, for example at a proximal end, or not coupled. One or both ends of the wires may be bent to be atraumatic. The spline pair 3727 may be shaped with two generally parallel splines 3722 which run alongside each other at their proximal and distal ends (e.g., along proximal and distal segments) but are separated by a greater distance along a central portion (e.g., an intermediate segment). As best seen in FIG. 37C, the splines 3722 circumferentially diverge at the beginning and end of a central portion of the spline 3722 (e.g., along proximal transitional segments and distal transitional segments) as they continue to extend radially outward. The convergence and divergence of the splines 3722 forms two short lengths during which the splines 3722 in a spline pair 3727 are not parallel. The splines 3722 of a spline pair 3727 run parallel within their central portions to form a generally hexagonal shape. The splines 3722 may share features with any of the patterns or configurations of expandable structures disclosed herein or variations thereof. As non-limiting examples, the central portions of the splines 3722 may be substantially parallel to the longitudinal axis of the expandable structure 3720, for example as shown in FIG. 36H, curve radially inward, for example as shown in FIG. 36E, radially outward, for example as shown in FIG. 36F, and/or have other configurations.

Some splines 3722 of the expandable structure 3720 may not include or lack or be devoid of or be free of electrodes 3724. After inserting the splines 3722 without electrodes 3724 through the proximal hub 3740, the splines 3722 may be wrapped with heat shrink tubing 3721, for example along their parallel and adjacent proximal and distal portions. The heat shrink tubing 3721 is then shrunk by heating. The heat shrink tubing 3721 may comprise, for example, polyethylene terephthalate (PET) or another suitable material. The heat shrink tubing 3721 can help inhibit rotation of the wrapped portions of the splines 3722 of a spline pair 3727 relative to each other. If the expandable structure 3720 is retracted through the pulmonary valve in an expanded state, the heat shrink tubing 3721 along the proximal portion of the splines 3722 may provide a more favorable proximally-facing surface than the splines 3722 for interaction with the valve tissue.

The wires forming the splines 3722 may be formed from a shape memory alloy such as Nitinol. In such cases, the wires are heated and programmed into a desired memory shape, such as the configuration depicted in FIG. 37D, then rapidly cooled. The wires may then be deformed as needed and inserted through the spline lumens 3745 and will return to their predetermined memory shape upon heating above a transition temperature. Once the wire is threaded through two adjacent spline lumens 3745 and returned to its programmed conformation, including the spline bend 3725 in the wire, the spline pair 3727 may be pulled distally until the spline bend snaps into place within a recess 3747 behind a proximal hub step 3748 (FIG. 37G).

FIG. 37E is a perspective view of a spline pair 3727. The spline pair 3727 comprises five electrodes 3724 positioned across the central portion of each splines 3722A, 3722B. The two splines 3722A, 3722B of a single spline pair 3727 may each comprise an electrode 3724, may each be devoid of electrodes 3724, or one of the splines 3722A, 3722B may comprise an electrode 3724 while the other of the splines 3722A, 3722B is devoid of electrodes.

FIG. 37F is an expanded view of the distal end of the spline pair 3727 of FIG. 37E. The splines 3722 comprising an electrode 3724 may be at least partially covered by a lining 3729, for example not at the proximal end and/or distal end. The lining 3729 may comprise PTFE. In embodiments in which the inner surfaces of the electrodes 3724 are not insulated, the lining 3729 may electrically insulate the splines 3722 from the electrodes 3724, which can inhibit cross-talk, activation of unintended electrodes, inefficient operation due to electrical leakage, etc. In embodiments in which the inner surfaces of the electrodes 3724 are insulated or other circumstances, the lining 3729 may be omitted. The splines 3722 not comprising an electrode 3724 may be free of a lining 3729, for example to provide better vessel wall apposition that is not prone to sliding. After inserting the splines 3722 through the proximal hub 3740, which may be before or after lining, lined spline wires may be wrapped with a spline tube 3723 that joins the two splines 3722A, 3722B of a spline pair 3727 at their proximal and distal ends. The spline tube 3723 may comprise two adjacent, yet, distinct lumens for each spline 3722 or it may comprise a single (e.g., oblong) lumen at its proximal and distal ends for receiving both splines. The spline tube 3723 may split at the proximal and distal points where the splines 3722A, 3722B diverge and cover each spline 3722A, 3722B individually along its central portion, such that the spline tube 3723 has two Y-shaped ends. Being spaced at the central portion of a spline pair 3727 may reduce the risk of thrombosis and/or provide better wall apposition by allowing the splines 3722 to abut the wall at circumferential points. The spline tube 3723 may span the expanse between the central portions of the splines 3722, which may provide a wider variety of electrode 3724 configurations (e.g., as described with respect to FIG. 4C) and/or provide better wall apposition by providing more apposition surface area. A plurality of spline tubes 3723 may be used, for example, one spline tube 3723 for each spline 3722. Spline tubes 3723 may optionally be coupled, for example at proximal and distal portions of a spline pair 3727. Spline tubes 3723 may be sized to be touching but not coupled. The spline tube 3723 may inhibit rotation of splines 3722A, 3722B of a spline pair 3727 relative to each other.

The individual electrodes 3724 may be generally cylindrical surrounding the circumference of central portions of the splines 3722. Other types and configurations of electrodes 3724 are also possible. For example, the electrodes 3724 may extend only partially around the circumference of the splines 3722 such that they face the outer diameter of the expandable structure 3720 (e.g., as described with respect to the electrode 4403).

The expandable structure 3720 may comprise five spline pairs 3727 spaced about the circumference of the expandable structure. The spline pairs 3727 may be evenly circumferentially spaced (e.g., as shown in FIG. 37C). Some of the spline pairs 3727 may be circumferentially clustered. For example, spline pairs 3727 comprising electrodes 3724 may be on a first side of a plane intersecting the longitudinal axis and spline pairs without electrodes 3724 may be on a second side of the plane opposite the first side. Two circumferentially adjacent spline pairs 3727 may each comprise a set of electrodes 3724, such as five electrodes 3724 per spline 3722, to form a 4×5 array of twenty electrodes 3724.

FIGS. 37Fi-37Fiii illustrate an example of electrical movement of electrodes. The expandable structure 3720, or other expandable members described herein, is expanded in a vessel. The electrodes may be selectively activated, for example as described herein, to determine a combination that stimulates the target nerve. In FIG. 37Fi, two electrodes in the first column have been found to capture a target nerve when activated. After some duration of treatment, stimulation of the target nerve may not be as effective as during the original selection. One option would be to contract, reposition, and reexpand the expandable structure 3720, and then repeat the selective activation process. Another non-mutually exclusive option is to electrically move the expandable structure 3720 to better capture the target nerve. In FIG. 37Fii, two electrodes in the fourth column have been found to capture the target nerve when activated. Changing the stimulation from the electrodes in the first column to the electrodes in the fourth column effectively moves or longitudinally shifts the expandable structure 3720 by the distance 3701. In FIG. 37Fiii, two electrodes in the first column but in the second and third rows have been found to capture the target nerve when activated. Changing the stimulation to these electrodes effectively circumferentially rotates the expandable structure 3720 by the distance 3703. Combinations of effective longitudinal movement and circumferential rotation are also possible. Although illustrated as bipolar operation in which two electrodes have opposite charges, monopolar operation (e.g., stimulation of one or more electrodes with the same charge in combination with a return electrode that is not an electrode of the electrode array (e.g., a chest pad, on a proximal portion of the catheter system 3700, on a separate catheter, etc.) is also possible. Although illustrated as simple bipolar operation for ease of explanation, guarded bipolar operation and other techniques are also compatible with electrical movement. Factors that may affect the precision with which an electrode array can capture a target nerve may include the total number of electrodes 3724, the span and shape of an electrode array, the proportioning of electrodes 3724 on individual splines 3722, the spacing of electrodes 3724 across the lengths of the splines 3722, and the circumferential spacing of the splines 3722, etc. An electrode array configured to allow electrical movement may advantageously reduce or eliminate physical or mechanical repositioning the expandable structure 3720, which could include contracting, moving, and reexpanding the expandable structure 3720. Physical movement can cause adverse events such as ischemic stroke (e.g., by causing debris to float loose or promoting thrombosis), damage to the vessel wall (e.g., promoting stenosis), etc. Physical movement can be time consuming, during which the subject may not be being treated.

Referring again to FIG. 37B, the expandable structure 3720 comprises a proximal hub 3740 and distal hub 3750 from which the splines 3722 extend. The proximal hub 3740 may comprise stainless steel or another suitable material. The distal hub 3750 may comprise stainless steel or another suitable material. The proximal hub 3740 and the distal hub 3750 may comprise the same material or different materials.

FIG. 37G is a perspective view of an example of a proximal hub 3740 of an expandable structure (e.g., the expandable structure 3720). FIG. 37H schematically illustrates a side cross-sectional view of the proximal hub 3740 of FIG. 37G. The proximal hub 3740 may comprise a biocompatible material such as, for example, stainless steel, nitinol, plastic, etc. The proximal hub 3740 may comprise a proximal portion 3741 and a distal portion 3742. The distal portion 3742 has a larger diameter than the proximal portion 3741 and may taper at its distal end to form a partially rounded surface 3749. A central lumen 3743 extends through both the proximal portion 3741 and the distal portion 3742, providing a channel from the proximal end of the proximal hub 3740 to the distal end of the proximal hub 3740 through which an actuation tube 3728 may slidingly extend. Although illustrated as having a circular cross-section, the central lumen 3743 may have other cross-sectional shapes (e.g., oval, arcuate, polygonal, etc.). The central lumen 3743 may include a lubricious coating or liner (e.g., comprising PTFE).

The proximal portion 3741 may be radially inward of the distal portion 3742. In some embodiments, a difference in diameter or outer dimension of the proximal portion 3741 and the distal portion 3742 may be approximately the thickness of a hinge 3726, which can allow the proximal hub 3740 to be coupled to a hinge 3726 while maintaining a uniform outer sheath 3711 (FIG. 37O) diameter if the outer sheath 3711 overlaps the distal portion 3742. In some embodiments, a difference in diameter or outer dimension of the proximal portion 3741 and the distal portion 3742 may be approximately the thickness of a hinge 3726 plus the thickness of an outer sheath 3711, which can allow the proximal hub 3740 to be coupled to a hinge 3726 while maintaining a uniform diameter if the outer sheath 3711 abuts the distal portion 3742. Other differences may be appropriate for other types of catheter shafts, for example not including a hinge 3711.

A plurality of peripheral lumens 3744 extends through both the proximal portion 3741 and distal portion 3742, providing a plurality of peripheral channels from the proximal end of the proximal hub 3740 to the distal end of proximal hub 3740 through which electrical connectors may extend and/or through which fluid may flow. The peripheral lumens 3744 may be radially outward of the central lumen 3743. The peripheral lumens 3744 may have a smaller diameter than the central lumen 3743. The peripheral lumens 3744 may each have the same diameter or at least one of the peripheral lumens 3744 may have a different diameter. Although illustrated as having a circular cross-section, the peripheral lumens 3744 may have other cross-sectional shapes (e.g., oval, arcuate, polygonal, etc.). The peripheral lumens 3744 may each have the same shape or at least one of the peripheral lumens 374 may have a different shape. For example, peripheral lumens 3744 configured for an electrical connector to extend therethrough may have one diameter or shape and peripheral lumens 3744 configured to deliver fluid may have another diameter or shape. Although the proximal hub 3740 is illustrated as having five peripheral lumens 3744, other quantities of peripheral lumens 3744 are also possible. For example, the proximal hub 3740 may include at least one peripheral lumen 3744 per spline pair 3727, at least one peripheral lumen 3744 per spline 3722, at least one peripheral lumen 3744 per spline 3722 comprising an electrode, at least one peripheral lumen 3744 per spline pair 3727 comprising an electrode, at least one peripheral lumen 3744 per electrical connector, etc. Although the proximal hub 3740 is illustrated as having five peripheral lumens 3744 equally spaced about the circumference of the proximal hub 3740, other arrangements of the peripheral lumens 3744 are also possible. Some peripheral lumens 3744 may be circumferentially bunched or grouped or clustered. For example, peripheral lumens 3744 configured for an electrical connector to extend therethrough may be circumferentially clustered and peripheral lumens 3744 configured to deliver fluid may be substantially equally circumferentially spaced about the remainder of the proximal hub 3740. A proximal hub 3740 comprising peripheral lumens 3744 that each have the same size, shape, and spacing may provide manufacturing flexibility and/or adaptability to a variety of designs. A proximal hub 3740 comprising at least one peripheral lumen 3744 having a different size, shape, and/or spacing may provide enhanced performance for a type of design.

The distal portion 3742 of the proximal hub 3740 may comprise spline lumens 3745. One or more splines 3722 may be positioned in each spline lumen 3745. In an example method of manufacture, a wire may be bent, for example as shown in FIG. 37D. The free ends of the wire may be inserted into the proximal ends of the spline lumens 3745 and then advanced distally until the bend 3725 contacts or is proximate to the proximal end of the distal portion 3742 of the proximal hub 3740. The bend 3725 in each spline pair 3727 can inhibit or prevent the spline pair 3727 from sliding distally because it contacts the proximal end of the distal portion 3742 of the proximal hub 3740.

The proximal portion 3741 may include recesses 3747 configured to accommodate or receive portions of splines 3722 extending proximal to the proximal end of the distal portion 3742 of the proximal hub 3740. The portions of the splines 3722 may comprise the bends 3725. The portions of the splines 3722 may comprise the free ends of the splines 3722, which may optionally be bent, for example to an atraumatic shape. If the recesses 3747 are flattened portions of an otherwise arcuate proximal portion 3741, the segment between the recesses 3747 and the radially outward surface may form steps 3748. The proximal portion 3740 may comprise one recess 3747 and one step 3748 per spline pair 3727. The proximal portion 3740 may comprise one recess 3747 and one step 3748 per two splines 3722, whether or not in a spline pair 3727. The proximal portion 3740 may comprise one recess 3747 and one step 3748 per spline 3722. The proximal portion 3740 may comprise one arcuate recess 3747 around or substantially around the circumference of the proximal portion 3740. The proximal portion 3740 may comprise one or more arcuate recesses 3747 for splines 3722 comprising an electrode 3724 and one or more recesses 3747 for splines 3722 lacking an electrode 3724.

The steps 3748 may limit the proximal motion of the proximal ends of the splines 3722. In implementations comprising a bend 3725, if the splines 3722 came out of the recesses 3747, then the surfaces that might interact with a vessel wall during retraction of an expandable structure 3720 comprising the splines 3722 and proximal hub 3740 would be atraumatic, and thus may not be prone to puncturing or otherwise adversely affecting the vessel. If the distal ends of the splines 3722 were straight wires and came out of the distal hub 3750, then the surfaces that might interact with a vessel wall during proximal retraction would be facing distally, the direction opposite retraction, and thus may not be prone to puncturing or otherwise adversely affecting the vessel. If the splines 3722 of the expandable structure 3720 have a portion that is bent radially outward, then the proximal and distal ends of the splines 3722 may be biased to be radially inward of an outward surface, and thus may not be prone to puncturing or otherwise adversely affecting the vessel.

The splines 3722 may be slidingly engaged with the spline lumens 3745. Upon proximal retraction of an actuation tube 3728, the steps 3748 may provide a counter force against the proximal ends of the splines 3722, forcing the splines 3722 to bend radially outward. The radially outward configuration may be different, for example, than an expanded configuration provided by shape memory. The splines 3722 may be fixably coupled to the spline lumens 3745. In certain such implementations, the interaction between the splines 3722 and the spline lumens 3745, independent of recesses 3747, steps 3748, and/or the proximal end of the distal section 3742 of the proximal hub 3740, can inhibit proximal and distal motion of the splines 3722 relative to the hub 3740. In some embodiments, friction between the splines 3722 and the spline lumens 3745 may provide additional or alternative counter force. The bends 3725 in the spline pairs 3727 form atraumatic proximal ends, which can be less dangerous to vasculature in a device failure scenario that results in the proximal ends of the splines 3722 coming free or misaligned such that they inadvertently contact the walls of the blood vessel. The spline pairs 3727 may be formed from individual wires or wires comprising a bend at their distal ends. In certain such embodiments, the splines 3722 may comprise a proximal bend or loop, the splines 3722 may be fixably coupled to the spline lumens 3745, and/or the splines lumens 3755 may comprise channels that are closed off at their proximal ends. The distal end of the distal portion 3742 of the proximal hub 3740 may be tapered such that the distal end of spline lumens 3745 open at an angle to a rounded surface 3749.

The angled open ends of the spline lumens 3745 at their distal ends may allow the splines 3722 to more easily bend radially outward, which may reduce stress on the wire when adopting an expanded configuration.

FIG. 37I is a perspective view of a distal end of the proximal hub 3740 of FIG. 37G. The wires or leads or conductors 3712 connecting the electrodes 3724 to the electrical socket 3799 may extend through the peripheral lumens 3744 of the proximal hub 3740. As illustrated in FIG. 37I, the conductors 3712 may be apportioned between the peripheral lumens 3744 such that the conductors 3712 for all of the electrodes of one or more splines 3722 extend through the same peripheral lumen 3744. For example, if the expandable structure 3720 comprises two adjacent spline pairs 3727 each comprising five electrodes 3724, the five conductors 3712A connected to the electrodes 3724 of a first spline 3722 may extend through a first peripheral lumen 3744A, the five conductors 3712B connected to the electrodes 3724 of a second spline 3722 in a spline pair 3727 with the first spline 3722 may extend through a second peripheral lumen 3744B, the five conductors 3712C connected to the electrodes 3724 of a third spline 3722 may extend through the second peripheral lumen 3744B, and the five conductors 3712D connected to the electrodes 3724 of a fourth spline 3722 in a spline pair 3727 with the third spline 3722 may extend through a third peripheral lumen 3744C. A fourth peripheral lumen 3744D and a fifth peripheral lumen 3744E may be free of conductors 3712. Other distributions of conductors 3712 in peripheral lumens 3744 are also possible. For another example, all of the conductors 3712 may extend through one peripheral lumen 3744. For yet another example, all of the conductors 3712 for each spline 3722 may extend through one peripheral lumen 3744 that is different for each spline 3722. For still another example, all of the conductors 3712 for two splines 3722 (e.g., in a spline pair 3727) may extend through one peripheral lumen 3744. A peripheral lumen 3744 free from conductors 3712 may be circumferentially between two peripheral lumens 3744 with conductors 3712 extending therethrough. Fluid flow through a peripheral lumen 3744 may be inversely proportional to the number of conductors 3712 occupying the peripheral lumen 3744, such that more fluid flows through peripheral lumens 3744 with fewer conductors 3712. Fluid flow through the device 3700 is described in further detail herein.

FIG. 37J schematically illustrates a side cross-sectional view of an example of a distal hub 3750 of an expandable structure (e.g., the expandable structure 3720). The distal hub 3750 may comprise a biocompatible material such as, for example, stainless steel, nitinol, plastic, etc. The distal ends of splines 3722 extend into the distal hub 3750. The distal hub 3750 may be generally cylindrical in shape, and may include an atraumatic (e.g., rounded) distal end 3754 and/or a tapered proximal end 3756. The tapered end 3756 may create angled open faces on the proximal end of the channels 3755 which allow the inserted splines 3722 to more easily bend in achieving an expanded configuration. The distal hub 3750 may comprise a central lumen 3753 configured to receive an actuator tube 3728. The actuator tube 3728 may be inserted into or through the central lumen 3753 and fixably coupled to the distal lumen 3753 by any suitable means, such as adhesive (e.g., cyanoacrylate), welding, soldering, combinations thereof, etc. The distal hub 3750 comprises a plurality of recesses 3755 configured to receive the distal ends of the splines 3722. A recess 3755 may have the same shape as the distal end of a spline 3722, for example being elongate and cylindrical. The distal hub 3750 may comprise a plurality of recesses 3755 each configured to receive the distal end of one spline 3722. The splines 3722 may be rigidly affixed to the distal hub 3750 by welding the distal hub 3750 after the distal ends of the splines 3722 are inserted into the recesses 3755. Welding may comprise applying a heat source around (e.g., 360° around) the outer circumference of the distal hub 3750. Welding may comprise using a laser and/or another suitable heat source. The splines 3722 may be welded to the distal hub 3750. Welding the outer circumference of the distal hub 3750 may, with or without welding the splines, heat stake the splines 3722 in the recesses 3755 by deformably reducing the inner diameters of the recesses 3755.

The actuation tube 3728 slidingly extends through the central lumen 3743 of the proximal hub 3740, then through a radially inner portion (e.g., the center) of the expandable structure 3720, then is fixably coupled to the central lumen 3753 of the distal hub 3750. The distal end of the actuation tube 3728 may be coupled to distal hub 3750 by any suitable means, such as adhesive (e.g., cyanoacrylate), welding, soldering, combinations thereof, etc. When the actuation tube 3728 is proximally retracted, the actuation tube 3728 proximally pulls the distal hub 3750 toward the proximal hub 3740, which is held in place by the catheter shaft assembly 3706. As the proximal hub 3740 and distal hub 3750 are brought closer together, the compressive force on the expandable structure 3720 forces the splines 3722 to expand radially outwardly, increasing the diameter and/or reducing the length of the expandable structure 3720. The diameter of the expandable structure may be greater than a shape set expanded shape of the expandable structure 3720. When the actuation tube 3728 is distally advanced, the actuation tube 3728 distally pushes the distal hub 3750 away from the proximal hub 3740, which is held in place by the catheter shaft assembly 3706. As the proximal hub 3740 and distal hub 3750 are brought further apart, the expansion force on the expandable structure 3720 forces the splines 3722 to retract radially inwardly, decreasing the diameter and/or increasing the length of the expandable structure 3720.

FIG. 37K shows a side view of an example of a proximal end 3702 of the catheter system 3700 of FIG. 37A. The proximal end 3702 comprises a handle 3710 and a portion of a catheter shaft assembly 3706 extending therefrom. The handle 3710 is configured to remain outside the body. The handle 3710 comprises a proximal part 3761 and a distal part 3762 movable relative to the proximal part 3761. The distal part 3762 may comprise a handle base 3763 and an outer handle 3770. The outer handle 3770 may include a grip portion (e.g., comprising a textured surface), which can enhance friction to provide better user grip. The proximal part 3761 may comprise an actuator 3780 and a hemostasis valve 3784. The proximal part 3761 and the distal part 3762 may be movably coupled by an actuation tube assembly 3790 and a securing member 3774 comprising a locking member 3776. Electrical conductors 3712 configured to supply signals to the electrodes 3724 may enter the handle 3710 via connector tubing 3798, which joins the handle 3710 to an electrical socket 3799. The outer handle 3770 may include a projection 3771 with a guide port through which the connector tubing 3798 may travel such that the connector tubing 3798 is secured along the side of the distal part 3762 of the handle 3710. The handle 3710 may be asymmetric with respect to the longitudinal axis of the catheter shaft assembly 3706, which can assist a user in approximating the amount of twisting or rotation in the attached catheter shaft assembly 3706.

FIG. 37L is a side cross-sectional view of the proximal end 3702 of FIG. 37K. The outer handle 3770 comprises a recess extending distally from its distal end that is configured to receive the handle base 3763. The proximal portion of the handle base 3763 may be partially inserted into the recess and fixably coupled to the handle base 3763.

The outer handle 3770 comprises a first lumen 3772 configured to slidably receive a portion of the actuation tube assembly 3790. The outer handle 3770 may include a second lumen 3773 configured to receive a securing member 3774 such as a pin, screw, piston, etc. The securing member 3774 may comprise, for example, a socket head cap screw comprising a threaded elongate section and a cap 3775. If the securing member 3774 is fixably coupled to the actuator 3780, the lumen 3773 may be devoid of threads so that the securing member 3774 may longitudinally slide through the lumen 3773. The threaded elongate section may interact with complementary threads in a lumen of the locking member 3776. If the securing member 3774 is rotatably coupled to the actuator 3780, the lumen 3773 may comprise complementary threads, and securing member 3774 may longitudinally slide through the lumen 3773 while rotating. The outer handle 3770 may comprise a shoulder extending into the second lumen 3773 configured to interact with an enlarged portion of the securing member 3774. For example, the shoulder may inhibit or prevent proximal retraction of the cap 3775, and thus the securing member 3774, beyond a certain length. Limiting longitudinal translation of the securing member 3774, which is fixably coupled to the actuator 3780, which is fixably coupled to the actuation tube 3728, can limit radial expansion of the expandable member 3720. Limiting radial expansion of the expandable member 3720 can enhance safety by reducing the likelihood of the expandable member 3720 expanding enough to puncture or rupture a vessel. The distal end of the lumen 3773 may be occluded, for example to inhibit debris from interfering with movement of the securing member 3774. The cap 3775 may comprise a tool interface, for example a hexagonal recess, a protruding nut, etc. The tool interface can be used during assembly (e.g., to couple the securing member 3774 to the actuator 3780 and/or during a procedure.

The actuator 3780 may comprise a first lumen 3781 aligned with the first lumen 3772 of the outer handle 3770. The first lumen 3781 may be configured to be coupled to a valve 3784 (e.g., a hemostasis valve 3784 (e.g., a luer lock)), for example by comprising complementary threads, being configured to be tapped, being configured to receive a press-fit, etc. The actuator 3780 may comprise a valve in communication with the first lumen 3781 that is monolithic with the actuator 3780. A portion of the actuation tube assembly 3790 is fixably coupled to at least one of the first lumen 3781 and the valve 3784. A lumen of the actuation tube assembly 3790 may be in fluid communication with a lumen of the valve 3784.

The actuator 3780 may comprise a second lumen 3782 configured to fixably couple the actuator 3780 to the securing member 3774. Depending on the shape and configuration of the securing member 3774, the second lumen 3782 may be aligned with the second lumen 3773 of the outer handle 3770. The second lumen 3782 may comprise threads configured to receive and secure an elongate threaded section of the securing member 3774. The securing member 3774 may be monolithic with and extend from a distal surface of the actuator 3780.

A locking member 3776 may optionally be positioned along the securing member 3774 between the actuator 3780 and the outer handle 3770. The locking member 3776 may comprise, for example, a locking tuohy (e.g., as illustrated in FIG. 36K), a nut, a wingnut, etc. The locking member 3776 comprises a threaded lumen configured to interact with the elongate threaded section of the securing member 3774. The locking member 3776 may comprise a textured outer surface configured to enhance grip of a user. The threads transmit rotational force on the locking member 3776 into longitudinal movement along the securing member 3774. When the locking member 3776 abuts a proximal end of the outer handle 3770, in what may be considered a locked position, the locking member 3776 inhibits or prevents the actuator 3780 (and thus the actuation tube assembly 3790 fixably coupled thereto) from moving distally. Locking the actuator 3780 can inhibit or prevent the splines 3722 of the expandable structure 3720 from radially compressing and losing wall apposition.

The locking member 3776 may comprise any suitable structure for preventing or inhibiting longitudinal motion of the securing member 3774 relative to the outer handle 3770. In some embodiments, the locking member 3776 may be a non-threaded structure. For example, the locking member 3776 may comprise a clamp, which is secured to the securing member 3774 via pressure and/or friction. The grip of the clamp locking member may be selectively loosenable and/or tightenable by the user. In some embodiments, a clamp locking member 3776 may be biased in a tightened position on the securing member 3774 by, for example, a spring. A clamp locking member 3776 may comprise a channel surrounding the circumference of the securing member 3774, and the diameter of the channel may be expanded or reduced by the turning of a screw that joins two ends of a clamp locking member 3776 to close the circumference around the securing member 3774. A clamp locking member 3776 may comprise a biased projection configured to frictionally engage the securing member 3774, and can be temporarily released by the user. A clamp locking member 3776 may be slideable or otherwise moveable along the securing member 3774 when in a loosened position and not slideable or otherwise moveable when in a tightened position. In some embodiments, a clamp locking member 3776 may be removable from the securing member 3774 and selectively reattached at a desired position along the length of the securing member 3774. A clamp locking member 3776 may inhibit or prevent the distal displacement of the securing member 3774 relative to the outer handle 3770 when a surface of the clamp locking member 3776 abuts the proximal end of the outer handle 3770, placing the handle 3710 in a locked position.

FIGS. 37Li-37Liii show an example method of operating a handle 3710 to radially expand an expandable member 3720. FIG. 37Li shows the handle 3710 in a compressed state in which the actuator 3780 abuts or is close to the locking member 3776, which abuts or is close to the outer handle 3770. As shown to the left, the expandable member 3720 may be in a self-expanded state. The actuation tube assembly 3790 may proximally retract upon radially outward self-expansion of the expandable structure 3720.

As shown in FIG. 37Lii, as the actuator 3780 is proximally retracted, the securing member 3774, which is fixably coupled to the actuator 3780, slides proximally through the second lumen 3773 of the outer handle 3770, the locking member 3776 stays in position on the securing member 3774 and thus is proximally retracted, and the actuator tube assembly 3790 slides proximally through the catheter shaft assembly 3706, the lumen 3764 of the handle base 3763, and the first lumen 3772 of the outer handle 3770. As the actuator tube assembly 3790 is proximally retracted, the distal hub 3750 to which the actuator tube 3728 is fixably coupled is proximally retracted, imparting a longitudinally compressive and radially expansive force on the splines 3722, which is expanded radially further than the self-expanded state. As the splines 3722 appose a vessel wall, the user can typically feel an opposition force in the actuator 3780, which is a benefit to a manual procedure such as illustrated in FIGS. 37Li-37Liii. Upon feeling the wall apposition, the user may adjust the expansion by further proximally retracting the actuator 3780 and/or by distally advancing the actuator 3780. Once the user is satisfied with the wall apposition provided by the splines 3722 of the expandable member 3720, the user may engage the locking member 3776.

As shown in FIG. 37Liii, the user rotates the locking member 3776. The threads of the threaded elongate section of the securing member 3774 and the locking member 3776 translate the rotational force into longitudinal force, and the locking member 3776 distally advances along the securing member 3774 until the locking member 3776 abuts a proximal surface of the outer handle 3770. If a distal force is applied to the actuator 3780, the actuator 3780 generally would not be able to distally move because the locking member 3776 is pressing against the proximal surface of the outer handle 3770.

FIGS. 37Li and 37Liv show another example method of operating a handle 3610 to radially expand an expandable member 3720. Referring again to FIG. 37Li, the handle 3710 is in a compressed state.

As shown in FIG. 37Liv, as the locking member 3776 is rotated, the threads of the threaded elongate section of the securing member 3774 and the locking member 3776 translate the rotational force into longitudinal force. The locking member 3776 bears against the proximal surface of the outer handle 3770, which forces the securing member 3774 to proximally retract.

As the securing member 3774 is proximally retracted, the securing member 3774 slides proximally through the second lumen 3773 of the outer handle 3770, the actuator 3780, which is fixably coupled to the securing member 3774, proximally retracts, and the actuator tube assembly 3790 slides proximally through the catheter shaft assembly 3706, the lumen 3764 of the handle base 3763, and the first lumen 3772 of the outer handle 3770. As the actuator tube assembly 3790 slides is proximally retracted, the distal hub 3750 to which the actuator tube 3728 is fixably coupled is proximally retracted, imparting a longitudinally compressive and radially expansive force on the splines 3722, which is expanded radially further than the self-expanded state. Throughout rotation of the locking member 3776, the locking member 3776 bears against the proximal surface of the outer handle 3770 such that, if a distal force is applied to the actuator 3780, the actuator 3780 generally would not be able to distally move because the locking member 3776 is pressing against the proximal surface of the outer handle 3770.

The force used to rotate the locking member 3776 may provide fine tuning as the locking member 3776 bears against the proximal surface of the outer handle 3770. Depending on the thread pitch, rotation of the locking member by a certain rotational amount may proximally retract the actuation tube assembly 3790 a certain amount and/or radially expand the expandable member 3720 a certain amount. For example, a 90° rotation of the locking member 3776 may radially expand the expandable member by a diameter of 1 mm in the absence of opposing forces. Finer and coarser pitches are also possible. A finer pitch allows finer tuning. A coarser pitch reduces the amount of rotation used to longitudinally move the components, which can reduce procedure time. The locking member 3776 may include indicia around its circumference to help the user identify the amount of rotation.

Combinations of the methods of FIGS. 37Li-37Liv are also possible. For example, the user may first manually retract the actuator 3780, for example to feel the wall apposition, rotate the locking member 3776 to abut a proximal end of the outer handle 3770, and then fine tune the amount of expansion by rotating the locking member 3776. For example, if the user desires to expand the expandable member 3720 by a diameter of 2 mm beyond wall apposition (e.g., the diameter of the vessel measure at systolic maximum), which can provide secure anchoring, the user can rotate the locking member 3776 by 180° after abutting the outer handle 3770.

FIG. 37M is a side cross-sectional view of example components of a handle base 3763. To provide example context, FIG. 37M also includes portions of the actuation shaft assembly 3790, part of the catheter shaft assembly 3706, and connector tubing 3798. The handle base 3763 comprises a lumen 3764 configured to receive a sealing element 3766, the actuation tube assembly 3790, and/or the catheter shaft assembly 3706. When the handle base 3763 is inserted into the recess of the outer handle 3770, the lumen 3764 is aligned with the first lumen 3772 of the outer handle 3770.

The catheter shaft assembly 3706 may be fixably coupled to the handle base 3763 by inserting the proximal end of the catheter shaft assembly 3706 into the lumen 3764 and then securing the catheter shaft assembly 3706 to the handle base 3763, for example by adhesive (e.g., cyanoacrylate), welding, soldering, combinations thereof, etc. The handle base 3763 may comprise a shoulder 3768 extending into the lumen 3764 configured to interact with the proximal end of the catheter shaft assembly 3706. For example, the shoulder 3768 may provide a stop for insertion of the catheter shaft assembly 3706 into the lumen 3764, which can facilitate manufacturing. The actuation tube assembly 3790 may comprise a plurality of components, for example including multiple types of tubing. Fewer components generally may reduce manufacturing complexity of the actuation tube assembly 3790. Multiple components can provide specialization of different portions of the actuation tube assembly 3790. If coupling components together is easier than modifying fewer components for particular functions, multiple components can reduce manufacturing complexity of the actuation tube assembly 3790. The actuation tube assembly 3790 illustrated in FIG. 37M comprises a first hypotube 3791, a second hypotube 3792, and the actuation tube 3728. The actuation tube assembly 3790 may comprise an actuation tube assembly lumen 3793 extending from the proximal end of the actuation tube assembly 3790 to the distal end of the actuation tube assembly 3790. The actuation tube assembly lumen 3793 may comprise segments in each component (e.g., the first hypotube 3791, second hypotube 3792, and actuation tube 3728) of the actuation tube assembly 3790, which may be aligned along a longitudinal axis of the actuation tube assembly 3790. The lumens of the components may be joined and/or aligned by, for example, positioning a component of a smaller outer diameter within the lumen of a component with a larger diameter inner diameter. The inner surfaces of the actuation tube 3728 and/or any of the other components comprising the actuation tube assembly lumen 3793 may comprise a lining (e.g., fluoropolymer (e.g., PTFE, PVDF, FEP, Viton, etc.)) to reduce friction with a guidewire inserted through the lumen 3793. The outer surfaces of the actuation tube 3728 and/or any of the other components comprising the actuation tube assembly 3790 may comprise a lining (e.g., fluoropolymer (e.g., PTFE, PVDF, FEP, Viton, etc.)) to reduce friction between the actuation tube assembly 3790 and the catheter shaft assembly 3706 or the lumen 3674 of the handle base 3763.

Referring again to FIG. 37L, a proximal end of the actuation tube assembly 3790, more specifically the proximal end of the first hypotube 3791, is fixably coupled to at least one of the actuator 3780 and the valve 3784. The first hypotube 3791 extends from the actuator 3780 into the proximal portion of lumen 3764 of the handle base 3763, through the sealing element 3766. The sealing element 3766 provides a fluid-tight seal between the actuation tube assembly 3790 and the handle base 3763. The first hypotube 3791 may be machined to include a first portion 3791A and a second portion 3791B having a smaller diameter than the first portion 3791A. The first hypotube 3791 may include one or a plurality of apertures 3794, which can provide fluid communication between the actuation tube assembly lumen 3793 and the lumen 3764. As described in further detail herein, fluid (e.g., saline, heparinized saline, contrast, etc.) injected into the lumen 3793 through the valve 3784 can flow through the lumen 3793 until the apertures 3794, and then may continue to flow through the lumen 3793 or out of the apertures 3794 and then through the lumen 3764. In some embodiments, the first hypotube 3791 may be devoid of apertures 3794 and configured such that fluid injected into the lumen 3793 flows only through the lumen 3793.

The first portion 3791A of the first hypotube 3791 may have an outer diameter that is slightly smaller than the inner diameter of the lumen 3764. Such a diameter difference can reduce (e.g., minimize) the space between the outer surface of the first portion 3791A and the inner surface of the handle base 3763 to reduce (e.g., minimize) fluid flowing out of the apertures 3794 from flowing proximally and/or can reduce friction between the first portion 3791A and the inner surface of the handle base 3763. The second portion 3791B of the first hypotube 3791 may provide an arcuate or toroidal gap or lumen between an outer surface of the second portion 3791B of the first hypotube 3791 and the inner surface of the handle base 3763. Such a diameter difference can promote fluid flowing out of the apertures 3794 to flow distally through the lumen 3764. The first hypotube 3791 may comprise a biocompatible material such as, for example, stainless steel, nitinol, plastic, etc. Although described as a hypotube, the first hypotube 3791 may be machined from a flat sheet, a solid rod, etc.

A proximal end of the lumen 3764 of the handle base 3763 may include an expanded diameter portion configured to receive a sealing element 3766 (e.g., comprising an o-ring, a shim, a gasket, etc.). The sealing element 3766 may be positioned between the first hypotube 3791 and the handle base 3763. The sealing element 3766 can seal a proximal end of the lumen 3764 to inhibit or prevent fluid flowing though the apertures 3794 from flowing out the handle base 3763.

A second hypotube 3792 may comprise an outer diameter that is slightly smaller than the inner diameter of the first hypotube 3791 such that a proximal end of the second hypotube may be inserted into a distal end of the first hypotube 3791. The second hypotube 3792 may be fixably coupled to the first hypotube 3791, for example by adhesive (e.g., cyanoacrylate), welding, soldering, combinations thereof, etc. The second hypotube 3792 may extend into a proximal end of the catheter shaft assembly 3706. The outer diameter of the second hypotube 3792 is less than the inner diameter of the lumen 3764, forming an arcuate or toroidal gap or lumen, which can provide an open segment for fluid to flow and conductors to extend. The second hypotube 3792 may comprise a biocompatible material such as, for example, stainless steel, nitinol, plastic, etc. Although described as a hypotube, the second hypotube 3792 may be machined from a flat sheet, a solid rod, etc.

The actuation tube 3728 extends from the proximal portion 3704 of the catheter system 3700 to the distal portion 3704 of catheter system 3700. The actuation tube 3728 may be fixably coupled to the second hypotube 3792, for example by adhesive (e.g., cyanoacrylate), welding, soldering, combinations thereof, etc. The second hypotube 3792 may comprise a lumen having an inner diameter that is slightly larger than the outer diameter of the actuation tube 3728 such that a proximal end of the actuation tube 3728 may extend into a distal end of the second hypotube 3792. The second hypotube 3792 may comprise a lumen having an inner diameter that is slightly larger than the outer diameter of the actuation tube 3728, and a distal end of the second hypotube 3793 may extend into a proximal end of the actuation tube 3728. The actuation tube 3728 may comprise a plurality of layers. For example, the actuation tube 3728 may comprise a flexible polymer (e.g., polyimide, polyamide, PVA, PEEK, Pebax, polyolefin, PET, silicone, etc.), a reinforcing layer (e.g., comprising a braid, a coil, etc.), and an inner liner (e.g., fluoropolymer (e.g., PTFE, PVDF, FEP, Viton, etc.)).

The second hypotube 3792 optionally may be omitted, for example by extending the first hypotube 3791 distally and/or extending the flexible polymer of the actuation tube 3728 proximally. The second hypotube 3792 may comprise a biocompatible material such as, for example, stainless steel, nitinol, plastic, etc.

The actuation tube assembly 3790 and the catheter shaft assembly 3706 combine to form two concentric lumens between the handle 3710 and the expandable structure 3720. The actuation tube assembly lumen 3793 of the actuation tube 3728 forms the inner lumen. The inner lumen 3793 may be in fluid communication with the hemostasis valve 3784. The distal terminus of the inner lumen 3793 is the distal end of the actuator tube assembly 3790, which is coupled to the proximal hub 3740. The hemostasis valve 3784 may allow insertion of a guidewire, which can extend through the actuation tube 3728 and distally beyond the distal hub 3750 of the expandable structure 3720. The outer lumen 3707 is arcuate or toroidal between the outer surface of the actuation tube assembly 3790 and the inner surface of the catheter shaft assembly 3706. The distal terminus of the outer lumen 3707 is the distal end of the catheter shaft assembly 3706, which is coupled to the proximal hub 3740.

The hemostasis valve 3784 may be used to inject fluids (e.g., saline, heparinized saline, contrast, etc.). Fluid may be injected into the hemostatsis valve 3784 (e.g., via IV bag, syringe, etc.). The fluid can flow through the first hypotube 3791 until the apertures 3794. The fluid may continue to flow through the inner lumen 3793 of the actuation tube assembly 3790 out of the distal hub 3750 and/or may flow through the apertures 3794 and then through the outer lumen 3707 out of the proximal hub 3740. Referring again to FIG. 37G-37I, the proximal hub 3740 comprises peripheral lumens 3743. Fluid flows out of the outer lumen 3707 through at least one of the peripheral lumens 3743. Fluid flow through a peripheral lumen 3743 may be inversely proportional to a level of occlusion of that peripheral lumen 3743 (e.g., due to occupation by conductors 3712). In some embodiments, the first hypotube 3791 may not comprise apertures 3794, and fluid may flow only through the inner lumen 3793 of the actuation tube assembly 37990 to the distal hub 3750.

Flushing fluid may provide a slight positive pressure within the lumens, which can inhibit blood from flowing into the catheter system 3700. Flushing fluid may wash the expandable structure 3720 and/or other portions of the catheter system 3700, which can inhibit thrombus formation during the medical procedure. If the fluid comprises contrast, flushing fluid can direct contrast to aid fluoroscopy and visualization of the expandable structure 3720 relative to the vessel.

The handle base 3763 may comprise an aperture 3765 extending through a sidewall into the lumen 3764, for example in communication with the arcuate or toroidal gap or lumen between the second hypotube 3792 and the handle base 3763. The conductors 3712 may extend from the electrical connector 3799, through the connector tubing 3798, through the aperture 3765, into the outer lumen 3707, through the proximal hub 3740 (e.g., as shown in FIG. 37I), and to the electrodes 3724.

FIG. 37N is a perspective view of a proximal end of an example of a catheter shaft assembly 3706 and second hypotube 3792. The catheter shaft assembly 3706 surrounds the actuation tube 3728 from the handle 3710 to the proximal hub 3740. The actuation tube 3828 may be proximally retracted and/or distally advanced relative to catheter shaft assembly 3706.

The catheter shaft assembly 3706 may comprise a plurality of layers. For example, the catheter shaft assembly 3706 may comprise a flexible polymer (e.g., polyimide, polyamide, PVA, PEEK, Pebax, polyolefin, PET, silicone, etc.), a reinforcing layer (e.g., comprising a braid, a coil, etc.), and an inner liner (e.g., fluoropolymer (e.g., PTFE, PVDF, FEP, Viton, etc.)). Different layers may be present along different longitudinal segments.

The flexible polymer may comprise, for example, polyimide, polyamide, PVA, PEEK, Pebax, polyolefin, PET, silicone, etc.). Different longitudinal sections of the tubing may have different durometers along the length of the catheter shaft assembly 3706. For example, the catheter shaft assembly 3706 may transition from a higher durometer, indicating a harder material, to a lower durometer, indicating a softer material, from proximal to distal. The lengths and durometers of the variable durometer sections may be matched to suit the different anatomical structures in which those sections will reside during a procedure. For example, the catheter shaft assembly 3706 may comprise at least five different durometer sections: a first section having a durometer of about 72 D having a length configured to extend from the handle 3710 into the body through a carotid vein proximal to the heart; a second section having a durometer of about 63 D and a third section having a durometer of about 55 D together having a length configured to pass through the right atrium and right ventricle; and a fourth section of having a durometer about 40 D and a fifth section having a durometer of about 25 D together having a length configured to extend through the pulmonary valve and into the right pulmonary artery. The flexibility of the fourth section and/or the fifth section may allow the catheter shaft assembly 3706 to bend and fixate the catheter shaft assembly, for example against a left side of the pulmonary trunk, which can aid in properly positioning the expandable member 3720 in a pulmonary artery. At least one of the fourth section and the fifth section may comprise a hinge 3726, for example as described herein, which can resist kinking if the catheter shaft assembly 3706 makes a sharp (e.g., 90°) turn, for example from the pulmonary trunk to the right pulmonary artery. The lengths of the five sections may be, in terms of percentage of the total length of the catheter shaft assembly 3706, between about 50-90% for the first section and between about 1 to 20% for each the remaining sections. For example, the lengths may be about 73%, 7.5%, 5.5%, 5.5%, and 8.5%, respectively. The first section may be longer or shorter depending on the total length of the catheter shaft assembly 3706, which may depend on the pathway to the pulmonary artery, the amount residing outside the body, etc.

The catheter shaft assembly 3706 may have a length between about 50 and 200 cm (e.g., about 50 cm, about 75 cm, about 100 cm, about 125 cm, about 150 cm, about 200 cm, ranges between such values, etc.). The length of the catheter shaft assembly 3706 may be suitable to position the expandable structure 3720 in a pulmonary artery from a peripheral vein such as a jugular vein, a femoral vein, a radial vein, or other suitable access location.

The flexibility of the catheter shaft assembly 3706 can be additionally or alternatively modulated by other means, such as reinforcing and adjusting various sections of the catheter shaft assembly 3706. For example, if the catheter shaft assembly 3706 comprises a reinforcing coil, a pitch of the coil may be varied. For another example, if the catheter shaft assembly 3706 comprises a reinforcing braid, a parameter (e.g., number, thickness, braid angle, etc.) of the braid wires in may be varied. For yet another example, the thickness may vary. For still another example, the composition may vary (e.g., different sections comprising at least one different material). Combinations of two or all variations is also possible. Rather than being discrete sections, the flexibility may transition from one section to the next section.

FIG. 37N shows the proximal end of catheter shaft assembly 3706 comprising a first segment 3708 and a second segment 3709 thicker than the first segment 3708. The change in thickness at the proximal end of the actuation shaft assembly 3706, for example the first segment 3708, may provide a mechanism of strain relief. The second segment 3709 may have an outer diameter configured to fit in the lumen 3764 of the handle base 3763 to be fixably coupled to the handle base 3763.

FIG. 37O is a side cross-sectional view of an example connection between a distal end of a catheter shaft assembly 3706 and a proximal hub 3740 of an expandable structure 3720. The distal end of the catheter shaft assembly 3706 may comprise a hinge 3726 configured to be fixably coupled to the proximal hub 3740.

The hinge 3726 may comprise, for example, a coil or series of interspaced coils that extend slightly beyond the distal end of other parts of the catheter shaft assembly 3760 such as the PTFE liner, wire braid, and flexible tubing. The coil hinge 3726 may comprise one or a plurality of wires (e.g., one wire, two wires, three wires, or more) configured in a helical pattern. The wires comprise helically wound coils having a uniform pitch. Each coil may occupy the space between the helical revolutions of the other coils. FIG. 37P is a perspective view of an end of an example of a hinge 3726 comprising three wires. The hinge 3726 may comprise a hypotube, for example cut to include a coil pattern and/or opposing circumferential slots.

The hinge 3726 may be positioned around the outer surface of the proximal section 3741 of the proximal hub 3740. The hinge 3726 may be fixably coupled to the proximal hub 3740 by adhesive (e.g., cyanoacrylate), welding, soldering, combinations thereof, etc. The distal end of the catheter shaft assembly 3706 may comprise layers that are proximally spaced from the distal end of the hinge 3726 by about 0.01 inches to about 0.1 inches (e.g., about 0.01 inches, 0.025 inches, 0.05 inches, 0.075 inches, 0.01 inches, ranges between such values, etc.), which can provide sufficient space for the hinge 3726 to be affixed (e.g., directly affixed) to the proximal hub 3740 without interference from those layers. The distal end of the flexible tubing, wire braid, liner, and/or other layers of the catheter shaft assembly 3706 may be longitudinally spaced from the proximal end of the proximal hub 3740, which can reduce transmission of forces on the catheter shaft assembly 3706, for example absorbed by the hinge 3726, from being transmitted to the expandable structure 3720.

The hinge 3726 may be covered by a hinge tube 3711, which may comprise urethane or another suitable material, and which extends from the distal end of the hinge 3726 past the proximal end of the hinge 3726, for example to inhibit pinching of tissue by the hinge 3726. The hinge tube 3711 may be heat cured to the hinge 3726 and outer circumference of other components of the catheter shaft assembly 3706. The hinge tube 3711 may be aligned substantially flush with or overlap the distal portion 3742 of the proximal hub 3740. The hinge tube 3711 may form a fluid seal with the proximal hub 3742, for example so that fluid flowing in the lumen 3707 exits the peripheral lumens 3744.

FIG. 37Q is a perspective view of an example handle 3701 of a catheter system (e.g., the catheter system 3700) in an unlocked configuration. FIG. 37R schematically illustrates a perspective cross-sectional view of the handle 3701 of FIG. 37Q along the line 37R-37R. In addition to the handle 3701, FIGS. 37Q and 37R show a portion of a catheter shaft assembly 3706 extending therefrom. The handle 3701 is configured to remain outside the body. The handle 3701 comprises an outer handle 3713 which the user may grasp. The outer handle 3713 comprises a lumen 3714 extending from the proximal end of the outer handle 3713 to the distal end of the handle outer 3713. The lumen 3714 may be configured to receive a tubular base 3715, which may be partially inserted into the lumen 3714 and fixably coupled to the outer handle 3713. The tubular base 3715 may be generally cylindrical in shape and may comprise a tapered distal end. Other geometries (e.g., polygonal) are also possible. The tubular base 3715 may extend out of the distal end of the lumen 3714 (as shown in FIGS. 37Q and 37R) or may be entirely received within the lumen 3714. The tubular base 3715 comprises a channel 3716 extending from the proximal end of the tubular base 3715 to the distal end of the tubular base 3715. The tubular base 3715 may comprise a shoulder 3717 extending into the channel 3716 configured to interact with the proximal end of the catheter shaft assembly 3706. The catheter shaft assembly 3706 may be fixably coupled to the tubular base 3715 by inserting the proximal end of the catheter shaft assembly 3706 into the channel 3716 and then securing the catheter shaft assembly 3706 to the tubular base 3715, for example by adhesive (e.g., cyanoacrylate), welding, soldering, combinations thereof, etc. The actuation tube assembly 3790 can be slidably received in the channel 3716 and portions of the actuation tube assembly 3790 can extend through the catheter shaft assembly 3706, for example as described herein. The tubular base 3715 may comprise an annular recess 3718 in the sidewall of the channel 3716 positioned near the proximal end of the channel 3716 configured to receive a sealing element (e.g., comprising an o-ring, a shim, a gasket, etc.) The sealing element may be positioned between the first hypotube 3791 and the tubular base 3715, and may inhibit or prevent fluid flowing through the apertures 3794 of the first hypotube 3791 from flowing out the tubular base 3715. In some embodiments, the annular recess 3718 may extend to the proximal end of the tubular base 3715.

The proximal end of the actuation shaft assembly 3790 can be coupled to an actuation pin 3730. The actuation pin 3730 comprises an actuation channel 3731 extending from the proximal end of the actuation pin 3730 to the distal end of the actuation pin 3730. The actuation channel 3731 is configured to receive the proximal end of the actuation tube assembly 3790 (e.g., the first hypotube 3791), which can be partially inserted into the actuation channel 3731 and fixably coupled to the actuation channel 3731, for example by adhesive (e.g., cyanoacrylate), welding, soldering, combinations thereof, etc. The actuation pin 3730 may comprise an expanded diameter grip 3732 for facilitating the grip of the user. The expanded diameter grip 3732 may comprise a textured surface. The actuation channel 3731 may comprise an expanded diameter portion at its proximal end configured to receive a tubing connector 3797. The tubing connector 3797 may be Y-shaped, including two intersecting channels. The channels of the tubing connector 3797 may be used for the insertion of a guidewire, electrical conductors, and/or the injection of fluids into the actuation tube assembly lumen 3793, as described elsewhere herein. The connector tubing 3797 may comprise a luer fitting including a single lumen.

The outer handle 3713 may comprise a void 3719 extending between an upper surface and a lower surface and intersecting the lumen 3714 of the outer handle 3713. In some embodiments, the void 3719 may extend to a side surface of the handle 3713 such that it opens to an upper surface, lower surface, and side surface of the outer handle 3713. The void 3719 may be configured to receive a locking member 3777. FIG. 37S is a perspective view of an example of the locking member 3777. The locking member 3777 may comprise a generally cylindrical body and a channel 3778 extending from a proximal side of the locking member 3777 to a distal side of the locking member 3777 through the generally cylindrical body. The locking member 3777 may comprise at least one projection 3789 extending radially inwardly from the sidewall of the channel 3778. If the locking member comprises two projections 3789, the two projections 3789 may be on opposite sides of the channel 3778. If the channel 3778 is oblong, the projection 3778 may be positioned along the longer-dimensioned length of the channel 3778 (e.g., at a central position along the longer-dimensioned length). The locking member 3777 may comprise a tab 3779 extending away from the channel 3778, for example in a direction perpendicular to the longitudinal axis of the channel 3778. The tab 3779 and generally cylindrical body may form a b-shape, d-shape, p-shape, or q-shape. The actuation pin 3730 may extend through the channel 3778. The handle 3701 may comprise a bushing 3796 configured to be received in the proximal end of the outer handle 3713 where the bushing 3796 may be affixed. The bushing 3796 may comprise a channel through which the actuation pin 3730 extends. The locking member 3777 may be rotatable about the longitudinal axis of the actuation pin 3730. The locking member 3777 can be configured to place the handle 3701 and the actuation tube assembly 3790 in a locked or unlocked configuration. In some embodiments, the degree of rotation of the locking member 3777 may be limited. As seen in the example of FIG. 37Q, the tab 3779 may only allow the locking member 3777 to rotate approximately a quarter-turn before the tab 3779 abuts a portion of the outer housing 3713.

FIG. 37T schematically illustrates an expanded perspective cross-sectional view of the handle 3701 of FIG. 37Q in an unlocked configuration in the area of the circle 37T of FIG. 37R. The actuation pin 3730 may comprise a series of ridges 3733 and intervening notches spaced along its outer circumference. The ridges 3733 may be perpendicular to the longitudinal axis of the actuation pin 3730. The ridges 3733 may extend away from the circumference of the actuation pin 3730 along two opposing sides of the actuation pin 3730. For example, the circumference of the actuation pin 3730 may be proportioned into approximate quarters, and the ridges 3733 may extend from two non-adjacent quarters of the circumference. The quarters of the circumference where the ridges 3733 do not extend may comprise flat surfaces extending along the length of the actuation pin 3730, as shown in FIG. 37Q (one of the flat surfaces is visible). The projection 3789 along the channel 3778 of the locking member 3777 may be configured to be received in a notch between two of the ridges 3733. The projection 3789 may be configured to mate with the outer circumference of the actuation pin 3730 when positioned in a notch. When in an unlocked configuration, the rotational orientation of the locking member 3777 positions the projection 3789 adjacent to a flattened surface of the actuation pin 3730. As shown in FIG. 37T, the projection 3789 is not positioned between the ridges 3733 in an unlocked configuration. The tab 3779 may be positioned in a first position (e.g., an upward position, extending away from the surface of the outer handle 3713), when in an unlocked configuration. In the unlocked configuration, the actuation pin 3730 may be translated in a proximal or distal direction by the user, which causes the translation of the actuation tube assembly 3790, which is rigidly affixed to the actuation pin 3730. The user may expand the expandable structure 3720 by pulling the actuation pin 3730 in a proximal direction. The user may compress the expandable structure 3720 by pushing the actuation pin 3730 in a distal direction. The expandable structure 3720 may assume a self-expanded state when in an unlocked configuration without a user pushing or pulling on the actuation pin 3730. The locking member 3777 may be devoid of a tab 3777, for example comprising a textured surface like a thumb wheel.

FIG. 37U is a perspective view of the handle 3701 of FIG. 37Q in a locked configuration. The user may place the handle 3701 in a locked configuration by moving the tab 3779 of the locking member 3777 to a second position to rotate the locking member 3777 approximately a quarter-turn around the actuation pin 3730. The outer handle 3713 may comprise a shoulder 3795 (FIG. 37Q) to limit the rotation of the tab 3779. In the locked configuration, the tab 3779 may no longer extend away from the surface of the handle 3701, but may be relatively flush with the surface of the handle 3701. The different positioning of the tab 3779 in unlocked and locked configurations, as seen in FIGS. 37Q and 37U, may provide a visually discernable indicator of the configuration the handle 3701.

FIG. 37V schematically illustrates a perspective cross-sectional view of the handle 3701 of FIG. 37U along the line 37V-37V. When in a locked configuration, the projections 3789 (two projections 3789 in the illustrated embodiment) have been rotated into two of the notches between the ridges 3733 of the actuation pin 3730, inhibiting or preventing the actuation pin 3730 and the actuation tube assembly 3730 coupled thereto from moving in a proximal direction and from moving in a distal direction. The locking of the handle 3730 can inhibit or prevent the expandable structure 3720 from further radially expanding and from radially compressing. The user may partially turn the tab 3779 at an approximate desired locking position and may then push or pull on the actuation pin 3779 until the projection 3789 falls into place between the ridges 3733. In some embodiments, the width of the projections 3789 may form a tight interference fit with the notches such that a "snap" is felt when locking or unlocking the locking member 3777. To unlock the locking member 3777, the user may place the tab 3779 back into an upright position, rotating approximately a quarter-turn in the opposite direction used to lock the locking member 3777. The locking member 3777 may be configured to be turned more or less than a quarter turn to switch between locked and unlocked configurations.

The handle 3701 can allow the user to quickly and/or easily adjust the expansion of the expandable structure 3720 by pushing or pulling the actuation pin 3730 a desired amount. The actuation pin 3730 and actuation tube assembly 3790 can be locked in position along the longitudinal axis according to discrete increments determined by the pitch of the series of ridges 3733 and intervening notches. The pitch and the projection 3789 can be modified to allow either narrower or broader tuning of the expansion and compression of the expandable structure 3720 (e.g., the widths can be smaller than shown in FIGS. 37Q-37U to provide more locking positions). In some embodiments, the locking member 3777 may comprise only one projection 3789 and/or the actuation pin 3730 may comprise only one flattened surface. In some embodiments, the actuation pin 3730 may comprise a textured surface (e.g., comprising grooves, bumps, flanges, etc.) configured to frictionally engage the locking member 3777. The projection 3789 and notches between ridges 3733 could be corresponding saw-tooth shapes. In such embodiments, the locking member 3777 may be configured to allow translation of the actuation pin 3730 (e.g., back to the self-expanded state of the expandable member 3720 in a failure event) in a locked configuration if enough force is applied to force the ridges 3733 over the saw tooth projection 3789.

FIG. 38A is a perspective view of an example of a catheter system 3800. The system 3800 may comprise a proximal portion configured to remain out of the body of a subject and a distal portion configured to be inserted into vasculature of a subject, for example as described with respect to the catheter system 3800. The system 3800 comprises an expandable structure 3820. The expandable portion 3820 is coupled to a catheter shaft 3806. In some embodiments, the system 3800 comprises a strain relief 3826 between the catheter shaft 3806 and the expandable structure 3820. The strain relief 3826 may be at least partially in a lumen of the catheter shaft 3806.

The expandable structure 3820 includes a plurality of splines 3822. The splines 3822 comprise a sinusoidal or wave or undulating or zig-sag shape. The sinusoidal shape may provide more flexibility in electrode positioning. For example, electrodes may be placed at peaks, troughs, and/or rising or falling portions. In some embodiments, electrodes are positioned proud of peaks, which can allow the electrodes to make close contact with vessel walls. The sinusoidal shape may provide better wall apposition, for example creating anchor points at peaks. At least one of the splines 3822 comprises an electrode array comprising a plurality of electrodes to form an electrode matrix. The number of electrodes in the electrode matrix, electrode sizing, electrode spacing, etc. may be in accordance with other systems described herein. In some embodiments, the splines 3822 comprise wires having a diameter between about 0.006 inches (approx. 0.15 mm) and about 0.015 inches (approx. 0.38 mm) (e.g., about 0.006 inches (approx. 0.15 mm), about 0.008 inches (approx. 0.2 mm), about 0.01 inches (approx. 0.25 mm), about 0.012 inches (approx. 0.3 mm), about 0.015 inches (approx. 0.38 mm), ranges between such values, etc.). In some embodiments, the splines 3822 may be cut from a hypotube and then shape set into the sinusoidal shape.

FIG. 38B is a perspective view of a portion of the catheter system 3800 of FIG. 38A in a collapsed state. The illustrated portion includes part of the catheter shaft 3806, the strain relief 3826, and the expandable structure 3820. The illustrated portion also includes an actuation member 3828, which can be coupled to an actuator mechanism to cause expansion or retraction of the expandable structure 3820. The actuation member 3828 may be in a lumen of the catheter shaft 3806. A guidewire 3815 is also shown in the lumen of the actuation member 3828. In some embodiments, the actuation member 3828 comprises a lumen capable of receiving a 0.018 inch guidewire 3815. The actuation member 3828 may comprise a tubular structure, for example as described with respect to the actuation tube assembly 3790. The actuation member 3828 may comprise a wire with or without a lumen.

FIG. 38C is a side view of a portion of the catheter system 3800 of FIG. 38A in an expanded state. Operation of the actuation mechanism 3612 can cause the expandable structure 3620 to expand and contract. For example, rotation and/or longitudinal movement of the actuation mechanism 3612 can cause the actuator wire 3628 to proximally retract, the catheter shaft 3606 to distally advance, or a combination thereof, each of which can push the splines 3622 radially outward. In some embodiments, the distal ends of the splines 3622 are coupled to a distal hub that is coupled to the actuator wire 3628, and the proximal ends of the splines 3622 are coupled to a proximal hub that is coupled to the catheter shaft 3606. In the expanded state, the expandable structure 3620 comprises splines 3622 that are spaced from each other generally parallel to a longitudinal axis at a radially outward position of the splines 3622. The parallel orientation of the splines 3622 can provide circumferential spacing of the splines 3622, for example in contrast to singular splines or wires that may circumferentially bunch. In some embodiments, the splines 3622 comprise wires having a diameter between about 0.006 inches (approx. 0.15 mm) and about 0.015 inches (approx. 0.38 mm) (e.g., about 0.006 inches (approx. 0.15 mm), about 0.008 inches (approx. 0.2 mm), about 0.01 inches (approx. 0.25 mm), about 0.012 inches (approx. 0.3 mm), about 0.015 inches (approx. 0.38 mm), ranges between such values, etc.).

In some embodiments, the diameter of the expandable structure 3820 in the expanded state is between about 15 mm and about 30 mm (e.g., about 15 mm, about 20 mm, about 22 mm, about 24 mm, about 26 mm, about 28 mm, about 30 mm, ranges between such values, etc.). In some embodiments, the splines 3822 may be self-expanding such that an actuation mechanism allows the splines to self-expand from a compressed state for navigation to a target site to an expanded state for treatment at the target site. In certain such embodiments, the diameter of the expandable structure 3820 in the expanded state may be oversized to most the intended vasculature of most subjects to ensure vessel wall apposition. In some embodiments, the splines 3822 may be non-self-expanding such that the splines only expand upon operation of an actuation mechanism. In some embodiments, the splines 3822 may be self-expanding, and an actuation mechanism may further expand the splines 3822, which may provide an adjustable expandable structure 3820 diameter usable for a range of vessel sizes, wall apposition forces, etc. Embodiments in which the expandable structure 3820 does not appose the wall in the event of an error could be advantageous for safety, for example as described with respect to the system 2200.

FIG. 38D is a partial side cross-sectional view of the expandable structure 3820. The expandable structure comprises a distal hub 3830 comprising a plurality of channels 3832 in which the distal segments of the splines 3822 are positioned. In some embodiments, the distal segments of the splines 3822 are not fixed such that they can slide in the channels 3832, which can allow each spline 3822 to move independently, which may accommodate curvature at a deployment site. In certain such embodiments, the distal ends of the splines 3822 comprise a stop member (e.g., an expanded diameter ball weld) that inhibits or prevents the distal segments from exiting the channels 3832 and the distal hub 3830. Such a system may also be used with other catheter systems and expandable structures described herein (e.g., the expandable structures 3620, 3630, 3640, 3650).

FIG. 38E is a partial side cross-sectional view of an expandable structure 3840. The expandable structure 3840 comprises a plurality of splines 3842 having a sinusoidal shape. The expandable structure 3840 comprises a plurality of electrodes 3844 at peaks of a plurality of three of the splines 3842 to form a 3×4 electrode matrix. In some embodiments in which three splines comprise electrodes, a middle or central spline may be different than the circumferentially adjacent splines. For example, the middle spline may comprise more or fewer peaks, peaks that are longitudinally offset, etc. Upon expansion of the expandable structure 3820, the electrodes of the electrode matrix may be selectively activated for testing nerve capture, calibration, and/or therapy, for example as described herein.

FIG. 39A is a side view of an example of an expandable structure 3900. The expandable structure 3900 may be incorporated into a catheter system such as the catheter systems described herein. The expandable structure 3900 comprises a plurality of splines 3902. The splines 3902 are bent to form parallel portions 3904 that are radially offset. The parallel portions 3904 may comprise electrodes, electrode structures, etc. In some embodiments, bent portions of the splines act as hinges to urge the offset parallel portions 3904 against vessel walls. The expandable structure 3900 may be self-expanding, expandable using an actuation mechanism, and combinations thereof, for example as described herein. FIG. 39A illustrates four splines 3902 that are circumferentially offset by about 90°, but other numbers of splines and offset are also possible.

FIG. 39B is an end view of an example of another expandable structure 3910. The expandable structure 3910 comprises six splines 3912, three of which are grouped on one side of a plane 3914 and three of which are grouped on the other side of the plane 3914. In some embodiments, one group of splines 3912 may comprise electrodes and the other group of splines 3912 may be free of electrodes and used for wall apposition, anchoring, etc. In some embodiments, FIG. 39B is representative of a portion of FIG. 36H. For example, the expandable structures 3900, 3910 may comprise a portion (e.g., half) of the splines described with respect to FIGS. 36A-36O.

FIG. 39C is an end view of an example of yet another expandable structure 3920. The expandable structure 3920 comprises six splines 3922 and six splines 3924. Like the splines 3902, the splines 3922 comprise radially offset parallel portions. The splines 3924 are each generally parallel to an adjacent spline up to the bend, and continue to extend radially outward.

FIG. 39D is an end view of an example of still another expandable structure 3930. The expandable structure 3930 comprises a first spline 3932, a second spline 3934, and six splines 3936. Like the splines 3902, the spline 3922 comprises a radially offset parallel portion Like the splines 3902, the spline 3924 also comprises a radially offset parallel portion that is radially offset in a different direction than the spline 3922. The splines 3936 are extend radially outward, with one spline 3936 circumferentially between the splines 3932, 3934. The splines 3932, 3934, and the spline 3936 circumferentially between the splines 3932, 3934 may comprise electrodes forming an electrode matrix. In some embodiments, FIG. 39D is representative of a portion of FIG. 36L. For example, the expandable structures 3900, 3910, 3920, 3930 may comprise a portion (e.g., half) of the splines described with respect to FIGS. 36A-36O.

The parallel portions of the expandable structures 3900, 3910, 3920, 3930 may be straight, recessed, crowned, sinusoidal, longitudinally offset, carrying a mesh, etc., for example as described herein.

FIG. 40A is a perspective view of an example of a strain relief 4026 for a catheter system. The strain relief 4026 can act like a flexible hinge to decouple catheter forces from an expandable structure, for example in the catheter systems described herein. The strain relief 4026 comprises a spring. The spring may comprise a variable helix, which can vary flexibility longitudinally. In some embodiments, the spring may be embedded in a polymer. In some embodiments, the polymer may have a durometer that varies longitudinally in longitudinal alignment with and/or longitudinally offset from helix variability. In some embodiments, a strain relief does not comprise a spring, but comprises a polymer having longitudinally varying durometer. In some embodiments, a plurality of helices of opposite sense may be braided to form a strain relief.

FIG. 40B is a perspective view of another example of a strain relief 4027 for a catheter system. The strain relief 4027 can act like a flexible hinge to decouple catheter forces from an expandable structure, for example in the catheter systems described herein. The strain relief 4027 comprises a cut hypotube. In the embodiment illustrated in FIG. 40B, the cut comprises a first helix 4002 having a first sense (e.g., winding clockwise) and a second helix 4004 having the same first sense. The first helix 4002 is longitudinally offset from the second helix 4004. In some embodiments, the cut pattern may comprise a variable helix, which can vary flexibility longitudinally. In some embodiments, the hypotube may be embedded in a polymer. In some embodiments, the polymer may have a durometer that varies longitudinally in longitudinal alignment with and/or longitudinally offset from helix variability. Other cut patterns are also possible. For example, the cut pattern may comprise a single helix. For another example, the cut pattern may comprise a plurality of transverse slots or kerfs connected by one or more struts. In sine embodiments, a cut hypotube may provide tensile strength.

FIG. 41A is a perspective view of an example of a catheter system 4100. The system 4100 comprises a proximal portion 4102 configured to remain out of the body of a subject and a distal portion 4104 configured to be inserted into vasculature of a subject. The distal portion 4104 comprises a first expandable structure 4120 and a second expandable structure 4122. The proximal portion comprises an actuation mechanism 4112. The proximal portion 4102 is coupled to the distal portion 4104 by a catheter shaft 4106. In some embodiments, the catheter shaft is slightly rigid such that the catheter shaft 4106 can appose a sidewall and help to anchor the system 4100 at a target position. The proximal portion 4102 may comprise an adapter comprising a plurality of ports, for example the Y-adapter comprising a first Y-adapter port 4116 and a second Y-adapter port 4118. The first Y-adapter port 4116 may be in communication with a lumen in fluid communication with the second expandable member. The second Y-adapter port 4118 may be used to couple an electrode matrix of the system 4100 to a stimulator system 4119. In some embodiments, the proximal portion 4102 comprises a stimulator system 4119. For example, the proximal portion 4102 may comprise electronics configured to provide stimulation to an electrode matrix, sensors (e.g., in communication with a fluid filled lumen of the catheter shaft 4106), electronics to receive data from sensors, electronics for closed loop control, electronics to provide feedback to a user (e.g., physician, nurse, subject), input mechanisms for a user (e.g., physician, nurse, subject), etc.

FIG. 41B is a perspective view of a portion 4104 of the catheter system 4100 of FIG. 41A in a collapsed and deflated state. FIG. 41C is a transverse cross-sectional side view of the portion 4104 of FIG. 41B. The illustrated distal portion 4104 includes part of the catheter shaft 4106, the first expandable structure 4120, the second expandable structure 4122, and a tubular member 4128. The first expandable structure 4120 includes a plurality of splines coupled to the catheter shaft 4106. The tubular member 4128 may be in a lumen of the catheter shaft 4106. In some embodiments, the distal ends of the splines are coupled to a distal hub that is coupled to the tubular member 4128, and the proximal ends of the splines are coupled to the catheter shaft 4106. Distal segments of the splines may be slidable in a distal hub, for example as described herein. The tubular member 4128 comprises a lumen 4129. The lumen 4129 is in fluid communication with the second expandable member 4122.

The second expandable member 4122 may be adjacent to the first expandable member 4120 (e.g., distance of 0 cm) or longitudinally (proximally or distally) spaced from the first expandable member 4120 by up to about 5 cm (e.g., about 0.25 cm, about 0.5 cm, about 1 cm, about 1.5 cm, about 2 cm, about 2.5 cm, about 3 cm, about 4 cm, about 5 cm, ranges between such values, etc.). The amount of spacing, if any, may at least partially depend on the location of a target site, the stiffness of the catheter shaft 4106, the number of splines of the first expandable member 4120, the expanded diameter of the first expandable member 4120, etc.

FIG. 41D is a side view of the portion of 4104 of FIG. 41B in an inflated state. Specifically, the second expandable member 4122 is inflated. In some embodiments, fluid (e.g., saline, contrast, etc.) may be injected into the lumen 4129 until the second expandable member 4122 radially expands. In some embodiments, the second expandable member 4122 may longitudinally expand. The inflated second expandable member 4122 may be a Swan-Ganz balloon, which can be used to float the distal portion 4104 to a target site such as a pulmonary artery. Rather than tracking a guidewire through the catheter system 4100, the catheter system 4100 may comprise an all-in-one system in which the second expandable member comprises an electrode matrix. In some embodiments, the catheter system 4100 may be devoid of a second expandable member 4122 and/or may be configured to track over a guidewire, which may be positioned in vasculature (e.g., in the right pulmonary artery 4143) prior to introduction of the catheter system 4100, for example as described herein using a Swan-Ganz technique, fluoroscopy-guided steering, etc.

FIG. 41E is a perspective view of the portion of 4104 of FIG. 41B in an expanded state. Specifically, the first expandable member 4120 is expanded. In some embodiments, operation of the actuation mechanism 4112 can cause the first expandable structure 4120 to expand and contract. For example, rotation and/or longitudinal movement of the actuation mechanism 4112 can cause the tubular member 4128 to proximally retract, the catheter shaft 4106 to distally advance, or a combination thereof, each of which can push the first expandable member 4120 radially outward. In certain such embodiments, the tubular member 4128 can inflate the second expandable member by flowing fluid through the lumen 4129 and can expand the first expandable member 4120 by proximally retracting. A dual function tubular member 4128 may reduce mass and/or complexity of the catheter system 4100. In some embodiments, different structures can be used to accomplish one or more of these functions. For example, in some embodiments, the splines may be self-expanding such that the actuation mechanism 4112 or another mechanism (e.g., retraction of a sheath over the splines) allows the splines to self-expand from a compressed state for navigation to a target site to an expanded state for treatment at the target site. In certain such embodiments, the diameter of the first expandable structure 4120 in the expanded state may be oversized to most the intended vasculature of most subjects to ensure vessel wall apposition. In some embodiments, the splines may be non-self-expanding such that the splines only expand upon operation of the actuation mechanism 4112. In some embodiments, the splines may be self-expanding, and the actuation mechanism 4112 may further expand the splines, which may provide an adjustable first expandable structure 4120 diameter usable for a range of vessel sizes, wall apposition forces, etc. Embodiments in which the first expandable structure 4120 does not appose the wall in the event of an error could be advantageous for safety, for example as described with respect to the system 2200. In some embodiments, the wires are not fixed distally (e.g., to a distal hub), which can allow each wire to move independently, which may accommodate curvature at a deployment site.

In the expanded state, the first expandable structure 4120 comprises splines that are circumferentially spaced from each other on one side of a plane that includes a longitudinal axis of the distal portion 4104. In some embodiments, the splines comprise wires having a diameter between about 0.006 inches (approx. 0.15 mm) and about 0.015 inches (approx. 0.38 mm) (e.g., about 0.006 inches (approx. 0.15 mm), about 0.008 inches (approx. 0.2 mm), about 0.01 inches (approx. 0.25 mm), about 0.012 inches (approx. 0.3 mm), about 0.015 inches (approx. 0.38 mm), ranges between such values, etc.). In some embodiments, the diameter of the expandable structure 4120 in the expanded state is between about 15 mm and about 30 mm (e.g., about 15 mm, about 20 mm, about 22 mm, about 24 mm, about 26 mm, about 28 mm, about 30 mm, ranges between such values, etc.).

The splines of the first expandable member 4120 may comprise an electrode array comprising a plurality of electrodes to form an electrode matrix. The number of electrodes in the electrode matrix, electrode sizing, electrode spacing, etc. may be in accordance with other systems described herein. For example, in some embodiments, the expandable structure 4120 comprises a mesh or membrane comprising electrodes that is stretched across two or more of the splines. Upon expansion of the first expandable structure 4120, the electrodes of the electrode matrix may be selectively activated for testing nerve capture, calibration, and/or therapy, for example as described herein.

FIG. 41F schematically illustrates the first expandable structure 4120 expanded in vasculature. The vasculature may include, for example, a pulmonary trunk 4132, a right pulmonary artery 4134, and a left pulmonary artery 4136. In some embodiments, the catheter shaft 4106 is asymmetric such that the catheter shaft 4106 can bend during floating to naturally align the first expandable structure 4120 with the right pulmonary artery 4134. After expansion of the first expandable structure 4120, the catheter system 4100 may be proximally retracted until the first expandable structure 4120 snaps into place. Upon positioning of the first expandable member 4120, electrodes on splines of the first expandable structure 4120 may be used to stimulate a target nerve 4138.

FIG. 41G schematically illustrates another example of the first expandable structure 4120 expanded in vasculature. The vasculature may include, for example, a pulmonary trunk 4132, a right pulmonary artery 4134, and a left pulmonary artery 4136. The bending and positioning of the tubular member 4128 against the left side of the pulmonary trunk 4132 may position and anchor the first expandable structure 4120 in the right pulmonary artery 4134 in a position for stimulating a target nerve 4138.

In some embodiments, expansion of the first expandable structure 4120 bends the distal portion 4104 relative to the catheter shaft 4106. This bending may advantageously help to anchor the distal portion 4104 at a target site. For example, the tubular member 4128 can appose a first side of a vessel and the catheter shaft 4106 can appose an opposite side of the vessel.

FIG. 42A is a side view of an example of an electrode structure 4224. The electrode structure 4224 may be used with expandable structures as described herein. In FIG. 42A, the electrode structure 4224 is shown on a spline 4222 of an expandable structure. The electrode structure 4224 comprises a plurality of electrodes 4202 and insulation 4204 around the electrodes 4202. The electrodes 4202 extend around the circumference of the electrode structure 4224. The electrode structure 4224 may be formed separately and then slid over the spline 4222.

FIG. 42B is a side view of another example of an electrode structure 4225. The electrode structure 4225 may be used with expandable structures as described herein. In FIG. 42B, the electrode structure 4225 is shown on a spline 4222 of an expandable structure. The electrode structure 4225 comprises a plurality of electrodes 4203 and insulation 4204 around the electrodes 4203. The electrodes 4203 extend partially around the circumference of the electrode structure 4225. The electrode structure 4225 further comprises insulation 4205 on an inner side, which can insulate the electrodes 4203 and direct energy radially outward. The electrode structure 4225 may be formed separately and then slid over the spline 4222.

FIG. 43A is a side view of an example of an electrode 4302. The electrode 4302 is a button electrode that may be coupled to a spline or a mesh. The electrode 4302 does not comprise insulation such that energy may be emitted in all directions.

FIG. 43B is a side view of another example of an electrode 4303. The electrode 4303 is a button electrode that may be coupled to a spline or a mesh. The electrode 4303 comprises insulation 4305 such that energy is emitted from uninsulated areas, which can provide directional control.

FIG. 44A is a side view of an example of an electrode 4402. The electrode 4402 is a barrel electrode that may be coupled to a spline or a mesh. The electrode 4303 does not comprise insulation such that energy may be emitted in all directions.

FIG. 44B is a side view of another example of an electrode 4403. The electrode 4403 is a barrel electrode that may be coupled to a spline or a mesh. The electrode 4403 comprises insulation 4405 such that energy is emitted from uninsulated areas, which can provide directional control. In some embodiments, the rotational position of the electrode 4403 around a spline is fixed, for example to direct energy radially outward.

FIG. 45 is a schematic diagram of neurostimulation of a nerve proximate to a vessel wall. An electrode 4508 is positioned in a vessel cavity 4506, and the vessel wall 4504 is proximate to or adjacent to a nerve 4502. The electrode 4508 is partially insulated (e.g., as in the electrode 4303) such that energy primarily radiates from one side. The electrode 4508 may have an area between about 1 $mm^2$ and about 3 $mm^2$. In some embodiments, the electrode 4508 comprises platinum iridium. In some embodiments, the uninsulated surface of the electrode 4508 is treated, for example to increase surface area. The energy radiates from the surface of the electrode 4508 and dissipates in the vessel wall 4504. A portion of the energy radiates out of the vessel wall 4504 and captures part of the nerve 4502. The nerve 4502 also dissipates the energy, which does not extend far beyond the nerve 4502, which could reduce the chances of capturing other undesired or unintended nerves, which could reduce side effects such as pain, cough, etc. The nerve may have a diameter 4503 between about 1 mm and about 2 mm. Even with insulation, some energy may be emitted from the opposite surface into the vessel cavity 4506, where blood or other materials may dissipate the energy.

Table 1 shows the correlation between changes in right ventricle contractility and left ventricle contractility after three different changes. The correlation was a heartbeat-by-heartbeat analysis. Pressure measurements, taken by a Millar catheter comprising a MEMS pressure sensor, in units of max(dP/dt) was used as a surrogate for contractility.

The first change, a dobutamine injection, provided a very high contractility increase greater than 500%. The average correlation between right ventricle contractility and left ventricle contractility was very good at 0.91, where 1.00 is a perfect correlation. Accordingly, if a subject is given a dobutamine injection, measuring changes to right ventricle contractility can provide accurate information about changes to left ventricle contractility. The first change was repeated three times.

The second change, calcium injection at 5 mL, provided a contractility increase of about 20%. FIG. 46A shows the left ventricle pressure in blue as measured by a Millar Mikro-Cath (MEMS) pressure sensor catheter, right ventricle pressure as measured by a pressure sensor in communication with a fluid filled lumen in yellow, and right ventricle pressure in purple as measured by a Millar Mikro-Cath (MEMS) pressure sensor catheter, as well as arterial pressure in green as measured in the aorta by a Millar Mikro-Cath (MEMS) pressure sensor catheter. The average correlation between right ventricle contractility and left ventricle contractility using a Millar (MEMS) sensor on a catheter was very good at 0.91. The average correlation between right ventricle contractility and left ventricle contractility using a fluid-filled lumen of a Swan-Ganz catheter in communication with an external pressure sensor was also very good at 0.87. Accordingly, under certain circumstances such as measurement of an animal (normal, non-HF ovine model) model, if a subject is given a calcium injection, measuring changes to right ventricle contractility with a MEMS sensor or a fluid filled lumen can provide accurate information about changes to left ventricle contractility.

The fourth change, neurostimulation as described herein, provided a contractility increase of about 28%. The correlation between right ventricle contractility and left ventricle contractility was very good at 0.90. Accordingly, if a subject is given neurostimulation, measuring changes to right ventricle contractility can provide accurate information about changes to left ventricle contractility. FIG. 46B shows the left ventricle contractility in teal and the right ventricle contractility in gold for the neurostimulation change in which the neurostimulation was applied after about 35 seconds and then cut off after being applied for about 2 minutes. In the first several beats after the calcium injection, the left ventricle contractility increased dramatically, but the right ventricle contractility only slightly increased. Thereafter, the left ventricle contractility tapered off logarithmically or exponentially, but the right ventricle contractility decreased very slowly. These differences help to show why the correlation between left ventricle contractility and right ventricle contractility are poorly correlated for calcium injections. The fourth change was not repeated.

TABLE 1

| Change | Average R-Value | Contractility % Increase |
| --- | --- | --- |
| Dobutamine Injection | 0.91 | >500 |
| Calcium Injection (5 mL) | 0.91 (Millar) | ~20 |
|  | 0.87 (Fluid Filled) |  |
| Neurostimulation | 0.90 | ~28 |

In some embodiments, a MEMS pressure sensor can be integrated into the catheter systems described herein, for example configured to reside in the right ventricle to measure right ventricle contractility, which can be accurately correlated to left ventricle contractility for neurostimulation. In some embodiments, an alternative pressure measurement system, for example a fluid-filled (e.g., saline-filled) lumen having a first end in communication with an external pressure sensor (e.g., connected via a luer fitting) and a second end in communication with an aperture configured to reside in the right ventricle to measure right ventricle contractility, which can be accurately correlated to left ventricle contractility for neurostimulation. MEMS pressure sensors may provide higher fidelity (more immediate feedback) than pressure sensing lumens. MEMS pressure sensors may occupy less catheter volume because they do not include a lumen, which can reduce the size of the catheter and/or provide additional space for other devices. MEMS pressure sensors may be easier to set up, for example compared to filling a lumen with fluid and correctly coupling the fluid filled lumen to a sensor. MEMS pressure sensors may be easier to place anatomically. Easier set up and/or placement may lead to more accurate results. MEMS pressure sensors may reduce or eliminate a whip effect in which curvature of a fluid filled lumen may kink when bending around a curve, which can provide inaccurate readings. Pressure sensing lumens may advantageously be well suited for long dwell times, as they are less likely to be affected by blood than MEMS sensors. In some embodiments, multiple pressure sensors, of the same type or different types, may be used, for example to provide a more accurate measurement (e.g., by taking an average or a weighted average of the measurements).

The accuracy of measurement of left ventricle contractility by measuring right ventricle contractility during neurostimulation can be used to monitor therapy efficacy. The accuracy of measurement of left ventricle contractility by measuring right ventricle contractility during neurostimulation can be used to monitor therapy efficacy. In some embodiments, left ventricle contractility, after correlation from a measurement of right ventricle contractility, can be used for closed loop control (e.g., neurostimulation parameter adjustments, turning neurostimulation on and/or off, etc.).

In some embodiments, pressure such as right ventricle pressure can be monitored for safety purposes. For example, right ventricle pressure, correlated left ventricle pressure, and optionally other measurements such as right atrium pressure can be used as a surrogate ECG signal for determining heart rate and/or arrhythmias. As described below, such variables may not be normally measurable during stimulation.

For another example, pressure can be used to determine if a catheter has moved, for example from the right ventricle into the right atrium or the superior vena cava, or from the pulmonary artery into the right ventricle. The system may be configured to trigger (e.g., automatically) certain events upon determination of movement, such as stopping stimulation, collapsing an electrode basket, releasing an anchor, etc.

FIG. 47A schematically illustrates an example electrocardiograph (ECG or EKG). The ECG includes a P wave, a Q wave, a R wave, a S wave, and a T wave, which are indicative of different events during a single heartbeat of a healthy patient. The P wave represent atrial depolarization, which causes the left atrium and the right atrium to push blood into the left ventricle and right ventricle, respectively. The flat period until the Q wave, the "PR Segment," and the start of the P wave to the start of the Q wave is the "PR Interval." The Q wave, the R wave, and the S wave, together the "QRS Complex," represent ventricular depolarization, which causes the right ventricle to push blood into the pulmonary artery and towards the lungs and which causes the left ventricle to push blood into the atrium for distribution to the body. The T wave represents repolarization of the left and right ventricles. The flat period until the T wave is the "ST Segment" during which the ventricles are depolarized, and collectively the QRS Complex, the ST Segment, and the T wave are the "QT Interval." Some ECGs also have a U wave after the T wave. The timing, amplitude, relative amplitude, etc. of the various waves, segments, intervals, and complexes can be used to diagnose various conditions of the heart. Electrical stimulation from the systems described herein may interfere with a normal ECG. In some embodiments, the ECG signal may be modified to account for such interference.

In some embodiments, the ECG may be monitored by the system so that stimulation is only applied during, for example, the period between the T wave and the P wave, the period between the S wave and the P wave, the period between the S wave and the Q wave, etc. The ECG may be artificially flatlined during periods of stimulation but unaffected during periods of non-stimulation. Some users may prefer to see a flatline or "blank" period rather than noise, an artificial signal, etc. In some embodiments, the ECG may be flatlined artificially high or low or show an irregular pattern during periods of stimulation so that a user of the ECG recognizes that the signal during such periods is not accurate. FIG. 47B is an example of a modified electrocardiograph. During stimulation, which occurs in the period between the S wave and the T wave, the ECG is artificially low.

FIG. 47C is an example of a monitored electrocardiograph. As discussed above, the stimulation is timed to heartbeats. Rather than relying on the heartbeat, including intrabeat duration, remaining regular, stimulation is applied for a portion of the time between heartbeats, after which the ECG is monitored for the next beat. For example, stimulation is applied for a short period after S wave (represented by "S" in FIG. 47C), followed by a monitoring period where the P wave should begin or be completed (represented by "M" in FIG. 47C). If the P wave is detected, then stimulation and monitoring are repeated. If the P wave is not detected in the monitoring period, which may be indicative that something is wrong, stimulation can be stopped. Stimulation may be restarted by a user after determining that conditions are appropriate for stimulation. Stimulation may be restarted automatically by the system after a certain number of normal heartbeats following the aberration.

In some embodiments, for example in which the stimulation system has a low duty cycle such as 1 second ON and 5 seconds OFF, 5 seconds ON and 10 seconds OFF, etc., the ECG may be halted during the period of stimulation and replaced with an alternative reading.

FIG. 47D is an example of a modified electrocardiograph. During stimulation, the entire electrocardiograph is flatlined. In some embodiments, the ECG may be flatlined artificially high or low so that a user of the ECG recognizes that the signal during such periods is not accurate.

FIG. 47E is another example of a modified electrocardiograph. During stimulation, the duration of which is known in advance, the electrocardiograph from the period preceding the stimulation is copied and presented again as the ECG during stimulation. FIG. 47F is still another example of a modified electrocardiograph. During stimulation, an artificial ECG, for example based on other patient data such as pressure, a perfect ECG, etc., is presented as the ECG during stimulation. In some embodiments based on pressure data, the artificial portion of the ECG may comprise or alternatively consist essentially of a R wave indicative of left ventricle contraction. The modified ECG of FIGS. 47E and 47F may allow integration with other machinery, for example which might alarm or function improperly if an ECG varied from a normal ECG.

FIG. 47G is yet another example of a modified electrocardiograph. During stimulation, an artificial ECG that is known to be artificial by visualization. For example, rather than waves with peaks, the waves may be represented as square waves. The modified ECG of FIG. 47G may allow integration with other machinery, for example which might alarm or function improperly if an ECG varied from a normal ECG, and/or can be visualized and clearly known to not be representative of actual ECG data.

In some embodiments, the effect of the stimulation on the ECG can be filtered out to present a true ECG during periods of stimulation.

Certain safety systems for the catheter systems are described herein, for example collapsing to a retracted state. In some embodiments, a parameter may be monitored, and certain events can be effected in response to a monitored parameter exceeding a threshold.

In some embodiments, the monitored parameter comprises pressure from a pressure sensor configured to be in the pulmonary artery. A pressure deviating from pulmonary artery pressure may indicate that the catheter has slid back such that electrodes may be in the right ventricle. Events that may be effected include stopping stimulation, collapsing an expandable member, and/or sounding an alarm. In some embodiments, right ventricle pressure may be monitored to confirm that the deviating pressure shows right ventricle pressure. Other combinations of sensor positions and vascular pressures, for example between a downstream cavity and an upstream cavity, are also possible. For example, right pulmonary artery to pulmonary artery, left pulmonary artery to pulmonary artery, pulmonary artery to right ventricle, right ventricle to right atrium, right atrium to superior vena cava, right atrium to inferior vena cava, superior vena cava to left brachiocephalic vein, superior vena cava to right brachiocephalic vein, left brachiocephalic vein to left internal jugular vein, right brachiocephalic vein to right internal jugular vein, combinations thereof, and the like.

In some embodiments, the monitored parameter comprises movement from a movement sensor. The pressure sensor may comprise, for example, a capacitive sensor, a magnetic sensor, a contact switch, combinations thereof, and the like. In some embodiments, the movement sensor is positioned at the access point (e.g., a left internal jugular vein). Movement greater than a certain distance (e.g., greater than about 0.5 cm, greater than about 1 cm, or greater than about 2 cm) may trigger effect events including stopping stimulation, collapsing an expandable member, and/or sounding an alarm. In some embodiments, a plurality of movement sensors spaced longitudinally along the system may be used to verify the detected movement.

In some embodiments, the monitored parameter comprises heart rate. As described herein, a pressure waveform may be used to monitor heart rate during stimulation. Other methods of monitoring heart rate during stimulation are also possible. If the heart rate changes by a certain amount or percentage, events that may be effected include stopping stimulation, collapsing an expandable member, and/or sounding an alarm.

In some embodiments, the monitored parameter comprises electrode impedance. If an electrode is configured to be pressed against a vessel wall, or spaced from the vessel wall by a distance, that configuration results in an impedance. If the impedance changes by a certain amount or percentage, events that may be effected include stopping stimulation, collapsing an expandable member, using an unused electrode, and/or sounding an alarm.

The catheter systems disclosed herein can be delivered, deployed, operated, and removed from the body according to any suitable method. FIGS. 48A-48H illustrate an example method for delivering and deploying a catheter system 4800 comprising an expandable structure 4820 including electrodes 4824. The catheter system 4800 may be the same or similar to the catheter system 3700 or other catheter systems disclosed herein. The catheter system 4800 may be delivered through a jugular vein to the superior vena cava, right atrium, right ventricle, through the pulmonary valve, and into the right pulmonary artery.

As shown in FIG. 48A, a syringe 4813 may be used to insert a needle 4814 for initially accessing the jugular vein 4815. A guidewire 4816 may then be inserted into the jugular vein 4815 through the needle 4814. As shown in FIG. 48B, the needle 4814 may be removed, and an introducer 4830 may be inserted into the jugular vein 4815 over the guidewire 4816, such that the introducer 4830 spans and maintains the opening into the jugular vein 4815. The introducer may comprise, for example, 11 French ARROW-FLEX® introducer from Teleflex, Inc. of Westmeath, Ireland, although other introducers may be used. The introducer may comprise a flexible shaft 4831 and a hemostasis valve 4832.

After the introducer 4830 is inserted into the jugular vein 4815, a Swan-Ganz catheter 4840 may be floated to the right pulmonary artery 4842, as illustrated in FIG. 48C. The Swan-Ganz catheter 4840 comprises an inflatable balloon 4841 at its distal end. The Swan-Ganz catheter 4842 may be inserted into the introducer 4830 over the guidewire 4816, and, once the balloon 4841 is distal to the introducer 4830, the balloon 4841 may be inflated. The inflated balloon 4841 is carried by the natural blood flow, pulling the distal tip of the Swan-Ganz catheter 4840 into the right pulmonary artery 4842. The guidewire 4816 may be distally advanced through a guidewire lumen of the Swan-Ganz catheter 4840 until the distal end of the guidewire 4816 is positioned in the right pulmonary artery 4842. Once the guidewire 4816 is in place, the balloon 4841 may be deflated and the Swan Ganz catheter 4840 can be proximally retracted out of the vasculature. The catheter assembly 4800 may include an inflatable balloon at its distal end such that the Swan Ganz catheter 4840 and the guidewire 4816 may be omitted.

An introducer sheath 4833 and dilator 4834 can be tracked over the guidewire 4816 to the pulmonary trunk or the right pulmonary artery 4842. When the introducer sheath 4833 is in place, the dilator 4834 can be withdrawn. The catheter system 4800 may be inserted through the introducer 4830, through the introducer sheath 4833, and tracked over the guidewire 4816 to the distal end of the introducer sheath 4833. If the expandable structure 4820 is self-expanding the expandable structure can be in a radially compressed state in the introducer sheath 4833 and in a radially expanded state out of the introducer sheath 4833. The expandable structure 4820 may prolapse from the distal end of the introducer sheath 4833 by distally advancing the expandable structure, proximally retracting the introducer sheath 4833, and/or combinations thereof. For example, if the distal end of the introducer sheath 4833 is in the pulmonary trunk, the expandable structure 4820 may be distally advanced and follow the guidewire 4816 into the right pulmonary artery 4842. FIG. 48D shows the expandable structure 4820 in a radially expanded configuration after exiting the distal end of the introducer sheath 4833.

The introducer sheath 4833 may be retracted to a position proximal or distal to the pulmonary valve 4847. If the catheter system 4800 includes a pressure sensor positioned in the right ventricle 4849, the distal end of the introducer sheath 4833 may be retracted to a position proximal to the pressure sensor, and thus proximal to the pulmonary valve 4847, to expose the pressure sensor to the right ventricle. The introducer sheath 4833 may be retracted to a position distal to the pulmonary artery 4847 such that proximal retraction of the expandable member 4820 causes the expandable member 4820 to be radially compressed by the introducer sheath 4833 and an expanded expandable member 4820 cannot cross the pulmonary valve 4847. If the introducer sheath 4833 is splittable, the introducer 4830 may be retracted from the body entirely and removed from the catheter shaft assembly 4806 by splitting along its circumference.

FIGS. 48D-48E show the expandable structure 4820 positioned within the right pulmonary artery 4842. In FIG. 48D, is in a self-expanded state after exiting the distal end of the introducer sheath 4833. In FIG. 48E, the expandable structure 4820 is in a further expanded state, for example due to retraction of an actuation tube. As seen in FIGS. 48D-48E, the durometer of the flexible tubing and/or the hinge of the catheter shaft assembly 4806 can allow a tight bend (approximately 90 degrees) as the catheter system 3800 transitions from the pulmonary artery trunk into the right pulmonary artery 4842. The catheter shaft assembly 4806 may be positioned firmly against the left side of the pulmonary artery trunk. Upon further expansion, for example 2 mm greater than the diameter of the right pulmonary artery 4842 in a maximum systolic state, the expandable structure 4820 is anchored. The neuromodulation procedure may occur over several days, so maintaining a position of the expandable structure 4820 by anchoring in the right pulmonary artery 4842 may provide consistency over the duration of the procedure.

The introducer 4830 may optionally be fixed relative to the patient during the procedure to inhibit or prevent inadvertent repositioning of the catheter system 4800. FIG. 48F shows an example of a handle 4810 of a catheter assembly 4800 that has been inserted into an introducer 4830. A silicone sleeve may be placed over the introducer 4830 and sutured to a surface outside the body of the patient and/or directly sutured to the patient. In some embodiments, the introducer 4830 is about 65 cm long and the catheter shaft assembly 4806 is about 100 cm long, leaving about 35 cm of neck 4835. After the introducer sheath 4833 is partially retracted, for example proximal to the pulmonary valve 4847, the neck 4835 may be reduce to about 15 to 20 cm. The introducer valve 4832 may form a secure connection between the introducer 4830 and the catheter shaft assembly 4806 of catheter system 4800, such that the catheter system 4800 is not easily moved relative to the introducer 4830. A silicone sleeve can optionally be placed over the actuation shaft assembly 4806 along the neck 4835 to maintain the desired spacing. An inadvertent dislocation of the expandable structure 4820 may be detected by a measured change in the heart contractility if the electrodes 4824 are shifted out of a proper stimulating position.

The electrode array 4829 of the expandable structure 4820 may be positioned toward the superior and posterior portion of the right pulmonary artery 4842 for stimulating one or more cardiopulmonary nerves. Fluoroscopy may be used to visualize the positioning of the catheter system 4800, including the expandable structure 4820, to ensure proper orientation is achieved, especially relating to the circumferential orientation the electrode array 4829. Fluoroscopy may be performed with or without contrast agents. FIG. 48G shows a fluoroscopic image of the catheter system 4800 inserted into right pulmonary artery 4842. The electrode array 4829 of expandable structure 4820 is visible without use of a contrast agent. Navigational guidance systems which incorporate positional sensors on catheters (e.g., NavX™, from St. Jude Medical Inc.) and/or cardiac mapping systems which map the electrophysiology of the heart surface may be used in conjunction with fluoroscopy or alternatively to fluoroscopy. Mapping performed additionally to fluoroscopy may be performed prior to or simultaneously with fluoroscopy. Pressure sensors or other means may be used to track positions of components of the catheter system, which can reduce or eliminate use of fluoroscopy.

FIG. 48H schematically depicts the activation of all of the electrodes 4824 on a single spline for stimulating a target nerve 4843, although actual stimulation protocols may include as few as two electrodes 4824, include electrodes 4824 on different splines, etc. The target nerve 4843 may be a cardiopulmonary nerve. In some embodiments, two electrodes 4824 positioned on either side of the target nerve 4843 may be activated. In some embodiments, the target nerve 4843 may be identified after positioning the expandable structure 4820 by "electrically moving" the catheter system 4800, in which the catheter system 4800 and the expandable structure 4820 are not physically repositioned, but the selection of "active" electrodes 4824 within the electrode array 4829 is shifted across the array 4829 or otherwise altered to better capture the target nerve 4843. The electrode array 4829 may be positioned so that the nerve is positioned between two or more electrodes (e.g., between two electrodes, between three electrodes, between four electrodes, etc.).

In some embodiments, a voltage pre-pulse may be applied to the tissue surrounding the target nerve 4843 immediately preceding a stimulation pulse. The pre-pulse may pre-polarize the nearby tissue and make it easier to stimulate the target nerve 4843 while avoiding stimulation of nearby pain nerves. For example, a stimulation protocol may include a smaller amplitude pulse with a first polarity (e.g., positive or anodic polarity) configured to pre-polarize the tissue followed immediately or almost immediately by a larger amplitude pulse of second polarity (e.g., negative or cathodic) configured to stimulate the target nerve 4843. The second polarity may be opposite the first polarity. The pre-pulse may be applied by the same or different electrodes 4824 of the electrode array 4829.

In some embodiments of use, the active electrodes which are to be used during the stimulation procedure are first identified by a fast titration. During a fast titration, the patient may be sedated to avoid pain so that the electrodes 4824 may be selectively activated at full power to determine which electrode or electrodes 4824 best capture the target nerve 4843. After the fast titration, the selected active electrodes 4824 may be activated with a lower power and increased to determine the optimal power setting for stimulating the target nerve 4843, during which the patient need not be sedated.

The electrodes 4824 may be activated in a monopolar or bipolar (e.g., guarded bipolar) fashion. Monopolar stimulation may use negative or positive polarity and includes the use of a return conductor. The return conductor may be at least 5 mm away from the electrodes. For example, the return conductor may be attached to or integrated with a portion of the catheter system 4800 or another catheter configured to be in the right ventricle 4849. For another example, the return conductor may be attached to or integrated with a portion of the catheter system 4800 or another catheter configured to be in the superior vena cava. For yet another example, the return conductor may be attached to or integrated with a portion of the catheter system 4800 or another catheter configured to be in the brachiocephalic or innominate vein. The current vector from the electrodes 4824 to the brachiocephalic vein may be away from at least one of the heart and the trachea, which may reduce side effects and/or increase patient tolerance. In certain such embodiments, the jugular vein assessed may be the left jugular vein. The return conductor may comprise a patch affixed to the skin.

Upon completion of the procedure, the catheter system 4800 may be removed from the body according to any suitable method. The actuation mechanism of the handle 4810 of the catheter system 4800 can be released so that the expandable structure 4820 can be in a self-expanded, but not further expanded, state. The expandable structure 4820 may then enter the introducer sheath 4833 by proximal retraction of the expandable member, distal advancement of the introducer sheath 4833, or a combination thereof. The introducer sheath 4833 may be retracted from the body with the catheter system 4800 in tow. The expandable structure 4820 may be retracted from the body through the introducer sheath 4833, and then the introducer sheath 4833 may be retracted.

The effectiveness of the neural stimulation on heart contractility, particularly of the left ventricle, can be monitored, for example, by measuring pressure within the heart. Pressure may be measured by a pressure sensor such as a fluid-filled column, a MEMS sensor, or another suitable type of pressure sensor. The pressure sensor may be attached to or integrated with the catheter system 4800, for example, along the catheter shaft assembly 4806. If the pressure sensor is attached to or integrated with the catheter system 4800, the sensor may be positioned in the right ventricle. The pressure in the right ventricle may be correlated to the pressure in the left ventricle, such that the left ventricular pressure and therefore left ventricle contractility may be sufficiently approximated. A pressure sensor may alternatively be inserted into the heart through another catheter, and may be placed in the right ventricle, in the left ventricle, or another suitable location. The left ventricular pressure may be used to optimize the effect of the neural stimulation on heart contractility over the course of the procedure. The heart contractility may be measurably increased, for example, by 5-12% during the procedure. A single catheter may comprise a plurality of sensors. For example, one sensor may be configured as above and a second sensor may be configured to reside in the right pulmonary artery. The sensor in the right pulmonary artery could provide a wedge pressure, which is a reading known to users from a Swan Ganz catheterization procedure. A sensor in the right pulmonary artery may be usable for safety. For example, if a pressure sensor in the right pulmonary artery migrated below the pulmonary valve, then stimulation could be shut off (e.g., immediately upon detection based on a change in pressure (e.g., percentage change or absolute change) and/or an absolute value of pressure (e.g., above or below a certain pressure)) in order to inhibit or prevent cardiac arrhythmias.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A method of using the trachea to facilitate positioning of electrodes in the right pulmonary artery, the method comprising:
    identifying under fluoroscopy a trachea bifurcating into a right pulmonary bronchus and a left pulmonary bronchus;
    identifying under fluoroscopy a pulmonary artery bifurcating into a right pulmonary artery and a left pulmonary artery;
    identifying a plane of bifurcation of the trachea, the plane of bifurcation of the trachea being along the right pulmonary artery;
    identifying a plane of bifurcation of the pulmonary artery, the plane of bifurcation of the trachea spaced from the plane of bifurcation of the pulmonary artery by a gap spanning the right pulmonary artery;
    expanding an expandable structure comprising stimulation electrodes in the right pulmonary artery along the gap and a first distance from the plane of bifurcation of the trachea;
    applying a signal to the stimulation electrodes to stimulate targeted nerves;
    after applying the signal, detecting a respiratory side effect; and
    after detecting the respiratory side effect, expanding the expandable structure comprising the stimulation electrodes in the right pulmonary artery along the gap and a second distance from the plane of bifurcation of the trachea, the second distance being greater than the first distance.

2. The method of claim 1, wherein the respiratory side effect comprises cough.

3. The method of claim 1, wherein expanding the expandable structure comprises allowing the expandable structure to self-expand.

4. The method of claim 3, wherein expanding the expandable structure comprises, after allowing the expandable structure to self-expand, further expanding the expandable structure.

5. The method of claim 1, wherein the nerves comprise at least one of the right dorsal medial common peroneal nerve, the right stellate CPN, or the left lateral cardiac nerve.

6. The method of claim 1, wherein the first distance is between 2 mm and 8 mm.

7. The method of claim 1, wherein the first distance is between 10% and 100% of a length of the right pulmonary artery and 8 mm.

8. A method of using the trachea to facilitate positioning of electrodes in the right pulmonary artery, the method comprising:
   identifying a trachea bifurcating into a right pulmonary bronchus and a left pulmonary bronchus;
   identifying a plane of bifurcation of the trachea;
   positioning stimulation electrodes in a right pulmonary artery a distance from the plane of bifurcation of the trachea, the distance being between 2 mm and 8 mm;
   applying a signal to the stimulation electrodes to stimulate targeted nerves;
   after applying the signal, detecting a respiratory side effect; and
   after detecting the respiratory side effect, positioning the stimulation electrodes in the right pulmonary artery a second distance from the plane of bifurcation of the trachea, the second distance being greater than the distance.

9. The method of claim 8, wherein identifying the trachea is under fluoroscopy.

10. The method of claim 8, wherein the respiratory side effect comprises cough.

11. The method of claim 10, wherein the second distance is between 4 mm and 8 mm.

12. The method of claim 11, wherein the nerves comprise at least one of the right dorsal medial common peroneal nerve, the right stellate CPN, or the left lateral cardiac nerve.

13. The method of claim 8, wherein the distance is between 10% and 100% of a length of the right pulmonary artery and 8 mm.

14. A method of using the trachea to facilitate positioning of electrodes in the right pulmonary artery, the method comprising:
   identifying a trachea;
   positioning stimulation electrodes in a right pulmonary artery a distance from the trachea, the distance being between 2 mm and 8 mm;
   applying a signal to the stimulation electrodes to stimulate targeted nerves;
   after applying the signal, detecting a respiratory side effect; and
   after detecting the respiratory side effect, positioning the stimulation electrodes in the right pulmonary artery a second distance from the trachea, the second distance being greater than the distance.

15. The method of claim 14, wherein identifying the trachea is under fluoroscopy.

16. The method of claim 14, wherein the respiratory side effect comprises cough.

17. The method of claim 16, wherein the second distance is between 4 mm and 8 mm.

18. The method of claim 17, wherein the nerves comprise at least one of the right dorsal medial common peroneal nerve, the right stellate CPN, or the left lateral cardiac nerve.

19. The method of claim 14, wherein the second distance is between 4 mm and 8 mm.

20. The method of claim 14, wherein the distance is between 10% and 100% of a length of the right pulmonary artery and 8 mm.

* * * * *